(12) United States Patent
Klosin et al.

(10) Patent No.: US 10,981,156 B2
(45) Date of Patent: Apr. 20, 2021

(54) CHROMIUM COMPLEX AND CATALYST THEREFROM

(71) Applicant: Dow Global Technologies LLC, Midland, MI (US)

(72) Inventors: Jerzy Klosin, Midland, MI (US); Kara A. Milbrandt, Freeland, MI (US); Scott D. Boelter, Saginaw, MI (US); David R. Wilson, Midland, MI (US); Mari S. Rosen, Midland, MI (US); Dean M. Welsh, Midland, MI (US); Peter M. Margl, Midland, MI (US); Kyoung Moo Koh, Midland, MI (US); David M. Pearson, Lake Jackson, TX (US); Rafael Huacuja, Rosharon, TX (US)

(73) Assignee: Dow Global Technologies LLC, Midland, MI (US)

(*) Notice: Subject to any disclaimer, the term of this patent is extended or adjusted under 35 U.S.C. 154(b) by 37 days.

(21) Appl. No.: 16/235,124

(22) Filed: Dec. 28, 2018

(65) Prior Publication Data
US 2019/0210013 A1 Jul. 11, 2019

Related U.S. Application Data

(62) Division of application No. 15/557,886, filed as application No. PCT/US2016/021700 on Mar. 10, 2016, now Pat. No. 10,207,262.
(Continued)

(51) Int. Cl.
*B01J 31/24* (2006.01)
*B01J 31/14* (2006.01)
(Continued)

(52) U.S. Cl.
CPC ......... *B01J 31/2433* (2013.01); *B01J 31/143* (2013.01); *B01J 31/188* (2013.01); *B01J 31/2208* (2013.01); *B01J 31/2438* (2013.01); *B01J 31/2457* (2013.01); *B01J 31/2476* (2013.01); *B01J 31/2495* (2013.01); *C07C 2/36* (2013.01); *C07F 9/6568* (2013.01); *C07F 9/6571* (2013.01); *C07F 9/65683* (2013.01);
(Continued)

(58) Field of Classification Search
None
See application file for complete search history.

(56) References Cited

U.S. PATENT DOCUMENTS 7,511,183 B2  3/2009  Blann et al.
8,962,903 B2  2/2015  Carter et al.
(Continued)

OTHER PUBLICATIONS

Stennett et al. (CHEMCATCHEM, 5, 2946-2954 (Year: 2013).*
(Continued)

*Primary Examiner* — Yun Qian
(74) *Attorney, Agent, or Firm* — Brooks, Cameron & Huebsch, PLLC

(57) ABSTRACT

The invention relates to oligomerization of olefins, such as ethylene, to higher olefins, such as a mixture of 1-hexene and 1-octene, using a catalyst system that comprises a) a source of chromium b) one or more activators and c) a phosphacycle-containing ligating compound. Additionally, the invention relates to a phosphacycle-containing ligating compound and a process for making said compound.

6 Claims, 4 Drawing Sheets

Related U.S. Application Data

(60) Provisional application No. 62/133,016, filed on Mar. 13, 2015.

(51) Int. Cl.

| | | |
|---|---|---|
| *B01J 31/18* | (2006.01) | |
| *C07C 2/36* | (2006.01) | |
| *C07F 9/6568* | (2006.01) | |
| *C07F 9/6584* | (2006.01) | |
| *C07F 11/00* | (2006.01) | |
| *C07F 17/02* | (2006.01) | |
| *C07F 9/6571* | (2006.01) | |
| *B01J 31/22* | (2006.01) | |

(52) U.S. Cl.
CPC ...... *C07F 9/65685* (2013.01); *C07F 9/65842* (2013.01); *C07F 9/65844* (2013.01); *C07F 9/65846* (2013.01); *C07F 9/65848* (2013.01); *C07F 9/657154* (2013.01); *C07F 11/005* (2013.01); *C07F 17/02* (2013.01); *B01J 2231/20* (2013.01); *B01J 2531/62* (2013.01); *B01J 2540/10* (2013.01); *B01J 2540/22* (2013.01); *B01J 2540/225* (2013.01); *B01J 2540/30* (2013.01); *B01J 2540/34* (2013.01); *B01J 2540/444* (2013.01); *C07C 2531/14* (2013.01); *C07C 2531/18* (2013.01); *C07C 2531/24* (2013.01)

(56) References Cited

U.S. PATENT DOCUMENTS

| | | |
|---|---|---|
| 9,499,456 B2 | 11/2016 | Overett et al. |
| 2006/0229480 A1 | 10/2006 | Blann et al. |
| 2007/0185357 A1 | 8/2007 | De Boer et al. |
| 2008/0039600 A1 | 2/2008 | Bollmann et al. |
| 2009/0306442 A1 | 12/2009 | Pretorius et al. |
| 2011/0086991 A1 | 4/2011 | Dixon et al. |
| 2014/0221645 A1 | 8/2014 | Sydora et al. |
| 2015/0284303 A1 | 10/2015 | Zoricak et al. |

OTHER PUBLICATIONS

Danan Dou, et al., "Synthesis and Reactivity of New Diborylphospbanes", Inorganic Chemistry, vol. 33, No. 10, May 1, 1994, pp. 2151-2160.

Mcguinness, "Olefin Oligomerization via Metallacycles: Dimerization, Trimerization, Tetramerization, and Beyond", Chemical Reviews, American Chemical Society, vol. 111, Mar. 9, 2011, pp. 2321-2341.

Velian, et al., "Facile Synthesis of Dibenzo-7[lambda]3-phosphanorbornadiene Derivatives Using Magnesium Anthracene", Journal of the American Chemical Society, vol. 134, No. 34, Aug. 15, 2012, pp. 13978-13981.

Gudat, et al., "Synthesis, Structure, and Chemical Reactivity of a Stable C, Me, -Substituted Phosphanylium Ion: (Pentamethylcyclopentadienyl)(t-butylamino)-phoshanylium Tetrachloroaluminate", Journal of The Chemical Society, Dalton Transactions, vol. 1989, No. 4, Jan. 1, 1989, pp. 693-700.

Fox, et al., "Bix-(2,5-diphenylphospholanes) with sp2 Carbon Linkers: Synthesis and Application in Asymmetric Hydrogenation", The Journal of Organic Chemistry, vol. 73, No. 3, Feb. 1, 2008, pp. 775-784.

Leeuwen, et al., "New Processes for the Selective Production of 1-Octene"; Coordination Chemistry Reviews, vol. 225, No. 13 (Oct. 4, 2010) 19 pgs.

Overett, et al., "Carbon-Bridged Diphosphine Ligands for Chromium-Catalysed Ethylene Tetramerisation and Trimerisation Reactions"; Journal of Molecular Catalysis A: Chemical, vol. 283, No. 1-2 (Mar. 18, 2008) 6 pgs.

International Search Report & Written Opinion for related PCT Application PCT/US2016/021700, dated Sep. 30, 2016 (37 pgs).

International Preliminary Report on Patentability for related PCT Application PCT/US2016/021700, dated Sep. 28, 2017 (24 pgs).

Chen, et al., "Synthesis of Cage Compounds Containing Boron, Germanium, and Phosphorus Atoms", Inorganic Chemistry, vol. 36, No, 5 (Feb. 1, 1997) (7 pgs).

Bailey, et al., "A simple Route to Azaborinylphosphines: Isoelectronic B—N Analogues of Arylphosphine Ligands", Chemical Communications—CHEMCON., vol. 50, No. 12 (Dec. 9, 2013) (3 pgs).

Driess, et al., "Darstellung, Struktur and Komplexierung von 2,2',5,5'-Tetrahydro-1,1'-bi(1 H-1, 2, 5-phosphadiborol)-Derivaten", Chemishce Berichte, vol. 124, No. 7, (Jul. 1, 1991) (7 pgs).

Kaufmann, et al., "Some Oxidative Addition Reactions with a Diphosphadibora [1.1.0] bicyclobutane: Formation of Cage Compounds and of an Unusual Trinuclear Coordination Compound of Palladium", Inorganica Chimica Acta, vol. 269, No. 1, (Mar. 3, 1998) (10 pgs).

Chen, et al., "Synthesis and Chemistry of Bis(borylphosphinp)silanes and -germanes", Inorganic Chemistry, vol. 38, No. 22 (Mar. 10, 1999) (7 pgs).

Stennett, et al., "N-N-Diphospholylamines—A New Family of Ligands for Highly Active, Chromium-Based, Selective Ethene Oligomesiration Catalysts"; ChemCatChem, vol. 5 (Year: 2013) (9 pgs).

\* cited by examiner

CHROMIUM COMPLEX AND CATALYST THEREFROM

This application is a Divisional of U.S. National Stage application Ser. No. 15/557,886, filed Sep. 13, 2017 and published as U.S. Publication No. 2018-0071725 A1 on Mar. 15, 2018, which claims priority to International Application Number PCT/US2016/021700, filed Mar. 10, 2016 and published as WO 2016/149024 on Sep. 22, 2016, which claims the benefit to U.S. Provisional Application 62/133,016, filed Mar. 13, 2015, the entire contents of which are incorporated herein by reference in its entirety.

The invention relates to oligomerization of olefins, such as ethylene, to higher olefins, such as a mixture of 1-hexene and 1-octene, using a catalyst system that comprises a) a source of chromium b) one or more activators and c) a phosphacycle-containing ligating compound. Additionally, the invention relates to a phosphacycle-containing ligating compound and a process for preparing said compound.

Numerous improvements in the ligating compounds for catalyst systems used in olefin oligomerization have been disclosed. However, problems still remain with catalyst efficiency, catalyst selectivity, formation of polymer byproduct, and deactivation of the catalyst under high temperature conditions. It would be advantageous to discover a catalyst system able to produce olefin oligomers with higher catalyst efficiency, higher catalyst selectivity, and less polymer byproduct formation.

It is believed that the rate of formation of $C_{10+}$ oligomers is related to the concentration of 1-hexene and/or 1-octene that are present in the reaction vessel in which the oligomerization occurs, such as disclosed in US Patent Application Publication 2015-0284303. Such reactions that maximize the concentration of 1-hexene and 1-octene in the reactor have provided poor product selectivity. In particular, the production of larger amounts of $C_{10+}$ oligomers has been observed under conditions that provide for a higher concentration of 1-hexene and/or 1-octene. The performance of chromium-bridged diphosphine catalysts is typically temperature dependent. The prior art generally discloses preferred operating temperatures of from 50 to 150° C., especially from 60 to 90° C. Very high activities (of greater than $2 \times 10^6$ grams of product per gram of catalyst per hour) have been reported at this temperature range. However, simple batch experiments have shown that this high activity, which leads to a high concentration of 1-hexene and 1-octene in the reactor, is also associated with a decrease in product selectivity—in particular, the production of a higher amount of $C_{10+}$ oligomers has been observed. Batch experiments have shown that product selectivity may be improved by lowering the reaction temperature, but a lower oligomerization temperature is not "sufficient" to minimize the $C_{10+}$ fraction.

Diphosphine ligands having a dioxyphosphacyclic group have been taught in WO2013168102 as being useful for the tetramerization of ethylene.

Surprisingly, it has been found that catalyst systems based on certain phosphacyclic ligating compounds desirably provide reduced polymer formation, and, in many cases, improved catalyst efficiency and selectivity.

SUMMARY OF THE INVENTION

The invention provides a process for selectively oligomerizing an olefin comprising contacting at least one olefin with a catalyst system under olefin oligomerization conditions sufficient to convert at least a portion of the at least one olefin to at least one oligomer of the at least one olefin, the catalyst system comprising, a) a source of chromium, b) one or more activators, and c) at least one phosphacycle-containing ligating compound $R_1R_2P—Y—X_1R_3(R_4)_m$ represented as:

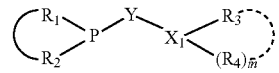

wherein:
P is phosphorus; $X_1$ is selected from nitrogen, phosphorus, oxygen, or sulfur; each of $R_1$ and $R_2$ is independently a substituted or unsubstituted hydrocarbon derivative, a substituted or unsubstituted heterohydrocarbon derivative, or a substituted or unsubstituted heteroatom group having from one to 50 non-hydrogen atoms; m is 0 or 1; $R_1$ and $R_2$ are linked together to form a divalent moiety represented as

which together with P forms a cyclic structure (phosphacycle) containing from 3 to 10 ring atoms; each of $R_3$ and $R_4$ is independently hydrogen, halogen, a substituted or unsubstituted hydrocarbon derivative, a substituted or unsubstituted heterohydrocarbon derivative, or a substituted or unsubstituted heteroatom group having from one to 50 non-hydrogen atoms; $R_3$ and $R_4$ are optionally linked together to form a divalent moiety represented as

wherein the optional character of the linkage is depicted by a dashed connection, which together with $X_1$ forms a cyclic structure containing from 3 to 10 ring atoms; Y, optionally linked together with one or more of $R_1$, $R_2$, $R_3$, or $R_4$ to form cyclic structures containing from 4 to 10 ring atoms, as represented by:

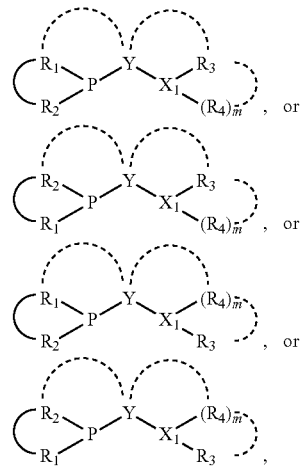

wherein the optional character of the linkages is depicted by a dashed connection, is a divalent linking group $[L(R_5)_q]_p$ between P and $X_1$ containing from one to 50 non-hydrogen atoms; $[L(R_5)_q]_p$ is represented by:

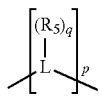

wherein each L is independently selected from the group consisting of boron, carbon, silicon, germanium, nitrogen, phosphorus, oxygen, and sulfur; p is an integer number from 1 to 6, preferably from 1 to 4; $R_5$ is independently hydrogen, halogen, substituted or unsubstituted hydrocarbon derivative, substituted or unsubstituted heterohydrocarbon derivative, or a substituted or unsubstituted heteroatom group; q is 0, 1, or 2; provided that the $[L]_p$ subunit of the divalent linking group $[L(R_5)_q]_p$ does not comprise an amidine (N—C═N) group; further provided that in at least one phosphacycle of the phosphacycle-containing ligating compound, both atoms directly bonded to P or $X_1$ are $sp^3$ hybridized; still further preferably provided that one or two phosphacycles comprising P or $X_1$, preferably comprising P, $R_1$, and $R_2$, or comprising $X_1$, $R_3$, and $R_4$, contain no P—N, P—O, or P—S bonds within the ring part of the phosphacycle; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; from two to ten, preferably from two to six, independently selected ligating compounds may be optionally linked together via their respective independently selected Y, $R_1$, $R_2$, $R_3$, $R_4$ or $R_5$ groups to form a poly(ligating compound) species. Preferably at least one, preferably two, phosphacycles do not contain more than one carbon-carbon unsaturated bond in each phosphacycle, preferably not more than one unsaturated bond in each phosphacycle.

Another embodiment of the invention provides a catalyst system for the oligomerization of olefins, the catalyst system comprising, a) a source of chromium, b) one or more activators, and c) at least one phosphacycle-containing ligating compound, as described herein.

Another embodiment of the invention provides a process to produce a catalyst system for the oligomerization of olefins, the catalyst system comprising, a) a source of chromium, b) one or more activators, and c) at least one phosphacycle-containing ligating compound, as described herein.

Another embodiment of the invention provides a phosphacycle-containing ligating compound-chromium complex comprising a) a source of chromium, and b) a phosphacycle-containing ligating compound, as described herein.

Another embodiment of the invention provides a process to produce a phosphacycle-containing ligating compound-chromium complex comprising a) a source of chromium, and b) a phosphacycle-containing ligating compound, as described herein.

Another embodiment of the invention provides a phosphacycle-containing ligating compound as described herein.

Another embodiment of the invention provides a process to produce a phosphacycle-containing ligating compound as described herein.

Another embodiment of the invention provides a catalyst system for the oligomerization of olefins, the catalyst system comprising, a) a source of chromium, b) one or more activators, and c) at least one poly(ligating compound) species, as described herein.

Another embodiment of the invention provides a process to produce a catalyst system for the oligomerization of olefins, the catalyst system comprising, a) a source of chromium, b) one or more activators, and c) at least one poly(ligating compound) species, as described herein.

Another embodiment of the invention provides a poly (ligating compound-chromium complex) species comprising a) a source of chromium, and b) a poly(ligating compound) species, as described herein.

Another embodiment of the invention provides a process to produce a poly(ligating compound-chromium complex) species comprising a) a source of chromium, and b) a poly(ligating compound) species, as described herein.

Another embodiment of the invention provides a poly (ligating compound) species as described herein.

Another embodiment of the invention provides a process to produce a poly(ligating compound) species as described herein.

DETAILED DESCRIPTION OF THE INVENTION

General Definitions

Figure 1:
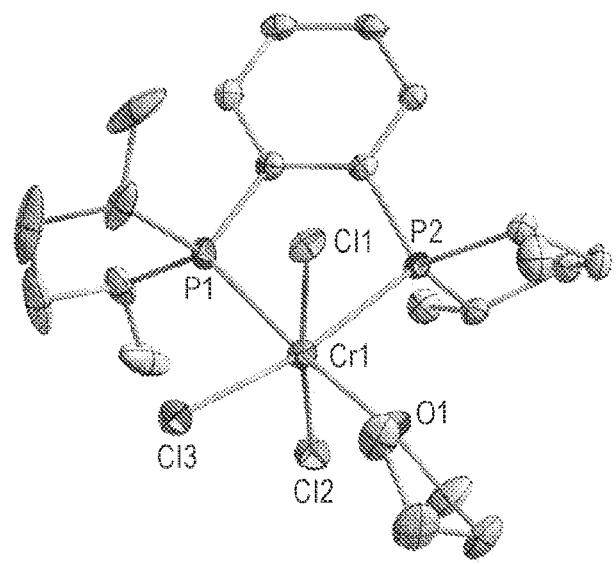
FIG. 1. Crystal structure of trichloro[1,2-bis[(2S,5S)-2,5-dimethylphospholano]benzene] (tetrahydrofuran)chromium, (3), drawn with 50% thermal ellipsoid probability. Hydrogen atoms are omitted for clarity. Carbon atoms are represented by gray thermal ellipsoids.

As used herein, "ring atom" means an atom that together with at least two other atoms forms a ring or cyclic structure.

As used herein, the term "hydrocarbon derivative", e.g., hydrocarbon derivative, substituted hydrocarbon derivative, hydrocarbon derivative-containing, refers to a group of compounds consisting of carbon and hydrogen only. Specifically, "hydrocarbon derivative" refers to the group consisting of hydrocarbyl, hydrocarbylene, hydrocarbylidene, and hydrocarbylidyne, the terms "hydrocarbyl", "hydrocarbylene", "hydrocarbylidene", and "hydrocarbylidyne" having the same meaning as established by the IUPAC (*International Union of Pure and Applied Chemistry*): Hydrocarbyl groups are univalent groups formed by removing a hydrogen atom from a hydrocarbon, e.g., methyl, ethyl, propyl, butyl, pentyl, hexyl, heptyl, octyl, cyclopentyl, cyclohexyl, cyclohexylmethyl, phenyl, benzyl, naphthyl. Hydrocarbylene groups are divalent groups formed by removing two hydrogen atoms from a hydrocarbon, the free valencies of which are not engaged in a double bond, e.g., 1,2-phenylene, —$CH_2CH_2CH_2$— (propane-1,3-diyl), —$CH_2$— (methylene), $C_6H_3C_6H_5$ (5-phenyl-1,3-phenylenediyl. Hydrocarbylidene groups are divalent groups formed by removing two hydrogen atoms from the same carbon atom of a hydrocarbon, the free valencies of which are engaged in a double bond, e.g., $CH_3CH$= (ethylidene), $C_6H_5CH$= (benzylidene).

Hydrocarbylidyne groups are trivalent groups formed by removing three hydrogen atoms from the same carbon atom of a hydrocarbon, the free valencies of which are engaged in a triple bond, e.g., $CH_3CH_2C$≡ (propylidyne), $C_6H_5C$≡ (benzylidyne). The term "hydrocarbon derivative" as used herein refers to hydrocarbon derivative radicals containing 1 to 50 carbon atoms, preferably 1 to 30 carbon atoms, more preferably 1 to 20 carbon atoms, most preferably 1 to 16 carbon atoms, including branched or unbranched, cyclic or acyclic, saturated or unsaturated species, such as alkyl groups, alkenyl groups, alkynyl groups, aryl groups, arylalkyl groups, cycloalkyl groups, alkanediyl groups, alkylenediyl groups, arylenediyl groups, alkylidene groups, and the like.

As used herein, the term "heterohydrocarbon derivative", e.g., heterohydrocarbon derivative, substituted heterohydrocarbon derivative, heterohydrocarbon derivative-containing, refers to a hydrocarbon derivative as defined above in which at least one carbon atom and, optionally, its attached hydrogen atoms in the hydrocarbon derivative are replaced with at least one heteroatom. Specifically, "heterohydrocarbon derivative" refers to the group consisting of heterohydrocarbyl, heterohydrocarbylene, heterohydrocarbylidene, and heterohydrocarbylidyne, the terms "heterohydrocarbyl", "heterohydrocarbylene", "heterohydrocarbylidene", and "heterohydrocarbylidyne" having the same meaning as defined above for the respective hydrocarbon derivatives, e.g., hydrocarbyl, hydrocarbylene, hydrocarbylidene, and hydrocarbylidyne, wherein at least one carbon atom and, optionally, its attached hydrogen atoms in the hydrocarbon derivative is replaced with at least one heteroatom. Heterohydrocarbyl groups are univalent groups formed by removing at least one carbon atom and, optionally, its attached hydrogen atoms from a hydrocarbyl group, and replacing it with at least one heteroatom, e.g., $CH_3O$— (methoxy), $CF_3$— (trifluoromethyl), $CH_3CH_2NH$— (ethylamino), $(CH_3CH_2)_2NC_6H_4$— (dimethylaminophenyl), $C_6H_5OC_6H_4CH_2$— (phenoxybenzyl), $CH_3OCH_2CH_2OCH_2$— (methoxyethoxymethyl), $C_5H_4N$— (pyridyl). Heterohydrocarbylene groups are divalent groups formed by removing at least one carbon atom and, optionally, its attached hydrogen atoms from a hydrocarbylene group and replacing it with at least one heteroatom, the free valencies of which heterohydrocarbylene group are not engaged in a double bond, e.g., —$CH_2CH_2N(CH_3)CH_2CH_2$— (methylaminodi-(2,1-ethane)diyl), —$CH_2CH_2OCH_2CH_2$— (oxydi-(2,1-ethane)diyl), —$CH_2CH_2CH_2CH_2O$— (4-butaneyl-1-oxy), —$OCH_2CH_2O$— (1,2-ethanediylbis(oxy)), —$CH_2CH(CF_3)CH_2$— (2-trifluoromethyl-1,3-propanediyl), —$CH_2COCH_2CH_2$— (2-oxo-1,4-butanediyl). Heterohydrocarbylidene groups are divalent groups formed by removing at least one carbon atom and, optionally, its attached hydrogen atoms from a hydrocarbylidene group and replacing it with at least one heteroatom, the free valencies of which heterohydrocarbylidene group are engaged in a double bond, e.g., $CH_3OCH_2CH$= (methoxyethylidene), $C_6H_3C_{12}CH$= (dichlorobenzylidene), $(CH_3)_2NCH$= (dimethylaminomethylidene), $C_6H_5CH_2N$= (benzylimine). Heterohydrocarbylidyne groups are trivalent groups formed by removing at least one carbon atom and, optionally, its attached hydrogen atoms from a hydrocarbylidyne group and replacing it with at least one heteroatom, the free valencies of which heterohydrocarbylidyne group are engaged in a triple bond, e.g., $CH_3OCH_2C$≡ (2-methoxyethylidyne), $(CH_3)_2NC_6H_4C$≡ (dimethylaminobenzylidyne).

More generally, the modifiers "hetero" and "heteroatom-containing", e.g., "heteroalkyl", "heteroaryl", "heterohydrocarbon derivative", "heteroatom-containing hydrocarbyl group", refer to a molecule or molecular fragment in which one or more carbon atoms and, optionally, its attached hydrogen atoms are replaced with a heteroatom. Thus, for example, the term "heteroalkyl" refers to an alkyl substituent that contains a heteroatom. When the term "heteroatom-containing" introduces a list of possible heteroatom-containing groups, it is intended that the term apply to every member of that group. That is, the phrase "heteroatom-containing alkyl, alkenyl, alkynyl, aryl, and arylalkyl" is to be interpreted as "heteroatom-containing alkyl, heteroatom-containing alkenyl, heteroatom-containing alkynyl, heteroatom-containing aryl, and heteroatom-containing arylalkyl." The free valence of the heterohydrocarbon derivative may reside on a heteroatom, as in methoxy ($CH_3O$—), diethylamino (($CH_3CH_2)_2N$—), or butylthio ($CH_3CH_2CH_2CH_2S$—), or it may reside on a carbon atom, as in N,N-dimethylaminoethyl (($CH_3)_2NCH_2CH_2$—), pyridylmethyl ($C_5H_4NCH_2$—), or methoxyethyl ($CH_3OCH_2CH_2$—). The term "heterohydrocarbon derivative" as used herein refers to heterohydrocarbon derivative radicals containing 1 to 50 carbon atoms, preferably 1 to 30 carbon atoms, more preferably 1 to 20 carbon atoms, most preferably 1 to 16 carbon atoms, including branched or unbranched, cyclic or acyclic, saturated or unsaturated species, e.g., heterohydrocarbyl groups, heteroalkyl groups, heteroalkenyl groups, and heteroaryl groups.

The term "heteroatom group" refers to an atom or molecular fragment comprising at least one heteroatom and no carbon atoms, for example, nitro (—$NO_2$), oxo (=O), and sulfonic acid (—$SO_3H$) groups. The heteroatom group contains from 1 to 40 atoms, preferably 1 to 10 atoms, more preferably 1 to 6 atoms.

As used herein, heteroatoms may be selected from the group consisting of B, Si, Ge, N, P, As, Sb, Bi, O, S, Se, F, Cl, Br, I, and transition metals, preferably from the group consisting of B, Si, Ge, N, P, O, S, Se, F, Cl, Br, I, and transition metals.

As used herein, the term "substituted", e.g., "substituted hydrocarbon derivative", "substituted heterohydrocarbon derivative", "substituted hydrocarbyl," "substituted heterohydrocarbyl", "substituted aryl," "substituted arylalkyl," "substituted alkyl," means that in the group in question (e.g., the hydrocarbon derivative, heterohydrocarbon derivative, hydrocarbyl, heterohydrocarbyl, aryl, arylalkyl, alkyl, or other moiety that follows the term "substituted"), at least one hydrogen atom bound to a carbon atom or to a heteroatom is replaced with one or more heteroatoms, unless another type of substitution is specifically stated, such as "alkyl-substituted" or "substituted by aryl". When the term "substituted" introduces a list of possible substituted groups, it is intended that the term apply to every member of that group. That is, the phrase "substituted alkyl, alkenyl, alkynyl, aryl, and arylalkyl" is to be interpreted as "substituted alkyl, substituted alkenyl, substituted alkynyl, substituted aryl, and substituted arylalkyl." Similarly, "optionally substituted alkyl, alkenyl, alkynyl, arylalkyl" is to be interpreted as "optionally substituted alkyl, optionally substituted alkenyl, optionally substituted alkynyl, and optionally substituted arylalkyl."

There is some overlap in terms of the definitions of "substituted hydrocarbon derivative" and "heterohydrocarbon derivative". For example, '2-fluoroethyl' is the 'ethyl' hydrocarbon derivative substituted with one fluorine atom. At the same time it may be classified as a heterohydrocarbon derivative formed by taking a propyl group ($CH_3CH_2CH_2$) and replacing the methyl ($CH_3$) carbon and its attached hydrogen atoms with a fluorine heteroatom. In either case, it will be clear to one skilled in the art that either classification is operative. In another example, 'pyridylmethyl' is the 'methyl' hydrocarbon derivative substituted with a pyridyl group. At the same time it may be classified as a heterohydrocarbon derivative formed by taking a benzyl group ($C_6H_5CH_2$) and replacing one of the ring carbons and its attached hydrogen atom with a nitrogen heteroatom. In either case, it will be clear to one skilled in the art that either classification is operative.

The term "alkyl" as used herein refers to a branched or unbranched, cyclic or acyclic saturated hydrocarbyl radical typically, although not necessarily, containing 1 to 50 carbon atoms, more preferably 1 to 25 carbon atoms, most preferably 1 to 16 carbon atoms, e.g., methyl, ethyl, n-propyl, isopropyl, n-butyl, isobutyl, sec-butyl, t-butyl, pentyl, hexyl, octyl, decyl, as well as cycloalkyl groups, e.g., cyclopropyl, cyclobutyl, cyclopentyl, cyclohexyl, cyclopentylmethyl, and cyclohexylethyl.

The term "alkenyl" as used herein refers to a branched or unbranched, cyclic or acyclic hydrocarbyl radical containing at least one double bond and typically, although not necessarily, containing 2 to 50 carbon atoms, more preferably 2 to 25 carbon atoms, most preferably 2 to 16 carbon atoms, e.g., ethenyl, n-propenyl, isopropenyl, n-butenyl, isobutenyl, 4-octenyl, 2-decenyl, cyclopentenyl, cyclopentadienyl, cyclohexenyl, and cyclohexadienyl.

The term "olefin" as used herein refers to branched or unbranched acyclic or cyclic hydrocarbons having one or more carbon-carbon double bonds, apart from the formal ones in aromatic compounds and typically, although not necessarily, containing 2 to 50 carbon atoms, more preferably 2 to 25 carbon atoms, most preferably 2 to 16 carbon atoms, e.g., ethene (ethylene), propene (propylene), 1-butene, 2-butene, isobutene, 1-hexene, 3-hexene, 1-octene, 2-decene, cyclopentene, cyclopentadiene, cyclohexene, and cyclohexadiene.

Under the term "α-olefins" as used herein refers olefins with terminal double bonds and typically, although not necessarily, containing 2 to 50 carbon atoms, more preferably 2 to 25 carbon atoms, most preferably 2 to 16 carbon atoms, e.g., ethylene, propylene, 1-butene, 1-pentene, 1-hexene, 1-heptene, 1-octene, and 1-decene.

The term "alkynyl" as used herein refers to a branched or unbranched, cyclic or acyclic hydrocarbon radical containing at least one triple bond and typically, although not necessarily, containing 2 to 50 carbon atoms, more preferably 2 to 25 carbon atoms, most preferably 2 to 16 carbon atoms, e.g., ethynyl, n-propynyl, isopropynyl, n-2-butynyl, isobutynyl, octynyl, 3-decynyl, cyclooctynyl.

The term "aromatic" is used in its usual sense, including unsaturation that is essentially delocalized across several bonds around a ring. The term "aromatic" as used herein refers to a group containing an aromatic ring or ring system typically, although not necessarily, containing 2 to 50 carbon atoms, preferably 2 to 25 carbon atoms, more preferably 2 to 16 carbon atoms. Typical neutral unsubstituted aromatic compounds include benzene, naphthalene, anthracene, phenanthrene, pyridine, pyrazine, imidazole, pyrazole, oxazole, thiophene, pyrrole, triazole, indole, and benzimidazole. Typical charged unsubstituted aromatic compounds include cyclopropenyl cation and cyclopentadienyl anion. The term "aryl" as used herein refers to groups containing an aromatic ring or ring system typically, although not necessarily, containing 2 to 50 carbon atoms, preferably 2 to 25 carbon atoms, more preferably 2 to 16 carbon atoms. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, terphenyl, anthracenyl, phenanthrenyl, pyridinyl, pyrazinyl, imidazolyl, pyrazolyl, oxazolyl, thienyl, pyrrolyl, triazolyl, indolyl, and benzimidazolyl. The aryl groups may be unsubstituted or may be substituted with halogen, preferably fluorine, chlorine, or bromine, more preferably fluorine or bromine, even more preferably fluorine; hydrocarbyl, such as alkyl, alkenyl, or alkynyl, heterohydrocarbyl; or heteroatom groups. In particular embodiments, aryl substituents (substituents on the aryl group) include 1 to 40 atoms other than hydrogen, preferably 1 to 20 atoms other than hydrogen, and more preferably 1 to 10 atoms other than hydrogen. Substituted aryl groups include tolyl (methylphenyl), xylyl (dimethylphenyl), mesityl (trimethylphenyl), ethylphenyl, styryl, allylphenyl, propynylphenyl, chlorophenyl, fluorophenyl, difluorophenyl, trifluorophenyl, tetrafluorophenyl, pentafluorophenyl, pentafluorobiphenyl, methoxyphenyl, ethoxyphenyl, dimethoxyphenyl, trifluoromethylphenyl, bis(trifluoromethyl)phenyl, dimethylaminophenyl, dimethylaminoethylphenyl, phenoxyphenyl, methylcarboxyphenyl, ethylcarboxyphenyl, methoxynaphthyl, nitrophenyl, dinitrophenyl, cyanophenyl, dicyanophenyl, chloropyridinyl, methylimidazolyl, phenylpyrrolyl, and ethylthienyl.

The term "arylalkyl" as used herein refers to substituted alkyl groups, the alkyl groups defined as above, wherein the substituent is one or more aryl groups and typically, although not necessarily, containing 2 to 50 carbon atoms, more preferably 2 to 25 carbon atoms, most preferably 2 to 16 carbon atoms, e.g., benzyl, tolylmethyl, xylylethyl, naphthylmethyl, anthracenylmethyl, 1-phenylethyl, 2-phenylethyl, diphenylmethyl, 2,2-diphenylethyl, phenylbutyl, fluorobenzyl, difluorobenzyl, trifluorobenzyl, chlorobenzyl, dichlorobenzyl, trichlorobenzyl, dimethylaminobenzyl, pyridylmethyl, diphenylpropyl, methoxybenzyl, and dinitrophenylethyl.

By "divalent", e.g., "divalent hydrocarbon derivative", "divalent heterohydrocarbon derivative", "divalent moiety", "divalent linking group", "divalent group", "divalent hydrocarbyl", "divalent heterohydrocarbyl", "divalent heteroatom group", "divalent alkyl", "divalent aryl", "divalent arylalkyl", is meant that the hydrocarbon derivative, heterohydrocarbon derivative, moiety, linking group, group, hydrocarbyl, heterohydrocarbyl, heteroatom group, alkyl, aryl, arylalkyl, or other moiety is bonded at two points (a 'diyl' group) to atoms, molecules or moieties with the two bonding points being covalent single bonds, or, alternatively, is bonded at one point (an 'ylidene' group) to an atom, molecule or moiety with the bonding point being a covalent double bond.

Phosphacycle-Containing Ligating Compound

In an embodiment of the invention, the invention comprises a phosphacycle-containing ligating compound ("ligating compound"). The ligating compound may be useful in the coordination, chelation, and sequestration of metals, and as precursors in forming ligating compound-metal complexes which are useful in catalysis, especially in hydroformylation, isomerization, hydrogenation, polymerization processes, especially the oligomerization of olefins such as ethylene. The ligating compound may be represented by:

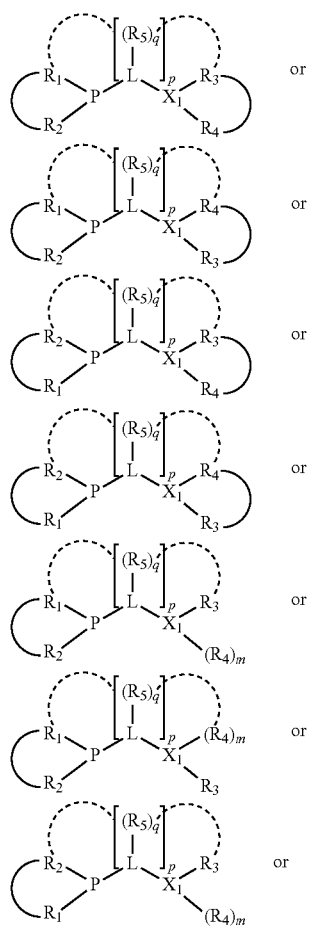

-continued

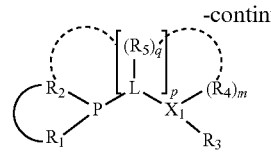

wherein P is phosphorus; $X_1$ is selected from nitrogen, phosphorus, oxygen, or sulfur, preferably nitrogen or phosphorus, more preferably phosphorus; m is 0 or 1; each L is independently selected from boron, carbon, silicon, germanium, nitrogen, phosphorus, oxygen, or sulfur, preferably carbon, nitrogen, phosphorus, oxygen, or sulfur, more preferably carbon or nitrogen; $R_1$ and $R_2$ are each independently selected from substituted or unsubstituted hydrocarbon derivatives, substituted or unsubstituted heterohydrocarbon derivatives, or a substituted or unsubstituted heteroatom group; $R_1$, P, and $R_2$ together form a phosphacycle; when $R_3$, $R_4$, and $X_1$ are linked together, they form a phosphacycle when $X_1$ is phosphorus and they form an azacycle when $X_1$ is nitrogen; two or more $R_1$, $R_2$, $R_3$, $R_4$ or $R_5$ groups are optionally linked together to form cyclic structures containing from 4 to 10 ring atoms, preferably from 4 to 7 ring atoms, wherein the optional character of the linkages is depicted by a dashed connection; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_1$, $R_2$, $R_3$, $R_4$ or $R_5$ groups to form a poly(ligating compound) species. $R_3$, $R_4$, and $R_5$ are each independently selected from hydrogen, halogen, substituted or unsubstituted hydrocarbon derivatives, substituted or unsubstituted heterohydrocarbon derivatives, or a substituted or unsubstituted heteroatom group; p is an integer number from 1 to 6, preferably from 1 to 4, more preferably from 1 to 3, most preferably from 1 to 2; q is 0, 1, or 2; provided that the $[L]_p$ subunit of the divalent linking group

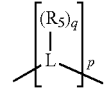

does not comprise an amidine (N—C═N) group; further provided that in at least one phosphacycle of the phosphacycle-containing ligating compound, both atoms directly bonded to P or $X_1$ are sp$^3$ hybridized; still further preferably provided that one or two phosphacycles comprising P or $X_1$, preferably comprising P, $R_1$, and $R_2$, or comprising $X_1$, $R_3$, and $R_4$, contain no P—N, P—O, or P—S bonds within the ring part of the phosphacycle. Preferably at least one, preferably two, phosphacycles do not contain more than one carbon-carbon unsaturated bond in each phosphacycle, preferably not more than one unsaturated bond in each phosphacycle. Phosphacycles or azacycles are ring or cyclic compounds comprising at least one phosphorus or nitrogen atom, respectively, in the ring or cycle.

Each $R_1$ and $R_2$ independently contains from 1 to 50 non-hydrogen atoms; each $R_3$, $R_4$, and $R_5$ independently contains from 0 to 50 non-hydrogen atoms; preferably each $R_5$ independently contains from 0 to 40 non-hydrogen atoms, more preferably from 0 to 20 non-hydrogen atoms, and most preferably from 0 to 12 non-hydrogen atoms; optionally, at least one $R_5$ group is a divalent group bonded to L via a double bond.

Preferably the ligating compound is represented by

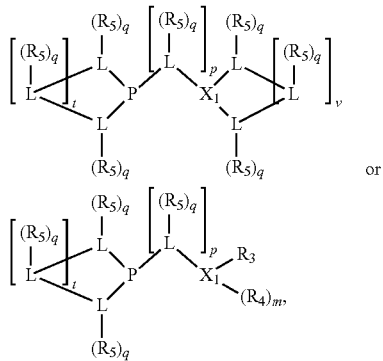

or wherein q is 0, 1, or 2; p is 1, 2, 3, or 4; t is 0, 1, 2, 3, or 4; v is 0, 1, 2, 3, or 4; m is 0 or 1; L, $R_3$, $R_4$, $R_5$, and $X_1$ are as defined above; further provided that in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_3$, $R_4$ or $R_5$ groups to form a poly(ligating compound) species.

Preferably $X_1$ is nitrogen or phosphorus; p=1, 2, 3, or 4; q=0, 1 or 2; v and t are each independently 1, 2, 3, or 4; $R_5$ are each independently hydrogen; halogen; $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms; $R_3$ and $R_4$ are each independently $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms, more preferably one atom; when $X_1$ and its two attached $R_3$ and $R_4$ groups form a cycle represented as:

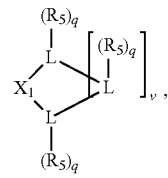

the cycle is an azacycle when $X_1$ is nitrogen and a phosphacycle when $X_1$ is phosphorus; P and its two attached $R_1$ and $R_2$ groups form a phosphacycle represented as:

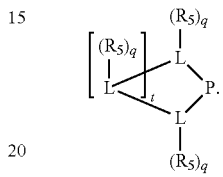

Preferably the L atoms of the phosphacycle or azacycle are each independently carbon, nitrogen, or oxygen; $[L(R_5)_q]_p$ is as defined above. Preferably all L atoms of either phosphacycle which are directly attached to the phosphorus of the phosphacycle are carbon; $[L(R_5)_q]_p$ is as defined above.

As is known to one skilled in the art, a carbon atom is chiral when the carbon atom is attached to four different types of atoms or groups of atoms, thus each ring carbon atom in the 4- to 7-membered phosphacycle or azacycle rings, respectively, is chiral when the ring carbon atom is attached to four different types of atoms or groups of atoms, that is, when its two attached $R_5$ groups and its two attached ring substituents differ from each other. The configuration around a chiral atom is considered to be S or R and depends on the arrangement of the atoms or groups of atoms attached to the atom. In the cases when t and v are each independently 1, 2, 3, or 4, L is carbon or nitrogen; and at least one L atom of the phosphacycle or azacycle is carbon, that at least one L which is carbon in each of the 4-, 5-, 6-, and 7-membered rings is potentially chiral. If a ring contains chiral carbon atoms, the ring itself may or may not be chiral; this, as is known to one skilled in the art, depends on the symmetry. The configurational possibilities of the phosphacycle or azacycle rings of the invention are: a) no carbon atom of the ring is chiral and the ring is not considered chiral; b) at least one of the carbon atoms of the ring is chiral, that is, either with an R-configuration or an S-configuration and the corresponding ring is considered have the R- or S-configuration for each chiral carbon. In the case that exactly one carbon atom in the ring is chiral, the carbon may have either the R configuration or the S configuration and the configuration of the ring is considered to be R or S, respectively. In the case that exactly two carbon atoms in the ring are chiral, the carbon atoms have the R,R; R,S; S,R; or S,S configurations, and the configurational possibilities of the ring are considered to be R,R; R,S; S,R; or S,S. In the case that exactly three carbon atoms in the ring are chiral, the carbon atoms may have the R,R,R; R,R,S; R,S,R; S,R,R; R,S,S; S,R,S; S,S,R; or S,S,S configurations, and the configurational possibilities of the ring are considered to be R,R,R; R,R,S; R,S,R; S,R,R; R,S,S; S,R,S; S,S,R; and S,S,S. One skilled in the art will recognize how to determine the R and S configurations of the atoms and the configurational possibilities of the rings with four, five, six, or more chiral carbon atoms.

In addition to the R and S designators indicating the configuration of the particular carbon atom, numerical designators may also be used to indicate the position in the ring of the particular carbon atom. As a matter of convention, the phosphorus atom or the nitrogen atom of the respective phosphacycle or azacycle attached to Y or to the $[L(R_5)_q]_p$ group representing Y is considered to be at the 1-position. For example, in the following six-membered phosphacycle which has the name of (2R,5S)-2-methyl-5-phenylphosphorinanyl:

(2R,5S)

P is at the 1-position, the carbon atom with the attached methyl group at the 2-position has an R-configuration as indicated by 2R, while the carbon atom with the attached phenyl group at the 5-position has an S-configuration as indicated by 5S.

The phosphorus atom of the phosphacycle is potentially chiral wherein the lone pair of electrons is relatively stable to inversion and is, therefore, counted as one of the four substituents on the phosphorus atom. The R-, S-, and achiral configurations of the phosphorus atoms of the ligating compounds, the ligating compound-chromium complexes, and the catalyst systems are embodiments of the invention although in this application the phosphorus atoms will not be given specific R- and S-configurational designations.

The above R and S configurational designators, as well as the numerical designators described above, clarify the configuration and position of selected atoms in the phosphacycles or azacycles of the invention. All possible R- and S-enantiomers are considered to be objects of the invention, including the cases when the configuration is not known. Unless otherwise so designated with a specific R- or S-configurational designation, e.g., in a name or in a caption, any drawing which appears to impute a particular stereo-orientation to an atom will be deemed to represent all possible stereo-orientations and that any and all R- or S-configurational enantiomers or stereoisomers of the ligating compounds, the ligating compound-chromium complexes, and the catalyst systems are considered to be embodiments of the invention. For example, in the depiction of the following fragment of a ligating compound:

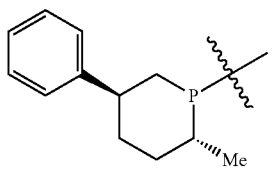

(2R,5S)

the carbon atom with the attached methyl group at the 2-position is specified to have an R-configuration and the carbon atom with the attached phenyl group at the 5-position is specified to have an S-configuration and thus the fragment has the (2R,5S) configuration, while the depiction of the same fragment:

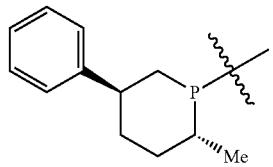 [SMILES: *P1C[C@H](c2ccccc2)CC[C@H]1C]

which does not specifically designate the configuration at the 2- and 5-positions with R or S descriptors, is considered to mean that the configurations are unspecified and all possible configurations of the fragment, that is, (2R,5R), (2R,5S), (2S,5R), and (2S,5S) are meant.

Preferred ligating compounds are represented by:

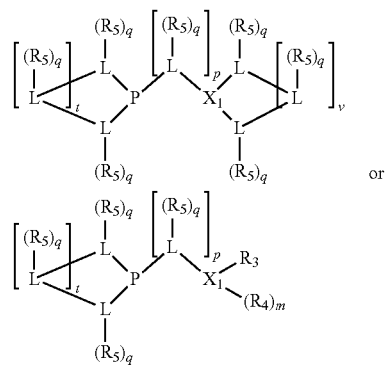

or wherein $[L(R_5)_q]$ of the phosphacycle or azacycle independently selected is $C(R_5)$, O, N, $N(R_5)$, or $C(R_5)_2$; $[L(R_5)_q]_p$ is as defined above; q is 0, 1, or 2; p is 1, 2, 3, or 4; t is 1, 2, 3, or 4; v is 1, 2, 3, or 4; m is 0 or 1, $X_1$ is nitrogen, phosphorus, or oxygen, preferably nitrogen or phosphorus, more preferably phosphorus; $R_5$ are each independently hydrogen; halogen; $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms; $R_3$ and $R_4$ are each independently $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms, more preferably one atom; further provided that in at least one phosphacycle of the phosphacycle-containing ligating compound, both atoms directly bonded to P or $X_1$ are $sp^3$ hybridized; two or more $R_3$, $R_4$ or R$_5$ groups are optionally linked together to form cyclic structures containing from 4 to 10 ring atoms, preferably from 4 to 7 ring atoms; two or more R$_5$ groups independently are linked together with at least one L atom to form a cyclic structure that contains from 3 to 10 ring atoms, preferably from 3 to 7 ring atoms; two R$_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected R$_3$, R$_4$ or R$_5$ groups to form a poly(ligating compound) species. More preferably p=1 or 2. More preferably all [L(R$_5$)$_q$] groups of either phosphacycle which are directly attached to the phosphorus of the phosphacycle are independently C(R$_5$) or C(R$_5$)$_2$.

The number of chiral ring atoms, not including the P or X$_1$ attached to [L(R$_5$)$_q$]$_p$, in each of the 4-, 5-, 6-, and 7-membered phosphacycle or azacycle rings in the ligating compound can range from zero (none) up to one less than the number of ring atoms in each ring. In some embodiments, no carbon atoms in either of the one or two 4-, 5-, 6-, and 7-membered phosphacycle or azacycle rings are chiral. In some embodiments, only one carbon atom in the one or two 4-, 5-, 6-, and 7-membered phosphacycle or azacycle rings is chiral. In some embodiments, only one carbon atom in each of the one or two 4-, 5-, 6-, and 7-membered phosphacycle or azacycle rings is chiral. In some embodiments, at least one of the carbon atoms in at least one of the one or two 4-, 5-, 6-, and 7-membered phosphacycle or azacycle rings is chiral. In some embodiments, at least one of the carbon atoms in each of the one or two 4-, 5-, 6-, and 7-membered phosphacycle or azacycle rings is chiral. In some embodiments, at least two of the carbon atoms in any one of the 4-, 5-, 6-, and 7-membered phosphacycle or azacycle rings are chiral. In some embodiments, at least two of the carbon atoms in at least one of the one or two 4-, 5-, 6-, and 7-membered phosphacycle or azacycle rings are chiral. In some embodiments, at least two of the carbon atoms in each of the one or two 4-, 5-, 6-, and 7-membered phosphacycle or azacycle rings are chiral. In some embodiments, exactly two of the carbon atoms in at least one of the one or two 4-, 5-, 6-, and 7-membered phosphacycle or azacycle rings are chiral. In some embodiments, exactly two of the carbon atoms in each of the one or two 4-, 5-, 6-, and 7-membered phosphacycle or azacycle rings are chiral. In some embodiments, at least three of the carbon atoms in any one of the 4-, 5-, 6-, and 7-membered phosphacycle or azacycle rings are chiral. In some embodiments, at least three of the carbon atoms in at least one of the one or two 4-, 5-, 6-, and 7-membered phosphacycle or azacycle rings are chiral. In some embodiments, at least three of the carbon atoms in each of the one or two 4-, 5-, 6-, and 7-membered phosphacycle or azacycle rings are chiral. In some embodiments, exactly three of the carbon atoms in at least one of the one or two 4-, 5-, 6-, and 7-membered phosphacycle or azacycle rings are chiral. In some embodiments, exactly three of the carbon atoms in each of the one or two 4-, 5-, 6-, and 7-membered phosphacycle or azacycle rings are chiral. In some embodiments, at least four of the carbon atoms in any one of the 5-, 6-, and 7-membered phosphacycle or azacycle rings are chiral. In some embodiments, at least four of the carbon atoms in at least one of the one or two 5-, 6-, and 7-membered phosphacycle or azacycle rings are chiral. In some embodiments, at least four of the carbon atoms in each of the one or two 5-, 6-, and 7-membered phosphacycle or azacycle rings are chiral. In some embodiments, exactly four of the carbon atoms in at least one of the one or two 5-, 6-, and 7-membered phosphacycle or azacycle rings are chiral. In some embodiments, exactly four of the carbon atoms in each of the one or two 5-, 6-, and 7-membered phosphacycle or azacycle rings are chiral. The ligating compound may or may not be optically active.

Preferably, when the ligating compound contains only one 4-, 5-, 6-, and 7-membered phosphacycle ring and no azacycle ring attached to [L(R$_5$)$_q$]$_p$, one, preferably two, L atoms in the phosphacycle ring attached to the P atom in the phosphacycle ring which is attached to [L(R$_5$)$_q$]$_p$ are carbon, and one, more preferably two, of these L atoms are chiral. Preferably, when the ligating compound contains two 4-, 5-, 6-, and 7-membered phosphacycle or azacycle rings attached to [L(R$_5$)$_q$]$_p$, one to four L atoms in the phosphacycle or azacycle rings attached to the P or N atoms in the phosphacycle or azacycle rings which are attached to [L(R$_5$)$_q$]$_p$ are carbon atoms, and one, preferably two, more preferably three, most preferably four of these L atoms are chiral.

In some embodiments, none of the 4-, 5-, 6-, and 7-membered phosphacycle or azacycle rings of the invention is chiral, preferably one or more 4-membered rings have chiral carbon atoms at the 2- and 4-positions, preferably both chiral carbon atoms have the R configuration or both have the S configuration; one or more 5-membered rings have chiral carbon atoms at the 2- and 5-positions, preferably both chiral carbon atoms have the R configuration or both have the S configuration; one or more 6-membered rings have chiral carbon atoms at the 2- and 6-positions, preferably both chiral carbon atoms have the R configuration or both have the S configuration; and one or more 7-membered rings have chiral carbon atoms at the 2- and 7-positions, preferably both chiral carbon atoms have the R configuration or both have the S configuration. Preferably one, more preferably two, 4-, 5-, 6-, and 7-membered phosphacycle or azacycle rings have exactly two chiral carbon atoms in each ring.

The ligating compound may comprise a single isomer or mixture of various isomers, including stereoisomers, whether configurational, conformational, geometric, or optical. Mixtures of ligating compounds comprising chiral ligating compounds which are racemic, enantioenriched, or enantiomerically pure are preferred.

The ligating compound having only one 4-, 5-, 6-, and 7-membered phosphacycle ring and no azacycle ring, and wherein the phosphacycle ring has two chiral carbons, may have the following configurational isomers: R,R; R,S; S,R; and S,S. In an embodiment of the invention, the ligating compound is a mixture of ligating compounds substantially comprising the R,S and S,R isomers of a single ligating compound in any proportion, more preferably the ligating compound is a mixture of ligating compounds substantially comprising the R,R and S,S isomers of a single ligating compound in any proportion.

When the ligating compound has one 4-, 5-, 6-, or 7-membered phosphacycle ring and one additional 4-, 5-, 6-, or 7-membered phosphacycle or azacycle ring wherein each ring has two chiral carbons, the ligating compound may have the following configurational isomers: R,R,R,R; R,R,R,S; R,R,S,R; R,S,R,R; S,R,R,R; R,R,S,S; R,S,R,S; S,R,R,S; R,S,S,R; S,R,S,R; S,S,R,R; R,S,S,S; S,R,S,S; S,S,R,S; S,S,S,R; and S,S,S,S; the configurational isomers of the ligating compound are a combination of the configurational isomers of the two phosphacycle and azacycle rings, each having the configurational choices of R,R; R,S; S,R; and S,S; each of the foregoing is an embodiment of the invention. Preferably both phosphacycle or azacycle rings of the ligating compound have the same configuration, for example, both are R,R or R,S or S,R or S,S, whereby preferred isomer configurations of the ligating compound are R,R,R,R; R,S,R,S; S,R,S,R; and S,S,S,S.

In a preferred embodiment of the invention, the ligating compound is a mixture substantially comprising the R,S,R,S and S,R,S,R isomers of a single ligating compound in any proportion, more preferably the ligating compound is a mixture substantially comprising the R,R,R,R and S,S,S,S isomers of a single ligating compound in any proportion.

Preferably $[L(R_5)_q]$ of the phosphacycle or azacycle independently selected is $C(R_5)$, N, $N(R_5)$, or $C(R_5)_2$; $X_1$ is phosphorus or nitrogen; t and v are each independently 1, 2, 3, or 4. Preferably one to six $[L(R_5)_q]$ groups of each 4-, 5-, 6-, and 7-membered phosphacycle or azacycle are $C(R_5)$ or $C(R_5)_2$, more preferably $C(R_5)_2$. Preferably at least one, more preferably two, even more preferably three, still more preferably four, $[L(R_5)_q]$ groups of each phosphacycle or azacycle are $C(R_5)_2$. Preferably at least one, more preferably two, $[L(R_5)_q]$ groups of each phosphacycle or azacycle are $C(R_5)$. Preferably one, more preferably two, of the $C(R_5)$ or $C(R_5)_2$ groups of at least one phosphacycle or azacycle are attached to a P or N atom in the phosphacycle or azacycle which is attached to $[L(R_5)_q]_p$. Preferably both $R_5$ groups of the one, more preferably two, $C(R_5)_2$ groups attached to a P or N atom in at least one phosphacycle or azacycle which is attached to $[L(R_5)_q]_p$ are identical; more preferably they are not identical. Preferably exactly one $R_5$ group of at least one, preferably two, $C(R_5)$ or $C(R_5)_2$ groups attached to a P or N atom in at least one phosphacycle or azacycle which is attached to $[L(R_5)_q]_p$ is hydrogen, more preferably exactly one $R_5$ group of at least one, preferably two, $C(R_5)$ or $C(R_5)_2$ groups attached to a P or N atom in at least one phosphacycle or azacycle which is attached to $[L(R_5)_q]_p$ is not hydrogen. Preferably both $C(R_5)$ or $C(R_5)_2$ groups attached to a P or N atom in at least one phosphacycle or azacycle which is attached to $[L(R_5)_q]_p$ are identical to each other. More preferably two $C(R_5)_q$ groups are attached to a P or N atom in each phosphacycle or azacycle which is attached to $[L(R_5)_q]_p$. More preferably all $[L(R_5)_q]$ groups of the phosphacycles or azacycle which are directly attached to the P or N atom in each phosphacycle or azacycle are independently $C(R_5)_q$ as represented by:

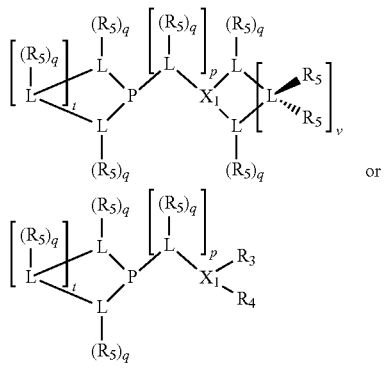

and their enantiomers wherein $C(R_5)_q$ is $C(R_5)$, $C(R_5)_2$, or $C(R_5)H$, preferably $C(R_5)H$; $X_1$ is phosphorus or nitrogen; preferably the $R_5$ groups of the $C(R_5)H$ groups attached to the P or N atom in each phosphacycle or azacycle which is attached to $[L(R_5)_q]_p$ are not hydrogen, and wherein, as mentioned above, both the R-configuration and the S-configuration are meant for $C(R_5)H$; further provided that in at least one phosphacycle of the phosphacycle-containing ligating compound, both atoms directly bonded to P or $X_1$ are sp$^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_3$, $R_4$ or $R_5$ groups to form a poly(ligating compound) species. Preferably both $C(R_5)H$ groups attached to the P or N atom in the phosphacycle or azacycle which is attached to $[L(R_5)_q]_p$ are the same. Preferably both $C(R_5)H$ groups attached to the P atom in the phosphacycle which is attached to $[L(R_5)_q]_p$ have the same R or S configuration. Preferably when $X_1$ is a P atom and $X_1$, $R_3$, and $R_4$ form a phosphacycle, the phosphacycle is identical to the phosphacycle formed by P, $R_1$ and $R_2$. Preferably the L atoms of phosphacycles or azacycles are independently carbon or nitrogen. Preferably at least two L atoms in each phosphacycle or azacycle are carbon. Preferably t and v are each independently 1, 2, or 3, preferably 1 or 2. Preferably at least one of t and v is 2, more preferably t is 2. In a preferred embodiment, t is 2; and at least one, preferably two, of L in the phosphacycle is carbon. In a preferred embodiment, t is 2; and at least one, preferably two, of L in the phosphacycle is nitrogen. In a preferred embodiment, v is 2; and at least one, preferably two, of L in the ring comprising $X_1$ are carbon. In a preferred embodiment, v is 2; and at least one, preferably two, of L in the ring comprising $X_1$ are nitrogen. More preferably $X_1$ is phosphorus. More preferably t and v are each 2. More preferably t and v are each 2 and $X_1$ is phosphorus. In a preferred embodiment, the $X_1$, $R_3$, and $R_4$ groups of $X_1R_3(R_4)_m$ do not form a cycle, m is 0 or 1, preferably m is 1; preferably $X_1$ is nitrogen, more preferably $X_1$ is phosphorus.

In preferred ligating compounds $X_1$ is phosphorus and 5-membered ligating compounds are represented by:

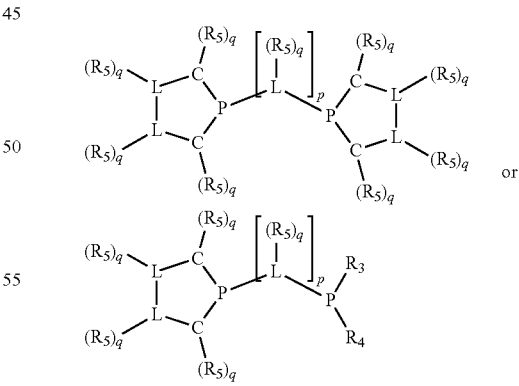

wherein q is 1 or 2; preferably $L(R_5)_q$ of the phosphacycles is $C(R_5)$, $N(R_5)$, or $C(R_5)_2$, preferably $[L(R_5)_q]_p$ is $C(R_5)$, $N(R_5)$, $C(R_5)_2$, $C(R_5)C(R_5)$ or $C(R_5)_2C(R_5)_2$, more preferably $N(R_5)$ or $C(R_5)C(R_5)$; the $C(R_5)_q$ attached to P is $C(R_5)$, $C(R_5)_2$, or $C(R_5)H$, preferably $C(R_5)H$; further provided that in at least one phosphacycle of the phosphacycle-containing ligating compound, both atoms directly bonded to P or $X_1$ are sp³ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_3$, $R_4$ or $R_5$ groups to form a poly(ligating compound) species. Preferably at least one, more preferably two, phosphacycles contain at least one, preferably two, $[L(R_5)_q]$ groups each which are $C(R_5)$ or $C(R_5)_2$. At most one bond in at least one phosphacycle is an unsaturated bond, preferably all bonds in at least one phosphacycle are saturated bonds. Preferably at least one, preferably two, 5-membered phosphacycles are saturated, meaning they contain no unsaturated bonds. Preferably one 5-membered phosphacycle is saturated, and one phosphacycle, preferably one 5-membered phosphacycle, has two unsaturated bonds, preferably exactly one unsaturated bond. Preferably one 5-membered phosphacycle has exactly one unsaturated bond, and one phosphacycle, preferably one 5-membered phosphacycle, has two unsaturated bonds, preferably exactly one unsaturated bond, more preferably no unsaturated bonds. Preferably the unsaturated bonds are carbon-carbon unsaturated bonds. Preferably the unsaturated bonds are carbon-nitrogen unsaturated bonds.

Saturated 5-membered phosphacycles are known as phospholanes when all four ring atoms besides phosphorus are carbon; azaphospholanes when three ring atoms besides phosphorus are carbon and one ring atom is nitrogen; diazaphospholanes when two ring atoms besides phosphorus are carbon and two ring atoms besides phosphorus are nitrogen. Unsaturated 5-membered phosphacycles with exactly one unsaturated bond, are known as dihydrophospholes when all four ring atoms besides phosphorus are carbon; dihydroazaphospholes when three ring atoms besides phosphorus are carbon and one L atom is nitrogen; dihydrodiazaphospholes when two ring atoms besides phosphorus are carbon and two ring atoms besides phosphorus are nitrogen. Unsaturated 5-membered phosphacycles with two unsaturated bonds are known as phospholes. The convention used herein for naming the 5-membered phosphacycles places the phosphorus at the 1-position, the two ring-atoms attached to phosphorus are at the 2- and 5-positions, while the remaining two ring-atoms not attached to phosphorus are at the 3- and 4-positions.

Preferred 5-membered phosphacycles of the ligating compound are independently selected, as represented by:

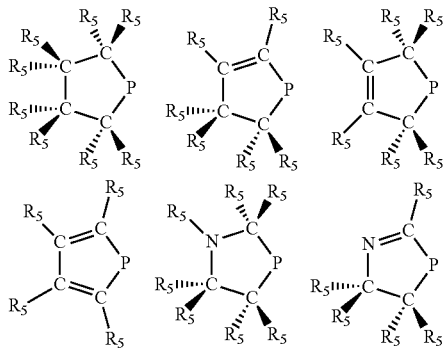

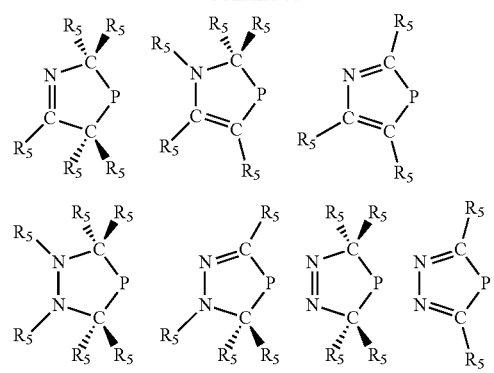

and their enantiomers.

Preferred 5-membered ring phosphacycle-containing ligating compounds may be built up by independently selecting one preferred 5-membered phosphacycle from above, connecting it to one valence of the $[L(R_5)_q]_p$ divalent linking group, and connecting the remaining free valence of the divalent linking group either to a second independently selected phosphacycle, preferably a preferred 5-membered phosphacycle from above, or to $X_1R_3R_4$, wherein $X_1$ is phosphorus or nitrogen, preferably phosphorus.

Non-limiting examples of preferred non-5-membered ring phosphacycle-containing ligating compounds are represented by:

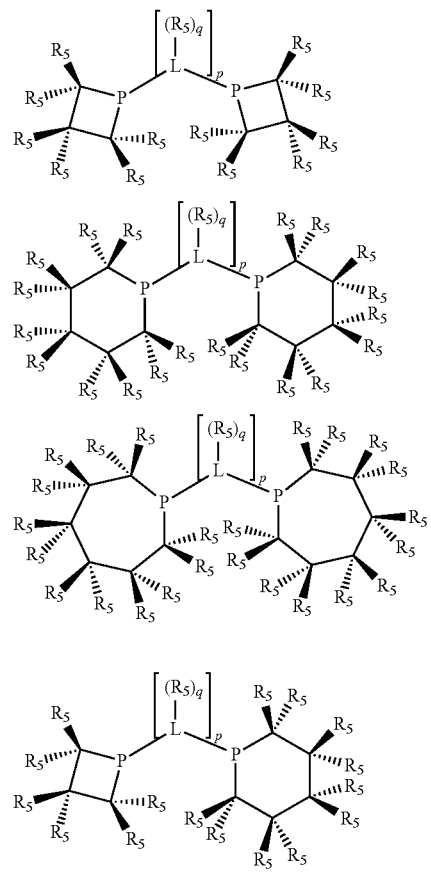

-continued

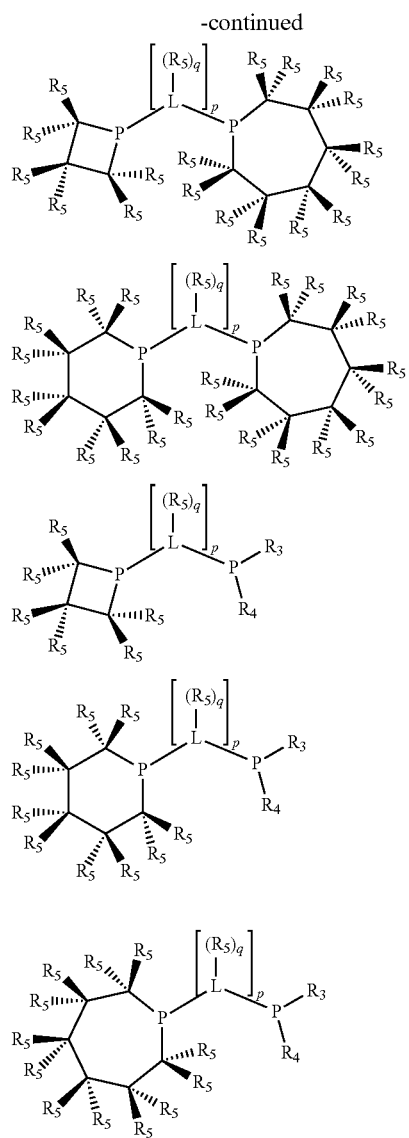

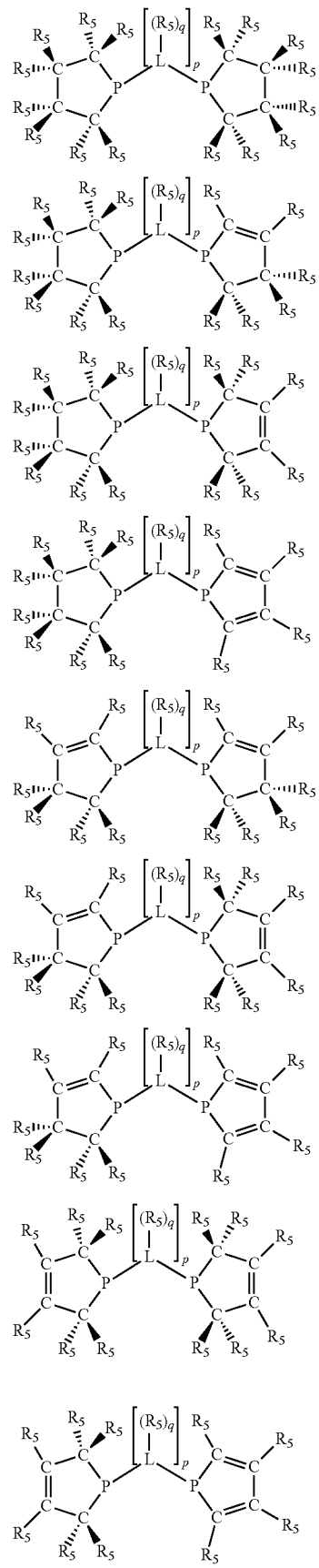

and their enantiomers wherein in at least one phosphacycle of the phosphacycle-containing ligating compound, both atoms directly bonded to P or $X_1$ are $sp^3$ hybridized; two or more $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_5$ groups to form a poly (ligating compound) species. Preferably the $[L(R_5)_q]_p$ divalent linking group is $NR_5$, $C(R_5)$, $C(R_5)C(R_5)$, $C(R_5)_2$ or $C(R_5)_2C(R_5)_2$, preferably $N(R_5)$.

Non-limiting examples of the preferred 5-membered ring phosphacycle-containing ligating compounds are represented by:

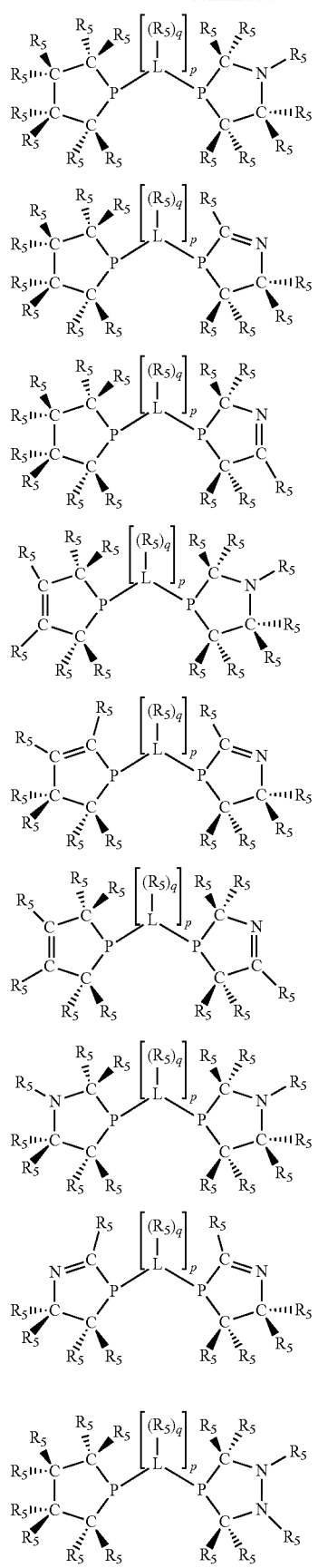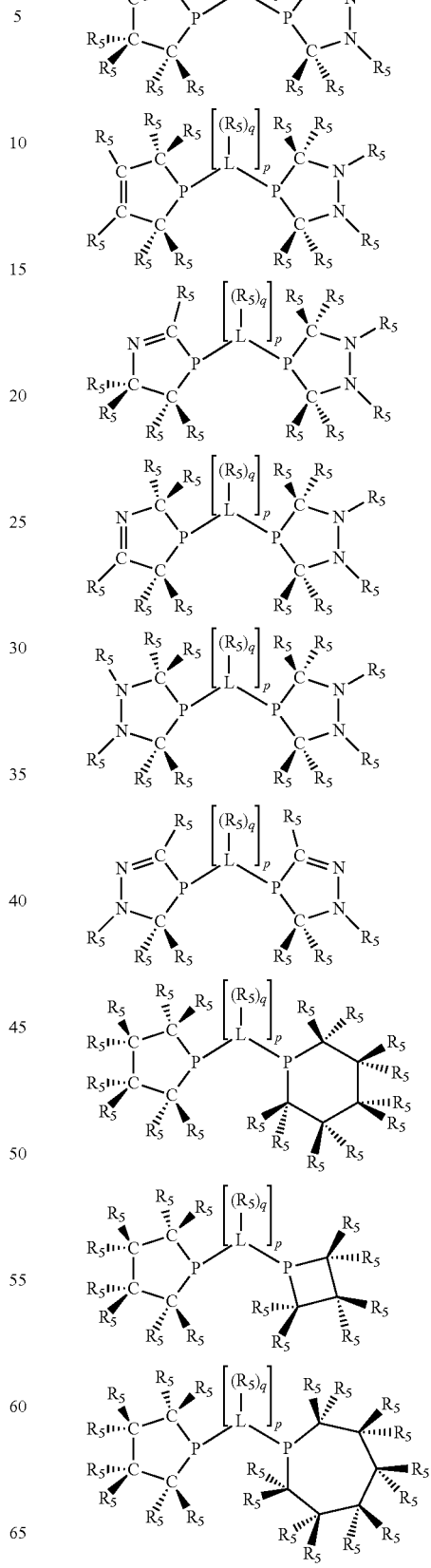

-continued
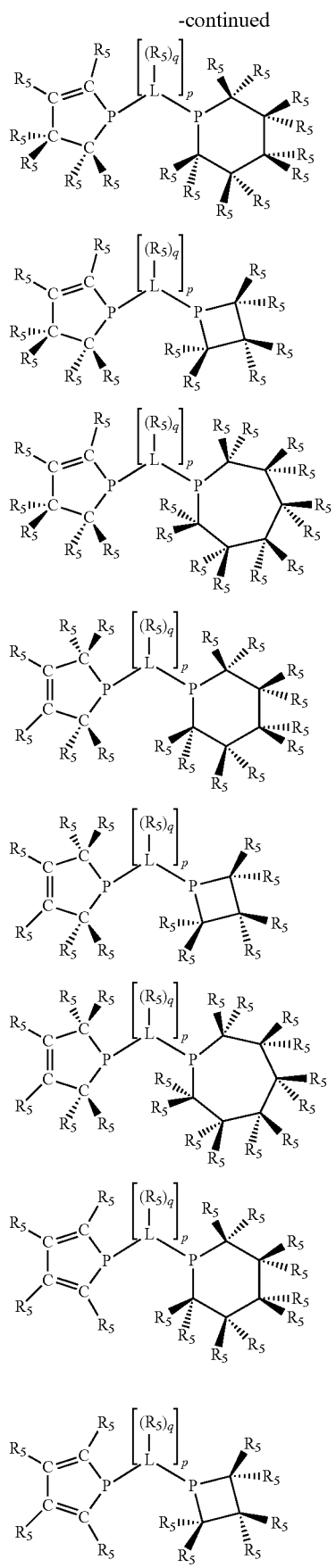
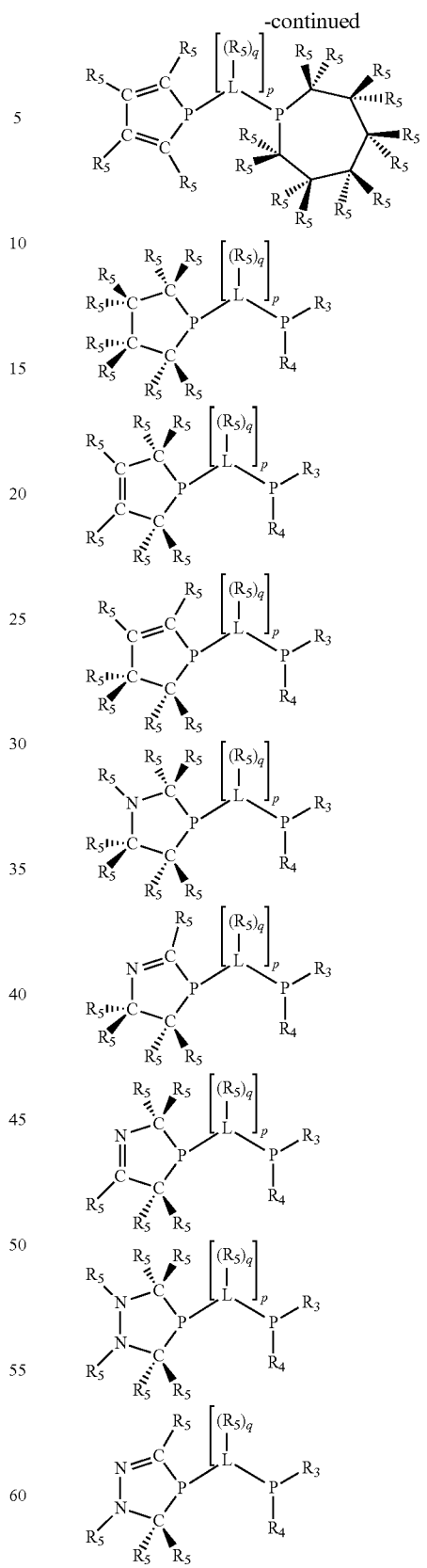
and their enantiomers wherein two or more $R_3$, $R_4$ or $R_5$ groups are optionally linked together to form cyclic structures containing from 4 to 10 ring atoms, preferably from 4 to 7 ring atoms; further provided that in at least one phosphacycle of the phosphacycle-containing ligating compound, both atoms directly bonded to P or $X_1$ are sp$^3$ hybridized; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_3$, $R_4$ or $R_5$ groups to form a poly(ligating compound) species. Preferably the $[L(R_5)_q]_p$ divalent linking group is $NR_5$, $C(R_5)$, $C(R_5)C(R_5)$, $C(R_5)_2$ or $C(R_5)_2C(R_5)_2$, preferably $N(R_5)$.

Preferably exactly one $R_5$ group in at least one, preferably two, $C(R_5)$ or $C(R_5)_2$ groups attached to the P atom in at least one, preferably two, phosphacycles is hydrogen. Representative, but not limiting, examples are:

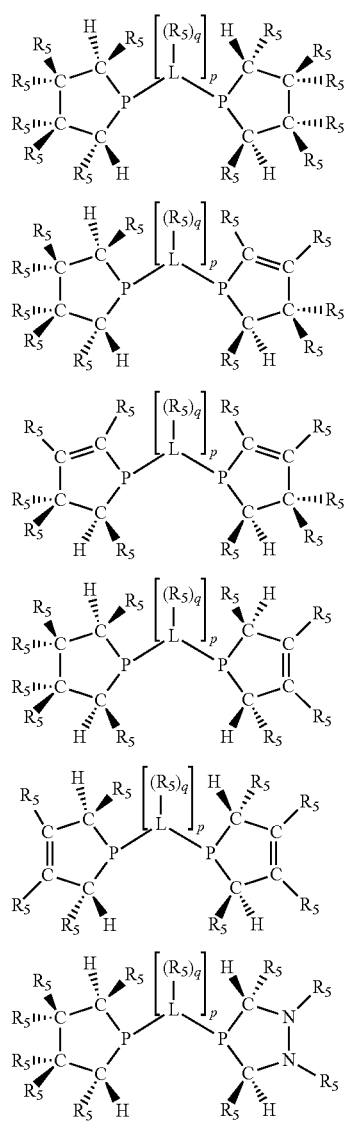

-continued

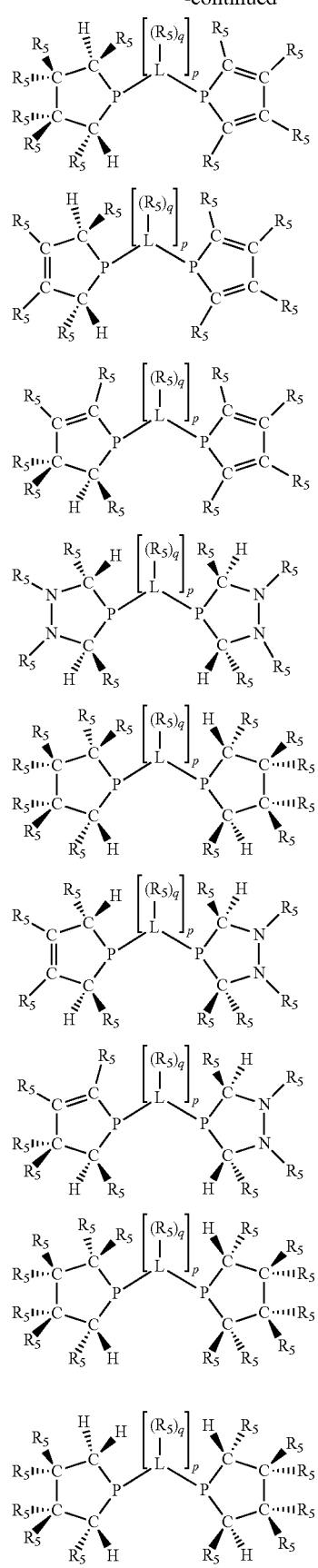

-continued
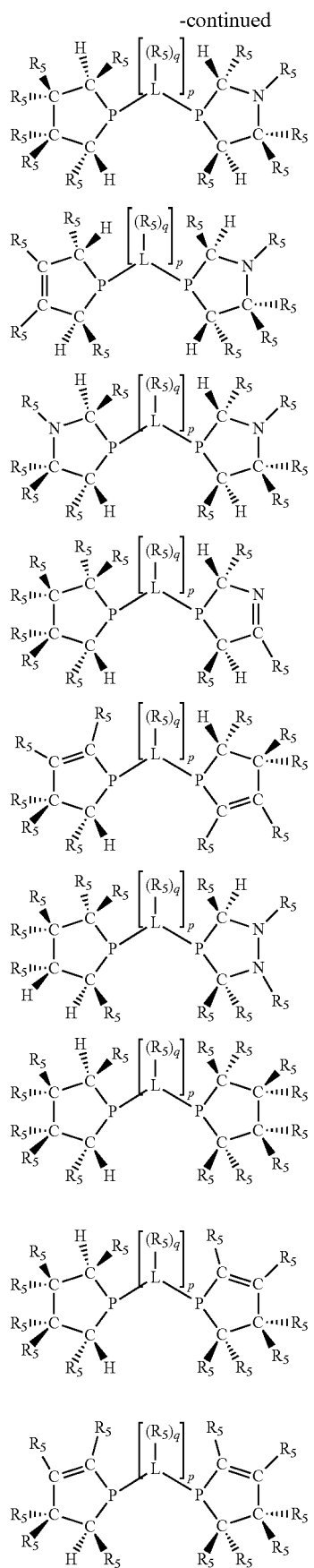
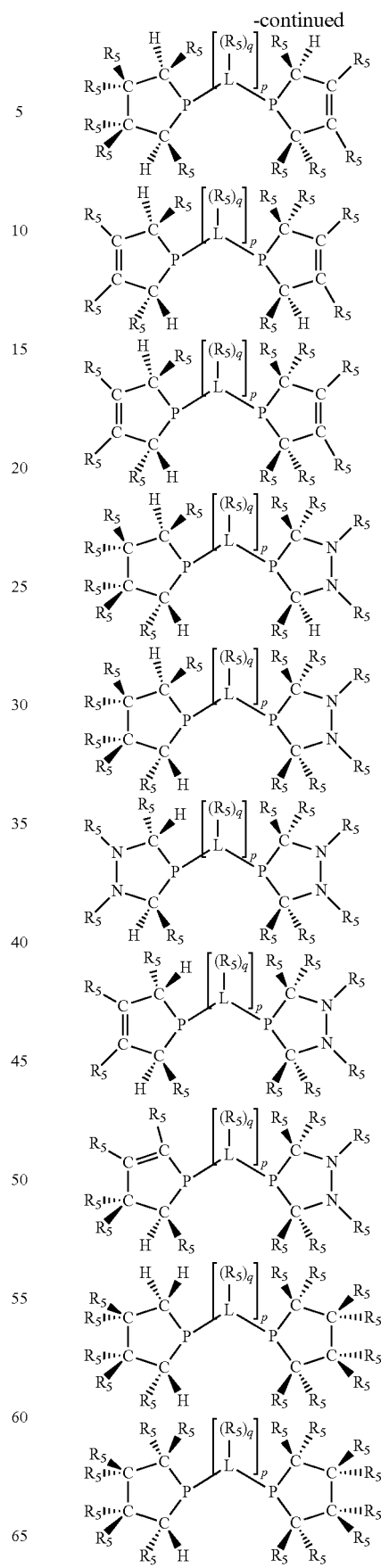

-continued
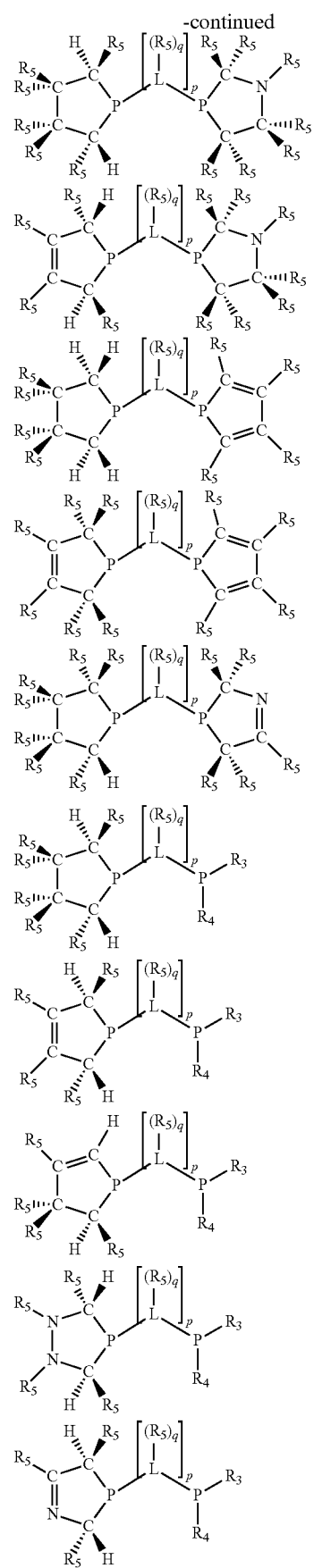
-continued
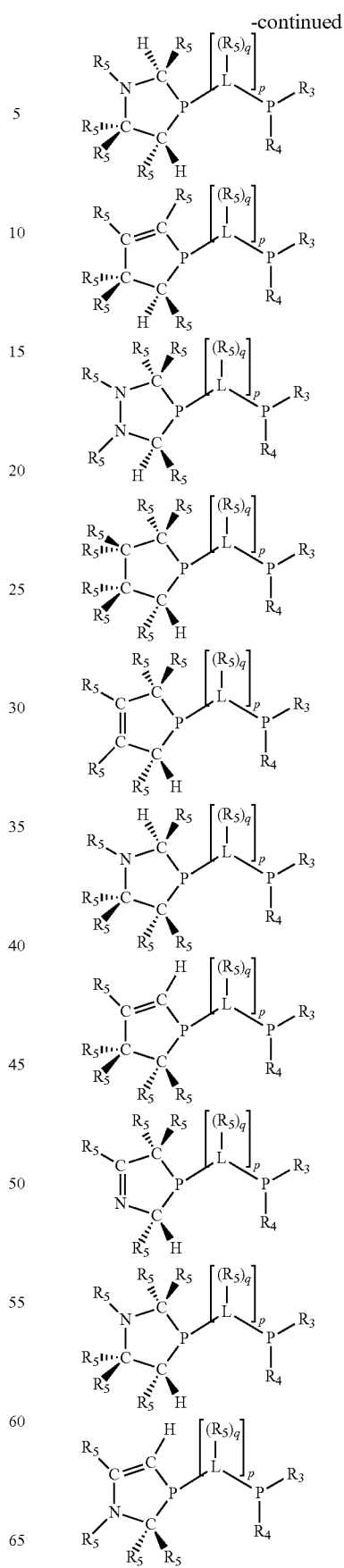

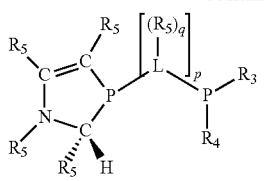

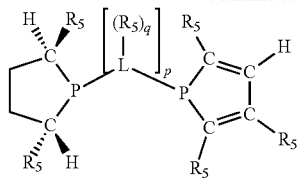

and their enantiomers wherein in at least one phosphacycle of the phosphacycle-containing ligating compound, both atoms directly bonded to P or $X_1$ are sp$^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two R groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_3$, $R_4$ or $R_5$ groups to form a poly(ligating compound) species.

Preferably any $R_5$ groups attached to the nitrogen atoms in the 5-membered phosphacycles are not hydrogen, preferably any $R_5$ groups attached to the nitrogen atoms in the 5-membered phosphacycles are hydrocarbyl, preferably $C_{1-4}$ alkyl, $C_{6-10}$ aryl, or $C_{7-10}$ arylalkyl, more preferably methyl, ethyl, phenyl, benzyl, or tolyl; preferably the $R_5$ groups attached to the ring carbon atom of the $C(R_5)$ or $C(R_5)_2$ groups at the 3- and 4-positions on the 5-membered phosphacycle are hydrogen atoms; preferably the $R_5$ groups attached to at least one of the ring carbon atoms of the $C(R_5)$ groups, wherein the ring carbon atoms of the $C(R_5)$ groups are bonded to another ring atom by means of an unsaturated bond, preferably carbon-carbon unsaturated bond, are hydrogen atoms or are part of an aromatic ring which is fused to the phosphacycle.

Representative, but not limiting, examples are:

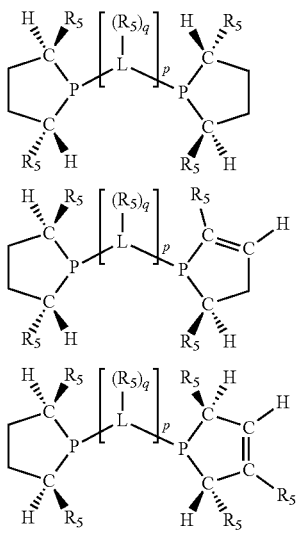

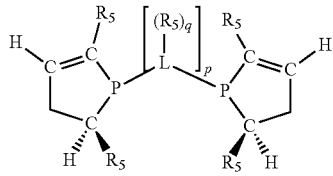

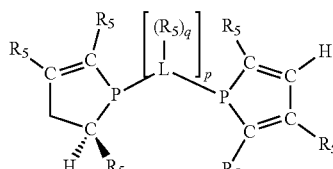

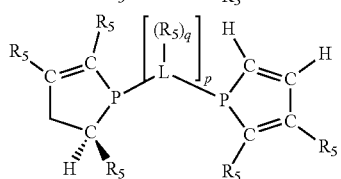

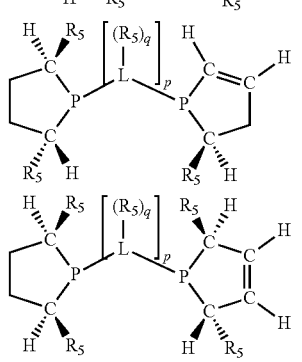

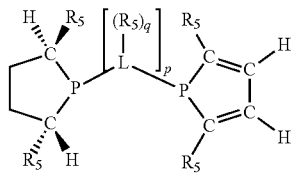

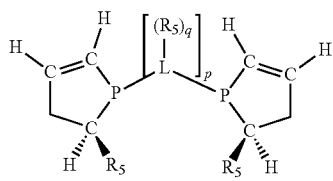

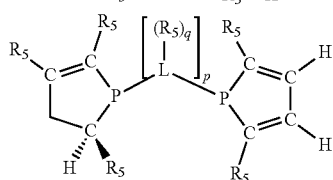

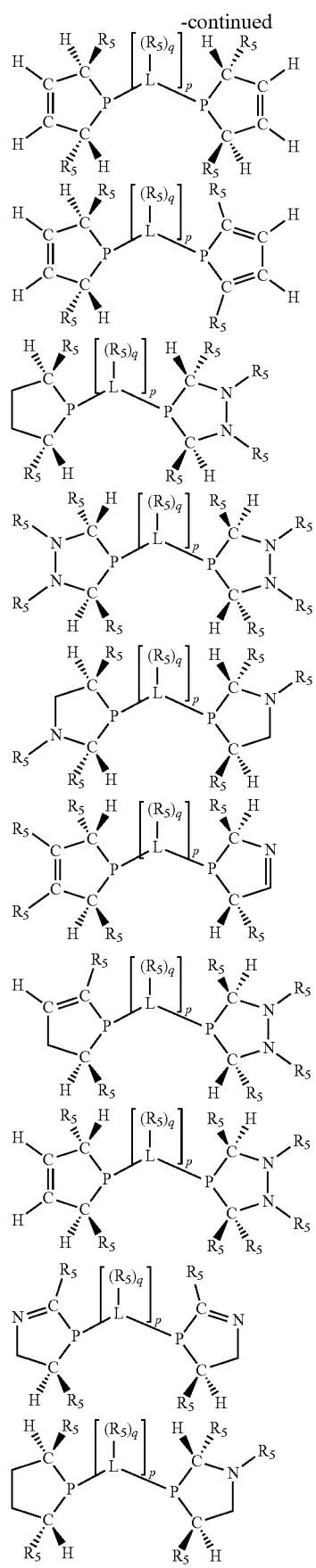
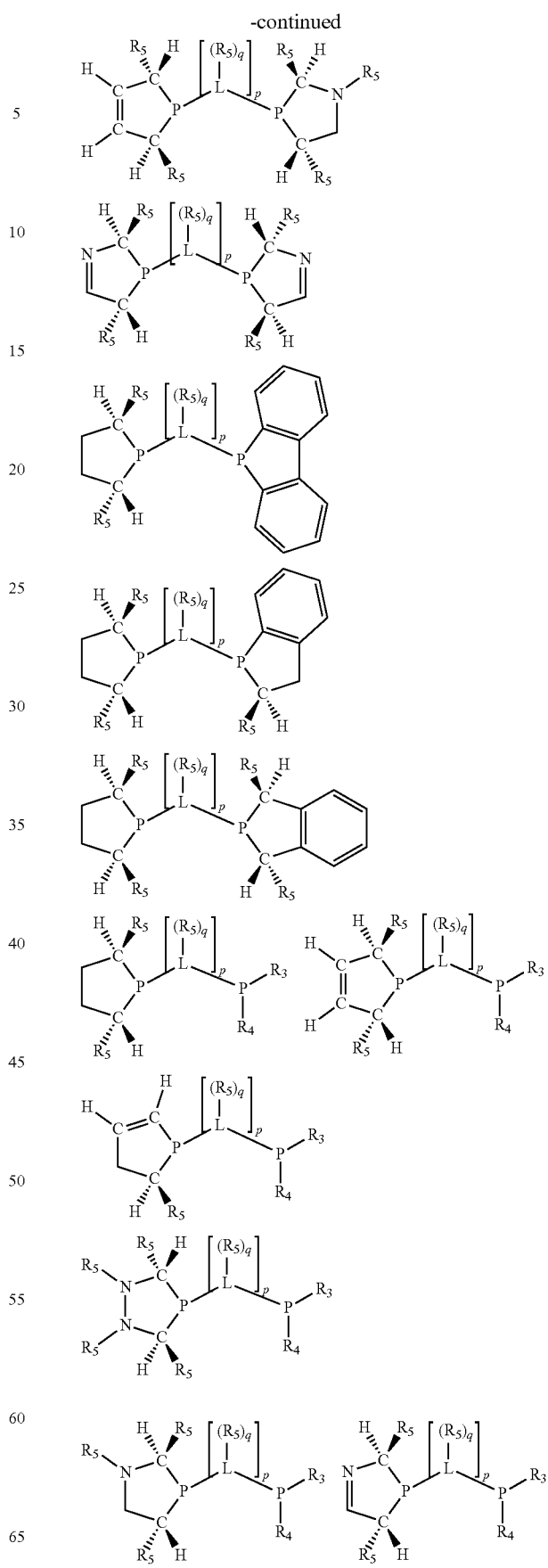

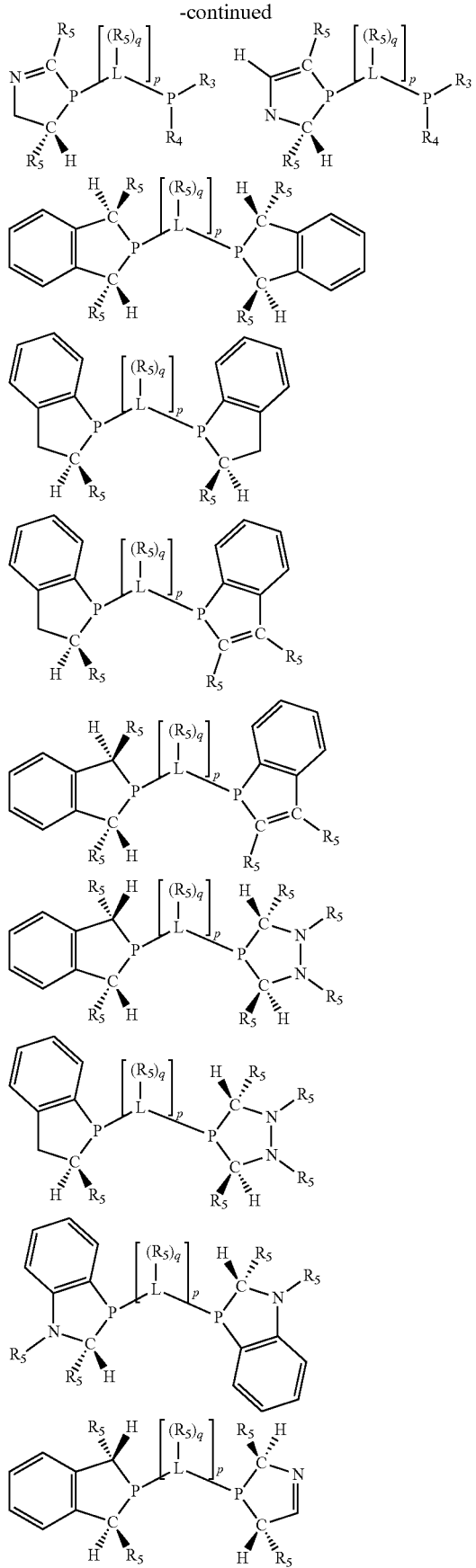

and their enantiomers.

Preferably at least one, preferably two, of the $R_5$ groups attached to the ring carbon atom of the $C(R_5)$ or $C(R_5)_2$ groups at the 2- and 5-positions on the 5-membered phosphacycle are independently alkyl, substituted alkyl, aryl, substituted aryl, arylalkyl, substituted arylalkyl, heteroaryl, or substituted heteroaryl, preferably aryl, substituted aryl, heteroaryl, or substituted heteroaryl, preferably aryl or substituted aryl; preferably exactly one $R_5$ group attached to the ring carbon atom of the C(R$_5$) or C(R$_5$)$_2$ group at each 2-position and at each 5-position on the 5-membered phosphacycle is alkyl, substituted alkyl, aryl, substituted aryl, arylalkyl, substituted arylalkyl, heteroaryl, or substituted heteroaryl, preferably aryl, substituted aryl, heteroaryl, or substituted heteroaryl, more preferably aryl or substituted aryl; preferably exactly one R$_5$ group attached to the ring carbon atom of any C(R$_5$)$_2$ groups at each 2-position and at each 5-position on the 5-membered phosphacycle is independently hydrogen, methyl, ethyl, propyl, butyl, or pentyl, preferably hydrogen or methyl, more preferably hydrogen; preferably R$_3$ and R$_4$ are independently alkyl, substituted alkyl, aryl, substituted aryl, arylalkyl, substituted arylalkyl, heteroaryl, or substituted heteroaryl, preferably aryl, substituted aryl, heteroaryl, or substituted heteroaryl, more preferably aryl or substituted aryl; preferably exactly one R$_5$ group attached to the ring carbon atom of the C(R$_5$) or C(R$_5$)$_2$ group at each 2-position and at each 5-position on the 5-membered phosphacycle is independently aryl or substituted aryl, exactly one R$_5$ group attached to the ring carbon atom of any C(R$_5$)$_2$ groups at each 2-position and at each 5-position on the 5-membered phosphacycle is a hydrogen, and R$_3$ and R$_4$ are independently alkyl, aryl, substituted aryl, arylalkyl, substituted arylalkyl, heteroaryl, or substituted heteroaryl, preferably aryl, substituted aryl, heteroaryl, or substituted heteroaryl, more preferably aryl or substituted aryl. Preferably the aryl, substituted aryl, heteroaryl, or substituted heteroaryl groups at the 2-position and the 5-position on the 5-membered phosphacycle are identical. Preferably R$_3$, R$_4$, and R$_5$ are each independently C$_{1-40}$ substituted or unsubstituted alkyl, preferably C$_{1-20}$ substituted or unsubstituted alkyl, more preferably C$_{1-12}$ substituted or unsubstituted alkyl; C$_{2-40}$ substituted or unsubstituted aryl, preferably C$_{2-20}$ substituted or unsubstituted aryl, more preferably C$_{2-12}$ substituted or unsubstituted aryl; C$_{2-40}$ substituted or unsubstituted arylalkyl, preferably C$_{2-20}$ substituted or unsubstituted arylalkyl, more preferably C$_{2-12}$ substituted or unsubstituted arylalkyl; C$_{2-40}$ substituted or unsubstituted heteroaryl, preferably C$_{2-20}$ substituted or unsubstituted heteroaryl, more preferably C$_{2-12}$ substituted or unsubstituted heteroaryl; preferably R$_5$ independently is C$_{1-4}$ alkyl, C$_{6-10}$ aryl, or C$_{7-10}$ arylalkyl when R$_5$ is attached to a ring nitrogen atom of the 5-membered ring phosphacycle; further provided that in at least one phosphacycle of the phosphacycle-containing ligating compound, both atoms directly bonded to P or X$_1$ are sp$^3$ hybridized; two or more R$_3$, R$_4$ or R$_5$ groups are optionally linked together to form cyclic structures containing from 4 to 10 ring atoms, preferably from 4 to 7 ring atoms; two or more R$_5$ groups independently are linked together with at least one L atom to form a cyclic structure that contains from 3 to 10 ring atoms, preferably from 3 to 7 ring atoms; two R$_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected R$_3$, R$_4$ or R$_5$ groups to form a poly(ligating compound) species.

In a preferred embodiment, R$_3$, R$_4$, and R$_5$ attached to a ring nitrogen atom of the 5-membered ring phosphacycle are Ar, R$_5$ attached to a ring nitrogen atom of the 5-membered ring phosphacycle is Ar', wherein Ar independently is C$_{2-40}$ substituted or unsubstituted aryl, preferably C$_{2-20}$ substituted or unsubstituted aryl, more preferably C$_{2-12}$ substituted or unsubstituted aryl; C$_{2-40}$ substituted or unsubstituted arylalkyl, preferably C$_{2-20}$ substituted or unsubstituted arylalkyl, more preferably C$_{2-12}$ substituted or unsubstituted arylalkyl; C$_{2-40}$ substituted or unsubstituted heteroaryl, preferably C$_{2-20}$ substituted or unsubstituted heteroaryl, more preferably C$_{2-12}$ substituted or unsubstituted heteroaryl, and Ar' independently is C$_{1-4}$ alkyl, C$_{6-10}$ aryl, or C$_{7-10}$ arylalkyl.

In preferred ligating compounds, L of the phosphacycles is carbon and 5-membered ligating compounds are represented by:

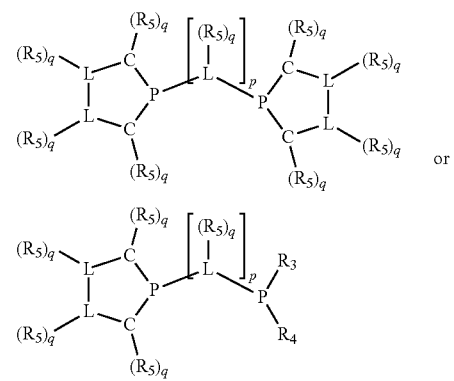

wherein q is 1 or 2; preferably [L(R$_5$)$_q$]$_p$ is C(R$_5$), N(R$_5$), C(R$_5$)$_2$, C(R$_5$)C(R$_5$) or C(R$_5$)$_2$C(R$_5$)$_2$, more preferably N(R$_5$) or C(R$_5$)C(R$_5$); the C(R$_5$)$_q$ attached to P is C(R$_5$), C(R$_5$)$_2$, or C(R$_5$)H, preferably C(R$_5$)H.

In preferred ligating compounds, [L(R$_5$)$_q$]$_p$ of the divalent linking group is NR$_5$ and 5-membered ligating compounds are represented by:

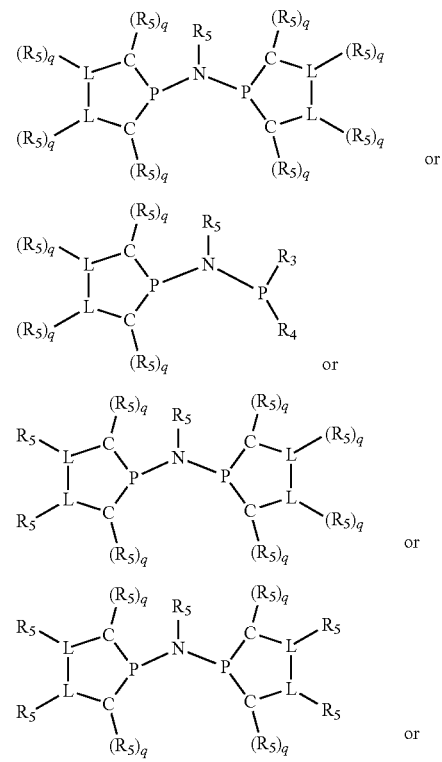

-continued

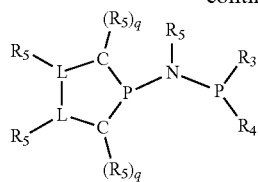

wherein q is 1 or 2; the $C(R_5)_q$ attached to P is $C(R_5)$, $C(R_5)_2$, or $C(R_5)H$, preferably $C(R_5)H$.

In preferred ligating compounds, $[L(R_5)_q]$ at the 3- and 4-positions of the phosphacycle ring are $CH_2$; $[L(R_5)_q]$ at the 2- and 5-positions of the phosphacycle ring are $CR_5H$; $[L(R_5)_q]_p$ of the divalent linking group is $NR_5$, and 5-membered ligating compounds are represented by:

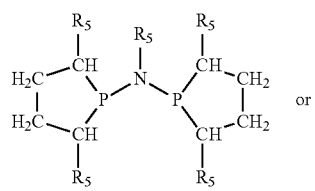

or

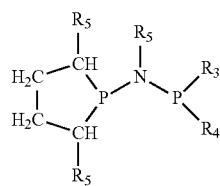

In preferred ligating compounds, $[L(R_5)_q]$ at the 2- and 5-positions of the phosphacycle ring are $CR_5H$; the carbon atoms at the 2- and 5-positions are chiral; preferably both carbon atoms at the 2- and 5-positions in each phosphacycle ring have the same R or S configuration; $[L(R_5)_q]_p$ of the divalent linking group is $NR_5$; preferably $[L(R_5)_q]$ at the 3- and 4-positions of the phosphacycle ring are $CH_2$, and 5-membered ligating compounds are represented by:

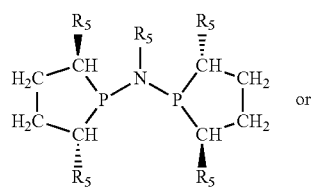

or

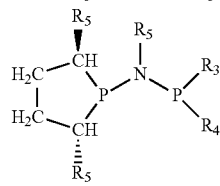

and their enantiomers.

Non-limiting examples of the ligating compounds are:

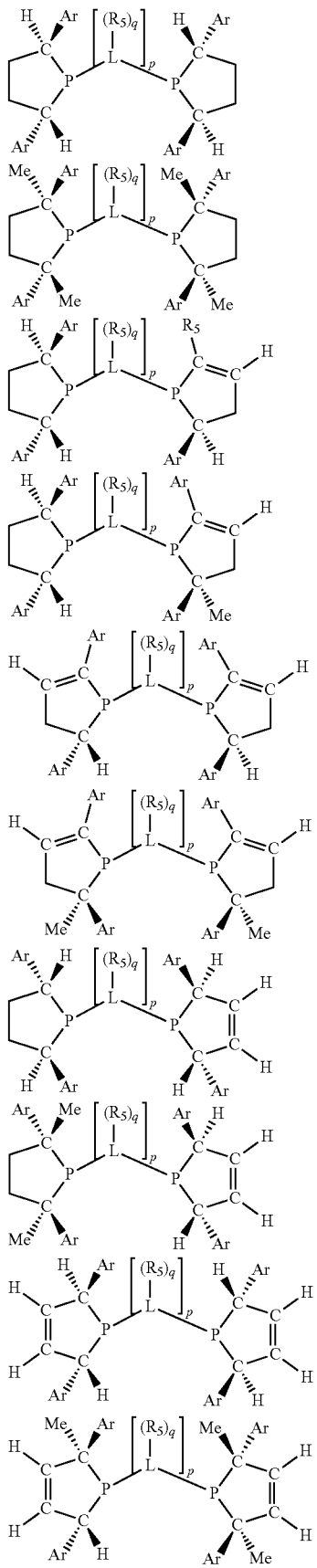

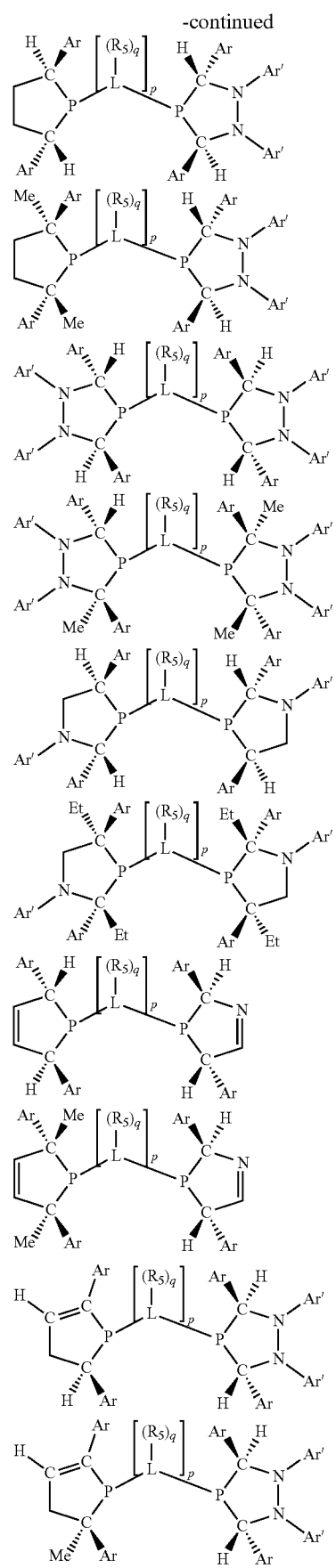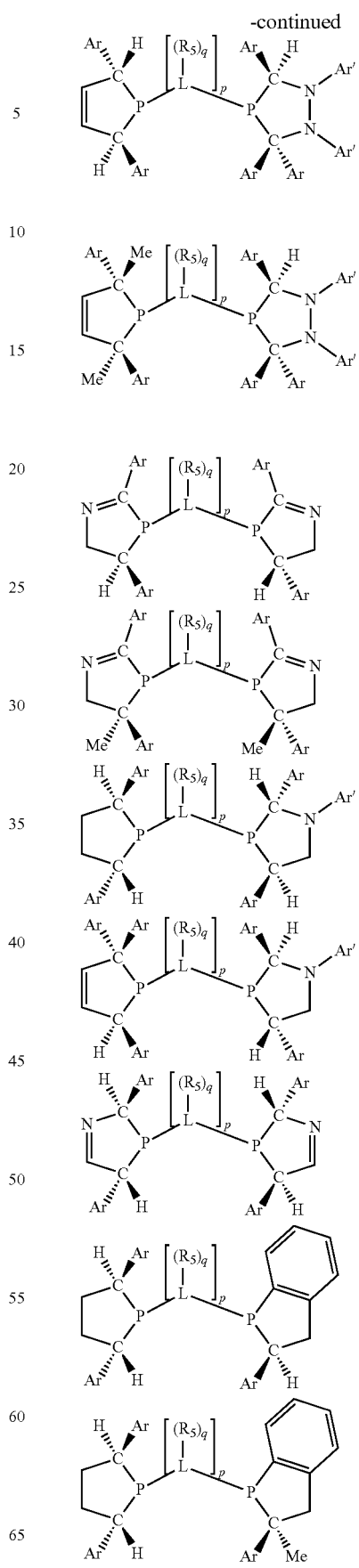

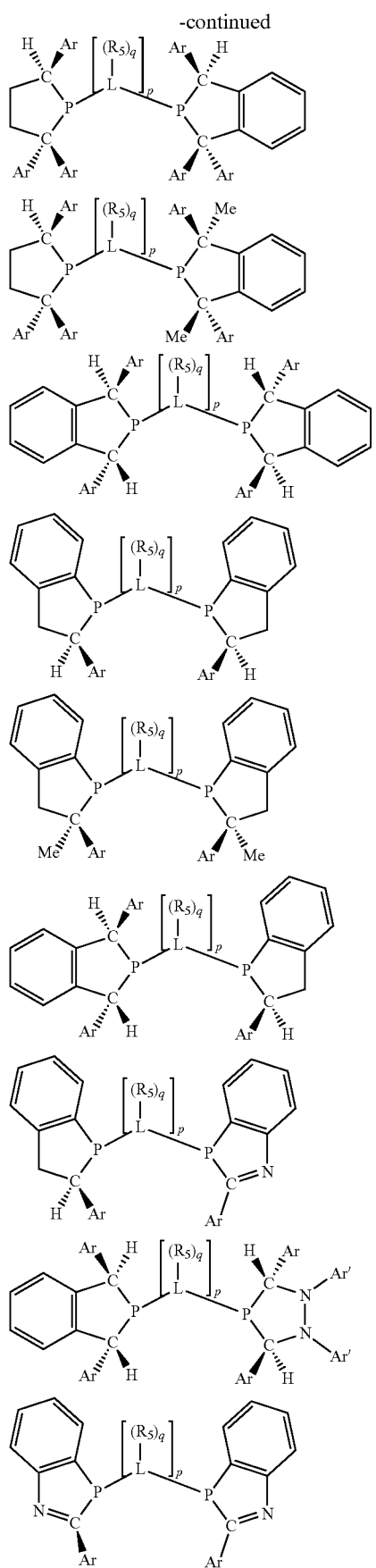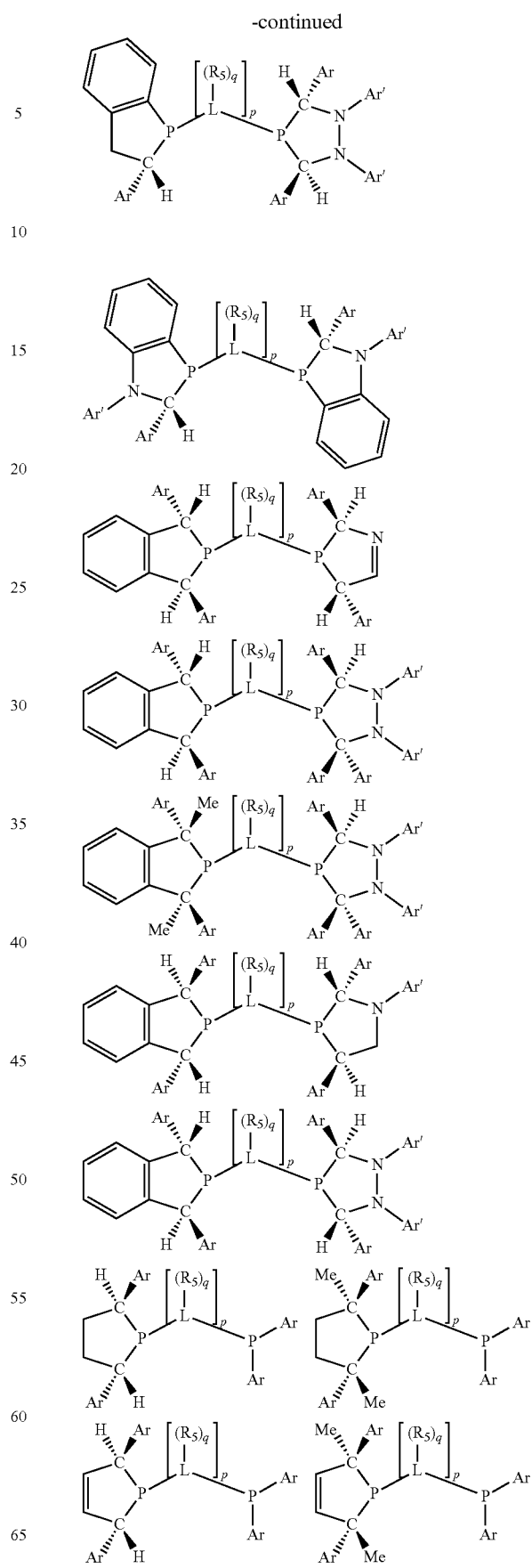

-continued
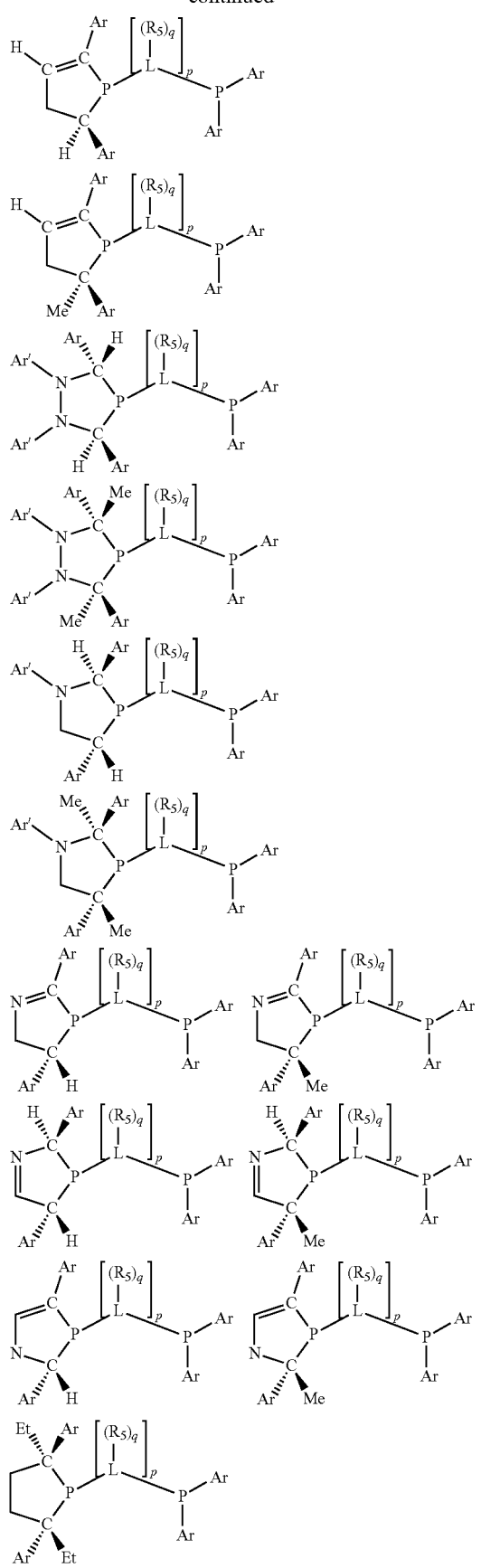
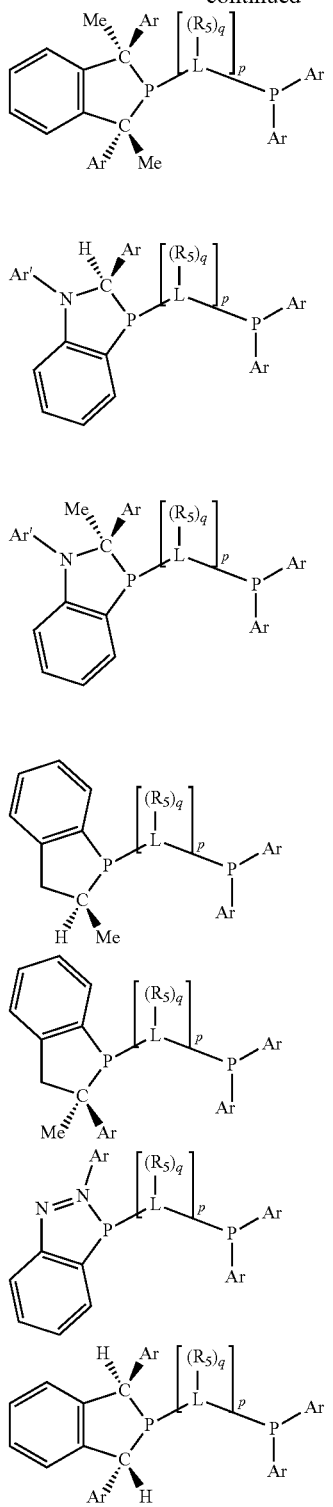
and their enantiomers.
In preferred ligating compounds, Ar at the 2- and 5-positions of the phosphacycle rings is phenyl optionally substituted with $R_5$; $[L(R_5)_q]_p$ of the divalent linking group is $NR_5$; preferably $[L(R_5)_q]$ at the 3- and 4-positions of the phosphacycle ring are $CH_2$, and 5-membered ligating compounds are represented by:

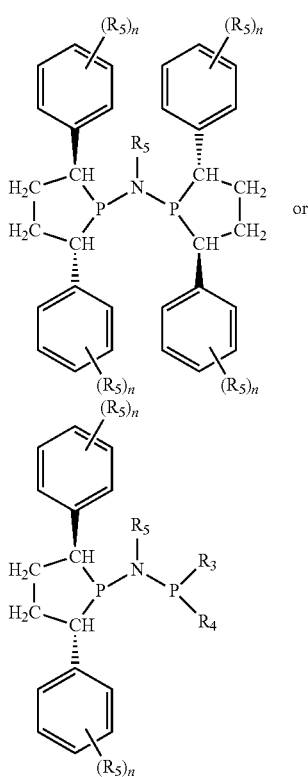

and their enantiomers wherein n independently selected is an integer from zero to five, preferably from zero to three.

Preferably Ar independently is $C_{2-40}$ substituted or unsubstituted aryl, preferably $C_{2-20}$ substituted or unsubstituted aryl, more preferably $C_{2-12}$ substituted or unsubstituted aryl; $C_{2-40}$ substituted or unsubstituted heteroaryl, preferably $C_{2-20}$ substituted or unsubstituted heteroaryl, more preferably $C_{2-12}$ substituted or unsubstituted heteroaryl. Preferably Ar is independently phenyl, substituted phenyl, furanyl, substituted furanyl, thienyl, substituted thienyl, pyrrolyl, substituted pyrrolyl, pyridinyl, and substituted pyridinyl, more preferably phenyl, substituted phenyl, and furanyl. In at least one phosphacycle of the phosphacycle-containing ligating compound, both atoms directly bonded to P or $X_1$ are $sp^3$ hybridized; Two or more Ar, Ar' or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected Ar, Ar' or $R_5$ groups to form a poly(ligating compound) species. When $PR_3R_4$ is non-cyclic (i.e., it does not form a phosphacycle), the atom of each $R_3$ or $R_4$ group directly attached to the phosphorus-atom is considered to be at the 1-position of that particular group for the purpose of numbering the positions of atoms or substituents in the $R_3$ or $R_4$ group. In a preferred embodiment of the ligating compounds wherein the $PR_3R_4$ group is non-cyclic, $R_3$ and $R_4$ independently are represented by alkyl, substituted alkyl, phenyl, substituted phenyl, furanyl, substituted furanyl, thienyl, substituted thienyl, pyrrolyl, substituted pyrrolyl, pyridinyl, and substituted pyridinyl; preferably the ligating compounds are represented by:

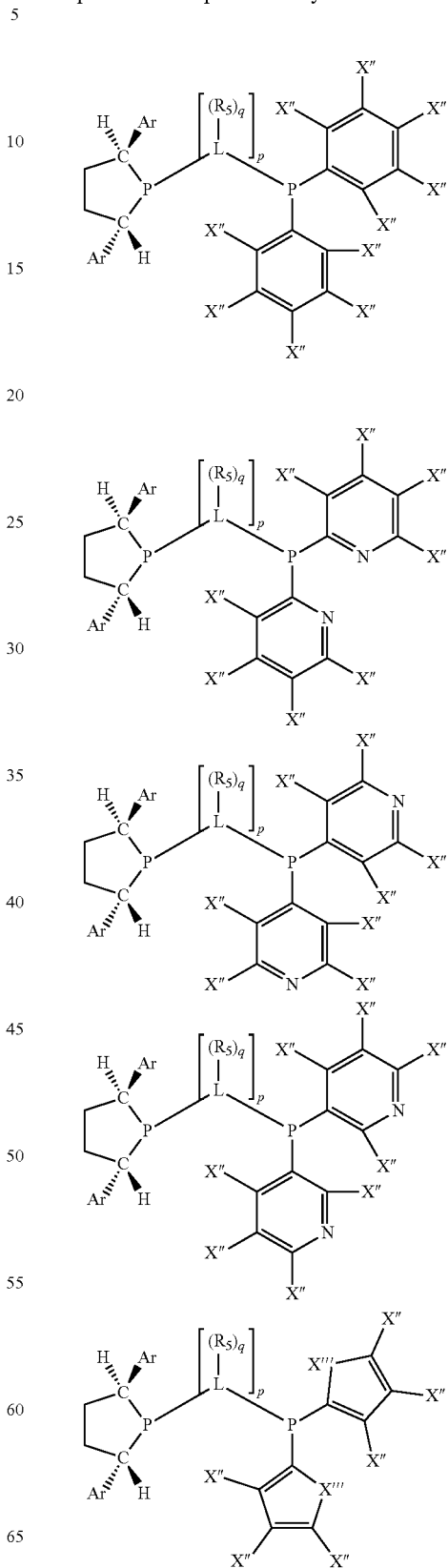

-continued

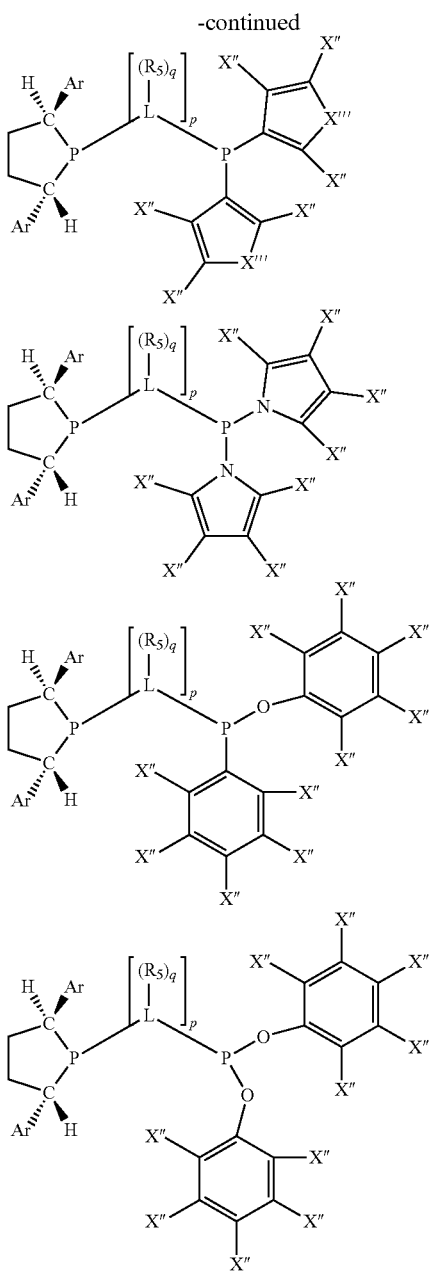

and their enantiomers wherein Ar independently is halogen; $C_{1-40}$ substituted or unsubstituted alkyl, preferably $C_{1-20}$ substituted or unsubstituted alkyl, more preferably $C_{1-12}$ substituted or unsubstituted alkyl, even more preferably $C_{1-6}$ substituted or unsubstituted alkyl, especially methyl, trifluoromethyl, methoxy, ethyl, ethoxy, propyl, isopropyl, n-butyl, i-butyl, s-butyl, t-butyl, pentyl, hexyl; $C_{2-40}$ substituted or unsubstituted aryl, preferably $C_{2-20}$ substituted or unsubstituted aryl, more preferably $C_{2-12}$ substituted or unsubstituted aryl, especially phenyl, fluorophenyl, difluorophenyl, trifluorophenyl, tolyl, dimethylphenyl, t-butylphenyl, di-t-butylphenyl, methoxyphenyl, ethoxyphenyl, di-t-butylmethoxyphenyl, cyanophenyl, nitrophenyl; $C_{2-40}$ substituted or unsubstituted heteroaryl, preferably $C_{2-20}$ substituted or unsubstituted heteroaryl, more preferably $C_{2-12}$ substituted or unsubstituted heteroaryl, especially substituted or unsubstituted pyridyl, thienyl, furanyl, pyrrolyl; X" independently is hydrogen; halogen, preferably fluorine, chlorine or bromine, more preferably fluorine or chlorine, even more preferably fluorine; $C_{1-40}$ substituted or unsubstituted alkyl, preferably $C_{1-20}$ substituted or unsubstituted alkyl, more preferably $C_{1-12}$ substituted or unsubstituted alkyl, even more preferably $C_{1-6}$ substituted or unsubstituted alkyl, especially methyl, trifluoromethyl, methoxy, ethyl, ethoxy, propyl, isopropyl, n-butyl, i-butyl, s-butyl, t-butyl, pentyl, hexyl; $C_{2-40}$ substituted or unsubstituted aryl, preferably $C_{2-20}$ substituted or unsubstituted aryl, more preferably $C_{2-12}$ substituted or unsubstituted aryl, especially phenyl, fluorophenyl, difluorophenyl, trifluorophenyl, tolyl, dimethylphenyl; $C_{2-40}$ substituted or unsubstituted arylalkyl, preferably $C_{2-20}$ substituted or unsubstituted arylalkyl, more preferably $C_{2-12}$ substituted or unsubstituted arylalkyl, especially benzyl, phenethyl, and methylbenzyl; nitro or cyano; further provided that in at least one phosphacycle of the phosphacycle-containing ligating compound, both atoms directly bonded to P or $X_1$ are $sp^3$ hybridized; two or more Ar, X" or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_1$, $R_2$, $R_3$, $R_4$ or $R_5$ groups to form a poly(ligating compound) species. X''' is independently N, O or S, preferably O. Preferably X" independently is hydrogen, fluorine, chlorine, methyl, methoxy, t-butyl, phenyl, nitro or cyano. Preferably $R_3$ and $R_4$ independently are substituted or unsubstituted phenyl or unsubstituted furanyl. Preferably $R_3$ or $R_4$ independently is substituted phenyl, and at least one X" on at least one, preferably each, substituted phenyl is halogen, preferably fluorine or chlorine, $C_{1-4}$ alkyl or substituted alkyl, preferably methyl, trifluoromethyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably fluorine; preferably at least one, more preferably each, substituted phenyl is substituted at the 2-position with cyano, nitro, fluorine, chlorine, bromine or iodine, preferably fluorine or chlorine, more preferably fluorine and is substituted at one or more of the 3-, 4-, 5-, 6-positions with cyano, nitro, fluorine, chlorine, bromine or iodine, preferably fluorine or chlorine, more preferably fluorine; preferably at least one, more preferably each, substituted phenyl is independently substituted at the 2-position and the 4-position with cyano, nitro, fluorine, chlorine, bromine or iodine, preferably fluorine or chlorine, more preferably fluorine; preferably at least one, more preferably each, substituted phenyl is substituted at the 2-position with cyano, nitro, fluorine, chlorine, bromine or iodine, preferably fluorine or chlorine, more preferably fluorine; preferably at least one, more preferably each, substituted phenyl is substituted at the 6-position with hydrogen, fluorine or chlorine, preferably hydrogen or fluorine, more preferably hydrogen; preferably at least one, more preferably each, substituted phenyl is substituted at the 2-position with fluorine, at the 4-position with hydrogen or fluorine, and at the 6-position with hydrogen. Preferably $R_3$ and $R_4$ independently are substituted or unsubstituted pyridinyl. Preferably $R_3$ or $R_4$ independently is substituted pyridinyl, and at least one X" on at least one, preferably each, substituted pyridinyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably fluorine; preferably at least one, more preferably each, substituted pyridinyl is substituted at the 2-position with cyano, nitro, fluorine, chlorine, bromine or iodine, preferably fluorine or chlorine, more preferably fluorine. Preferably $R_3$ and $R_4$ independently are substituted or unsubstituted pyridinyl. Preferably $R_3$ or $R_4$ independently is substituted pyridinyl, and at least one X" on at least one, preferably each, substituted pyridinyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably fluorine. Preferably $R_3$ and $R_4$ independently are substituted or unsubstituted pyrrolyl. Preferably $R_3$ or $R_4$ independently is substituted pyrrolyl, and at least one X" on at least one, preferably each, substituted pyrrolyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably methyl. Preferably $R_3$ and $R_4$ independently are substituted or unsubstituted furanyl. Preferably $R_3$ or $R_4$ independently is substituted furanyl, and at least one X" on at least one, preferably each, substituted furanyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably methyl. Preferably $R_3$ and $R_4$ independently are substituted or unsubstituted thienyl. Preferably $R_3$ or $R_4$ independently is substituted thienyl, and at least one X" on at least one, preferably each, substituted thienyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably methyl.

Non-limiting examples of the ligating compounds are:

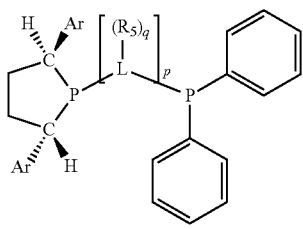

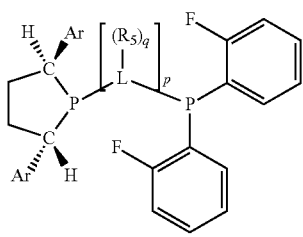

-continued

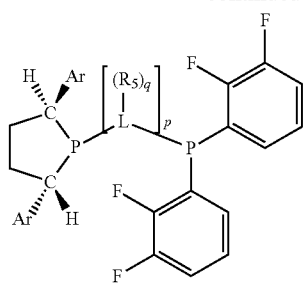

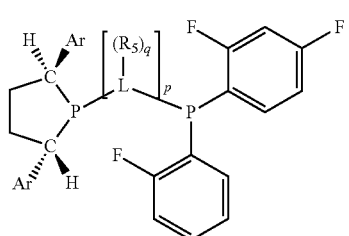

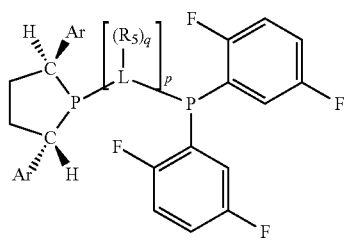

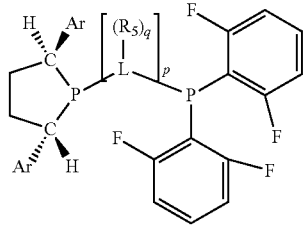

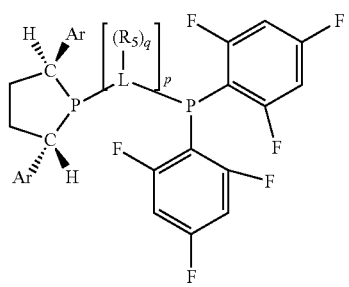

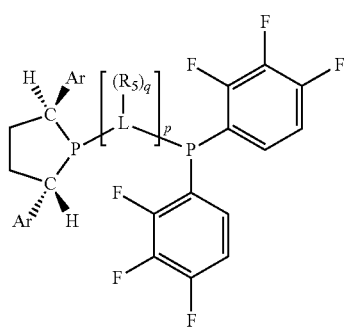

-continued
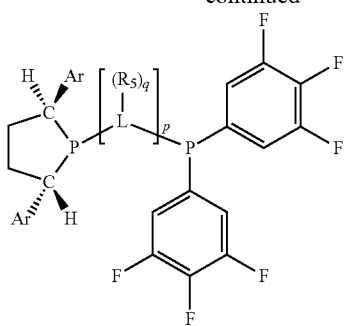
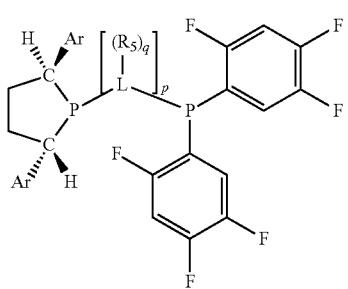
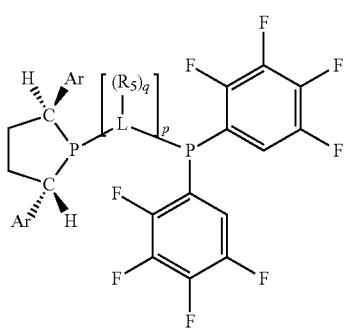
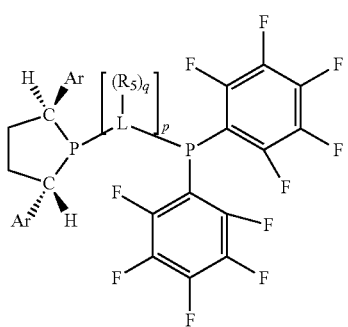
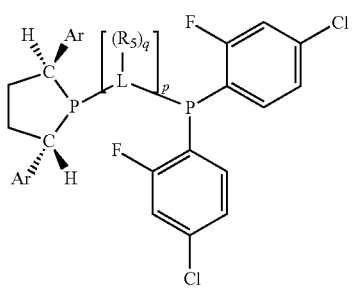
-continued
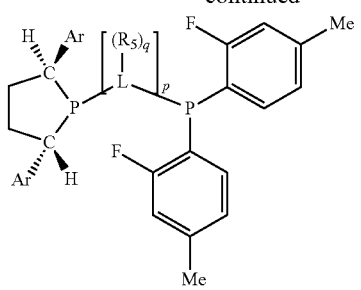
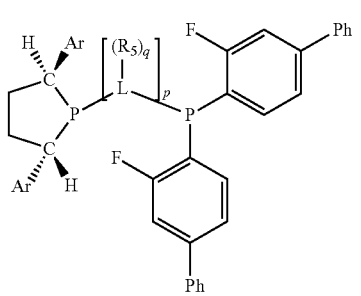
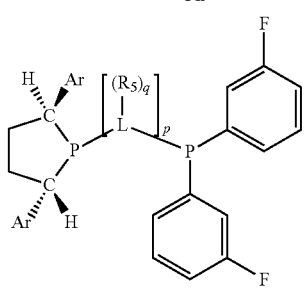
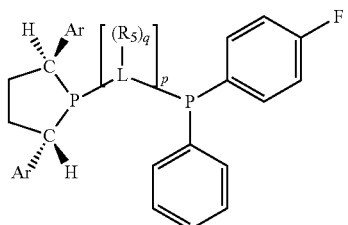
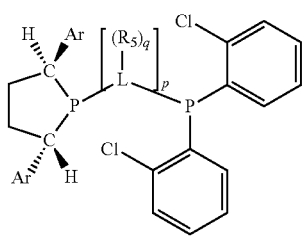
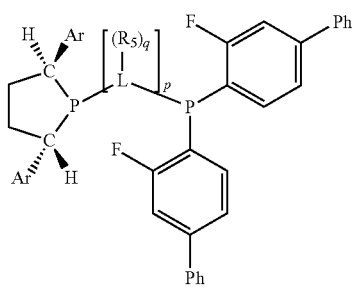

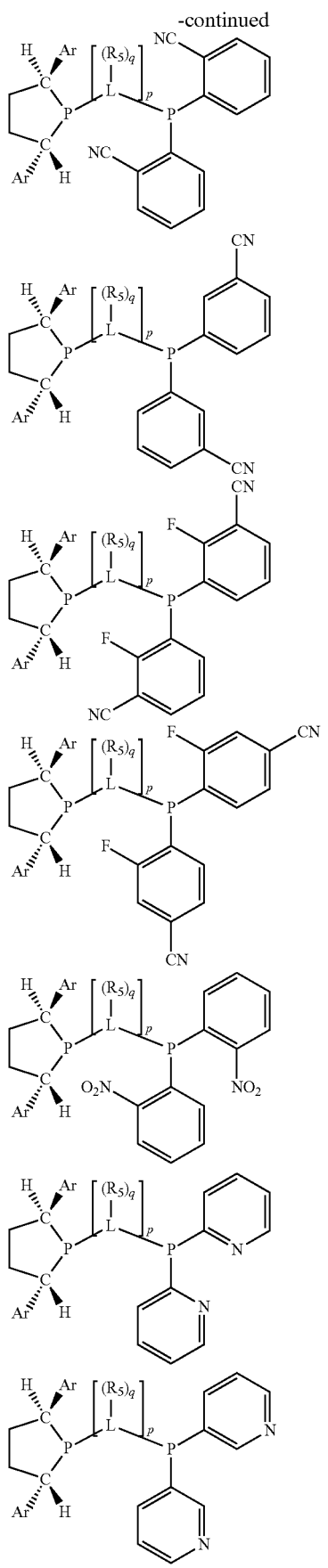
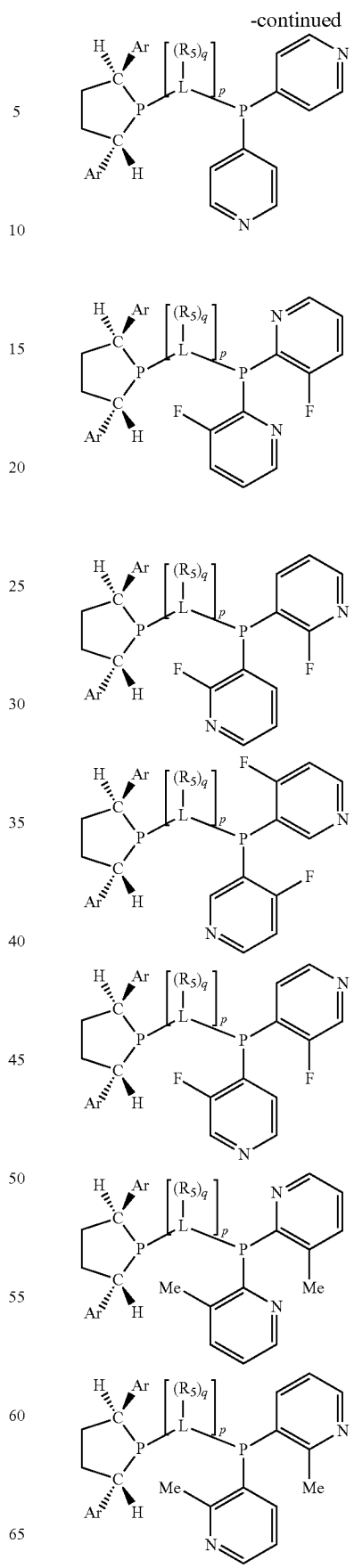

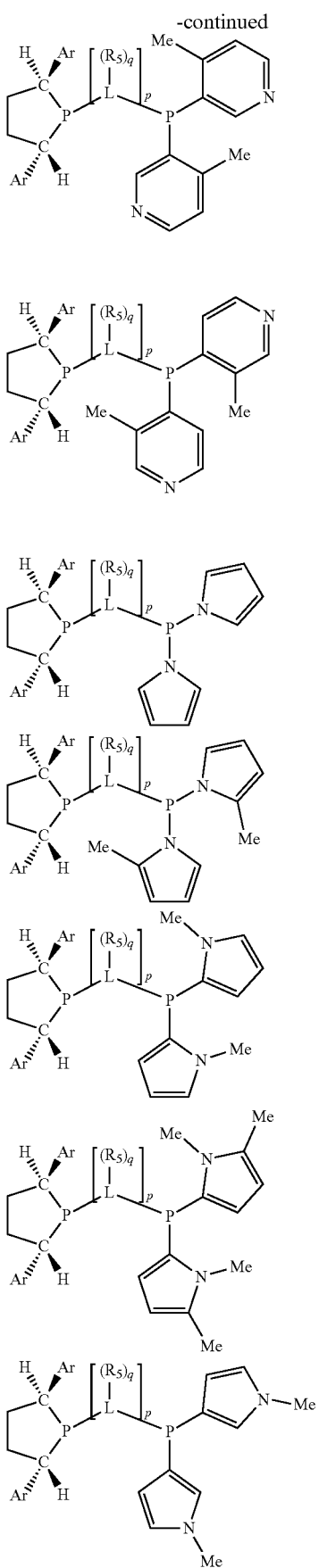
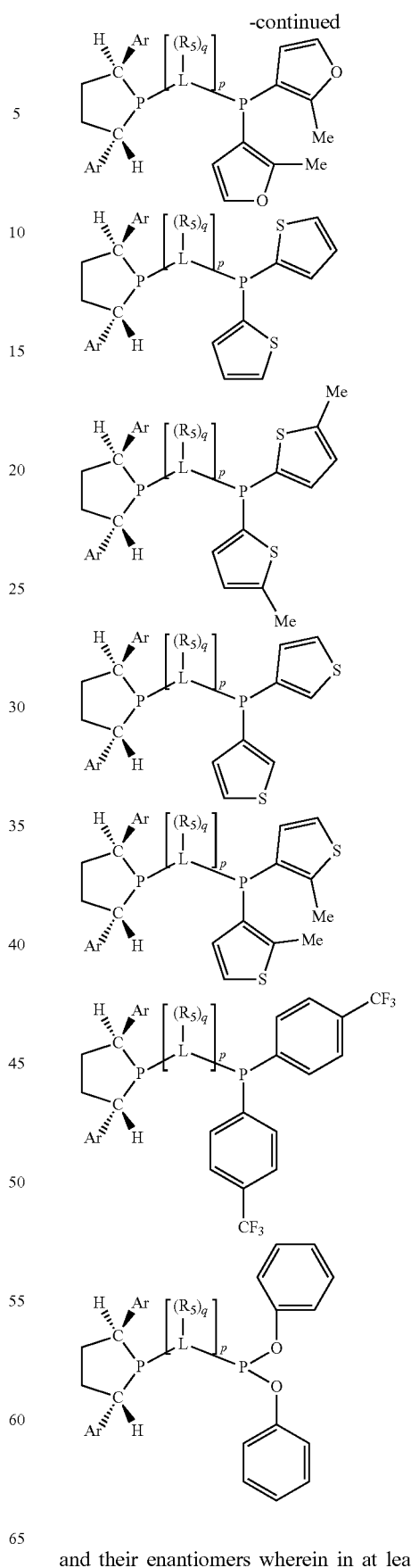
and their enantiomers wherein in at least one phosphacycle of the phosphacycle-containing ligating compound, both atoms directly bonded to P or $X_1$ are $sp^3$ hybridized; two or more Ar or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected Ar or $R_5$ groups to form a poly(ligating compound) species.

In preferred ligating compounds, Ar at the 2- and 5-positions of the phosphacycle rings is phenyl optionally substituted with $R_5$; $[L(R_5)_q]_p$ of the divalent linking group is $NR_5$, and 5-membered ligating compounds are represented by:

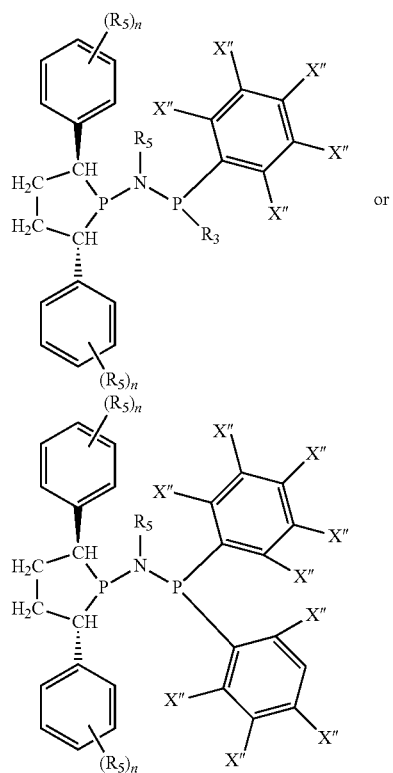

or and their enantiomers, wherein n independently selected is an integer from zero to five, preferably from zero to three, more preferably zero to one; $R_5$ is halogen, $C_{1-40}$ substituted or unsubstituted alkyl, $C_{1-40}$ substituted or unsubstituted aryl; preferably fluorine, chlorine, bromine, $C_{1-20}$ substituted or unsubstituted alkyl, $C_{1-20}$ substituted or unsubstituted aryl; more preferably fluorine, chlorine, $C_{1-12}$ substituted or unsubstituted alkyl, $C_{1-12}$ substituted or unsubstituted aryl; $R_3$ is $C_{1-40}$ substituted or unsubstituted alkyl, $C_{1-40}$ substituted or unsubstituted aryl; preferably $C_{1-20}$ substituted or unsubstituted alkyl, $C_{1-20}$ substituted or unsubstituted aryl; more preferably $C_{1-12}$ substituted or unsubstituted alkyl, $C_{1-12}$ substituted or unsubstituted aryl; X" is hydrogen, halogen, $C_{1-4}$ alkyl or substituted alkyl, $C_{6-10}$ aryl or substituted aryl, cyano or nitro, preferably hydrogen, fluorine, chlorine, bromine, methyl, ethyl, propyl, butyl, phenyl, tolyl, xylyl, methoxy, ethoxy, propoxy, trifluoromethyl or t-butyl, cyano, more preferably hydrogen, fluorine, chlorine, methyl, ethyl, propyl, butyl, phenyl, tolyl, methoxy, ethoxy, propoxy, trifluoromethyl, cyano, even more preferably hydrogen, fluorine, methyl, or methoxy.

In preferred ligating compounds, X" at the 2-position of the phenyl ring attached to P is fluorine, X" at the 6-position of the phenyl ring attached to P is hydrogen, and 5-membered ligating compounds are represented by:

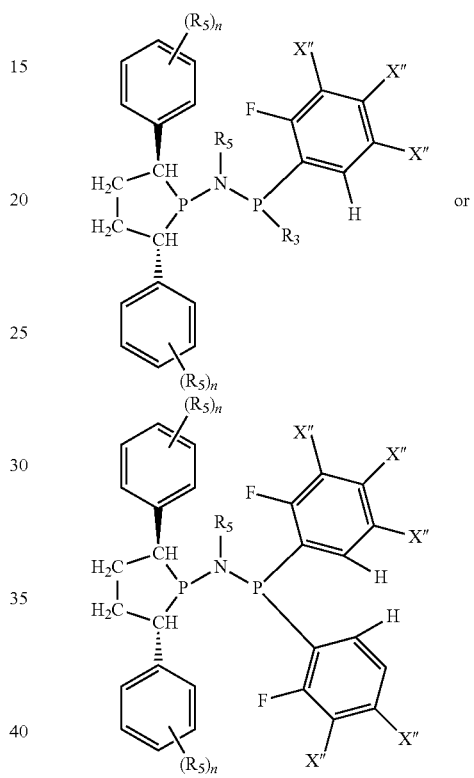

and their enantiomers, wherein n independently selected is an integer from zero to five, preferably from zero to three, more preferably zero to one; $R_5$ is halogen, $C_{1-40}$ substituted or unsubstituted alkyl, $C_{1-40}$ substituted or unsubstituted aryl; preferably fluorine, chlorine, bromine, $C_{1-20}$ substituted or unsubstituted alkyl, $C_{1-20}$ substituted or unsubstituted aryl; more preferably fluorine, chlorine, $C_{1-12}$ substituted or unsubstituted alkyl, $C_{1-12}$ substituted or unsubstituted aryl; $R_3$ is $C_{1-40}$ substituted or unsubstituted alkyl, $C_{1-40}$ substituted or unsubstituted aryl; preferably $C_{1-20}$ substituted or unsubstituted alkyl, $C_{1-20}$ substituted or unsubstituted aryl; more preferably $C_{1-12}$ substituted or unsubstituted alkyl, $C_{1-12}$ substituted or unsubstituted aryl; X" is hydrogen, halogen, $C_{1-4}$ alkyl or substituted alkyl, $C_{6-10}$ aryl or substituted aryl, cyano or nitro, preferably hydrogen, fluorine, chlorine, bromine, methyl, ethyl, propyl, butyl, phenyl, tolyl, xylyl, methoxy, ethoxy, propoxy, trifluoromethyl or t-butyl, cyano, more preferably hydrogen, fluorine, chlorine, methyl, ethyl, propyl, butyl, phenyl, tolyl, methoxy, ethoxy, propoxy, trifluoromethyl, cyano, even more preferably hydrogen, fluorine, methyl, or methoxy.

The group Y, which links P and $X_1$ together in the ligating compounds, is a divalent linking group $[L(R_5)_q]_p$, wherein p is an integer number from 1 to 6, preferably from 1 to 4, preferably 1, 2, or 3, more preferably 1 or 2; q is 0, 1, or 2; consisting of the linking part [L]$_p$ and the R$_5$ pendant groups wherein the R$_5$ pendant groups independently selected are attached to the L atoms of the [L]$_p$ linking part. The linking part [L]$_p$ consists of 1 to 6, preferably of 1 to 4, preferably 1, 2, or 3, more preferably 1 or 2 L atoms; L is independently selected from the group consisting of boron, carbon, silicon, germanium, nitrogen, phosphorus, oxygen, and sulfur. Preferably L is independently selected from carbon, nitrogen, phosphorus, oxygen, and sulfur. Preferred linking parts [L]$_p$, each L independently selected, are B, C, N, O, P, S, Si, C—C, C=C, C—N, C=N, C—Si, N—N, C—C—C, C—C=C, C—N—C, C—P—C, C—N=C, C—Si—C, N—C—N, C—N—N, C=N—N, C—N=N, C—O—C, and C—S—C, preferably provided that the linking part [L]$_p$ is not amidine, N—C=N. In an embodiment of the invention, each L(R$_5$)$_q$ group is independently —N—, —N(R$_5$)—, —P(R$_5$)—, —P(O)(R$_5$)—, —P(S)(R$_5$)—, —C(O)—, —C(R$_5$)—, —C(R$_5$)$_2$—, —Si(R$_5$)$_2$—, —O—, —S—, S(O)—, and —SO$_2$—, preferably N, N(R$_5$), C(R$_5$), or C(R$_5$)$_2$.

In some embodiments, the linking part [L]$_p$ consists of C and the divalent linking group is [C(R$_5$)$_q$] wherein q is 1 or 2. Representative, but not limiting, [C(R$_5$)$_q$] linking groups include:

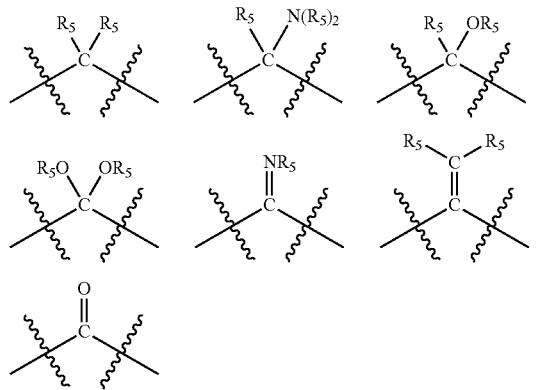

Specific, but not limiting, [C(R$_5$)$_q$] linking groups include:

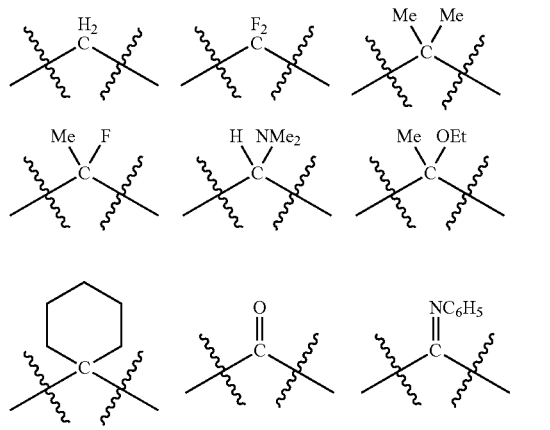

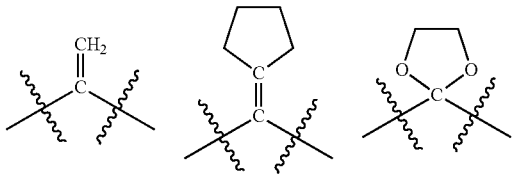

In some embodiments, the linking part [L]$_p$ is not C and the divalent linking group is not [C(R$_5$)$_q$] wherein q is 1 or 2.

In some embodiments, the linking part [L]$_p$ consists of C—C and the divalent linking group is [C(R$_5$)$_q$]2 wherein q independently is 1 or 2 and at least one q is 2. Representative, but not limiting, [C(R$_5$)$_q$]2 linking groups include:

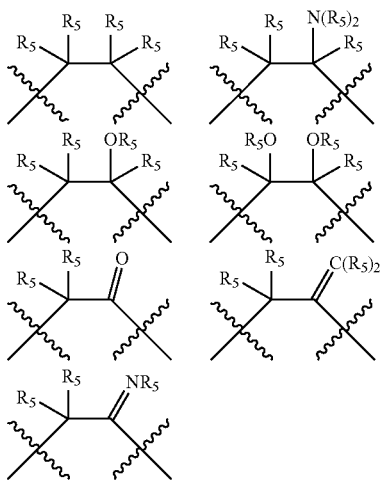

Specific, but not limiting, [C(R$_5$)$_q$]2 linking groups include:

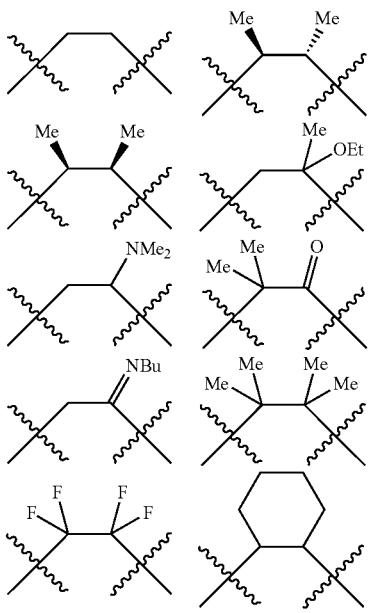

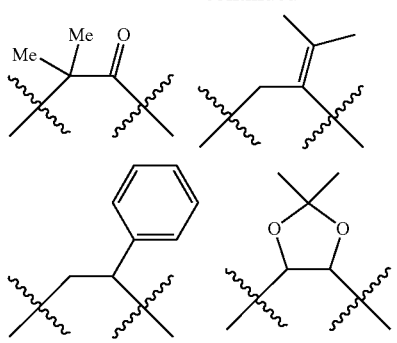

In some embodiments, the linking part $[L]_p$ is not C—C and the divalent linking group is not $[C(R_5)_q]2$ wherein q independently is 1 or 2 and at least one q is 2.

In some embodiments the linking part $[L]_p$ consists of C—C and the divalent linking group is $[C(R_5)]2$ wherein both carbon atoms are connected with a carbon-carbon unsaturated bond, or both carbon atoms are connected to their respectively $R_5$ groups with unsaturated bonds. Representative, but not limiting, $[C(R_5)]2$ linking groups include:

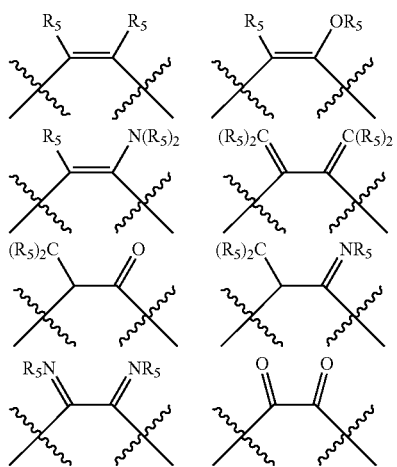

Specific, but not limiting, $[C(R_5)]2$ linking groups include:

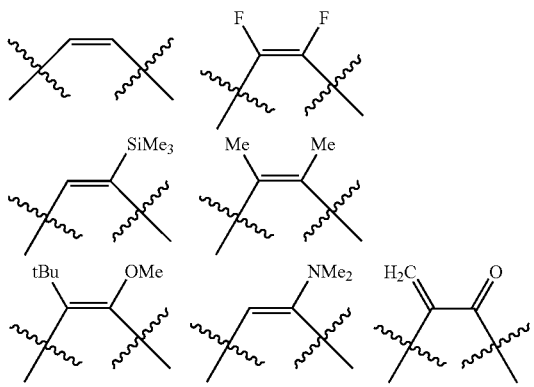

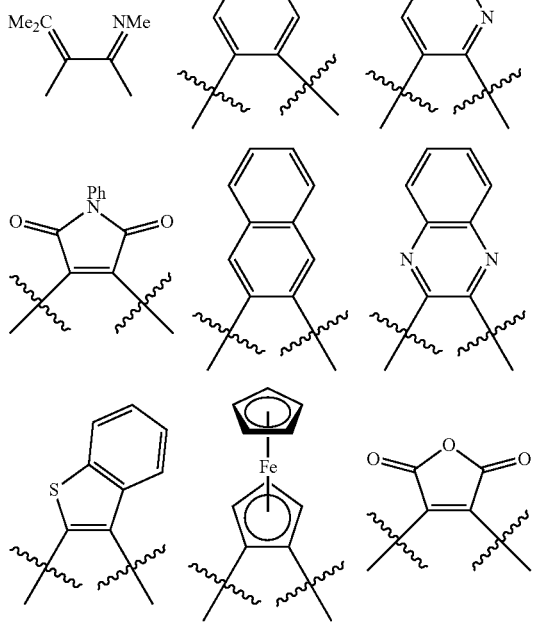

In some embodiments the linking part $[L]_p$ is not C—C and the divalent linking group is not $[C(R_5)]2$ wherein both carbon atoms are connected with a carbon-carbon unsaturated bond, or both carbon atoms are connected to their respectively $R_5$ groups with unsaturated bonds.

In some embodiments, the linking part $[L]_p$ consists of N or N—N and the divalent linking group is $[NR_5]$ or $[NR_5]2$. Representative, but not limiting, $[NR_5]$ or $[NR_5]2$ linking groups include:

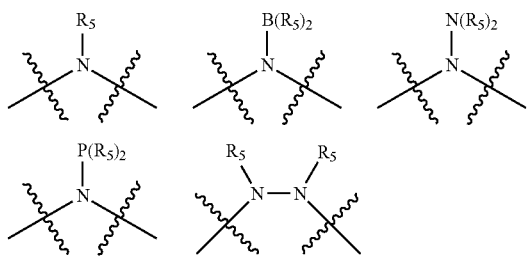

Specific, but not limiting, $[NR_5]$ or $[NR_5]2$ linking groups include:

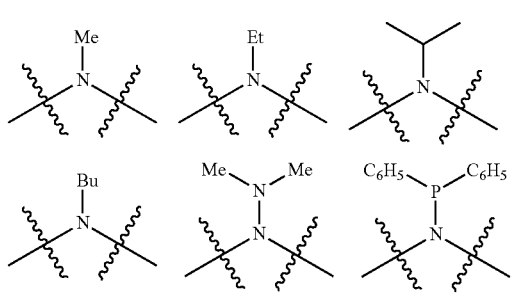

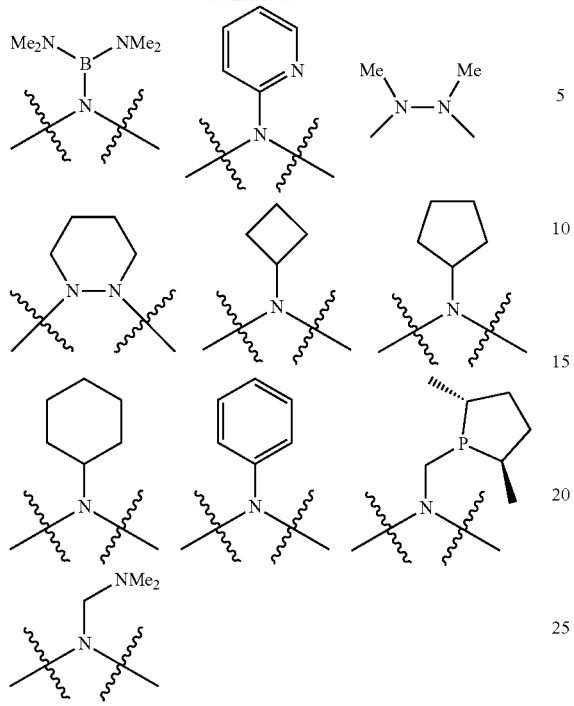

In some embodiments, the linking part $[L]_p$ is neither N nor N—N and the divalent linking group is neither $[NR_5]$ nor $[NR_5]2$. Preferably $[NR_5]$ does not comprise

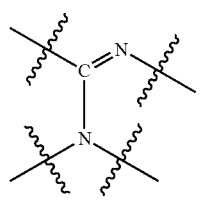

It will be appreciated that a diphosphinoimine compound of the form $R_1R_2P—P(=NR_5)R_3(R_4)$ ('P—P=N') is a rearranged isomer of the diphosphinoamine compound $R_1R_2P—NR_5—PR_3(R_4)$ ('P—N—P') claimed in the present invention, as shown by Dyson et al in Inorganica Chimica Acta 359 (2006) 2635-2643 and may isomerize to the P—N—P form in the presence of transition metals, such as chromium in the instant application.

Similarly, it may be possible that a ligating compound of the form $R_1R_2P—Y—XR_3(R_4)_m$ or $R_1R_2P-[L(R_5)_q]_p—X_1R_3(R_4)_m$ where Y or $[L(R_5)_q]_p$ is $—N(R_5)—$ and $X_1R_3(R_4)_m$ is $PR_3R_4$, exists in its isomeric 'P—P=N' form. Regardless of the structural formulation of the ligating compound in its pure and isolated form, it and its use are embodiments of the present invention, especially if it exists in the 'P—N—P' form when used in an oligomerization process, more especially when it is bound to chromium in an oligomerization process.

In some embodiments, the linking part $[L]_p$ consists of C—N and the divalent linking group is $[C(R_5)_qN(R_5)_q]$ wherein q independently is 1 or 2 for $C(R_5)_q$ and 0 or 1 for $N(R_5)_q$. Representative, but not limiting, $[C(R_5)_qN(R_5)_q]$ linking groups include:

Specific, but not limiting, $[C(R_5)_qN(R_5)_q]$ linking groups include:

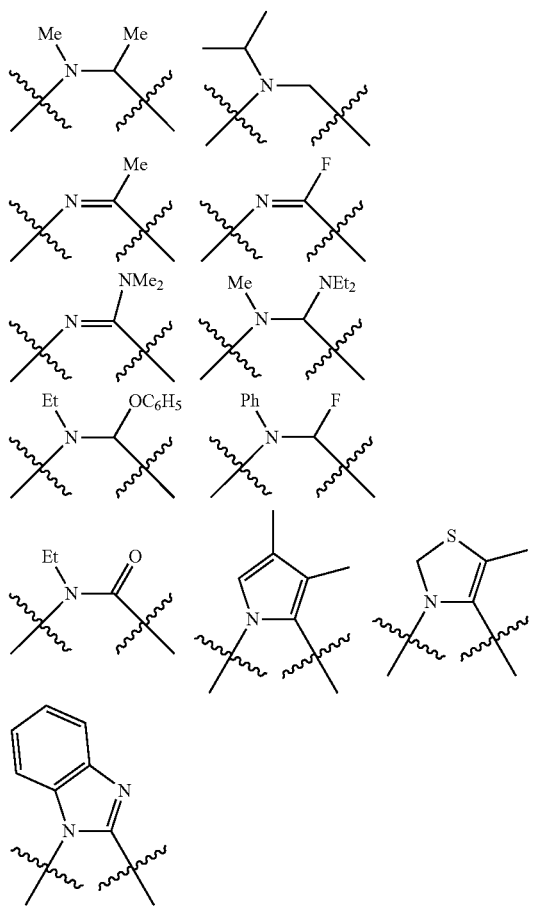

In some embodiments, the linking part $[L]_p$ is not C—N and the divalent linking group is not $[C(R_5)_qN(R_5)_q]$ wherein q independently is 1 or 2 for $C(R_5)_q$ and 0 or 1 for $N(R_5)_q$. Preferably $[C(R_5)_qN(R_5)_q]$ does not comprise

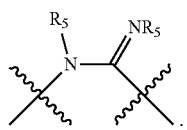

In some embodiments, the L atoms of the linking part $[L]_p$ are selected from the group consisting of B, O, S, Si, and C wherein at least one L is not C; p is 1, 2, 3, or 4; and the divalent linking group is $[(C(R_5)_2)_k X'_r (C(R_5)_2)_{k'}]$ wherein X' independently selected is $BR_5$, O, S, SO, $SO_2$, or $Si(R_5)_2$; k is 0 or 1; k' is 0 or 1; r is 1, 2, or 3. Preferably r+k+k'1, 2, or 3.

Representative, but not limiting, $[(C(R_5)_2)_k X'_r (C(R_5)_2)_{k'}]$ linking groups include:

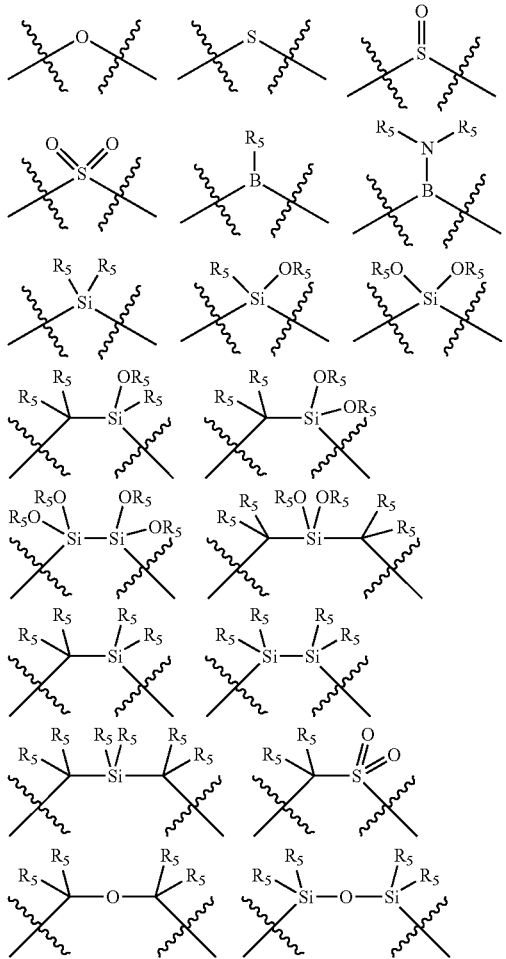

Specific, but not limiting, $[(C(R_5)_2)_k X'_r (C(R_5)_2)_{k'}]$ linking groups include:

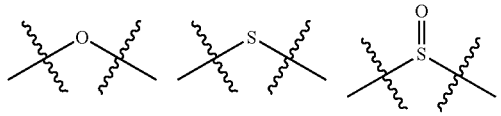

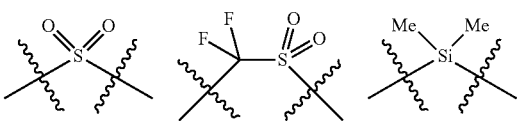

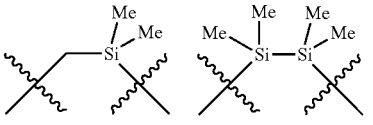

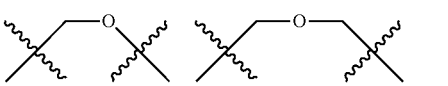

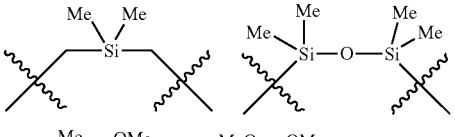

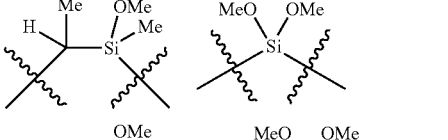

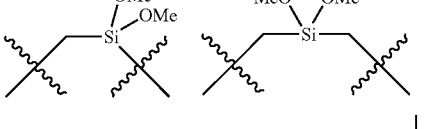

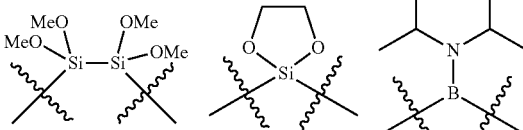

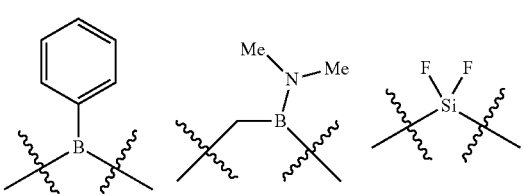

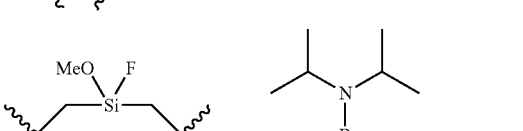

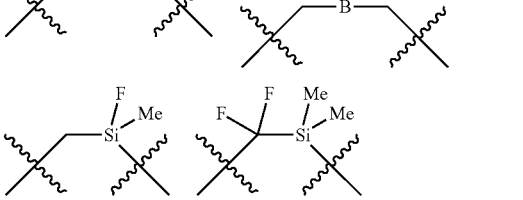

In some embodiments, the L atoms of the linking part $[L]_p$ are not selected from the group consisting of B, O, S, Si, and C wherein at least one L is not C; p is 1, 2, 3, or 4; and the divalent linking group is not $[(C(R_5)_2)_k X'_r (C(R_5)_2)_{k'}]$ wherein X' independently selected is $BR_5$, O, S, SO, $SO_2$, or $Si(R_5)_2$; k is 0 or 1; k' is 0 or 1; r is 1, 2, or 3.

In preferred ligating compounds, represented by:

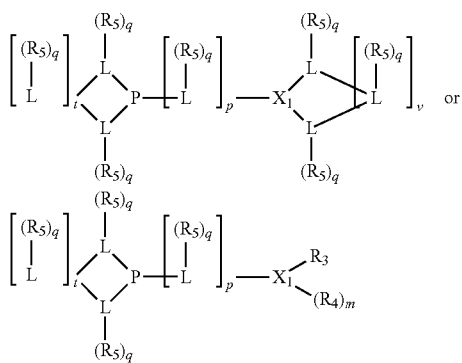

the L atoms are connected to each other, independently for each connection, with single bonds or with unsaturated bonds with the proviso that in at least one phosphacycle of the ligating compound, both atoms directly bonded to P or $X_1$ are $sp^3$ hybridized; preferably least one phosphacycle does not contain more than one carbon-carbon unsaturated bond, preferably not more than one unsaturated bond, more preferably at least one, preferably two, phosphacycles contain no unsaturated bonds; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compounds may be linked together via their respective independently selected $R_3$, $R_4$ or $R_5$ groups to form a poly(ligating compound) species. In an embodiment of the invention no two $R_5$, $R_3$, or $R_4$ groups are linked together to form a cyclic structure. In an embodiment of the invention at least two $R_5$ groups are linked together to form a cyclic structure. Preferably at least one $R_5$ group on a first $L(R_5)_q$ group is linked together with at least one $R_5$ group on an adjacent second $L(R_5)_q$ group together with the L atom from the first $L(R_5)_q$ group and the L atom from the adjacent second $L(R_5)_q$ group to form an

cyclic structure containing from 4 to 10 atoms, preferably 4 to 7 atoms, in the ring part of the

cyclic structure. Preferably the

ring is a substituted or unsubstituted, saturated or unsaturated hydrocarbyl group, such as cyclopentanediyl, cyclohexanediyl, dioxolanediyl, tetrahydrofurandiyl, pyrrolidinediyl, piperidinediyl, piperazinediyl, pyrazolidinediyl. Preferably the

ring is a substituted or unsubstituted alkenyl or aromatic group, such as cyclopentenediyl, cyclohexenediyl, cyclopentadienediyl, phenylene, naphthalenediyl, pyridinediyl, pyrrolediyl, imidazoldiyl, pyridazinediyl, pyridazinedionediyl, quinoxalinediyl, thiazolediyl, thiophenediyl, furandiyl, or cyclopentadienyl-diyl, wherein preferably the cyclopentadienyl group is part of an $\eta^5$-bonded transition metal complex, wherein preferably the $\eta^5$-bonded transition metal complex comprises Fe, Ti, Zr, or Hf.

In an embodiment of the invention, two $R_5$ groups on the same $L(R_5)_q$ group, wherein q=2, are linked together to form an

cyclic structure containing from 3 to 10 atoms, preferably 3 to 7 atoms, in the ring part of the

cyclic structure. Preferably the

ring is a substituted or unsubstituted, saturated or unsaturated hydrocarbyl group, such as cyclobutanediyl, cyclopentanediyl, cyclohexanediyl, tetrahydrofurandiyl, or cyclopentenediyl.

In preferred ligating compounds of the invention, at least one $R_5$ group on a $L(R_5)_q$ group from at least one of the

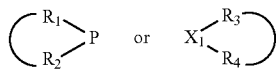

groups or at least one $R_5$ group on a

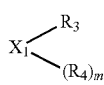

group, wherein the $R_3$ or $R_4$ group may be represented as $L(R_5)_q(R_5)$, is linked together with at least one $R_5$ group from the $[L(R_5)_q]_p$ divalent bridging group between P and $X_1$ to form an

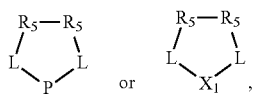

respectively, cyclic structure containing from 5 to 10 atoms, preferably 5 to 7 atoms, in the ring part of the

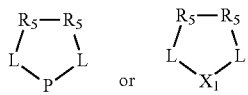

cyclic structure.

R$_3$, R$_4$, and R$_5$ independently selected are hydrogen, fluoro, chloro, bromo, cyano; substituted or unsubstituted hydrocarbon derivatives, preferably substituted or unsubstituted alkyl groups having 1-20, preferably 1-12, more preferably 1-6, non-hydrogen atoms, preferably methyl, trifluoromethyl, ethyl, propyl, isopropyl, n-butyl, i-butyl, s-butyl, t-butyl, pentyl, hexyl, cyclopentyl, cyclohexyl; preferably substituted or unsubstituted unsaturated groups, including alkylidene, alkenyl, aryl, or arylalkyl groups, having 2-20, preferably 2-12, more preferably 2-8, still more preferably 2-6, non-hydrogen atoms, preferably vinyl, methylidene, ethylidene, allyl, phenyl, 2-methylphenyl, 3-methylphenyl, 4-methylphenyl, 2,4-dimethylphenyl, 2,6-dimethylphenyl, 2,4,6-trimethylphenyl, 2-isopropylphenyl, 2,6-diisopropylphenyl, 2,6-diisopropyl-4-methylphenyl, 2-fluorophenyl, 4-fluorophenyl, 2-trifluoromethylphenyl, naphthyl, anthracenyl, biphenyl, benzyl, naphthylmethyl phenethyl, biphenylmethyl; substituted or unsubstituted heterohydrocarbon derivatives having 1-20, preferably 1-12, more preferably 1-6, non-hydrogen atoms, preferably methoxy, ethoxy, propoxy, isopropoxy, butoxy, phenoxy, methylthio, ethylthio, acetyl, dimethylboryl, diphenylboryl, bis(dimethylamino)boryl, dimethylamino, diethylamino, 2-dimethylaminoethyl, 2-methoxyphenyl, 3-methoxyphenyl, 4-methoxyphenyl, 2,6-dimethoxyphenyl, 2,6-dimethoxy-4-methylphenyl, 2-dimethylaminophenyl, phenylamino, phenylmethylamino, acetamide, formylamino, benzamido, benzoyl, methylcarboxamide, dimethylcarboxamide, methoxymethyl, ethoxymethyl, phenoxymethyl, methoxyethyl, ethoxyethyl, phenoxyethyl, phospholanylmethyl, diethylphospholanylmethyl, 2-furanyl, 3-furanyl, pyrrolyl, imidazolyl, pyrrolidinyl, piperidinyl, pyridinyl, pyridazinyl, pyrazolidinyl, pyrazinyl, thienyl, thiazolyl, trimethylsilyl, trimethylsilylmethyl, dimethylphenylsilyl, methylsulfinyl, ethylsulfinyl, methylsulfonyl, ethylsulfonyl; or a substituted or unsubstituted heteroatom group having 1-6 non-hydrogen atoms, preferably a nitro group, one oxygen atom, or one sulfur atom. R$_3$ and R$_4$ preferably are substituted or unsubstituted aryl or arylalkyl groups, more preferably substituted or unsubstituted aryl groups. When two or more R$_3$, R$_4$, or R$_5$ groups, independently selected, are linked together, the moiety they form is di- or polyvalent, depending on how many R$_3$, R$_4$, or R$_5$ groups are linked together. For example, if two R$_3$, R$_4$, or R$_5$ groups are linked together, the moiety is divalent; if three R$_3$, R$_4$, or R$_5$ groups are linked together, the moiety is trivalent. When two or more R$_3$, R$_4$, or R$_5$ groups, independently selected, are linked together, the linked R$_3$, R$_4$, or R$_5$ groups are not hydrogen, fluoro, chloro, bromo or cyano.

In some embodiments, ligating compounds of the present invention include the following compositions:

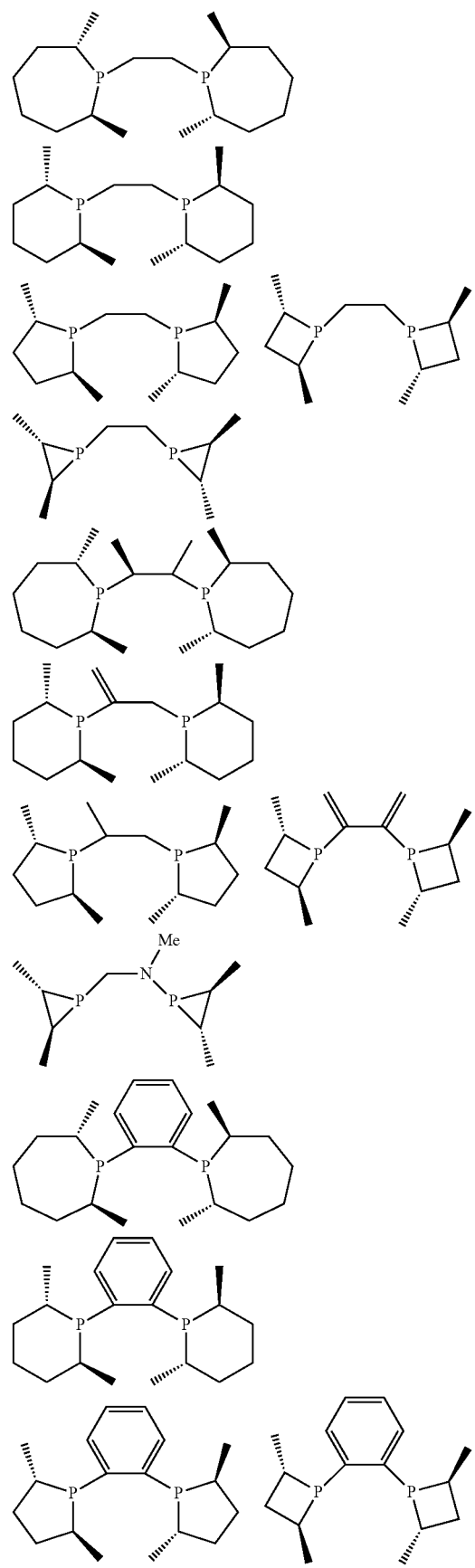

-continued
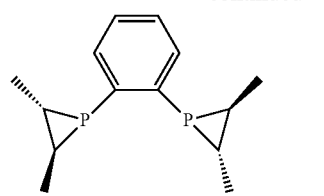
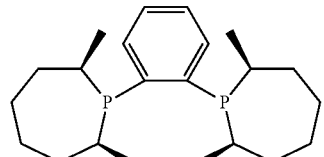
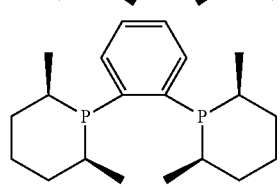
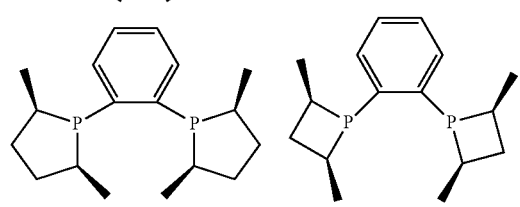
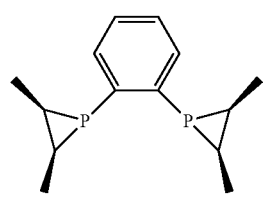
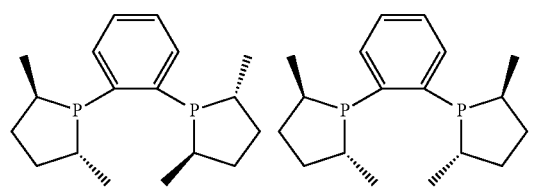
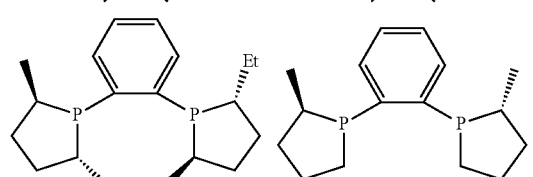
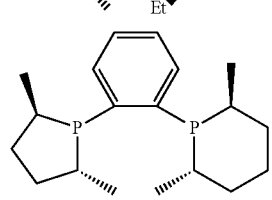
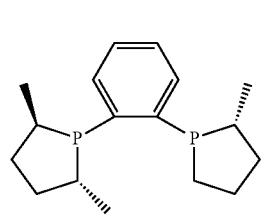
-continued
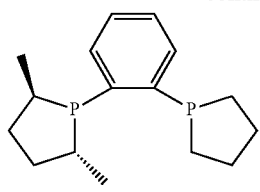
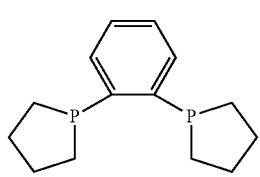
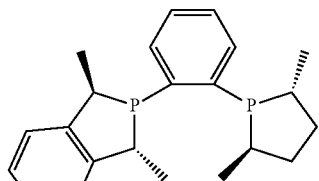
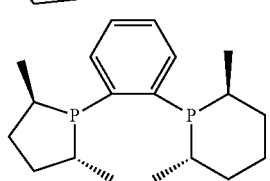
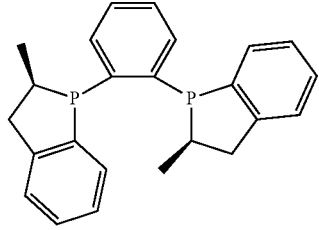
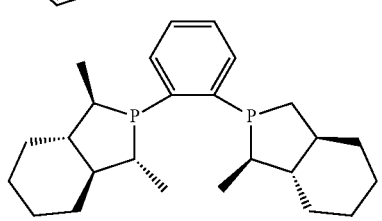
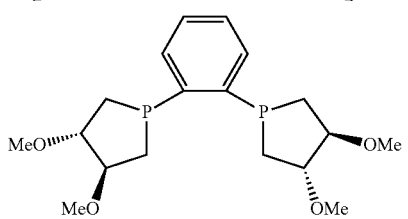
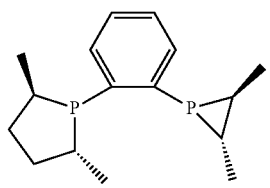

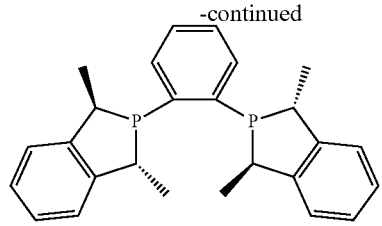
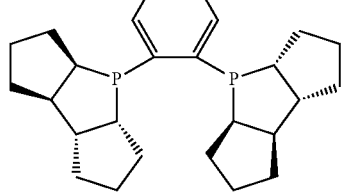
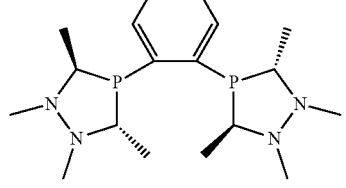
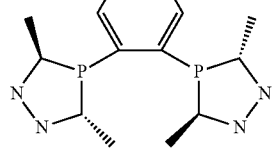
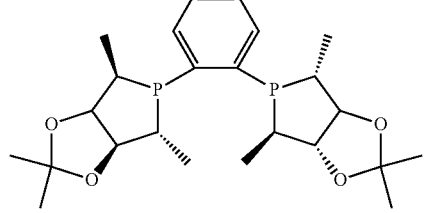
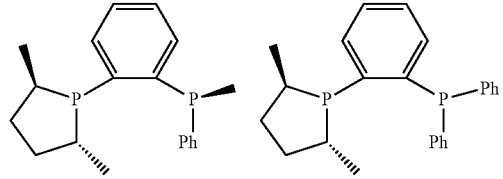
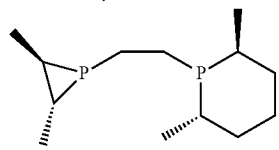
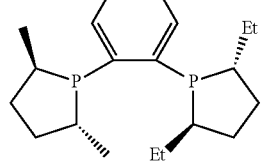
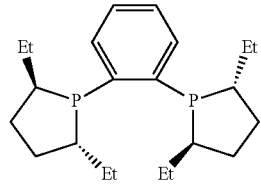
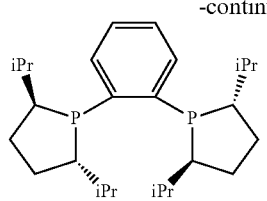
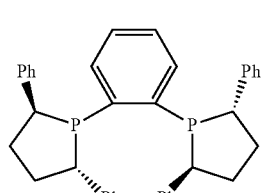
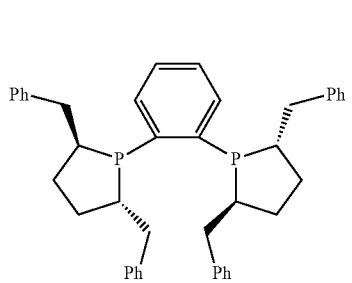
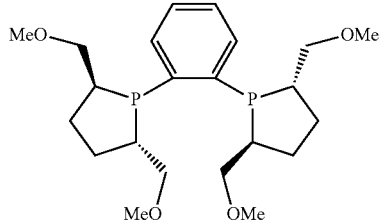
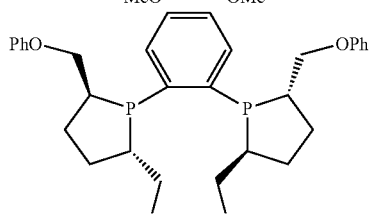
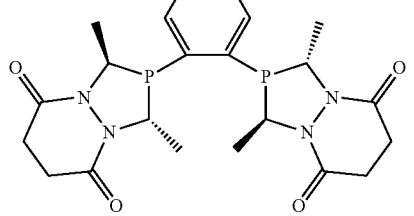
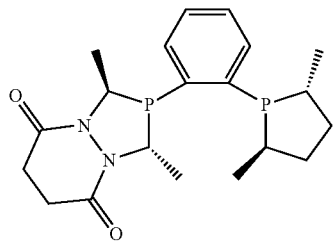

79
-continued
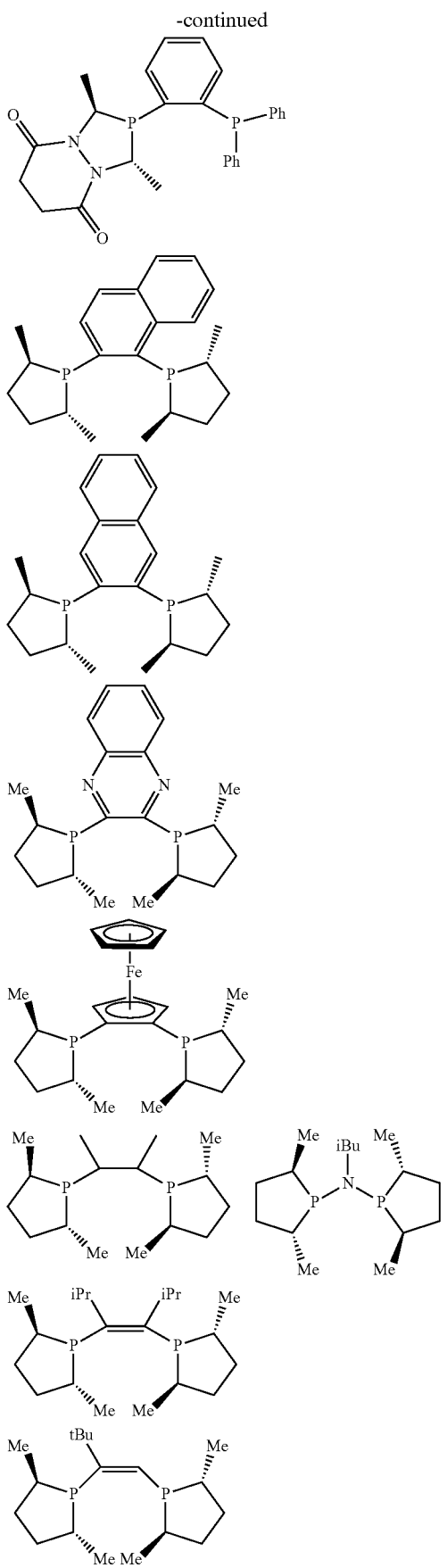
80
-continued
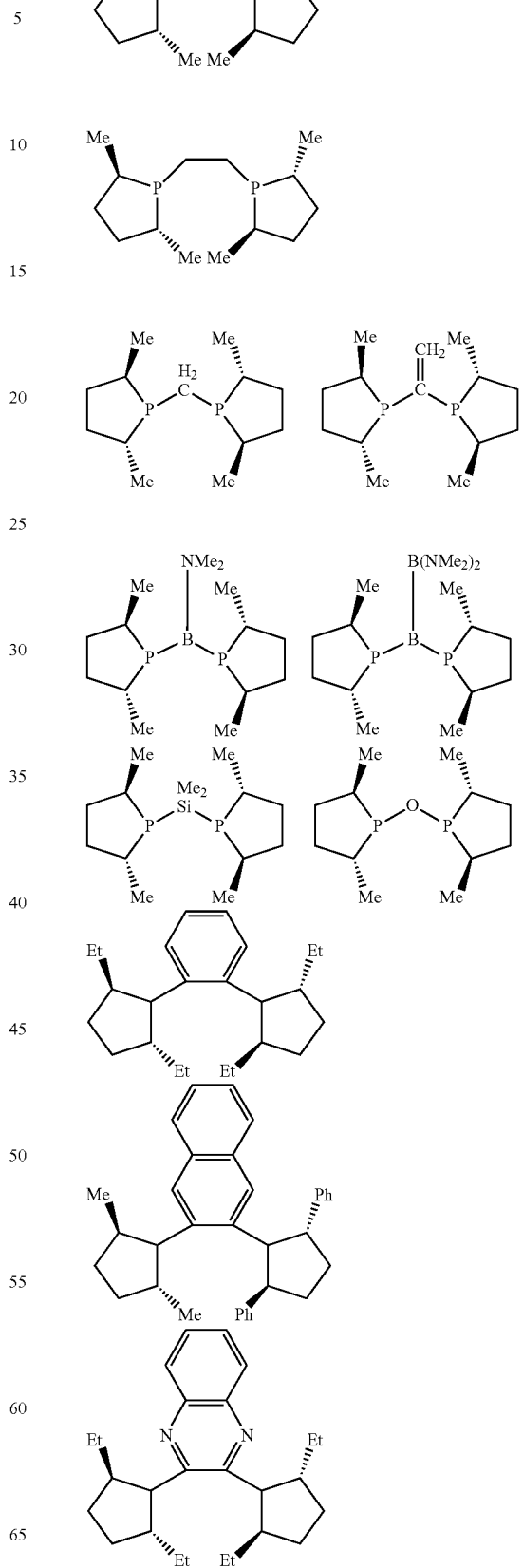

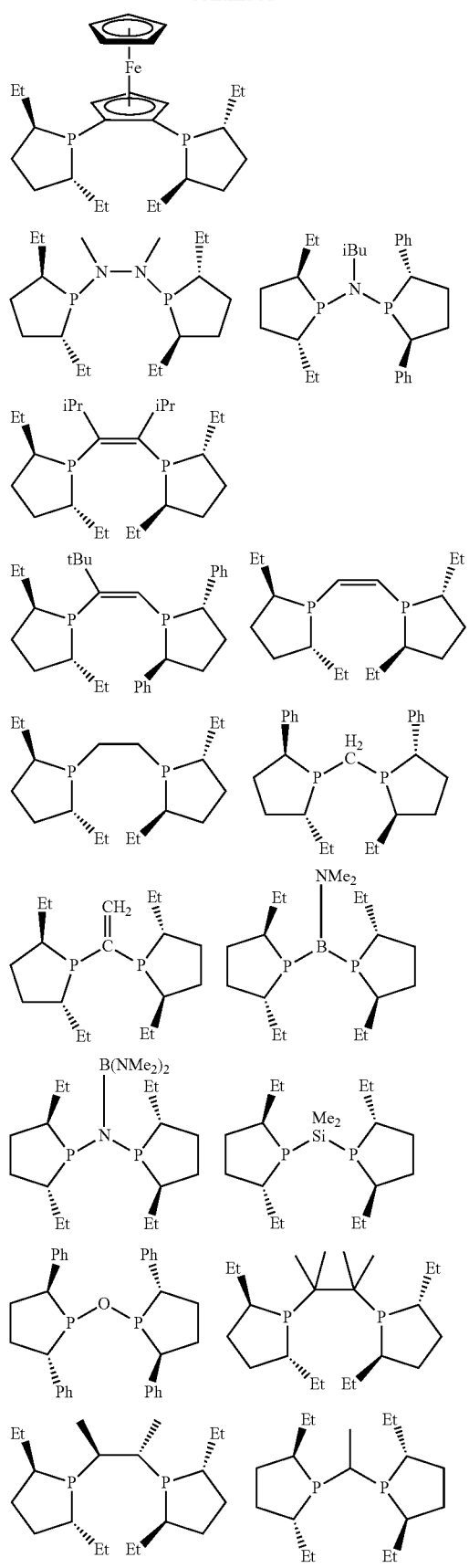
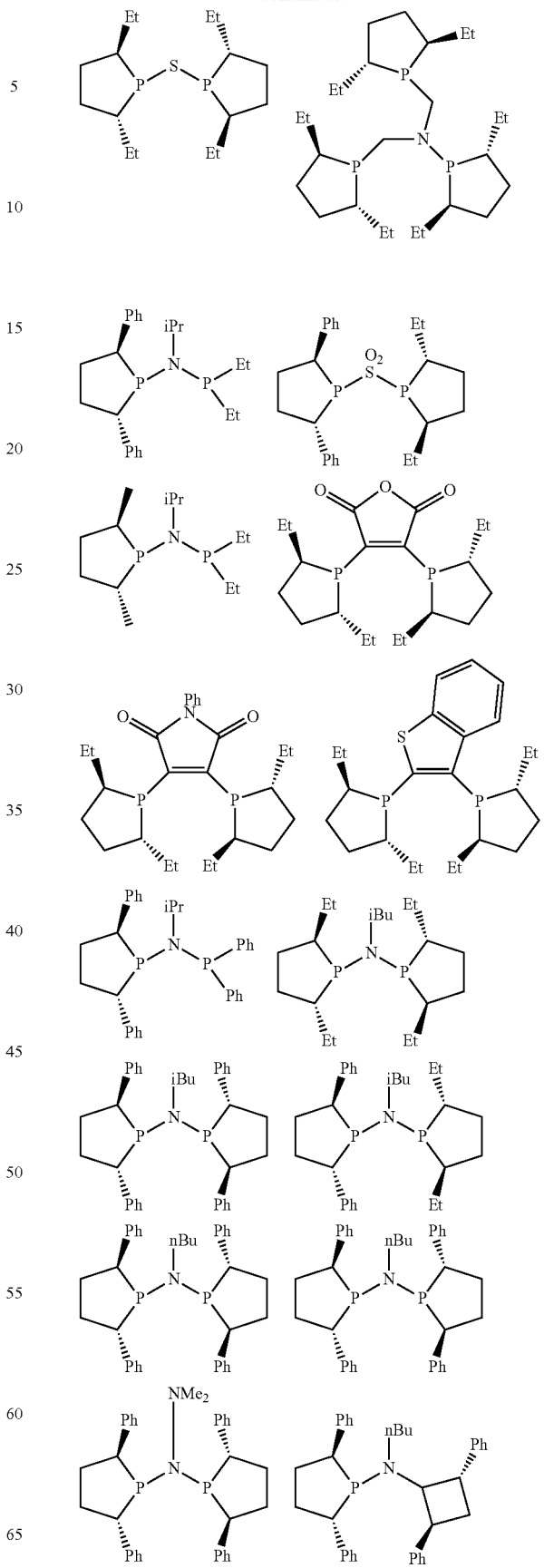

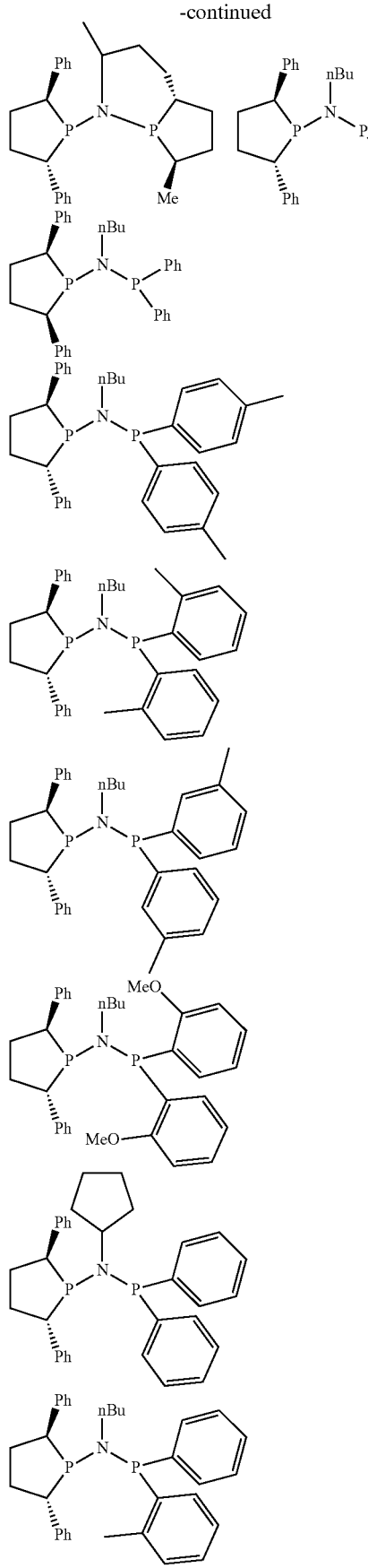
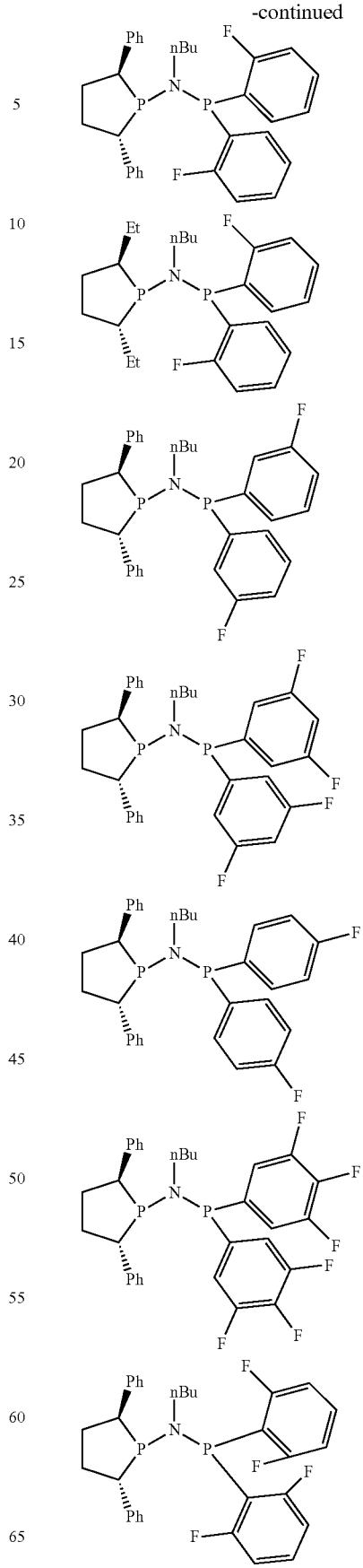

85
-continued
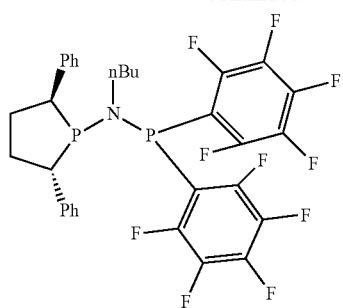
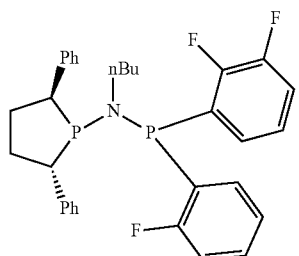
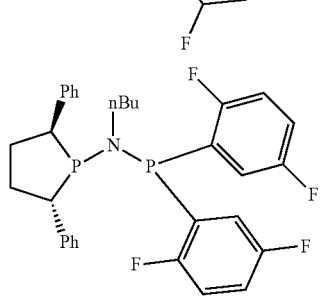
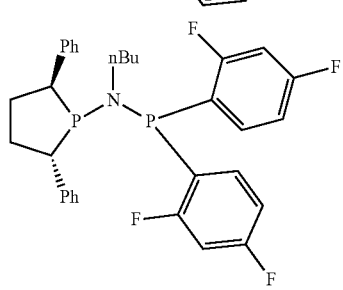
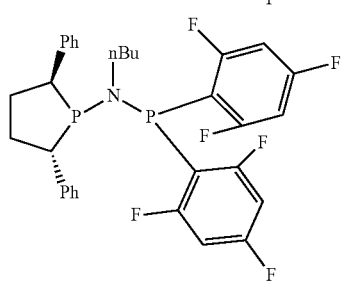
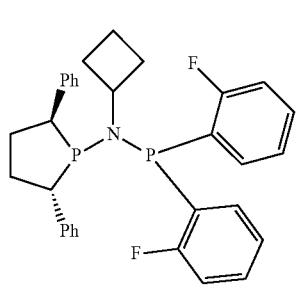
86
-continued
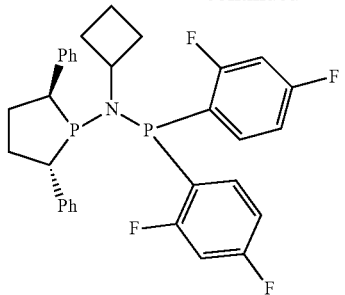
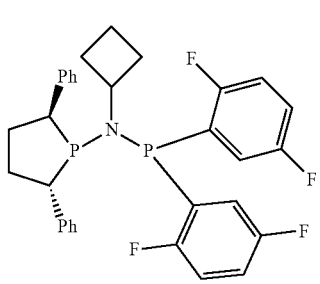
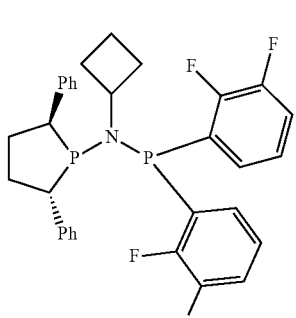
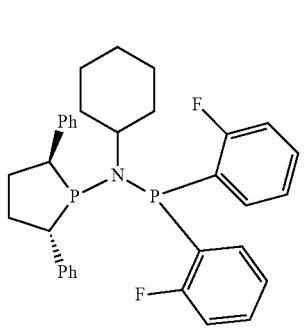
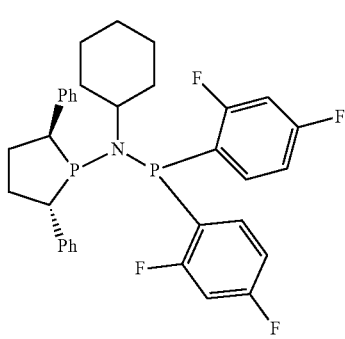

87
-continued
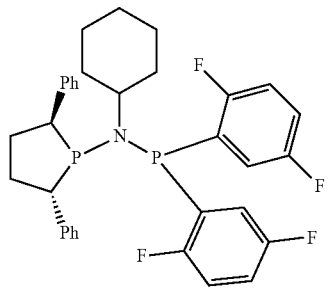
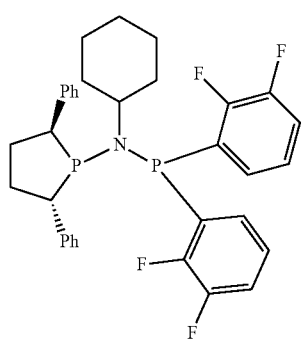
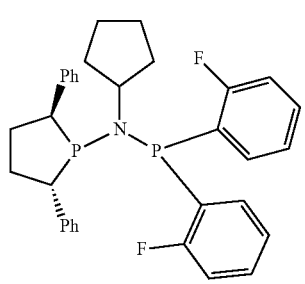
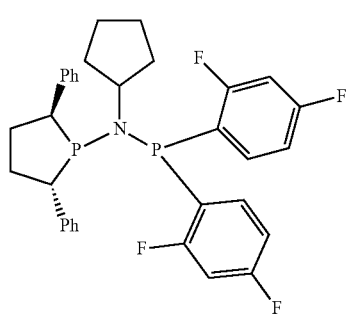
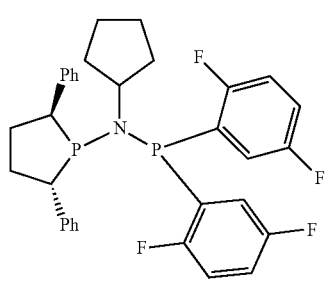
88
-continued
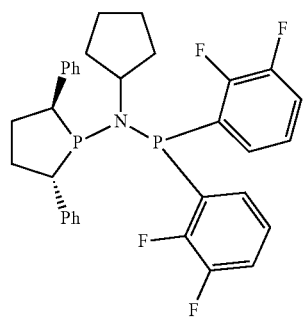
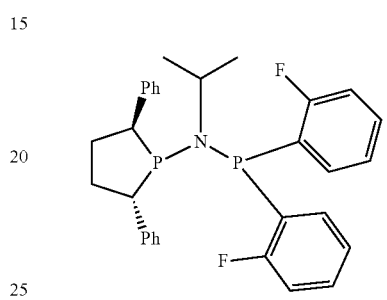
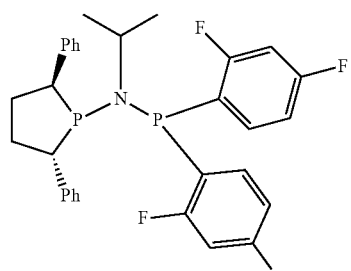
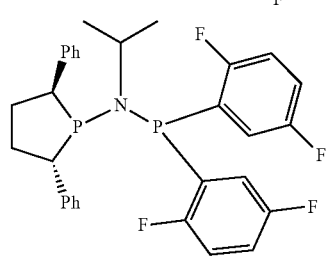
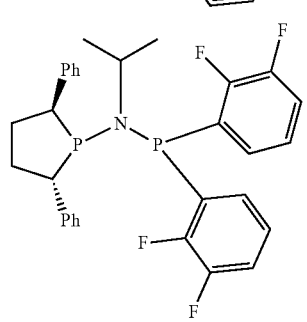
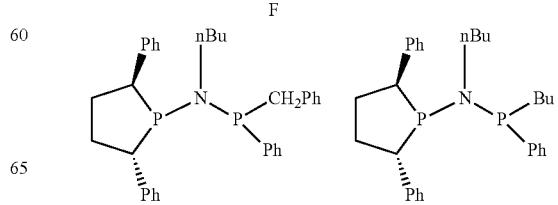

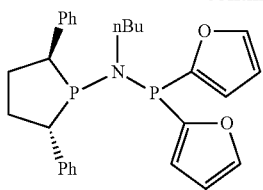
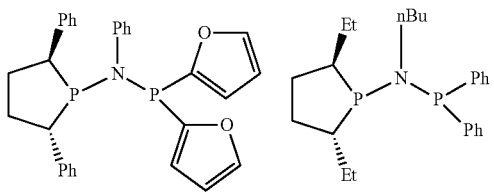
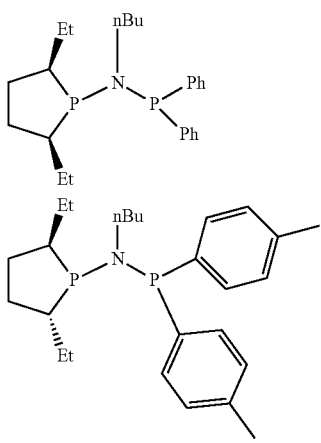
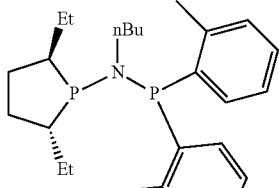
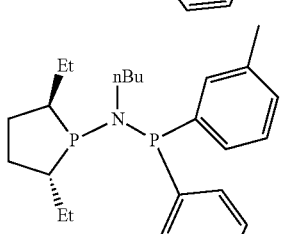
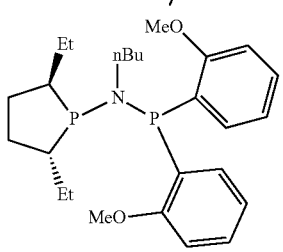
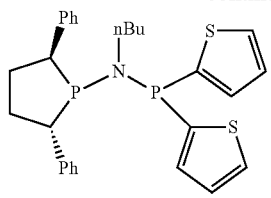
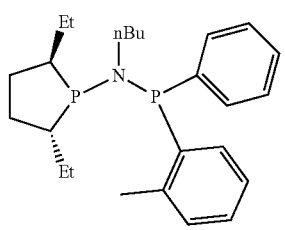
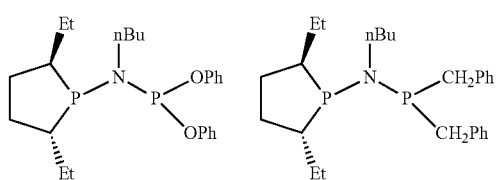
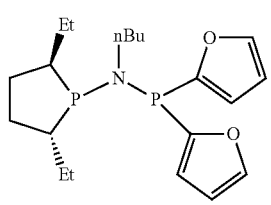
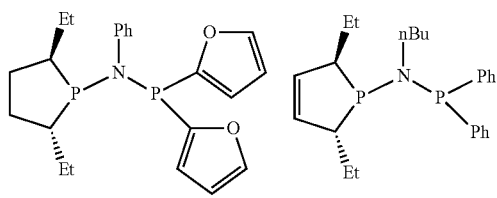
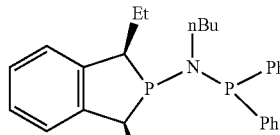
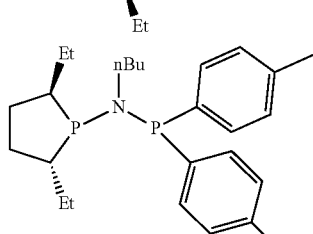
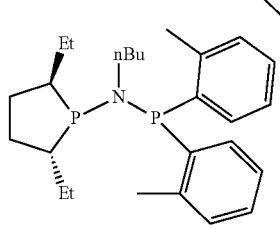

91
-continued
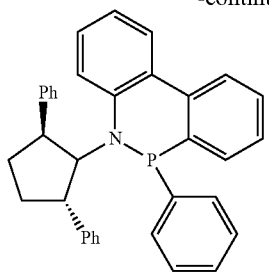
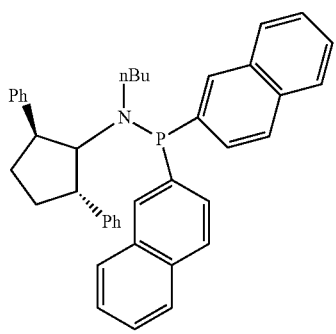
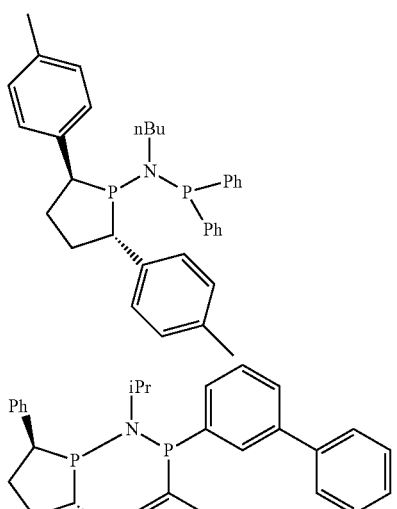
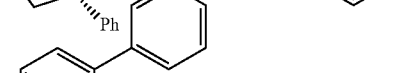
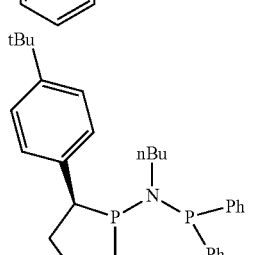
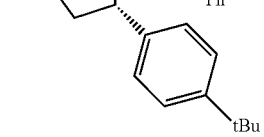
92
-continued
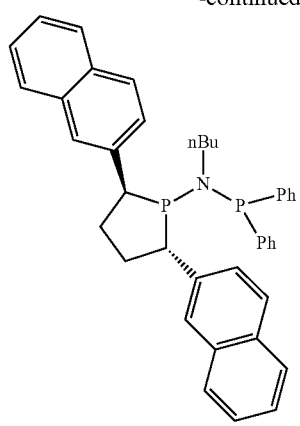
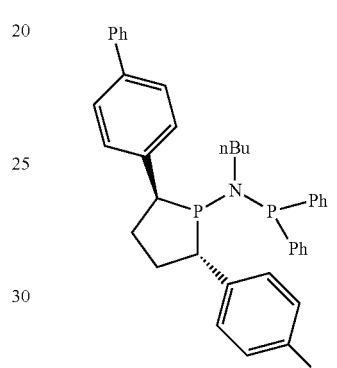
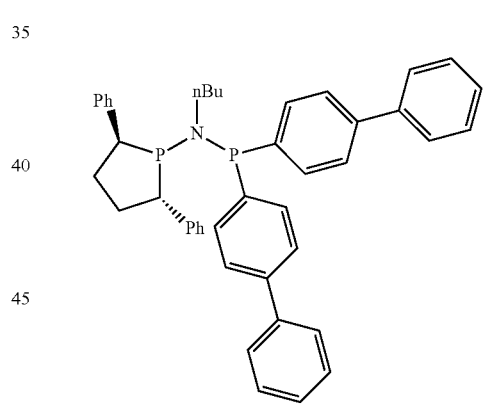
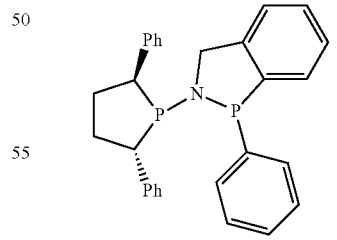
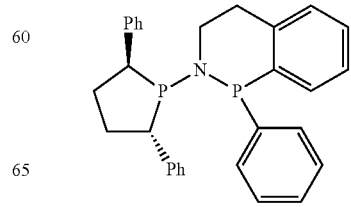

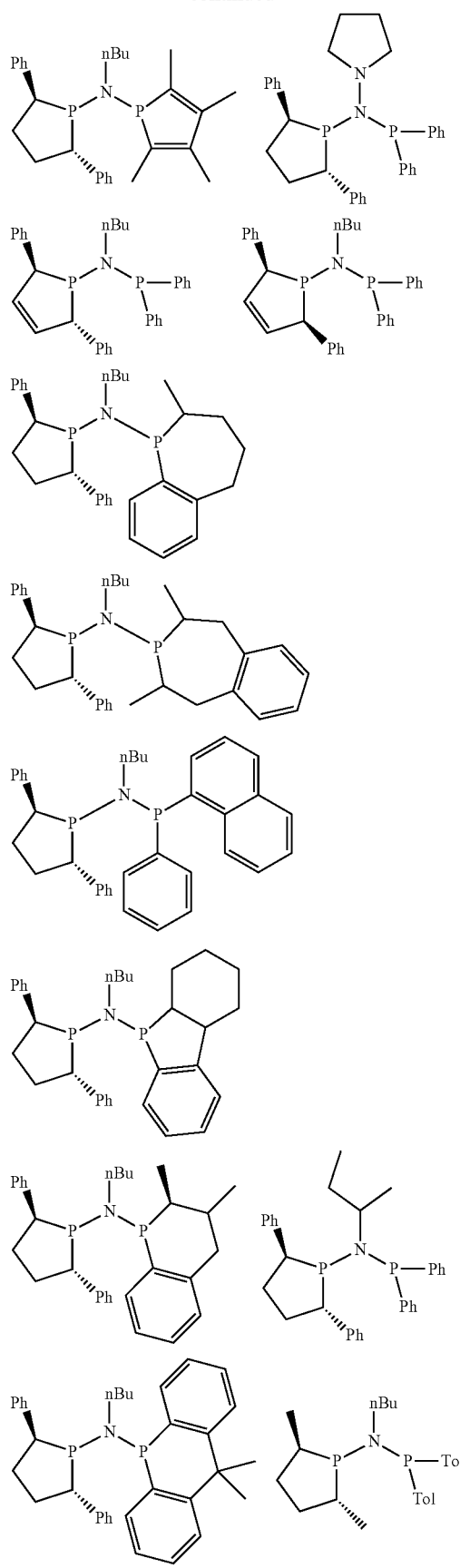
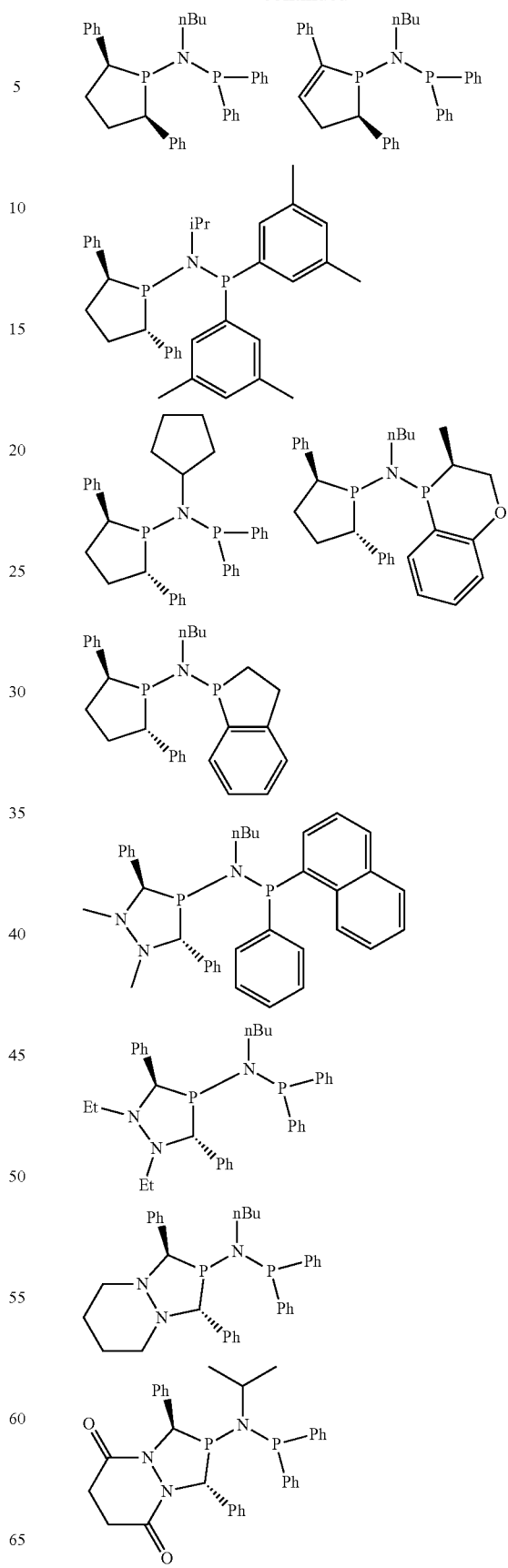

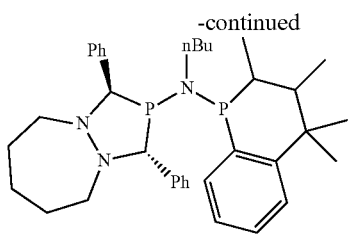
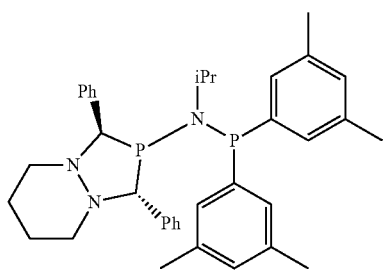
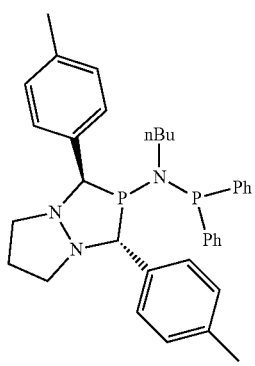
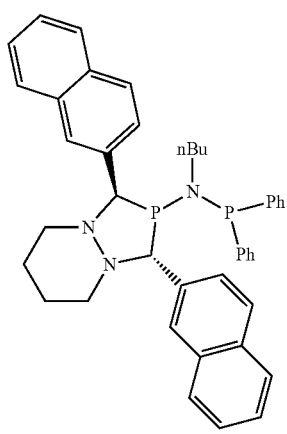
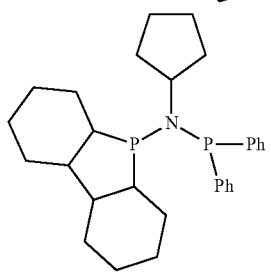
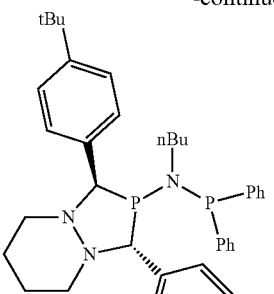
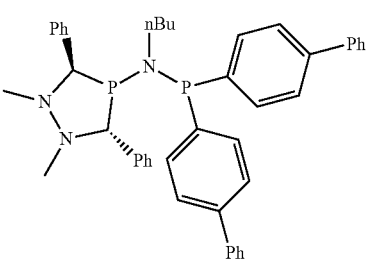
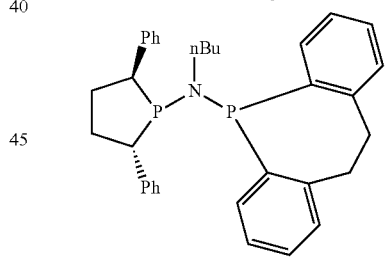
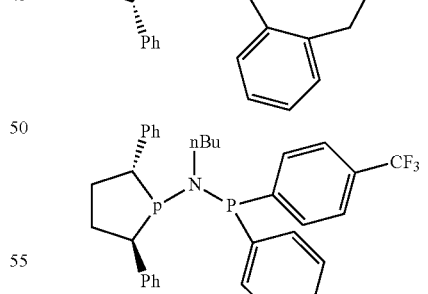
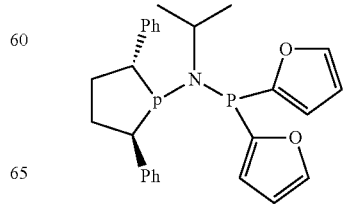

-continued
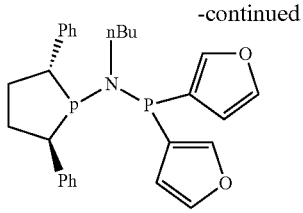
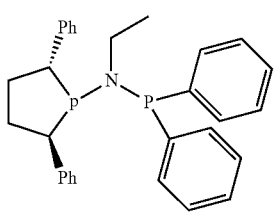
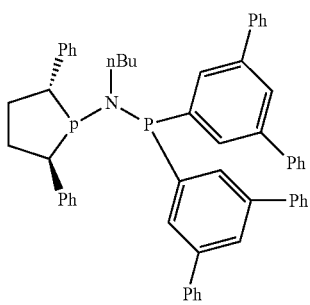
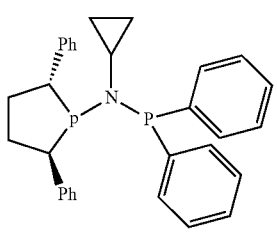
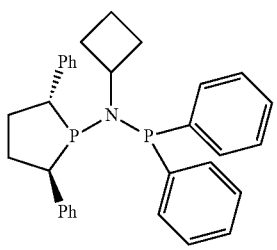
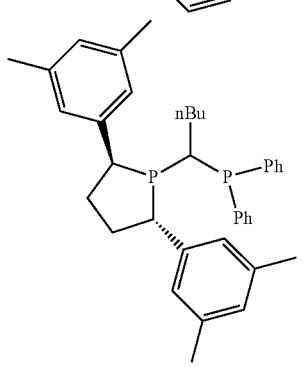
-continued
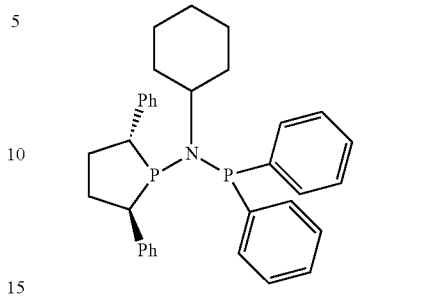
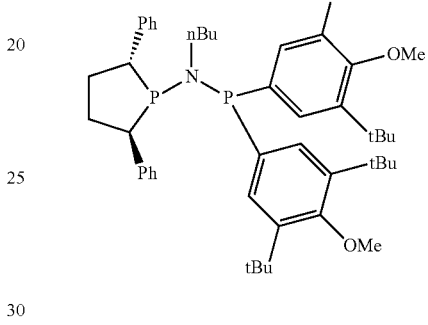
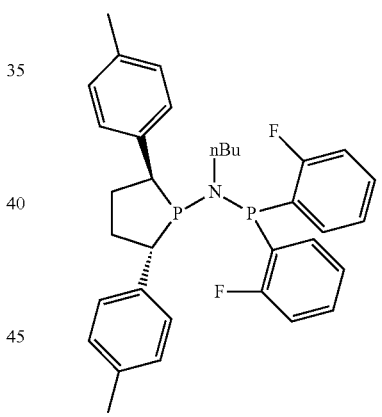
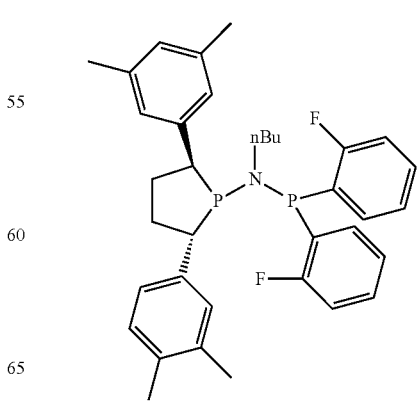

99
-continued
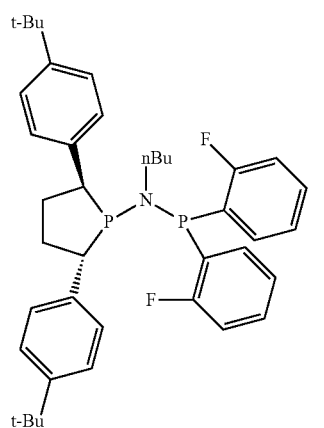
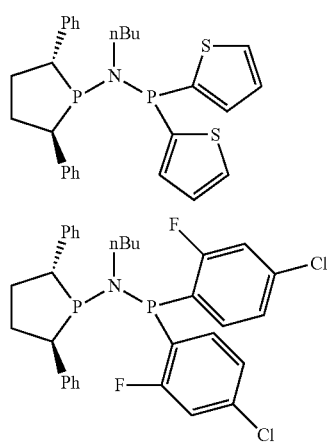
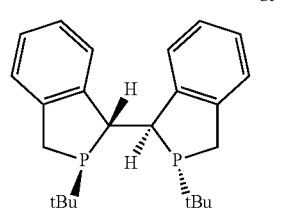
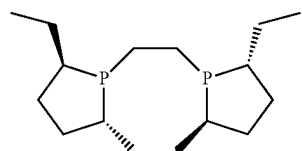
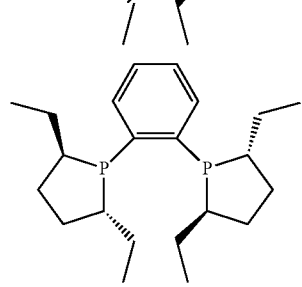
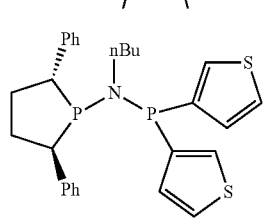
100
-continued
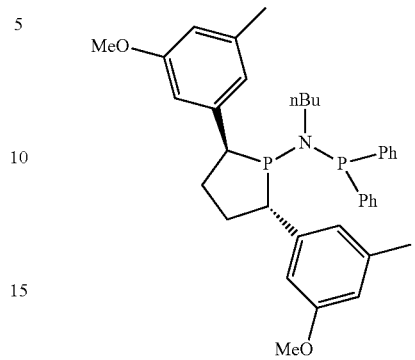
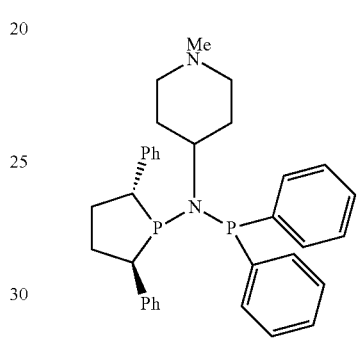
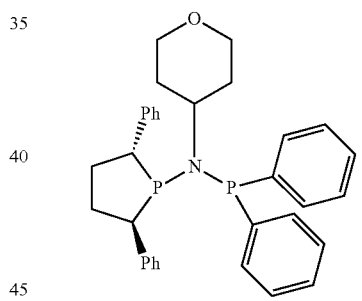
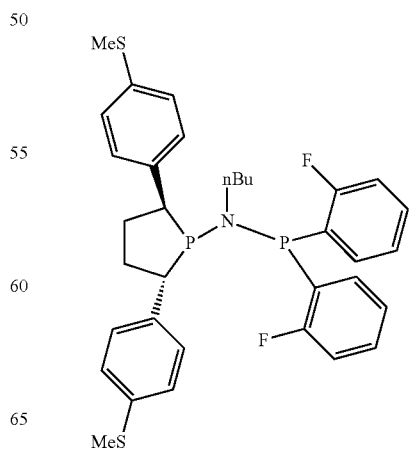

101
-continued
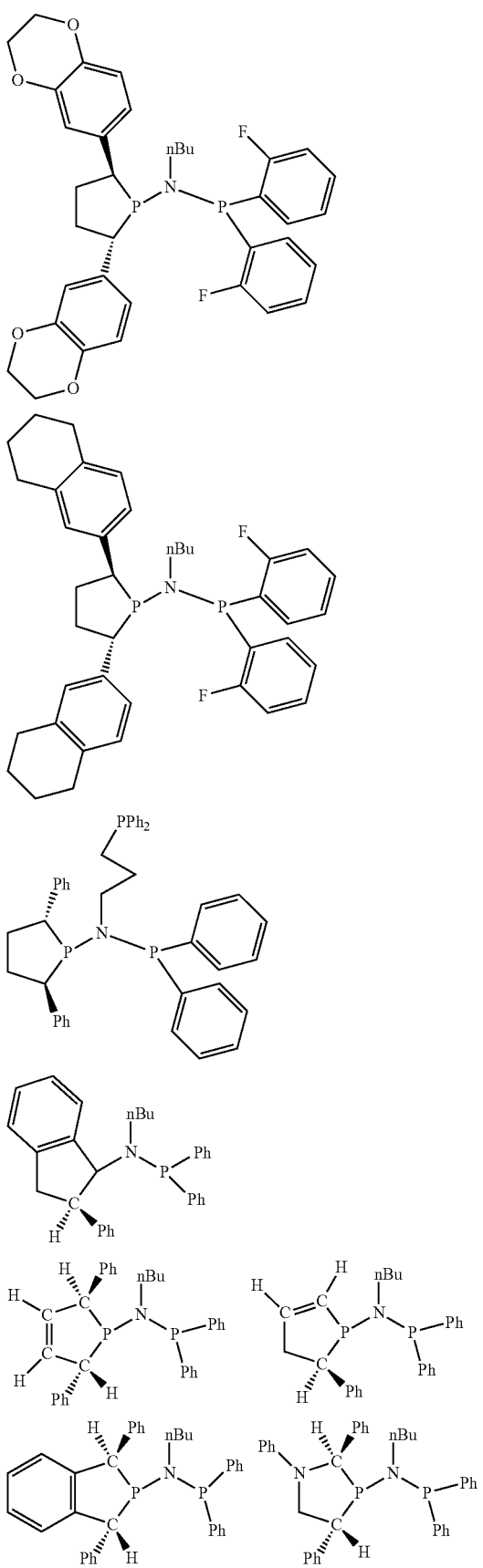
102
-continued
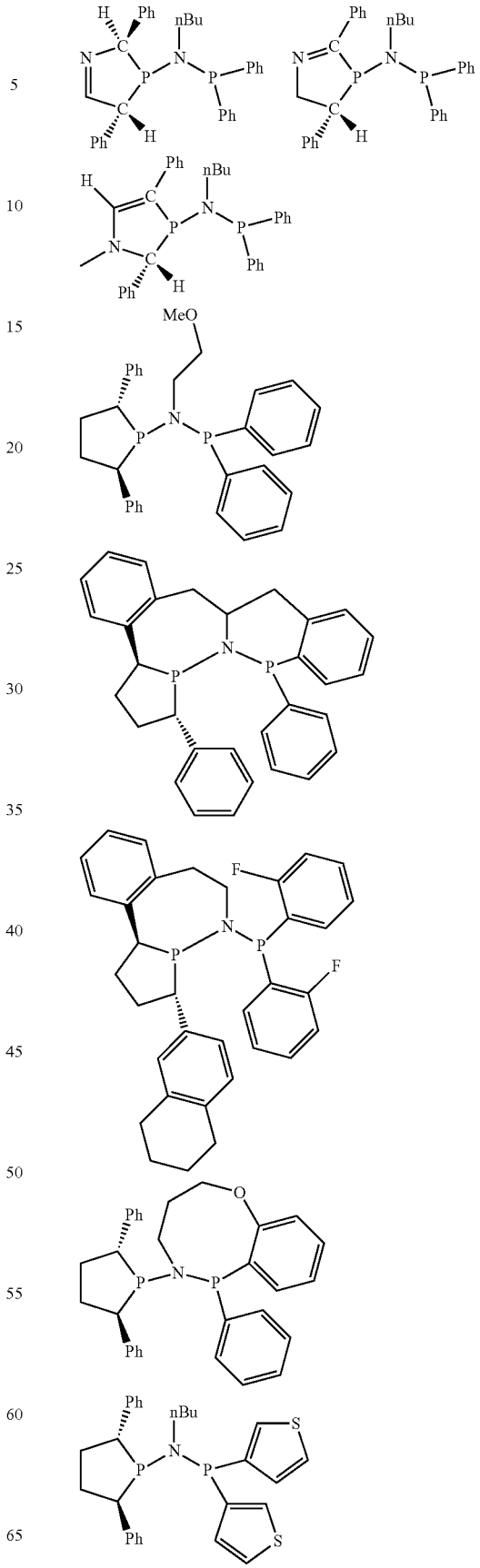

103

-continued

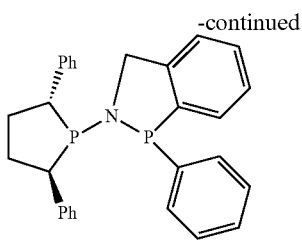

and their enantiomers. Optionally from two to ten, preferably from two to six, independently selected ligating compounds may be linked together via their respective independently selected Ar, Ar', X", Y, $R_1$, $R_2$, $R_3$, $R_4$ or $R_5$ groups to form a poly(ligating compound) species. The poly(ligating compound) species may take the form of dendrimers, oligomers or polymers of the ligating compound. The poly(ligating compound) species may be a linear, branched, or cyclic dendrimer, oligomer or polymer, wherein each monomer unit is an individual independently selected ligating compound. In one embodiment all of the individual ligating compounds are the same as each other. In one embodiment the individual ligating compounds are not all the same as each other.

104

The ligating compounds may be linked to form the poly(ligating compound) species by removing one or more independently selected atoms, preferably one atom, from one or more of the respective independently selected Ar, Ar', X", Y, $R_1$, $R_2$, $R_3$, $R_4$ or $R_5$ groups of each ligating compound to provide one or more free valencies on each ligating compound and then linking the ligating compounds having one or more free valencies to each other at the free valence sites to form the poly(ligating compound). In one embodiment the ligating compounds are linked via their corresponding independently selected Ar, Ar', X", Y, $R_1$, $R_2$, $R_3$, $R_4$ or $R_5$ groups (e.g., $R_1$ from one ligating compound is linked with $R_1$ from another ligating compound or Y from one ligating compound is linked with Y from another ligating compound). In one embodiment the ligating compounds are linked, but not via their corresponding independently selected Ar, Ar', S", Y, $R_1$, $R_2$, $R_3$, $R_4$ or $R_5$ groups (e.g., $R_2$ from one ligating compound is linked with a group from another ligating compound other than $R_2$).

Specific, but non-limiting, examples of the poly(ligating compound) include:

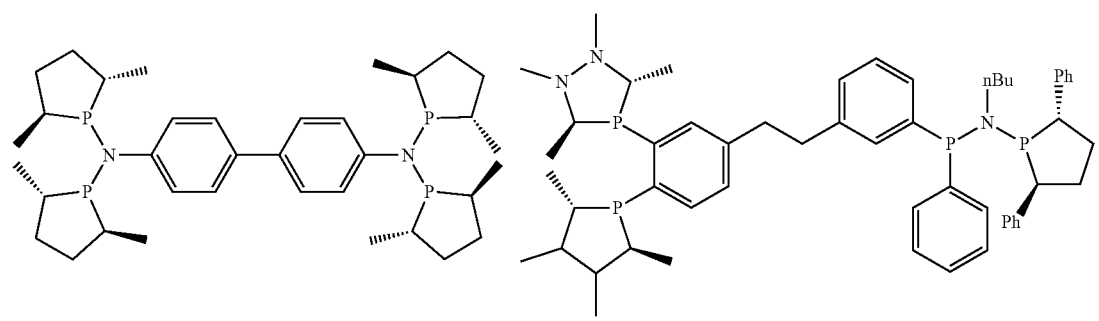

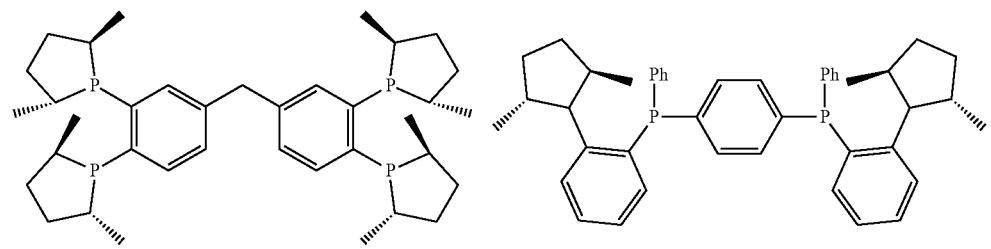

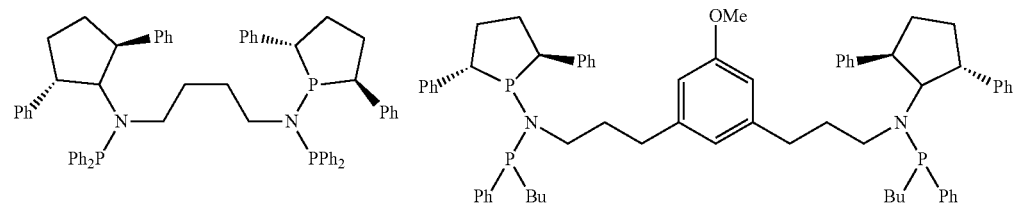

105
-continued
106
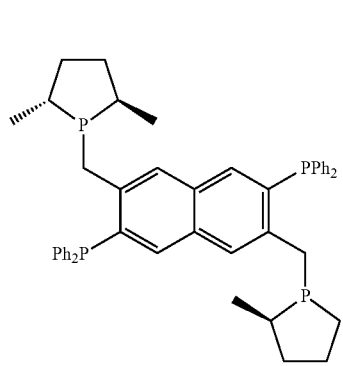
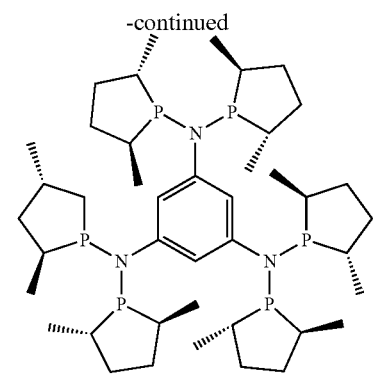
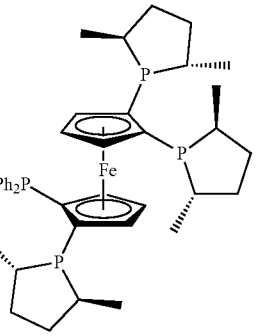
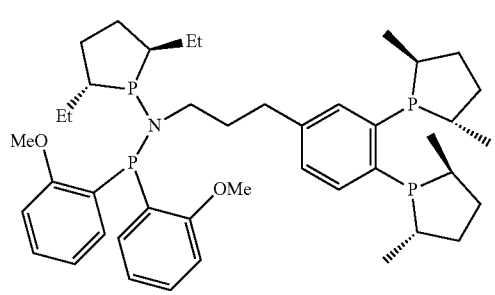
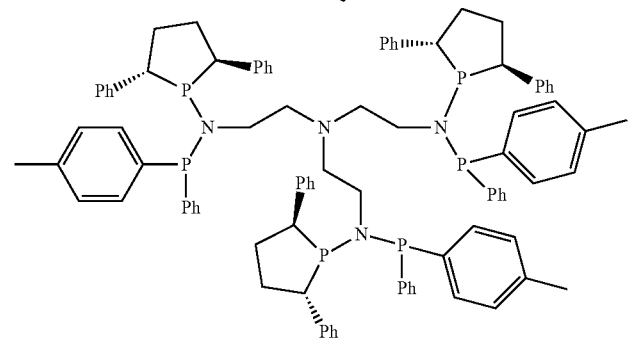
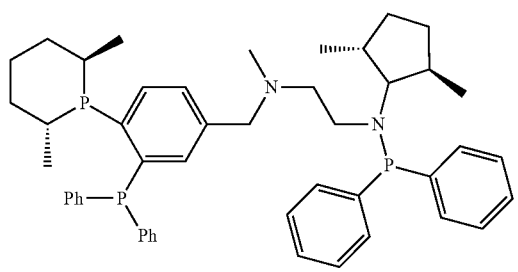
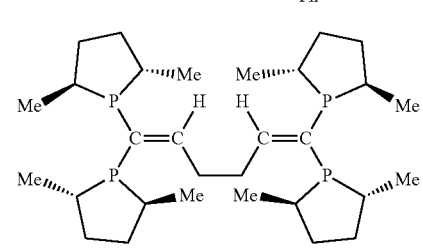
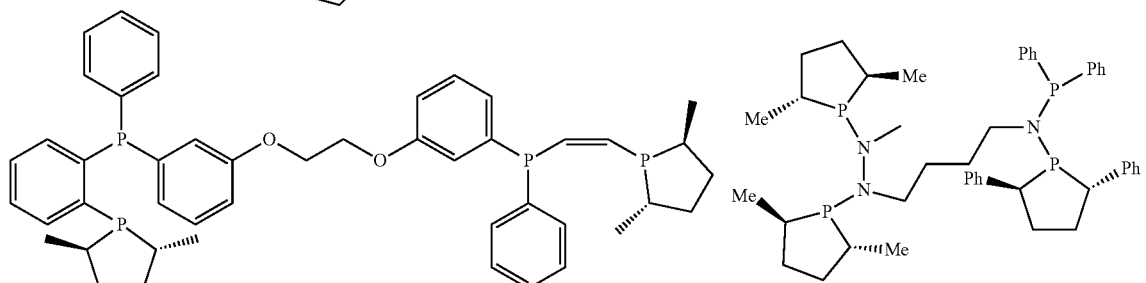
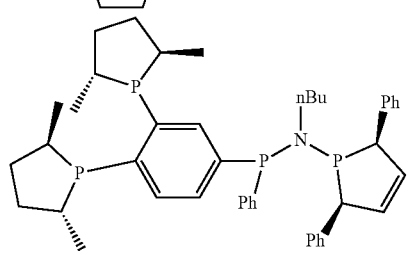
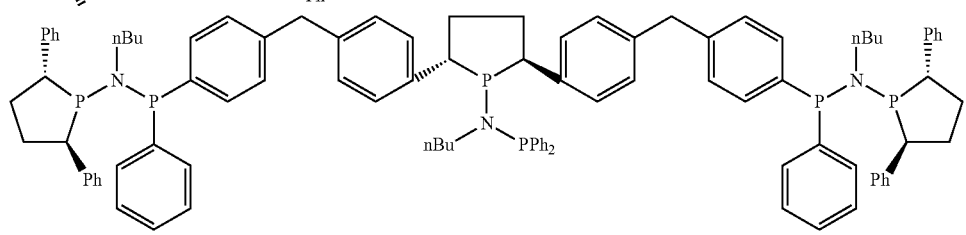

-continued

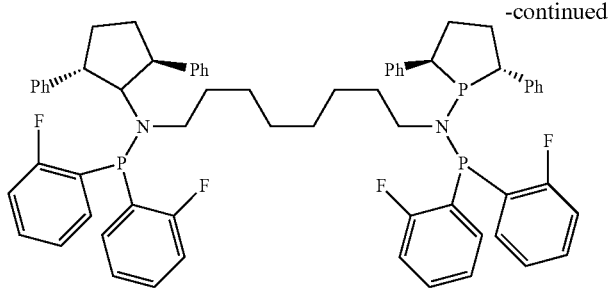

and their enantiomers.

Preparation of the Ligating Compounds

According to an even further aspect of the invention, there is provided a process to prepare a ligating compound, represented as:

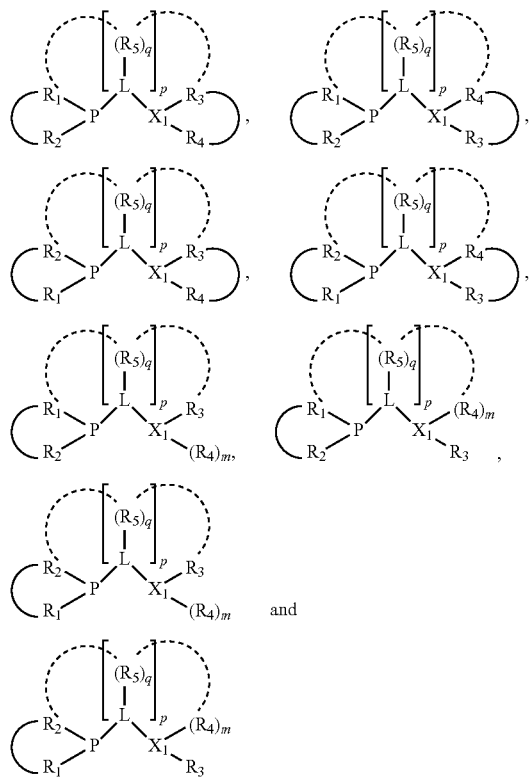

as described above, the steps of the process comprising a) contacting approximately one equivalent of

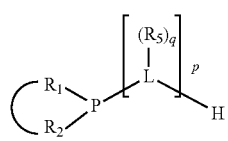

or silyl derivative thereof with approximately one equivalent of a

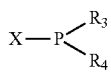

cyclic or acyclic precursor, or b) contacting approximately one equivalent of

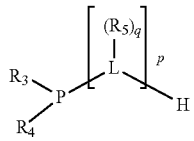

or silyl derivative thereof with approximately one equivalent of a

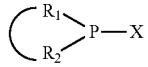

cyclic precursor; optionally in the presence of at least one equivalent of a proton scavenger; X is a leaving group; and optionally isolating the product.

The ligating compounds and subunits and precursor materials thereof, as represented in this section ("Preparation of the ligating compounds") for the sake of brevity without the dashed connections depicting the optional character of the linkages, may be prepared by any one of several methods. In general, the method of preparation is selected based on the nature of the subunits of the ligating compound, that is,

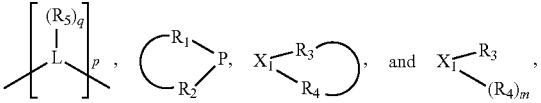

and the availability (commercial or through synthesis) of suitable precursor materials. In general, the preparation may be achieved by contacting a hydrogen-, halide- or other leaving group derivative, or alkali metal-, alkaline earth metal-, or alkaline earth metal-halide derivative of

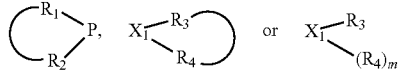

with a suitable hydrogen-, halide- or other leaving group derivative, or alkali metal-, alkaline earth metal-, or alkaline earth metal-halide derivative of

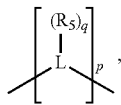

optionally in the presence of a proton scavenger, such as an amine. The halide or other leaving group preferably is chloride, bromide, iodide, sulfate, sulfonate, such as methanesulfonate (mesylate), p-toluenesulfonate (tosylate), or trifluoromethanesulfonate (triflate), or carboxylate, such as acetate or benzoate. The alkali metal preferably is lithium, sodium, or potassium. The alkaline earth metal is magnesium or calcium, preferably magnesium. The alkaline earth metal-halide preferably is magnesiumchloride, magnesiumbromide, or magnesiumiodide.

The

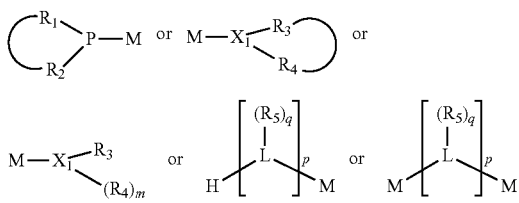

alkali-, alkaline earth, or alkaline earth metal-halide derivatives of

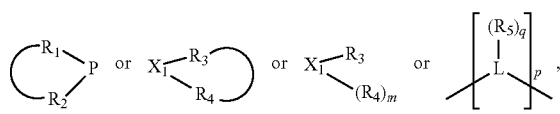

respectively, preferably may be prepared by combining

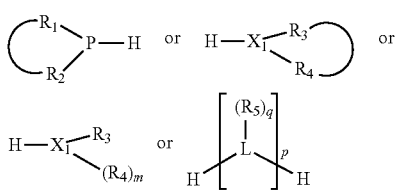

with a strong base comprising M, such as sodium hydride, potassium hydride, methyllithium, butyllithium, potassium t-butoxide, potassium t-amylate, dibutylmagnesium, butyloctylmagnesium, methylmagnesium bromide, ethylmagnesium iodide, or isopropylmagnesium chloride, wherein M is an alkali metal, alkaline earth metal, or alkaline earth metal-halide.

The proton scavenger preferably is a trihydrocarbylamine, such as triethylamine or ethyldiisopropylamine, or an aromatic amine, such as pyridine or lutidine. In the case that

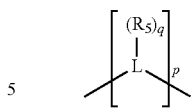

is $R_5N$, and $R_5NH_2$ is used as the hydrogen derivative of

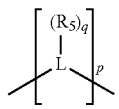

in the process to prepare the ligating compound, the proton scavenger may advantageously be $R_5NH_2$.

In an embodiment, the invention provides a process to prepare the ligating compounds

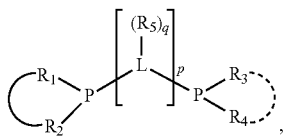

similar to the manner of Nifant'ev et al. ("The synthesis and structure of phosphorus(III)-phosphorylated 2-aminopyridines and their derivatives", Nifant'ev, E. E.; Negrebetskii, V. V.; Gratchev, M. K.; Kurochkina, G. I.; Bekker, A. R.; Vasyanina, L. K.; Sakharov, S. G., *Phosphorus, Sulfur and Silicon and the Related Elements* 1992, 66, 261-71), the steps comprising contacting cyclic or acyclic group precursors such as halide-, sulfonate-, or other leaving group derivatives of

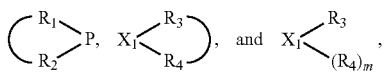

such as

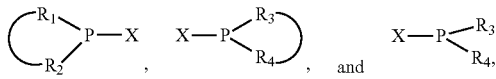

wherein X is a leaving group, preferably chloride, bromide, iodide, mesylate, tosylate, or triflate, more preferably chloride or iodide, even more preferably iodide, and further wherein

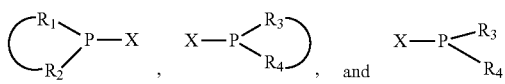

are selected according to the desired ligating compound to be obtained, with

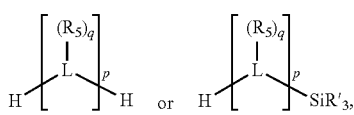

wherein L-H independently is NH, PH, OH, or SH, and R' independently selected is hydrogen, $C_{1-6}$ hydrocarbyl, or halide, preferably in the presence of a proton scavenger. This embodiment allows the preparation of unsymmetrical ligating compounds, wherein

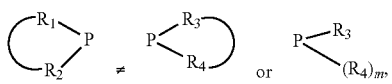

as well as symmetric ligating compounds, wherein

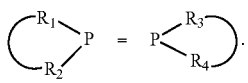

Not desiring to be bound to any particular method, the symmetric ligating compound may be prepared by contacting approximately two equivalents of the

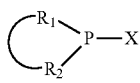

cyclic precursor with approximately one equivalent of

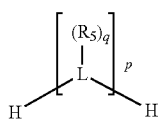

in the presence of preferably at least two equivalents of a proton scavenger.

Not desiring to be bound to any particular method, the unsymmetrical ligating compound, wherein

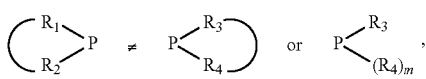

is obtained by first contacting preferably either approximately one equivalent of

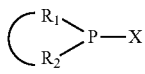

cyclic precursor or one equivalent of

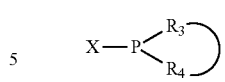

cyclic or

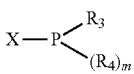

acyclic precursor with preferably approximately one or more equivalents of linking group precursor

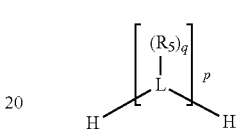

or silyl derivative thereof, represented as

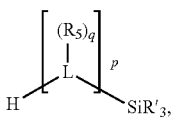

preferably in the presence of at least one equivalent, preferably at least five equivalents, more preferably at least ten equivalents of a proton scavenger in a first reaction to give a first product represented as

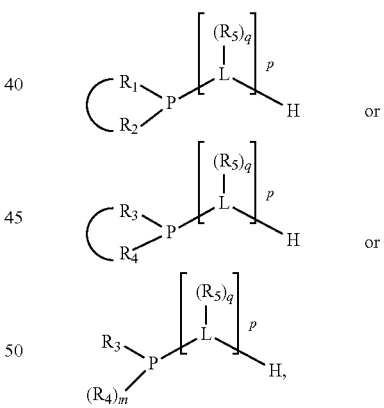

or silyl derivatives thereof, represented as

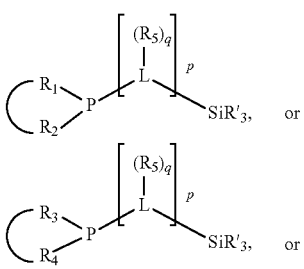

-continued

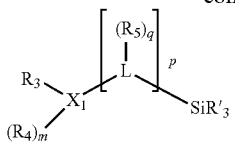

then contacting this first product with preferably approximately one equivalent of the other selected

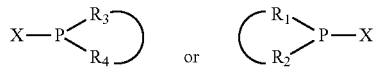

cyclic or

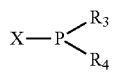

acyclic precursor preferably in the presence of at least one equivalent, more preferably five equivalents, even more preferably ten equivalents of a proton scavenger. Preferably the linking group precursor

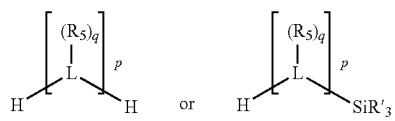

can serve as the proton scavenger in the first reaction to give the first product, wherein at least one additional equivalent, preferably at least additional five equivalents, more preferably at least ten additional equivalents of the linking group precursor are used, optionally in the presence of a proton scavenger, preferably a trihydrocarbylamine or aromatic amine.

In a less preferred (due to the greater statistical possibility of forming symmetric ligating compounds) embodiment for producing the unsymmetrical ligating compounds, the

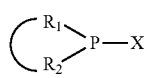

cyclic precursor and the

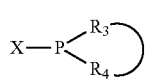

cyclic or

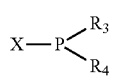

acyclic precursor may be contacted concurrently with

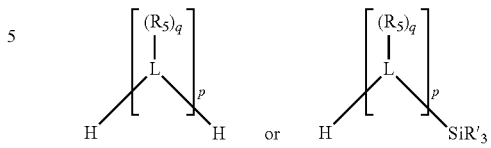

in the presence of preferably at least two equivalents of a proton scavenger.

Preferably the

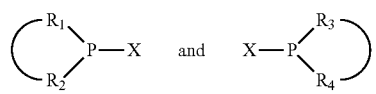

cyclic precursors are represented as

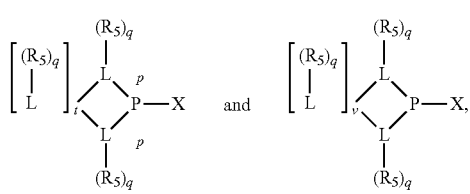

respectively, preferably

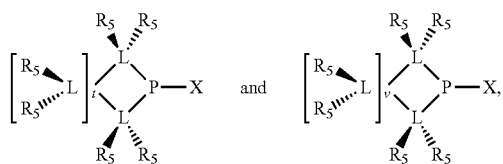

more preferably

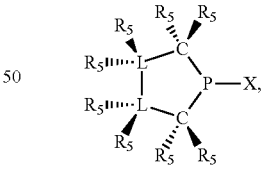

wherein X is a leaving group, preferably halide, more preferably chloride or iodide, still more preferably

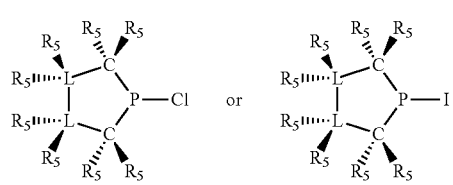

wherein L preferably is nitrogen or carbon, more preferably carbon; the
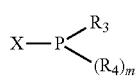
acyclic precursor is represented as
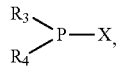
preferably
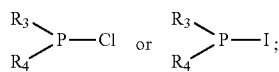
the linking group precursors
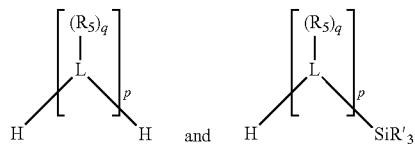
are represented as $R_5NH_2$ and $R_5NH(SiR'_3)$, respectively;
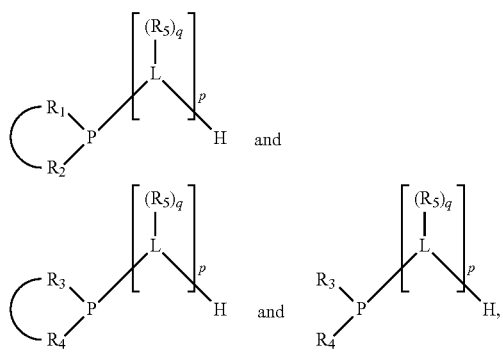
or silyl derivatives thereof, represented as
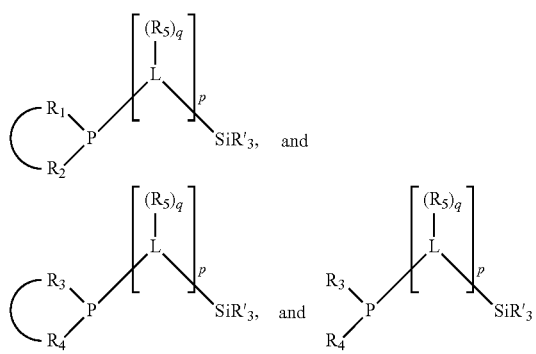
are represented as
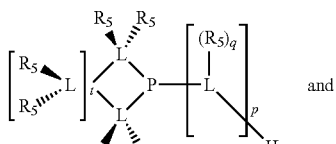
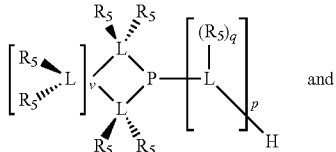
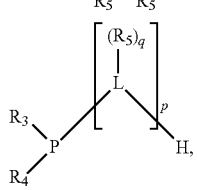
or silyl derivatives thereof, represented as
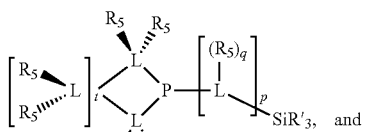
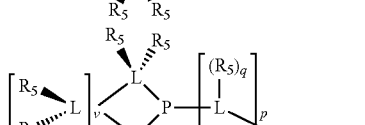
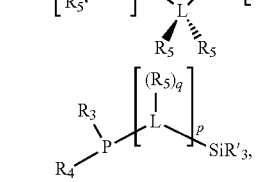
respectively, preferably as
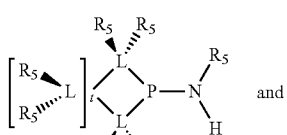
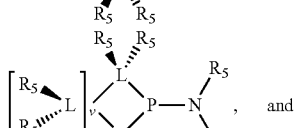 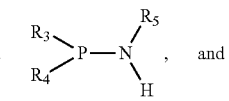
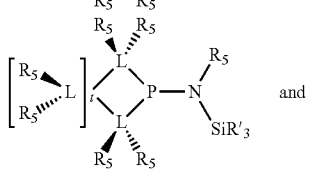

-continued

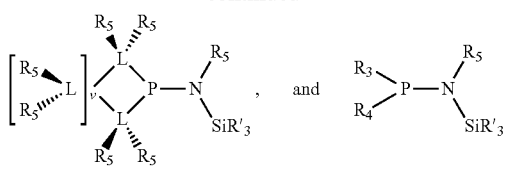

respectively, wherein $R_1$, $R_2$, $R_3$, $R_4$, $R_5$, L, t, p, q, and n are as described above; R' independently is selected is hydrogen, $C_{1-6}$ hydrocarbyl, or halide; more preferably

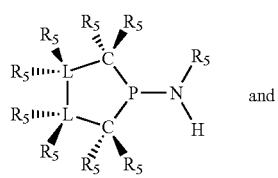

and

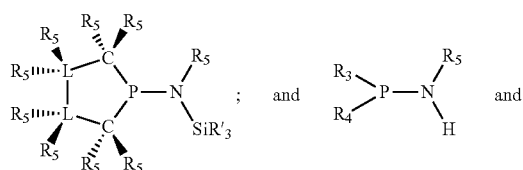

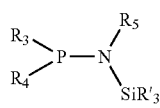

wherein L is nitrogen or carbon, preferably L is carbon, preferably the phosphacycle is a 5-membered phospholane wherein both atoms directly bonded to P are sp³ hybridized and the phospholane is not 8-aza-1-phosphatricylo[3.3.0.0²,⁶]octane, more preferably represented as

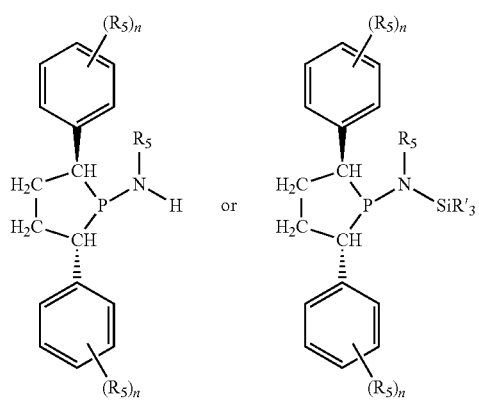

wherein $R_5$, R', and n are as described above.

In an embodiment, the invention provides a process for the preparation of a first product

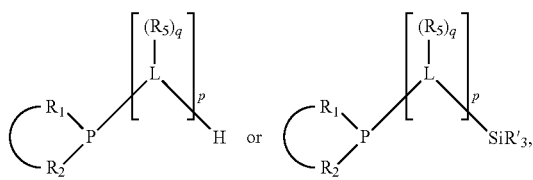

the steps of the process comprising contacting preferably approximately one equivalent of

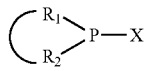

cyclic precursor with preferably approximately one or more equivalents of linking group precursor

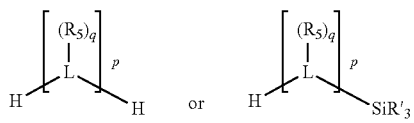

optionally in the presence of at least one equivalent, preferably at least five equivalents, more preferably at least ten equivalents of a proton scavenger, and optionally isolating the product. Preferably the linking group precursor

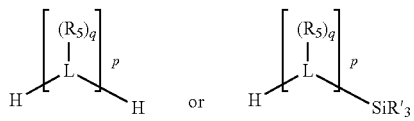

can serve as the proton scavenger in the first reaction to give the first product, wherein at least one additional equivalent, preferably at least additional five equivalents, more preferably at least ten additional equivalents of the linking group precursor are used, optionally in the presence of a proton scavenger, preferably a trihydrocarbylamine or aromatic amine.

Preferably the

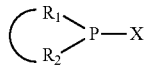

cyclic precursor is represented as

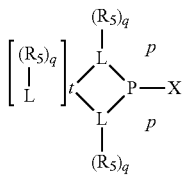

wherein X is a leaving group, preferably
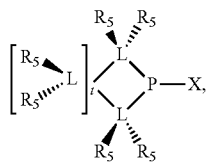
more preferably
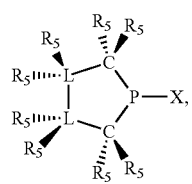
still more preferably
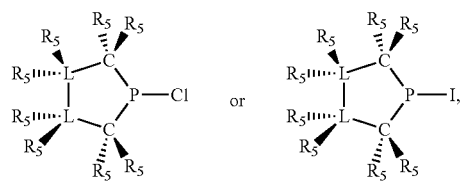
even still more preferably
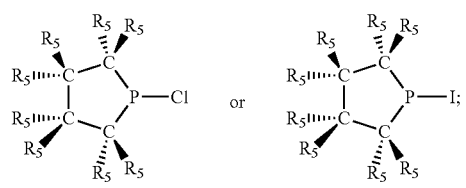
preferably the linking group precursor
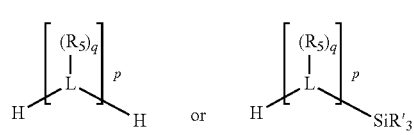
are represented as $R_5NH_2$ or $R_5NH(SiR'_3)$;
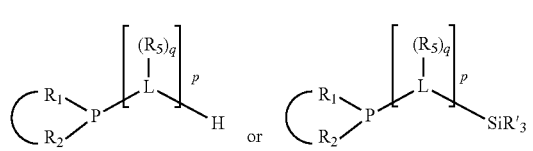
is represented as
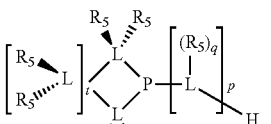
or
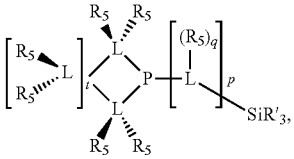
preferably as
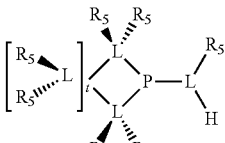
or
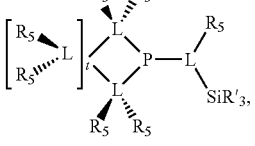
more preferably or
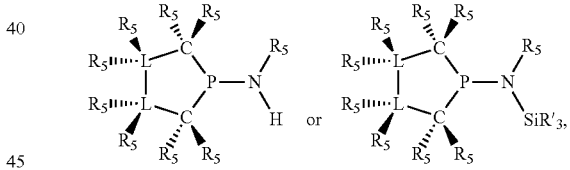
even still more preferably
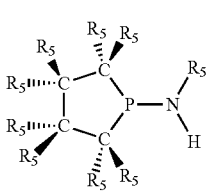
or
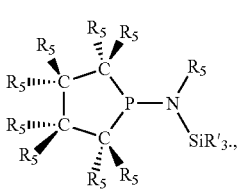

most preferably by

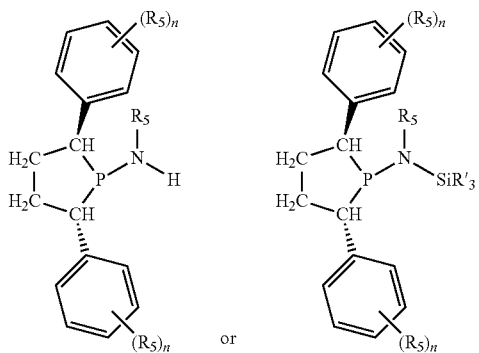

or

In an embodiment, the invention provides a process for the preparation of the ligating compound, the steps of the process comprising contacting preferably approximately one equivalent of

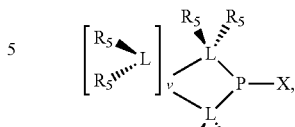

with preferably approximately one equivalent of a

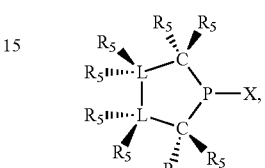

cyclic or acyclic precursor, preferably acyclic precursor, optionally in the presence of at least one equivalent, more preferably five equivalents, even more preferably ten equivalents of a proton scavenger and optionally isolating the product. Preferably the

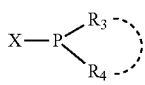

cyclic precursor is represented as

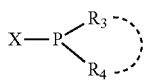

wherein X is a leaving group, preferably

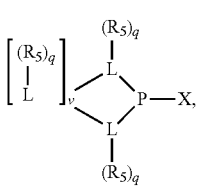

more preferably

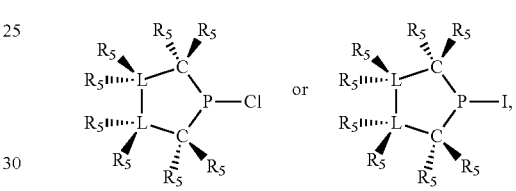

more preferably still more preferably

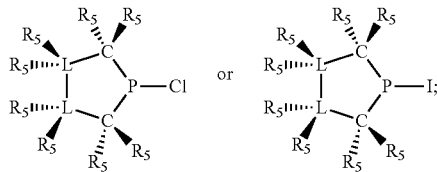

even still more preferably

Preferably the

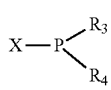

acyclic precursor is represented as

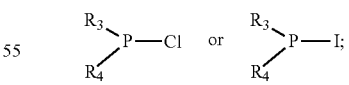

In an embodiment, the invention provides a process for the preparation of a first product

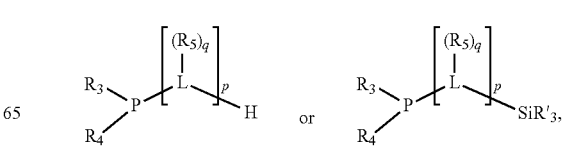

the steps of the process comprising contacting preferably approximately one equivalent of the

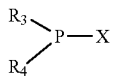

acyclic precursor with preferably approximately one or more equivalents of linking group precursor

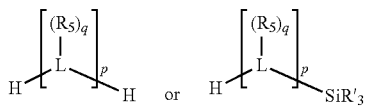

optionally in the presence of at least one equivalent, preferably at least five equivalents, more preferably at least ten equivalents of a proton scavenger, and optionally isolating the product. Preferably the linking group precursor

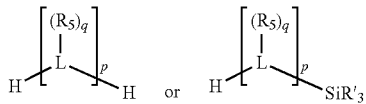

can serve as the proton scavenger in the first reaction to give the first product, wherein at least one additional equivalent, preferably at least additional five equivalents, more preferably at least ten additional equivalents of the linking group precursor are used, optionally in the presence of a proton scavenger, preferably a trihydrocarbylamine or aromatic amine.

Preferably the

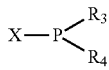

acyclic precursor is represented as

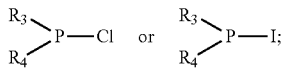

preferably the linking group precursor

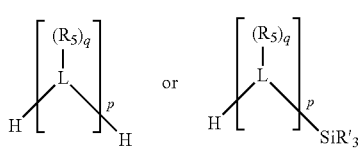

is represented as $R_5NH_2$ or $R_5NH(SiR'_3)$; preferably

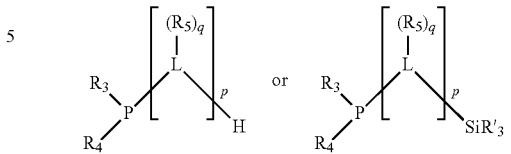

is represented as

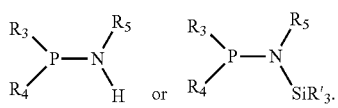

In an embodiment, the invention provides a process for the preparation of the ligating compound, the steps of the process comprising contacting preferably approximately one equivalent of a

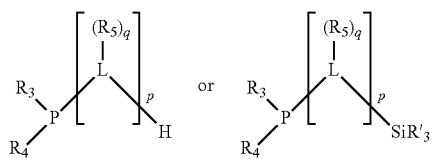

with preferably approximately one equivalent of a

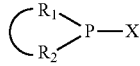

cyclic precursor wherein X is a leaving group, optionally in the presence of at least one equivalent, more preferably five equivalents, even more preferably ten equivalents of a proton scavenger and optionally isolating the product. Preferably the cyclic precursor is represented as

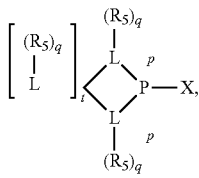

preferably

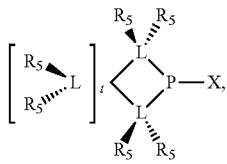

more preferably

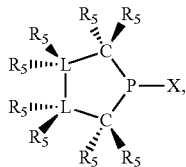

still more preferably

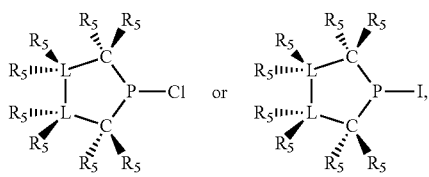

even still more preferably

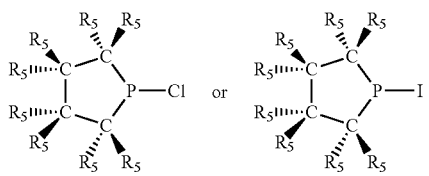

In a non-limiting specific example, 1-chloro-2,5-diphenylphospholane is contacted with isopropylamine in the presence of triethylamine to give the symmetric product N-isopropyl-[bis(2,5-diphenylphospholane)amine].

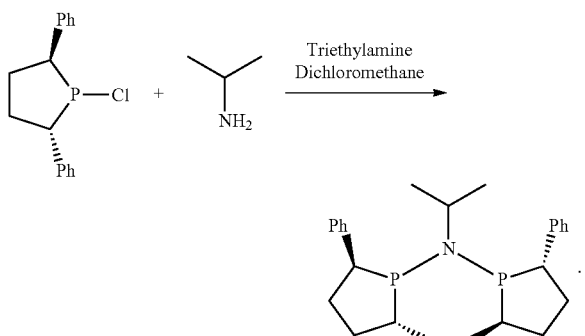

In a non-limiting specific example, 1-chloro-2,5-diphenylphospholane is contacted with ten equivalents of n-butylamine to give N-butyl-(2,5-diphenylphospholane)amine as a first product, which is contacted with chlorodiphenylphosphine in the presence of triethylamine to give N-butyl-(2,5-diphenylphospholane)(diphenylphosphino)amine.

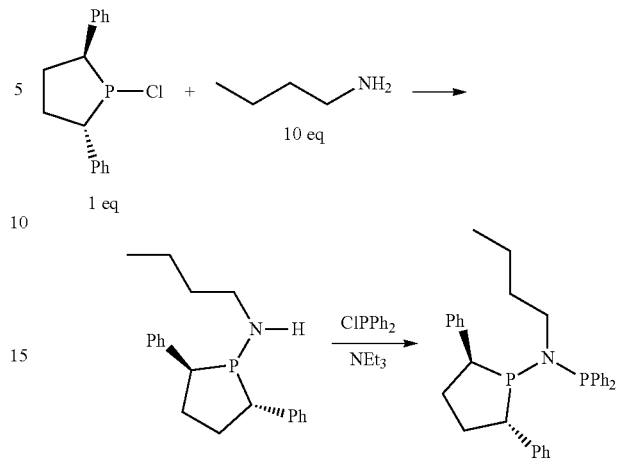

In one embodiment of the process to prepare the ligating compounds, 5-membered-ring analogs of the intermediate

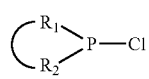

cyclic precursor, represented as

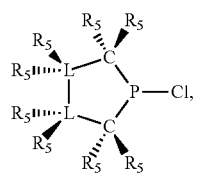

may be prepared in an overall 7-step process as disclosed in a specific example by combining Fox et al. ("Bis-(2,5-diphenylphospholanes) with sp² Carbon Linkers: Synthesis and Application in Asymmetric Hydrogenation", Fox, M. E.; Jackson, M.; Lennon, I. C.; Klosin, J.; Abboud, K. A. *J. Org. Chem.* 2008, 73, 775-784.) and Guillen et al. ("Synthesis and first applications of a new family of chiral monophosphine ligand: 2,5-diphenylphospholanes", Guillen, F.; Rivard, M.; Toffano, M.; Legros, J.-Y.; Daran, J.-C.; Fiaud, J.-C. *Tetrahedron* 2002, 58, 5895-5904) wherein 1,4-diphenylbutadiene is cyclized with Cl₂PNMe₂ to give a first product which is hydrogenated to give N,N-dimethyl-2,5-diphenyl-1-phospholanamine-1-oxide as a second product, the second product is isomerized to give a third product as an approximately racemic mixture of R,R and S,S products. It requires four steps (hydrolysis, Step 4; chlorination, Step 5; reduction, Step 6; and chlorination, Step 7) to convert the third product into the seventh product, the cyclic phosphine chloride:

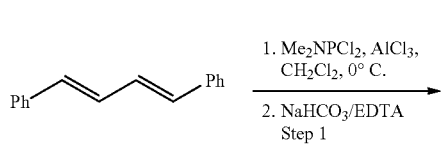

127
-continued

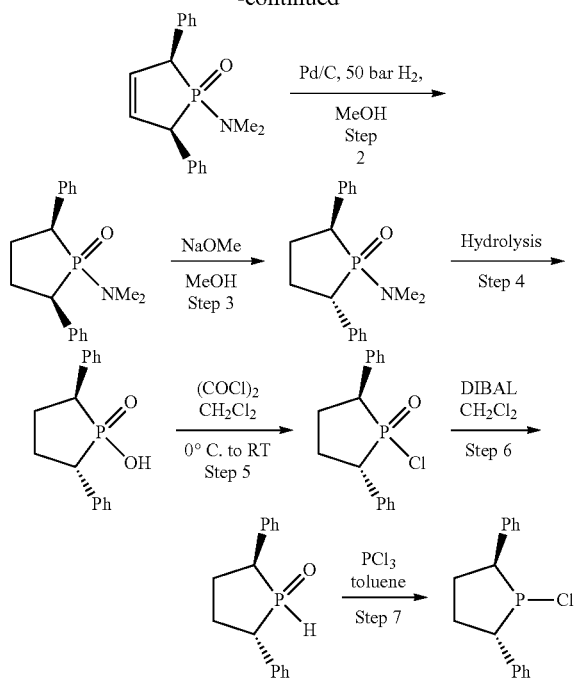

In an embodiment, the invention provides an improved process to prepare the cyclic phosphine halide represented as

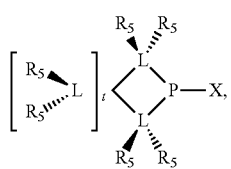

the steps of the process comprising contacting a cyclic phosphinic amide represented as

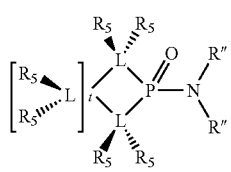

with at least one hydrido-silicon compound represented as R'$_3$SiH and at least one silicon halide compound represented as R'$_3$SiX in the presence of one or more bases, and optionally isolating the product. The improved process provides the cyclic phosphine halide from the cyclic phosphinic amide in one chemical step, as represented below:

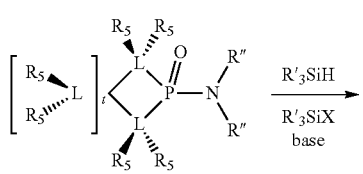

128
-continued

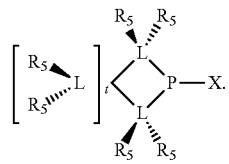

The intermediate cyclic phosphinic amide precursor (obtainable for 5-membered cyclic phosphinic amides according to Guillen et al. from the corresponding 1,3-butadiene compound

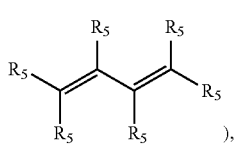

is represented as:

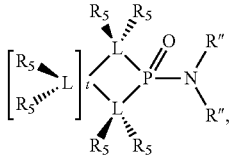

preferably

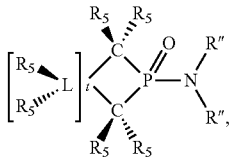

more preferably

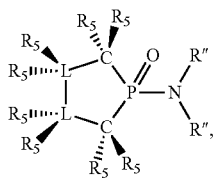

even more preferably

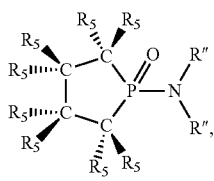

wherein R$_5$=hydrogen, aryl, substituted aryl, arylalkyl, or substituted arylalkyl, preferably hydrogen, aryl, or substituted aryl, more preferably at least two R$_5$ are aryl or substituted aryl and at least two $R_5$ are hydrogen; and R"=alkyl, preferably $C_{1-6}$ alkyl, more preferably methyl or ethyl; still more preferably

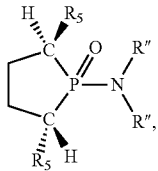

even more preferably

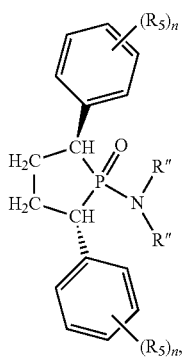

wherein $R_5$=aryl, substituted aryl, arylalkyl, or substituted arylalkyl, preferably aryl or substituted aryl; and R" is methyl or ethyl, even more preferably

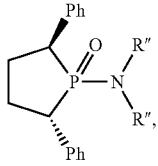

even still more preferably

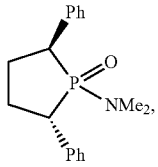 [SMILES: CN(C)P1(=O)[C@H](c2ccccc2)CC[C@H]1c1ccccc1]

corresponding to the product of Step 3 of the state-of-the-art process above; the cyclic phosphine halide, preferably chloride, is represented as

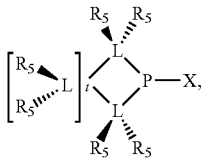

preferably

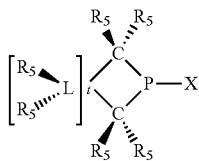

more preferably

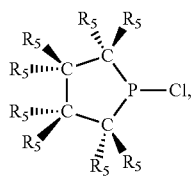

wherein X is halide, preferably chloride, bromide or iodide, more preferably chloride or bromide, even more preferably chloride; R' independently selected is hydrogen, $C_{1-6}$ hydrocarbyl, or halide; $R_5$ independently is hydrogen, $C_{1-20}$ aryl, $C_{1-20}$ substituted aryl, $C_{1-20}$ arylalkyl, or $C_{1-20}$ substituted arylalkyl, preferably hydrogen, $C_{1-12}$ aryl, $C_{1-12}$ substituted aryl, $C_{1-12}$ arylalkyl, or $C_{1-12}$ substituted arylalkyl, more preferably $C_{1-12}$ aryl, or $C_{1-12}$ substituted aryl, more preferably at least two $R_5$ are $C_{1-12}$ aryl or $C_{1-12}$ substituted aryl and at least two $R_5$ are hydrogen, still more preferably

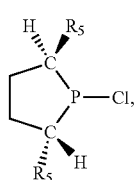

wherein $R_5$=$C_{1-12}$ aryl, $C_{1-12}$ substituted aryl, $C_{1-12}$ arylalkyl, or substituted $C_{1-12}$ arylalkyl, preferably $C_{1-12}$ aryl or $C_{1-12}$ substituted aryl, even more preferably

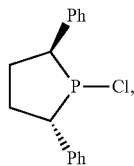

corresponding to the product of Step 7 of the state-of-the-art process above; the at least one hydrido-silicon compound is represented as $R'_3SiH$ and the at least one silicon halide compound is represented as $R'_3SiX$, wherein L, $R_5$, and t are as described above; R" independently selected is hydrogen; $C_{1-20}$, preferably $C_{1-12}$, more preferably $C_{1-6}$, hydrocarbon derivative, preferably R" is $C_{1-20}$, preferably $C_{1-12}$, more preferably $C_{1-6}$, hydrocarbyl, more preferably $C_{1-12}$, more preferably $C_{1-6}$, alkyl or $C_{2-20}$, more preferably $C_{2-12}$ aryl or arylalkyl, still more preferably methyl, ethyl, propyl, isopropyl, butyl, phenyl, preferably methyl, ethyl, isopropyl; R' independently selected is hydrogen, $C_{1-20}$, preferably $C_{1-12}$, more preferably $C_{1-6}$, hydrocarbyl, $C_{1-20}$, preferably $C_{1-12}$, more preferably $C_{1-6}$, heterohydrocarbyl or halide, e.g., chloride, bromide, iodide, preferably chloride or bromide, more preferably chloride; more preferably R' is hydrogen, methyl, ethyl, propyl, butyl, allyl, vinyl, t-butyl, phenyl, tolyl, chloride, bromide, iodide, dimethylamido (($CH_3$)$_2$N), diethylamido (($CH_3CH_2$)$_2$N), methoxy, ethoxy, propoxy, phenoxy, more preferably hydrogen, chloride, methyl, ethyl, phenyl; X is chloride, bromide, iodide, preferably chloride; each base of the one or more bases is independently a hydrocarbylamine, preferably a hydrocarbylamine not having N—H bonds that interfere substantially with the transformation of the intermediate cyclic phosphinic amide into the cyclic phosphine halide, preferably a trihydrocarbylamine or an aromatic amine, preferably a $C_{1-12}$ trihydrocarbylamine or a $C_{1-12}$ aromatic amine, more preferably triethylamine, ethyldiisopropylamine, pyridine, 2-methylpyridine, 3-methylpyridine, 4-methylpyridine, lutidine, pyrimidine, pyrazole, dimethylphenylamine, N,N-dimethylaminopyridine, 1,8-diazabicyclo[5.4.0]undec-7-ene, or methylimidazole, even more preferably pyridine.

In a preferred embodiment, the at least one hydrido-silicon compound and the at least one silicon halide compound is at least one hydrido-silicon halide compound, preferably one hydrido-silicon halide compound, represented as R'$_2$SiHX. Preferably R'$_3$SiH is $CH_3SiH_3$, $CH_3CH_2SiH_3$, $(C_2H_3)SiH_3$, $((CH_3)_2CH)SiH_3$, $(CH_3CH_2CH_2)SiH_3$, $(CH_2CHCH_2)SiH_3$, $(CH_3CH_2CH_2CH_2)SiH_3$, $((CH_3)_3C)SiH_3$, $C_6H_5SiH_3$, $CH_3CH_2CH_2CH_2CH_2CH_2CH_2CH_2SiH_3$, $H_3SiCH_2CH_2SiH_3$, $(CH_3)_2SiH_2$, $(CH_3CH_2)_2SiH_2$, $(CH_3)(C_2H_3)SiH_2$, $((CH_3)_2CH)_2SiH_2$, $(CH_3CH_2CH_2)_2SiH_2$, $(CH_3CH_2CH_2CH_2)_2SiH_2$, $((CH_3)_3C)_2SiH_2$, $((CH_3)_3C)(CH_3)SiH_2$, $(C_6H_5)(CH_3)SiH_2$, $(C_6H_5)_2SiH_2$, $(CH_3C_6H_4)_2SiH_2$, $H_2(CH_3)SiCH_2CH_2Si(CH_3)H_2$, $(CH_3)_3SiH$, $(CH_3CH_2)_3SiH$, $((CH_3)_2CH)_3SiH$, $(CH_3CH_2)(CH_3)_2SiH$, $((CH_3)_2CH)(CH_3)_2SiH$, $(CH_2CHCH_2)(CH_3)_2SiH$, $(CH_3CH_2CH_2)_3SiH$, $(CH_3CH_2CH_2CH_2)_3SiH$, $(C_6H_5CH_2)(CH_3)_2SiH$, $(C_6H_5)_3SiH$, $(CH_3C_6H_4)_3SiH$, $(C_6H_5)(CH_3)_2SiH$, $(C_6H_5)_2(CH_3)SiH$, $(CH_3)_2(CH_2Cl)SiH$, $(CH_3)_2(C_2H_3)SiH$, $(CH_2CH_2)((CH_3)_2SiH)_2$, $((CH_3)_3C)(CH_3)_2SiH$, $((CH_3)_3C)_2(CH_3)SiH$, $((CH_3)_3C)(C_6H_5)_2SiH$, $H(CH_3)_2SiCH_2CH_2Si(CH_3)_2H((CH_3)_2SiH)_{20}$, $((CH_3CH_2)_2SiH)_{20}$, $((CH_3)(C_6H_5)SiH)_{20}$, $((C_6H_5)_2SiH)_{20}$, $(((CH_3)_2CH)_2SiH)_2O$ or $H_3SiSiH_3$, more preferably $CH_3SiH_3$, $CH_3CH_2SiH_3$, $((CH_3)_2CH)SiH_3$, $((CH_3)_3C)SiH_3$, $C_6H_5SiH_3$, $(CH_3)_2SiH_2$, $(CH_3CH_2)_2SiH_2$, $((CH_3)_2CH)_2SiH_2$, $((CH_3)_3C)_2SiH_2$, $((CH_3)_3C)(CH_3)SiH_2$, $(C_6H_5)(CH_3)SiH_2$, $(C_6H_5)_2SiH_2$, $(CH_3C_6H_4)_2SiH_2$, $(CH_3)_3SiH$, $(CH_3CH_2)_3SiH$, $((CH_3)_2CH)SiH$, $(C_6H_5)_3SiH$, $(CH_3C_6H_4)_3SiH$, $(C_6H_5)(CH_3)_2SiH$, $(C_6H_5)_2(CH_3)SiH$, $((CH_3)_3C)(CH_3)_2SiH$ or $((CH_3)_3C)_2(CH_3)SiH$, even more preferably $CH_3SiH_3$, $CH_3CH_2SiH_3$, $((CH_3)_2CH)SiH_3$, $C_6H_5SiH_3$, $(CH_3)_2SiH_2$, $(CH_3CH_2)_2SiH_2$, $((CH_3)_2CH)_2SiH_2$, $((CH_3)_3C)_2SiH_2$, $(C_6H_5)_2SiH_2$, $(CH_3)_3SiH$, $(CH_3CH_2)_3SiH$, $((CH_3)_2CH)_3SiH$ or $(C_6H_5)_3SiH$, still more preferably $CH_3SiH_3$, $C_6H_5SiH_3$, $(CH_3)_2SiH_2$, $(C_6H_5)_2SiH_2$, $(CH_3)_3SiH$ or $(C_6H_5)_3SiH$; preferably R'$_3$SiX is $CH_3SiCl_3$, $CH_3CH_2SiCl_3$, $(C_2H_3)SiCl_3$, $((CH_3)_2CH)SiCl_3$, $(CH_3CH_2CH_2)SiCl_3$, $(CH_2CHCH_2)SiCl_3$, $(CH_3CH_2CH_2CH_2)SiCl_3$, $((CH_3)_3C)SiCl_3$, $C_6H_5SiCl_3$, $CH_3CH_2CH_2CH_2CH_2CH_2CH_2CH_2SiCl_3$, $Cl_3SiSiCl_3$, $Cl_3SiCH_2CH_2SiCl_3$, $(CH_3)_2SiCl_2$, $(CH_3CH_2)_2SiCl_2$, $(CH_3)(C_2H_3)SiCl_2$, $((CH_3)_2CH)_2SiCl_2$, $(CH_3CH_2CH_2)_2SiCl_2$, $(CH_3CH_2CH_2CH_2)_2SiCl_2$, $((CH_3)_3C)_2SiCl_2$, $((CH_3)_3C)(CH_3)SiCl_2$, $(C_6H_5)(CH_3)SiCl_2$, $(C_6H_5)_2SiCl_2$, $(CH_3C_6H_4)_2SiCl_2$, $Cl_2(CH_3)SiCH_2CH_2Si(CH_3)Cl_2$, $(CH_3)_3SiCl$, $(CH_3)_3SiI$, $(CH_3CH_2)_3SiCl$, $((CH_3)_2CH)_3SiCl$, $(CH_3CH_2)(CH_3)_2SiCl$, $((CH_3)_2CH)(CH_3)_2SiCl$, $(CH_2CHCH_2)(CH_3)_2SiCl$, $(CH_3CH_2CH_2)_3SiCl$, $(CH_3CH_2CH_2CH_2)_3SiCl$, $(C_6H_5CH_2)(CH_3)_2SiCl$, $(C_6H_5)_3SiCl$, $(CH_3C_6H_4)_3SiCl$, $(C_6H_5)(CH_3)_2SiCl$, $(C_6H_5)_2(CH_3)SiCl$, $(CH_3)_2(CH_2Cl)SiCl$, $(CH_3)_2(C_2H_3)SiCl$, $(CH_2CH_2)((CH_3)_2SiCl)_2$, $((CH_3)_3C)(CH_3)_2SiCl$, $((CH_3)_3C)_2(CH_3)SiCl$, $((CH_3)_3C)(C_6H_5)_2SiCl$, $Cl(CH_3)_2SiCH_2CH_2Si(CH_3)_2Cl((CH_3)_2SiCl)_{20}$, $((CH_3CH_2)_2SiCl)_{20}$, $((CH_3)(C_6H_5)SiCl)_{20}$, $((C_6H_5)_2SiCl)_2O$ or $(((CH_3)_2CH)_2SiCl)_{20}$, more preferably $CH_3SiCl_3$, $CH_3CH_2SiCl_3$, $((CH_3)_2CH)SiCl_3$, $((CH_3)_3C)SiCl_3$, $C_6H_5SiCl_3$, $(CH_3)_2SiCl_2$, $(CH_3CH_2)_2SiCl_2$, $((CH_3)_2CH)_2SiCl_2$, $((CH_3)_3C)_2SiCl_2$, $((CH_3)_3C)(CH_3)SiCl_2$, $(C_6H_5)(CH_3)SiCl_2$, $(C_6H_5)_2SiCl_2$, $(CH_3C_6H_4)_2SiCl_2$, $(CH_3)_3SiCl$, $(CH_3)_3SiI$, $(CH_3CH_2)_3SiCl$, $((CH_3)_2CH)_3SiCl$, $(C_6H_5)_3SiCl$, $(CH_3C_6H_4)_3SiCl$, $(C_6H_5)(CH_3)_2SiCl$, $(C_6H_5)_2(CH_3)SiCl$, $((CH_3)_3C)(CH_3)_2SiCl$ or $((CH_3)_3C)_2(CH_3)SiCl$, even more preferably $CH_3SiCl_3$, $(CH_3)_3SiI$, $CH_3CH_2SiCl_3$, $((CH_3)_2CH)SiCl_3$, $C_6H_5SiCl_3$, $(CH_3)_2SiCl_2$, $(CH_3CH_2)_2SiCl_2$, $((CH_3)_2CH)_2SiCl_2$, $((CH_3)_3C)_2SiCl_2$, $(C_6H_5)_2SiCl_2$, $(CH_3)_3SiCl$, $(CH_3CH_2)_3SiCl$, $((CH_3)_2CH)_3SiCl$ or $(C_6H_5)_3SiCl$, still more preferably $CH_3SiCl_3$, $(CH_3)_3SiI$, $C_6H_5SiCl_3$, $(CH_3)_2SiCl_2$, $(C_6H_5)_2SiCl_2$, $(CH_3)_3SiCl$, $(C_6H_5)_3SiCl$; preferably R'$_2$SiHX is $HSiCl_3$, $H_2SiCl_2$, $H_3SiCl$, $(CH_3)_2SiHCl$, $(CH_3CH_2)_2SiHCl$, $(CH_2CH_2)_2SiHCl$, $((CH_3)_2CH)_2SiHCl$, $(CH_3CH_2CH_2)_2SiHCl$, $(CH_3CH_2CH_2CH_2)_2SiHCl$, $((CH_3)_3C)_2SiHCl$, $((CH_3)_3C)(CH_3)_2SiHCl$, $(C_6H_5)(CH_3)_2SiHCl$, $(C_6H_5)_2SiHCl$, $(CH_3C_6H_4)_2SiHCl$, $Cl(CH_3)HSiCH_2CH_2SiH(CH_3)Cl$, $CH_3SiHCl_2$, $CH_3CH_2SiHCl_2$, $(C_2H_3)SiHCl_2$, $((CH_3)_2CH)SiHCl_2$, $(CH_3CH_2CH_2)SiHCl_2$, $(CH_2CHCH_2)SiHCl_2$, $(CH_3CH_2CH_2CH_2)SiHCl_2$, $((CH_3)_3C)SiHCl_2$, $C_6H_5SiHCl_2$, $Cl_2HSiCH_2CH_2SiHCl_2$, $Cl_2HSiSiHCl_2$, $CH_3SiH_2Cl$, $CH_3CH_2SiH_2Cl$, $(C_2H_3)SiH_2Cl$, $((CH_3)_2CH)SiH_2Cl$, $(CH_3CH_2CH_2)SiH_2Cl$, $(CH_2CHCH_2)SiH_2Cl$, $(CH_3CH_2CH_2CH_2)SiH_2Cl$, $((CH_3)_3C)SiH_2Cl$, $C_6H_5SiH_2Cl$, $ClH_2SiCH_2CH_2SiH_2Cl$ or $ClH_2SiSiH_2Cl$, more preferably $HSiCl_3$, $H_2SiCl_2$, $(CH_3)_2SiHCl$, $(CH_3CH_2)_2SiHCl$, $((CH_3)_2CH)_2SiHCl$, $((CH_3)_3C)_2SiHCl$, $((CH_3)_3C)(CH_3)_2SiHCl$, $(C_6H_5)(CH_3)_2SiHCl$, $(C_6H_5)_2SiHCl$, $CH_3SiHCl_2$, $CH_3CH_2SiHCl_2$, $((CH_3)_2CH)SiHCl_2$, $((CH_3)_3C)SiHCl_2$, $C_6H_5SiHCl_2$, $CH_3SiH_2Cl$, $CH_3CH_2SiH_2Cl$, $((CH_3)_2CH)SiH_2Cl$, $((CH_3)_3C)SiH_2Cl$ or $C_6H_5SiH_2Cl$, even more preferably $HSiCl_3$, $H_2SiCl_2$, $(CH_3)_2SiHCl$, $(C_6H_5)(CH_3)SiHCl$, $(C_6H_5)_2SiHCl$, $CH_3SiHCl_2$, $C_6H_5SiHCl_2$, $CH_3SiH_2Cl$ or $C_6H_5SiH_2Cl$, still more preferably $HSiCl_3$, $H_2SiCl_2$, $(CH_3)_2SiHCl$, $(C_6H_5)_2SiHCl$ or $CH_3SiHCl_2$, $HSiCl_3$ is most highly preferred. Mixtures of the foregoing may also be used.

In an embodiment of the one-step improved process to convert the intermediate cyclic phosphinic amide into the cyclic phosphine halide product using R'$_3$SiH, R'$_3$SiX or R'$_2$SiHX compounds, the cyclic phosphine halide product can be separated or purified from the silicon-containing co-products which result by extracting or partitioning the cyclic phosphine halide into the high polarity solvent phase of a high polarity solvent/low polarity two-phase solvent mixture and extracting or partitioning the silicon-containing co-products into the low polarity solvent phase of a two-phase high polarity solvent/low polarity solvent mixture, preferably wherein the high polarity solvent phase comprises one or more solvents selected from $C_{2-8}$ nitriles, such as acetonitrile, propanenitrile, butanenitrile, benzenenitrile; $C_{1-10}$ amides, such as formamide, N,N-dimethylformamide, N,N-diethylformamide, N,N-dimethylacetamide, N,N-diethylacetamide, N,N-dimethylbenzamide; $C_{1-8}$ carboxylic acids, such as formic acid, acetic acid, propanoic acid, butanoic acid, malonic acid; $C_{1-8}$ alcohols, such as methanol, ethanol, propanol, isopropanol, n-butanol, t-butanol; dimethylsulfoxide; preferably acetonitrile, propanenitrile, formamide, N,N-dimethylformamide, N,N-dimethylacetamide, acetic acid or dimethylsulfoxide, more preferably acetonitrile, and the low polarity solvent phase comprises one or more solvents selected from $C_{6-12}$ aromatic hydrocarbons, $C_{4-12}$ saturated hydrocarbons or $C_{4-10}$ ethers, preferably $C_{4-8}$ saturated hydrocarbons, $C_{6-8}$ aromatic hydrocarbons or $C_{6-8}$ ethers, more preferably butane, pentane, cyclopentane, hexane, cyclohexane, methylcyclopentane, heptane, methylcycloheptane, octane, 2,2,4,-trimethylpentane, benzene, toluene, diisopropyl ether or dibutyl ether, even more preferably butane, pentane, hexane, still more preferably pentane. Preferably the two-phase high polarity solvent/low polarity solvent mixture components are selected such that the high polarity solvent and the low polarity solvent are immiscible in each other, such that a two-phase solvent mixture is provided, e.g., pentane/acetonitrile, diethyl ether/dimethylsulfoxide, hexane/dimethylformamide. After the cyclic phosphine halide and the silicon-containing co-product mixture has been extracted or partitioned in the high polarity solvent/low polarity solvent mixture and the high polarity and low polarity solvent phases have been separated, the cyclic phosphine halide can be recovered by methods known to one of ordinary skill in the art, such as evaporating off the solvent. Alternatively the cyclic phosphine halide product can be separated or purified from the silicon-containing co-products by washing the cyclic phosphine halide/silicon-containing co-product mixture with one or more low polarity solvents, preferably pentane, hexane, heptane or cyclohexane, more preferably pentane. Preferably the cyclic phosphine halide product is purified by partitioning the cyclic phosphine chloride and reaction coproducts in a two-phase acetonitrile/hexane solvent mixture.

This improved process for the conversion of the intermediate cyclic phosphinic amide into the cyclic phosphine halide reduces the number of steps required from four to one.

In one embodiment of the process to prepare the ligating compounds, similar to the manner of Fox et al., halide- or other leaving group derivatives of

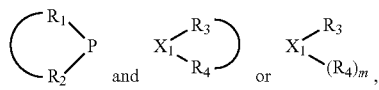

such as

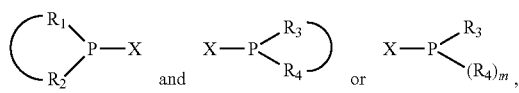

wherein X is a leaving group, are contacted with

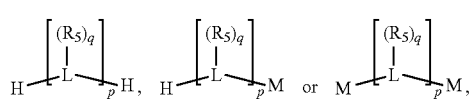

wherein L-H independently is CH, NH, PH, OH, or SH, to prepare the desired ligating compound

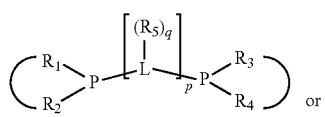

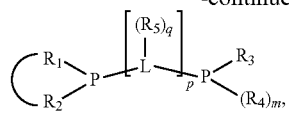

respectively. This embodiment allows the preparation of unsymmetrical ligating compounds, wherein

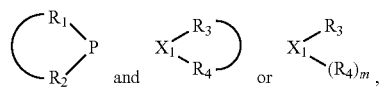

as well as symmetric ligating compounds, wherein

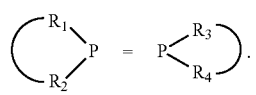

Not desiring to be bound to any particular method, the symmetric ligating compound may be prepared by combining approximately two equivalents of the

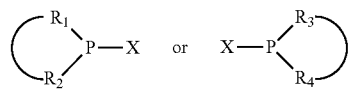

cyclic precursor with approximately one equivalent of

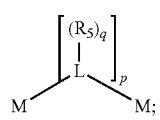

whereas the unsymmetrical ligating compound, wherein

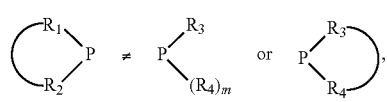

preferably obtained by first combining either approximately one equivalent of

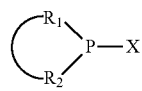

cyclic precursor or approximately one equivalent of

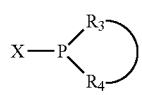

cyclic or

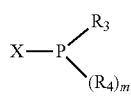

acyclic precursor with approximately one equivalent of

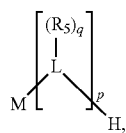

then combining the product of the just-mentioned first reaction with a strong base comprising M to form

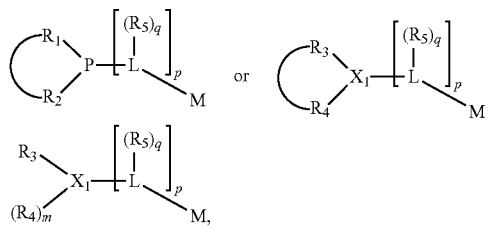

respectively, which is then contacted with either approximately one equivalent of a different

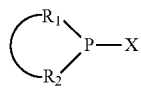

cyclic precursor or approximately one equivalent of a different

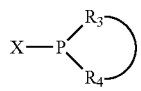

cyclic or

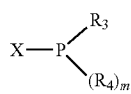

acyclic precursor. The

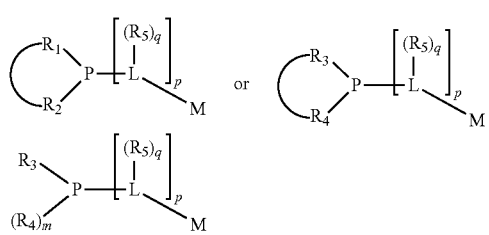

intermediates may also be formed by combination of approximately one equivalent of

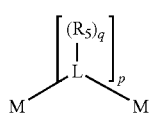

with approximately one equivalent of

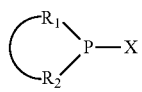

cyclic precursor or approximately one equivalent of

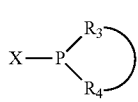

cyclic or

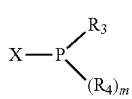

acyclic precursor

In another non-limiting embodiment of the process to prepare the ligating compounds,

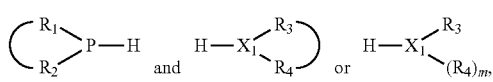

wherein

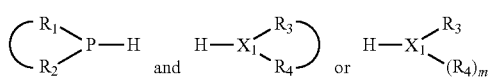

may be selected according to the desired ligating compound to be obtained, may be contacted with a halide or other leaving group derivative of

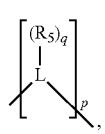

such as

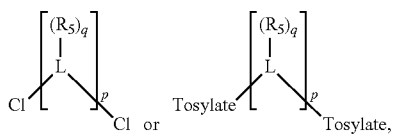

in the presence of preferably at least two equivalents of a proton scavenger to give the ligating product. As above, symmetric or unsymmetrical products may be obtained by choice of stoichiometry and precursors. Such chemistry is analogous to that disclosed in Montag et al. ("The unexpected role of CO in C—H oxidative addition by a cationic rhodium(I) complex", Montag, M.; Schwartsburd, L.; Cohen, R.; Leitus, G; Ben-David, Y.; Martin, J. M. L.; Milstein, D., *Angew. Chem., Int. Ed.* 2007, 46, 1901-1904) wherein 1,3-bis(bromomethyl)benzene and diisopropylphosphine are contacted with triethylamine to prepare 1,3-bis(diisopropylphosphinomethyl)benzene.

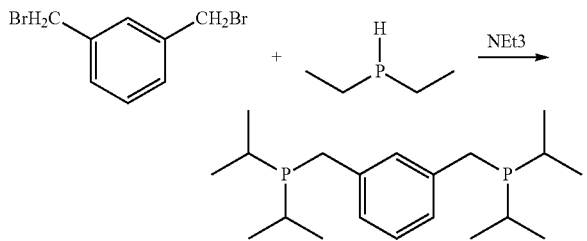

In another non-limiting embodiment of the process to prepare the ligating compounds, a halide- or other leaving group derivative of

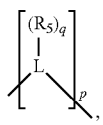

such as

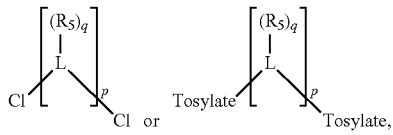

preferably when the leaving group is attached to L when L is P, C, Si, Ge, or B, may be contacted with an alkali metal-, alkaline earth metal-, or alkaline earth metal-halide derivative of

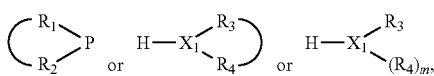

such as

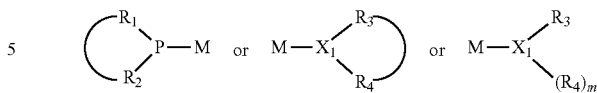

to give the ligating product. As above, symmetric or unsymmetrical products may be obtained by choice of stoichiometry and precursors. A non-limiting specific example of this embodiment of the process to prepare the ligating compounds is disclosed in Coleman et al. ("Coordination chemistry of cis,cis and trans,trans 1,1'-[1,2-phenylenebis(methylene)]bis(2,2,3,4,4-pentamethylphosphetane)" Coleman, D.; Edwards, P. G.; Kariuki, B. M.; Newman, P. D. *Dalton Trans.* 2010, 39, 3842-3850), wherein the lithium derivative of 2,2,3,4,4-pentamethylphosphetane trihydroboron is contacted with 1,2-bis(chloromethyl)benzene and the resulting product is treated sequentially with $HBF_4$ and $NaHCO_3$ to give 1,1'-[1,2-phenylenebis(methylene)]bis-(2,2,3,4,4-pentamethylphosphetane).

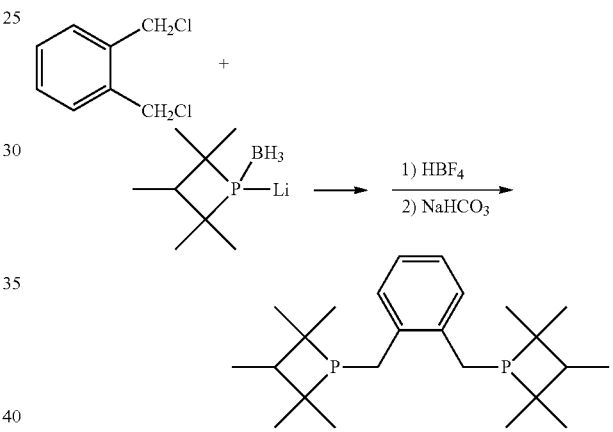

In another non-limiting embodiment of the process to prepare the ligating compounds, silyl derivatives of

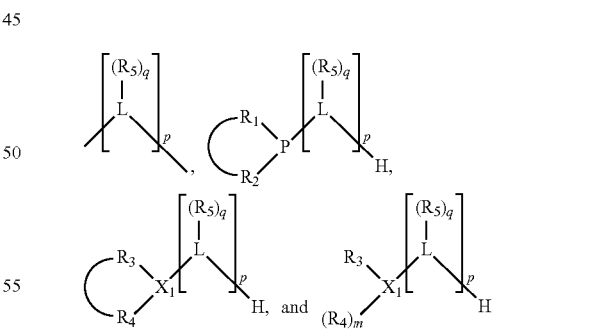

such as

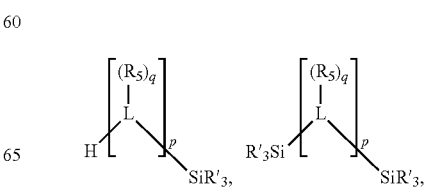

-continued

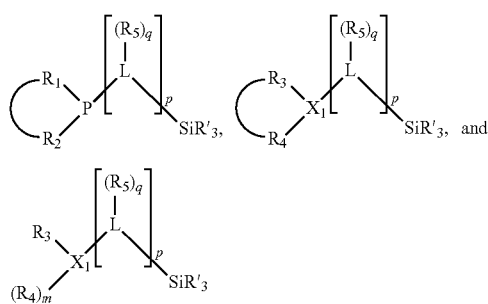

may be contacted with

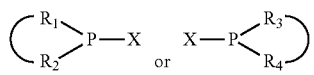

cyclic or

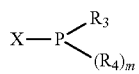

acyclic precursors, wherein X is a leaving group, preferably chloride, bromide, iodide, mesylate, tosylate, or triflate, preferably chloride or iodide; preferably at least one L is N or O, preferably N, such that L-SiR'$_3$ is N—SiR'$_3$ or O—SiR'$_3$, preferably N—SiR'$_3$. A non-limiting specific example of the reaction to form a P—N bond by combining a P—Cl bond-containing compound with a N-silyl bond-containing compound is disclosed in Bettermann et al. ("Reaction of N- or O-trimethylsilylated ethanolamine derivatives with phosphorus(III)-halogen compounds. Intramolecular donor-acceptor interactions in compounds $CH_3OCH_2CH_2N(CH_3)PCl_2$, $(CH_3)_2NCH_2CH_2OPCl_2$, $(CH_3)_2NCH_2CH_2N(CH_3)P(C_6H_5)_2$, $(CH_3)_2NCH_2CH_2N(CH_3)P(C_6H_5)Cl$, and $(CH_3)_2NCH_2CH_2N(CH_3)PCl_2$" Bettermann, G.; Schomburg, D.; Schmutzler, R. *Phosphorus Sulfur Related Elements* 1986, 28, 327-336), wherein $N^1N^1N^2$-trimethyl-$N^2$-(trimethylsilyl)-1,2-ethanediamine is contacted with chlorodiphenylphosphine to give (2-(dimethylamino)ethyl(methyl)amino)diphenylphosphine.

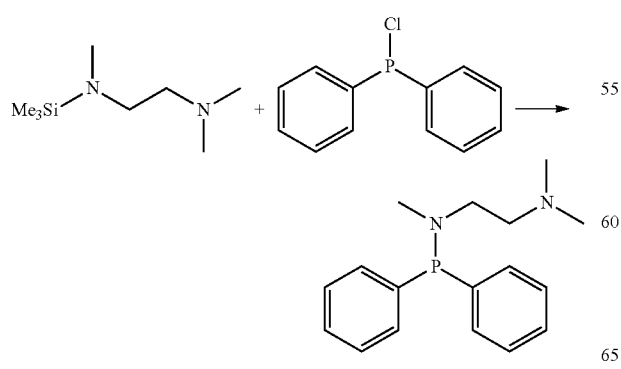

In an embodiment of the invention, a process is provided represented as

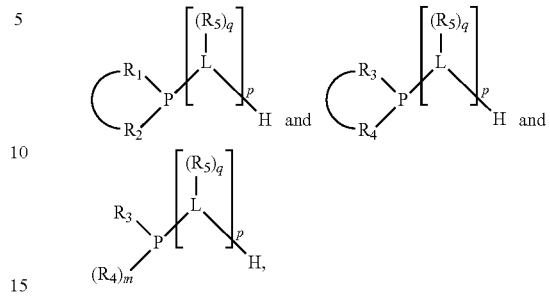

and silyl derivatives thereof, represented as

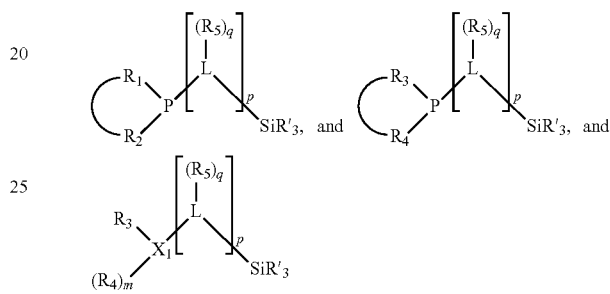

as described above, more preferably represented as

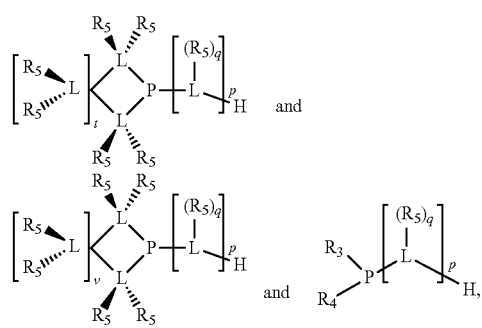

or silyl derivatives thereof, represented as

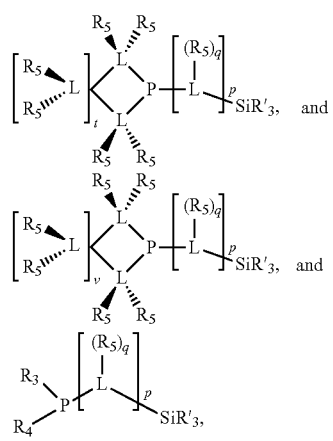

respectively, preferably as

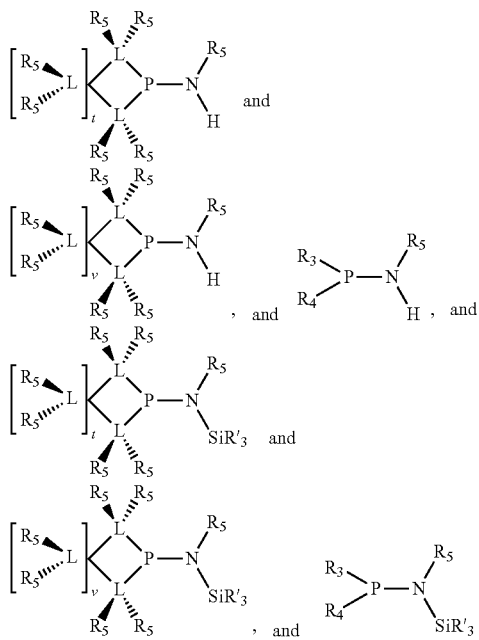

respectively, wherein $R_1$, $R_2$, $R_3$, $R_4$, $R_5$, L, t, p, q, and n are as described above; R' independently selected is hydrogen, $C_{1-6}$ hydrocarbyl, or halide; more preferably

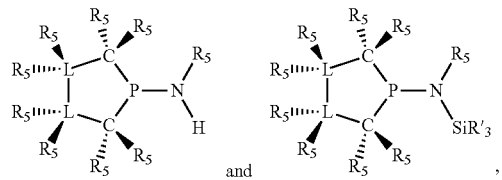

and the phosphacycle is not 8-aza-1-phosphatricylo[3.3.0.0$^{2,6}$]octane; preferably L is nitrogen or carbon, more preferably L is carbon; even more preferably

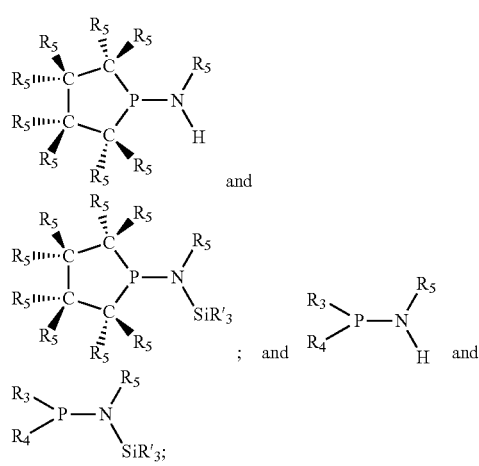

phosphacycle is not 8-aza-1-phosphatricylo[3.3.0.0$^{2,6}$]octane; preferably L is nitrogen, preferably the phosphacycle is a 5-membered phospholane wherein both atoms directly bonded to P are sp$^3$ hybridized and the phospholane is not 8-aza-1-phosphatricylo[3.3.0.0$^{2,6}$]octane, more preferably represented as

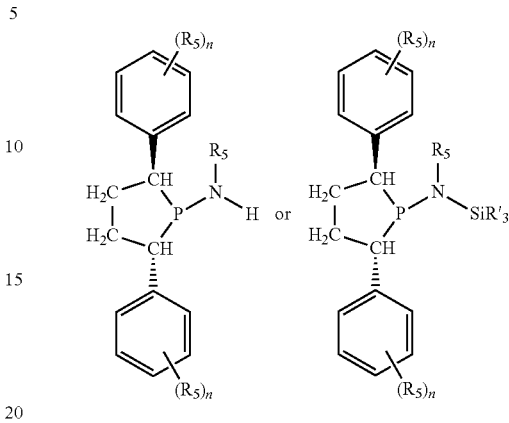

wherein $R_5$, R', and n are as described above.

In one embodiment of the process to prepare the ligating compounds, the leaving group of the cyclic or acyclic phosphine precursor is chloride, bromide, iodide, mesylate, tosylate, or trifluoromethanesulfonate, preferably chloride or iodide, more preferably chloride. In one embodiment of the above methods to produce the ligating compound or any of the intermediate compounds, the cyclic or acyclic phosphine precursor is a cyclic or acyclic phosphine chloride which is advantageously employed due to its ready availability, either commercially or through synthesis. In another embodiment of the above methods to produce the ligating compound or any of the intermediate compounds, the cyclic or acyclic phosphine precursor is a cyclic or acyclic phosphine iodide which is preferred in some embodiments over the corresponding cyclic or acyclic phosphine chloride due to its greater reactivity with N—H or N—Si bonds. In one embodiment of the process to prepare the ligating compounds, the cyclic or acyclic phosphine chloride may be converted into the corresponding cyclic or acyclic phosphine iodide, the process comprising contacting the cyclic phosphine chloride with an iodide source wherein the iodide source is selected from the group comprising LiI, NaI, KI, MgI$_2$, CaI$_2$, SmI$_2$(THF)$_2$, R'''$_4$NI, R'''$_3$SiI, R'''$_2$SiI$_2$, R'''SiI$_3$, and SiI$_4$, wherein THF is tetrahydrofuran, R''' independently selected is hydrogen; $C_{1-20}$, preferably $C_{1-12}$, more preferably $C_{1-6}$ hydrocarbyl, preferably $C_{1-12}$, more preferably $C_{1-6}$, alkyl or $C_{2-20}$, more preferably $C_{2-12}$ aryl or arylalkyl, still more preferably methyl, ethyl, isopropyl, t-butyl, phenyl, tolyl, benzyl, preferably methyl, t-butyl, and phenyl, and isolating the cyclic or acyclic phosphine iodide product. Preferably the iodide source is trimethylsilyl iodide.

In another non-limiting embodiment of the process to prepare the ligating compounds, the preparation of the ligating compound may be achieved by combining

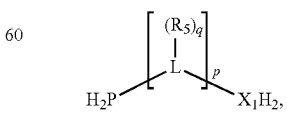

wherein $X_1H_2$ is either PH$_2$ or NH$_2$, with a) a strong base comprising M, and with b) leaving group-containing derivatives of

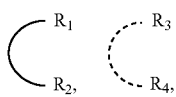

such as cyclic sulfate derivatives, such as

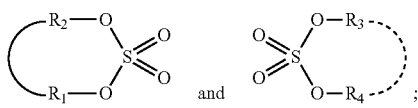

or sulfonate derivatives, such as

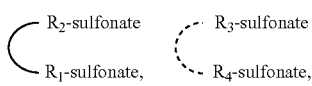

$R_3$-sulfonate or $R_4$-sulfonate, preferably wherein sulfonate is mesylate, tosylate, or triflate; or halide derivatives, such as

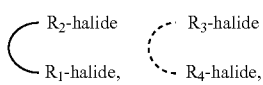

$R_3$-halide, or $R_4$-halide, wherein the halide is Cl, Br, or I;

is a divalent moiety in which $R_1$ and $R_2$ are linked together and

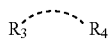

is a divalent moiety in which $R_3$ and $R_4$ are linked together. A non-limiting specific example of this embodiment of the process to prepare the ligating compounds is disclosed in Bonnaventure et al. ("Probing the Importance of the Hemilabile Site of Bis(phosphine) Monoxide Ligands in the Copper-Catalyzed Addition of Diethylzinc to N-Phosphinoylimines: Discovery of New Effective Chiral Ligands" Bonnaventure, I.; Charette, A. B. *J. Org. Chem.*, 2008, 73, 6330-6340), wherein 1,2-bis(phosphino)benzene is contacted with butyllithium and 2,5-dimethyl-1,3,2-dioxathiepane 2,2-dioxide to give 1,1'-(1,2-phenylene)bis[2,5-dimethylpholane].

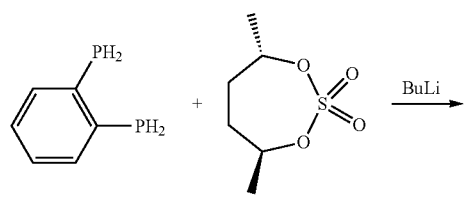

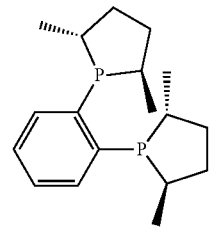

As is known to one skilled in the art, the yield and purity of the ligating compound may be dependent to some extent on the reaction conditions, such as the temperature, the solvents employed, and the order of addition in which the precursors are contacted with each other. Some minor experimentation, such as is known to be undertaken by one skilled in the art, may be desirable for optimization of the yield and purity, for example, in some cases it may be desirable to use any one or more of the reaction components in excess, such as 0.01 to 0.5-fold excess, or 0.5-5-fold excess, even as high as, or higher than 5-20-fold excess, in order to increase the rate of the reaction and to improve the conversion.

In an embodiment of the invention the poly(ligating compound) may be prepared using coupling reactions to link two or more ligating compounds together. For example, Suzuki cross-coupling reactions can couple a ligating compound having an organoboronic acid group with a ligating compound having an organohalide group. An example of the coupling reaction between a compound having an arylboronic acid group with a compound having an arylhalide group is described in Song et al., ("Palladium catalyzed Suzuki-Miyaura coupling with aryl chlorides using a bulky phenanthryl N-heterocyclic carbene ligand", Song, C.; Ma, Y.; Chai, Q.; Ma, C.; Jiang, W.; Andrus, M. B. *Tetrahedron*, 2005, 61, 7438-7446.) As described above in an embodiment, ligating compounds may be prepared beginning with dihydrocarbylphosphine halide compounds. In an embodiment, ligating compounds having an arylhalide group may be prepared beginning with a diarylphosphine halide having an arylhalide group which themselves can be prepared as described by De Pater et al. ("(Perfluoro)alkylsilyl-Substituted 2-[Bis(4-aryl)phosphino]pyridines: Synthesis and Comparison of Their Palladium Complexes in Methoxycarbonylation of Phenylacetylene in Regular Solvents and Supercritical $CO_2$", De Pater, J. J. M.; Maljaars, C. E. P.; De Wolf, E.; Lutz, M.; Spek, A. L.; Deelman, B.-J.; Elsevier, C. J.; Van Koten, G. *Organometallics* 2005, 24, 5299-5310.) In an embodiment, ligating compounds having an arylboronic acid group may be prepared by contacting a ligating compound having an arylhalide group with butyllithium, then with a boronic ester. The general reaction for preparing an arylboronic acid compound from an arylhalide in this manner has been described by Moleele et al. ("Methodology for the synthesis of 1,2-disubstituted arylnaphthalenes from α-tetralones", Moleele, S. S.; Michael, J. P.; De Koning, C. B. *Tetrahedron* 2006, 62, 2831-2844.)

As described above in an embodiment, ligating compounds may be prepared by contacting a primary amine with cyclic and/or acyclic phosphine halide precursors. In an embodiment related thereto, the poly(ligating compound) species can be prepared by contacting a compound having two or more primary amine groups, such as 1,6-diaminohexane, with cyclic or acyclic phosphine halide precursors.

Ligating Compound-Chromium Complexes

In some embodiments, the invention provides a ligating compound-metal complex which is useful in catalysis, especially in hydroformylation, isomerization, hydrogenation, polymerization processes, especially the oligomerization of olefins such as ethylene. In some embodiments, the invention provides a ligating compound-chromium complex which is useful in the oligomerization of olefins such as ethylene. The ligating compound-chromium complex is a composition comprising a) a source of chromium and b) a phosphacycle-containing ligating compound as described herein.

While not wishing to be bound by any particular theory or physical description of the complex, it is believed that the ligating compound is bound to the chromium atom in the ligating compound-chromium complex in a bidentate fashion, but it is within the scope of the invention to envision other modes of bonding in addition to bidentate ligand bonding.

The ligating compound-chromium complex $R_1R_2P$—Y—$XR_3(R_4)_m$[Cr] may be represented as

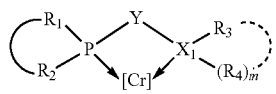

wherein:

P is phosphorus; $X_1$ is selected from nitrogen, phosphorus, oxygen, or sulfur; each of $R_1$ and $R_2$ is independently a substituted or unsubstituted hydrocarbon derivative, a substituted or unsubstituted heterohydrocarbon derivative, or a substituted or unsubstituted heteroatom group having from one to 50 non-hydrogen atoms; m is 0 or 1; $R_1$ and $R_2$ are linked together to form a divalent moiety represented as

which together with P forms a cyclic structure (phosphacycle) containing from 3 to 10 ring atoms; each of $R_3$ and $R_4$ is independently hydrogen, halogen, a substituted or unsubstituted hydrocarbon derivative, a substituted or unsubstituted heterohydrocarbon derivative, or a substituted or unsubstituted heteroatom group having from one to 50 non-hydrogen atoms; $R_3$ and $R_4$ are optionally linked together to form a divalent moiety represented as

wherein the optional character of the linkage is depicted by a dashed connection, which together with $X_1$ forms a cyclic structure containing from 3 to 10 ring atoms; [Cr] comprises a chromium atom from the source of chromium along with any ancillary ligands, that is, the ligands attached to the chromium atom not including the ligating compound; Y, optionally linked together with one or more of $R_1$, $R_2$, $R_3$, or $R_4$ to form cyclic structures containing from 4 to 10 ring atoms, as represented by:

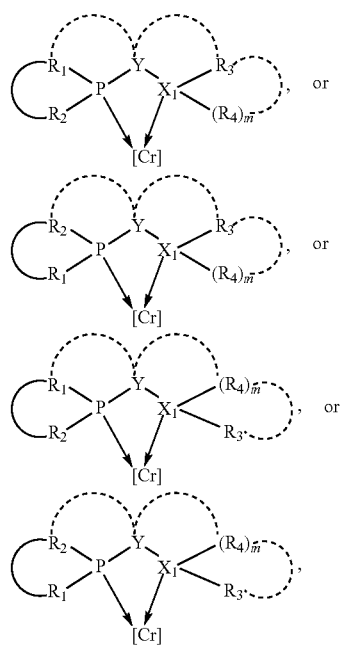

wherein the optional character of the linkages is depicted by a dashed connection, is a divalent linking group $[L(R_5)_q]_p$ between P and $X_1$ containing from one to 50 non-hydrogen atoms; $[L(R_5)_q]_p$ is represented by:

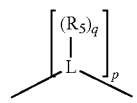

wherein each L is independently selected from the group consisting of boron, carbon, silicon, germanium, nitrogen, phosphorus, oxygen, and sulfur; p is an integer number from 1 to 6, preferably from 1 to 4; $R_5$ is independently hydrogen, halogen, substituted or unsubstituted hydrocarbon derivative, substituted or unsubstituted heterohydrocarbon derivative, or a substituted or unsubstituted heteroatom group; q is 0, 1, or 2; provided that the $[L]_p$ subunit of the divalent linking group $[L(R_5)_q]_p$ does not comprise an amidine (N—C=N) group; further provided that in at least one phosphacycle of the phosphacycle-containing ligating compound-chromium complex, both atoms directly bonded to P or $X_1$ are sp$^3$ hybridized; still further preferably provided that one or two phosphacycles comprising P or $X_1$, preferably comprising P, $R_1$, and $R_2$, or comprising $X_1$, $R_3$, and $R_4$, contain no P—N, P—O, or P—S bonds within the ring part of the phosphacycle; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; from two to ten, preferably from two to six, independently selected ligating compound-chromium complexes may be optionally linked together via their respective independently selected Y, $R_1$, $R_2$, $R_3$, $R_4$ or $R_5$ groups to form a poly(ligating compound-chromium complex) species. Preferably at least one, preferably two, phosphacycles do not contain more than one carbon-carbon unsaturated bond in each phosphacycle, preferably not more than one unsaturated bond in each phosphacycle.

The phosphacycle-containing ligating compound-chromium complex may be present as a monomer, represented as:

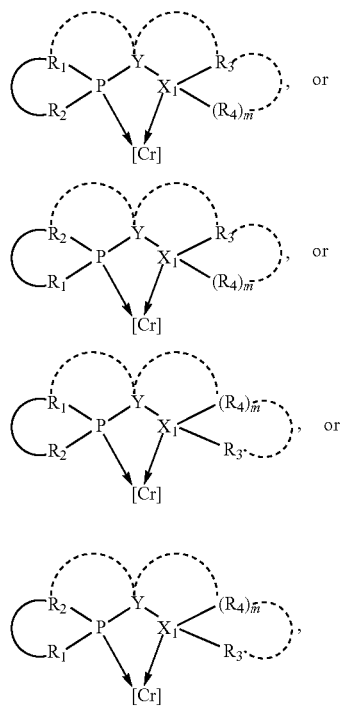

or as a dimer, represented as:

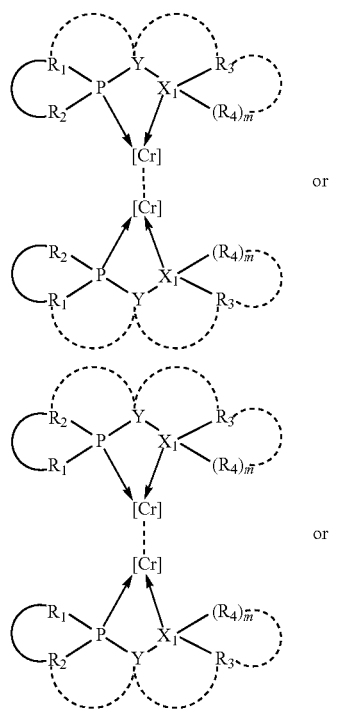

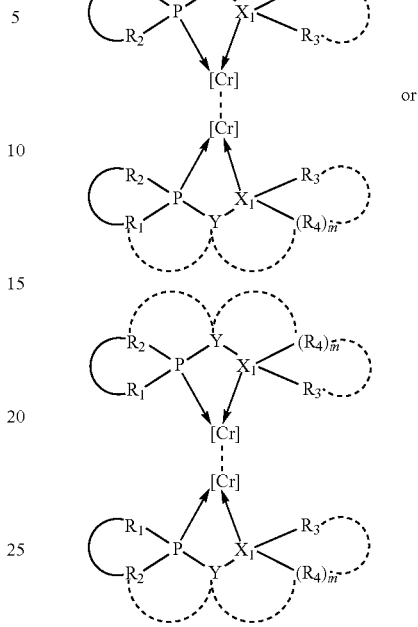

wherein [Cr]—[Cr] represents the two [Cr] groups and the linkage between them in the dimer form of the ligating compound-chromium complex.

In an embodiment of the invention, the invention comprises a phosphacycle-containing ligating compound-chromium complex ("ligating compound-chromium complex") as represented by:

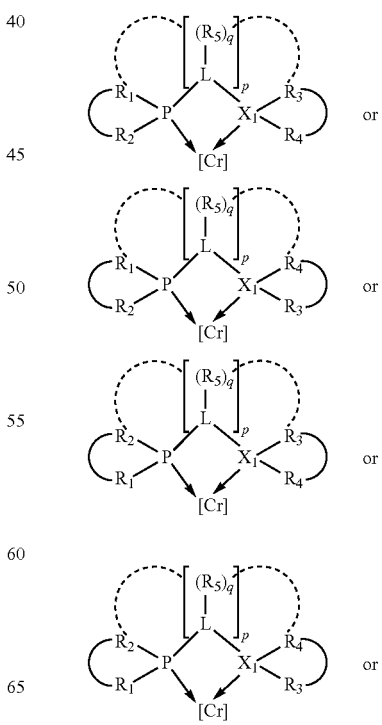

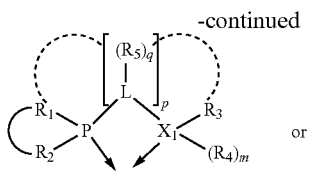

or


or

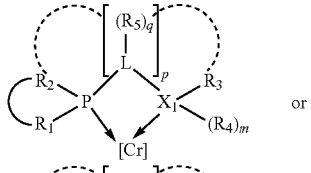

or

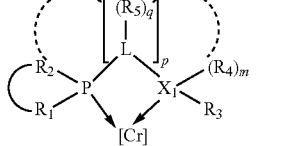

wherein P is phosphorus; $X_1$ is selected from nitrogen, phosphorus, oxygen, or sulfur, preferably nitrogen or phosphorus, more preferably phosphorus; m is 0 or 1; each L is independently selected from boron, carbon, silicon, germanium, nitrogen, phosphorus, oxygen, or sulfur, preferably carbon, nitrogen, phosphorus, oxygen, or sulfur, more preferably carbon or nitrogen; $R_1$ and $R_2$ are each independently selected from substituted or unsubstituted hydrocarbon derivatives, substituted or unsubstituted heterohydrocarbon derivatives, or a substituted or unsubstituted heteroatom group; $R_1$, P, and $R_2$ together form a phosphacycle; when $R_3$, $R_4$, and $X_1$ are linked together, they form a phosphacycle when $X_1$ is phosphorus and they form an azacycle when $X_1$ is nitrogen; two or more $R_1$, $R_2$, $R_3$, $R_4$ or $R_5$ groups are optionally linked together to form cyclic structures containing from 4 to 10 ring atoms, preferably from 4 to 7 ring atoms wherein the optional character of the linkages is depicted by a dashed connection; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_1$, $R_2$, $R_3$, $R_4$ or $R_5$ groups to form a poly(ligating compound-chromium complex) species; $R_3$, $R_4$, and $R_5$ are each independently selected from hydrogen, halogen, substituted or unsubstituted hydrocarbon derivatives, substituted or unsubstituted heterohydrocarbon derivatives, or a substituted or unsubstituted heteroatom group; p is an integer number from 1 to 6, preferably from 1 to 4, more preferably from 1 to 3, most preferably from 1 to 2; q is 0, 1, or 2; provided that the $[L]_p$ subunit of the divalent linking group

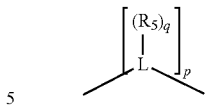

does not comprise an amidine (N—C=N) group; further provided that in at least one phosphacycle of the phosphacycle-containing ligating compound, both atoms directly bonded to P or $X_1$ are $sp^3$ hybridized; still further preferably provided that one or two phosphacycles comprising P or $X_1$, preferably comprising P, $R_1$, and $R_2$, or comprising $X_1$, $R_3$, and $R_4$, contain no P—N, P—O, or P—S bonds within the ring part of the phosphacycle. Preferably at least one, preferably two, phosphacycles do not contain more than one carbon-carbon unsaturated bond in each phosphacycle, preferably not more than one unsaturated bond in each phosphacycle. Phosphacycles or azacycles are ring or cyclic compounds comprising at least one phosphorus or nitrogen atom, respectively, in the ring or cycle.

Each $R_1$ and $R_2$ independently contains from 1 to 50 non-hydrogen atoms; each $R_3$, $R_4$, and $R_5$ independently contains from 0 to 50 non-hydrogen atoms; preferably each $R_5$ independently contains from 0 to 40 non-hydrogen atoms, more preferably from 0 to 20 non-hydrogen atoms, and most preferably from 0 to 12 non-hydrogen atoms; optionally, at least one $R_5$ group is a divalent group bonded to L via a double bond.

Preferably the phosphacycle-containing ligating compound-chromium complex is represented by

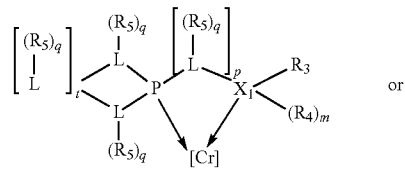

or

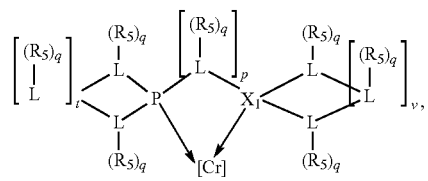

wherein q is 0, 1, or 2; p is 1, 2, 3, or 4; t is 0, 1, 2, 3, or 4; v is 0, 1, 2, 3, or 4; m is 0 or 1; L, $R_3$, $R_4$, $R_5$, and $X_1$ are as defined above; further provided that in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species.

Preferably $X_1$ is nitrogen or phosphorus; p=1, 2, 3, or 4; q=0, 1 or 2; v and t are each independently 1, 2, 3, or 4; $R_5$ are each independently hydrogen; halogen; $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms; $R_3$ and $R_4$ are each independently $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms, more preferably one atom; when $X_1$ and its two attached $R_3$ and $R_4$ groups form a cycle represented as:

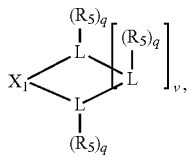

the cycle is an azacycle when $X_1$ is nitrogen and a phosphacycle when $X_1$ is phosphorus; P and its two attached $R_1$ and $R_2$ groups form a phosphacycle represented as:

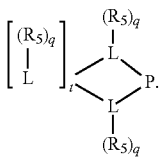

Preferably the L atoms of the phosphacycle or azacycle are each independently carbon, nitrogen, or oxygen; $[L(R_5)_q]_p$ is as defined above. Preferably all L atoms of either phosphacycle which are directly attached to the phosphorus of the phosphacycle are carbon; $[L(R_5)_q]_p$ is as defined above. Preferred phosphacycle-containing ligating compound-chromium complexes are represented by:

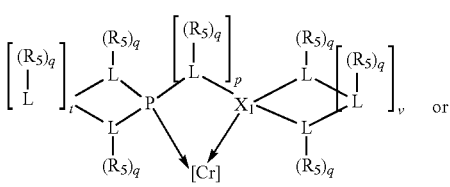 or

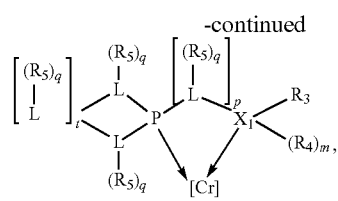

wherein $[L(R_5)_q]$ of the phosphacycle or azacycle independently selected is $C(R_5)$, O, N, $N(R_5)$, or $C(R_5)_2$; $[L(R_5)_q]_p$ is as defined above; q is 0, 1, or 2; p is 1, 2, 3, or 4; t is 1, 2, 3, or 4; v is 1, 2, 3, or 4; m is 0 or 1, $X_1$ is nitrogen, phosphorus, or oxygen, preferably nitrogen or phosphorus, more preferably phosphorus; $R_5$ are each independently hydrogen; halogen; $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms; $R_3$ and $R_4$ are each independently $C_{1-40}$ substituted or unsubstituted hydrocarbon derivative, preferably $C_{1-20}$ substituted or unsubstituted hydrocarbon derivative, more preferably $C_{1-12}$ substituted or unsubstituted hydrocarbon derivative; $C_{1-40}$ substituted or unsubstituted heterohydrocarbon derivative, preferably $C_{1-20}$ substituted or unsubstituted heterohydrocarbon derivative, more preferably $C_{1-12}$ substituted or unsubstituted heterohydrocarbon derivative; or a heteroatom group having one to four atoms, preferably one to three atoms, more preferably one atom; further provided that in at least one phosphacycle of the phosphacycle-containing ligating compound, both atoms directly bonded to P or $X_1$ are sp$^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species. More preferably p=1 or 2. More preferably all $[L(R_5)_q]$ groups of either phosphacycle which are directly attached to the phosphorus of the phosphacycle are independently $C(R_5)$ or $C(R_5)_2$.

The number of chiral ring atoms, not including the P or $X_1$ attached to $[L(R_5)_q]_p$, in each of the 4-, 5-, 6-, and 7-membered phosphacycle or azacycle rings in the ligating compound-chromium complex can range from zero (none) up to one less than the number of ring atoms in each ring. In some embodiments, no carbon atoms in either of the one or two 4-, 5-, 6-, and 7-membered phosphacycle or azacycle rings are chiral. In some embodiments, only one carbon atom in the one or two 4-, 5-, 6-, and 7-membered phosphacycle or azacycle rings is chiral. In some embodiments, only one carbon atom in each of the one or two 4-, 5-, 6-, and 7-membered phosphacycle or azacycle rings is chiral. In some embodiments, at least one of the carbon atoms in at least one of the one or two 4-, 5-, 6-, and 7-membered phosphacycle or azacycle rings is chiral. In some embodiments, at least one of the carbon atoms in each of the one or two 4-, 5-, 6-, and 7-membered phosphacycle or azacycle rings is chiral. In some embodiments, at least two of the carbon atoms in any one of the 4-, 5-, 6-, and 7-membered phosphacycle or azacycle rings are chiral. In some embodiments, at least two of the carbon atoms in at least one of the one or two 4-, 5-, 6-, and 7-membered phosphacycle or azacycle rings are chiral. In some embodiments, at least two of the carbon atoms in each of the one or two 4-, 5-, 6-, and 7-membered phosphacycle or azacycle rings are chiral. In some embodiments, exactly two of the carbon atoms in at least one of the one or two 4-, 5-, 6-, and 7-membered phosphacycle or azacycle rings are chiral. In some embodiments, exactly two of the carbon atoms in each of the one or two 4-, 5-, 6-, and 7-membered phosphacycle or azacycle rings are chiral. In some embodiments, at least three of the carbon atoms in any one of the 4-, 5-, 6-, and 7-membered phosphacycle or azacycle rings are chiral. In some embodiments, at least three of the carbon atoms in at least one of the one or two 4-, 5-, 6-, and 7-membered phosphacycle or azacycle rings are chiral. In some embodiments, at least three of the carbon atoms in each of the one or two 4-, 5-, 6-, and 7-membered phosphacycle or azacycle rings are chiral. In some embodiments, exactly three of the carbon atoms in at least one of the one or two 4-, 5-, 6-, and 7-membered phosphacycle or azacycle rings are chiral. In some embodiments, exactly three of the carbon atoms in each of the one or two 4-, 5-, 6-, and 7-membered phosphacycle or azacycle rings are chiral. In some embodiments, at least four of the carbon atoms in any one of the 5-, 6-, and 7-membered phosphacycle or azacycle rings are chiral. In some embodiments, at least four of the carbon atoms in at least one of the one or two 5-, 6-, and 7-membered phosphacycle or azacycle rings are chiral. In some embodiments, at least four of the carbon atoms in each of the one or two 5-, 6-, and 7-membered phosphacycle or azacycle rings are chiral. In some embodiments, exactly four of the carbon atoms in at least one of the one or two 5-, 6-, and 7-membered phosphacycle or azacycle rings are chiral. In some embodiments, exactly four of the carbon atoms in each of the one or two 5-, 6-, and 7-membered phosphacycle or azacycle rings are chiral. The ligating compound-chromium complex may or may not be optically active.

Preferably, when the ligating compound-chromium complex contains only one 4-, 5-, 6-, and 7-membered phosphacycle ring and no azacycle ring attached to $[L(R_5)_q]_p$, one, preferably two, L atoms in the phosphacycle ring attached to the P atom in the phosphacycle ring which is attached to $[L(R_5)_q]_p$ are carbon, and one, more preferably two, of these L atoms are chiral. Preferably, when the ligating compound-chromium complex contains two 4-, 5-, 6-, and 7-membered phosphacycle or azacycle rings attached to $[L(R_5)_q]_p$, one to four L atoms in the phosphacycle or azacycle rings attached to the P or N atoms in the phosphacycle or azacycle rings which are attached to $[L(R_5)_q]_p$ are carbon atoms, and one, preferably two, more preferably three, most preferably four of these L atoms are chiral.

In some embodiments, none of the 4-, 5-, 6-, and 7-membered phosphacycle or azacycle rings of the invention is chiral, preferably one or more 4-membered rings have chiral carbon atoms at the 2- and 4-positions, preferably both chiral carbon atoms have the R configuration or both have the S configuration; one or more 5-membered rings have chiral carbon atoms at the 2- and 5-positions, preferably both chiral carbon atoms have the R configuration or both have the S configuration; one or more 6-membered rings have chiral carbon atoms at the 2- and 6-positions, preferably both chiral carbon atoms have the R configuration or both have the S configuration; and one or more 7-membered rings have chiral carbon atoms at the 2- and 7-positions, preferably both chiral carbon atoms have the R configuration or both have the S configuration. Preferably one, more preferably two, 4-, 5-, 6-, and 7-membered phosphacycle or azacycle rings have exactly two chiral carbon atoms in each ring.

The ligating compound-chromium complexes may comprise a single isomer or mixture of various isomers, including stereoisomers, whether configurational, conformational, geometric, or optical. Mixtures of ligating compound-chromium complexes comprising chiral ligating compound-chromium complexes which are racemic, enantioenriched, or enantiomerically pure are preferred.

The ligating compound-chromium complexes having only one 4-, 5-, 6-, and 7-membered phosphacycle ring and no azacycle ring, and wherein the phosphacycle ring has two chiral carbons, may have the following configurational isomers: R,R; R,S; S,R; and S,S. In an embodiment of the invention, the ligating compound-chromium complex is a mixture of ligating compound-chromium complexes substantially comprising the R,S and S,R isomers of a single ligating compound-chromium complex in any proportion, more preferably the ligating compound-chromium complex is a mixture of ligating compound-chromium complexes substantially comprising the R,R and S,S isomers of a single ligating compound-chromium complex in any proportion.

When the ligating compound-chromium complex contains a ligating compound having one 4-, 5-, 6-, or 7-membered phosphacycle ring and one additional 4-, 5-, 6-, or 7-membered phosphacycle or azacycle ring wherein each ring has two chiral carbons, the ligating compound-chromium complex may have the following configurational isomers: R,R,R,R; R,R,R,S; R,R,S,R; R,S,R,R; S,R,R,R; R,R,S,S; R,S,R,S; S,R,R,S; R,S,S,R; S,R,S,R; S,S,R,R; R,S,S,S; S,R,S,S; S,S,R,S; S,S,S,R; and S,S,S,S; the configurational isomers of the ligating compound-chromium complex are a combination of the configurational isomers of the two phosphacycle and azacycle rings, each having the configurational choices of R,R; R,S; S,R; and S,S; each of the foregoing is an embodiment of the invention. Preferably both phosphacycle or azacycle rings of the ligating compound-chromium complex have the same configuration, for example, both are R,R or R,S or S,R or S,S, whereby preferred isomer configurations of the ligating compound-chromium complex are R,R,R,R; R,S,R,S; S,R,S,R; and S,S,S,S.

In a preferred embodiment of the invention, the ligating compound-chromium complex is a mixture substantially comprising the R,S,R,S and S,R,S,R isomers of a single ligating compound-chromium complex in any proportion, more preferably the ligating compound-chromium complex is a mixture substantially comprising the R,R,R,R and S,S,S,S isomers of a single ligating compound-chromium complex in any proportion.

Preferably $[L(R_5)_q]$ of the phosphacycle or azacycle independently selected is $C(R_5)$, N, $N(R_5)$, or $C(R_5)_2$; $X_1$ is phosphorus or nitrogen; t and v are each independently 1, 2, 3, or 4. Preferably one to six $[L(R_5)_q]$ groups of each 4-, 5-, 6-, and 7-membered phosphacycle or azacycle are $C(R_5)$ or $C(R_5)_2$, more preferably $C(R_5)_2$. Preferably at least one, more preferably two, even more preferably three, still more preferably four, $[L(R_5)_q]$ groups of each phosphacycle or azacycle are $C(R_5)_2$. Preferably at least one, more preferably two, $[L(R_5)_q]$ groups of each phosphacycle or azacycle are $C(R_5)$. Preferably one, more preferably two, of the $C(R_5)$ or $C(R_5)_2$ groups of at least one phosphacycle or azacycle are attached to a P or N atom in the phosphacycle or azacycle which is attached to $[L(R_5)_q]_p$. Preferably both $R_5$ groups of the one, more preferably two, $C(R_5)_2$ groups attached to a P or N atom in at least one phosphacycle or azacycle which is attached to $[L(R_5)_q]_p$ are identical; more preferably they are not identical. Preferably exactly one $R_5$ group of at least one, preferably two, $C(R_5)$ or $C(R_5)_2$ groups attached to a P or N atom in at least one phosphacycle or azacycle which is attached to $[L(R_5)_q]_p$ is hydrogen, more preferably exactly one $R_5$ group of at least one, preferably two, $C(R_5)$ or $C(R_5)_2$ groups attached to a P or N atom in at least one phosphacycle or azacycle which is attached to $[L(R_5)_q]_p$ is not hydrogen. Preferably both $C(R_5)$ or $C(R_5)_2$ groups attached to a P or N atom in at least one phosphacycle or azacycle which is attached to $[L(R_5)_q]_p$ are identical to each other. More preferably two $C(R_5)_q$ groups are attached to a P or N atom in each phosphacycle or azacycle which is attached to $[L(R_5)_q]_p$. More preferably all $[L(R_5)_q]$ groups of the phosphacycles or azacycle which are directly attached to the P or N atom in each phosphacycle or azacycle are independently $C(R_5)_q$ as represented by:

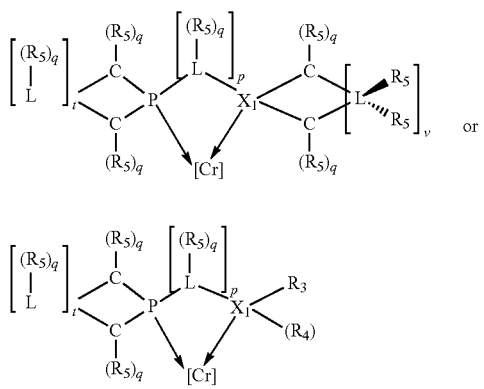

and their enantiomers wherein $C(R_5)_q$ is $C(R_5)$, $C(R_5)_2$, or $C(R_5)H$, preferably $C(R_5)H$; $X_1$ is phosphorus or nitrogen; preferably the $R_5$ groups of the $C(R_5)H$ groups attached to the P or N atom in each phosphacycle or azacycle which is attached to $[L(R_5)_q]_p$ are not hydrogen, and wherein, as mentioned above, both the R-configuration and the S-configuration are meant for $C(R_5)H$; further provided that in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species. Preferably both $C(R_5)H$ groups attached to the P or N atom in the phosphacycle or azacycle which is attached to $[L(R_5)_q]_p$ are the same. Preferably both $C(R_5)H$ groups attached to the P atom in the phosphacycle which is attached to $[L(R_5)_q]_p$ have the same R or S configuration. Preferably when $X_1$ is a P atom and $X_1$, $R_3$, and $R_4$ form a phosphacycle, the phosphacycle is identical to the phosphacycle formed by P, $R_1$ and $R_2$. Preferably the L atoms of phosphacycles or azacycles are independently carbon or nitrogen. Preferably at least two L atoms in each phosphacycle or azacycle are carbon. Preferably t and v are each independently 1, 2, or 3, preferably 1 or 2. Preferably at least one of t and v is 2, more preferably t is 2. In a preferred embodiment, t is 2; and at least one, preferably two, of L in the phosphacycle is carbon. In a preferred embodiment, t is 2; and at least one, preferably two, of L in the phosphacycle is nitrogen. In a preferred embodiment, v is 2; and at least one, preferably two, of L in the ring comprising $X_1$ are carbon. In a preferred embodiment, v is 2; and at least one, preferably two, of L in the ring comprising $X_1$ are nitrogen. More preferably $X_1$ is phosphorus. More preferably t and v are each 2. More preferably t and v are each 2 and $X_1$ is phosphorus. In a preferred embodiment, the $X_1$, $R_3$, and $R_4$ groups of $X_1R_3(R_4)_m$ do not form a cycle, m is 0 or 1, preferably m is 1; preferably $X_1$ is nitrogen, more preferably $X_1$ is phosphorus. In preferred phosphacycle-containing ligating compound-chromium complexes $X_1$ is phosphorus and 5-membered ligating compound-chromium complexes are represented by:

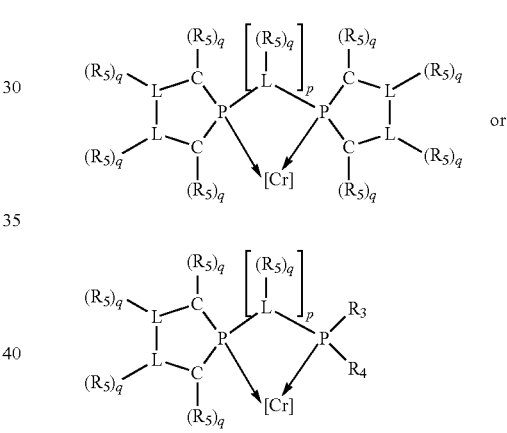

wherein q is 1 or 2; preferably $L(R_5)_q$ of the phosphacycles is $C(R_5)$, $N(R_5)$, or $C(R_5)_2$, preferably $[L(R_5)_q]_p$ is $C(R_5)$, $N(R_5)$, $C(R_5)_2$, $C(R_5)C(R_5)$ or $C(R_5)_2C(R_5)_2$, more preferably $N(R_5)$ or $C(R_5)C(R_5)$; the $C(R_5)_q$ attached to P is $C(R_5)$, $C(R_5)_2$, or $C(R_5)H$, preferably $C(R_5)H$; further provided that in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species. Preferably at least one, more preferably two, phosphacycles contain at least one, preferably two, $[L(R_5)_q]$ groups each which are $C(R_5)$ or $C(R_5)_2$. At most one bond in at least one phosphacycle is an unsaturated bond, preferably all bonds in at least one phosphacycle are saturated bonds. Preferably at least one, preferably two, 5-membered phosphacycles are saturated, meaning they contain no unsaturated bonds. Preferably one 5-membered phosphacycle is saturated, and one phosphacycle, preferably one 5-membered phosphacycle, has two unsaturated bonds, preferably exactly one unsaturated bond. Preferably one 5-membered phosphacycle has exactly one unsaturated bond, and one phosphacycle, preferably one 5-membered phosphacycle, has two unsaturated bonds, preferably exactly one unsaturated bond, more preferably no unsaturated bonds. Preferably the unsaturated bonds are carbon-carbon unsaturated bonds. Preferably the unsaturated bonds are carbon-nitrogen unsaturated bonds.

Preferred 5-membered phosphacycles of the phosphacycle-containing ligating compound-chromium complex are independently selected, as represented by:

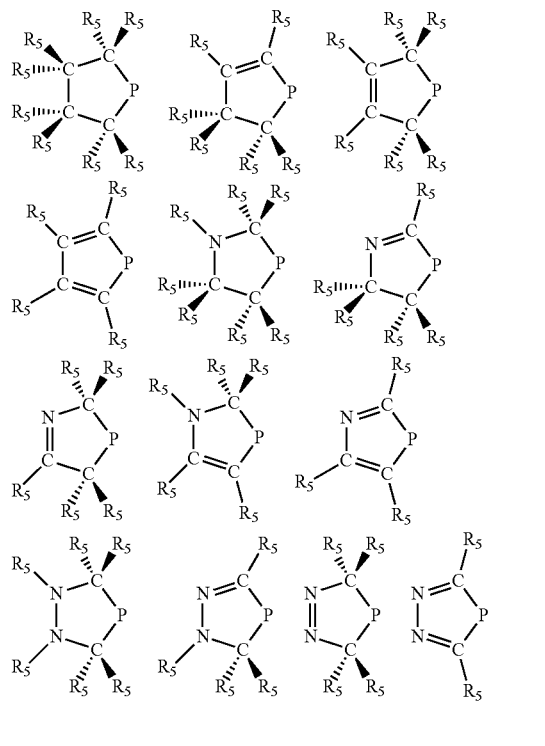

and their enantiomers.

Preferred 5-membered ring phosphacycle-containing ligating compound-chromium complexes may be built up by independently selecting one preferred 5-membered phosphacycle from above, connecting it to one valence of the $[L(R_5)_q]_p$ divalent linking group, and connecting the remaining free valence of the divalent linking group either to a second independently selected phosphacycle, preferably a preferred 5-membered phosphacycle from above, or to $X_1R_3R_4$, wherein $X_1$ is phosphorus or nitrogen, preferably phosphorus, to form a ligating compound and then combining the ligating compound with a source of chromium to introduce the [Cr] group.

Non-limiting examples of preferred non-5-membered ring phosphacycle-containing ligating compound-chromium complexes are represented by:

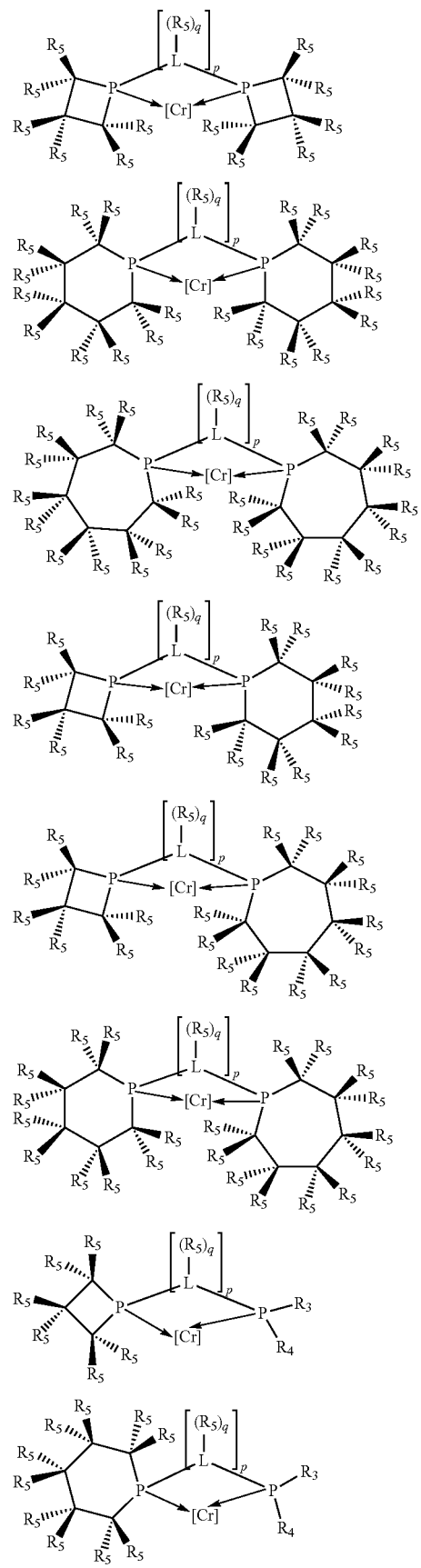

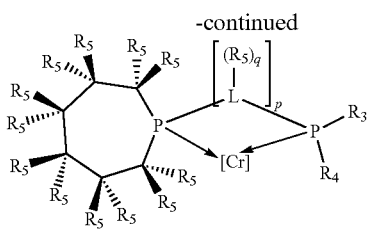

and their enantiomers wherein in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species. Preferably the $[L(R_5)_q]_p$ divalent linking group is $NR_5$, $C(R_5)$, $C(R_5)C(R_5)$, $C(R_5)_2$ or $C(R_5)_2C(R_5)_2$, preferably $N(R_5)$.

Non-limiting examples of the preferred 5-membered ring phosphacycle-containing ligating compound-chromium complexes are represented by

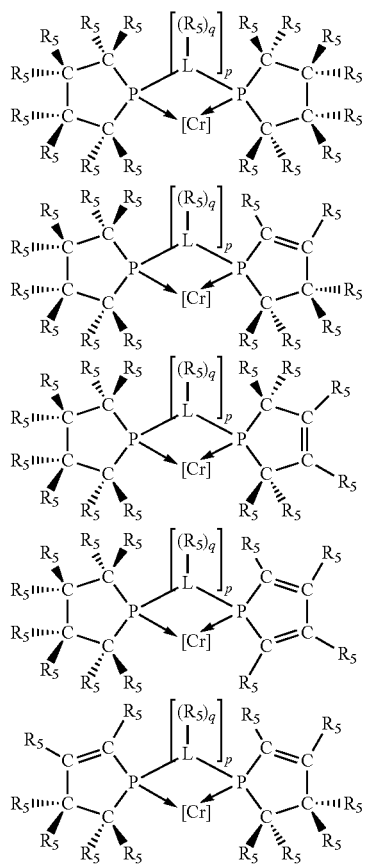

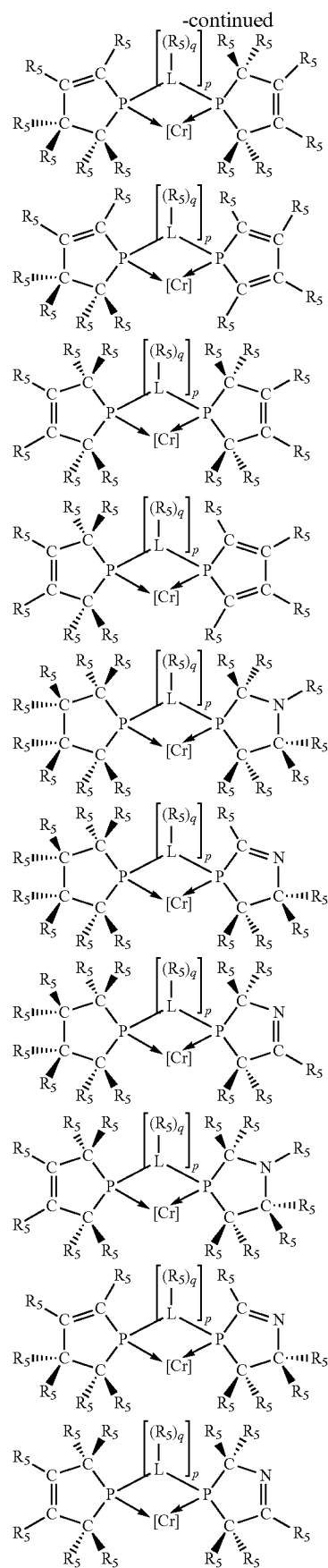

-continued
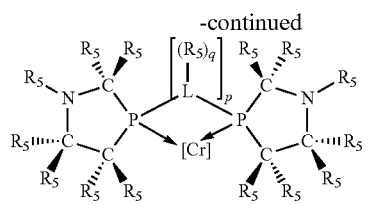
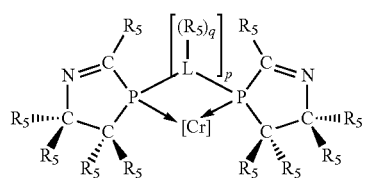
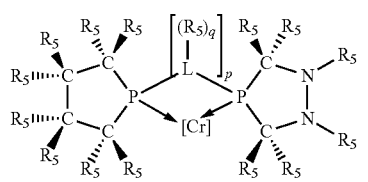
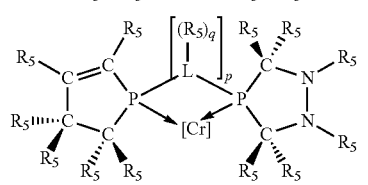
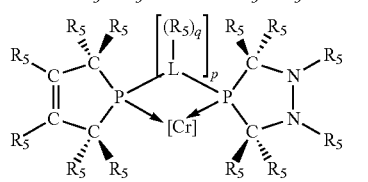
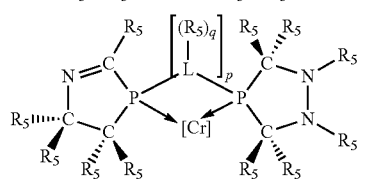
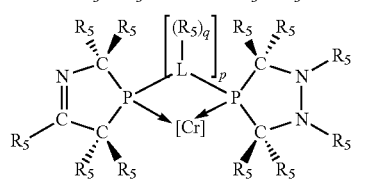
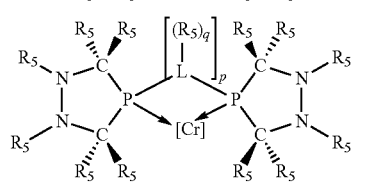
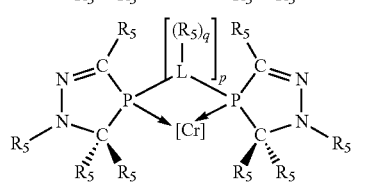
-continued
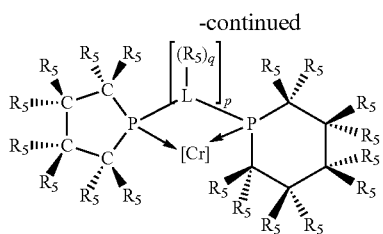
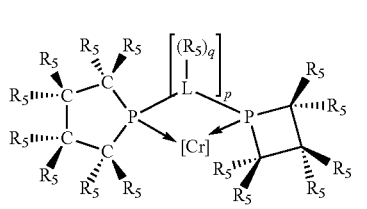
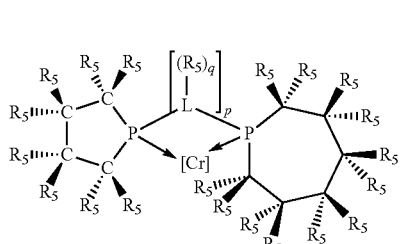
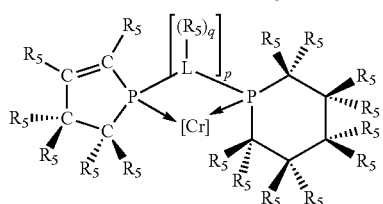
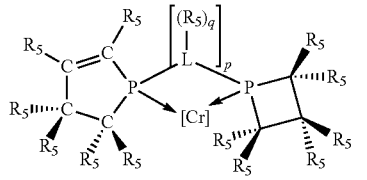
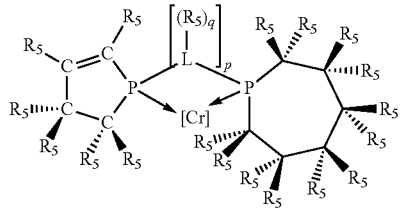
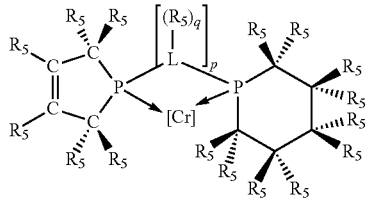
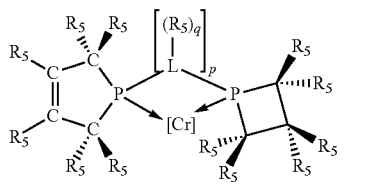

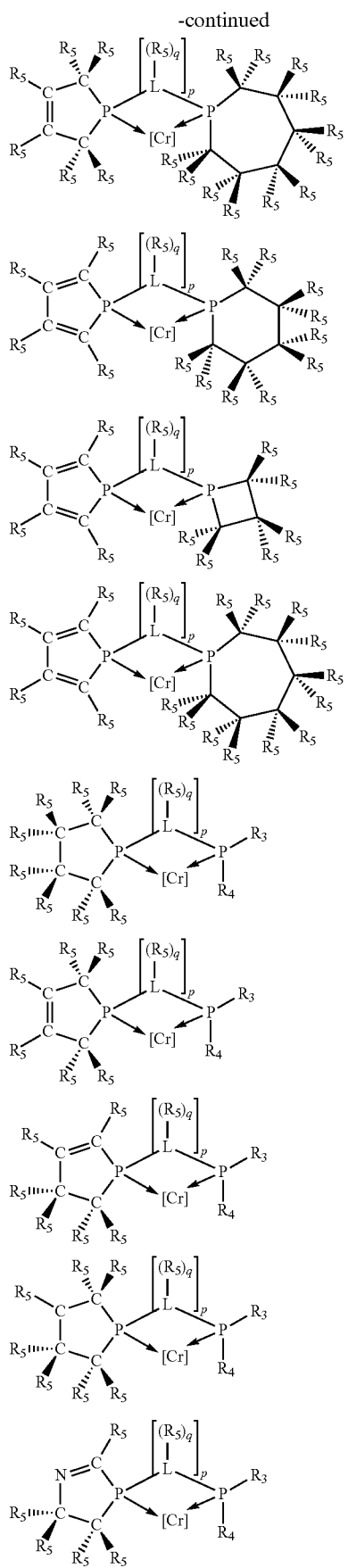

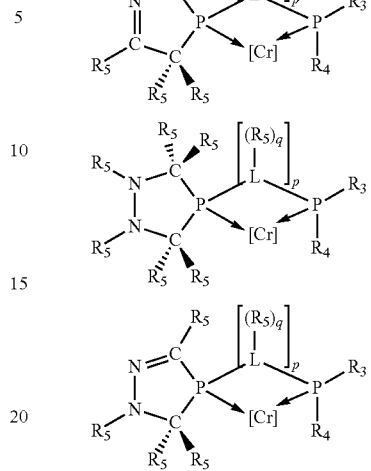

and their enantiomers wherein in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species. Preferably the $[L(R_5)_q]_p$ divalent linking group is $NR_5$, $C(R_5)$, $C(R_5)C(R_5)$, $C(R_5)_2$ or $C(R_5)_2C(R_5)_2$, preferably $N(R_5)$.

Preferably exactly one $R_5$ group in at least one, preferably two, $C(R_5)$ or $C(R_5)_2$ groups attached to the P atom in at least one, preferably two, phosphacycles is hydrogen.

Representative, but not limiting, examples are:

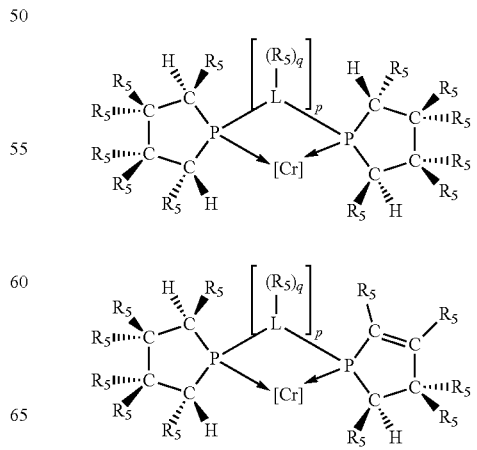

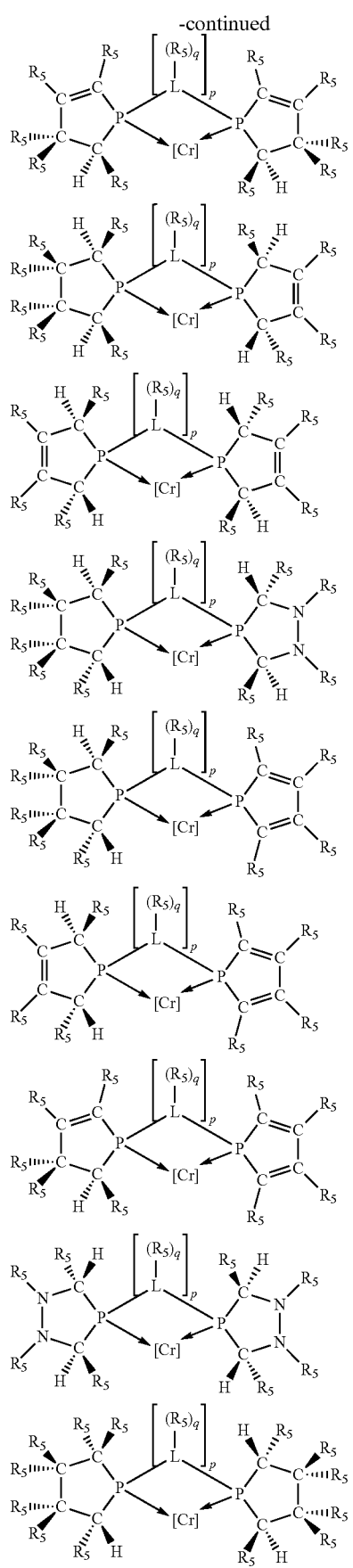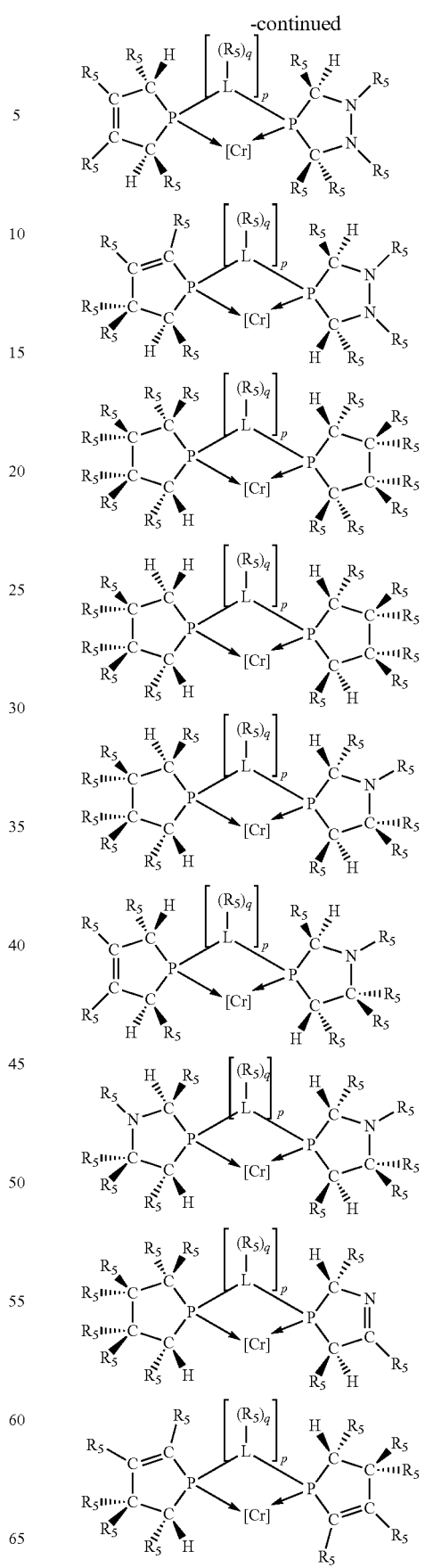

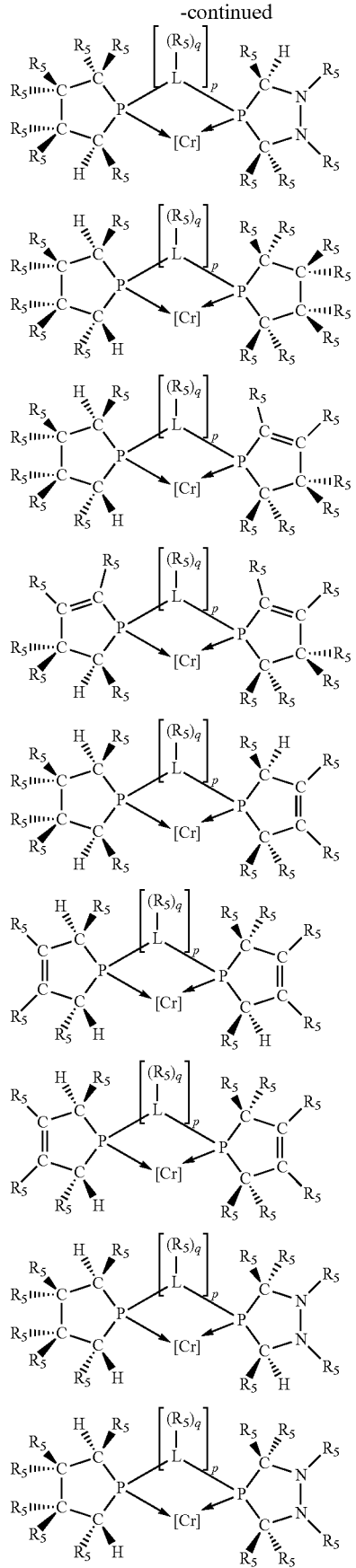
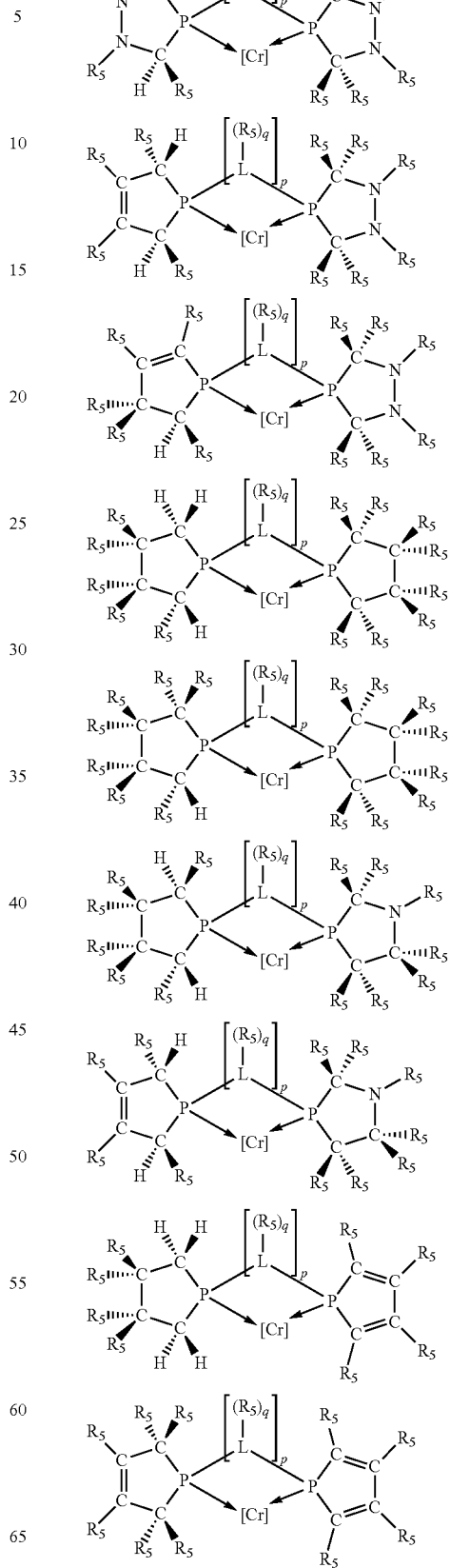

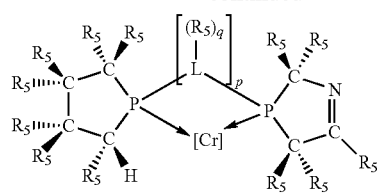
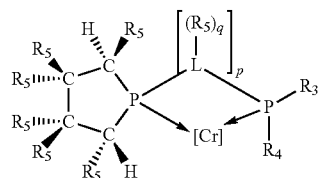
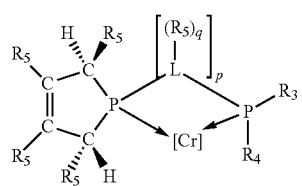
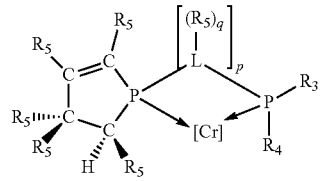
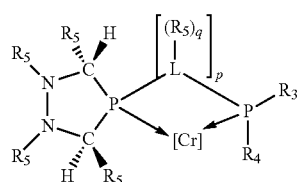
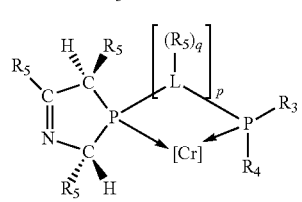
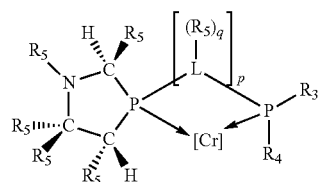
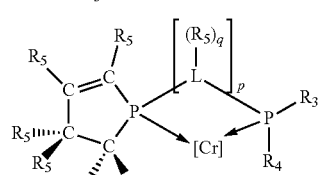
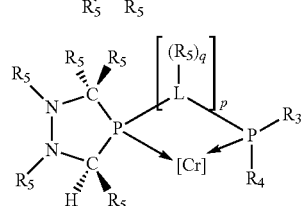
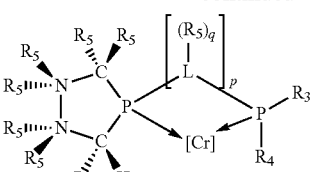
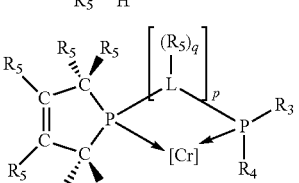
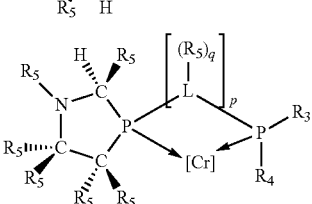
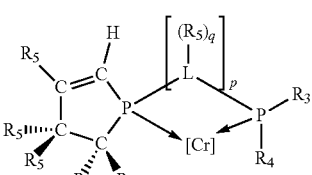
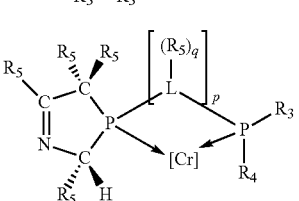
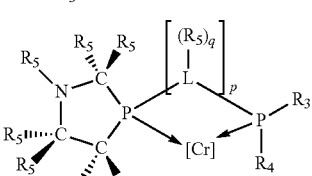
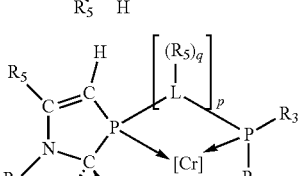
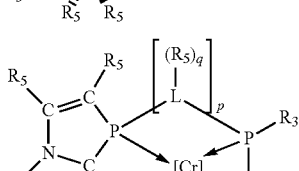
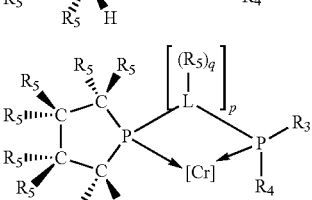

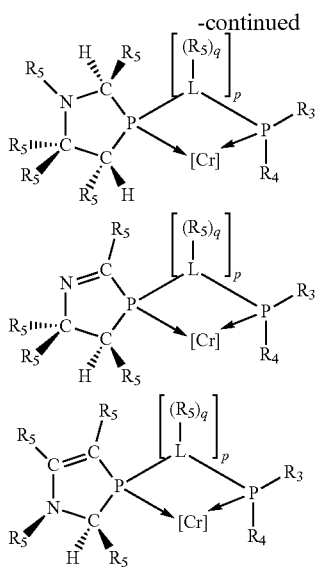

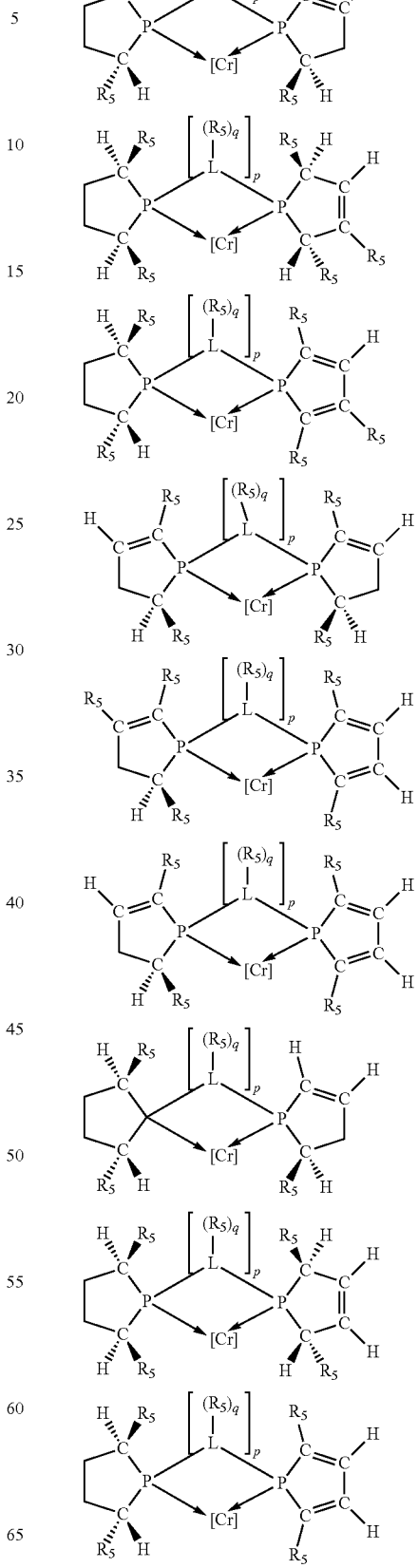

and their enantiomers wherein in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species.

Preferably any $R_5$ groups attached to the nitrogen atoms in the 5-membered phosphacycles are not hydrogen, preferably any $R_5$ groups attached to the nitrogen atoms in the 5-membered phosphacycles are hydrocarbyl, preferably $C_{1-4}$ alkyl, $C_{6-10}$ aryl, or $C_{7-10}$ arylalkyl, more preferably methyl, ethyl, phenyl, benzyl, or tolyl; preferably the $R_5$ groups attached to the ring carbon atom of the $C(R_5)$ or $C(R_5)_2$ groups at the 3- and 4-positions on the 5-membered phosphacycle are hydrogen atoms; preferably the $R_5$ groups attached to at least one of the ring carbon atoms of the $C(R_5)$ groups, wherein the ring carbon atoms of the $C(R_5)$ groups are bonded to another ring atom by means of an unsaturated bond, preferably carbon-carbon unsaturated bond, are hydrogen atoms or are part of an aromatic ring which is fused to the phosphacycle.

Representative, but not limiting, examples are:

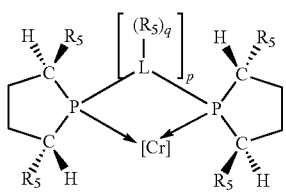

-continued
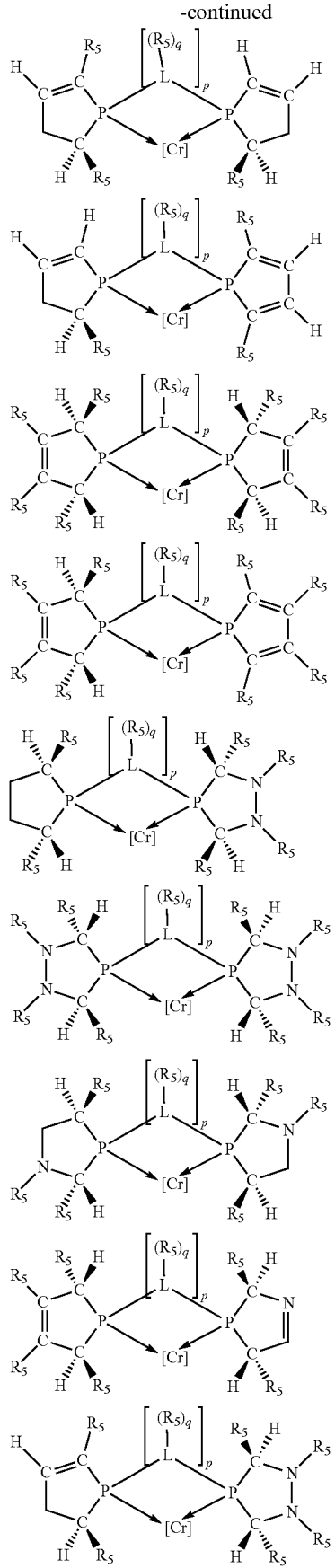
-continued
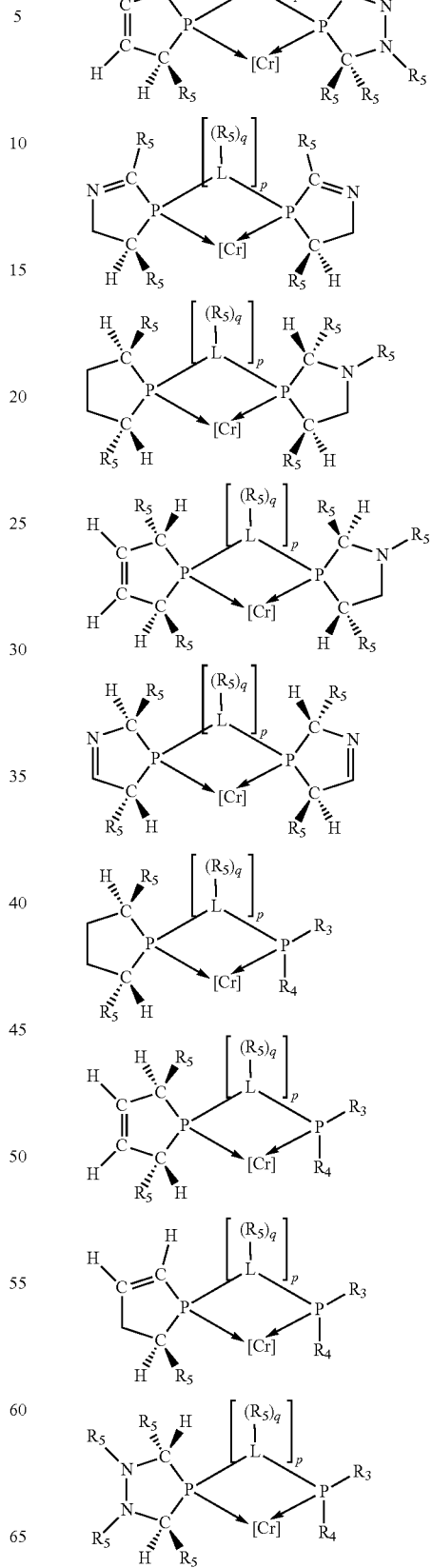

-continued
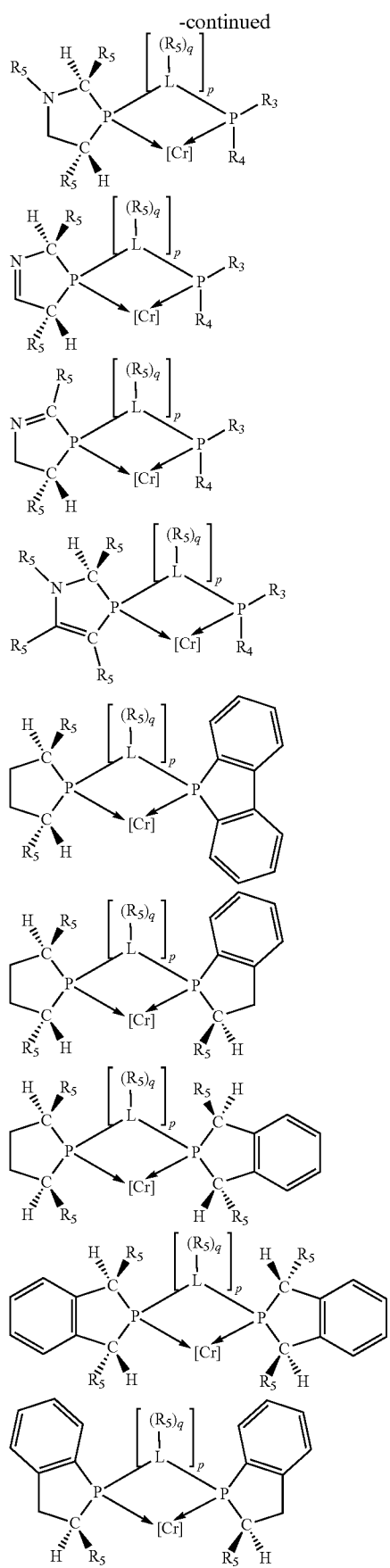
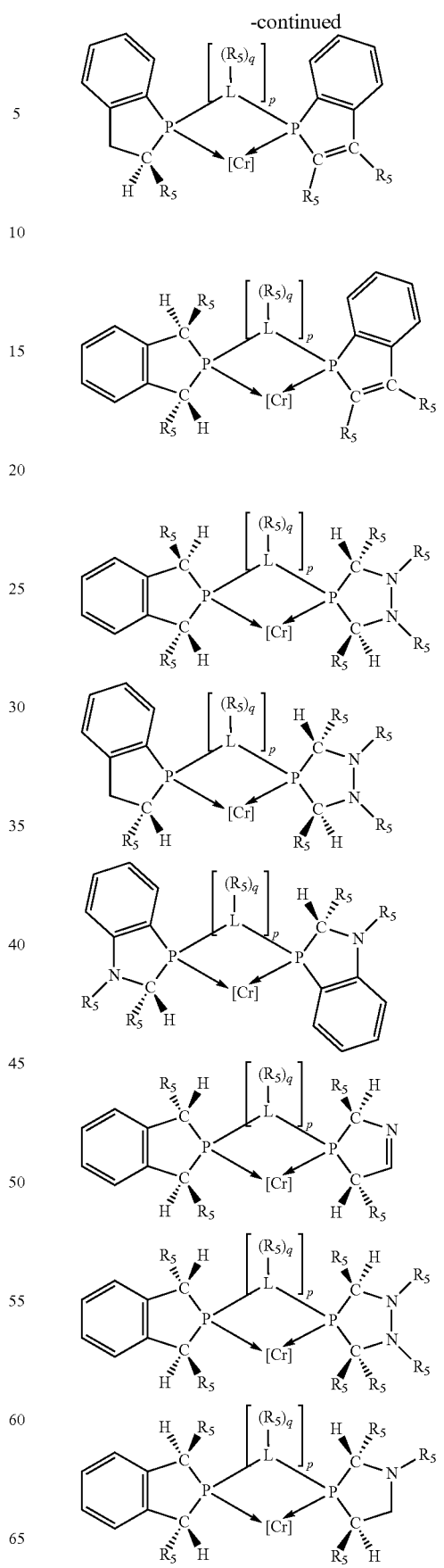

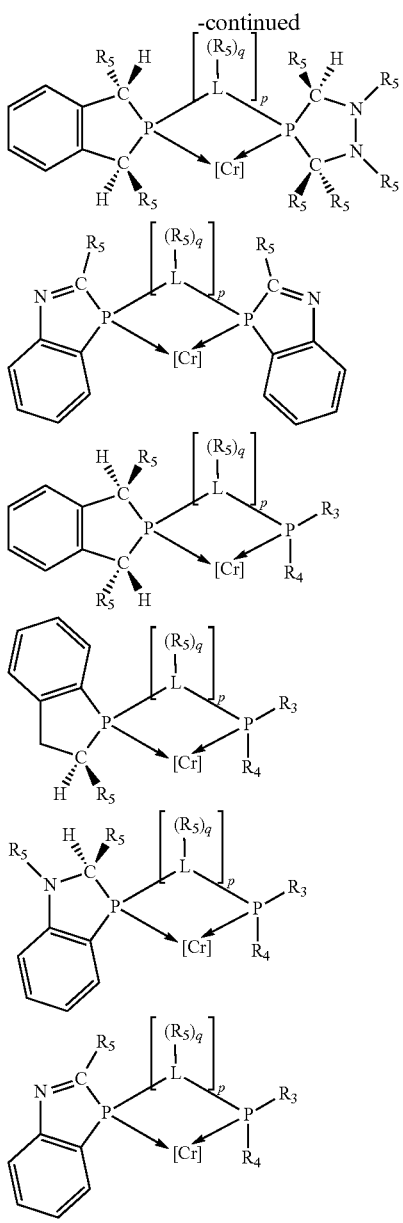

and their enantiomers.

Preferably at least one, preferably two, of the $R_5$ groups attached to the ring carbon atom of the $C(R_5)$ or $C(R_5)_2$ groups at the 2- and 5-positions on the 5-membered phosphacycle are independently alkyl, substituted alkyl, aryl, substituted aryl, arylalkyl, substituted arylalkyl, heteroaryl, or substituted heteroaryl, preferably aryl, substituted aryl, heteroaryl, or substituted heteroaryl, preferably aryl or substituted aryl; preferably exactly one $R_5$ group attached to the ring carbon atom of the $C(R_5)$ or $C(R_5)_2$ group at each 2-position and at each 5-position on the 5-membered phosphacycle is alkyl, substituted alkyl, aryl, substituted aryl, arylalkyl, substituted arylalkyl, heteroaryl, or substituted heteroaryl, preferably aryl, substituted aryl, heteroaryl, or substituted heteroaryl, more preferably aryl or substituted aryl; preferably exactly one $R_5$ group attached to the ring carbon atom of any $C(R_5)_2$ groups at each 2-position and at each 5-position on the 5-membered phosphacycle is independently hydrogen, methyl, ethyl, propyl, butyl, or pentyl, preferably hydrogen or methyl, more preferably hydrogen; preferably $R_3$ and $R_4$ are independently alkyl, substituted alkyl, aryl, substituted aryl, arylalkyl, substituted arylalkyl, heteroaryl, or substituted heteroaryl, preferably aryl, substituted aryl, heteroaryl, or substituted heteroaryl, more preferably aryl or substituted aryl; preferably exactly one $R_5$ group attached to the ring carbon atom of the $C(R_5)$ or $C(R_5)_2$ group at each 2-position and at each 5-position on the 5-membered phosphacycle is independently aryl or substituted aryl, exactly one $R_5$ group attached to the ring carbon atom of any $C(R_5)_2$ groups at each 2-position and at each 5-position on the 5-membered phosphacycle is a hydrogen, and $R_3$ and $R_4$ are independently alkyl, aryl, substituted aryl, arylalkyl, substituted arylalkyl, heteroaryl, or substituted heteroaryl, preferably aryl, substituted aryl, heteroaryl, or substituted heteroaryl, more preferably aryl or substituted aryl. Preferably the aryl, substituted aryl, heteroaryl, or substituted heteroaryl groups at the 2-position and the 5-position on the 5-membered phosphacycle are identical. Preferably $R_3$, $R_4$, and $R_5$ are each independently $C_{1-40}$ substituted or unsubstituted alkyl, preferably $C_{1-20}$ substituted or unsubstituted alkyl, more preferably $C_{1-12}$ substituted or unsubstituted alkyl; $C_{2-40}$ substituted or unsubstituted aryl, preferably $C_{2-20}$ substituted or unsubstituted aryl, more preferably $C_{2-12}$ substituted or unsubstituted aryl; $C_{2-40}$ substituted or unsubstituted arylalkyl, preferably $C_{2-20}$ substituted or unsubstituted arylalkyl, more preferably $C_{2-12}$ substituted or unsubstituted arylalkyl; $C_{2-40}$ substituted or unsubstituted heteroaryl, preferably $C_{2-20}$ substituted or unsubstituted heteroaryl, more preferably $C_{2-12}$ substituted or unsubstituted heteroaryl; preferably $R_5$ independently is $C_{1-4}$ alkyl, $C_{6-10}$ aryl, or $C_{7-10}$ arylalkyl when $R_5$ is attached to a ring nitrogen atom of the 5-membered ring phosphacycle; further provided that in at least one phosphacycle of the phosphacycle-containing ligating compound, both atoms directly bonded to P or $X_1$ are $sp^3$ hybridized; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species.

In a preferred embodiment, $R_3$, $R_4$, and $R_5$ attached to a ring nitrogen atom of the 5-membered ring phosphacycle are Ar, $R_5$ attached to a ring nitrogen atom of the 5-membered ring phosphacycle is Ar', wherein Ar independently is $C_{2-40}$ substituted or unsubstituted aryl, preferably $C_{2-20}$ substituted or unsubstituted aryl, more preferably $C_{2-12}$ substituted or unsubstituted aryl; $C_{2-40}$ substituted or unsubstituted arylalkyl, preferably $C_{2-20}$ substituted or unsubstituted arylalkyl, more preferably $C_{2-12}$ substituted or unsubstituted arylalkyl; $C_{2-40}$ substituted or unsubstituted heteroaryl, preferably $C_{2-20}$ substituted or unsubstituted heteroaryl, more preferably $C_{2-12}$ substituted or unsubstituted heteroaryl, and Ar' independently is $C_{1-4}$ alkyl, $C_{6-10}$ aryl, or $C_{7-10}$ arylalkyl.

In preferred ligating compound-chromium complexes L of the phosphacycles is carbon and 5-membered ligating compound-chromium complexes are represented by:

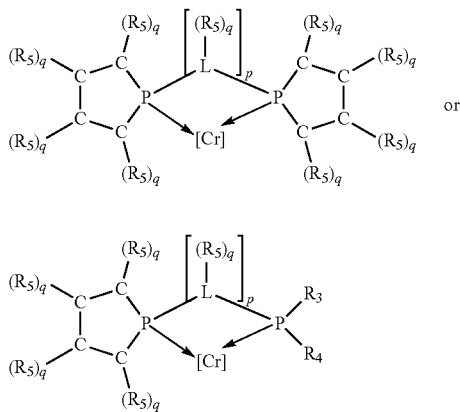

wherein q is 1 or 2; preferably $[L(R_5)_q]_p$ is $C(R_5)$, $N(R_5)$, $C(R_5)_2$, $C(R_5)C(R_5)$ or $C(R_5)_2C(R_5)_2$, more preferably $N(R_5)$ or $C(R_5)C(R_5)$; the $C(R_5)_q$ attached to P is $C(R_5)$, $C(R_5)_2$, or $C(R_5)H$, preferably $C(R_5)H$.

In preferred ligating compound-chromium complexes, $[L(R_5)_q]_p$ of the divalent linking group is $NR_5$ and 5-membered phosphacycle-containing ligating compound-chromium complexes are represented by:

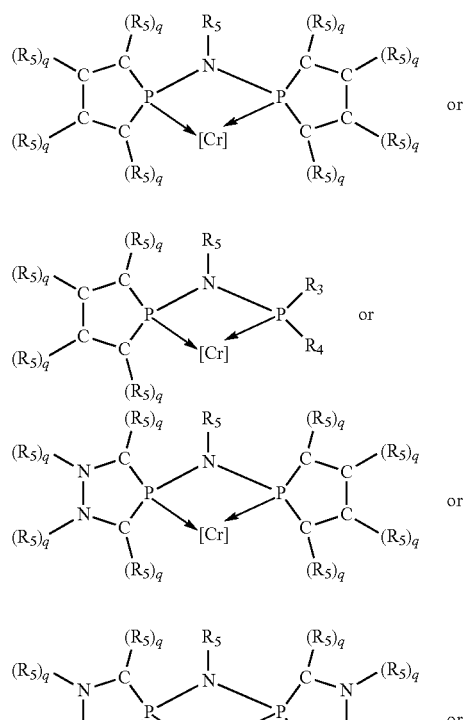

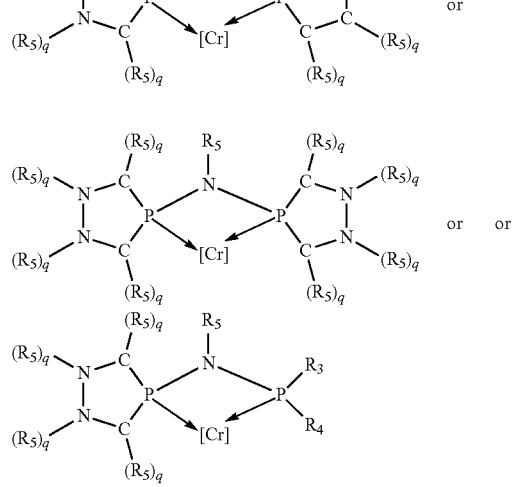

wherein q is 1 or 2; the $C(R_5)_q$ attached to P is $C(R_5)$, $C(R_5)_2$, or $C(R_5)H$, preferably $C(R_5)H$.

In preferred ligating compound-chromium complexes, $[L(R_5)_q]$ at the 3- and 4-positions of the phosphacycle ring are $CH_2$; $[L(R_5)_q]$ at the 2- and 5-positions of the phosphacycle ring are $CR_5H$; $[L(R_5)_q]_p$ of the divalent linking group is $NR_5$, and 5-membered phosphacycle-containing ligating compound-chromium complexes are represented by:

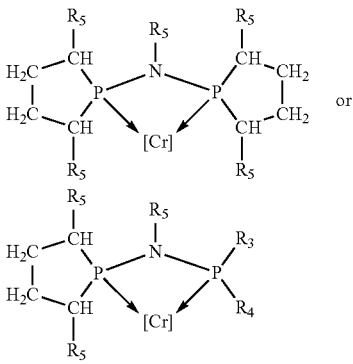

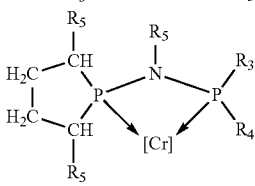

In preferred ligating compound-chromium complexes, $[L(R_5)_q]$ at the 2- and 5-positions of the phosphacycle ring are $CR_5H$; the carbon atoms at the 2- and 5-positions are chiral; preferably both carbon atoms at the 2- and 5-positions in each phosphacycle ring have the same R or S configuration; $[L(R_5)_q]_p$ of the divalent linking group is $NR_5$; preferably $[L(R_5)_q]$ at the 3- and 4-positions of the phosphacycle ring are $CH_2$, and 5-membered phosphacycle-containing ligating compound-chromium complexes are represented by:

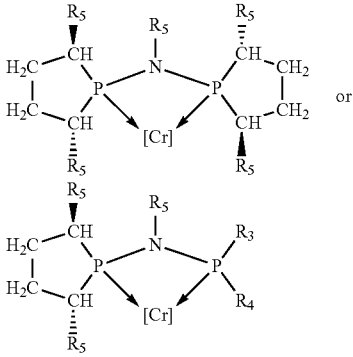

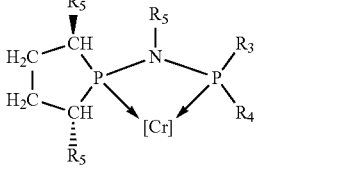

and their enantiomers.

Non-limiting examples of the phosphacycle-containing ligating compound-chromium complexes are:

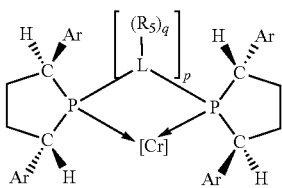

181
-continued
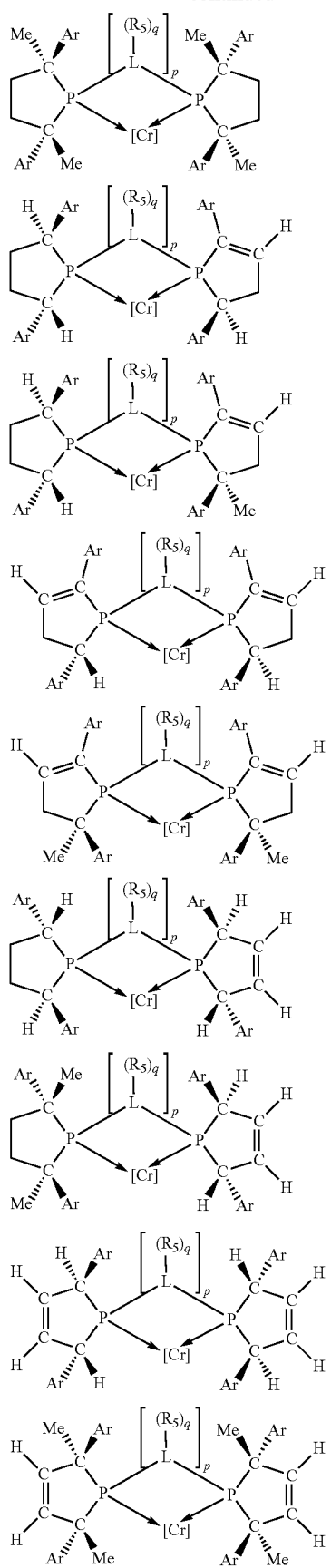
182
-continued
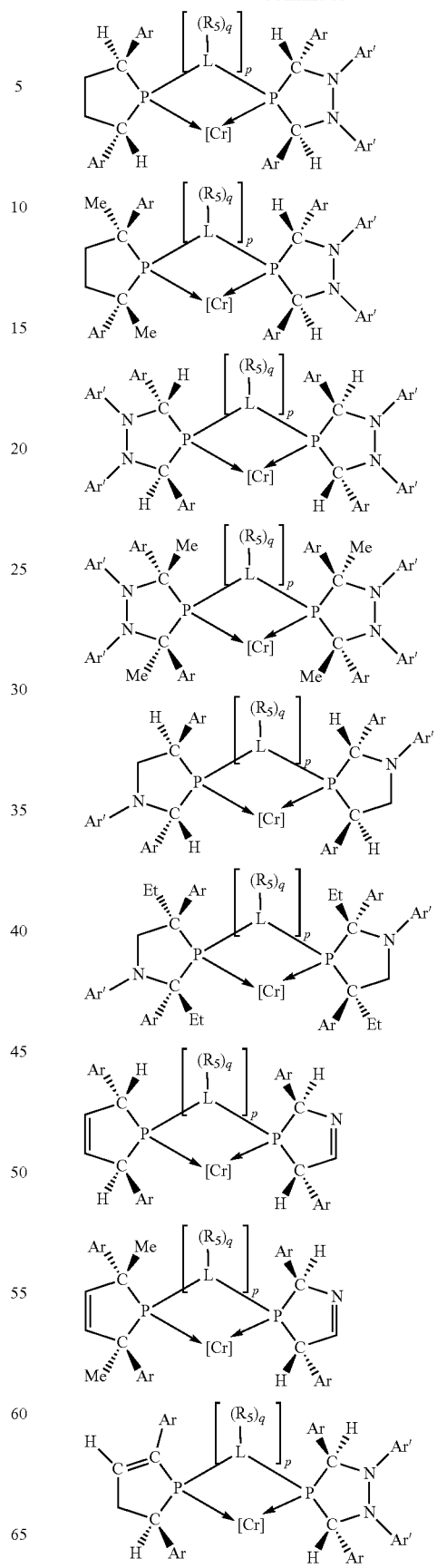

-continued
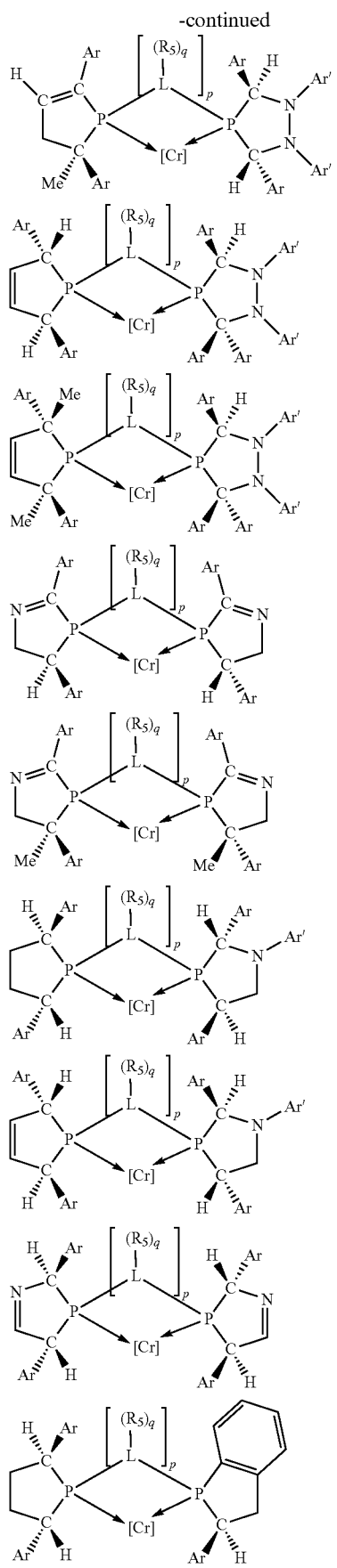
-continued
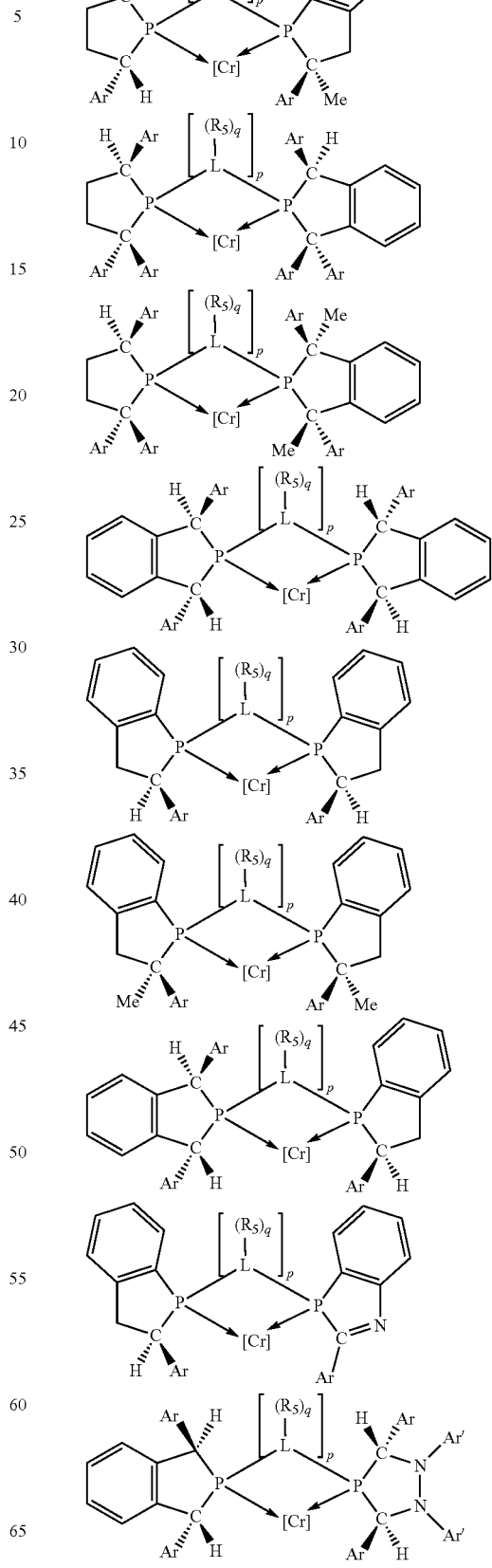

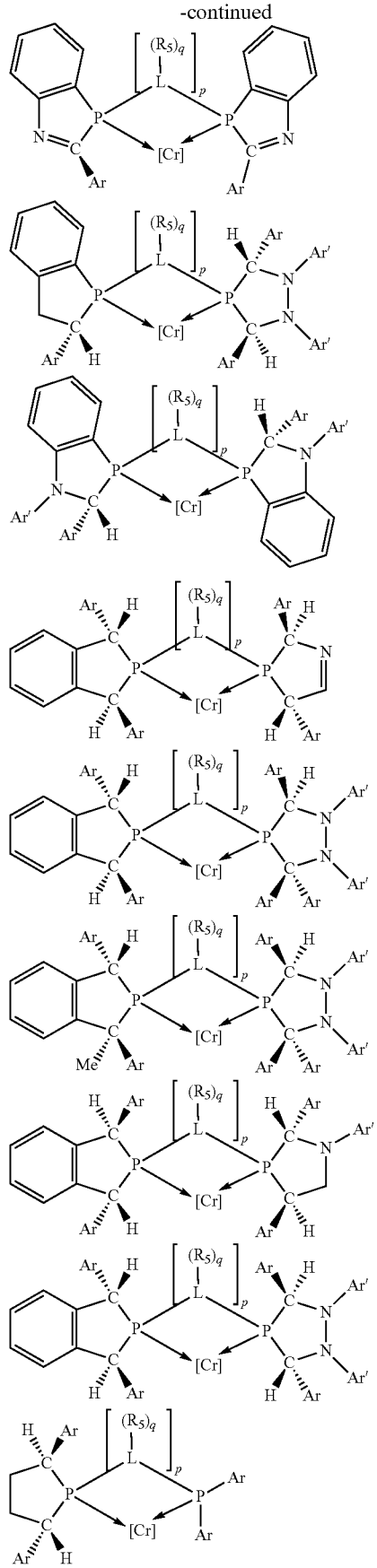
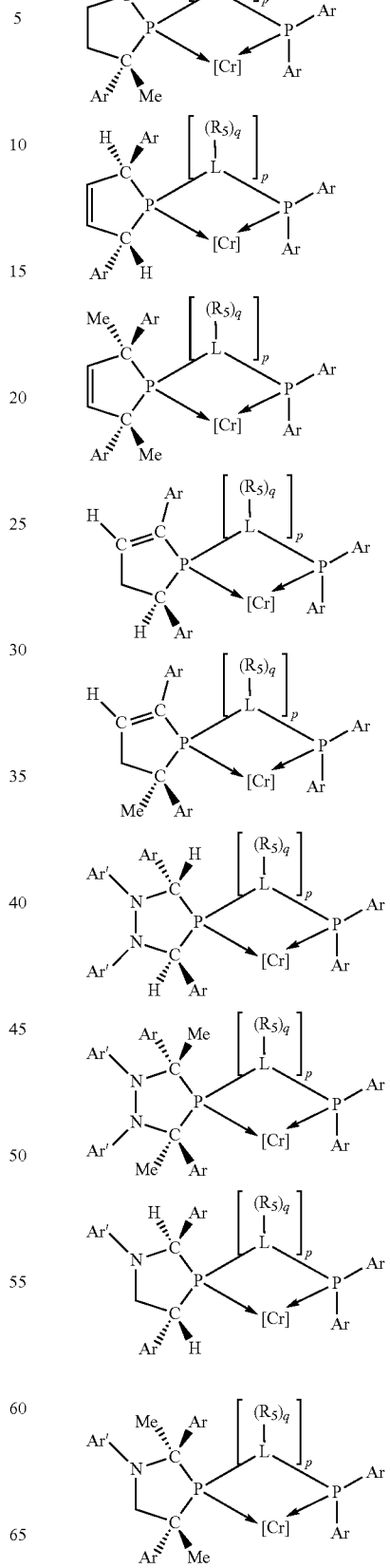

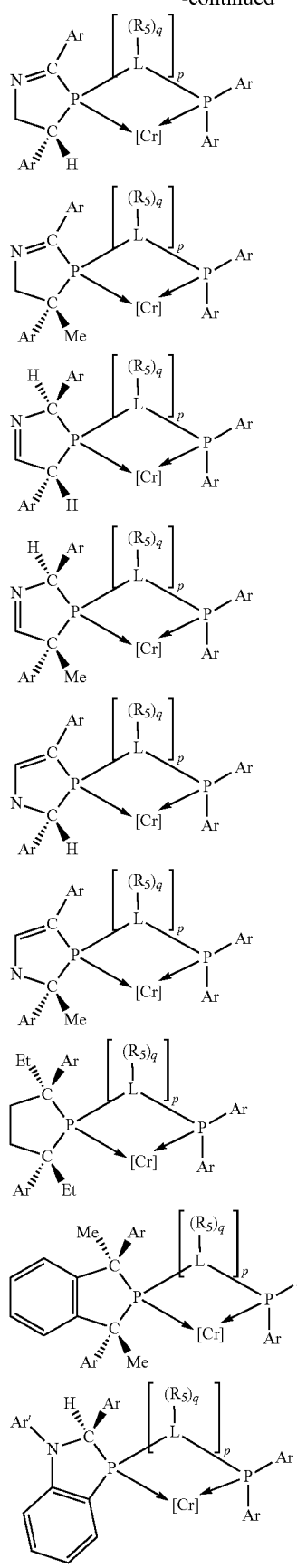
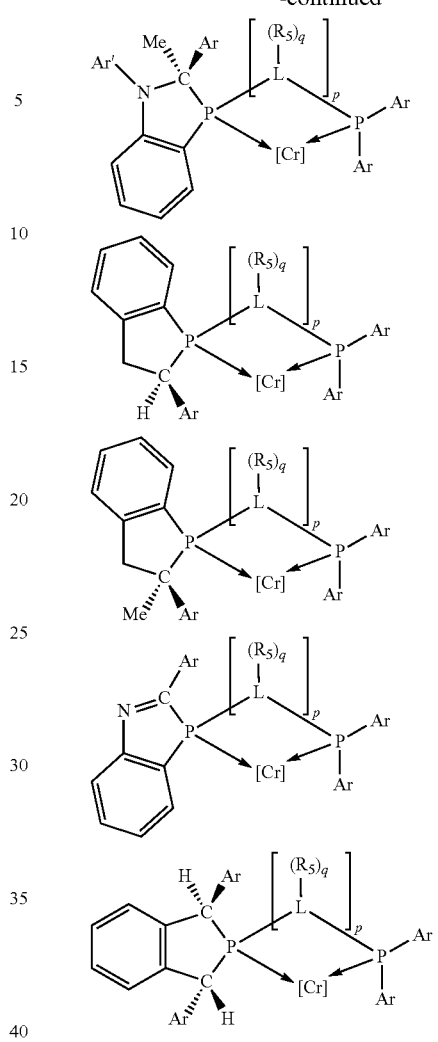

and their enantiomers.

In preferred phosphacycle-containing ligating compound chromium complexes, Ar at the 2- and 5-positions of the phosphacycle rings is phenyl optionally substituted with $R_5$; $[L(R_5)_q]_p$ of the divalent linking group is $NR_5$; preferably $[L(R_5)_q]$ at the 3- and 4-positions of the phosphacycle ring are $CH_2$, and 5-membered phosphacycle-containing ligating compound chromium complexes are represented as:

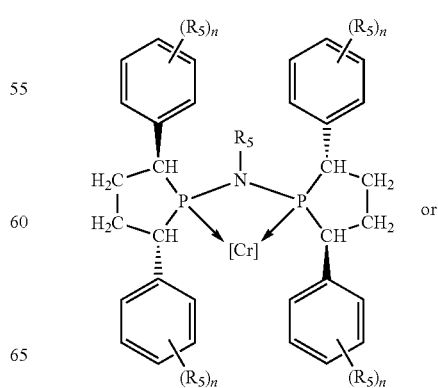

or

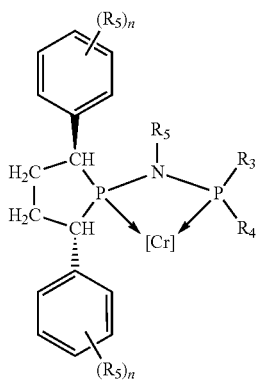

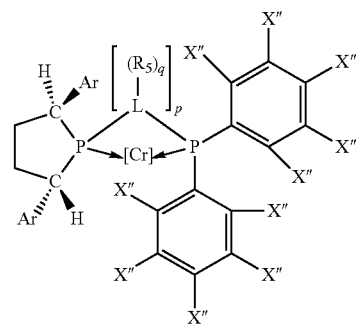

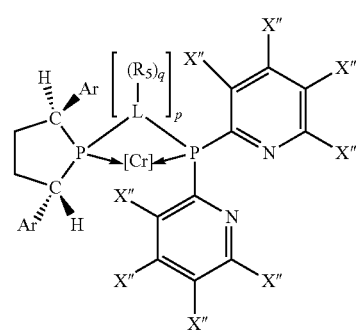

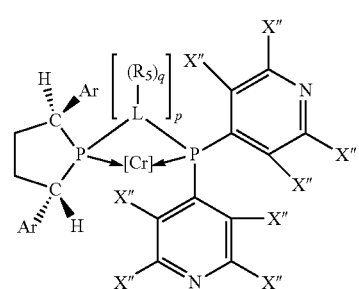

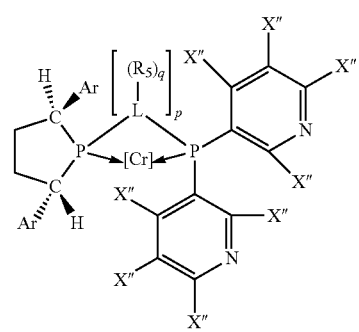

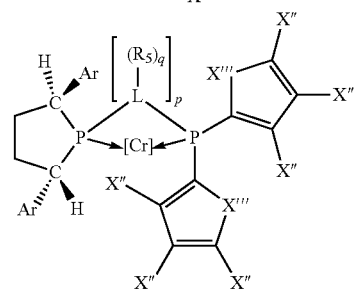

and their enantiomers wherein n independently selected is an integer from zero to five, preferably from zero to three.

Preferably Ar independently is $C_{2-40}$ substituted or unsubstituted aryl, preferably $C_{2-20}$ substituted or unsubstituted aryl, more preferably $C_{2-12}$ substituted or unsubstituted aryl; $C_{2-40}$ substituted or unsubstituted heteroaryl, preferably $C_{2-20}$ substituted or unsubstituted heteroaryl, more preferably $C_{2-12}$ substituted or unsubstituted heteroaryl; preferably Ar is independently phenyl, substituted phenyl, furanyl, substituted furanyl, thienyl, substituted thienyl, pyrrolyl, substituted pyrrolyl, pyridinyl, and substituted pyridinyl, more preferably phenyl, substituted phenyl, and furanyl; further provided that in at least one phosphacycle of the phosphacycle-containing ligating compound, both atoms directly bonded to P or $X_1$ are $sp^3$ hybridized; two or more Ar, Ar' or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected Ar, Ar' or $R_5$ groups to form a poly(ligating compound-chromium complex) species. When $PR_3R_4$ is non-cyclic (i.e., it does not form a phosphacycle), the atom of each $R_3$ or $R_4$ group directly attached to the phosphorus-atom is considered to be at the 1-position of that particular group for the purpose of numbering the positions of atoms or substituents in the $R_3$ or $R_4$ group. In a preferred embodiment of the ligating compound-chromium complexes wherein the $PR_3R_4$ group is non-cyclic, $R_3$ and $R_4$ independently are represented by alkyl, substituted alkyl, phenyl, substituted phenyl, furanyl, substituted furanyl, thienyl, substituted thienyl, pyrrolyl, substituted pyrrolyl, pyridinyl, and substituted pyridinyl; preferably the phosphacycle-containing ligating compound chromium complexes are represented by -continued

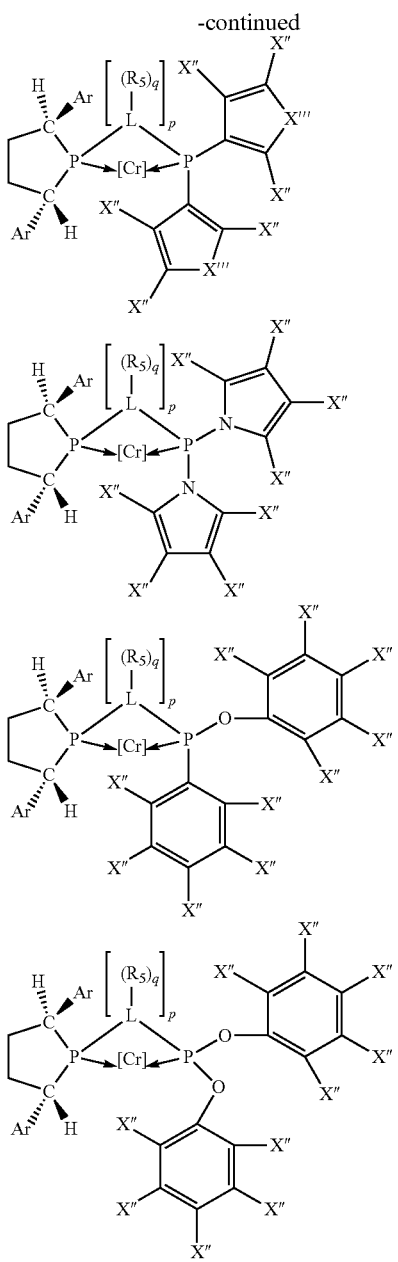

and their enantiomers wherein Ar independently is halogen; $C_{1-40}$ substituted or unsubstituted alkyl, preferably $C_{1-20}$ substituted or unsubstituted alkyl, more preferably $C_{1-12}$ substituted or unsubstituted alkyl, even more preferably $C_{1-6}$ substituted or unsubstituted alkyl, especially methyl, trifluoromethyl, methoxy, ethyl, ethoxy, propyl, isopropyl, n-butyl, i-butyl, s-butyl, t-butyl, pentyl, hexyl; $C_{2-40}$ substituted or unsubstituted aryl, preferably $C_{2-20}$ substituted or unsubstituted aryl, more preferably $C_{2-12}$ substituted or unsubstituted aryl, especially phenyl, fluorophenyl, difluorophenyl, trifluorophenyl, tolyl, dimethylphenyl, t-butylphenyl, di-t-butylphenyl, methoxyphenyl, ethoxyphenyl, di-t-butyl-methoxyphenyl, cyanophenyl, nitrophenyl; $C_{2-40}$ substituted or unsubstituted heteroaryl, preferably $C_{2-20}$ substituted or unsubstituted heteroaryl, more preferably $C_{2-12}$ substituted or unsubstituted heteroaryl, especially substituted or unsubstituted pyridyl, thienyl, furanyl, pyrrolyl; X" independently is hydrogen; halogen, preferably fluorine, chlorine or bromine, more preferably fluorine or chlorine, even more preferably fluorine; $C_{1-40}$ substituted or unsubstituted alkyl, preferably $C_{1-20}$ substituted or unsubstituted alkyl, more preferably $C_{1-12}$ substituted or unsubstituted alkyl, even more preferably $C_{1-6}$ substituted or unsubstituted alkyl, especially methyl, trifluoromethyl, methoxy, ethyl, ethoxy, propyl, isopropyl, n-butyl, i-butyl, s-butyl, t-butyl, pentyl, hexyl; $C_{2-40}$ substituted or unsubstituted aryl, preferably $C_{2-20}$ substituted or unsubstituted aryl, more preferably $C_{2-12}$ substituted or unsubstituted aryl, especially phenyl, fluorophenyl, difluorophenyl, trifluorophenyl, tolyl, dimethylphenyl; $C_{2-40}$ substituted or unsubstituted arylalkyl, preferably $C_{2-20}$ substituted or unsubstituted arylalkyl, more preferably $C_{2-12}$ substituted or unsubstituted arylalkyl, especially benzyl, phenethyl, and methylbenzyl; nitro or cyano; further provided that in at least one phosphacycle of the phosphacycle-containing ligating compound, both atoms directly bonded to P or $X_1$ are $sp^3$ hybridized; two or more Ar, X" or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected Ar, X" or $R_5$ groups to form a poly(ligating compound-chromium complex) species. X''' is independently N, O or S, preferably O. Preferably X" independently is hydrogen, fluorine, chlorine, methyl, methoxy, t-butyl, phenyl, nitro or cyano. Preferably $R_3$ and $R_4$ independently are substituted or unsubstituted phenyl or unsubstituted furanyl. Preferably $R_3$ or $R_4$ independently is substituted phenyl, and at least one X" on at least one, preferably each, substituted phenyl is halogen, preferably fluorine or chlorine, $C_{1-4}$ alkyl or substituted alkyl, preferably methyl, trifluoromethyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably fluorine; preferably at least one, more preferably each, substituted phenyl is substituted at the 2-position with cyano, nitro, fluorine, chlorine, bromine or iodine, preferably fluorine or chlorine, more preferably fluorine and is substituted at one or more of the 3-, 4-, 5-, 6-positions with cyano, nitro, fluorine, chlorine, bromine or iodine, preferably fluorine or chlorine, more preferably fluorine; preferably at least one, more preferably each, substituted phenyl is independently substituted at the 2-position and the 4-position with cyano, nitro, fluorine, chlorine, bromine or iodine, preferably fluorine or chlorine, more preferably fluorine; preferably at least one, more preferably each, substituted phenyl is substituted at the 2-position with cyano, nitro, fluorine, chlorine, bromine or iodine, preferably fluorine or chlorine, more preferably fluorine; preferably at least one, more preferably each, substituted phenyl is substituted at the 6-position with hydrogen, fluorine or chlorine, preferably hydrogen or fluorine, more preferably hydrogen; preferably at least one, more preferably each, substituted phenyl is substituted at the 2-position with fluorine, at the 4-position with hydrogen or fluorine, and at the 6-position with hydrogen. Preferably $R_3$ and $R_4$ independently are substituted or unsubstituted pyridinyl. Preferably $R_3$ or $R_4$ independently is substituted pyridinyl, and at least one X" on at least one, preferably each, substituted pyridinyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably fluorine; preferably at least one, more preferably each, substituted pyridinyl is substituted at the 2-position with cyano, nitro, fluorine, chlorine, bromine or iodine, preferably fluorine or chlorine, more preferably fluorine. Preferably $R_3$ and $R_4$ independently are substituted or unsubstituted pyridinyl. Preferably $R_3$ or $R_4$ independently is substituted pyridinyl, and at least one X" on at least one, preferably each, substituted pyridinyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably fluorine. Preferably $R_3$ and $R_4$ independently are substituted or unsubstituted pyrrolyl. Preferably $R_3$ or $R_4$ independently is substituted pyrrolyl, and at least one X" on at least one, preferably each, substituted pyrrolyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably methyl. Preferably $R_3$ and $R_4$ independently are substituted or unsubstituted furanyl. Preferably $R_3$ or $R_4$ independently is substituted furanyl, and at least one X" on at least one, preferably each, substituted furanyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably methyl. Preferably $R_3$ and $R_4$ independently are substituted or unsubstituted thienyl. Preferably $R_3$ or $R_4$ independently is substituted thienyl, and at least one X" on at least one, preferably each, substituted thienyl is halogen, preferably fluorine or chlorine, $C_{1-4}$ alkyl, preferably methyl or t-butyl, $C_{1-4}$ alkoxy, preferably methoxy or ethoxy, $C_{6-10}$ aryl, preferably phenyl or tolyl, cyano or nitro, more preferably fluorine, chlorine or methyl, even more preferably methyl.

Non-limiting examples of the phosphacycle-containing ligating compound chromium complexes are:

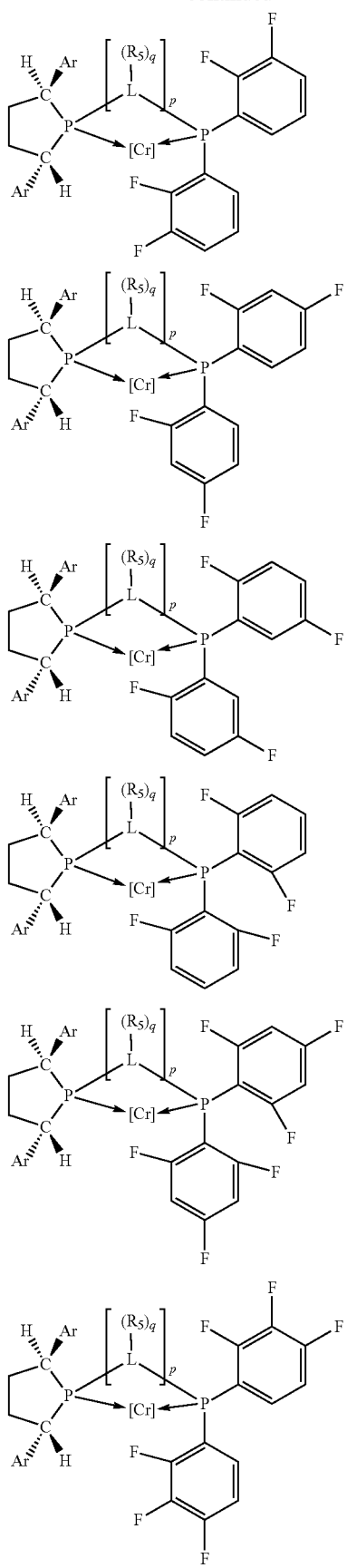

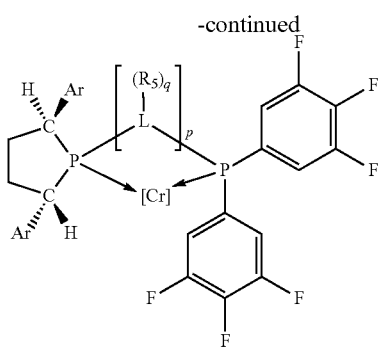
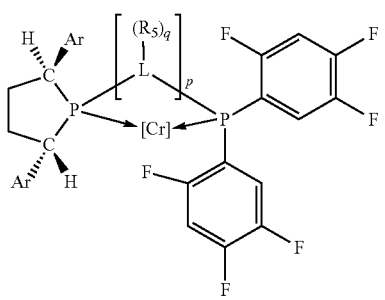
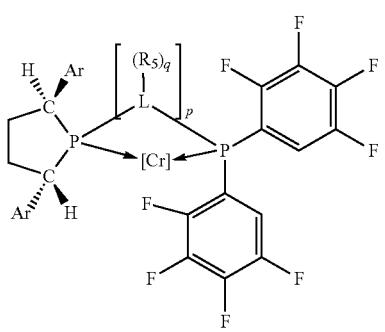
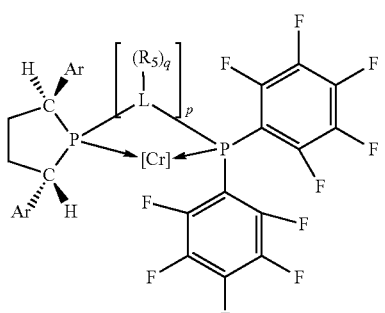
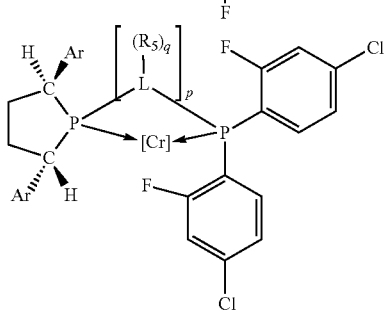
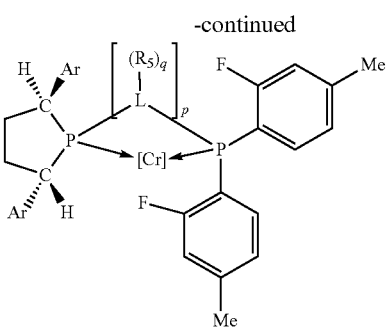
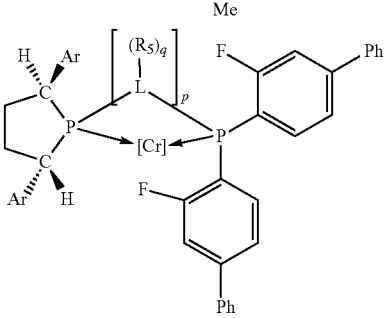
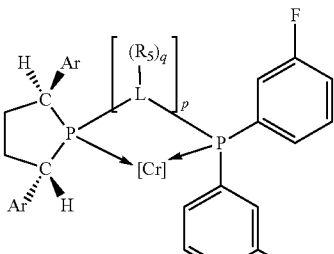
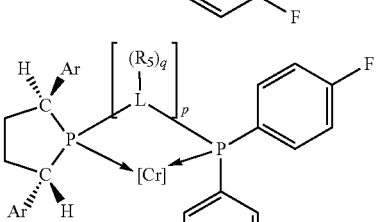
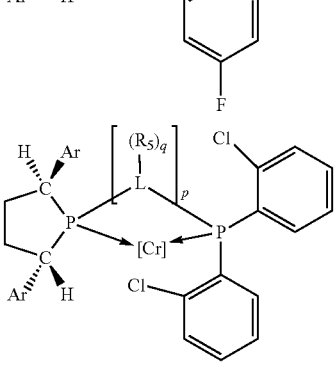
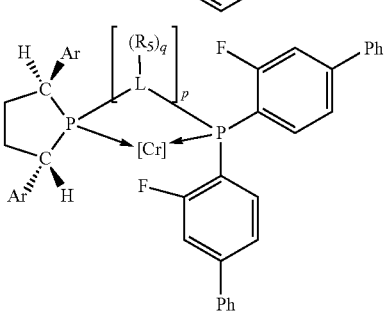

197
-continued
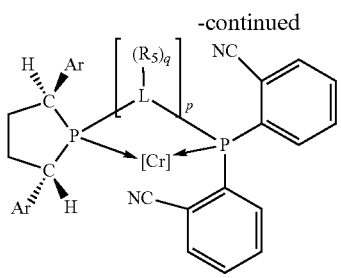
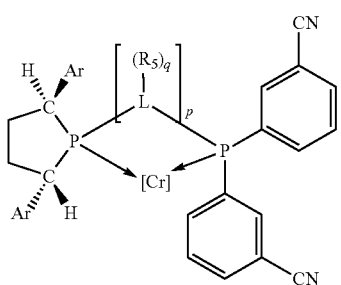
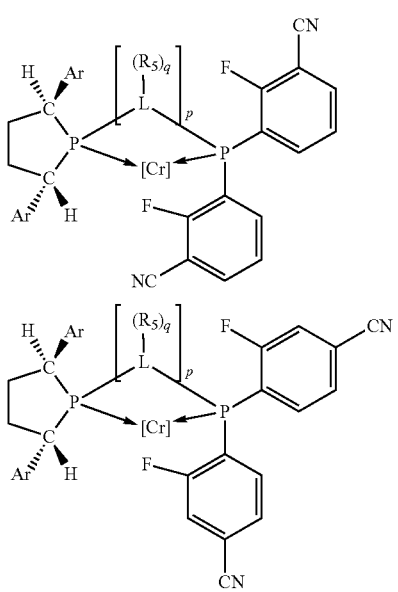
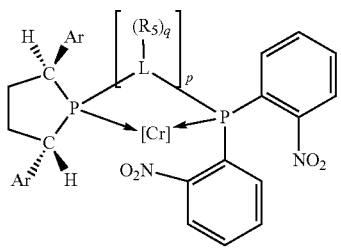
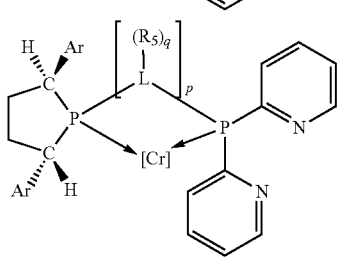
198
-continued
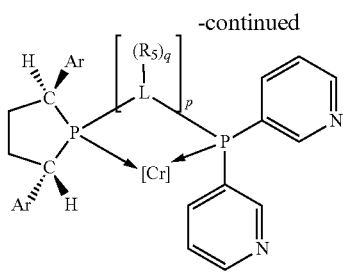
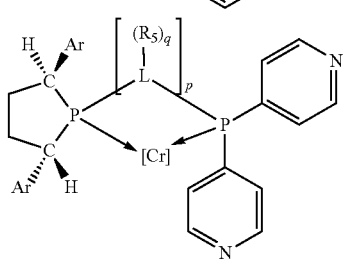
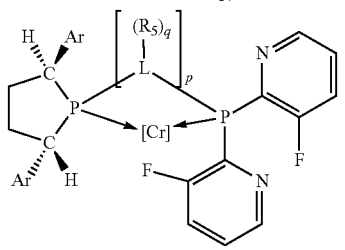
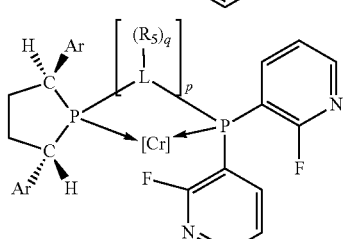
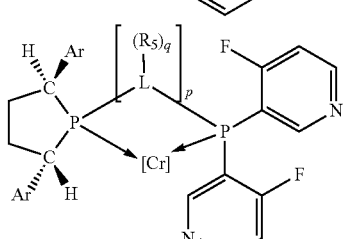
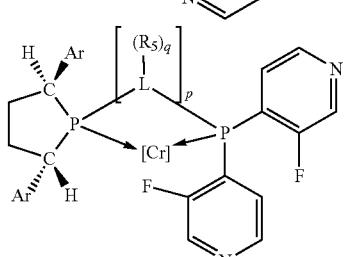
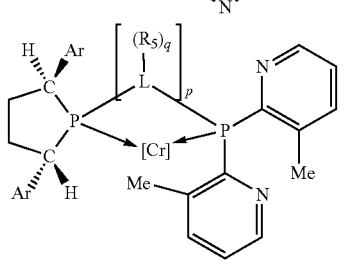

199
-continued
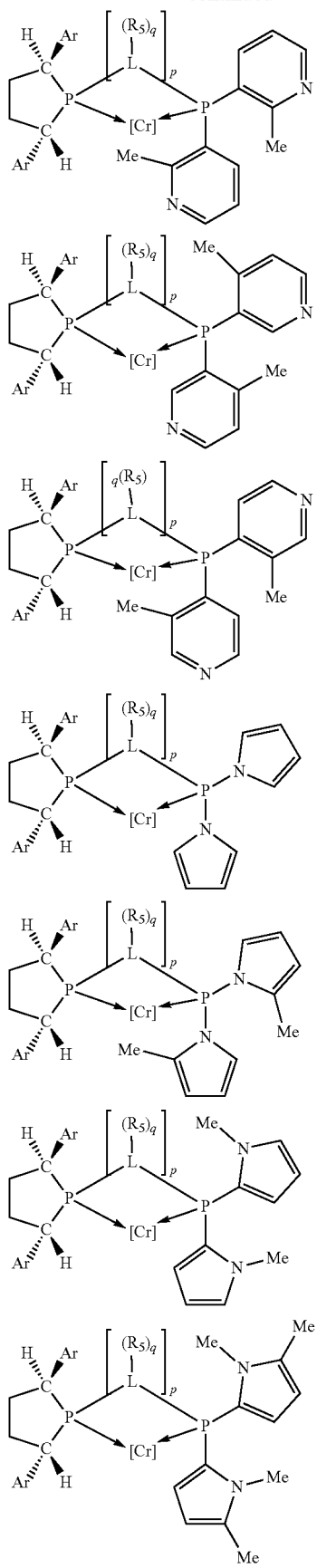
200
-continued
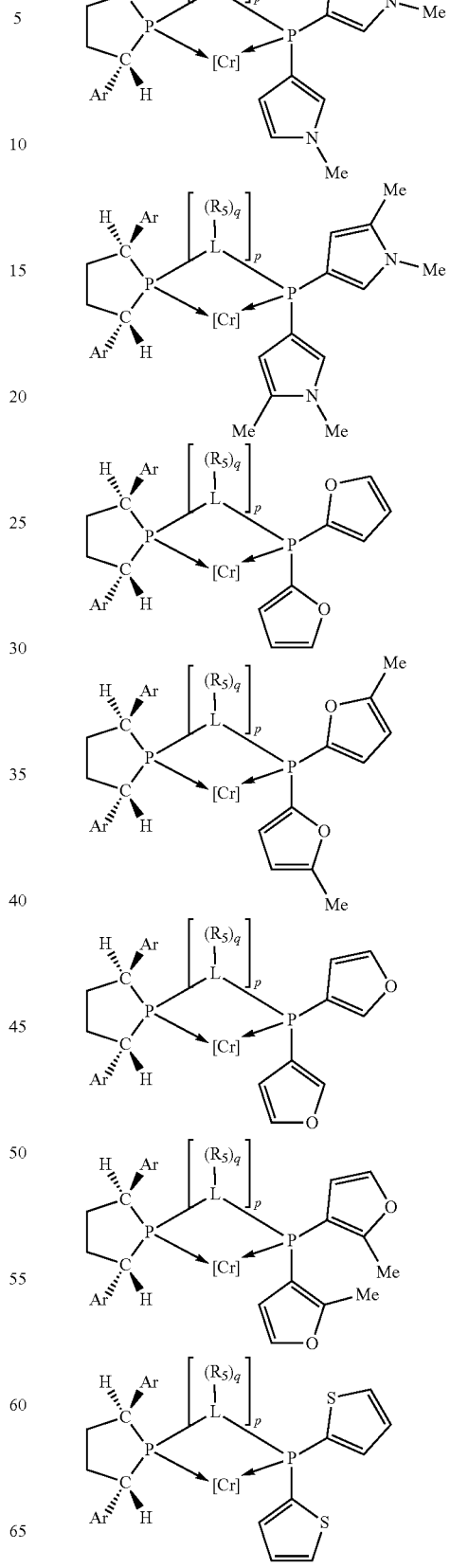

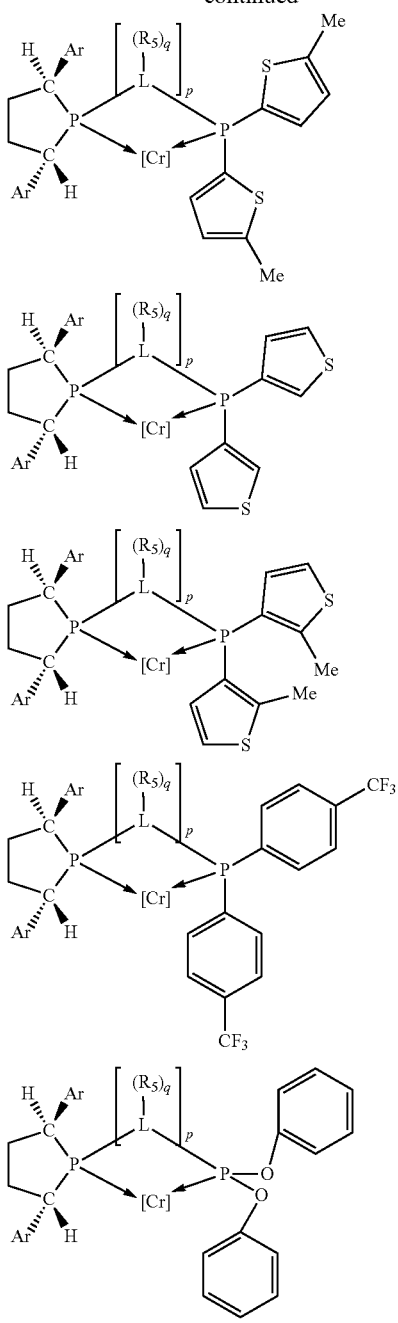

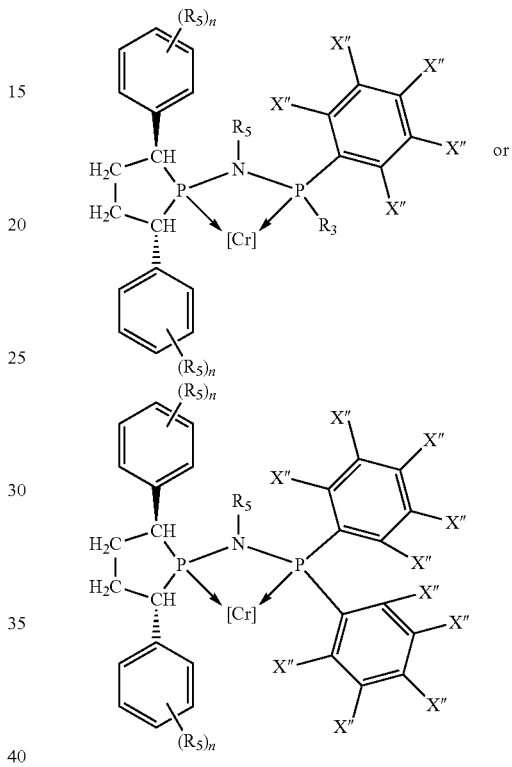

linked together via their respective independently selected Ar or $R_5$ groups to form a poly(ligating compound-chromium complex) species.

In preferred ligating compound-chromium complexes, Ar at the 2- and 5-positions of the phosphacycle rings is phenyl optionally substituted with $R_5$; $[L(R_5)_q]_p$ of the divalent linking group is $NR_5$, and 5-membered phosphacycle-containing ligating compound chromium complexes are represented by:

and their enantiomers, wherein n independently selected is an integer from zero to five, preferably from zero to three, more preferably zero to one; $R_5$ is halogen, $C_{1-40}$ substituted or unsubstituted alkyl, $C_{1-40}$ substituted or unsubstituted aryl; preferably fluorine, chlorine, bromine, $C_{1-20}$ substituted or unsubstituted alkyl, $C_{1-20}$ substituted or unsubstituted aryl; more preferably fluorine, chlorine, $C_{1-12}$ substituted or unsubstituted alkyl, $C_{1-12}$ substituted or unsubstituted aryl; $R_3$ is $C_{1-40}$ substituted or unsubstituted alkyl, $C_{1-40}$ substituted or unsubstituted aryl; preferably $C_{1-20}$ substituted or unsubstituted alkyl, $C_{1-20}$ substituted or unsubstituted aryl; more preferably $C_{1-12}$ substituted or unsubstituted alkyl, $C_{1-12}$ substituted or unsubstituted aryl; X" is hydrogen, halogen, $C_{1-4}$ alkyl or substituted alkyl, $C_{6-10}$ aryl or substituted aryl, cyano or nitro, preferably hydrogen, fluorine, chlorine, bromine, methyl, ethyl, propyl, butyl, phenyl, tolyl, xylyl, methoxy, ethoxy, propoxy, trifluoromethyl or t-butyl, cyano, more preferably hydrogen, fluorine, chlorine, methyl, ethyl, propyl, butyl, phenyl, tolyl, methoxy, ethoxy, propoxy, trifluoromethyl, cyano, even more preferably hydrogen, fluorine, methyl, or methoxy.

In preferred ligating compound-chromium complexes, X" at the 2-position of the phenyl ring attached to P is fluorine, X" at the 6-position of the phenyl ring attached to P is hydrogen, and 5-membered phosphacycle-containing ligating compound chromium complexes are represented by:

and their enantiomers wherein in at least one phosphacycle of the phosphacycle-containing ligating compound, both atoms directly bonded to P or $X_1$ are $sp^3$ hybridized; two or more Ar or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be

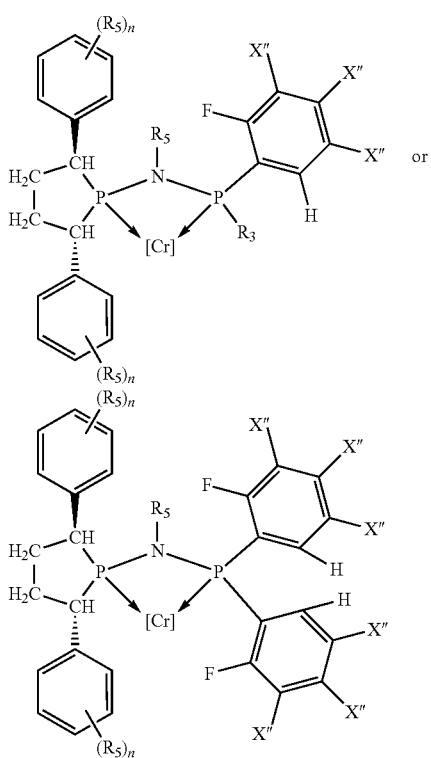

and their enantiomers, wherein n independently selected is an integer from zero to five, preferably from zero to three, more preferably zero to one; $R_5$ is halogen, $C_{1-40}$ substituted or unsubstituted alkyl, $C_{1-40}$ substituted or unsubstituted aryl; preferably fluorine, chlorine, bromine, $C_{1-20}$ substituted or unsubstituted alkyl, $C_{1-20}$ substituted or unsubstituted aryl; more preferably fluorine, chlorine, $C_{1-12}$ substituted or unsubstituted alkyl, $C_{1-12}$ substituted or unsubstituted aryl; $R_3$ is $C_{1-40}$ substituted or unsubstituted alkyl, $C_{1-40}$ substituted or unsubstituted aryl; preferably $C_{1-20}$ substituted or unsubstituted alkyl, $C_{1-20}$ substituted or unsubstituted aryl; more preferably $C_{1-12}$ substituted or unsubstituted alkyl, $C_{1-12}$ substituted or unsubstituted aryl; X" is hydrogen, halogen, $C_{1-4}$ alkyl or substituted alkyl, $C_{6-10}$ aryl or substituted aryl, cyano or nitro, preferably hydrogen, fluorine, chlorine, bromine, methyl, ethyl, propyl, butyl, phenyl, tolyl, xylyl, methoxy, ethoxy, propoxy, trifluoromethyl or t-butyl, cyano, more preferably hydrogen, fluorine, chlorine, methyl, ethyl, propyl, butyl, phenyl, tolyl, methoxy, ethoxy, propoxy, trifluoromethyl, cyano, even more preferably hydrogen, fluorine, methyl, or methoxy.

The group Y, which links P and $X_1$ together in the ligating compound-chromium complexes, is a divalent linking group $[L(R_5)_q]_p$, wherein p is an integer number from 1 to 6, preferably from 1 to 4, preferably 1, 2, or 3, more preferably 1 or 2; q is 0, 1, or 2; consisting of the linking part $[L]_p$ and the $R_5$ pendant groups wherein the $R_5$ pendant groups independently selected are attached to the L atoms of the $[L]_p$ linking part. The linking part $[L]_p$ consists of 1 to 6, preferably of 1 to 4, preferably 1, 2, or 3, more preferably 1 or 2 L atoms; L is independently selected from the group consisting of boron, carbon, silicon, germanium, nitrogen, phosphorus, oxygen, and sulfur. Preferably L is independently selected from carbon, nitrogen, phosphorus, oxygen, and sulfur. Preferred linking parts $[L]_p$, each L independently selected, are B, C, N, O, P, S, Si, C—C, C=C, C—N, C=N, C—Si, N—N, C—C—C, C—C=C, C—N—C, C—P—C, C—N=C, C—Si—C, N—C—N, C—N—N, C=N—N, C—N=N, C—O—C, and C—S—C, preferably provided that the linking part $[L]_p$ is not amidine, N—C=N. In an embodiment of the invention, each $L(R_5)_q$ group is independently —N—, —N($R_5$)—, —P($R_5$)—, —P(O)($R_5$)—, —P(S)($R_5$)—, —C(O)—, —C($R_5$)—, —C($R_5$)$_2$—, —Si($R_5$)$_2$—, —O—, —S—, S(O)—, and —SO$_2$—, preferably N, N($R_5$), C($R_5$), or C($R_5$)$_2$.

In some embodiments, the linking part $[L]_p$ consists of C and the divalent linking group is $[C(R_5)_q]$ wherein q is 1 or 2. Representative, but not limiting, $[C(R_5)_q]$ linking groups include:

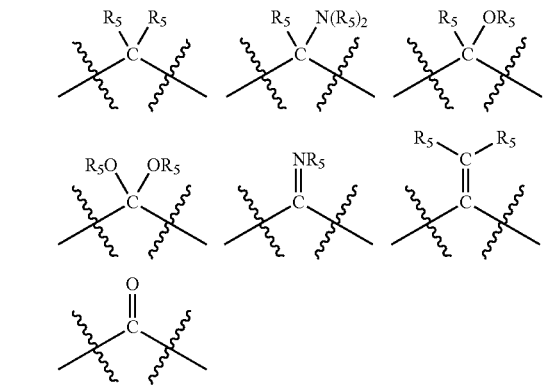

Specific, but not limiting, $[C(R_5)_q]$ linking groups include:

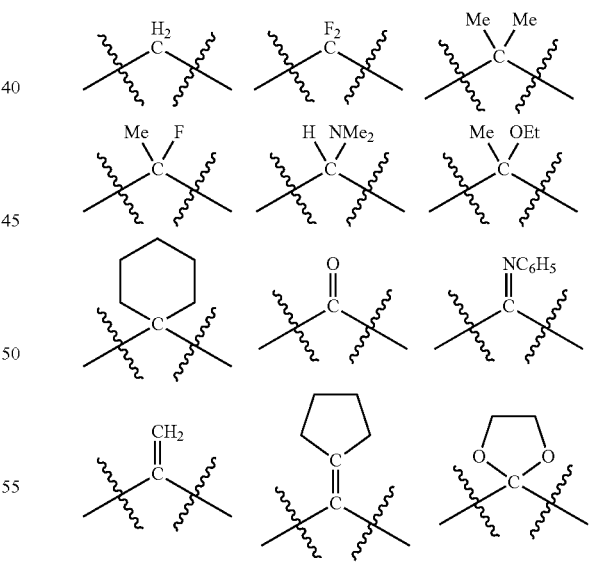

In some embodiments, the linking part $[L]_p$ is not C and the divalent linking group is not $[C(R_5)_q]$ wherein q is 1 or 2.

In some embodiments, the linking part $[L]_p$ consists of C—C and the divalent linking group is $[C(R_5)_q]2$ wherein q independently is 1 or 2 and at least one q is 2. Representative, but not limiting, $[C(R_5)_q]2$ linking groups include:

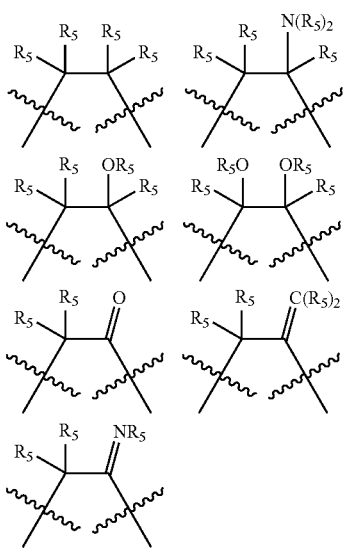

Specific, but not limiting, $[C(R_5)_q]2$ linking groups include:

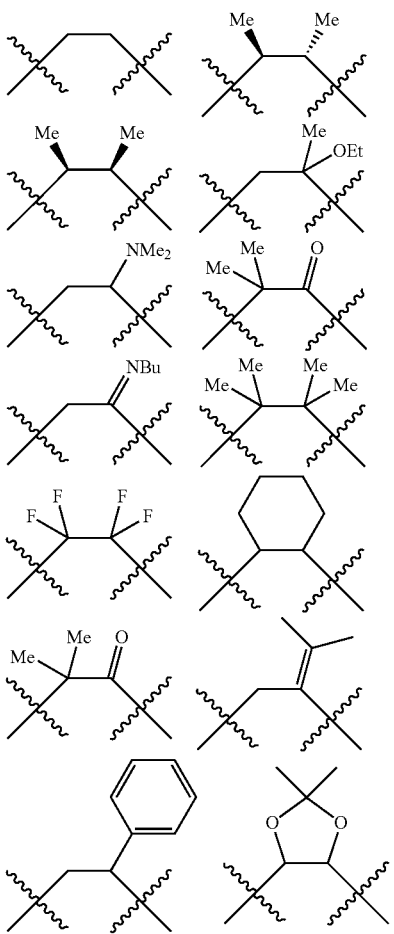

In some embodiments, the linking part $[L]_p$ is not C—C and the divalent linking group is not $[C(R_5)_q]2$ wherein q independently is 1 or 2 and at least one q is 2.

In some embodiments the linking part $[L]_p$ consists of C—C and the divalent linking group is $[C(R_5)]2$ wherein both carbon atoms are connected with a carbon-carbon unsaturated bond, or both carbon atoms are connected to their respectively $R_5$ groups with unsaturated bonds. Representative, but not limiting, $[C(R_5)]2$ linking groups include:

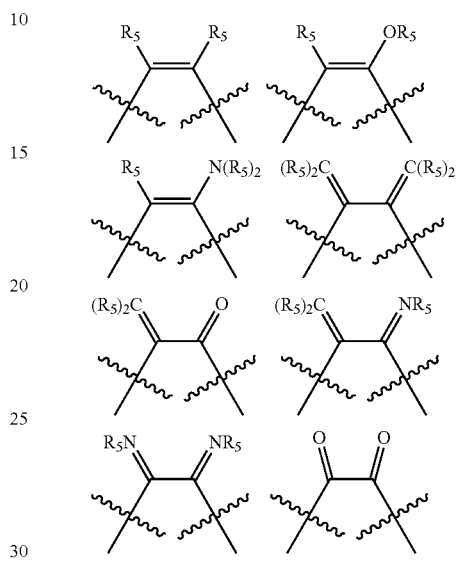

Specific, but not limiting, $[NR_5]$ or $[NR_5]2$ linking groups include:

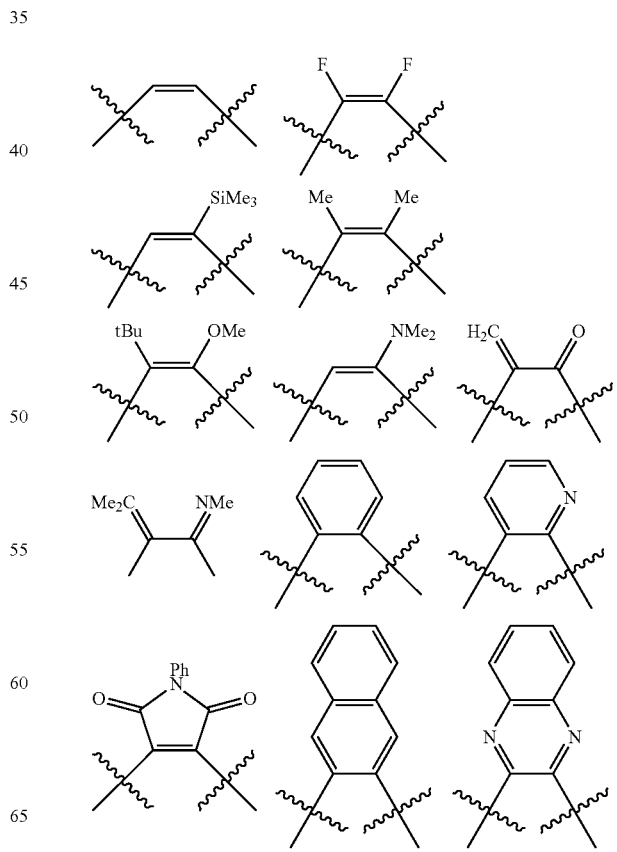

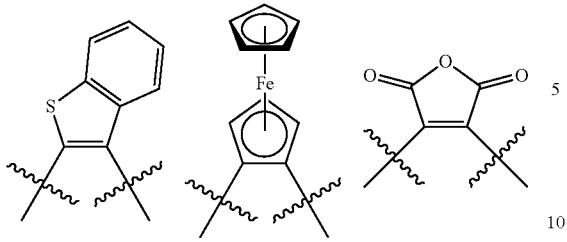

In some embodiments the linking part $[L]_p$ is not C—C and the divalent linking group is not $[C(R_5)]_2$ wherein both carbon atoms are connected with a carbon-carbon unsaturated bond, or both carbon atoms are connected to their respectively $R_5$ groups with unsaturated bonds.

In some embodiments, the linking part $[L]_p$ consists of N or N—N and the divalent linking group is $[NR_5]$ or $[NR_5]_2$. Representative, but not limiting, $[NR_5]$ or $[NR_5]_2$ linking groups include:

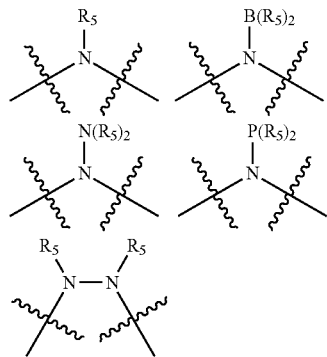

Specific, but not limiting, $[NR_5]$ or $[NR_5]_2$ linking groups include:

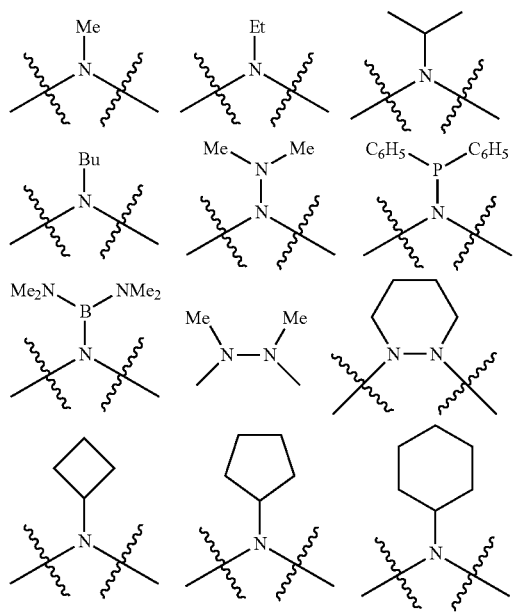

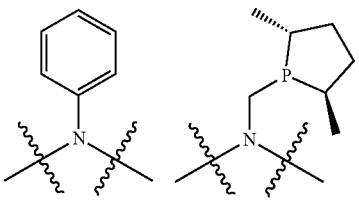

In some embodiments, the linking part $[L]_p$ is neither N nor N—N and the divalent linking group is neither $[NR_5]$ nor $[NR_5]2$. Preferably $[NR_5]$ does not comprise

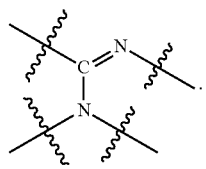 [SMILES: */N=C(/*)N(*)*]

It will be appreciated that a diphosphinoimine compound of the form $R_1R_2P$—$P(=NR_5)R_3(R_4)$ ('P—P=N') is a rearranged isomer of the diphosphinoamine compound $R_1R_2P$—$NR_5$—$PR_3(R_4)$ ('P—N—P') claimed in the present invention, as shown by Dyson et al in Inorganica Chimica Acta 359 (2006) 2635-2643 and may isomerize to the P—N—P form in the presence of transition metals, such as chromium in the instant application.

Similarly, it may be possible that a ligating compound of the form $R_1R_2P$—Y—$X_1R_3(R_4)_m$ or $R_1R_2P$-$[L(R_5)_q]_p$—$X_1R_3(R_4)_m$ where Y or $[L(R_5)_q]_p$ is —$N(R_5)$— and $X_1R_3(R_4)_m$ is $PR_3R_4$, exists in its isomeric 'P—P=N' form. Regardless of the structural formulation of the ligating compound in its pure and isolated form, it and its use are embodiments of the present invention, especially if it exists in the 'P—N—P' form when used in an oligomerization process, more especially when it is bound to chromium in an oligomerization process.

In some embodiments, the linking part $[L]_p$ consists of C—N and the divalent linking group is $[C(R_5)_qN(R_5)_q]$ wherein q independently is 1 or 2 for $C(R_5)_q$ and 0 or 1 for $N(R_5)_q$. Representative, but not limiting, $[C(R_5)_qN(R_5)_q]$ linking groups include:

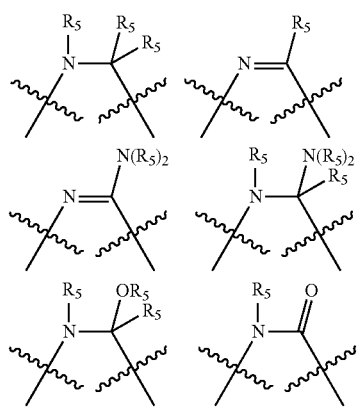

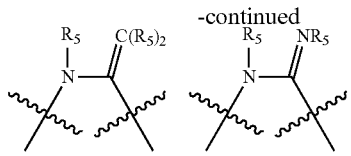

Specific, but not limiting, [C(R$_5$)$_q$N(R$_5$)] linking groups include:

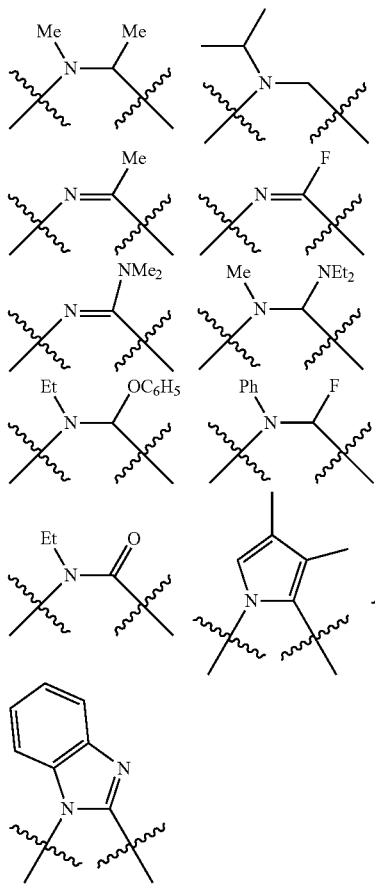

In some embodiments, the linking part [L]$_p$ is not C—N and the divalent linking group is not [C(R$_5$)$_q$N(R$_5$)$_q$] wherein q independently is 1 or 2 for C(R$_5$)$_q$ and 0 or 1 for N(R$_5$)$_q$. Preferably [C(R$_5$)$_q$N(R$_5$)$_q$] does not comprise

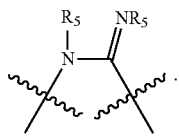

In some embodiments, the L atoms of the linking part [L]$_p$ are selected from the group consisting of B, O, S, Si, and C wherein at least one L is not C; p is 1, 2, 3, or 4; and the divalent linking group is [(C(R$_5$)$_2$)$_k$X'$_r$(C(R$_5$)$_2$)$_{k'}$] wherein X' independently selected is BR$_5$, O, S, SO, SO$_2$, or Si(R$_5$)$_2$; k is 0 or 1; k' is 0 or 1; r is 1, 2, or 3. Preferably r+k+k'1, 2, or 3.

Representative, but not limiting, [(C(R$_5$)$_2$)$_k$X'$_r$(C(R$_5$)$_2$)$_{k'}$] linking groups include:

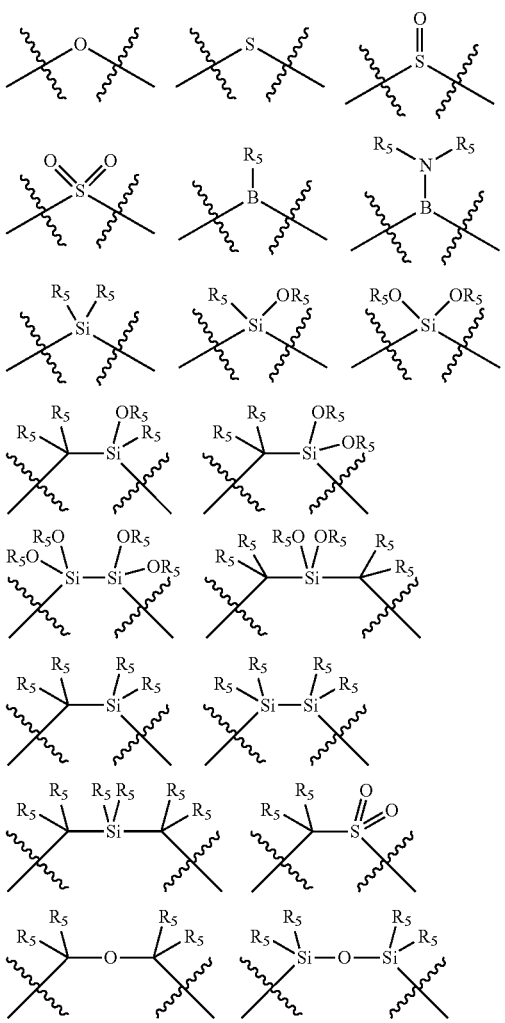

Specific, but not limiting, [(C(R$_5$)$_2$)$_k$X'$_r$(C(R$_5$)$_2$)$_{k'}$] linking groups include:

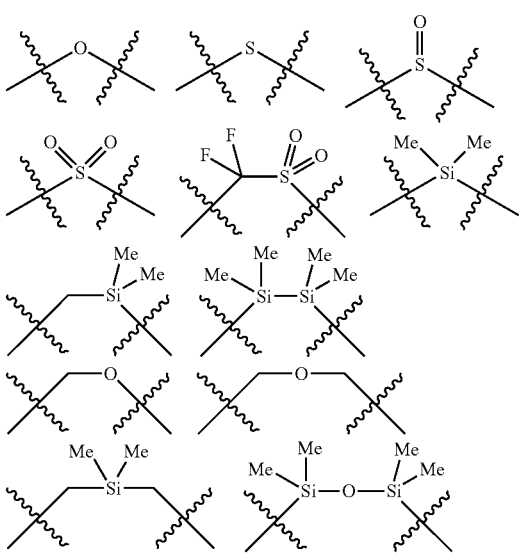

-continued

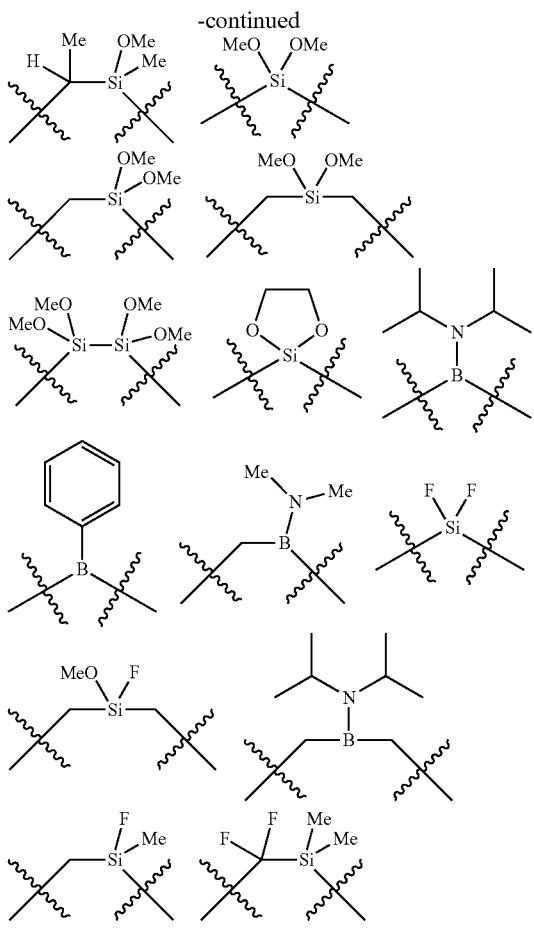

In some embodiments, the L atoms of the linking part $[L]_p$ are not selected from the group consisting of B, O, S, Si, and C wherein at least one L is not C; p is 1, 2, 3, or 4; and the divalent linking group is not $[(C(R_5)_2)_k X'_r (C(R_5)_2)_{k'}]$ wherein X' independently selected is $BR_5$, O, S, SO, $SO_2$, or $Si(R_5)_2$; k is 0 or 1; k' is 0 or 1; r is 1, 2, or 3.

In preferred phosphacycle-containing ligating compound chromium complexes, represented by:

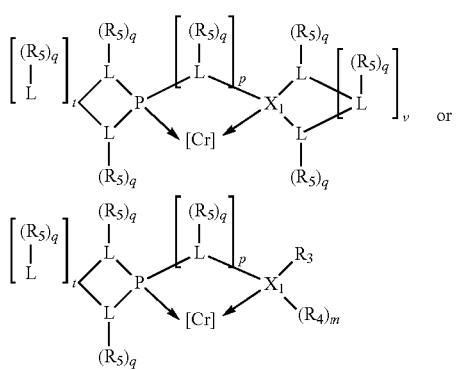

the L atoms are connected to each other, independently for each connection, with single bonds or with unsaturated bonds with the proviso that in at least one phosphacycle of the ligating compound, both atoms directly bonded to P or $X_1$ are $sp^3$ hybridized; preferably at least one phosphacycle does not contain more than one carbon-carbon unsaturated bond, preferably not more than one unsaturated bond, more preferably at least one, preferably two, phosphacycles contain no unsaturated bonds; two or more $R_3$, $R_4$ or $R_5$ groups are optionally linked together to form cyclic structures containing from 4 to 10 ring atoms, preferably from 4 to 7 ring atoms; two or more $R_5$ groups independently are linked together with at least one L atom to form a cyclic structure that contains from 3 to 10 ring atoms, preferably from 3 to 7 ring atoms; two $R_5$ groups attached to the same L atom may be optionally linked together to form a cyclic structure that contains from 3 to 10 ring atoms, preferably from 3 to 7 ring atoms; optionally from two to ten, preferably from two to six, independently selected ligating compound-chromium complexes may be linked together via their respective independently selected $R_3$, $R_4$ or $R_5$ groups to form a poly(ligating compound-chromium complex) species. In an embodiment of the invention no two $R_5$, $R_3$, or $R_4$ groups are linked together to form a cyclic structure. In an embodiment of the invention at least two $R_5$ groups are linked together to form a cyclic structure. Preferably at least one $R_5$ group on a first $L(R_5)_q$ group is linked together with at least one $R_5$ group on an adjacent second $L(R_5)_q$ group together with the L atom from the first $L(R_5)_q$ group and the L atom from the adjacent second $L(R_5)_q$ group to form an

cyclic structure containing from 4 to 10 atoms, preferably 4 to 7 atoms, in the ring part of the

cyclic structure. Preferably the

ring is a substituted or unsubstituted, saturated or unsaturated hydrocarbon group, such as cyclopentanediyl, cyclohexanediyl, dioxolanediyl, tetrahydrofurandiyl, pyrrolidinediyl, piperidinediyl, piperazinediyl, pyrazolidinediyl. Preferably the

ring is a substituted or unsubstituted alkenyl or aromatic group, such as cyclopentenediyl, cyclohexenediyl, cyclopentadienediyl, phenylene, naphthalenediyl, pyridinediyl, pyrrolediyl, imidazoldiyl, pyridazinediyl, pyridazinedionediyl, quinoxalinediyl, thiazolediyl, thiophenediyl, furandiyl, or cyclopentadienyl-diyl, wherein preferably the cyclopentadienyl group is part of an $\eta^5$-bonded transition metal complex, wherein preferably the $\eta^5$-bonded transition metal complex comprises Fe, Ti, Zr, or Hf.

In preferred ligating compound-chromium complexes of the invention, two $R_5$ groups on the same $L(R_5)_q$ group, wherein q=2, are linked together to form an

cyclic structure containing from 3 to 10 atoms, preferably 3 to 7 atoms, in the ring part of the

cyclic structure. Preferably the

ring is a substituted or unsubstituted, saturated or unsaturated hydrocarbyl group, such as cyclobutanediyl, cyclopentanediyl, cyclohexanediyl, tetrahydrofurandiyl, or cyclopentenediyl.

In preferred ligating compound-chromium complexes of the invention, at least one $R_5$ group on a $L(R_5)_q$ group from at least one of the

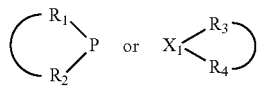

groups or at least one $R_5$ group on a

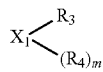

group, wherein the $R_3$ or $R_4$ group may be represented as $L(R_5)_q(R_5)$, is linked together with at least one $R_5$ group from the $[L(R_5)_q]_p$ divalent bridging group between P and $X_1$ to form an

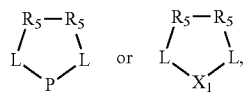

respectively, cyclic structure containing from 5 to 10 atoms, preferably 5 to 7 atoms, in the ring part of the

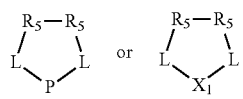

cyclic structure.

$R_3$, $R_4$, and $R_5$ independently selected are hydrogen, fluoro, chloro, bromo, cyano; substituted or unsubstituted hydrocarbon derivatives, preferably substituted or unsubstituted alkyl groups having 1-20, preferably 1-12, more preferably 1-6, non-hydrogen atoms, preferably methyl, trifluoromethyl, ethyl, propyl, isopropyl, n-butyl, i-butyl, s-butyl, t-butyl, pentyl, hexyl, cyclopentyl, cyclohexyl; preferably substituted or unsubstituted unsaturated groups, including alkylidene, alkenyl, aryl, or arylalkyl groups, having 2-20, preferably 2-12, more preferably 2-8, still more preferably 2-6, non-hydrogen atoms, preferably vinyl, methylidene, ethylidene, allyl, phenyl, 2-methylphenyl, 3-methylphenyl, 4-methylphenyl, 2,4-dimethylphenyl, 2,6-dimethylphenyl, 2,4,6-trimethylphenyl, 2-isopropylphenyl, 2,6-diisopropylphenyl, 2,6-diisopropyl-4-methylphenyl, 2-fluorophenyl, 4-fluorophenyl, 2-trifluoromethylphenyl, naphthyl, anthracenyl, biphenyl, benzyl, naphthylmethyl phenethyl, biphenylmethyl; substituted or unsubstituted heterohydrocarbon derivatives having 1-20, preferably 1-12, more preferably 1-6, non-hydrogen atoms, preferably methoxy, ethoxy, propoxy, isopropoxy, butoxy, phenoxy, methylthio, ethylthio, acetyl, dimethylboryl, diphenylboryl, bis(dimethylamino)boryl, dimethylamino, diethylamino, 2-dimethylaminoethyl, 2-methoxyphenyl, 3-methoxyphenyl, 4-methoxyphenyl, 2,6-dimethoxyphenyl, 2,6-dimethoxy-4-methylphenyl, 2-dimethylaminophenyl, phenylamino, phenylmethylamino, acetamide, formylamino, benzamido, benzoyl, methylcarboxamide, dimethylcarboxamide, methoxymethyl, ethoxymethyl, phenoxymethyl, methoxyethyl, ethoxyethyl, phenoxyethyl, phospholanylmethyl, diethylphospholanylmethyl, 2-furanyl, 3-furanyl, pyrrolyl, imidazolyl, pyrrolidinyl, piperidinyl, pyridinyl, pyridazinyl, pyrazolidinyl, pyrazinyl, thienyl, thiazolyl, trimethylsilyl, trimethylsilylmethyl, dimethylphenylsilyl, methylsulfinyl, ethylsulfinyl, methylsulfonyl, ethylsulfonyl; or a substituted or unsubstituted heteroatom group having 1-6 non-hydrogen atoms, preferably a nitro group, one oxygen atom, or one sulfur atom. $R_3$ and $R_4$ preferably are substituted or unsubstituted aryl or arylalkyl groups, more preferably substituted or unsubstituted aryl groups. When two or more $R_3$, $R_4$, or $R_5$ groups, independently selected, are linked together, the moiety they form is di- or polyvalent, depending on how many $R_3$, $R_4$, or $R_5$ groups are linked together. For example, if two $R_3$, $R_4$, or $R_5$ groups are linked together, the moiety is divalent; if three $R_3$, $R_4$, or $R_5$ groups are linked together, the moiety is trivalent. When two or more $R_3$, $R_4$, or $R_5$ groups, independently selected, are linked together, the linked $R_3$, $R_4$, or $R_5$ groups are not hydrogen, fluoro, chloro, bromo or cyano.

In some embodiments, phosphacycle-containing ligating compound chromium complexes of the present invention include the following compositions:

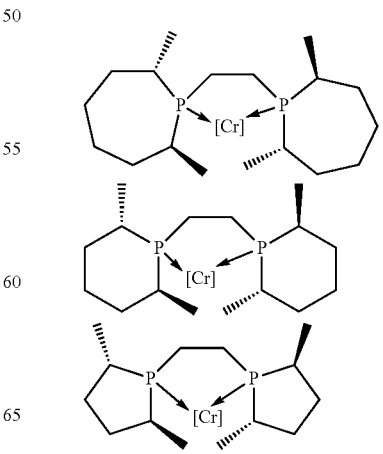

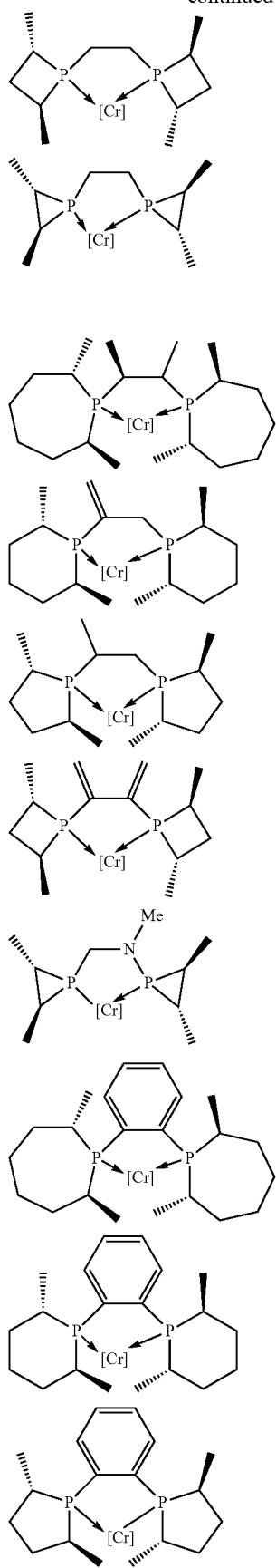
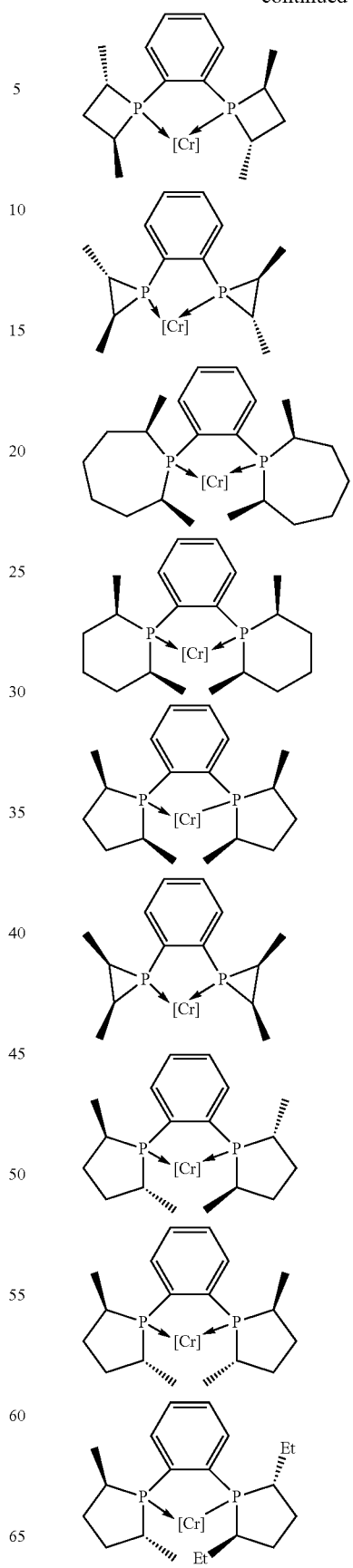

217
-continued
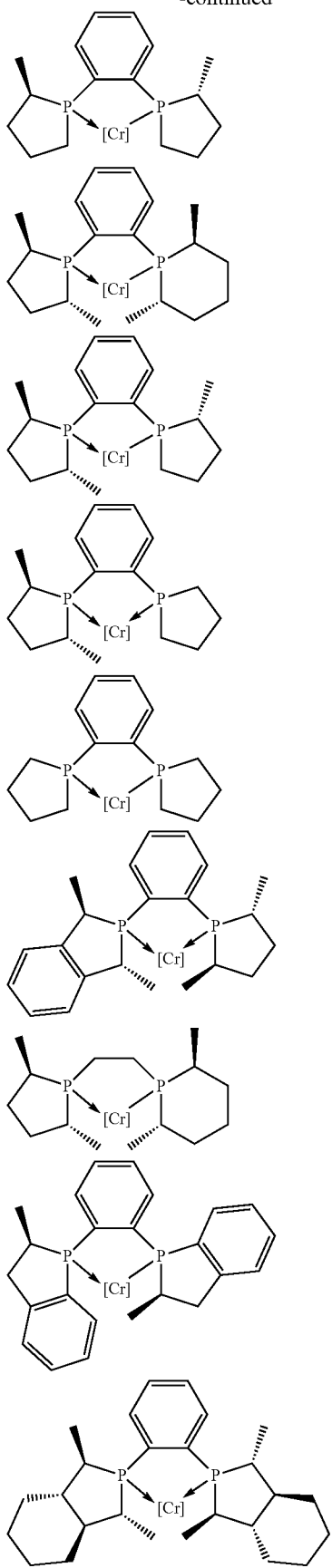
218
-continued
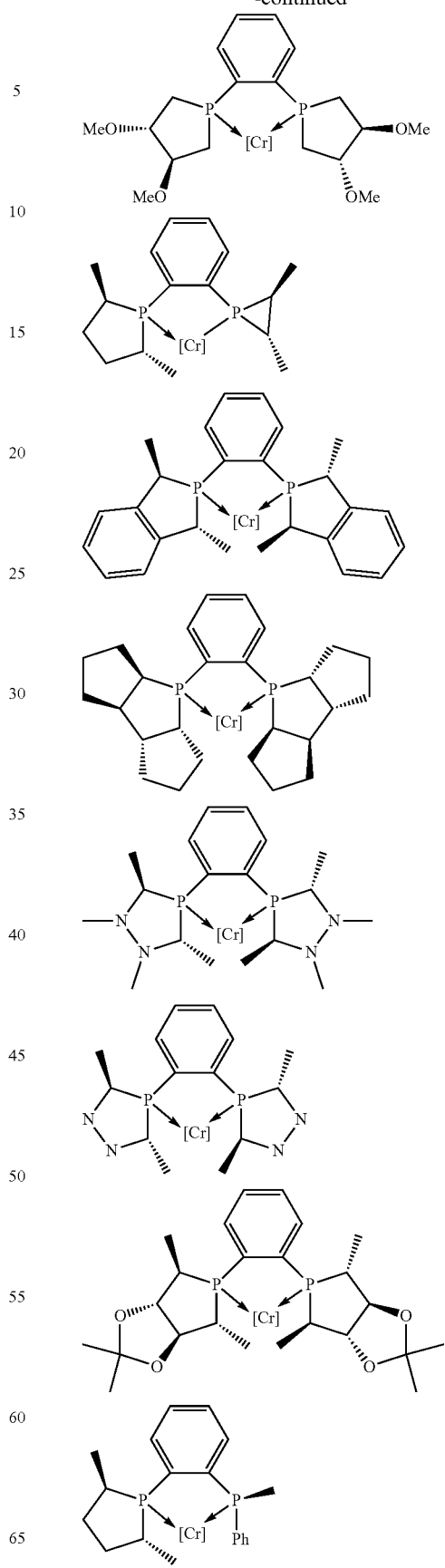

219
-continued
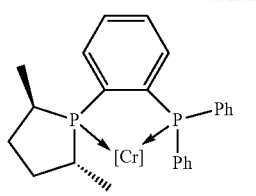
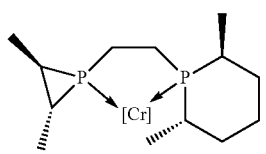
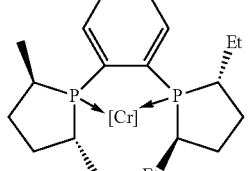
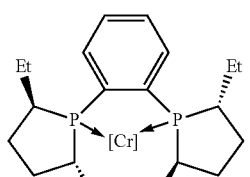
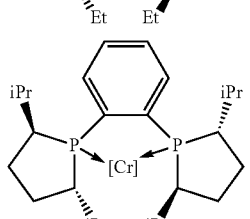
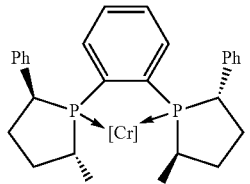
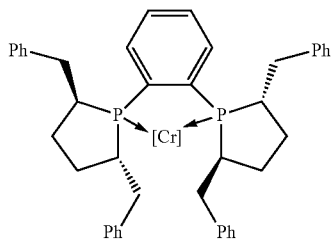
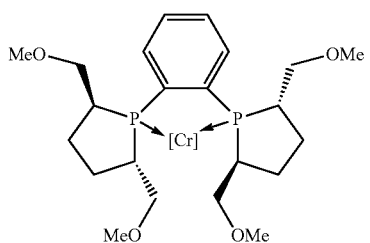
220
-continued
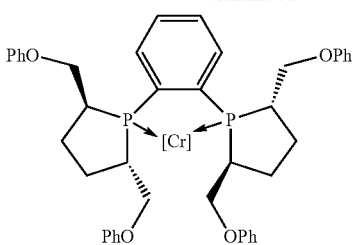
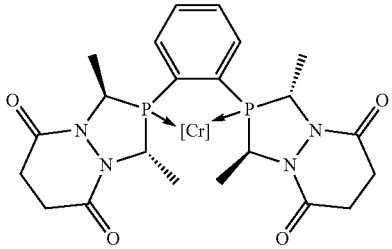
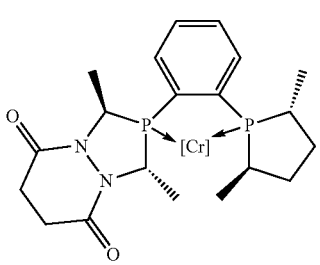
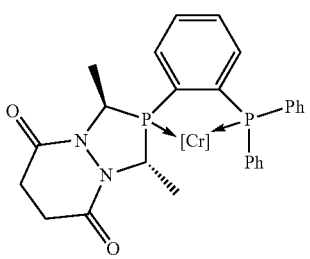
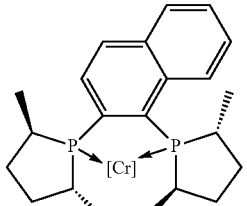
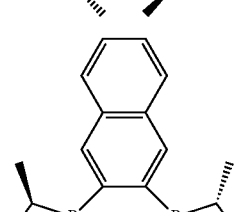
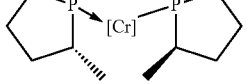

221
-continued
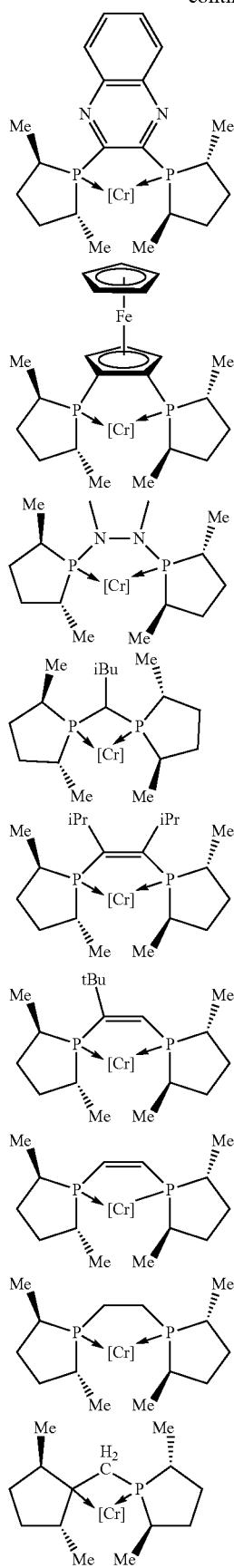
222
-continued
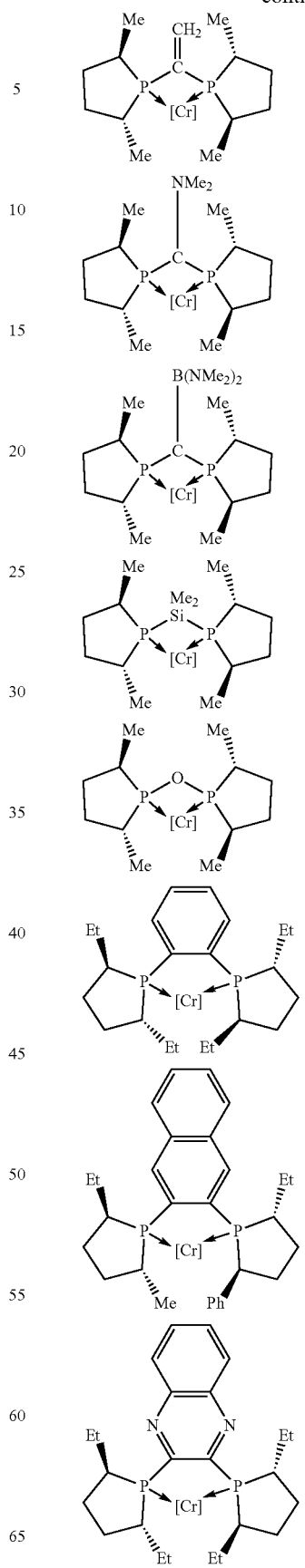

223
-continued
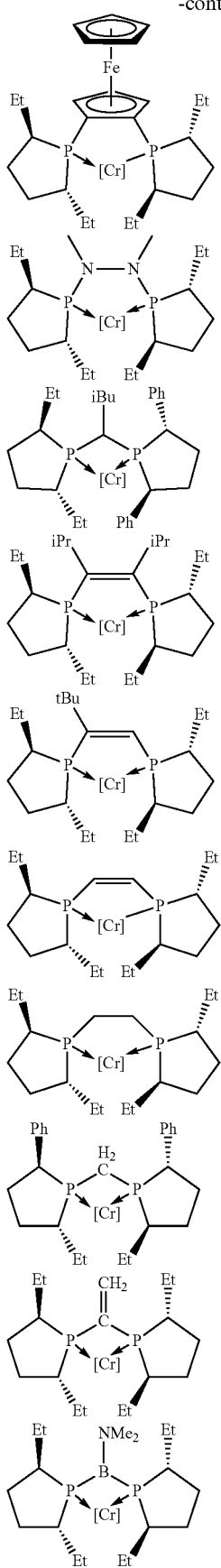
224
-continued
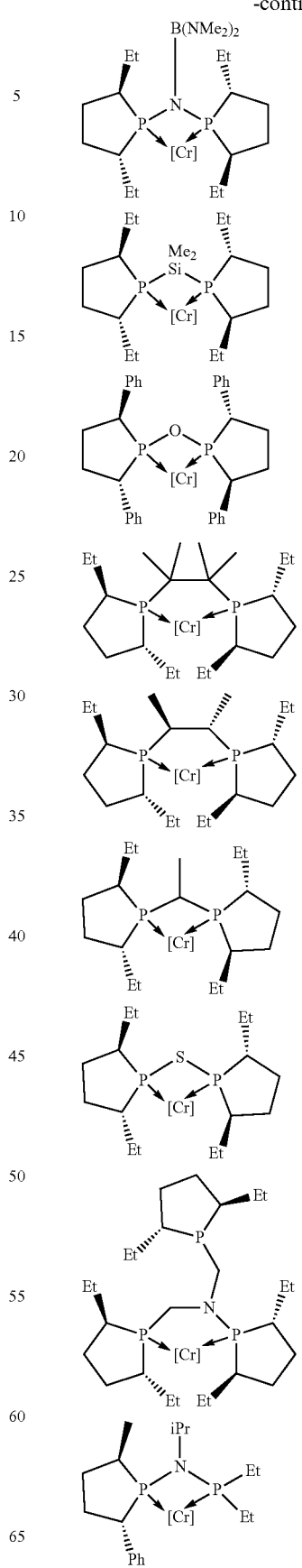

225
-continued
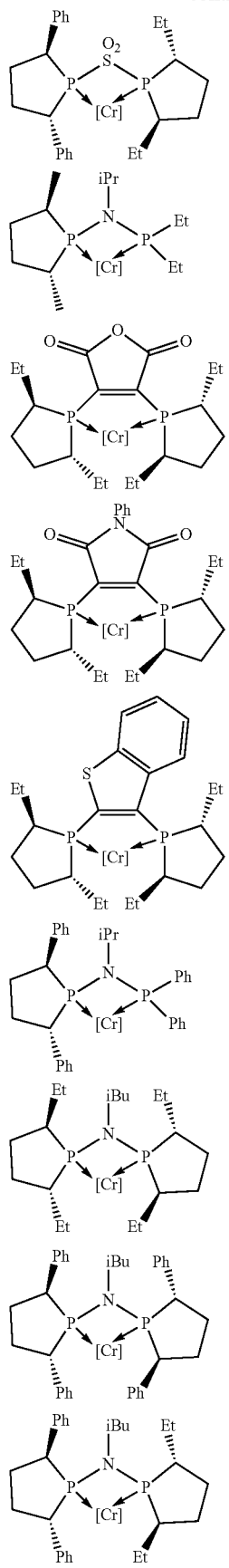
226
-continued
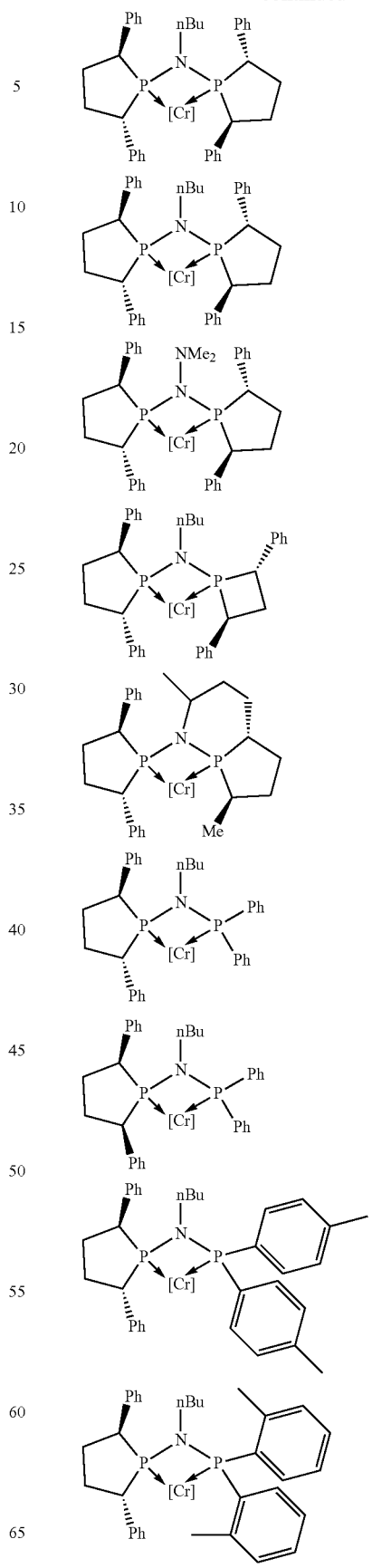

227
-continued
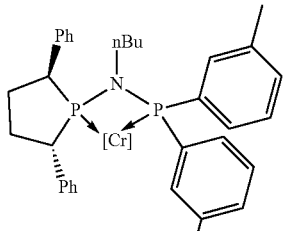
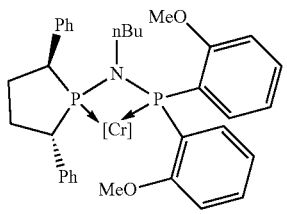
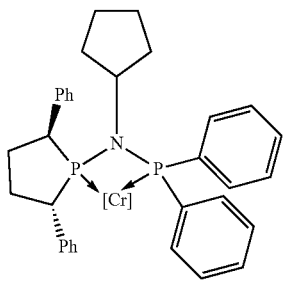
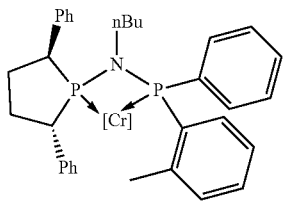
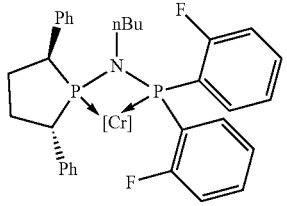
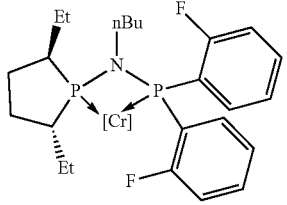
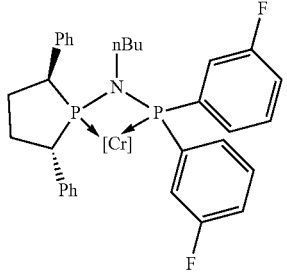
228
-continued
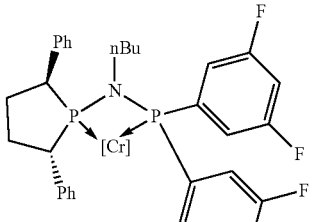
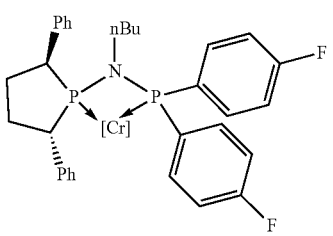
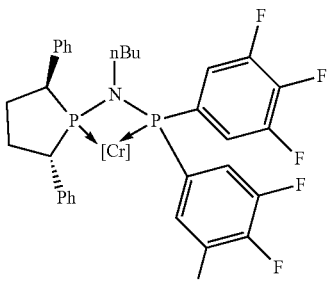
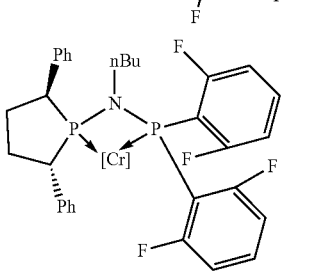
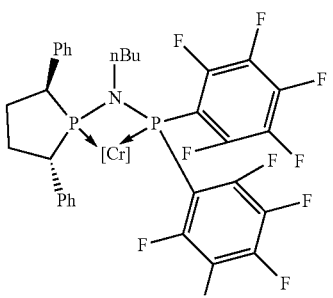
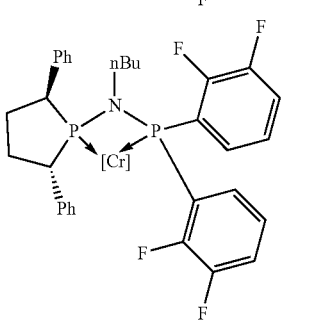

-continued
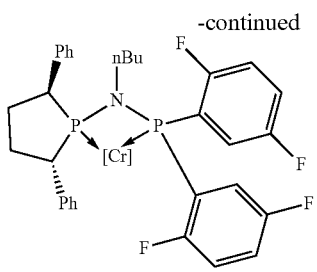
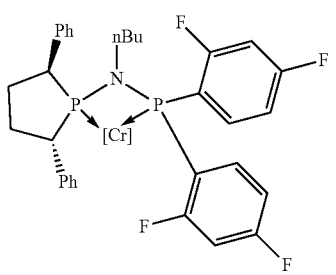
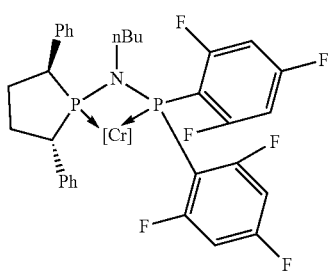
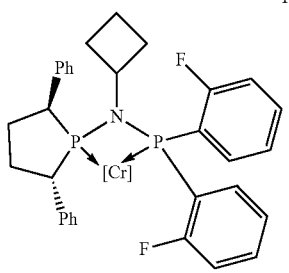
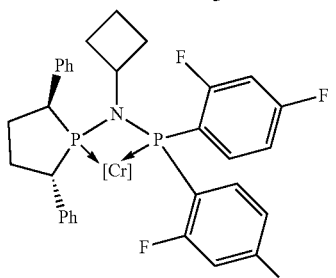
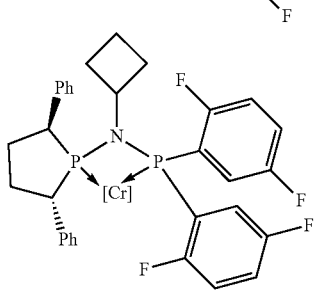
-continued
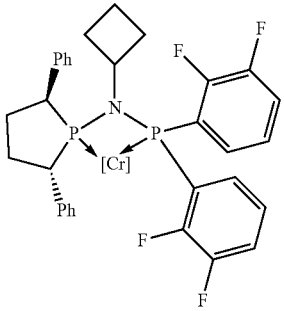
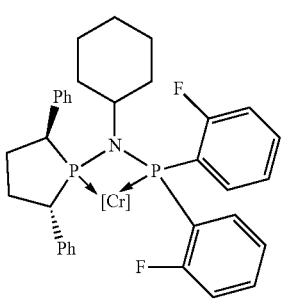
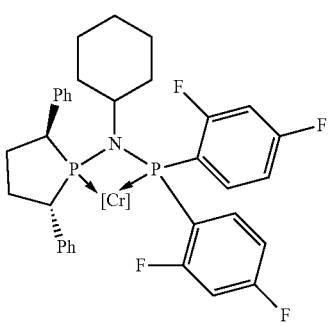
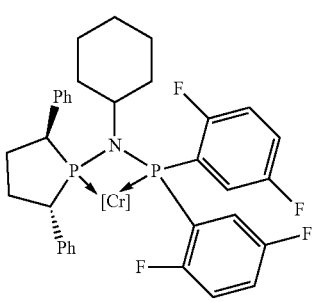
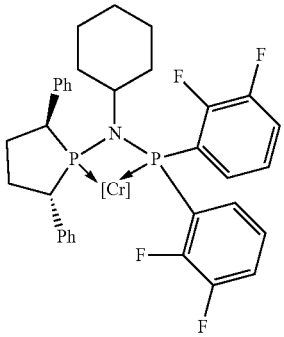

231
-continued
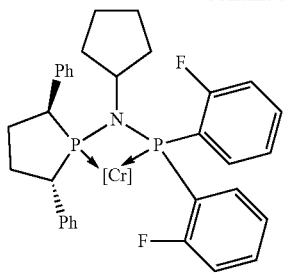
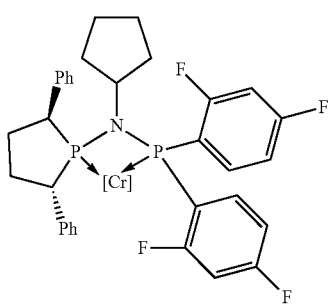
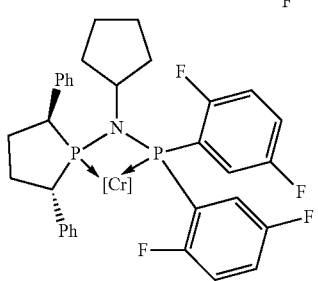
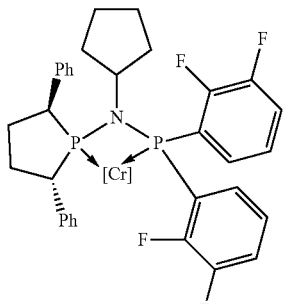
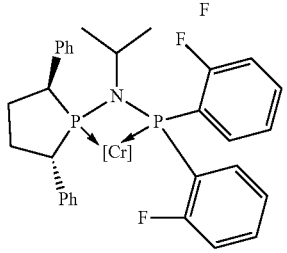
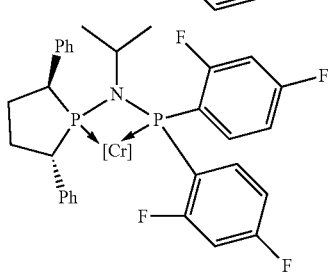
232
-continued
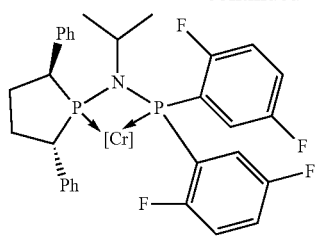
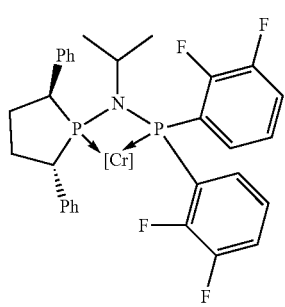
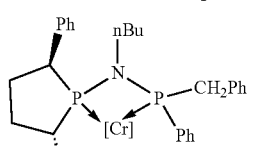
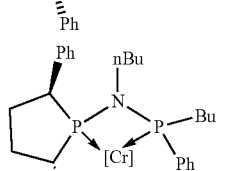
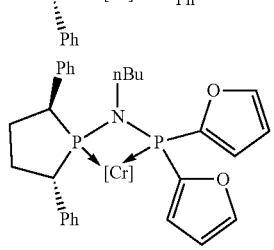
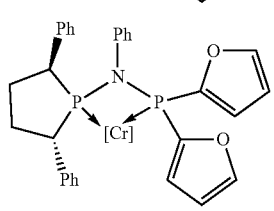
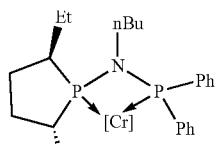
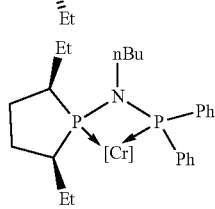

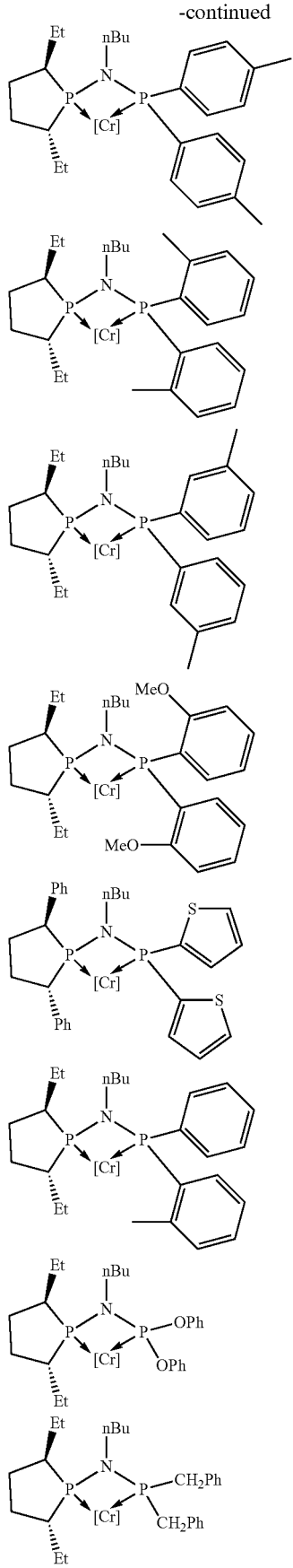
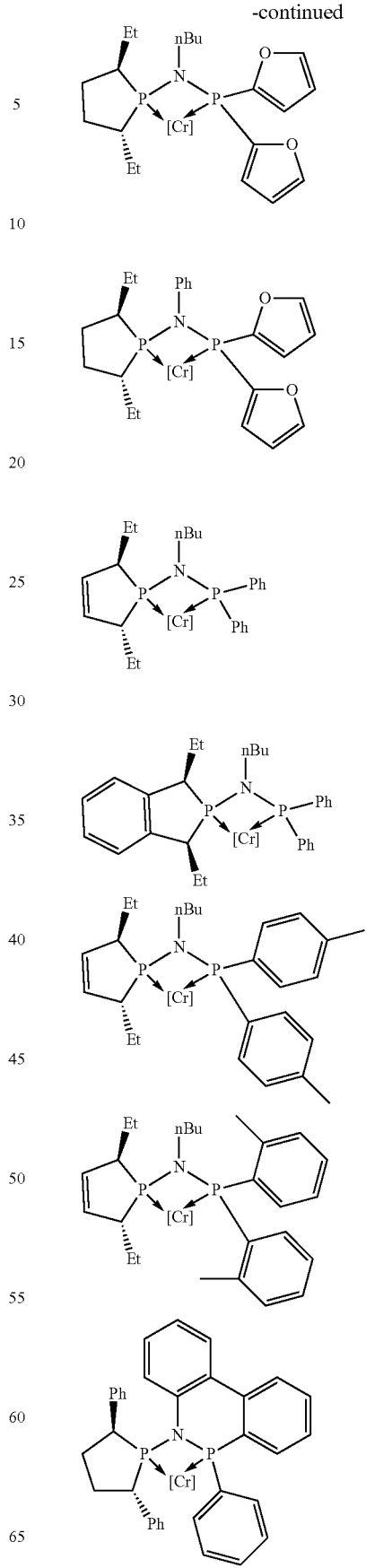

235
-continued
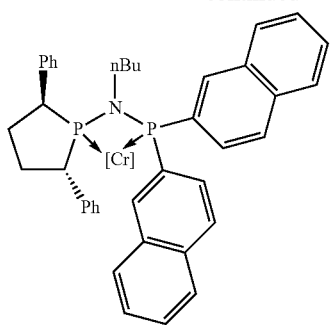
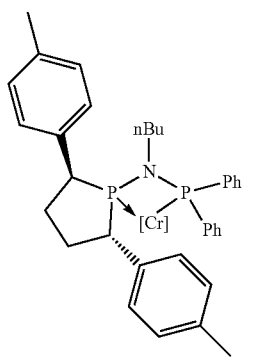
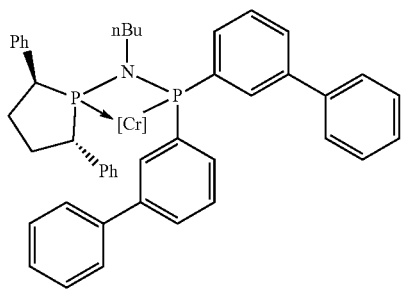
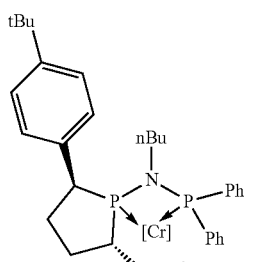
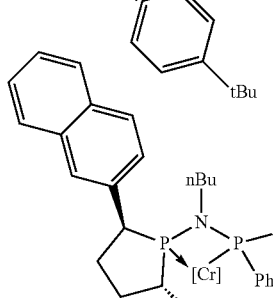
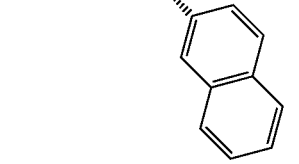
236
-continued
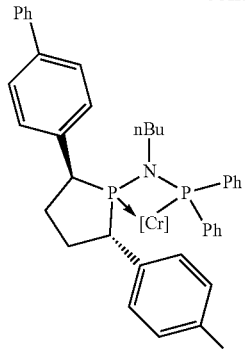
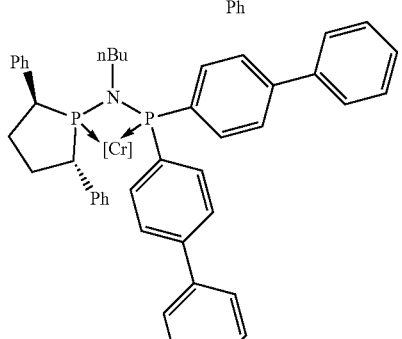
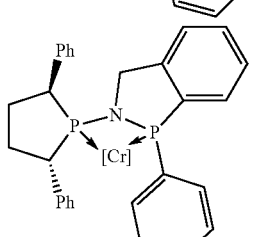
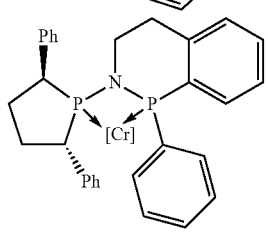
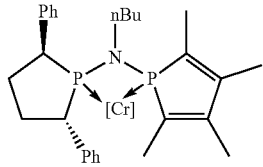
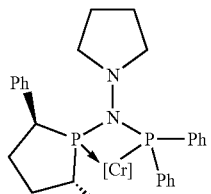
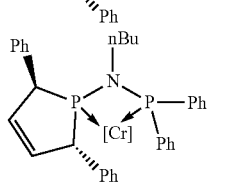

237
-continued
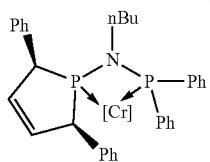
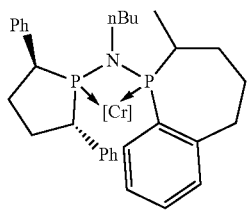
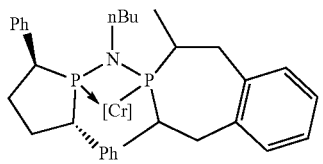
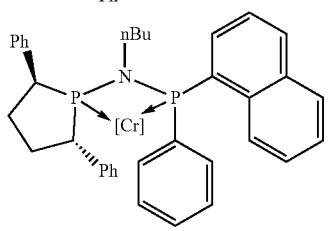
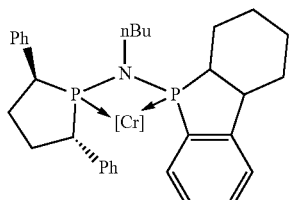
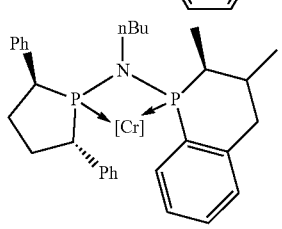
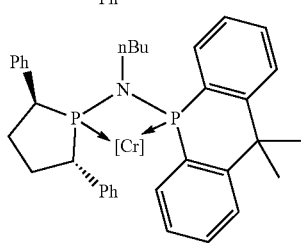
238
-continued
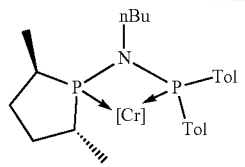
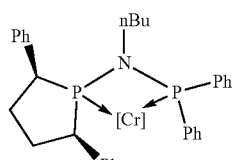
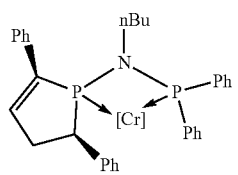
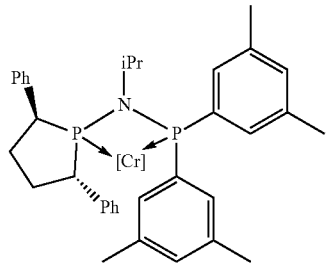
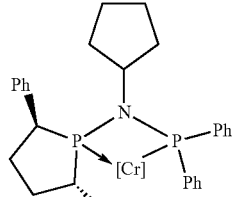
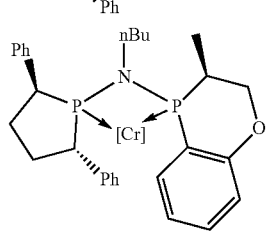
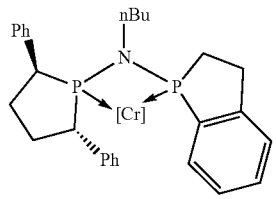
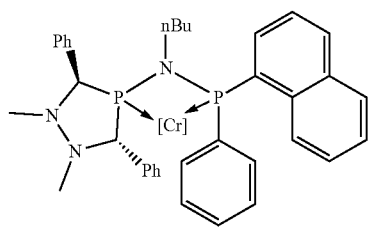

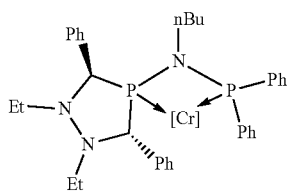
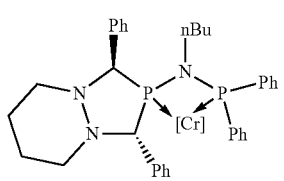
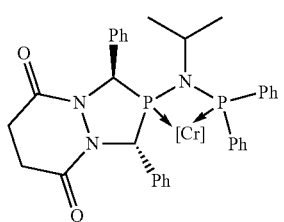
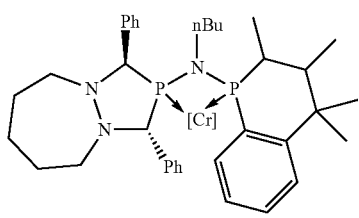
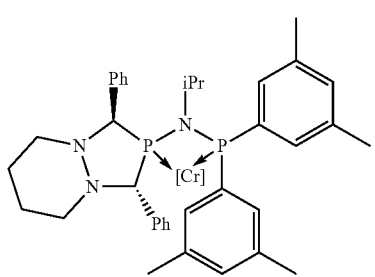
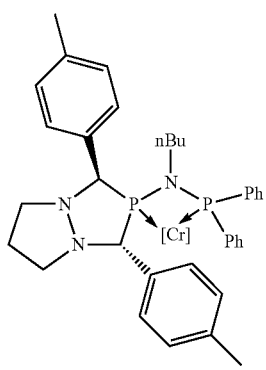
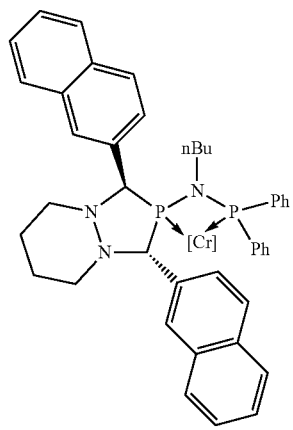
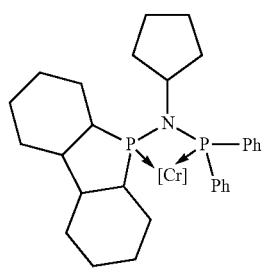
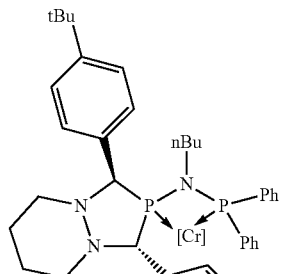
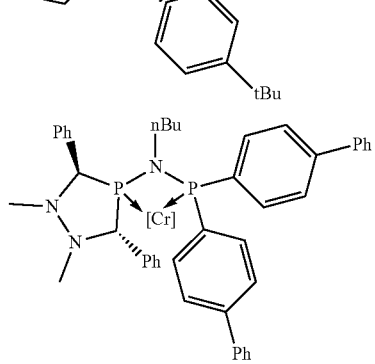

241
-continued
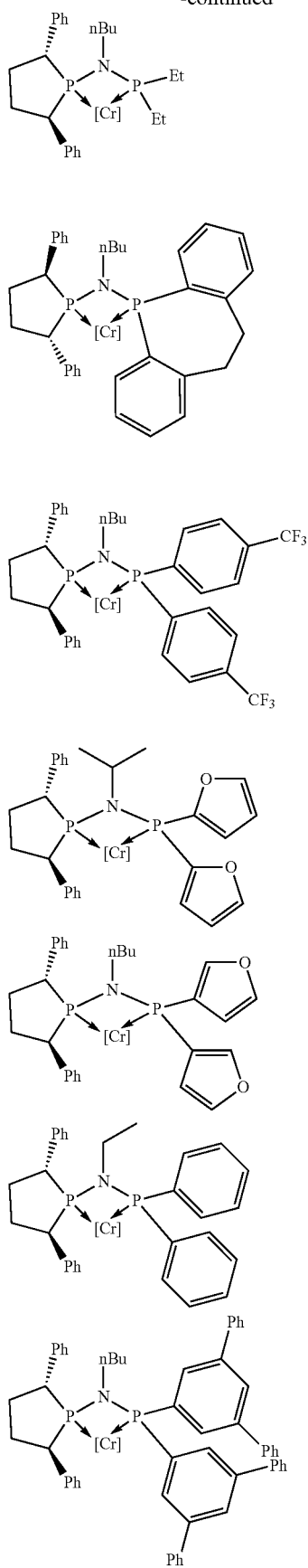
242
-continued
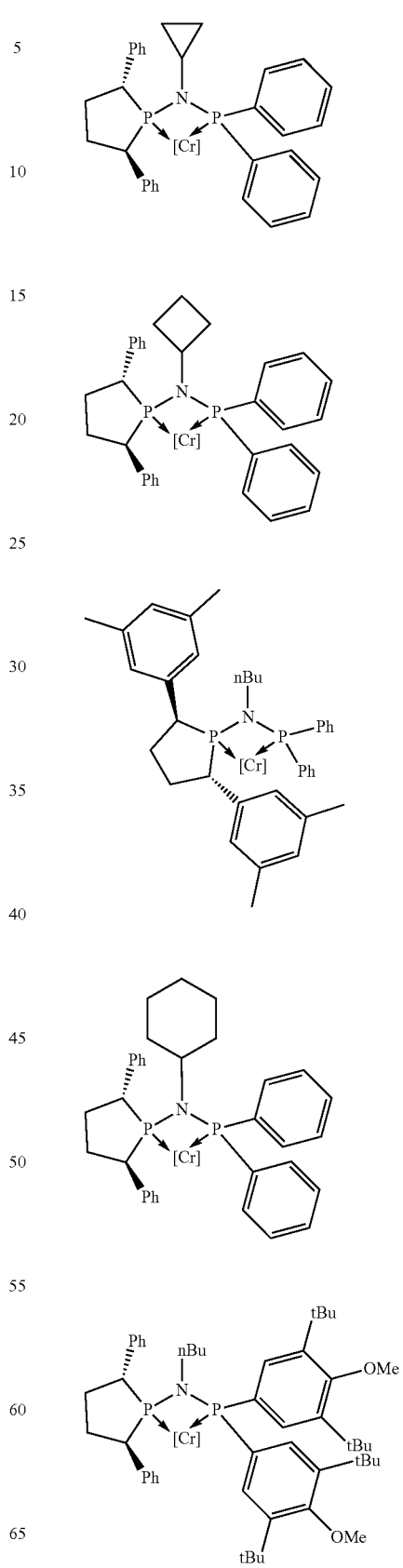

243
-continued
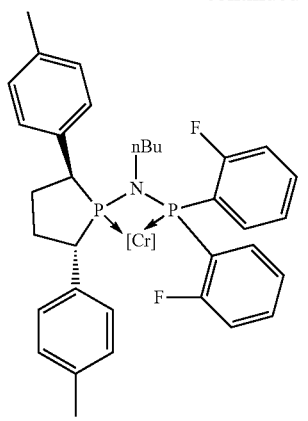
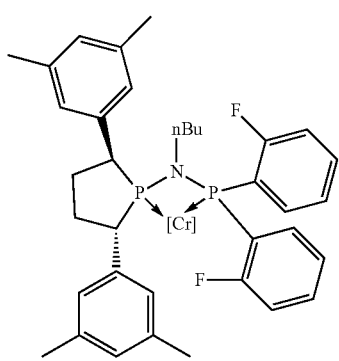
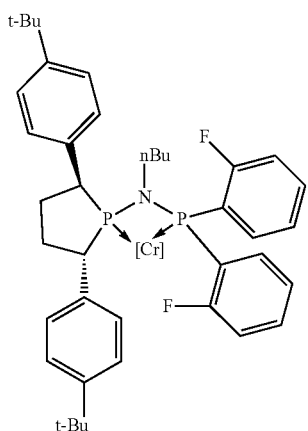
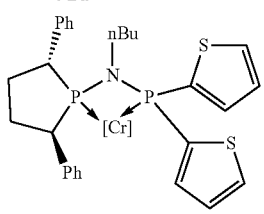
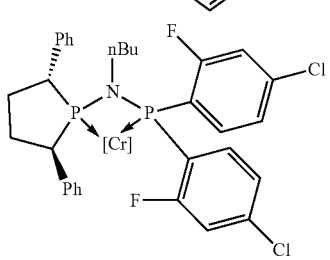
244
-continued
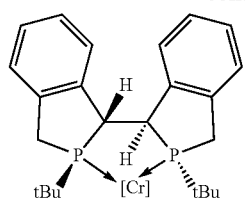
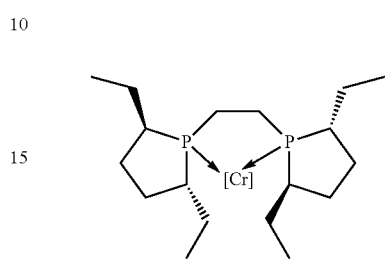
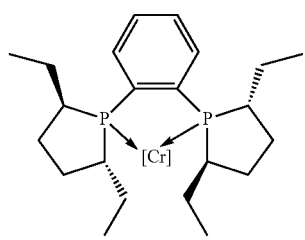
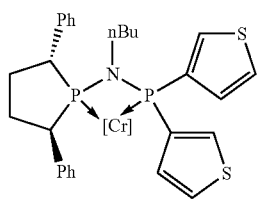
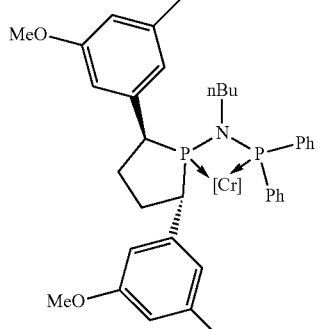
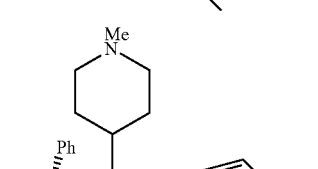
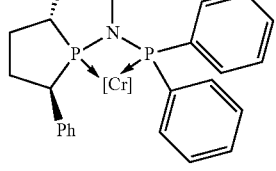

245
-continued
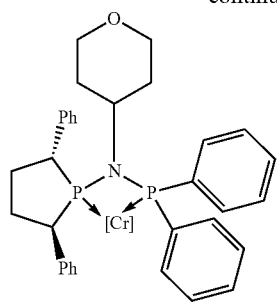
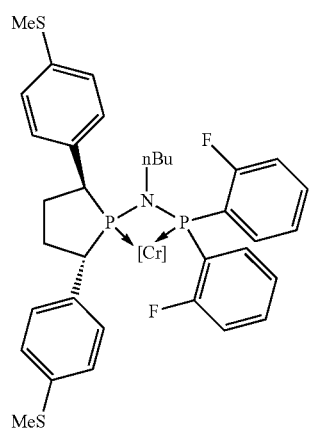
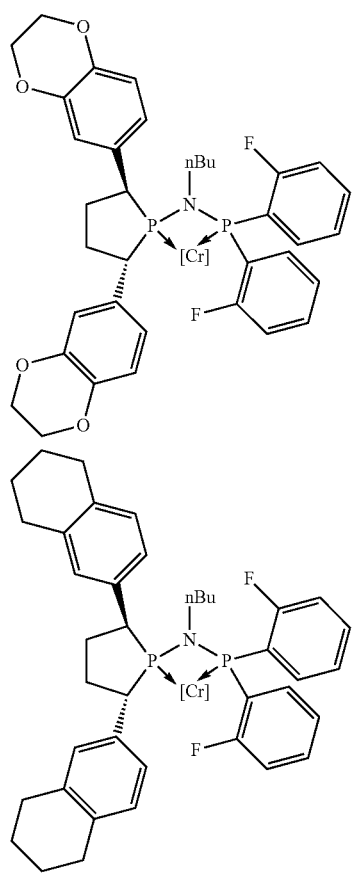
246
-continued
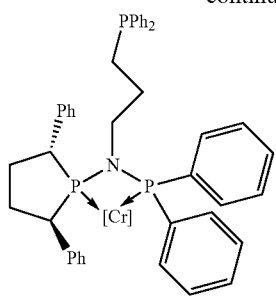
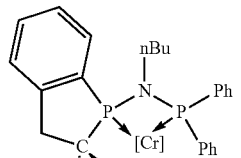
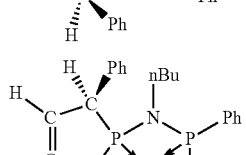
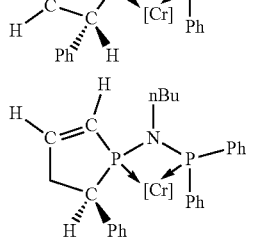
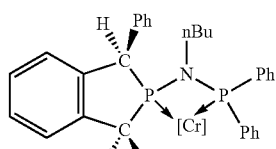
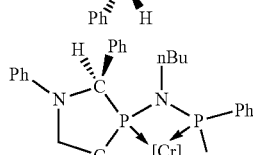
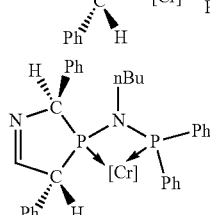
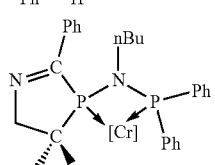
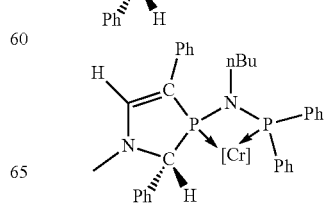

-continued

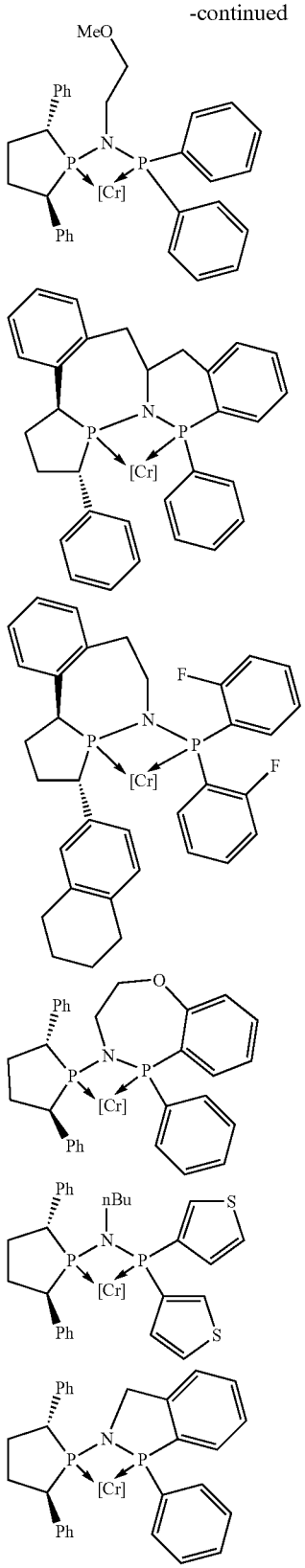

and their enantiomers.

The [Cr]—[Cr] linkage between the two [Cr] groups in the dimer form of the ligating compound-chromium complex is not limited to represent a Cr—Cr bond, but rather represents that the two independently selected [Cr] units are connected or associated through bonding interactions, for example, a Cr—Cr bond; bridging anionic ligands between the chromium atoms, such as bridging halide ligands, especially chloride, bromide, and iodide; bridging hydride ligands; bridging hydrocarbyl ligands, especially methyl, ethyl, ethanediyl, butanediyl, hexanediyl, octanediyl; bridging carboxylate ligands, especially acetate, octoate, 2-ethylhexaneoate; bridging sulfonate ligands, especially methanesulfonate, benzenesulfonate, toluenesulfonate, trifluoromethylsulfonate; bridging oxide or sulfide ligands; bridging hydroxide ligands; bridging alkoxide ligands, especially methoxide, ethoxide, propoxide, butoxide; bridging cyanide ligands; or bridging amido ligands, especially dimethylamido, diethylamido, diisopropylamido; bridging neutral Lewis bases between the chromium atoms, such as bridging carbonyl (CO); bridging phosphines, especially trimethylphosphine, triethylphosphine, triphenylphosphine; bridging ethers, especially diethyl ether, tetrahydrofuran; or bridging thioethers; bridging ligands having multiple anionic and/or neutral sites connecting the chromium atoms, wherein one chromium atom is attached to one site and another chromium atom is attached to another site, such as amido-imine ligands, diphosphine ligands, dicarboxylate ligands; ionic bonding interactions, such as when a ligating compound-chromium complex bearing a positive charge is associated with a ligating compound-chromium complex bearing a negative charge. In one embodiment, the dimer may be formed by connecting two independently selected ligating compound-chromium complexes by covalent bonding interactions between their respective $R_1$, $R_2$, $R_3$, $R_4$, $R_5$, or L groups.

The ancillary ligands attached to the chromium atom in [Cr], that is, the ligands attached to the chromium atom, not including the ligating compound, can include anionic or neutral ligands. The anionic or neutral ligands attached to the chromium atom in [Cr] can arise from the source of chromium, from the optional at least one solvent in which the ligating compound and the source of chromium may be contacted to form the ligating compound-chromium complex, from the ligating compound, from the at least one activator, or from other optional components that may be added. Anionic ligands attached to the chromium atom in [Cr] are selected from the group comprising halide anions, especially chloride, bromide, or iodide; β-ketonates, such as acetylacetonate, hexafluoroacetylacetonate, methylacetylacetonate, 3-acetylpentane-2,4-dionate; carboxylate anions, such as formate, acetate, propionate, benzoate, 2-ethylhexanoate, or trifluoroacetate; sulfonates, such as methanesulfonate, benzenesulfonate, p-toluenesulfonate, trifluoromethanesulfonate; hydrocarbyl groups and derivatives thereof, such as methyl, ethyl, propyl, butyl, allyl, neopentyl, phenyl, mesityl, benzyl, or trimethylsilylmethyl; and amide anions, such as dimethylamide, diethylamide, diisopropylamide; alkoxide anions, such as methoxide, ethoxide, or phenoxide; oxide or sulfide. Neutral ligands attached to the chromium atom in [Cr] are selected from the group comprising neutral Lewis bases, including, but not limited to ethers, such as THF (tetrahydrofuran) or diethyl ether; alcohols, such as methanol or ethanol; nitriles, such as acetonitrile or benzonitrile; amines, such as triethylamine or ethylenediamine; phosphines, such as trimethylphosphine, triethylphosphine, triphenylphosphine, or bis(dimethylphosphino)ethane; imines, such as N-ethylidene-benzenamine or N-(1-methylethylidene)-2-propanamine; water; carbonyl (CO); preferably carbonyl and THF.

Optionally from two to ten, preferably from two to six, independently selected ligating compound-chromium complexes may be linked together via their respective independently selected Ar, Ar', X", Y, $R_1$, $R_2$, $R_3$, $R_4$ or $R_5$ groups to form a poly(ligating compound-chromium complex) species. The poly(ligating compound-chromium complex) species may take the form of dendrimers, oligomers or polymers of the ligating compound-chromium complexes. The poly(ligating compound-chromium complex) species may be a linear, branched, or cyclic dendrimer, oligomer or polymer, wherein each monomer unit is an individual independently selected ligating compound-chromium complex. In one embodiment all of the individual ligating compound-chromium complexes are the same as each other. In one embodiment the individual ligating compound-chromium complexes are not all the same as each other.

The ligating compound-chromium complexes may be linked to form the poly(ligating compound-chromium complex) species by removing one or more independently selected atoms, preferably one atom, from one or more of the respective independently selected Ar, Ar', X", Y, $R_1$, $R_2$, $R_3$, $R_4$ or $R_5$ groups of each ligating compound-chromium complex to provide one or more free valencies on each ligating compound-chromium complex and then linking the ligating compound-chromium complexes having one or more free valencies to each other at the free valence sites to form the poly(ligating compound-chromium complex) species. In one embodiment the ligating compound-chromium complexes are linked via their corresponding independently selected Ar, Ar', X", Y, $R_1$, $R_2$, $R_3$, $R_4$ or $R_5$ groups (e.g., $R_1$ from one ligating compound-chromium complex is linked with $R_1$ from another ligating compound-chromium complex or Y from one ligating compound-chromium complex is linked with Y from another ligating compound-chromium complex). In one embodiment the ligating compound-chromium complexes are linked, but not via their corresponding independently selected Ar, Ar', X", Y, $R_1$, $R_2$, $R_3$, $R_4$ or $R_5$ groups (e.g., $R_2$ from one ligating compound-chromium complex is linked with a group from another ligating compound-chromium complex other than $R_2$).

In an embodiment, the poly(ligating compound-chromium complex) species may be formed by combining a poly(ligating compound) with a chromium source.

In an embodiment, the poly(ligating compound-chromium complex) species may be formed by contacting individual ligating compound-chromium complexes, whereby each individual ligating compound-chromium complex possesses at least one functional group on at least one Ar, Ar', X", Y, $R_1$, $R_2$, $R_3$, $R_4$ or $R_5$ group which can combine with a functional group of another individual ligating compound-chromium complex to form a bond.

In an embodiment, the poly(ligating compound-chromium complex) species may be formed by linking ligating compound-chromium complexes using the ancillary ligands which are part of [Cr], for example, ligating compound-chromium complexes which dimerize via bridging chloride ligands. While not wishing to be bound by any particular theory, it is believed that a poly(ligating compound-chromium complex) species formed by linking ligating compound-chromium complexes using the ancillary ligands which are part of [Cr] is prone to dissociation under oligomerization conditions, whereas a poly(ligating compound-chromium complex) species in which the individual ligating compound-chromium complexes are linked via their respective Ar, Ar', X", Y, $R_1$, $R_2$, $R_3$, $R_4$ or $R_5$ groups is believed not to dissociate under oligomerization conditions into its individual ligating compound-chromium complexes.

Specific, but non-limiting, examples of the poly(ligating compound-chromium complex) species include:

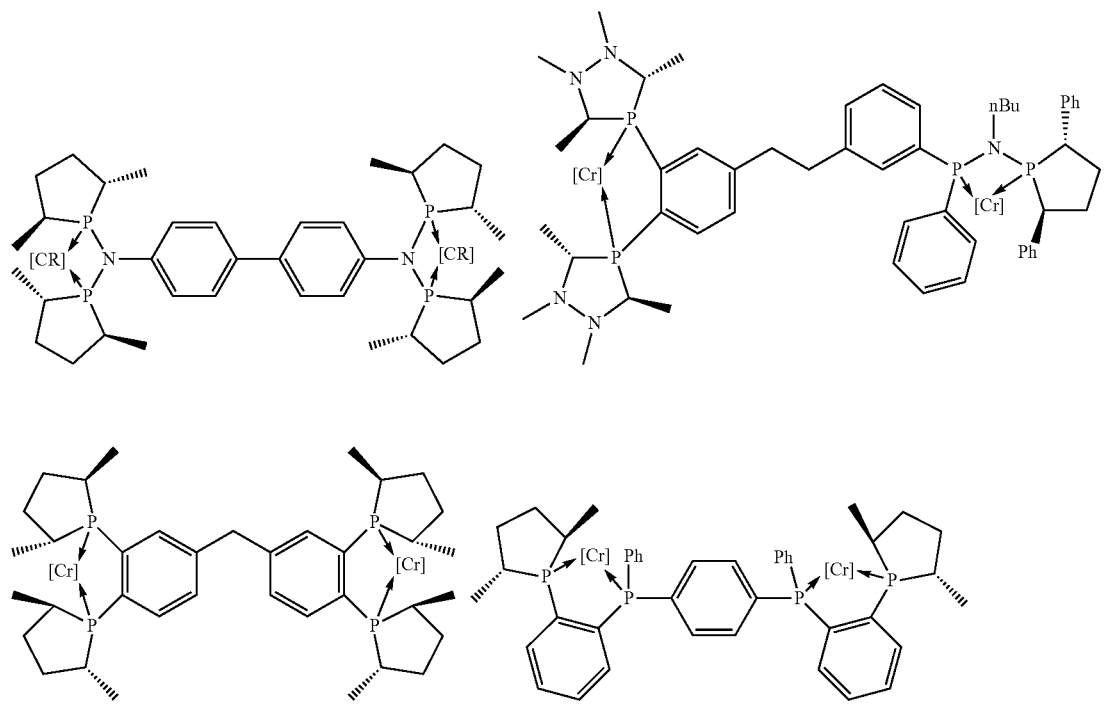

251  252
-continued
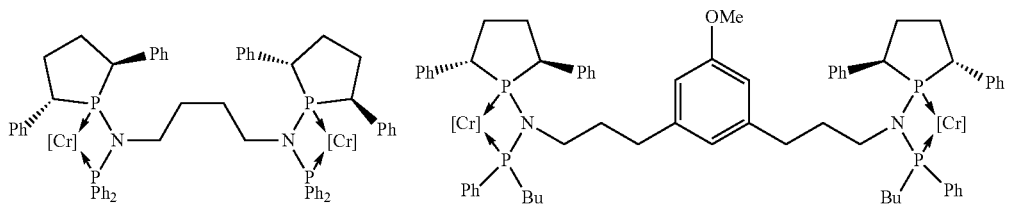
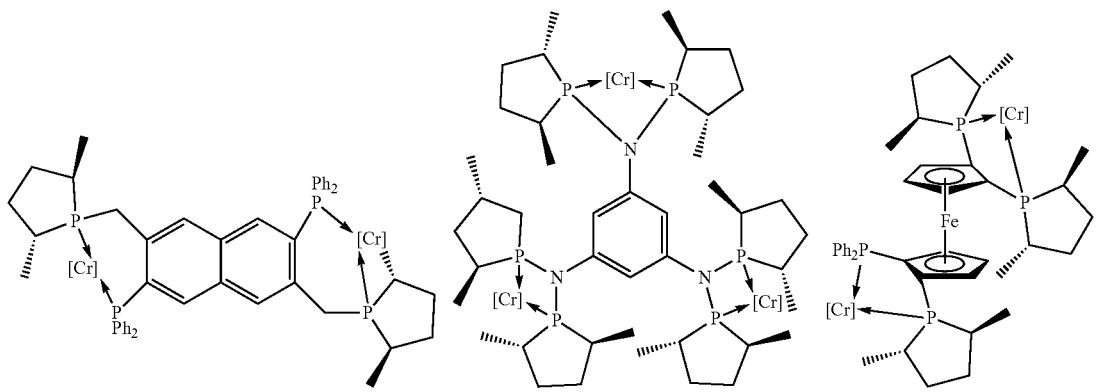
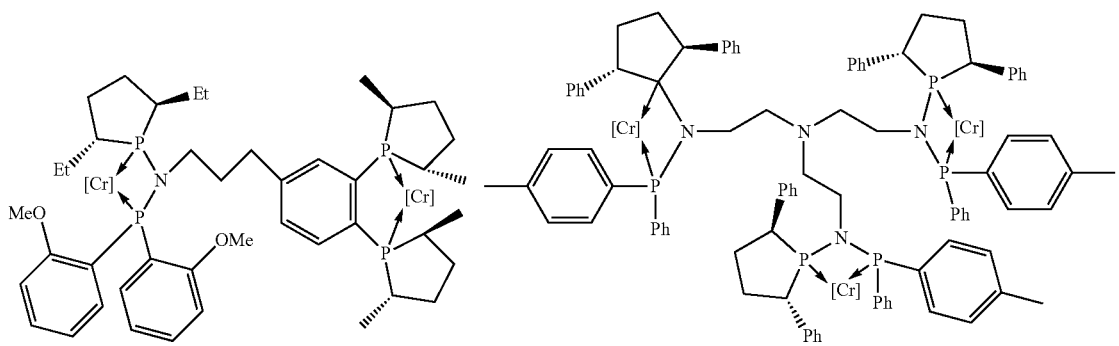
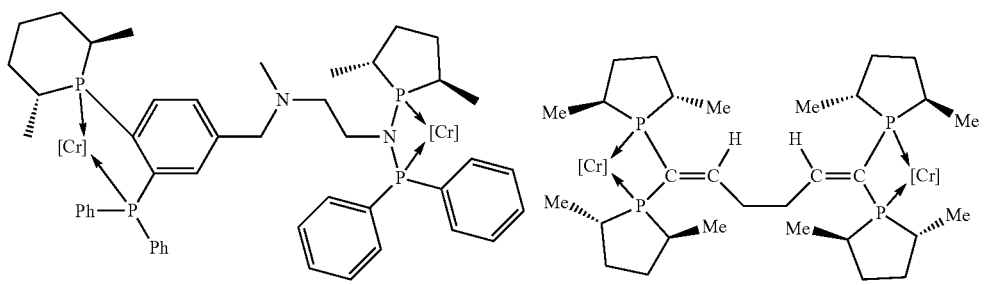
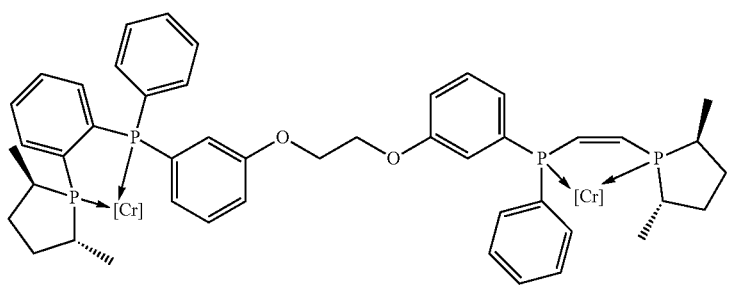

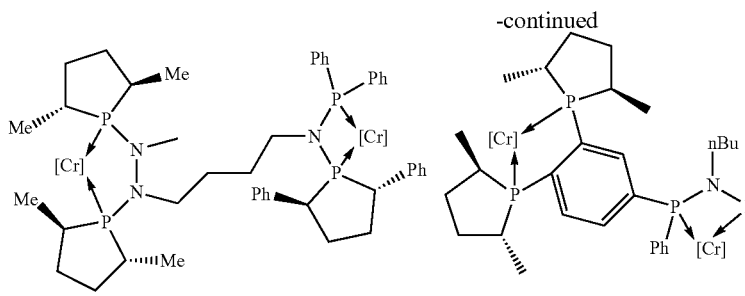
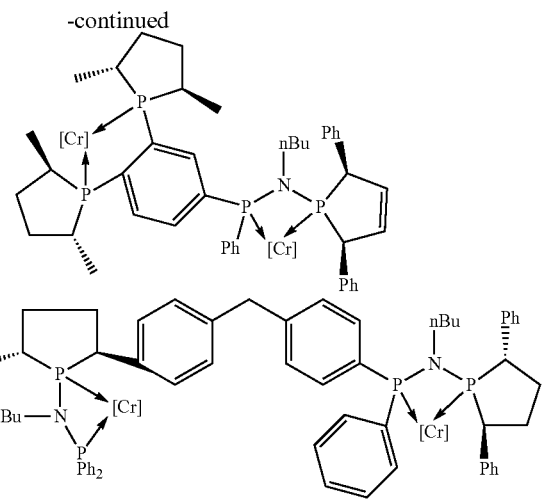
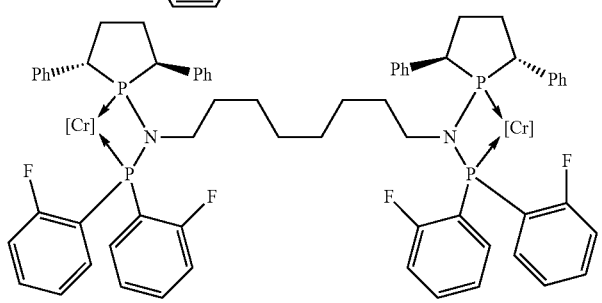

and their enantiomers.

Preparation of the Ligating Compound-Chromium Complex

In some embodiments, the invention provides a process to prepare the ligating compound-chromium complexes which are useful in the oligomerization of olefins such as ethylene. The ligating compound-chromium complex may be prepared by combining in any order a) a source of chromium and b) a phosphacycle-containing ligating compound as described herein, optionally in the presence of at least one solvent.

The ligating compound-chromium complex formed by combining the source of chromium and b) a phosphacycle-containing ligating compound optionally may or may not be isolated; optionally the ligating compound-chromium complex may be formed in situ, for example, in the oligomerization reactor.

The preparation of the ligating compound-chromium complex may be carried out at temperatures ranging from −100° C. to 250° C., preferably from −78° C. to 150° C., more preferably from 0° C. to 110° C., even more preferably from 20° C. to 80° C. The optional at least one solvent in which the ligating compound and the source of chromium are contacted to form the ligating compound-chromium complex may be any inert solvent, especially inert solvents selected from the group comprising pentane, hexane, heptane, octane, nonane, decane, cyclohexane, cycloheptane, methylcyclopentane, methylcyclohexane, 1-hexene, 1-octene, benzene, toluene, xylene, ethylbenzene, cumene, mesitylene, commercial saturated hydrocarbons mixtures, such as Isopar-E™, THF, diethyl ether, chloroform, methylene chloride, dichloroethane, trichloroethane, tetrachloroethane, chlorobenzene, 1,2-dichlorobenzene, chlorobenzene, and 1,2-dichlorobenzene, or mixtures thereof. Preferably the process to prepare the ligating compound-chromium complex is carried out under inert atmosphere conditions. Depending on the reaction conditions, the ligating compound-chromium complex may form as a monomer or as a dimer. For example, the reaction of 1,2-bis[(2S,5S)-2,5-dimethylphospholano]benzene, (Me-DuPhos), with $CrCl_3(THF)_3$), (trichlorotris(tetrahydrofuran)chromium), in THF gives the monomeric ligating compound-chromium complex Me-DuPhos-$CrCl_3$(THF), while in hot toluene the dimeric ligating compound-chromium complex (Me-DuPhos-$CrCl_3)_2$ forms. In some cases the dimer form of a ligating compound-chromium complex may be obtained upon recrystallization of the monomer form.

The source of chromium and the ligating compound may be contacted in proportions to provide Cr:ligating compound ratios from 1000:1 to 1:1000, preferably from 100:1 to 1:100, more preferably from 10:1 to 1:10, even more preferably from 1.3:1 to 1:1.3, still even more preferably from 1.1:1 to 1:1.1

The terms 'inert solvent' and 'inert atmosphere' mean that the solvent, respectively, atmosphere, do not interfere substantially with the formation of the ligating compound-chromium complex; preferably this means that the solvent, respectively, atmosphere, are substantially free of oxygen and/or other components which could interfere with formation of the ligating compound-chromium complex or could cause decomposition of the ligating compound or ligating compound-chromium complex.

The preparation of the ligating compound-chromium complex may optionally be carried out in the presence of an activator. The preparation of the ligating compound-chromium complex may occur as part of the process to prepare the catalyst system for the oligomerization of olefins.

It will be appreciated from Dyson et al Inorganica Chimica Acta 359 (2006) 2635-2643) that the isomeric 'P—P=N' form of the phosphacycle-containing ligating compound $R_1R_2P-Y-X_1R_3(R_4)_m$ or $R_1R_2P-[L(R_5)_q]_p-X_1R_3(R_4)_m$, where Y or $[L(R_5)_q]_p$ is $-N(R_5)$ — and $X_1R_3(R_4)_m$ is $PR_3R_4$, may be used in any method to prepare the ligating compound-chromium complex, including in the methods discussed above, especially if it exists in the 'P—N—P' form when used in an oligomerization process, more especially when it is bound to chromium in an oligomerization process.

Source of Chromium

Sources of chromium, sometimes referred to as "chromium precursors", are known in the literature. Illustrative publications include U.S. Pat. Nos. 7,378,537 and 7,425,661. To the extent permitted by US law, these references are incorporated herein.

In one embodiment, the source of chromium is selected from a group comprising $CrCl_3(THF)_3$ (trichlorotris(tetrahydrofuran)chromium), $CrBr_3(THF)_3$, $CrI_3(THF)_3$, $CrCl_3$, $CrBr_3$, $CrI_3$, $CrCl_2$, $CrCl_2(THF)_2$, $Cr(acac)_3$, (chromium (III) acetylacetonate), $Cr(acetate)_3$ (chromium (III) acetate), $Cr(2$-ethylhexanoate$)_3$ (chromium (III) 2-ethylhexanoate), $(THF)_3CrMeCl_2$, $(Mes)_3Cr(THF)$, $((TFA)_2Cr(OEt)_2)_2$, $(THF)_3CrPh_3$, $Cr(NMe_3)_2Cl_3$, $Cr(neopentyl)_3(THF)_3$, $Cr(CH_2-C_6H_4$-o-$NMe)_3$, $Cr(TFA)_3$, $Cr(CH(SiMe_3)_2)_3$, $Cr(Mes)_2(THF)_3$, $Cr(Mes)_2(THF)Cr(Mes)_2(THF)_2$, $Cr(Mes)Cl(THF)_2$, $Cr(Mes)Cl(THF)_{0.5}$, $Cr(p$-tolyl$)Cl_2(THF)_3$, $Cr(diisopropylamide)_3$, $Cr(picolinate)_3$, $CrCl_2(THF)_2$, $Cr(NO_3)_3$, $Cr(hexafluoroacetylacetonato)_3$, $(THF)_3Cr(\eta^2$-2,2"biphenyl)Br, $Cr(CO)_6$, $Cr(CO)_3(THF)_3$, $Cr(CO)_3(NCCH_3)_3$, (benzene)$Cr(CO)_3$, (toluene)$Cr(CO)_3$ and mixtures thereof. The source of chromium is preferably selected from a group consisting of $CrCl_3(THF)_3$, $CrCl_3$, $Cr(acac)_3$, $Cr(acetate)_3$, $Cr(2$-ethylhexanoate$)_3$, $CrCl_2$, $CrCl_2(THF)_2$, $Cr(CO)_6$, and mixtures thereof. In the foregoing formulae, "Mes" means mesityl or 2,4,6-trimethylphenyl, "TFA" means trifluoroacetate and "acac" means acetylacetonato.

Catalyst System

In some embodiments, the invention provides an oligomerization catalyst system for the oligomerization of olefins, wherein the catalyst system is a composition comprising a) a source of chromium, b) one or more activators, and c) at least one, preferably one, phosphacycle-containing ligating compound as described herein. Preferably the catalyst system is the composition comprising one or more activators and at least one, preferably one, phosphacycle-containing ligating compound-chromium complex wherein the at least one, preferably one, ligating compound-chromium complex comprises a source of chromium and at least one, preferably one, phosphacycle-containing ligating compound.

Another embodiment of the catalyst system for the oligomerization of olefins is the composition prepared by combining a) the source of chromium, b) one or more activators, and c) at least one, preferably one, phosphacycle-containing ligating compound together in any order, optionally in the presence of at least one solvent, either in the reactor in which the oligomerization process of this invention is carried out or not in the reactor, either in the presence or absence of at least one olefin, preferably in the presence of the at least one olefin, preferably ethylene, to be oligomerized, optionally the phosphacycle-containing ligating compound-chromium complex is formed in situ by combining the phosphacycle-containing ligating compound and the chromium source, optionally the phosphacycle-containing ligating compound and the chromium source are combined in situ.

Another embodiment of the catalyst system for the oligomerization of olefins is the composition prepared by a) combining the one or more activators with at least one, preferably one, ligating compound and b) combining the resulting combination with the source of chromium.

Another embodiment of the catalyst system for the oligomerization of olefins is the composition prepared by a) combining the one or more activators with the source of chromium and b) combining the resulting combination with at least one, preferably one, ligating compound.

Another embodiment of the catalyst system for the oligomerization of olefins is the composition prepared by combining the source of chromium, the one or more activators, and at least one, preferably one, ligating compound concurrently.

Another embodiment of the catalyst system for the oligomerization of olefins is the composition prepared by a) combining a source of chromium with at least one, preferably one, ligating compound and b) not isolating the resulting combination, and c) combining the combination with the one or more activators.

Another embodiment of the catalyst system for the oligomerization of olefins is the composition prepared by a) combining a source of chromium with at least one, preferably one, ligating compound and b) isolating the resulting combination Another embodiment of the catalyst system for the oligomerization of olefins is the composition prepared by a) combining a source of chromium with at least one, preferably one, ligating compound and b) not isolating the resulting combination.

A more preferred embodiment of the catalyst system for the oligomerization of olefins is the composition prepared by combining a) at least one, preferably one, isolated ligating compound-chromium complex (as described above), which is prepared by combining the source of chromium with at least one, preferably one, ligating compound, optionally in the presence of at least one solvent, and isolating the product; with b) the one or more activators, optionally in the presence of one or more solvents.

In some embodiments, the invention provides a process to prepare a catalyst system for the oligomerization of olefins, wherein the catalyst system is a composition comprising a) a source of chromium, b) one or more activators, and c) at least one phosphacycle-containing ligating compound as described herein. Preferably the catalyst system is the composition comprising one or more activators and at least one, preferably one, phosphacycle-containing ligating compound-chromium complex wherein the ligating compound-chromium complex comprises a source of chromium and at least one, preferably one, phosphacycle-containing ligating compound.

Another embodiment of the invention provides a process to prepare a catalyst system for the oligomerization of olefins, the steps of the process comprising combining a) the source of chromium, b) one or more activators, and c) at least one phosphacycle-containing ligating compound together in any order, optionally in the presence of at least one solvent, either in the reactor in which the oligomerization process of this invention is carried out or not in the reactor, either in the presence or absence of at least one olefin, preferably in the presence of the at least one olefin, preferably ethylene, to be oligomerized.

Another embodiment of the invention provides a process to prepare a catalyst system for the oligomerization of olefins, the steps of the process comprising a) combining the one or more activators with at least one ligating compound and b) combining the resulting combination with the source of chromium.

Another embodiment of the invention provides a process to prepare a catalyst system for the oligomerization of olefins, the steps of the process comprising a) combining the one or more activators with the source of chromium and b) combining the resulting combination with at least one ligating compound.

Another embodiment of the invention provides a process to prepare a catalyst system for the oligomerization of olefins, the steps of the process comprising combining the source of chromium, the one or more activators, and at least one ligating compound concurrently.

Another embodiment of the invention provides a process to prepare a catalyst system for the oligomerization of olefins, the steps of the process comprising a) combining a source of chromium with at least one, preferably one, ligating compound, optionally in situ, and b) not isolating the resulting combination, and c) combining the combination with the one or more activators.

Another embodiment of the invention provides a process to prepare a catalyst system for the oligomerization of olefins, steps of the process comprising a) combining a source of chromium with at least one, preferably one, ligating compound, optionally in situ, and b) isolating the resulting combination.

Another embodiment of the invention provides a process to prepare a catalyst system for the oligomerization of olefins, steps of the process comprising a) combining a source of chromium with at least one, preferably one, ligating compound, optionally in situ, and b) not isolating the resulting combination.

A more preferred embodiment of the invention provides a process to prepare a catalyst system for the oligomerization of olefins, the steps of the process comprising a) combining the source of chromium with at least one ligating compound, optionally in the presence of at least one solvent, b) isolating a ligating compound-chromium complex, c) combining the isolated a ligating compound-chromium complex with one or more activators.

In one embodiment, the invention provides a process to prepare a catalyst system for the oligomerization of olefins in the oligomerization reactor (in situ) or outside (ex situ) of the oligomerization reactor, optionally in the presence of at least one oligomerization solvent and optionally in the presence of at least one olefin, preferably in the presence of the at least one olefin, preferably ethylene, to be oligomerized. Preferably the source of chromium, one or more activators, and at least one phosphacycle-containing ligating compound are contacted in the oligomerization reactor in any order. More preferably at least one, preferably one, ligating compound-chromium complex and one or more activators are contacted in the oligomerization reactor.

In the composition and process of the invention, the chromium (either from the source of chromium or from the ligating compound-chromium complex), the one or more activators, and the phosphacycle-containing ligating compound (including from the ligating compound-chromium complex) may be in such proportions relative to each other to provide chromium:ligating compound molar ratios from 10:1 to 1:10, more preferably from 1.3:1 to 1:1.3, still more preferably from 1.1:1 to 1:1.1; and chromium:activator (e.g., aluminum, boron, gallium compounds) molar ratios from 100:1 to 1:10,000, preferably from 1:1 to 1:3000, more preferably from 1:1 to 1:1000, still more preferably from 1:1 to 1:500.

Typically the chromium (either from the source of chromium or from the ligating compound-chromium complex), the one or more activators, and the phosphacycle-containing ligating compound (including from the ligating compound-chromium complex) are contacted (both in situ and ex situ) to provide chromium:ligating compound molar ratios from 10:1 to 1:10, more preferably from 1.3:1 to 1:1.3, still more preferably from 1.1:1 to 1:1.1; and chromium: activator (e.g., aluminum, boron, gallium compounds) molar ratios from 100:1 to 1:10,000, preferably from 1:1 to 1:3000, more preferably from 1:1 to 1:1000, still more preferably from 1:1 to 1:500.

The preparation of the catalyst system may be carried out at temperatures ranging from −80° C. to 110° C., preferably from 0° C. to 80° C., more preferably from 20° C. to 70° C. The optional at least one solvent may be any inert solvent, especially inert solvents selected from the group consisting of hydrocarbons, e.g., pentane, hexane, heptane, octane, nonane, decane, cyclohexane, cycloheptane, methylcyclopentane, methylcyclohexane, 1-hexene, 1-octene, benzene, toluene, xylene, ethylbenzene, cumene, mesitylene, or commercial saturated hydrocarbons mixtures, such as Isopar-E™; neutral Lewis bases, e.g., THF, diethyl ether, alcohols, such as methanol or ethanol, acetonitrile; chlorinated hydrocarbons, e.g., chloroform, methylene chloride, dichloroethane, trichloroethane, tetrachloroethane, chlorobenzene, 1,2-dichlorobenzene; and ionic liquids, or mixtures thereof. Preferably the at least one solvent is selected from the group consisting of saturated hydrocarbons and chlorinated hydrocarbons or mixtures thereof. Especially preferred are methylcyclohexane, chlorobenzene, and 1,2-dichlorobenzene.

Activators

In some embodiments, the invention provides a process for selectively oligomerizing an olefin comprising an activated catalyst system comprising combining a) a source of chromium, b) one or more activators, and c) at least one phosphacycle-containing ligating compound.

An embodiment of the invention comprises a process for forming an activated catalyst system comprising combining a) a source of chromium, b) one or more activators, and c) at least one phosphacycle-containing ligating compound.

As is described below, the source of chromium, the one or more activators, and the ligating compound may be contacted in any order. In some embodiments, the source of chromium and the ligating compound may be contacted in the absence of any activators and a resulting ligating compound-chromium complex which may or may not be isolated is contacted with one or more activators. In some embodiments, the ligating compound may be contacted with the one or more activators and the resulting combination may be contacted with the chromium source. In an embodiment of the invention, an activating technique may be used in place of the one or more activators.

The activators ("activating co-catalysts") and activating techniques are such as those that are known in the art for use with metal-based olefin polymerization reactions. Suitable activators for use herein include neutral Lewis acids, especially Group 13 metal and metalloid compounds; polymeric or oligomeric alumoxanes (also known as aluminoxanes); non-polymeric, non-coordinating, ion-forming compounds (including the use of such compounds under oxidizing conditions); and aluminates. A suitable activating technique is bulk electrolysis as disclosed in U.S. Pat. No. 6,465,384.

Preferred neutral Lewis acid activators are Group 13 metal and metalloid compounds containing from 1 to 3 hydrocarbon derivative, preferably hydrocarbyl, substituents as described herein, especially wherein the Group 13 metal and metalloid compounds are selected from compounds of boron, aluminum, and gallium. More preferred Group 13 metal compounds are (hydrocarbyl)aluminum, (hydrocarbyl)gallium, (hydrocarbyl)boron, (substituted hydrocarbyl)aluminum, (substituted hydrocarbyl)gallium and (substituted hydrocarbyl)boron compounds, especially mono(hydrocarbyl)-substituted-aluminum, di(hydrocarbyl)-substituted-aluminum, tri(hydrocarbyl)-substituted-aluminum, (hydrocarbyl)-substituted-gallium, di(hydrocarbyl)-substituted-gallium, tri(hydrocarbyl)-gallium, or tri (hydrocarbyl)-boron compounds, more especially alkyl aluminum, alkyl gallium, aryl and arylalkyl boron compounds or mixtures thereof. The term "alkyl aluminum" means a monoalkyl aluminum dihydride, monoalkylaluminum dihalide, or monoalkylaluminum dialkoxide, a dialkyl aluminum hydride, dialkyl aluminum halide, or a dialkyl aluminum alkoxide, or a trialkylaluminum. The term "alkyl gallium" means a monoalkyl gallium dihydride, monoalkyl gallium dihalide, or monoalkyl gallium dialkoxide, a dialkyl gallium hydride, dialkyl gallium halide, or a dialkyl gallium alkoxide, or a trialkyl gallium. The term "aryl boron" means a monoaryl boron dihydride, a monoaryl boron dihalide, a monoaryl boron dialkoxide, a monoaryl boron dialkyl, a diaryl boron alkyl, a diaryl boron hydride, a diaryl boron halide, a diaryl boron alkoxide, or a trialkyl boron. The term "arylalkyl boron" means a monoarylalkyl boron dihydride, a monoarylalkyl boron dihalide, a monoarylalkyl boron dialkoxide, a monoarylalkyl boron dialkyl, a diarylalkyl boron alkyl, a diarylalkyl boron hydride, a diarylalkyl boron halide, a diarylalkyl boron alkoxide, or a triarylalkyl boron. Still more preferred are $((C_{1-10})$alkyl)aluminum dihydride, $((C_{1-10})$alkyl)aluminum dihalide, $((C_{1-10})$alkyl)aluminum dialkoxide, di$((C_{1-10})$alkyl)aluminum hydride, di$((C_{1-10})$alkyl)aluminum alkoxide, di$((C_{1-10})$alkyl)aluminum halide, tri$((C_{1-10})$alkyl)aluminum, $((C_{1-10})$alkyl)gallium dihydride, $((C_{1-10})$alkyl)gallium dihalide, $((C_{1-10})$alkyl)gallium dialkoxide, di$((C_{1-10})$alkyl)gallium hydride, di$((C_{1-10})$alkyl) gallium alkoxide, di$((C_{1-10})$alkyl)gallium halide, tri$((C_{1-10})$ alkyl)gallium, $((C_{6-18})$aryl)boron dihydride, $((C_{6-18})$aryl)boron dialkyl, $((C_{6-18})$aryl)boron dihalide, $((C_{6-18})$aryl)boron dialkoxide, di$((C_{6-18})$aryl)boron hydride, di$((C_{6-18})$aryl)boron alkyl, di$((C_{6-18})$aryl)boron halide, di$((C_{6-18})$aryl)boron alkoxide, tri$((C_{6-18})$aryl)aluminum, tri$((C_{6-18})$aryl)boron, $((C_{6-18})$arylalkyl)boron dihydride, $((C_{6-18})$arylalkyl)boron dialkyl, $((C_{6-18})$arylalkyl)boron dihalide, $((C_{6-18})$arylalkyl) boron dialkoxide, di$((C_{6-18})$arylalkyl)boron hydride, di$((C_{6-18})$arylalkyl)boron alkyl, di$((C_{6-18})$arylalkyl)boron halide, di$((C_{6-18})$arylalkyl)boron alkoxide, tri$((C_{6-18})$arylalkyl)aluminum, tri$((C_{6-18}$ is)arylalkyl)boron, or tri$((C_{6-18})$ aryl)gallium compounds and halogenated (including perhalogenated) derivatives thereof, even more especially tris (fluoro-substituted phenyl)borane compounds, tris(fluoro-substituted phenyl)aluminum compounds, and tris(fluoro-substituted phenyl)gallium compounds, still even more especially tris(pentafluorophenyl)borane, tris(pentafluorophenyl)aluminum, and tris(pentafluorophenyl)gallium, or mixtures thereof.

Preferred alkyl aluminum activators include trimethylaluminum (TMA), triethylaluminum, tripropylaluminum, triisopropylaluminum, tributylaluminum, triisobutylaluminum (TIBA), trihexylaluminum, trioctylaluminum, ethyldiisopropylaluminum methylaluminum dichloride, ethylaluminum dichloride, isobutylaluminum dichloride, dimethylaluminum chloride, diethylaluminum chloride, diisobutylaluminum chloride, diethylaluminum hydride, diisobutylaluminum hydride, methylaluminum sesquichloride, ethylaluminum sesquichloride, isobutylaluminum sesquichloride, methylaluminum di(2,6-t-butyl-4-methylphenoxide), dimethylaluminum isopropoxide, diethylaluminum ethoxide, diisobutylaluminum (2,6-t-butyl-4-methylphenoxide), and mixtures thereof.

Preferred alkyl gallium compounds include trimethylgallium, triethylgallium, tripropylgallium, triisopropylgallium, diethylgallium chloride, and dimethyl(2,4-pentanedionato) gallium.

Aluminoxanes and their preparations are known at, for example, U.S. Pat. No. 6,103,657. Aluminoxanes, a subset of (hydrocarbyl)aluminum compounds, are well known in the art as typically polymeric or oligomeric, usually oligomeric, compounds which can be prepared by the controlled addition of water to a (hydrocarbyl)aluminum compound, especially an alkylaluminum compound, for example, trimethylaluminum. Examples of preferred polymeric or oligomeric alumoxanes are methylaluminoxane (MAO) (MAO is also referred to as methalumoxane and methylalumoxane in the literature), triisobutylaluminum-modified methylalumoxane, and isobutylalumoxane, as well as tetraethyl-g-oxodialuminum and tetraisobutyl-g-oxodialuminum.

Preferred alumoxanes are those which are commercially available so as to reduce costs. It will be recognized by those skilled in the art that commercially available alkylaluminoxanes may contain a proportion of trialkylaluminum. For instance, commercial MAO usually contains approximately 10 wt % trimethylaluminum (TMA), and commercial "modified MAO" (or "MMAO") contains both TMA and TIBA. Preferred aluminoxanes include MAO and MMAO.

Preferred non-coordinating, ion-forming compounds, some of which are described in WO 2007/039851, may include a cation and an anion component, and may be represented by the following formula:

where $(Cat)^{d'+}$ is a cation having the charge d'+; $A^{d'-}$ is a non-coordinating anion having the charge d'– and d' is an integer from 1 to 3.

$A^{d'-}$ preferably can be a borate anion, especially an organoborate anion, an aluminate anion, a gallate anion, or a tantalate anion. Preferably d' is 1; $A^{d'-}$ is $[A'(R^9)_4]^-$, wherein A' is boron, aluminum, or gallium, and; $R^9$ independently at each occurrence is selected from the group consisting of hydride, halide, di$(C_{1-18})$ alkylamido, $(C_{1-18})$ hydrocarbyl, halosubstituted-$(C_{1-18})$ hydrocarbyl, $(C_{1-18})$ alkoxide, $(C_{2-18})$ aryloxide, and $(C_{2-18})$ arylalkyloxide. Preferably $R^9$ is selected from $(C_{1-18})$ halosubstituted-alkyl, $(C_{2-18})$ halosubstituted-aryl, $(C_{2-18})$ halosubstituted-arylalkyl, $(C_{1-18})$ halosubstituted-alkoxide, $(C_{2-18})$ halosubstituted-aryloxide and $(C_{2-18})$ halosubstituted-arylalkyloxide. More preferably $R^9$ is selected from $(C_{1-18})$ fluorosubstituted-alkyl, $(C_{2-18})$ fluorosubstituted-aryl, $(C_{2-18})$ fluorosubstituted-arylalkyl, $(C_{1-18})$ fluorosubstituted-alkoxide, $(C_{2-18})$ fluorosubstituted-aryloxide, and $(C_{2-18})$ fluorosubstituted-arylalkyloxide. Preferably $R^9$ is selected from H, F, $(CH_3)_2N$, $(CH_3CH_2)_2N$, $((CH_3)_2CH)_2N$, methyl, ethyl, propyl, isopropyl, butyl, isobutyl, phenyl, benzyl, trifluoromethyl, 2,2,2-trifluoroethyl, pentafluoroethyl, 1,1,1,3,3,3-hexafluoro-2-propyl, heptafluoro-isopropyl, nonafluoro-t-butyl, tetrafluorophenyl, pentafluorophenyl, 3,5-bis (trifluoromethyl)phenyl, methoxy, ethoxy, propoxy, isopropoxy, butoxy, phenoxy, trifluoromethoxy, 2,2,2-trifluoroethoxy, pentafluoroethoxy, 1,1,1,3,3,3-hexafluoro-2- propoxy, heptafluoro-isopropoxy, nonafluoro-t-butoxy, tetrafluorophenoxy, pentafluorophenoxy, or two $R^9$ groups taken together are catechol or tetrafluorocatechol. Preferably A' is boron; $R^9$ is H, fluoro, heptafluoro-isopropyl, nonafluoro-t-butyl, tetrafluorophenyl, pentafluorophenyl, or 3,5-bis(trifluoromethyl)phenyl; preferably at least one $R^9$ is fluoro, preferably at least one $R^9$ is pentafluorophenyl, more preferably at least two $R^9$ are pentafluorophenyl, even more preferably at least three $R^9$ are pentafluorophenyl, most preferably four $R^9$ are pentafluorophenyl. Preferably A' is aluminum or gallium; $R^9$ is fluoro, pentafluorophenyl, 3,5-bis(trifluoromethyl)phenyl, 1,1,1,3,3,3-hexafluoro-2-propoxy, heptafluoro-isopropoxy, nonafluoro-t-butoxy, pentafluorophenoxy, or two $R^9$ groups taken together are tetrafluorocatechol.

Illustrative, but non-limiting, examples of the anion component $A^{d'-}$ are $[B\{OC(CF_3)_3\}_4]^-$, $[B(OC_6F_5)_4]^-$, $[B(C_6F_4O_2)_2]^-$, $[BF\{OC(CF_3)_3\}_3]^-$, $[BH\{OC(CF_3)_3\}_3]^-$, $[B\{OC(CF_3)_3\}_6]^-$, $[B(OC_6F_5)_6]^-$, $[B(C_6F_5)_4]^-$, $[B\{3,5\text{-}(CF_3)_2C_6H_3\}_4]^-$, $[BF(C_6F_5)_3]^-$, $[BF\{3,5\text{-}(CF_3)_2C_6H_3\}_3]^-$, $[Al\{OCH(CF_3)_2\}_4]^-$, $[Al\{OCF(CF_3)_2\}_4]^-$, $[Al\{OC(CF_3)_3\}_4]^-$, $[Al(OC_6F_5)_4]^-$, $[Al(C_6F_4O_2)_2]^-$, $[AlF\{OCH(CF_3)_2\}_3]^-$, $[AlF\{OCF(CF_3)_2\}_3]^-$, $[AlF\{OC(CF_3)_3\}_3]^-$, $[AlH\{OC(CF_3)_3\}_3]^-$, $[Al_2F\{OCH(CF_3)_2\}_6]^-$, $[Al_2F\{OC(CF_3)_3\}_6]^-$, $[AlF(C_6F_5)_3]^-$, $[AlF\{3,5\text{-}(CF_3)_2C_6H_3\}_3]^-$, $[Al(C_6F_5)_4]^-$, $[Al\{3,5\text{-}(CF_3)_2C_6H_3\}_4]^-$, $[Ga\{OCH(CF_3)_2\}_4]^-$, $[Ga\{OCF(CF_3)_2\}_4]^-$, $[Ga\{OC(CF_3)_3\}_4]^-$, $[Ga(OC_6F)_4]^-$, $[Ga(C_6F_4O_2)_2]^-$, $[GaF\{OCH(CF_3)_2\}_3]^-$, $[GaF\{OCF(CF_3)_2\}_3]^-$, $[GaF\{OC(CF_3)_3\}_3]^-$, $[Ga_2F\{OCH(CF_3)_2\}_6]^-$, $[Ga_2F\{OC(CF_3)_3\}_6]^-$, $[GaF(C_6F_5)_3]^-$, $[GaF\{3,5\text{-}(CF_3)_2C_6H_3\}_3]^-$, $[Ga(C_6F_5)_4]^-$, $[Ga\{3,5\text{-}(CF_3)_2C_6H_3\}_4]^-$, and $[Ta(OC_6F_5)_6]^-$.

Preferably $(Cat)^{d'+}$ can be represented by $(L'\text{-}H)^{d'+}$, where L' is a neutral Lewis base; H is hydrogen; $(L'\text{-}H)^{d'+}$ is a Brønsted acid having the charge d'+; and d' is an integer from 1 to 3; preferably d' is 1. More preferably $(Cat)^{d'+}$ can be represented by $[(R)_xL^*\text{-}H]^+$ or $[(R^{10})_3C]^+$ or $[M]^+$ wherein the cation $[(R)_xL^*\text{-}H]^+$ is a Brønsted acid with a +1 positive charge; H is hydrogen; each R, independently chosen, is H, halide, $C_{2-20}$ dialkylamido, $C_{1-20}$ hydrocarbyl, or $C_{1-20}$ heterohydrocarbyl; L* is an atom selected from the group consisting of N, P, and S; x' is 3 for L*=N or P and x' is 2 for L*=S; the cation $[(R^{10})_3C]^+$ is a carbenium cation with a +1 positive charge; each $R^{10}$, independently chosen, is H, $C_{1-20}$ hydrocarbyl, or $C_{1-20}$ heterohydrocarbyl; the cation $[M]^+$ is a metal-containing cation with a +1 positive charge.

Preferably R is independently a $C_{1-20}$ hydrocarbon derivative, or $C_{1-20}$ heterohydrocarbon derivative, preferably $C_{1-20}$ hydrocarbyl, or $C_{1-20}$ heterohydrocarbyl. Preferably L* is nitrogen; x' is 3; at least one of R comprises at least 6 carbon atoms and provided further that the total number of carbon atoms in $(R)_{x'}$ collectively is greater than 12. More preferably at least one of R is a $C_{6-12}$ aryl, $C_{6-12}$ arylalkyl, or $C_{14-20}$ alkyl. Preferably $[(R)_xL^*\text{-}H]^+$ is bis(($C_{1-20}$)hydrocarbyl)ammonium or tris(($C_{1-20}$)hydrocarbyl)ammonium. As used herein, the term "ammonium" means a nitrogen cation that is $((C_{1-20})\text{hydrocarbyl})_4N^+$ (a tetrakis(($C_{1-20}$)hydrocarbyl) ammonium cation), $((C_{1-20})\text{hydrocarbyl})_3N(H)^+$ (a tris(($C_{1-20}$)hydrocarbyl)ammonium cation), $((C_{1-20})\text{hydrocarbyl})_2N(H)_2^+$ (a bis(($C_{1-20}$)hydrocarbyl)ammonium cation), $((C_{1-20})\text{hydrocarbyl})N(H)_3^+$ (a mono(($C_{1-20}$)hydrocarbyl) ammonium cation), or $N(H)_4^+$ (ammonium cation), wherein each ($C_{1-20}$)hydrocarbyl independently selected may be the same or different. Illustrative, but non-limiting, examples of the cation component $[(R)_xL^*\text{-}H]^+$ are di(octadecyl)ammonium, dimethylanilinium, dihexylanilinium, di(octadecyl) ammonium, methyldi(octadecyl)ammonium, (hexadecyl) (methyl)octadecylammonium, dimethylimidazolium, ethylmethylimidazolium, di-t-butylimidazolium, Preferably $R^{10}$ is $C_{1-12}$ alkyl, $C_{6-16}$ aryl, $C_{6-16}$ arylalkyl, or $C_{6-16}$ heteroaryl. Preferably at least one $R^{10}$ is substituted or unsubstituted $C_{6-20}$ aryl, more preferably two $R^{10}$, independently selected, are substituted or unsubstituted $C_{6-20}$ aryl, even more preferably all three $R^{10}$ independently selected, are substituted or unsubstituted $C_{6-20}$ aryl. Preferably $R^{10}$ is phenyl, 4-methylphenyl, 2,4-dimethylphenyl, 2,4,6-trimethylphenyl, 4-methoxyphenyl, 4-dimethylaminophenyl or 2,6-dimethoxyphenyl. Preferably $[(R^{10})_3C]^+$ is triphenylcarbenium (trityl).

Preferably the $[M]^+$ metal-containing cation is $Ag^+$ or a substituted or unsubstituted ferrocenium cation.

Preferred non-coordinating, ion-forming compounds $(Cat)^{d'+} A^{d'-}$ wherein d'=1 may be selected by pairing a desired $(Cat)^+$ with a desired $A^-$, to give $[(R)_xL^*\text{-}H]^+ A^-$, $[(R^{10})_3C]^+ A^-$, or $[M]^+ A^-$. Illustrative, but non-limiting, examples of these non-coordinating, ion-forming compounds include methyldi(octadecyl)ammonium tetrakis (pentafluorophenyl)borate, dimethylanilinium tetrakis(nonafluoro-t-butoxy)aluminate, trioctylammonium tetrakis (pentafluorophenyl)borate, (hexadecyl)(methyl)(octadecyl) ammonium tetrakis(pentafluorophenyl)borate, (hexadecyl) (methyl)(octadecyl)ammonium $[B\{3,5\text{-}(CF_3)_2C_6H_3\}_4]^-$, ethylmethylimidazolium $[Al\{OCH(CF_3)_2\}_4]^-$, triphenylcarbenium tetrakis(tetrafluorophenyl)borate, ferrocenium $[Ga(OC_6F_5)_4]^-$, tris(4-methoxyphenyl)carbenium $[BF(C_6F_5)_3]^-$, and $Ag^+ [Ta(OC_6F_5)_6]^-$. In some embodiments, organoboron activators represented as $[(R)_xL^*\text{-}H]^+ [B(R^9)_4]^-$ are described in WO 2010/092554.

One or more activators are used to form the catalyst system with the ligating compound and the source of chromium. Preferably at least two activators are used in combination. Also preferred are combinations of such neutral Lewis acid mixtures with a polymeric or oligomeric alumoxane, and combinations of a single neutral Lewis acid, especially tris(pentafluorophenyl)borane with a polymeric or oligomeric alumoxane. In some embodiments, the at least two activators come from the same class (neutral Lewis acids with neutral Lewis acids; polymeric or oligomeric alumoxanes with polymeric or oligomeric alumoxanes; non-polymeric, non-coordinating, ion-forming compounds with non-polymeric, non-coordinating, ion-forming compounds), for example, triethylaluminum with tris(pentafluorophenyl) borane; MAO with MMAO; methyldi(octadecyl)ammonium tetrakis(pentafluorophenyl)borate with triphenylcarbenium tetrakis(nonafluoro-t-butoxy)aluminate; $Ag^+$ $[Al(OC_6F_5)_4]^-$ with ferrocenium $[B\{3,5\text{-}(CF_3)_2C_6H_3\}_4]^-$. More preferably the at least two activators come from at least two different classes, for example, triethylaluminum with MMAO; diethylaluminum chloride with triphenylcarbenium $[Al\{OCF(CF_3)_2\}_4]^-$; MMAO with dimethylhexylammonium [Al $\{OCF(CF_3)_2\}_4]^-$; MAO with methyldi(octadecyl)ammonium $[B\{3,5\text{-}(CF_3)_2C_6H_3\}_4]^-$; triethylaluminum with MMAO and tetrakis(pentafluorophenyl)borate. Preferred combinations of activators include mixtures of neutral Lewis acids comprising a combination of a tri(($C_{1-4}$)alkyl)aluminum and a halogenated tri(($C_{6-16}$) aryl)boron compound, especially tris(pentafluorophenyl)borane. Combinations of one or more of the foregoing activators and activating techniques are also contemplated.

The activators or combination of activators may be added to the reaction media (e.g., ethylene and/or diluents and/or solvent) at any time, either prior to the addition of the catalyst system or any components thereof, or at the same time as the catalyst system or any components thereof, or as part of the catalyst system, or after the catalyst system or any components thereof have been added. Such techniques are known in the art of oligomerization and are disclosed in more detail in for example, U.S. Pat. Nos. 5,491,272; 5,750,817; 5,856,257; 5,910,619; and 5,919,996, as well as WO 2008/146215 and WO 2007/007272. To the extent permitted by US law, these references are incorporated herein.

Many activators and activating techniques have been previously taught with respect to different metal-ligand complexes in the following U.S. Pat. Nos. 5,064,802; 5,153,157; 5,296,433; 5,321,106; 5,350,723; 5,425,872; 5,625,087; 5,721,185; 5,783,512; 5,883,204; 5,919,983; 6,696,379; and 7,163,907. To the extent permitted by US law, these references are incorporated herein. Examples of suitable hydrocarbyloxides are disclosed in U.S. Pat. No. 5,296,433. Examples of suitable Brønsted acid salts for addition polymerization catalysts are disclosed in U.S. Pat. Nos. 5,064,802; 5,919,983; 5,783,512. Examples of suitable salts of a cationic oxidizing agent and a non-coordinating, compatible anion as activators for addition polymerization catalysts are disclosed in U.S. Pat. No. 5,321,106. Examples of suitable carbenium salts as activators for addition polymerization catalysts are disclosed in U.S. Pat. No. 5,350,723. Examples of suitable silylium salts as activators for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these activators are also described in a portion of U.S. Pat. No. 6,515,155 B1 beginning at column 50, at line 39, and going through column 56, at line 55, only the portion of which is incorporated by reference herein. Activators for olefin oligomerization may be selected from activators taught above for olefin polymerization.

In the composition of the invention, the chromium (either from the source of chromium or from the ligating compound-chromium complex), the one or more activators, and the phosphacycle-containing ligating compound (including from the ligating compound-chromium complex) may be in such proportions relative to each other to provide chromium: ligating compound molar ratios from about 10:1 to 1:10, more preferably from about 1.3:1 to 1:1.3, still more preferably from about 1.1:1 to 1:1.1; and chromium:activator (e.g., aluminum compounds, including aluminoxane, boron compounds, including borates, gallium compounds, non-coordinating, ion-forming compounds)) molar ratios from about 100:1 to 1:50,000, preferably from about 1:1 to 1:10,000, preferably from about 1:1 to 1:3000, more preferably from about 1:1 to 1:1000, still more preferably from about 1:1 to 1:500. In a particularly preferred embodiment when the activator is selected from boron compounds or non-coordinating, ion-forming compounds, the chromium: activator molar ratios range from about 1:1 to 1:100, preferably, from about 1:1 to 1:10, more preferably from about 1:1 to 1:2. In a particularly preferred embodiment when the activator is selected from aluminum compounds, including aluminoxane compounds, the chromium:activator molar ratios range from about 1:1 to 1:10,000, preferably from abut 1:1 to 1:3000, more preferably from about 1:1 to 1:1000, even more preferably from about 1:1 to 1:500.

When one or more alumoxanes alone or one or more tri(($C_{1-4}$)hydrocarbyl)aluminum compounds alone or together in combination are used as the activator, preferably the number of moles of the one or more alumoxanes or of the one or more tri(($C_{1-4}$)hydrocarbyl)aluminum compounds or of the one or more alumoxanes and the one or more tri(($C_{1-4}$)hydrocarbyl)aluminum compounds used in combination that are employed is at least 100 times the number of moles of the one or more sources of chromium or of the ligating compound-chromium complex. When tris(pentafluorophenyl)borane alone is used as the activator, preferably the number of moles of the tris(pentafluorophenyl)borane that are employed to the total number of moles of the one or more sources of chromium or of the ligating compound-chromium complex is from 0.5:1 to 10:1, more preferably from 1:1 to 6:1, still more preferably from 1:1 to 5:1. The remaining activators are generally employed in approximately mole quantities equal to or up to ten times the total mole quantities of the one or more sources of chromium or of the ligating compound-chromium complex.

The activator compound may optionally be a solid material, or be supported on an insoluble solid material, for example, aluminoxanes such as MAO and borate activators may be supported on inorganic oxides such as alumina, silica, $MgCl_2$ or the like.

The process may further include the use of activator compounds that may act as reducing or oxidizing agents, such as sodium or zinc metal and the like, (hydrocarbyl)zinc or (substituted hydrocarbyl)zinc compounds, (hydrocarbyl) magnesium or (substituted hydrocarbyl)magnesium compounds, hydrocarbyl- or substituted hydrocarbyllithium compounds, and the like, or oxygen-containing compounds, for example oxygen and the like, or chloride-containing compounds, for example methylene chloride, chloroform, and the like. Hydrocarbyl- and substituted hydrocarbylzinc compounds include monohydrocarbylzinc halide or alkoxide compounds and dihydrocarbylzinc compounds such as methylzinc chloride, ethylzinc chloride, isopropylzinc bromide, 2-cyanoethylzinc bromide, allylzinc chloride, cyclopentylzinc chloride, benzylzinc bromide, phenylzinc chloride, isobutylzinc ethoxide, and propylzinc methoxide, 4-dimethylaminophenylzinc bromide, bromo(2-ethoxy-2-oxoethyl)zinc bromide, dimethylzinc, diethylzinc, divinylzinc, diallylzinc, dipropylzinc, diisopropylzinc, dibutylzinc, dioctylzinc, diphenylzinc, and dibenzylzinc. The process also includes the optional use of a zinc species as an additive, as described in WO 2011/048527, which is herein incorporated by reference.

Hydrocarbyl- and substituted hydrocarbylmagnesium compounds include monohydrocarbylmagnesium halide or alkoxide compounds and dihydrocarbylmagnesium compounds such as methylmagnesium chloride, ethylmagnesium bromide, butylmagnesium iodide, propylmagnesium chloride, isopropylmagnesium chloride, phenylmagnesium bromide, 4-dimethylaminophenylmagnesium bromide, benzylmagnesium butoxide, dibutylmagnesium, dioctylmagnesium, butylethylmagnesium, diisopropylmagnesium, dihexylmagnesium, and dibenzylmagnesium.

Hydrocarbyl- and substituted hydrocarbyllithium compounds include methyllithium, ethyllithium, propyllithium, isopropyllithium, n-butyllithium, s-butyllithium, i-butyllithium, t-butyllithium, pentyllithium, 2,2-methylpropyllithium, hexyllithium, octyllithium, 2-ethylhexyllithium, allyllithium, propynyllithium, vinyllithium, phenyllithium, cyclopentyllithium, cyclohexyllithium, benzyllithium, 4-dimethylaminophenyllithium, and 4-methoxyphenyllithium.

Mixtures of the foregoing hydrocarbyl- and substituted hydrocarbylzinc compounds, hydrocarbyl- and substituted hydrocarbylmagnesium compounds, and hydrocarbyl- and substituted hydrocarbyllithim compounds are also envisioned, especially in combination with alkylaluminum compounds.

A further advantageous use of the activator compounds is to exert a beneficial effect of scavenging contaminants such as adventitious oxygen or water that may be present.

Oligomerization Process

In some embodiments, the invention provides a process for selectively oligomerizing an olefin comprising placing at least one olefin in operative contact with a catalyst system as described above under conditions sufficient to convert at least a portion of the at least one olefin to at least one oligomer of the at least one olefin, the catalyst system comprising, a) a source of chromium, b) one or more activators, and c) at least one phosphacycle-containing ligating compound as described herein. As described above, the catalyst system may comprise an isolated ligating compound-chromium complex. The components of the catalyst system may be contacted in any order.

The oligomerization process includes a process for the trimerization and/or tetramerisation of at least one olefin, preferably at least one α-olefin. In one embodiment, two or more different types of ligands may be used to alter the relative amounts of 1-hexene and 1-octene being produced. For example, one or more ligands that produce predominantly 1-hexene may be used in combination with one or more ligands that produce predominantly 1-octene in order to achieve a specific 1-hexene:1-octene production ratio.

The at least one olefin to be oligomerized may comprise a single olefin or mixture of olefins. In one embodiment of the invention it may comprise a single olefin. The olefin may include multiple carbon-carbon double bonds, but preferably it comprises a single carbon-carbon double bond. The at least one olefin may comprise an α-olefin with 2 to 30 carbon atoms, preferably 2 to 10 carbon atoms. In the process of the invention, the at least one olefin to be oligomerized may be selected from the group comprising ethylene (ethene), propylene (propene), 1-butene, isobutene, 1-pentene, 1-hexene, 1-heptene, 1-octene, 1-nonene, 1-decene, 1-dodecene, 2-methyl-1-propene, 3-methyl-1-butene, 3-methyl-1-pentene, 4-methyl-1-pentene, styrene, p-methyl styrene, or mixtures thereof. Preferably the at least one olefin comprises ethylene, propylene, 1-hexene, or 1-octene, more preferably ethylene. Mixtures of olefins may be used to form mixed oligomeric products, preferably ethylene in combination with 1-hexene and/or 1-octene. The product stream comprises the oligomeric products that are formed according to the invention.

Preferably the at least one oligomer comprises hexene or octene, preferably a mixture of 1-octene and 1-hexene. The ratio of the mass of hexene or octene, preferably a mixture of 1-octene and 1-hexene, formed in the oligomerization process to the total mass of reaction products (product stream) of the oligomerization process (weight fraction) ranges from ten percent by weight to 100 percent by weight, preferably from 50 percent by weight to 100 percent by weight, more preferably from 70 percent by weight to 100 percent by weight, even more preferably from 80 percent by weight to 100 percent by weight, still even more preferably from 85 percent by weight to 100 percent by weight, most preferably from 90 percent by weight to 100 percent by weight.

The 1-hexene:1-octene ratio by weight may be selected by the choice of catalyst system and oligomerization conditions and ranges from 1000:1 to 1:1000, preferably from 100:1 to 1:100, more preferably from 10:1 to 1:10, even more preferably from 4:1 to 1:10, even still more preferably from 2:1 to 1:5. The 1-hexene:1-octene ratio by weight may range from 1000:1 to 100:1; from 100:1 to 10:1; and from 10:1 to 3:1; preferably from 3:1 to 2:1; from 2:1 to 1:1; and from 1:1 to 1:2; more preferably from 1:2 to 1:3; and from 1:3 to 1:4; even more preferably from 1:4 to 1:10; from 1:10 to 1:100; and from 1:100 to 1:1000.

The reaction products of the oligomerization process may, depending on the nature of the catalyst system and the reaction conditions, in addition to 1-hexene and 1-octene, also comprise different quantities of polymer byproduct ("polymer", e.g., olefin waxes, polyethylene); cyclics and $C_6$ and $C_8$ isomers (for example, methylcyclopentane, methylenecyclopentane, allylcyclopentane, propylcyclopentane, or hexadiene); specific higher oligomers, especially $C_{10-18}$ olefin oligomers, which may arise from the mixed oligomerization of ethylene, 1-hexene, or 1-octene. The amount of polymer byproduct produced in the trimerization and tetramerization of ethylene using the process of the present invention is typically at most about 10 wt %. Lower levels of solid olefin waxes and polyethylene, including as low as none, produced in the trimerization and tetramerization of ethylene are desirable in commercial operations as this can reduce the amount of fouling of the reactor equipment, reduce the amount of waste by-products and reduce the amount of operational "downtime" due to maintenance and cleaning of the reactor equipment. Preferably the polymer byproduct has a total mass fraction with respect to the total mass of reaction products within a range of zero percent by weight to 10 percent by weight, preferably from zero percent by weight to five percent by weight, and more preferably from zero percent by weight to two percent by weight, even more preferably from zero percent by weight to one percent by weight, most preferably from zero percent by weight to one-half of one percent by weight.

In an embodiment, the oligomerization can be carried out in the presence of additives to control selectivity, enhance activity and reduce the amount of polymer formed in the oligomerization process. In an embodiment, hydrogen ($H_2$), silanes, a halide source (especially the halide sources disclosed in U.S. Pat. No. 7,786,336, Zhang et al.), and the like may be used in the catalytic composition or otherwise introduced into the process. In some embodiments, the amount of polymer produced in the method to oligomerize olefins can be reduced by providing and/or controlling a partial pressure or concentration of hydrogen, silanes, and/or a halide source to the olefin production process. While it should be noted that the presence of hydrogen, silanes, and/or a halide source is not necessarily required to produce an oligomerization product having an acceptable quantity of polymer, the amount of polymer produced by the oligomerization process may be further reduced by the presence of hydrogen, silanes, and/or a halide source. Other (optional) additives include antistatic agents (such as the polysulfone polymer sold under the trademark Stadis®) and/or fluorocarbons to mitigate reaction fouling. The use of hydrogen is especially preferred.

The oligomer product as described herein, may be prepared using the disclosed catalyst system in a homogeneous liquid phase reaction in the presence or absence of an inert solvent, and/or in a slurry reaction where the catalyst system is in a form that displays little or no solubility, and/or in a two-phase liquid/liquid reaction, and/or in a bulk phase reaction in which neat reagent and/or product olefins serve as the dominant medium, and/or in a gas phase reaction, using conventional equipment and contacting techniques.

The oligomerization process may be carried out in an inert solvent or mixture of inert solvents. The inert solvent or mixture of inert solvents is sometimes referred to as the makeup solvent. An inert solvent is one that does not interfere substantially with the oligomerization process, especially inert solvents selected from the group consisting of hydrocarbons, e.g., butane, pentane, hexane, heptane, octane, nonane, decane, cyclohexane, methylcyclopentane, methylcyclohexane, 1-hexene, 1-octene, benzene, toluene, xylene, ethylbenzene, mesitylene, cumene, or commercial saturated hydrocarbons mixtures, such as Isopar-E™, particularly saturated $C_6$-$C_{20}$ (acyclic and cyclic) hydrocarbons such as pentane, hexane, heptane, octane, Isopar-E™, cyclopentane, cyclohexane, methylcyclohexane; neutral Lewis bases, e.g., THF, diethyl ether, acetonitrile; chlorinated hydrocarbons, e.g., chloroform, methylene chloride, dichloroethane, trichloroethane, tetrachloroethane, chlorobenzene, 1,2-dichlorobenzene; and ionic liquids. Preferably the inert solvent or mixture of inert solvents is selected from the group consisting of saturated hydrocarbons and chlorinated hydrocarbons or mixtures thereof. Especially preferred are cyclohexane, methylcyclohexane, chlorobenzene, and 1,2-dichlorobenzene. Mixtures of the foregoing are also suitable.

The makeup solvent may be introduced into the oligomerization reactor in the form of a feed stream comprising the olefin to be oligomerized or may be added separately.

According to another aspect of the invention there is provided a process for the oligomerization of olefins wherein the product of the oligomerization process is an olefin or mixture of olefins, especially 1-hexene and 1-octene, and makes up more than 30 wt % of the product stream of the process based on the weight of the product stream.

In one aspect of the process of the invention, an olefinic feed stream ("feed stream") comprising at least one olefin to be oligomerized is provided, wherein the at least one olefin is selected from the group comprising ethylene (ethene), propylene (propene), 1-butene, isobutene, 1-pentene, 1-hexene, 1-heptene, 1-octene, 1-nonene, 1-decene, 1-dodecene, 2-methyl-1-propene, 3-methyl-1-butene, 3-methyl-1-pentene, 4-methyl-1-pentene, styrene, p-methyl styrene, or mixtures thereof. Preferably the at least one olefin comprises ethylene, propylene, 1-hexene, or 1-octene, more preferably ethylene.

According to another aspect of the invention the oligomerization process includes the step of contacting a feed stream comprising the olefin to be oligomerized with the catalyst system as described above and wherein the product or product stream of the oligomerization process comprises an olefin or mixture of olefins, especially 1-hexene and/or 1-octene, and the olefin or mixture of olefins, especially 1-hexene and/or 1-octene, makes up from 10 wt % to 100 wt %, preferably from 20 wt % to 100 wt %, preferably from 30 wt % to 100 wt %, preferably from 40 wt % to 100 wt %, preferably from 50 wt % to 100 wt %, preferably from 60 wt % to 100 wt %, preferably from 85 wt % to 100 wt % of the total product formed or product stream of the process, wherein the product stream of the process comprises the reaction products of the oligomerization process, catalyst system residues, optional solvent, and any optional additives employed in the process.

The feed stream comprising the olefin to be oligomerized can be introduced into the process according to the invention in a continuous or batch fashion. The feed stream can be introduced into the process in either liquid or gaseous form. In addition to the olefin to be oligomerized, the feed stream may comprise makeup solvent and components from the recycle stream. The recycle stream may comprise recycled solvent, recycled olefin, as well as various recycled oligomerization products, including 1-hexene, 1-octene, methylcyclopentane, methylenecyclopentane, higher oligomers which may arise from the mixed oligomerization of ethylene, 1-hexene, or 1-octene, and polymer. Preferably the recycle stream does not comprise polymer, or comprises only de minimis amounts of polymer.

If desired, at least some of the components from the recycle stream may be introduced into the process separately from the feed stream or, alternatively, at least some of the components from the recycle stream may be introduced into the process together with the feed stream. Preferably the at least one olefin to be oligomerized makes up from 5 wt % to 100 wt % of the feed stream, preferably from 20 wt % to 100 wt % of the feed stream, more preferably from 50 wt % to 100 wt % of the feed stream, even more preferably from 75 wt % to 100 wt % of the feed stream, still more preferably from 90 wt % to 100 wt % of the feed stream, and yet even more preferably from 95 wt % to 100 wt % of the feed stream based on total weight of the feed stream, not including the solvent.

The oligomerization process may be carried out at pressures from atmospheric to 50 000 kPa (500 barg). Ethylene pressures in the range of 1000-7000 kPa (10-70 barg) are preferred. Particularly preferred pressures range from 3000-5000 kPa (30-50 barg). The oligomerization process may be carried out at temperatures from −100° C. to 250° C., preferably at temperatures from 15° C. to 130° C., more preferably at temperatures from 35° C. to 100° C., still more preferably from 40° C. to 90° C., even still more preferably from 50° C. to 80° C.

Although the catalyst system, its individual components, reagents, solvents, and reaction products may be employed on a once-through basis, any of these materials can, and are indeed preferred to be recycled to some extent in order to minimize production costs, especially with regard to the solvents and unreacted olefins to be oligomerized.

In an embodiment of the invention, the catalyst system or its individual components, in accordance with the invention, may also be immobilized by supporting it on a support material, for example, silica, alumina, zirconia, titania, $MgCl_2$, NaCl, zeolites, clays, including artificial hectorite or smectorite clays such as Laponite™ RD, carbon, e.g., graphite, grapheme, or carbon black, or mixtures thereof, or on a polymer, for example polyethylene, polypropylene, polystyrene, or poly(aminostyrene). An advantage of an immobilized catalyst system is that the oligomerization process can be carried out such that the feed stream and the product stream flow continuously or semi-continuously through the reactor, while the catalyst system remains substantially in the reactor. The catalyst system can be formed in situ in the presence of the support material, or the support can be pre-impregnated or premixed, simultaneously or sequentially, with one or more of the components of the catalyst system or the oligomerization catalyst. In some cases the support material can also act as a component of the activator. This approach would also facilitate the recovery of the catalyst system or any of its components from the reaction mixture for reuse. The concept was, for example, successfully demonstrated with a chromium-based ethylene trimerization catalyst by T. Monoi and Y. Sasaki, *J. Mol. Cat. A: Chem.*, 2002, 187, 135-141. In some cases the support can also act as a catalyst system component, for example where such supports contain aluminoxane functionalities or other activators or where the support is capable of performing similar chemical functions as an activator. In an embodiment of the invention, the immobilization on the support may include chemical bonding of the phosphacycle-containing ligating compound with the support, for example, via a functional group. The phosphacycle-containing ligating compound may include a polymeric moiety to render the catalyst system or the reaction product of the source of chromium and the said ligating compound to be soluble at higher temperatures and insoluble at lower temperatures, e.g. 25° C. This approach may enable the recovery of the complex from the reaction mixture for reuse and has been used for other catalyst as described by D. E. Bergbreiter et al., J. Am. Chem. Soc., 1987, 109, 177-179. In a similar vein the catalyst system or the ligating compound can also be immobilized by binding the catalyst system or the ligating compound to silica, silica gel, polysiloxane or alumina backbone as, for example, demonstrated by C. Yuanyin et al., Chinese J. React. Pol., 1992, 1(2), 152-159 for immobilizing platinum complexes.

An embodiment of the invention is a phosphacycle-containing ligating compound-containing polymeric support (e.g., polystyrene (PS), poly(methyl methacrylate) (PMMA), poly(methyl acrylate) (PMA)) having amino- or phosphino functionality present by means of which the phosphacycle-containing ligating compound is chemically bonded to the polymeric support. In a non-limiting example the phosphacycle-containing ligating compound-containing polymeric support can be formed in that the nitrogen atom of the dihydroaminoalkyl group of a dihydroaminoalkyl-functionalized PS, PPM, or PMA support is incorporated into the Y group of a phosphacycle-containing ligating compound. In another non-limiting example, a phosphacycle-containing ligating compound-containing polymeric support is formed upon polymerization of a vinylaryl, methacrylate, or acrylate monomer functionalized with a phosphacycle-containing ligating compound. An embodiment of the invention is a supported catalyst system comprising a phosphacycle-containing ligating compound-containing polymeric support, a source of chromium, and at least one activator. In an embodiment of the invention the supported catalyst system can be formed by contacting a phosphacycle-containing ligating compound-containing polymeric support with a source of chromium and at least one activator.

In some embodiments, the invention provides a tandem oligomerization, preferably trimerization and/or tetramerization, and polymerization process wherein the olefin in the form of ethylene is oligomerized using the catalyst system of the invention to produce a monomer mixture comprising monomers selected from 1-hexene and 1-octene and at least one monomer from the mixture is copolymerized in situ with ethylene using the polymerization catalyst and wherein oligomerization and polymerization take place in the same reaction medium.

In some embodiments, the invention provides a polymerization process wherein the feed stream of the polymerization process comprises at least part of the oligomer product of the oligomerization process.

The oligomerization process of the invention may be carried out in a plant which includes any type of reactor, especially a mixed reactor. Examples of such reactors include, but are not limited to, batch reactors, semi-batch reactors and continuous reactors. The plant may include, in combination a) a reactor, b) at least one inlet line into this reactor for olefin reactant and the catalyst system, c) effluent lines from this reactor for oligomerization reaction products, and d) at least one separator to separate the desired oligomerization reaction products, wherein the catalyst system comprises a source of chromium, a phosphacycle-containing ligating compound, and at least one activator, as described herein. The term "mixed reactor" is meant to convey its conventional meaning—i.e., a reactor that contains an agitator or mixing system. A continuously stirred tank reactor ("CSTR") is generally preferred. However, a loop reactor in which mixing is provided by a circulating pump is also suitable (and such reactors are well known to those skilled in the art and are in commercial use). The use of a CSTR is generally preferred as it is desirable to maintain essentially homogenous reactor conditions—i.e., as will be appreciated by those skilled in the art, a well-mixed CSTR will provide homogenous reactor conditions (in contrast to a plug flow, or tubular reactor, in which the reactor conditions are typically very different at the inlet and discharge). More than one CSTR may be used.

Although a single CSTR is preferred, it is also within the scope of this invention to (optionally) use an additional tubular reactor. If the tubular reactor is employed, it would be placed downstream of the CSTR. The tubular reactor (if used) would provide some additional ethylene conversion, thereby reducing the need to recover/recycle ethylene from the discharge.

The term "continuous flow" is meant to convey its conventional meaning—i.e. reactants are continuously added to the reactor and product is continuously withdrawn.

In another embodiment of the process the reactor and a separator may be contacted to facilitate the simultaneous formation of reaction products and separation of these compounds from the reactor. This process principle is commonly known as reactive distillation. When the catalyst system exhibits no solubility in the solvent or reaction products, and is fixed in the reactor so that it does not exit the reactor with the reactor product, solvent and unreacted olefin, the process principle is commonly known as catalytic distillation.

As described herein, the catalyst system may be formed in situ in the reactor or may be preformed outside of the reactor and then added into the reactor. Advantageously the oligomerization process may be carried out under inert conditions, that is, under substantial absence of oxygen and/or other species which interfere with the oligomerization process.

While not wishing to be bound by theory, it is believed that the 1-hexene and/or 1-octene that are produced during the reaction may themselves become reactants for a secondary reaction that may produce the $C_{10+}$ oligomers that are formed under the conditions of the process. In one embodiment of the invention, the oligomerization process may form specific higher $C_{10-18}$ olefin oligomers which arise from the mixed oligomerization of ethylene, 1-hexene, or 1-octene. While such $C_{10-18}$ oligomers can be used in making surfactants for aqueous detergent formulations, most of the $C_{10+}$ oligomers have comparatively low value so it is desirable to limit the amount of them that is produced.

In an embodiment of the process of the invention, product selectivity can be improved in a continuous process using certain specific conditions. More specifically, selectivity can be increased by using a low chromium concentration and by maintaining low 1-hexene and/or 1-octene concentrations in the reactor. Further improvements may be achieved using lower oligomerization temperatures, so low temperatures are preferred (even though a low temperature is not "sufficient" for a continuous process). Low temperatures are preferred in order to increase the 1-octene: 1-hexene ratio. In this embodiment, the present invention provides: A continuous flow process for the oligomerization of ethylene, said process comprising I) adding ethylene and solvent to a mixed reactor and contacting said ethylene under oligomerization conditions with a catalyst system as described above; II)

removing a product discharge stream comprising 1-hexene, 1-octene, $C_{10+}$ oligomers, solvent, and optional polymer from said reactor; and III) controlling the flow of said solvent to said reactor such that the product discharge stream contains from 1 to 30 combined weight % of 1-hexene and 1-octene, preferably from 2 to 25 combined weight % of 1-hexene and 1-octene, more preferably from 3 to 20 combined weight % of 1-hexene and 1-octene based on the weight of the product discharge stream (reaction products of the oligomerization process, catalyst system residues, solvent, and any optional additives employed in the process) wherein said process is further characterized by being conducted at a catalyst concentration of from 0.01 to 50 micromolar Cr, preferably 0.05 to 20 micromolar Cr, more preferably 0.1 to 5 micromolar Cr. Another preferred element of this embodiment of the present invention is the use of ethylene concentrations, based on vapor-liquid equilibrium, of 3 to 15 weight %, especially from 5 to 10 weight %.

As noted above, this embodiment of the process of the invention requires that the 1-octene concentration in the reactor is controlled/limited. In a continuous flow process, the concentration of 1-octene in the reactor can be controlled by adjusting the solvent flow rate and the rate of reaction. For example, increasing the solvent flow will dilute the 1-octene concentration and decreasing the catalyst concentration will decrease the rate of reaction. Low catalyst concentrations (less than $50 \times 10^{-6}$ moles of Cr per liter, preferably less than $5 \times 10^{-6}$ moles of Cr per liter) are required in this process and low temperatures are preferred wherein the reactor temperature is preferably from 25 to 100° C., more preferably from 35 to 85° C., even more preferably from 40 to 70° C. Suitable solvents include the solvents described above, particularly saturated $C_6$-$C_{20}$ (acyclic and cyclic) hydrocarbons such as pentane, hexane, heptane, octane, Isopar-E™, cyclopentane, cyclohexane, methylcyclohexane, and unsubstituted and substituted aromatic hydrocarbons such as toluene, xylene, ethylbenzene, cumene, mesitylene, chlorobenzene, and dichlorobenzene.

For safety and or product quality reasons it is often desirable to deactivate the catalyst system at some point in the oligomerization process, for example, after completion of a desired level of oligomerization or in case of a runaway reaction. In an embodiment of the invention, the catalyst system will be deactivated upon completion of the oligomerization either in the reactor, upon its leaving the reactor or shortly thereafter. In general, many polar compounds (such as water, alcohols and carboxylic acids) will deactivate the catalyst. The use of alcohols, amines and/or carboxylic acids is preferred—and combinations of these are contemplated. Preferred deactivators include water, methanol, ethanol, propanol, butanol, methylamine, dimethylamine, ethylamine, diethylamine, propylamine, dipropylamine, butylamine, dibutylamine, formic acid, acetic acid, propanoic acid, or butanoic acid. It is generally found that the quantity employed to deactivate the catalyst is sufficient to provide a deactivator to metal (from catalyst+activator) mole ratio between about 0.1 to about 4, especially from 1 to 2 (thus, when MAO is the activator, the deactivator is provided on a ratio based on moles of Cr+moles of Al). The deactivator may be added to the oligomerization product stream before or after the volatile unreacted reagents/diluents and product components are separated. In the event of a runaway reaction (e.g., rapid temperature rise) the deactivator can be immediately fed to the oligomerization reactor to terminate the reaction. The deactivation system may also include a basic compound (such as sodium hydroxide) to minimize isomerization of the products (as deactivation conditions may facilitate the isomerization of desirable alpha olefins to undesired internal olefins).

Polymer removal (and, optionally, catalyst removal) preferably follows catalyst deactivation. Two types of polymer may exist, namely polymer that is dissolved in the process solvent and non-dissolved polymer that is present as a solid or "slurry".

Solid/non-dissolved polymer may be separated using one or more of the following types of equipment: centrifuge; cyclone (or hydrocyclone), a decanter equipped with a skimmer or a filter. Preferred equipment include so-called "self-cleaning filters" sold under the name V-auto strainers, self-cleaning screens such as those sold by Johnson Screens Inc. of New Brighton, Minn. and centrifuges such as those sold by Alfa Laval Inc. of Richmond, Va. (including those sold under the trademark Sharples®).

Soluble polymer may be separated from the final product by two distinct operations. Firstly, low molecular weight polymer that remains soluble in the heaviest product fraction ($C_{20+}$) may be left in that fraction. This fraction will be recovered as "bottoms" from the distillation operations (described below). This solution may be used as a fuel for a power generation system.

An alternative polymer separation comprises polymer precipitation caused by the removal of the solvent from the solution, followed by recovery of the precipitated polymer using a conventional extruder. The technology required for such separation/recovery is well known to those skilled in the art of solution polymerization and is widely disclosed in the literature.

In another embodiment, the residual catalyst is treated with an additive that causes some or all of the catalyst to precipitate. The precipitated catalyst is preferably removed from the product at the same time as by-product polymer is removed (and optionally using the same equipment). Many of the catalyst deactivators listed above will also cause catalyst precipitation. In a preferred embodiment, a solid sorbent (such as clay, silica or alumina) is added to the deactivation operation to facilitate removal of the deactivated catalyst by filtration or centrifugation.

Reactor fouling (caused by deposition of polymer and/or catalyst residue) can, if severe enough, cause the process to be shut down for cleaning. The deposits may be removed by known means, especially the use of high pressure water jets or the use of a hot solvent flush.

The use of an aromatic solvent (such as chlorobenzene) for solvent flushing is generally preferred because they are good solvents for polyethylene.

The invention will now be further described by means of the following non-limiting examples.

EXAMPLES

All preparation reactions carried out at temperatures below −50° C. were conducted outside of a glovebox under inert atmosphere using Schlenk line techniques. All preparation reactions carried out under elevated pressure were conducted outside of a glovebox. Depending on the elevated pressure preparation reaction, the reactor involved may have been charged in a glovebox. Unless otherwise specified, all other reactions were conducted in inert (nitrogen or argon) atmosphere gloveboxes. All commercial chemicals were obtained from Sigma-Aldrich Corporation, Acros Organics, Strem Corporation, Oakwood Chemical, Oxchem Corporation, or Thermo Fisher Scientific, Inc.

Solvents used in the preparation reactions were purified as follows: Non-chlorinated solvents (e.g., tetrahydrofuran (THF), toluene, hexane, diethyl ether) were purified in a manner similar to the method of Pangborn et al. ("*Safe and Convenient Procedure for Solvent Purification*" Pangborn, A. B.; Giardello, M. A.; Grubbs, R. H.; Rosen, R. K.; Timmers, F. J. *Organometallics* 1996, 15, 1518-1520) by passing the degassed solvents through columns of activated A204 alumina and supported copper-based reactive scavenger (Q5 reactant) to remove water and trace oxygen, respectively. Other solvents (pentane, methylene chloride, chloroform, chlorobenzene) were dried by storing over activated molecular sieves or by passing through activated A2 alumina. The solvents were stored over activated molecular sieves. The A2 alumina and A204 alumina were activated by heating under a dry nitrogen stream at 300° C. for 8 h. The molecular sieves were activated by heating under a dry nitrogen stream at 250° C. for 4 h.

Ambient temperature within the gloveboxes may vary within the range of 25 degrees centigrade (° C.) to 30° C. Unless otherwise specified, the NMR data was obtained at room temperature with a Varian 400 MHz or 500 MHz apparatus. The multiplicity and coupling constants of the peaks from the NMR spectra, based on appearance and obtained by first order analysis, are reported as follows: s, singlet; d, doublet; t, triplet; q, quartet; p, pentet. In some cases the spectra may be second order. The unit for "grams" is abbreviated as "g"; the unit for "millimoles" is abbreviated as "mmol".

Experimental Information for Phosphacycle Ligands and their Cr Complexes

Ligating Compound Preparation Examples

Preparation of ((rac)-N-(diphenylphosphanyl)-N-methyl-2,5-diphenylphospholan-1-amine), L553

Step 1. Preparation of 1-[(N,N)-dimethylamino]-1-r-oxo-2-t,5-t-diphenyl-phosphol-3-ene

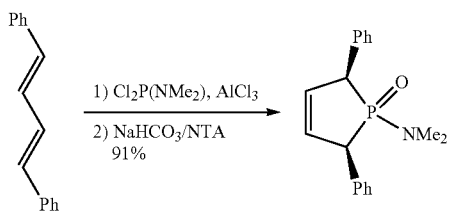

In a glovebox, a 200-mL jar was charged with aluminum chloride (22.84 g, 171.3 mmol) and 50 mL of anhydrous methylene chloride. The jar was placed in a freezer at −30° C. for 15 minutes then removed. Dimethylphosphoramidous dichloride (25.00 g, 171.3 mmol) was added to a stirred suspension. Once everything was dissolved, the jar was removed from the glovebox and the contents transferred to a 500-mL three-necked round bottom flask equipped with an addition funnel and nitrogen inlet. The flask and its contents were cooled in an ice bath. 1,4-Diphenylbutadiene (32.12 g, 155.7 mmol) was dissolved in anhydrous methylene chloride (~200 mL) in the glovebox, transferred to the addition funnel, and slowly added under nitrogen atmosphere to the reaction mixture over a 45 minute period. After 1 h, reaction completion was shown by $^{31}$P NMR spectroscopy. The solution was transferred to an addition funnel and added slowly to a chilled mixture of NTA (nitrilotriacetic acid) (37.21 g, 194.6 mmol) in 300 mL of aqueous saturated NaHCO$_3$ solution. The biphasic mixture was stirred vigorously for 1 h at 0° C. while under nitrogen and checked by $^{31}$P NMR spectroscopy for completion. Once complete the mixture was filtered through Celite and transferred to a separatory funnel. The organic layer was separated. The aqueous layer was extracted with methylene chloride (2×100 mL). The organic layers were washed with saturated NaHCO$_3$(100 mL), 1 M HCl (100 mL), and brine (100 mL), dried over MgSO$_4$, concentrated down and dried to yield the product as a light orange solid. Yield (42.2 g, 91.3%). The product was stored in a drybox. $^1$H NMR (400 MHz, C$_6$D$_6$) δ 7.23 (ddt, J=8.1, 2.3, 1.2 Hz, 4H), 7.09 (tq, J=6.8, 0.8 Hz, 4H), 7.04-6.98 (m, 2H), 6.09 (dd, J=27.9, 1.0 Hz, 2H), 4.26-4.14 (m, 2H), 1.81 (d, J=8.1 Hz, 6H). $^{13}$C NMR (101 MHz, C$_6$D$_6$) δ 136.91 (d, J=8.2 Hz), 131.05 (d, J=15.8 Hz), 129.01 (d, J=2.6 Hz), 127.71 (d, J=4.7 Hz), 127.15 (d, J=2.7 Hz), 50.09, 49.38, 36.47 (d, J=1.5 Hz). $^{31}$P NMR (162 MHz, C$_6$D$_6$) δ 66.51.

Step 2. Preparation of 1-[(N,N)-dimethylamino]-1-r-oxo-2-t,5-t-diphenyl-phospholane

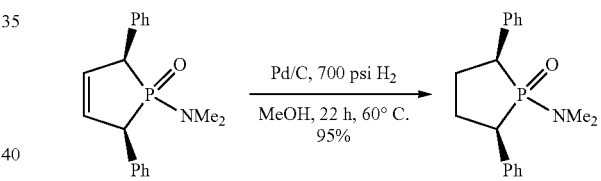

In a reaction not carried out in a glovebox, a clean, leak-tested, 250-mL pressure reactor equipped with a bottom filter was charged with 1-[(N,N)-dimethylamino]-1-r-oxo-2-t,5-t-diphenyl-phosphol-3-ene (37.00 g, 124.4 mmol), 5% Pd—C (3.973 g, 37.33 mmol), and methanol (~150 mL). The reactor was pressurized to 700 pounds per square inch (psi) (4.83 megapascals (MPa)) with hydrogen gas and heated to 60° C. with 700 rpm stirring. After 2.5 hours the reaction was sampled and the conversion was analyzed by $^{31}$P NMR spectroscopy to be 91%. The reactor was repressurized with hydrogen to 708 psi (4.88 MPa) and the reaction was allowed to continue overnight. The reaction mixture was checked again at 22 hours and determined to be complete. The reactor was emptied into a round bottom flask through a bottom filter yielding a clear, pale yellow solution. The reactor was washed out with methanol (2×20 mL) and those washings also collected. The combined solutions were concentrated down to yield the product as a light yellow solid. Yield (35.6 g, 95.4%). $^1$H NMR (400 MHz, C$_6$D$_6$) δ 7.25-7.21 (m, 4H), 7.15-7.08 (m, 4H), 7.02 (tt, J=7.3, 1.5 Hz, 2H), 3.55 (dt, J=22.7, 7.5 Hz, 2H), 2.20-1.87 (m, 4H), 1.76 (dd, J=8.1, 1.6 Hz, 6H). $^{13}$C NMR (101 MHz, C$_6$D$_6$) δ 138.15 (d, J=5.5 Hz), 128.92 (d, J=2.0 Hz), 127.68 (d, J=4.9 Hz), 126.76 (d, J=2.4 Hz), 46.53, 45.81, 35.82 (d, J=2.3 Hz), 26.80 (d, J=12.9 Hz). $^{31}$P NMR (162 MHz, C$_6$D$_6$) δ 63.80.

Step 3. Preparation of (rac)-1-(dimethylamino)-2,5-diphenylphospholane 1-oxide

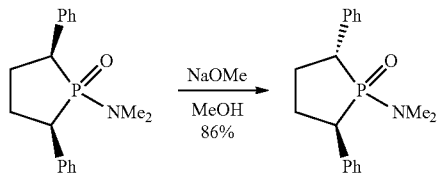 [SMILES: CN(C)P1(=O)[C@@H](c2ccccc2)CC[C@H]1c1ccccc1 ; CN(C)P1(=O)[C@@H](c2ccccc2)CC[C@@H]1c1ccccc1 ; "NaOMe"]

A 400-mL jar was charged with 1-[(N,N)-dimethylamino]-1-r-oxo-2-t,5-t-diphenyl-phospholane (35.00 g, 116.9 mmol), methanol (250 mL), and a stir bar and placed in a freezer a few hours. The cold jar was removed from the freezer, a thermocouple was added to the jar, and a 25 wt % solution of sodium methoxide in methanol (63.16 g, 292.3 mmol) (2.5 equivalents) was added slowly while monitoring the temperature to avoid a large exotherm. The reaction temperature started at −12° C. and rose to −3° C. by the end of the addition. After the reactants had dissolved (5 minutes), an aliquot was removed for analysis. The sample was treated with a few drops of 1 M HCl and extracted with toluene. The solution was concentrated and analyzed by $^{31}$P NMR which showed reaction was 33% converted to the desired product. The reaction was checked again after 2 hours and was determined to be 75% converted to the desired product. After 4 hours total reaction time the reaction was sampled again and determined to be complete. The reaction mixture was removed from the glovebox, hydrolyzed slowly with HCl (1 M, 150 mL), and extracted with toluene. The organic layers were washed with water and brine, dried over anhydrous magnesium sulfate, filtered and concentrated to yield the product as a light yellow solid. Yield (28.7 g, 82.0%). $^1$H NMR (400 MHz, C$_6$D$_6$) δ 7.42 (dddd, J=8.3, 1.8, 1.2, 0.5 Hz, 2H), 7.25-7.21 (m, 2H), 7.18-7.09 (m, 4H), 7.10-7.01 (m, 2H), 3.49 (ddd, J=24.5, 12.9, 7.5 Hz, 1H), 2.91-2.80 (m, 1H), 2.05 (d, J=8.8 Hz, 6H), 1.99-1.84 (m, 3H), 1.62-1.48 (m, 1H). $^{13}$C NMR (101 MHz, C$_6$D$_6$) δ 137.82 (dd, J=30.4, 4.9 Hz), 129.56 (d, J=5.1 Hz), 128.57 (dd, J=5.9, 1.9 Hz), 127.44 (d, J=5.0 Hz), 126.82 (d, J=2.0 Hz), 126.46 (d, J=2.6 Hz), 48.07, 47.33, 43.08, 42.31, 35.69 (d, J=2.4 Hz), 30.36 (d, J=11.8 Hz), 27.30 (d, J=9.0 Hz). $^{31}$P NMR (162 MHz, C$_6$D$_6$) δ 56.39.

Step 4. Preparation of (rac)-1-chloro-2,5-diphenylphospholane

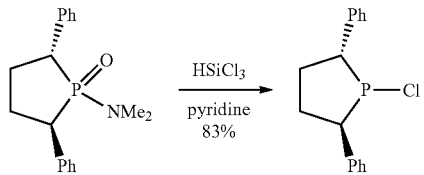 [SMILES: CN(C)P1(=O)[C@@H](c2ccccc2)CC[C@@H]1c1ccccc1 ; "HSiCl3" ; ClP1[C@@H](c2ccccc2)CC[C@@H]1c1ccccc1]

(rac)-1-(Dimethylamino)-2,5-diphenylphospholane 1-oxide (12.0 g, 40.1 mmol) was mixed in toluene (125 mL). Pyridine (4.05 mL, 50.1 mmol) and trichlorosilane (4.50 mL, 44.1 mmol) were added and the mixture was stirred overnight (~24 h) at ambient temperature. Pentane (20 mL) was added to the resulting slurry and the mixture was filtered through a disposable fritted filter. The filtrate was concentrated to dryness. The resulting yellow oil was dissolved in acetonitrile (anhydrous grade, stored over molecular sieves, 140 mL) and washed with pentane (2×30 mL). The acetonitrile layer was then concentrated to dryness. The liquid was then dissolved in hexanes (50 mL) and passed through a small plug of acidic alumina. The alumina was rinsed with another 40 mL of hexanes. The filtrate was concentrated to yield the product as a yellow liquid. Yield (6.1 g, 84%). $^1$H NMR (400 MHz, C$_6$D$_6$) δ 7.21-6.91 (m, 10H), 3.69 (td, J=8.8, 2.3 Hz, 1H), 3.06 (ddd, J=33.4, 12.3, 5.7 Hz, 1H), 2.44-2.18 (m, 2H), 2.05-1.90 (m, 1H), 1.58-1.43 (m, 1H). $^{13}$C NMR (101 MHz, C$_6$D$_6$) δ 141.93 (d, J=19.6 Hz), 137.09, 129.06, 128.55, 128.27 (d, J=44.7 Hz), 126.80 (d, J=2.3 Hz), 58.18 (d, J=32.2 Hz), 53.66 (d, J=32.9 Hz), 34.70 (d, J=2.7 Hz), 31.93 (d, J=3.2 Hz). $^{31}$P NMR (162 MHz, C$_6$D$_6$) δ 137.59.

Step 5. Preparation of (rac)-N-butyl-2,5-diphenylphospholan-1-amine

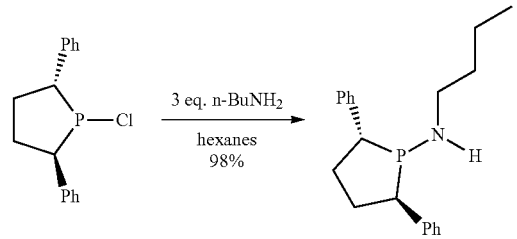 [SMILES: ClP1[C@@H](c2ccccc2)CC[C@@H]1c1ccccc1 ; "3 eq. n-BuNH2" ; CCCCNP1[C@@H](c2ccccc2)CC[C@@H]1c1ccccc1]

A solution of (rac)-1-chloro-2,5-diphenylphospholane (5.30 g, 19.2 mmol) in hexanes (50 mL) was added to n-butylamine (5.72 mL, 57.8 mmol) in 150 mL of hexanes. After stirring for 30 minutes, a sample was removed for NMR spectroscopic analysis. Analysis showed complete conversion to the desired product. The resulting slurry was filtered through a plug of neutral alumina. The alumina was rinsed with an additional 25 mL of hexanes. The filtrate was concentrated under vacuum to yield the product as a light yellow oil. Yield (5.9 g, 98%). $^1$H NMR (400 MHz, C$_6$D$_6$) δ 7.26 (dt, J=8.0, 1.6 Hz, 2H), 7.20-7.06 (m, 6H), 7.06-6.96 (m, 2H), 3.00 (ddd, J=21.7, 12.5, 6.0 Hz, 1H), 2.87 (dt, J=12.6, 6.6 Hz, 1H), 2.43-2.26 (m, 1H), 2.22-2.04 (m, 2H), 2.01 (qd, J=7.2, 5.5 Hz, 1H), 1.78 (qdd, J=12.5, 5.1, 2.6 Hz, 1H), 1.52 (qdd, J=12.6, 5.1, 2.5 Hz, 1H), 1.03-0.93 (m, 1H), 0.92-0.74 (m, 4H), 0.61 (t, J=7.1 Hz, 3H). $^{13}$C NMR (101 MHz, C$_6$D$_6$) δ 144.33 (d, J=18.3 Hz), 140.20, 128.69 (d), 128.45 (d, J=1.3 Hz), 128.20 (d, J=3.4 Hz), 127.92, 125.74 (dd, J=37.2, 2.2 Hz), 55.75 (d, J=14.3 Hz), 50.39 (d, J=23.1 Hz), 47.67 (d, J=22.6 Hz), 35.43 (d, J=6.6 Hz), 34.18 (d, J=2.7 Hz), 31.71 (d, J=2.2 Hz), 19.98, 14.05. $^{31}$P NMR (162 MHz, C$_6$D$_6$) δ 73.36.

Step 6. Preparation of (rac)-N-(diphenylphosphanyl)-N-methyl-2,5-diphenylphospholan-1-amine, L553

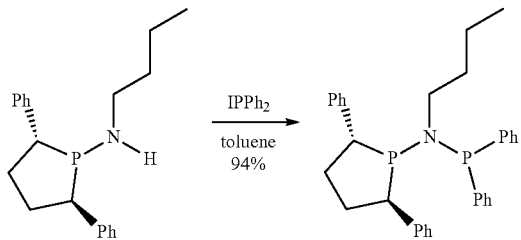 [SMILES: CCCCNP1[C@@H](c2ccccc2)CC[C@@H]1c1ccccc1 ; CCCCN(P(c1ccccc1)c1ccccc1)P1[C@@H](c2ccccc2)CC[C@@H]1c1ccccc1 ; "IPPh2"]

(rac)-N-Butyl-2,5-diphenylphospholan-1-amine (0.25 g, 0.93 mmol) and triethylamine (142 uL, 1.02 mmol) were dissolved in toluene (5 mL). Iodophenylphosphine (0.29 g, 0.93 mmol) was also dissolved in toluene (5 mL). The two solutions were cooled in the freezer to −30° C. The iododiphenylphosphine solution was added dropwise to the solution of (rac)-N-butyl-2,5-diphenylphospholan-1-amine and triethylamine causing immediate solid formation. The sample was analyzed by $^{31}$P-NMR which showed complete conversion to the product. The solution was filtered and the filtrate was concentrated under reduced pressure. The residue was dissolved in ether (15 mL) and filtered again before concentrating to a thick yellow oil. Pentane (5 mL) was added to the oil, the solution was stirred for 1 minute, and then concentrated again, yielding the desired product as a white solid. Yield (3.8 g, 94%). $^1$H NMR (400 MHz, $C_6D_6$) δ 7.53-7.38 (m, 4H), 7.37-7.20 (m, 4H), 7.20-7.04 (m, 8H), 7.04-6.84 (m, 5H), 4.08 (ddt, J=12.1, 7.5, 4.5 Hz, 1H), 3.35 (ddd, J=23.9, 13.2, 5.6 Hz, 1H), 3.23-2.85 (m, 3H), 2.56-2.34 (m, 1H), 2.32-2.10 (m, 1H), 1.76-1.46 (m, 1H), 0.83-0.51 (m, 3H), 0.43 (d, J=14.2 Hz, 3H). $^{13}$C NMR (101 MHz, $C_6D_6$) δ 144.40 (d, J=21.0 Hz), 140.58 (d, J=22.2 Hz), 139.18 (d, J=2.4 Hz), 138.55 (d, J=16.6 Hz), 133.10 (d, J=20.2 Hz), 132.07 (d, J=20.1 Hz), 128.84 (dd, J=3.5, 1.7 Hz), 128.46, 128.32 (t, J=4.8 Hz), 128.21-128.03 (m), 127.60, 127.54, 55.48 (dd, J=21.9, 18.5 Hz), 54.29 (dd, J=31.8, 4.8 Hz), 51.82 (dd, J=22.9, 3.4 Hz), 36.64 (d, J=2.3 Hz), 33.58 (d, J=6.5 Hz), 32.87 (dd, J=7.7, 3.4 Hz), 19.59, 13.40. $^{31}$P NMR (162 MHz, $C_6D_6$) δ 98.98 (d, J=23.5 Hz), 57.64 (d, J=23.4 Hz). HRMS (ESI-TOF) m/z: [M+H]+ Calcd for $C_{32}H_{35}NP_2$ 496.2318; Found 496.2327.

Preparation of (rac)-N-butyl-N-(diethylphosphanyl)-2,5-diphenylphospholan-1-amine, L565

Preparation of (rac)-N-butyl-N-(diethylphosphanyl)-2,5-diphenylphospholan-1-amine, L565

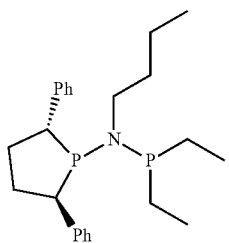 [SMILES: CCCCN(P(CC)CC)P1[C@@H](c2ccccc2)CC[C@@H]1c1ccccc1]

(rac)-N-Butyl-2,5-diphenylphospholan-1-amine (0.25 g, 0.80 mmol) and triethylamine (112 μL, 0.80 mmol) were combined with toluene (3 mL). Chlorodiethylphosphine (98 μL, 0.80 mmol) was added and the cloudy mixture was stirred for 2 h at room temperature. $^{31}$P NMR spectroscopy indicated complete conversion to the product. Volatiles were removed under vacuum and the residue mixed with ether and passed through a small plug of activated neutral alumina. Volatiles were removed from the filtrate to yield the product as a colorless oil. Yield (0.27 g, 84%). $^1$H NMR (400 MHz, $C_6D_6$) δ 7.47-7.32 (m, 4H), 7.22 (dt, J=15.8, 7.7 Hz, 4H), 7.15-7.00 (m, 2H), 3.88 (ddt, J=11.8, 7.8, 4.1 Hz, 1H), 3.29 (ddd, J=24.4, 13.1, 5.8 Hz, 1H), 2.97-2.58 (m, 3H), 2.51-2.32 (m, 1H), 2.12 (tt, J=10.6, 5.3 Hz, 1H), 1.75-1.50 (m, 1H), 1.50-1.28 (m, 2H), 1.27-0.90 (m, 8H), 0.86-0.63 (m, 6H), 0.64-0.44 (m, 1H). $^{13}$C NMR (101 MHz, $C_6D_6$) δ 144.65 (d, J=21.2 Hz), 140.45 (d, J=2.6 Hz), 128.86 (dd, J=3.5, 1.7 Hz), 128.73, 128.64, 128.36, 126.09 (d, J=2.4 Hz), 125.60 (d, J=1.9 Hz), 54.29 (dd, J=21.5, 13.6 Hz), 51.73 (dd, J=24.4, 1.9 Hz), 50.90 (dd, J=23.3, 3.4 Hz), 36.39 (d, J=3.5 Hz), 35.32 (dd, J=5.8, 2.5 Hz), 32.86 (dd, J=6.4, 3.1 Hz), 23.63-22.02 (m), 20.44, 14.19, 10.48 (d, J=17.1 Hz), 9.53 (d, J=24.0 Hz). $^{31}$P NMR (162 MHz, $C_6D_6$) δ 92.21 (s, br), 60.09 (d, J=19.2 Hz). HRMS (ESI-TOF) m/z: [M+H]+ Calcd for $C_{24}H_{35}NP_2$ 400.2318. Found 400.2310.

Preparation of rac-N-butyl-N-(bis(4-methylphenyl)phosphinyl)-2,5-diphenylphospholan-1-amine, L592

Step 1. Preparation of bis(4-methylphenyl)iodophosphine

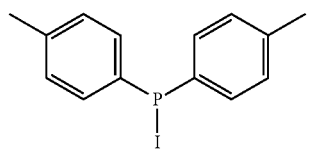

Iodotrimethylsilane (0.50 g, 2.5 mmol) was added to a solution of bis(4-methylphenyl)chloro phosphine (0.50 g, 2.0 mmol) in toluene (5.0 mL). The orange mixture was stirred at ambient conditions overnight. The reaction mixture was filtered to remove the dark precipitate which was suspended in the solution after the reaction. The solvent and unreacted iodotrimethylsilane were removed under vacuum and the product was obtained as a yellowish liquid. Yield (0.50 g, 73%). $^1$H NMR (400 MHz, $C_6D_6$) δ 7.53 (t, 4H), 6.76 (m, 4H), 1.91 (d, J=0.9 Hz, 6H). $^{13}$C NMR (101 MHz, $C_6D_6$) δ 140.37, 134.08 (d, J=23.3 Hz), 129.60 (d, J=6.5 Hz), 21.07. $^{31}$P NMR (162 MHz, $C_6D_6$) δ 43.08 (s).

Step 2. Preparation of rac-N-butyl-N-(bis (4-methylphenyl)phosphinyl)-2,5-diphenylphospholan-1-amine, L592

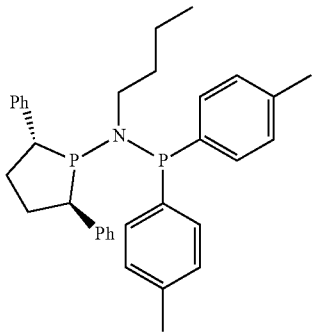 [SMILES: CCCCN(P(c1ccc(C)cc1)c1ccc(C)cc1)P1[C@@H](c2ccccc2)CC[C@@H]1c1ccccc1]

A cold solution (−30° C.) of triethylamine (0.089 g, 0.88 mmol) in toluene-d₈ (2.0 mL) was added to a cold (−30° C.) solution of rac-N-butyl-2,5-diphenylphospholan-1-amine (0.28 g, 0.88 mmol) in toluene-d₈ (2.0 mL) and the resulting reaction mixture was stirred for 10 min. The reaction mixture was placed in a freezer at −30° C. for 30 minutes. To this cooled reaction mixture was added a cold (−30° C.) solution of the bis(4-methylphenyl)iodophosphine (0.30 g, 0.88 mmol) in 2.0 mL of toluene-d8 with formation of a white precipitate. The reaction mixture was stirred for 30 min at ambient temperature. Volatiles were The volatiles were removed under vacuum. The crude product was dissolved in toluene (10 mL). The solution was passed through 5-cm plug of activated neutral alumina and the volatiles were removed under vacuum, giving solid product which was recrystallized from cold pentane at −30° C. to produce pure product. Yield 0.20 g (43%). $^1$H NMR (400 MHz, C$_6$D$_6$) δ 7.45 (dt, J=7.1, 1.2 Hz, 2H), 7.37-7.31 (m, 2H), 7.29 (dt, J=8.0, 1.4 Hz, 2H), 7.23-7.10 (m, 5H), 7.04 (ddt, J=7.9, 6.8, 1.3 Hz, 2H), 6.98-6.92 (m, 2H), 6.87-6.77 (m, 3H), 4.09 (m, 1H), 3.41-3.26 (m, 1H), 3.16-2.87 (m, 3H), 2.52-2.32 (m, 1H), 2.16 (m, 1H), 2.05 (s, 3H), 2.00 (s, 3H), 1.66-1.43 (m, 1H), 0.94 (m, 1H), 0.61 (m, 3H), 0.40 (t, J=7.0 Hz, 3H). $^{13}$C NMR (101 MHz, C$_6$D$_6$) δ 144.89 (d, J=21.3 Hz), 139.65 (d, J=2.2 Hz), 138.21 (d, J=13.5 Hz), 137.76 (d, J=21.0 Hz), 135.79 (d, J=15.6 Hz), 133.61 (d, J=20.5 Hz), 132.45 (d, J=20.1 Hz), 129.35-129.08 (m), 128.75 (d, J=4.3 Hz), 128.71-128.58 (m), 128.46, 125.97 (d, J=2.5 Hz), 125.61 (d, J=1.8 Hz), 55.62 (dd, J=21.8, 18.7 Hz), 54.48 (dd, J=31.9, 4.9 Hz), 52.29 (dd, J=22.9, 3.3 Hz), 36.97 (d, J=2.2 Hz), 34.33-33.06 (m), 21.15 (d, J=3.4 Hz), 19.99, 13.75. $^{31}$P NMR (162 MHz, C$_6$D$_6$) δ 99.33 (d, J=22.8 Hz), 57.72 (d, J=22.8 Hz).

Preparation of N-butyl-N-((2S,5 S)-2,5-diphenylphospholan-1-yl)-10,11-dihydro-5H-dibenzo[b,f]-phosphepin-5-amine, L593

Step 1. Preparation of 1,2-bis(2-bromophenyl)ethane

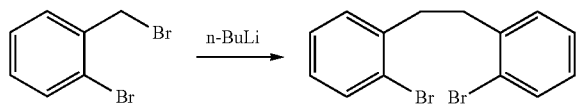

A solution of 2-bromobenzyl bromide (33.36 g, 133.5 mmol) in THF (200 mL) was cooled in a dry ice bath to −78° C. n-Butyllithium (1.42 M, 47.0 mL, 66.7 mmol) was added slowly dropwise over 40 minutes. The solution was allowed to stir for about 3 hours, then gradually allowed to warm up. When the temperature reached about −20° C., water (40 mL) was slowly added and the reaction mixture was allowed to warm to ambient temperature. Workup: The organic solution was washed with water (3×250 mL) and sat. aq. NaCl solution (125 mL). The combined organics were dried over anhydrous magnesium sulfate. The solution was filtered, and concentrated (rotavap) to give a white solid. The proton and carbon NMR spectra of this crude product agree with the literature. The product was recrystallized from hot hexane to give 18.48 g, 81.4%, in a first crop. Second crop: 2.62 g. Total: 21.10 g, 92.97%. $^1$H NMR (400 MHz, CDCl$_3$) δ 7.55 (dd, J=7.8, 1.1 Hz, 2H), 7.24-7.17 (m, 4H), 7.07 (ddd, J=8.0, 6.7, 2.4 Hz, 2H), 3.05 (s, 4H). $^{13}$C NMR (101 MHz, CDCl$_3$) δ 140.54, 132.77, 130.60, 127.79, 127.41, 124.46, 36.42.

Step 2. Preparation of 1,2-bis(2-lithiophenyl)ethane-diethyl ether adduct

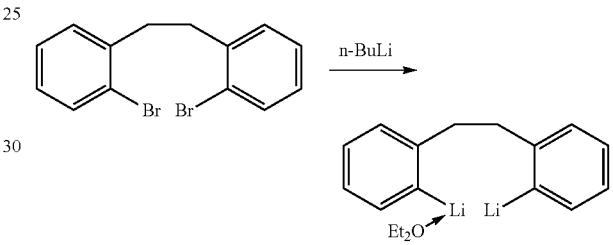

n-Butyllithium (16.5 mL, 2.44 M, 40.3 mmol) was slowly added to a solution of 1,2-bis(2-bromophenyl)ethane (6.540, 19.23 mmol) in ether (80 mL) cooled in a dry ice bath (precipitate forms). The reaction mixture was allowed to warm to ambient temperature and was stirred overnight. The resulting white precipitate was filtered out, washed with ether and dried to give a white powder (4.5606 g, 88.4%, based on the monoether adduct, as shown by the $^1$H NMR spectrum). $^1$H NMR (500 MHz, THF-d$_8$) δ 7.86 (dd, J=6.2, 1.2 Hz, 2H), 6.80 (d, J=7.2 Hz, 2H), 6.72 (td, J=7.2, 1.8 Hz, 2H), 6.67 (ddd, J=7.3, 6.3, 1.3 Hz, 2H), 3.39 (q, J=7.0 Hz, 4H), 3.07 (s, 4H), 1.15-1.09 (m, 6H). $^{13}$C NMR (126 MHz, THF-d$_8$) δ 185.70, 158.67, 143.91, 125.48, 124.03, 122.34, 66.30, 43.46, 15.68.

Step 3. Preparation of N,N-dimethyl-10,11-dihydro-5H-dibenzo[b,f]phosphepin-5-amine

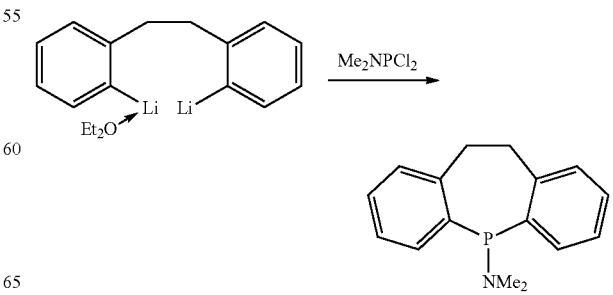

The dilithium salt 1,2-bis(2-lithiophenyl)ethane-diethyl ether adduct (4.000 g, 14.86 mmol) was suspended in ether (60 mL) and cooled to −30° C. in the freezer. Dimethylphosphoramidous dichloride (2.17 g, 14.86 mmol) was added slowly dropwise and the reaction mixture was allowed to warm to ambient temperature and stir overnight. The $^{31}$P NMR spectrum showed very little starting NMe$_2$PCl$_2$ compound to be present along with a major peak at 75 ppm, presumably due to the desired product. The volatiles were removed under reduced pressure. The white residue was extracted with copious amounts of hexane, filtered, and the volatiles were removed under reduced pressure to give a white solid having low solubility in hexane. The solids were dissolved in hot hexane and allowed to cool while standing at ambient temperature. Large crystals formed. The supernatant was pipetted off, the residue was washed with 3 mL of hexane, and the solids were dried under reduced pressure (2.231 g, 58.8%). By $^{31}$P NMR the compound was about 85% pure, with about 15% of other phosphorus species being present. $^1$H NMR (400 MHz, CDCl$_3$) δ 7.38 (td, J=7.3, 1.6 Hz, 2H), 7.24 (tt, J=7.5, 1.5 Hz, 2H), 7.19 (tdd, J=7.2, 1.6, 0.6 Hz, 2H), 7.12 (ddd, J=7.3, 3.8, 1.0 Hz, 2H), 3.41-3.29 (m, 2H), 3.06-2.97 (m, 2H), 2.96 (d, J=8.0 Hz, 6H). $^{13}$C NMR (101 MHz, CDCl$_3$) δ 143.14 (d, J=13.8 Hz), 139.86 (d, J=18.0 Hz), 129.59 (d, J=2.3 Hz), 129.34 (d, J=11.0 Hz), 127.22 (d, J=1.0 Hz), 125.51 (d, J=3.2 Hz), 43.23 (d, J=16.7 Hz), 34.20 (d, J=7.2 Hz). $^{31}$P NMR (162 MHz, CDCl$_3$) δ 72.90.

Step 4. Preparation of 5-chloro-10,11-dihydro-5H-dibenzo[b,f]phosphepin

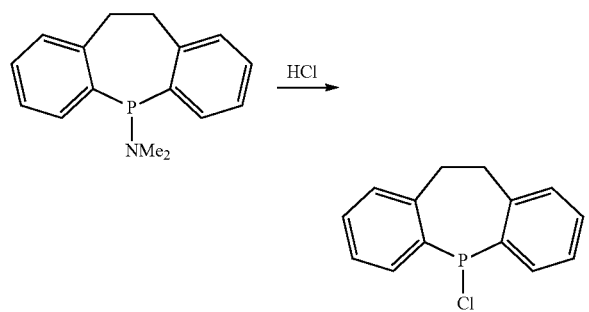

Anhydrous HCl (15 mL, 2.0 M, ether solution, 30.0 mmol) was added to a solution of the solids from Step 3 immediately above comprising mostly N,N-dimethyl-10,11-dihydro-5H-dibenzo[b,f]phosphepin-5-amine dissolved in a mixture of hexane (60 mL) and ether (40 mL) with immediate formation of precipitate. The mixture was stirred for several hours. $^1$H and $^{31}$P NMR spectra showed the reaction has not quite gone to completion, however the mixture is cleaner than it started out: The 15% of other species is gone and only desired P—Cl product and starting P—N are present. Additional HCl solution (5 mL) was added. The reaction mixture was filtered and the volatiles were removed under reduced pressure to give white solid which was washed with hexane and dried under reduced pressure. By NMR it is about 85% pure, so it was recrystallized from boiling ether. The solution was allowed to cool to ambient temperature overnight. The supernatant was pipetted from the crystalline material which had formed and the product was dried under reduced pressure. Yield of colorless crystals/powder was about 1.24 g, 33.84%, of 95% pure material. An additional less-pure crop was obtained from the supernatant. $^1$H NMR (500 MHz, CDCl$_3$) δ 7.87 (ddd, J=13.3, 7.6, 1.5 Hz, 1H), 7.37 (td, J=7.5, 1.4 Hz, 1H), 7.28 (tt, J=7.5, 1.5 Hz, 1H), 7.22 (dt, J=7.6, 1.7 Hz, 1H), 3.64-3.55 (m, 1H), 3.28-3.19 (m, 1H). $^{13}$C NMR (126 MHz, CDCl$_3$) δ 144.71 (d, J=4.8 Hz), 135.80 (d, J=37.2 Hz), 134.17 (d, J=46.4 Hz), 131.07, 130.15, 126.13 (d, J=13.3 Hz), 34.03 (d, J=5.1 Hz). $^{31}$P NMR (202 MHz, CDCl$_3$) δ 92.26.

Step 5. Preparation of 5-iodo-10,11-dihydro-5H-dibenzo[b,f]phosphepin

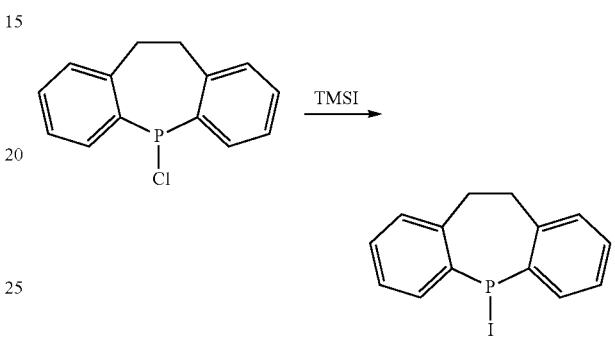

Iodotrimethylsilane (1.30 g, 6.54 mmol) was added quickly dropwise to a solution of 5-chloro-10,11-dihydro-5H-dibenzo[b,f]phosphepin (1.24 g, 5.03 mmol) in toluene (50 mL). The reaction solution immediately turned yellow. The solution was stirred for several hours. By $^{31}$P NMR, the reaction was complete. The volatiles were removed under reduced pressure to give the product as a bright yellow powder, Yield: 1.7641 g, 103.8%, of product which by $^{31}$P NMR is 97% pure. $^1$H NMR (500 MHz, CDCl$_3$) δ 7.83 (dd, J=17.2, 7.6 Hz, 2H), 7.37 (t, J=7.3 Hz, 3H), 7.28-7.16 (m, 4H), 3.76 (s, 2H), 3.28 (s, 3H). $^{13}$C NMR (126 MHz, CDCl$_3$) δ 147.26 (d, J=2.3 Hz), 135.67 (d, J=63.7 Hz), 132.67 (d, J=41.5 Hz), 131.86, 130.43, 125.93 (d, J=18.5 Hz), 34.65. $^{31}$P NMR (202 MHz, CDCl$_3$) δ 38.80.

Step 6. Preparation of N-butyl-N-((2S,5S)-2,5-diphenylphospholan-1-yl)-10,11-dihydro-5H-dibenzo[b,f]-phosphepin-5-amine, L593

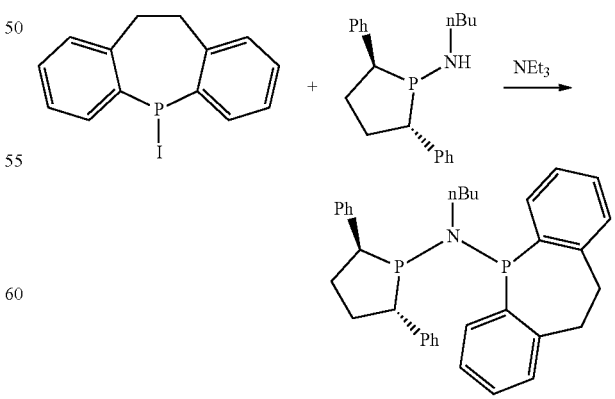

A solution of N-butyl-2,5-diphenylphospholan-1-amine (0.186 g, 0.60 mmol) and triethylamine (0.301 g, 2.98 mmol) in toluene (10 mL) was cooled in the freezer for several hours. 5-Iodo-10,11-dihydro-5H-dibenzo[b,f]phosphepin (0.201 g, 0.60 mmol) was added dropwise. The yellow color of the 5-Iodo-10,11-dihydro-5H-dibenzo[b,f] phosphepin disappeared quickly and precipitate gradually formed. The reaction mixture was stirred overnight. The mixture was filtered and the volatiles were removed under reduced pressure to give a viscous oil that solidified on standing under reduced pressure overnight. The yield was 0.3195 g, 103%. The product looked good on the basis of its $^{31}$P NMR spectrum. $^1$H NMR (400 MHz, CDCl$_3$) δ 7.45 (d, J=7.4 Hz, 2H), 7.40-7.29 (m, 4H), 7.28-7.22 (m, 4H), 7.22-7.15 (m, 2H), 7.14-6.96 (m, 4H), 6.71 (dt, J=14.9, 1.7 Hz, 1H), 6.34 (t, J=7.4 Hz, 1H), 4.08-3.96 (m, 1H), 3.56 (dddd, J=24.6, 14.3, 5.8, 2.0 Hz, 1H), 3.36 (ddd, J=16.2, 9.4, 7.0 Hz, 2H), 2.99 (tdd, J=15.0, 7.4, 4.4 Hz, 4H), 2.66-2.50 (m, 2H), 2.35 (tq, J=10.7, 5.3, 4.5 Hz, 1H), 1.84-1.64 (m, 2H), 1.09 (dq, J=16.8, 6.7, 5.0 Hz, 1H), 1.01-0.90 (m, 1H), 0.90-0.79 (m, 1H), 0.66 (t, J=7.3 Hz, 3H). $^{13}$C NMR (101 MHz, CDCl$_3$) δ 144.80 (d, J=21.8 Hz), 143.45 (d, J=14.7 Hz), 142.88 (d, J=14.1 Hz), 138.79 (d, J=2.0 Hz), 138.42 (d, J=27.0 Hz), 136.97 (d, J=23.0 Hz), 130.98 (d, J=3.0 Hz), 130.87 (d, J=2.2 Hz), 129.38 (d, J=1.6 Hz), 129.14 (d, J=1.9 Hz), 128.74 (dd, J=3.3, 1.6 Hz), 128.64 (d, J=9.5 Hz), 128.44, 128.38 (d, J=1.4 Hz), 127.58 (d, J=1.3 Hz), 126.84, 125.79 (d, J=2.6 Hz), 125.73 (d, J=1.9 Hz), 125.47 (d, J=2.3 Hz), 124.96 (d, J=2.8 Hz), 54.89 (d, J=2.6 Hz), 54.74 (d, J=12.5 Hz), 54.58 (dd, J=15.2, 7.7 Hz), 52.63 (dd, J=22.1, 3.1 Hz), 37.77 (d, J=1.8 Hz), 34.42 (dd, J=10.6, 7.3 Hz), 33.73 (d, J=14.0 Hz), 32.84 (dd, J=8.0, 3.4 Hz), 20.23, 13.80. $^{31}$P NMR (162 MHz, CDCl$_3$) δ 97.48, 72.33. High resolution mass spec: Expected (M+1) 522.2473. Found (M+1) 522.2494

Preparation of (rac)-N-(bis(4-(trifluoromethyl)phenyl)phosphanyl)-N-butyl-2,5-diphenylphospholan-1-amine, L594

Step 1. Preparation of bis(4-(trifluoromethyl)phenyl)iodophosphine

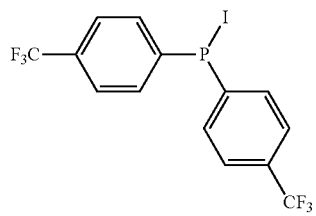 [SMILES: FC(F)(F)c1ccc(P(I)c2ccc(C(F)(F)F)cc2)cc1]

Bis(4-(trifluoromethyl)phenyl)chlorophosphine (0.55 g, 1.5 mmol) was dissolved in toluene (3.0 mL). Iodotrimethylsilane (0.26 mL, 1.9 mmol) was added and the orange solution was stirred at ambient temperature for 2 h. A dark oily material formed during the reaction. The reaction mixture was decanted to remove the dark material and the volatiles were removed to yield the product as a pale yellow oil. Yield (0.42 g, 61%). $^1$H NMR (400 MHz, C$_6$D$_6$) δ 7.32-7.20 (m, 4H), 7.19-7.09 (m, 4H). $^{13}$C NMR (101 MHz, C$_6$D$_6$) δ 139.55 (d, J=40.6 Hz), 134.24 (d, J=23.6 Hz), 132.24 (d, J=32.7 Hz), 131.96 (d, J=10.7 Hz), 125.66 (dd, J=6.2, 3.6 Hz). $^{31}$P NMR (162 MHz, C$_6$D$_6$) δ 29.46-29.26 (m).

Step 2. Preparation of (rac)-N-(bis(4-(trifluoromethyl)phenyl)phosphanyl)-N-butyl-2,5-diphenylphospholan-1-amine, L594

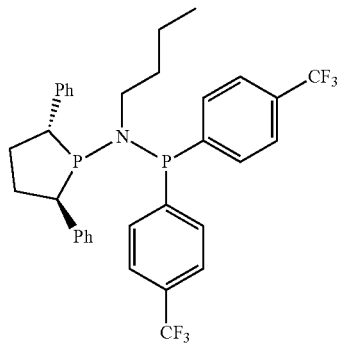 [SMILES: CCCCN(P(c1ccc(C(F)(F)F)cc1)c1ccc(C(F)(F)F)cc1)P1[C@@H](c2ccccc2)CC[C@@H]1c1ccccc1]

(rac)-N-Butyl-2,5-diphenylphospholan-1-amine (0.14 g, 0.45 mmol) and triethylamine (69 uL, 0.50 mmol) were combined and dissolved in toluene (2.0 mL). Bis(4-(trifluoromethyl)phenyl)iodophosphine (0.20 g, 0.45 mmol) was separately dissolved in toluene (2.0 mL). The two solutions were cooled in the freezer to −30° C. The bis(4-(trifluoromethyl)phenyl)iodophosphine solution was added dropwise to the solution of (rac)-N-butyl-2,5-diphenylphospholan-1-amine and triethylamine causing immediate solid formation. After 30 minutes, the volatiles were removed under vacuum. The material was extracted with ether and filtered through a small alumina plug. The solvent was removed to yield the crude product. Pentane was added to the solid and the mixture was placed in the freezer at −30° C. After 1.5 h, the pentane was decanted from the solid product and the process was repeated with cold pentane. The residual solvent was removed under reduced pressure to yield the product as a white solid. Yield (0.16 g, 56%). $^1$H NMR (400 MHz, C$_6$D$_6$) δ 7.28-7.17 (m, 6H), 7.16-6.87 (m, 10H), 6.71-6.55 (m, 2H), 3.88-3.66 (m, 1H), 3.20 (ddd, J=24.9, 13.2, 5.8 Hz, 1H), 3.01-2.61 (m, 3H), 2.43-2.18 (m, 1H), 2.05 (tt, J=10.8, 5.3 Hz, 2H), 1.58-1.34 (m, 1H), 1.07-0.76 (m, 1H), 0.76-0.50 (m, 3H), 0.44-0.31 (m, 3H). $^{13}$C NMR (101 MHz, C$_6$D$_6$) δ 144.87 (d, J=24.5 Hz), 143.78 (d, J=20.7 Hz), 143.16 (d, J=19.8 Hz), 139.10 (d, J=2.7 Hz), 133.35 (d, J=20.8 Hz), 132.77 (d, J=20.7 Hz), 130.82 (dd, J=38.3, 32.4 Hz), 129.08-128.96 (m), 128.92, 128.69, 128.59, 126.56 (d, J=2.5 Hz), 126.07 (d, J=1.8 Hz), 125.27 (dd, J=5.4, 3.9 Hz), 124.83 (dd, J=6.1, 3.7 Hz), 123.49 (d, J=8.1 Hz), 56.68-55.17 (m), 54.82 (d, J=26.0 Hz), 51.45 (dd, J=23.1, 3.6 Hz), 36.83 (d, J=3.4 Hz), 34.50-33.77 (m), 33.19 (dd, J=6.1, 3.4 Hz), 19.96, 13.69. $^{31}$P NMR (162 MHz, C$_6$D$_6$) δ 98.44 (d, J=20.9 Hz), 57.13 (d, J=20.5 Hz). $^{19}$F NMR (376 MHz, C$_6$D$_6$) δ −62.56 (d, J=20.7 Hz). HRMS (ESI-TOF) m/z: [M+H]+ Calcd for C$_{34}$H$_{33}$F$_6$NP$_2$ 632.2065; Found 632.2080.

Preparation of rac-(2R,5R)—N-butyl-N-((2R,5R)-2,5-diphenylphospholan-1-yl)-2,5-diphenylphospholan-1-amine, L596

Step 1. Preparation of rac-(2R,5R)-1-iodo-2,5-diphenylphospholane

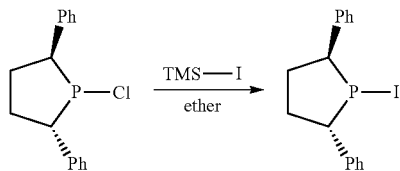

(2S,5S)-1-Chloro-2,5-diphenylphospholane (2.0 g, 7.28 mmol) was dissolved in anhydrous ether (30 mL). Iodotrimethylsilane (1.24 mL, 8.74 mmol) was added and the solution was stirred for 1 h. The solution was passed through a filter and the filtrate was concentrated under vacuum to yield the product as a yellow oil. $^1$H NMR (400 MHz, C$_6$D$_6$) δ 7.35-6.69 (m, 10H), 3.61 (s, 2H), 2.10 (h, J=6.6 Hz, 2H), 1.89 (s, 2H). $^{13}$C NMR (101 MHz, C$_6$D$_6$) δ 128.44 (d, J=1.4 Hz), 127.41, 127.35, 126.48 (d, J=2.6 Hz), 51.47, 34.70. $^{31}$P NMR (162 MHz, C$_6$D$_6$) δ 111.51.

Step 2. Preparation of rac-(2R,5R)—N-butyl-N-((2R,5R)-2,5-diphenylphospholan-1-yl)-2,5-diphenylphospholan-1-amine, L596

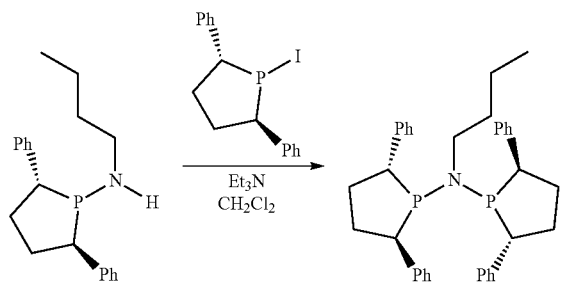 [SMILES: "Et3NCH2Cl2" ; CCCCNP1[C@@H](c2ccccc2)CC[C@@H]1c1ccccc1 ; IP1[C@@H](c2ccccc2)CC[C@@H]1c1ccccc1 ; CCCCN(P1[C@@H](c2ccccc2)CC[C@@H]1c1ccccc1)P1[C@@H](c2ccccc2)CC[C@@H]1c1ccccc1]

N-Butyl-2,5-diphenylphospholan-1-amine (0.68 g, 2.18 mol) is dissolved in methylene chloride (35 mL) and triethylamine (0.61 mL, 4.37 mmol). (rac)-1-Iodo-2,5-diphenylphospholane (0.80 g, 0.2.18 mmol) was also dissolved in methylene chloride (10 mL). The two solutions were chilled to −30° C. before being slowly combined. The sample was analyzed by $^{31}$P NMR spectroscopy which showed complete reaction to mostly one product. The reaction solution was concentrated to dryness under vacuum. The residue was slurried in hexane (40 mL) and was filtered. The solid was rinsed with additional hexane (10 mL). The filtrate was concentrated to ~20 mL under vacuum whereupon a large amount of white solid precipitated from the cold solution. The solid was collected by filtration and dried under high vacuum. $^1$H NMR (400 MHz, C$_6$D$_6$) δ 7.14 (m, 8H), 7.07-6.99 (m, 8H), 6.95 (d, J=7.6 Hz, 4H), 3.25-3.00 (m, 4H), 2.58-2.38 (m, 2H), 2.31-2.13 (m, 1H), 2.13-1.95 (m, 6H), 1.62-1.43 (m, 2H), 1.07-0.88 (m, 1H), 0.68-0.51 (m, 2H), 0.48 (t, 3H). $^{13}$C NMR (101 MHz, C$_6$D$_6$) δ 144.32 (d, J=19.0 Hz), 140.86, 128.84-128.56 (m), 128.49, 126.04, 125.66, 52.78 (t, J=11.8 Hz), 49.32 (d, J=21.0 Hz), 35.22-34.24 (m), 30.91 (t, J=4.4 Hz), 20.16, 13.77. $^{31}$P NMR (162 MHz, C$_6$D$_6$) δ 91.12. HRMS (ESI-TOF) m/z: [M+H]+ Calcd for C$_{36}$H$_{41}$NP$_2$ 550.2787; Found 550.2797.

Preparation of (rac)-N-(di(furan-2-yl)phosphanyl)-N-isopropyl-2,5-diphenylphospholan-1-amine, L601

Step 1. Preparation of (rac)-N-isopropyl-2,5-diphenylphospholan-1-amine

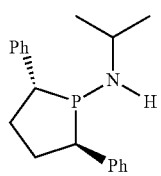 [SMILES: CC(C)NP1[C@@H](c2ccccc2)CC[C@@H]1c1ccccc1]

A solution of (rac)-1-chloro-2,5-diphenylphospholane (0.80 g, 2.9 mmol) in hexanes (5 mL) was added to a solution of isopropylamine (2.5 mL, 29 mmol) in hexanes (5 mL) resulting in immediate precipitation of a white solid. After stirring for 1 h, the mixture was checked by $^{31}$P NMR spectroscopy which showed complete conversion to a new product. The mixture was filtered and the volatiles removed under vacuum to yield the product as a yellow oil. Yield (0.81 g, 94%). $^1$H NMR (400 MHz, C$_6$D$_6$) δ 7.38-7.32 (m, 2H), 7.29-7.17 (m, 4H), 7.14-7.02 (m, 4H), 3.07 (ddd, J=22.2, 12.5, 6.0 Hz, 1H), 2.96-2.78 (m, 1H), 2.59 (m, 1H), 2.23-1.98 (m, 2H), 1.79 (m, J=12.5, 5.1, 2.6 Hz, 1H), 1.58 (m, 1H), 1.00 (dd, J=10.6, 7.2 Hz, 1H), 0.80 (d, J=6.3 Hz, 3H), 0.46 (d, J=6.4 Hz, 3H). $^{13}$C NMR (101 MHz, C$_6$D$_6$) δ 144.42 (d, J=18.7 Hz), 140.39 (d, J=1.4 Hz), 128.76, 128.45 (d, J=1.4 Hz), 128.41 (d, J=3.4 Hz), 127.96 (d, J=8.1 Hz), 126.00 (d, J=2.6 Hz), 125.68 (d, J=1.9 Hz), 57.01 (d, J=14.8 Hz), 50.20 (d, J=22.1 Hz), 49.12 (d, J=25.3 Hz), 34.09 (d, J=3.0 Hz), 31.83 (d, J=2.1 Hz), 25.92 (dd, J=50.4, 5.8 Hz). $^{31}$P NMR (162 MHz, C$_6$D$_6$) δ 67.37.

Step 2. Preparation of di(furan-2-yl)iodophosphine

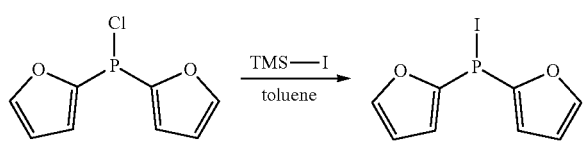

Chlorodi(furan-2-yl) phosphine (2.0 mL, 13 mmol) was dissolved in toluene (10 mL). Iodotrimethylsilane (2.19 mL, 15.4 mmol) was added and the orange solution was stirred at ambient temperature. After 2 h, the reaction was checked by $^{31}$P NMR spectroscopy which showed complete conversion to a new product. The solvent was removed under vacuum to yield the product as a red oil. Yield (3.5 g, 92%). $^1$H NMR (400 MHz, C$_6$D$_6$) δ 7.27 (dd, J=1.8, 0.8 Hz, 2H), 6.73 (dt, J=3.5, 0.9 Hz, 2H), 5.99 (dd, J=3.5, 1.8 Hz, 2H). $^{13}$C NMR (101 MHz, C$_6$D$_6$) δ 149.03 (d, J=3.9 Hz), 146.66 (d, J=37.9 Hz), 122.81 (d, J=28.1 Hz), 111.85 (d, J=5.5 Hz). $^{31}$P NMR (162 MHz, C$_6$D$_6$) δ −39.35.

Step 3. Preparation of (rac)-N-(di(furan-2-yl)phosphanyl)-N-isopropyl-2,5-diphenylphospholan-1-amine, L601

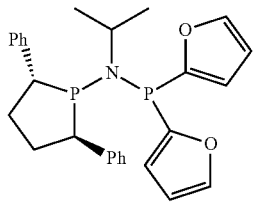 [SMILES: CC(C)N(P(c1ccco1)c1ccco1)P1[C@@H](c2ccccc2)CC[C@@H]1c1ccccc1]

(rac)-N-Isopropyl-2,5-diphenylphospholan-1-amine (0.30 g, 1.0 mmol) and triethylamine (0.155 mL, 1.11 mmol) were dissolved in toluene (2 mL). Di(furan-2-yl)iodophosphine (0.315 g, 1.01 mmol) was also dissolved in toluene (2 mL). The two solutions were cooled in the freezer to −30° C. The di(furan-2-yl)iodophosphine solution was added dropwise to the solution of (rac)-N-isopropyl-2,5-diphenylphospholan-1-amine and triethylamine causing immediate formation of precipitate. The sample was analyzed by $^{31}$P NMR spectroscopy which showed complete conversion to the product. The solvent was removed. The residue was extracted with ether and passed through a short plug of alumina. The solvent was removed to yield the product as a white solid. Yield (0.36 g, 77%). $^1$H NMR (400 MHz, C$_6$D$_6$) δ 7.41-7.25 (m, 4H), 7.26-7.16 (m, 3H), 7.09-7.00 (m, 4H), 7.00-6.90 (m, 1H), 6.42 (dd, J=3.3, 0.7 Hz, 1H), 6.09-5.98 (m, 2H), 5.95 (dt, J=3.4, 1.8 Hz, 1H), 4.40-4.12 (m, 1H), 3.90-3.64 (m, 1H), 3.33 (ddd, J=25.9, 13.2, 5.6 Hz, 1H), 3.15-2.90 (m, 1H), 2.53-2.34 (m, 1H), 2.26-2.07 (m, 1H), 1.79-1.48 (m, 1H), 0.75 (dd, J=25.9, 6.6 Hz, 6H). $^{13}$C NMR (101 MHz, C$_6$D$_6$) δ 146.28 (d, J=4.3 Hz), 146.03 (d, J=2.7 Hz), 144.41 (d, J=20.9 Hz), 129.14 (t, J=3.0 Hz), 128.70 (d, J=1.3 Hz), 128.45 (d, J=8.1 Hz), 128.38 (d, J=1.2 Hz), 125.79 (dd, J=49.0, 2.3 Hz), 119.74 (d, J=26.2 Hz), 119.13 (d, J=16.4 Hz), 110.86 (d, J=2.7 Hz), 110.47 (d, J=5.7 Hz), 53.88 (dd, J=23.9, 6.9 Hz), 50.27 (dd, J=21.3, 4.8 Hz), 36.01 (d, J=3.2 Hz), 33.23 (dd, J=8.1, 3.4 Hz), 24.05 (d, J=14.3 Hz), 23.61 (d, J=11.7 Hz). $^{31}$P NMR (162 MHz, C$_6$D$_6$) δ 75.57, 10.79 (d, J=38.6 Hz). HRMS (ESI-TOF) m/z: [M+H]+ Calcd for C$_{27}$H$_{29}$NO$_2$P$_2$ 462.1747; Found 462.1730.

Preparation of rac-N-butyl-N-(bis(4-fluorophenyl)phosphinyl)-2,5-diphenylphospholan-1-amine, L603

Step 1. Preparation of bis(4-methylphenyl)iodophosphine

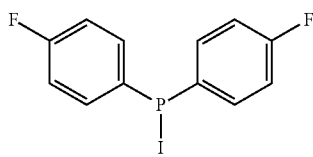 [SMILES: Fc1ccc(P(I)c2ccc(F)cc2)cc1]

Iodotrimethylsilane (0.49 g, 2.5 mmol) was added to a solution of bis(4-fluorophenyl)chlorophosphine (0.50 g, 1.9 mmol) in toluene (5.0 mL) with rapid formation of orange color. The reaction mixture was stirred at room temperature overnight, then filtered to remove the dark precipitate which was suspended in the solution after the reaction. The volatiles were removed under vacuum and a yellowish liquid was obtained. Yield (0.52 g, 76%). $^1$H NMR (400 MHz, C$_6$D$_5$CD$_3$) δ 7.27 (m, 4H), 6.70-6.51 (m, 4H). $^{13}$C NMR (101 MHz, C$_6$D$_5$CD$_3$) δ 165.04 (d, J=1.0 Hz), 162.54, 137.05, 135.54 (dd, J=24.9, 8.3 Hz), 130.85 (dd, J=38.9, 3.5 Hz), 115.57 (dd, J=21.3, 7.1 Hz). $^{31}$P NMR (162 MHz, C$_6$D$_5$CD$_3$) δ 36.68 (t, J=5.0 Hz). $^{19}$F NMR (376 MHz, C$_6$D$_6$) δ −109.22−−109.69 (m).

Step 2. Preparation of rac-N-butyl-N-(bis(4-fluorophenyl)phosphinyl)-2,5-diphenylphospholan-1-amine, L603

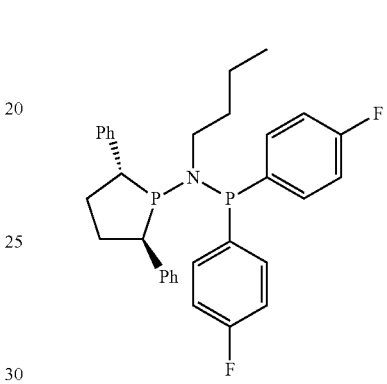

A cold solution (−30° C.) of triethylamine (0.068 g, 0.67 mmol) in toluene-d$_8$ (1.4 mL) was added to a cold (−30° C.) solution of rac-N-butyl-2,5-diphenylphospholan-1-amine (0.21 g, 0.67 mmol) in toluene-d$_8$ (2.1 mL) and the resulting mixture was stirred for 10 min. The mixture was placed in a freezer at −30° C. for 30 minutes. To this cooled mixture was added a cold (−30° C.) solution of the bis(4-fluorophenyl)iodophosphine (0.23 g, 0.67 mmol) in toluene-d$_8$ (2.3 mL) with formation of a white precipitate. The reaction mixture was stirred for 30 min at ambient temperature. The volatiles were removed under vacuum. The crude product was redissolved in toluene (10 mL). The solution was passed through a 5-cm plug of activated neutral alumina and the solvent was evaporated under vacuum giving solid product which was recrystallized from cold pentane at −30° C. to produce the pure product. Yield 0.22 g (61%). $^1$H NMR (400 MHz, C$_6$D$_5$CD$_3$) δ 7.33-7.26 (m, 2H), 7.22-7.02 (m, 9H), 6.98 (t, J=7.3 Hz, 1H), 6.80-6.70 (m, 2H), 6.70-6.49 (m, 4H), 3.87 (m, 1H), 3.24 (m, 1H), 3.04-2.72 (m, 2H), 2.47-2.27 (m, 1H), 2.15 (m, 1H), 1.54 (ddt, J=12.8, 4.6, 2.1 Hz, 1H), 1.02-0.81 (m, 1H), 0.65 (m, 2H), 0.47 (t, J=7.1 Hz, 3H). $^{13}$C NMR (101 MHz, C$_6$D$_5$CD$_3$) δ 143.83 (d, J=20.8 Hz), 139.02 (d, J=2.7 Hz), 137.05, 134.85 (d, J=7.9 Hz), 134.63 (d, J=7.8 Hz), 134.09 (d, J=7.7 Hz), 133.87 (d, J=7.8 Hz), 128.32, 128.27, 128.12, 125.83 (d, J=2.5 Hz), 125.39 (d, J=1.9 Hz), 115.28 (d, J=6.0 Hz), 115.07 (d, J=6.0 Hz), 114.56 (d, J=6.6 Hz), 53.83 (d, J=28.7 Hz), 51.29 (d, J=19.9 Hz), 36.45, 33.65 (d, J=5.4 Hz), 32.79, 13.38. $^{31}$P NMR (162 MHz, C$_6$D$_5$CD$_3$) δ 98.19 (d, J=22.4 Hz), 58.38-54.20 (m). $^{19}$F NMR (376 MHz, C$_6$D$_5$CD$_3$) δ −112.24−−112.40 (m), −112.71 (m).

289

Preparation of (2S,5S)—N-(bis(2-fluorophenyl)phosphanyl)-N-butyl-2,5-diphenylpholan-1-amine, Ligand 604

Step 1. Preparation of bis(2-fluorophenyl)dimethylaminophosphine

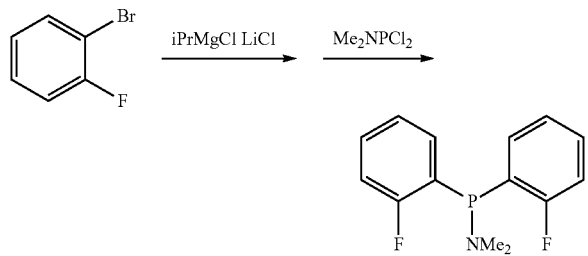

1-Bromo-2-fluorobenzene (18.50 g, 105.7 mmol) was added slowly dropwise to a chilled (−85 to −80° C. (liquid nitrogen/acetone bath)) solution of n-butyllithium (42.0 mL, 2.38 M, 99.9 mmol) in ether (200 mL) such that the temperature did not exceed −78° C. The temperature was allowed to increase to between −78 and −75° C. for one hour with formation of white precipitate. The reaction mixture was cooled to −85° C. A solution of dimethylphosphoramidous dichloride (7.295 g, 49.98 mmol) in ether (10 mL) was added very slowly dropwise such that the temperature did not exceed −80° C. Dry ice was added to the bath and the reaction mixture was allowed to stir overnight while warming to ambient temperature. $^{31}$P and $^{19}$F NMR spectra showed the product to be about 99.5% desired product. The reaction mixture was filtered and the volatiles were removed under reduced pressure. The residue was extracted with hexane, filtered, and the volatiles were removed under reduced pressure to give the product as a pale yellow oil, 12.72 g, 95.95%. $^{1}$H NMR (400 MHz, CDCl$_3$) δ 7.34 (ddddd, J=8.3, 7.3, 5.5, 1.9, 1.0 Hz, 1H), 7.23 (tddd, J=5.6, 4.6, 2.4, 1.3 Hz, 1H), 7.15 (tt, J=7.5, 1.0 Hz, 1H), 7.05 (dddd, J=9.4, 8.2, 4.1, 1.1 Hz, 1H). $^{13}$C NMR (101 MHz, CDCl$_3$) δ 163.47 (dd, J=244.5, 16.1 Hz), 132.23 (t, J=5.9 Hz), 130.65 (d, J=8.2 Hz), 124.85 (td, J=20.2, 2.0 Hz), 124.17 (d, J=3.4 Hz), 115.10 (d, J=23.3 Hz). $^{31}$P NMR (162 MHz, CDCl$_3$) δ 44.59 (t, J=45.7 Hz). $^{19}$F NMR (376 MHz, CDCl$_3$) δ −105.77 (ddt, J=45.6, 11.6, 6.2 Hz).

Steps 2 and 3. Preparation of bis(2-fluorophenyl)chlorophosphine and bis(2-fluorophenyl)iodophosphine

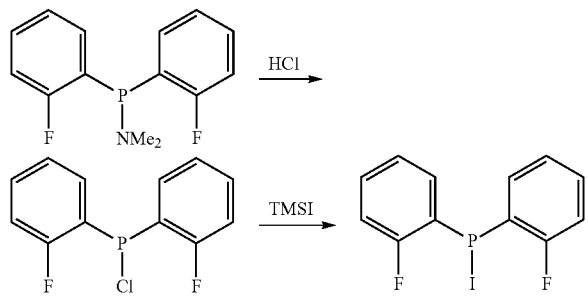

290

Iodotrimethylsilane (TMSI) (7.11 g, 34.5 mmol) was added to a solution of bis(2-fluorophenyl)dimethylaminophosphine (8.100 g, 30.54 mmol) in hexane (40 mL). $^{31}$P and $^{19}$F NMR spectra taken immediately after mixing showed slight (a few ppm) chemical shifts from the starting material. The reaction mixture was stirred over several days. An aliquot was removed and devolatilized: The NMR spectra showed that no reaction had taken place. HCl solution (35 mL, 2.0 M, 70 mmol) was added with formation of copious precipitate. NMR spectra showed that the starting material was all consumed. The reaction mixture was filtered. NMR spectra showed only bis(2-fluorophenyl)chlorophosphine, but not any bis(2-fluorophenyl)iodophosphine. The volatiles were removed under reduced pressure, the residue was dissolved in ether and iodotrimethylsilane (7.00 g, 34.98 mmol) was added. After stirring for several hours, the volatiles were removed under reduced pressure. The residue was extracted with hexane, filtered, and the volatiles were removed under reduced pressure to give bis(2-fluorophenyl)iodophosphine as a yellow-orange oil. Yield was 10.17 g, 95.65%. NMR spectra for bis(2-fluorophenyl)chlorophosphine: $^{1}$H NMR (400 MHz, CDCl$_3$) δ 7.57 (tdd, J=7.5, 5.6, 1.7 Hz, 1H), 7.44 (ddddd, J=8.0, 7.2, 5.3, 1.8, 0.6 Hz, 1H), 7.22 (tt, J=7.6, 0.9 Hz, 1H), 7.06 (dddd, J=9.5, 8.3, 4.4, 1.1 Hz, 1H). $^{13}$C NMR (101 MHz, CDCl$_3$) δ 163.57 (dd, J=247.9, 19.0 Hz), 132.96 (d, J=8.9 Hz), 132.83 (tdd, J=10.2, 3.2, 1.3 Hz), 124.69 (dt, J=3.3, 1.5 Hz), 124.50-123.86 (m), 115.51 (d, J=23.0 Hz). $^{31}$P NMR (162 MHz, CDCl$_3$) δ 61.33 (t, J=64.9 Hz). $^{19}$F NMR (376 MHz, CDCl$_3$) δ −105.22 (dm, J=65.5 Hz). NMR spectra for bis(2-fluorophenyl)iodophosphine: $^{1}$H NMR (400 MHz, CDCl$_3$) δ 7.59 (tdd, J=7.4, 5.0, 1.7 Hz, 1H), 7.44 (ddddd, J=8.1, 7.3, 5.4, 1.8, 0.8 Hz, 1H), 7.19 (tt, J=7.5, 1.0 Hz, 1H), 7.06 (dddd, J=9.5, 8.2, 4.4, 1.1 Hz, 1H). $^{13}$C NMR (101 MHz, CDCl$_3$) δ 163.31 (dd, J=248.2, 18.8 Hz), 136.30 (dd, J=8.8, 3.1 Hz), 133.08 (d, J=8.6 Hz), 124.87-124.72 (m), 120.54 (ddd, J=45.4, 17.1, 1.9 Hz), 115.46 (d, J=22.8 Hz). $^{31}$P NMR (162 MHz, CDCl$_3$) δ 11.95 (t, J=63.7 Hz). $^{19}$F NMR (376 MHz, CDCl$_3$) δ −101.52 (ddt, J=63.5, 9.5, 6.2 Hz).

Step 4. Preparation of (2S,5S)—N-(bis(2-fluorophenyl)phosphanyl)-N-butyl-2,5-diphenylpholan-1-amine, Ligand 604

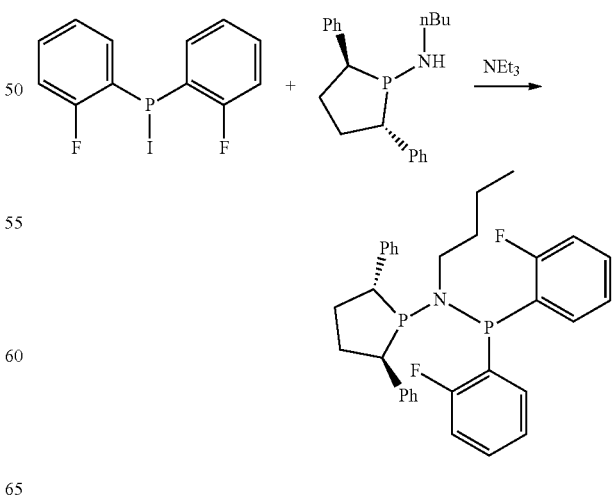

A solution of bis(2-fluorophenyl)iodophosphine (0.229, 0.660 mmol) in CDCl$_3$ (2 mL) was added slowly to a solution of N-butyl-2,5-diphenylphospholan-1-amine (0.205 g, 0.66 mmol) and triethylamine (0.500 g, 4.94 mmol) in CDCl$_3$ (5 mL). The solvents were removed under reduced pressure to give a solid. The residue was extracted with hexane and ether and filtered and the volatiles were removed under reduced pressure. The solids were washed with hexane and dried under reduced pressure to give the product as a colorless solid. $^1$H NMR (400 MHz, C$_6$D$_6$) δ 7.43 (dt, J=8.0, 1.5 Hz, 2H), 7.36 (dt, J=7.1, 1.6 Hz, 2H), 7.24 (t, J=7.8 Hz, 2H), 7.09 (tq, J=7.3, 1.3 Hz, 1H), 7.04 (ddd, J=5.9, 4.1, 1.7 Hz, 1H), 6.99 (dd, J=8.3, 6.9 Hz, 2H), 6.91-6.79 (m, 3H), 6.73 (dddd, J=9.6, 8.2, 4.2, 1.2 Hz, 1H), 6.70-6.63 (m, 3H), 6.60 (td, J=7.4, 1.2 Hz, 1H), 4.40 (ddt, J=12.3, 8.4, 4.6 Hz, 1H), 3.36-3.16 (m, 1H), 3.16-2.94 (m, 3H), 2.66-2.48 (m, 1H), 2.10 (tt, J=10.5, 5.2 Hz, 1H), 1.59 (qd, J=12.6, 5.0 Hz, 1H), 1.08-0.94 (m, 1H), 0.70-0.45 (m, 3H), 0.36 (t, J=7.2 Hz, 3H). $^{13}$C NMR (101 MHz, C$_6$D$_6$) δ 164.56 (dd, J=245.2, 18.7 Hz), 162.79 (dd, J=244.5, 16.6 Hz), 144.84 (d, J=21.1 Hz), 139.02 (d, J=1.9 Hz), 133.54 (dd, J=7.4, 5.1 Hz), 133.38 (t, J=4.8 Hz), 131.62 (d, J=8.5 Hz), 130.01 (d, J=8.1 Hz), 128.83 (dd, J=3.9, 1.9 Hz), 128.73, 128.63, 128.35 (d, J=1.1 Hz), 126.60 (ddd, J=27.1, 18.7, 1.6 Hz), 125.96 (ddd, J=23.1, 18.6, 2.4 Hz), 125.95 (dd, J=15.9, 2.3 Hz), 124.39 (d, J=3.1 Hz), 124.26 (d, J=3.3 Hz), 115.51 (d, J=23.9 Hz), 114.79 (d, J=23.1 Hz), 55.31 (td, J=9.1, 3.1 Hz), 55.00 (d, J=3.5 Hz), 52.62 (dd, J=22.4, 4.4 Hz), 37.04, 34.14 (d, J=7.3 Hz), 32.81 (dd, J=8.6, 3.5 Hz), 19.91, 13.64. $^{31}$P NMR (162 MHz, C$_6$D$_6$) δ 103.28 (d, J=28.9 Hz), 32.93 (ddd, J=54.9, 42.6, 28.7 Hz). $^{19}$F NMR (376 MHz, C$_6$D$_6$) δ −103.52 (dm, J=41.8 Hz), —104.72 (dm, J=54.7 Hz). HRMS: Expected (M+1): 532.2128. Found (M+1): 532.2137.

Preparation of (rac)-N-(diphenylphosphanyl)-N-ethyl-2,5-diphenylphospholan-1-amine, L606

Step 1. Preparation of (rac)-N-ethyl-2,5-diphenylphospholan-1-amine

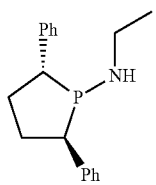 [SMILES: CCNP1[C@@H](c2ccccc2)CC[C@@H]1c1ccccc1]

A solution of (rac)-1-chloro-2,5-diphenylphospholane (0.40 g, 1.5 mmol) in hexanes (5.0 mL) was added to a solution of ethylamine (2 M) in THF (3.6 mL, 7.3 mmol), resulting in immediate precipitation of a white solid. After stirring overnight, the volatiles were removed under vacuum. The residue was slurried with hexanes and filtered. The volatiles were removed under vacuum to yield the product as a yellow oil. Yield (0.40, 96%). $^1$H NMR (400 MHz, C$_6$D$_6$) δ 7.32-7.24 (m, 2H), 7.23-6.97 (m, 8H), 2.99 (ddd, J=21.7, 12.6, 6.0 Hz, 1H), 2.91-2.78 (m, 1H), 2.48-2.29 (m, 1H), 2.28-1.92 (m, 3H), 1.87-1.65 (m, 1H), 1.63-1.40 (m, 1H), 0.90 (q, J=7.0 Hz, 1H), 0.46 (t, J=7.1 Hz, 3H). $^{13}$C NMR (101 MHz, C$_6$D$_6$) δ 144.08, 143.89, 139.83, 128.34, 128.06 (d, J=1.4 Hz), 127.75 (d, J=11.7 Hz), 125.60 (d, J=2.6 Hz), 125.22 (d, J=1.9 Hz), 55.43 (d, J=14.1 Hz), 50.08 (d, J=23.2 Hz), 42.11 (d, J=23.7 Hz), 33.97 (d, J=2.6 Hz), 31.33 (d, J=2.1 Hz), 18.10 (d, J=7.2 Hz). $^{31}$P NMR (162 MHz, C$_6$D$_6$) δ 72.81.

Step 2. Preparation of (rac)-N-(diphenylphosphanyl)-N-ethyl-2,5-diphenylphospholan-1-amine, L606

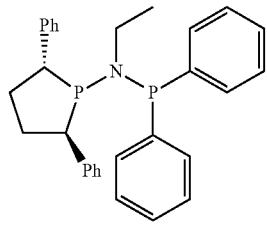 [SMILES: CCN(P(c1ccccc1)c1ccccc1)P1[C@@H](c2ccccc2)CC[C@@H]1c1ccccc1]

(rac)-N-Ethyl-2,5-diphenylphospholan-1-amine (0.15 g, 0.53 mmol) and triethylamine (81 uL, 0.58 mmol) were dissolved in toluene (5.0 mL). Iododiphenylphosphine (0.17 g, 0.53 mmol) was also dissolved in toluene (5 mL). The two solutions were cooled in the freezer to −30° C. The iododiphenylphosphine solution was added dropwise to the solution of (rac)-N-ethyl-2,5-diphenylphospholan-1-amine and triethylamine causing immediate formation of precipitate. After stirring at ambient temperature for 30 minutes, the volatiles were removed under vacuum. The residue was extracted with ether and the mixture was filtered through a plug of activated neutral alumina. The solvent was removed under vacuum to yield the final product. Yield (0.19 g, 77%). $^1$H NMR (400 MHz, C$_6$D$_6$) δ 7.43-7.28 (m, 4H), 7.28-7.13 (m, 4H), 7.13-6.86 (m, 10H), 6.85-6.70 (m, 2H), 4.01 (ddt, J=12.1, 7.5, 4.5 Hz, 1H), 3.49-3.19 (m, 1H), 3.10-2.79 (m, 3H), 2.53-2.24 (m, 1H), 2.13 (tt, J=10.7, 5.3 Hz, 1H), 1.73-1.39 (m, 1H), 0.45-0.27 (m, 3H). $^{13}$C NMR (101 MHz, C$_6$D$_6$) δ 144.28 (d, J=21.0 Hz), 140.54 (d, J=22.2 Hz), 139.18 (d, J=2.5 Hz), 138.61 (d, J=16.4 Hz), 132.91 (d, J=20.0 Hz), 132.10 (d, J=20.3 Hz), 128.77 (dd, J=3.6, 1.8 Hz), 128.38, 128.34, 128.21, 128.12 (d, J=5.6 Hz), 128.03, 127.59, 125.73 (d, J=2.6 Hz), 125.35 (d, J=1.9 Hz), 55.15 (dd, J=21.9, 18.4 Hz), 51.53 (dd, J=22.8, 3.4 Hz), 48.71 (dd, J=32.0, 4.2 Hz), 36.44 (d, J=2.7 Hz), 32.83 (dd, J=7.5, 3.3 Hz), 16.64 (d, J=7.3 Hz). $^{31}$P NMR (162 MHz, C$_6$D$_6$) δ 97.75 (d, J=19.7 Hz), 58.57 (d, J=19.9 Hz). HRMS (ESI-TOF) m/z: [M+H]+ Calcd for C$_{30}$H$_{31}$NP$_2$ 468.2005; Found 468.1999.

Preparation of (rac)-N-butyl-N-(bis([1,1':3',1''-terphenyl]-5'-yl)phosphanyl)-2,5-diphenylphospholan-1-amine, L607

Step 1. Preparation of bis(3,5-diphenylphenyl)iodophosphine

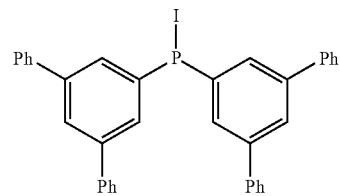 [SMILES: IP(c1cc(-c2ccccc2)cc(-c2ccccc2)c1)c1cc(-c2ccccc2)cc(-c2ccccc2)c1]

Iodotrimethylsilane (0.16 mL, 1.1 mmol) was added to a solution of bis(3,5-diphenylphenyl)chlorophosphine (0.50 g, 0.95 mmol) in toluene (2.0 mL). After 2 h stirring at ambient temperature, the orange solution was filtered and the volatiles were removed to yield a yellow solid. The product was washed with pentane, filtered, and dried under reduced pressure. The crude product was used as-is in the next step. Yield (0.45 g, 59%). $^1$H NMR (400 MHz, Benzene-$d_6$) δ 8.13 (dd, J=7.7, 1.7 Hz, 3H), 7.68-7.55 (m, 3H), 7.40-7.28 (m, 7H), 7.25-6.89 (m, 13H). $^{31}$P NMR (162 MHz, $C_6D_6$) δ 39.07.

Step 2. Preparation of (rac)-N-butyl-N-(bis([1,1':3',1''-terphenyl]-5'-yl)phosphanyl)-2,5-diphenylphospholan-1-amine, L607

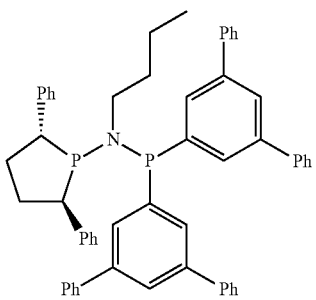 [SMILES: CCCCN(P(c1cc(-c2ccccc2)cc(-c2ccccc2)c1)c1cc(-c2ccccc2)cc(-c2ccccc2)c1)P1[C@@H](c2ccccc2)CC[C@@H]1c1ccccc1]

(rac)-N-Butyl-2,5-diphenylphospholan-1-amine (0.15 g, 0.48 mmol) and triethylamine (0.74 uL, 0.53 mmol) were dissolved in toluene (5.0 mL). Bis(3,5-diphenylphenyl)iodophosphine (0.30 g, 0.48 mmol) was also dissolved in toluene (5.0 mL). The two solutions were cooled in the freezer to −30° C. The bis(3,5-diphenylphenyl)iodophosphine solution was added dropwise to the solution of (rac)-N-butyl-2,5-diphenylphospholan-1-amine (0.15 g, 0.48 mmol) and triethylamine causing immediate formation of precipitate. The volatiles were removed under vacuum and the residue was extracted with ether. The mixture was filtered through a plug of neutral activated alumina. The ether was removed under vacuum to yield a white solid. The solid was triturated with pentane and dried to yield the pure product as a white solid. Yield (0.2 g, 52%). $^1$H NMR (400 MHz, $C_6D_6$) δ 7.91 (dd, J=6.5, 1.7 Hz, 2H), 7.81-7.71 (m, 1H), 7.70-7.59 (m, 1H), 7.48 (dd, J=7.2, 1.8 Hz, 4H), 7.46-7.34 (m, 8H), 7.32-7.24 (m, 2H), 7.21-6.89 (m, 17H), 6.63 (t, J=7.4 Hz, 1H), 4.31 (ddt, J=12.3, 7.4, 4.7 Hz, 1H), 3.49-3.07 (m, 4H), 2.57-2.29 (m, 1H), 2.31-2.05 (m, 1H), 1.74-1.35 (m, 1H), 1.22-0.97 (m, 1H), 0.67-0.43 (m, 2H), 0.35 (t, J=7.2 Hz, 3H). $^{13}$C NMR (101 MHz, $C_6D_6$) δ 144.46 (d, J=21.3 Hz), 142.51 (d, J=5.3 Hz), 142.10 (d, J=6.1 Hz), 141.33 (d, J=20.0 Hz), 140.22 (d, J=19.0 Hz), 139.07 (d, J=2.2 Hz), 131.41 (d, J=21.0 Hz), 130.01 (d, J=20.2 Hz), 129.09 (d, J=15.6 Hz), 128.85, 128.78, 128.53, 127.71 (d, J=8.0 Hz), 127.63, 127.21 (d, J=25.6 Hz), 126.15 (dd, J=5.5, 2.1 Hz), 56.05 (dd, J=21.8, 19.9 Hz), 55.37 (d, J=6.7 Hz), 55.04 (d, J=6.8 Hz), 52.66 (dd, J=22.6, 3.2 Hz), 37.19, 34.51 (d, J=7.6 Hz), 33.57 (d, J=5.7 Hz), 19.99, 13.90. $^{31}$P NMR (162 MHz, $C_6D_6$) δ 98.25 (d, J=24.2 Hz), 59.04 (d, J=24.6 Hz). HRMS (ESI-TOF) m/z: [M+H]+ Calcd for $C_{56}H_{51}NP_2$ 800.3570; Found 800.3557.

Preparation of rac-N-cyclopropyl-N-(diphenylphosphanyl)-2,5-diphenylphospholan-1-amine, L608

Step 1. Preparation of rac-N-cyclopropyl-2,5-diphenylphospholan-1-amine

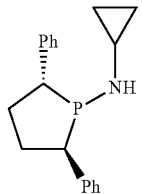 [SMILES: c1ccc([C@H]2CC[C@H](c3ccccc3)P2NC2CC2)cc1]

A solution of cyclopropylamine (0.43 mL, 6.6 mmol) in hexanes (5.00 mL) was added to a solution of rac-1-chloro-2,5-diphenyl-phospholane (0.60 g, 2.2 mmol) in hexane (5.00 mL). The mixture was stirred at room temperature overnight. The solids were removed by filtration using a disposable filter funnel and the solution was passed through a 5-cm plug of activated neutral alumina. Solvent was evaporated under vacuum to produce a white solid. Yield 0.27 g (41.5%). $^1$H NMR (400 MHz, $C_6D_5CD_3$) δ 7.24 (dt, J=8.0, 1.6 Hz, 2H), 7.17 (td, J=7.3, 1.7 Hz, 4H), 7.13-7.08 (m, 2H), 7.08-7.00 (m, 2H), 2.96 (ddd, J=22.2, 12.6, 5.9 Hz, 1H), 2.78 (ddd, J=12.4, 7.3, 5.7 Hz, 1H), 2.13 (ddddd, J=14.4, 12.6, 7.2, 5.1, 1.5 Hz, 1H), 2.07-1.97 (m, 1H), 1.75 (qdd, J=12.5, 5.1, 2.4 Hz, 1H), 1.62-1.44 (m, 3H), 0.11-0.00 (m, 3H), —0.06 (tdt, J=6.3, 3.5, 2.4 Hz, 1H). $^{13}$C NMR (101 MHz, $C_6D_5CD_3$) δ 143.88 (d, J=19.1 Hz), 139.70, 128.28 (d, J=1.1 Hz), 128.03 (d, J=1.2 Hz), 127.83 (d, J=3.4 Hz), 127.55, 127.46, 125.55 (d, J=2.5 Hz), 125.28 (d, J=1.9 Hz), 55.11 (d, J=14.2 Hz), 50.16 (d, J=24.0 Hz), 34.12 (d, J=1.9 Hz), 31.18 (d, J=2.3 Hz), 27.50 (d, J=22.3 Hz), 9.22 (d, J=11.6 Hz), 8.05 (d, J=8.0 Hz). $^{31}$P NMR (162 MHz, $C_6D_5CD_3$) δ 67.73.

Step 2. Preparation of rac-N-cyclopropyl-N-(diphenylphosphanyl)-2,5-diphenylphospholan-1-amine, L608

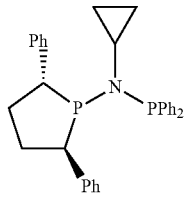

A cold solution (−30° C.) of triethylamine (0.034 g, 0.34 mmol) in toluene-$d_8$ (0.69 mL) was added to a cold (−30° C.) solution of rac-N-cyclopropyl-2,5-diphenylphospholan-1-amine (2) (0.10 g, 0.34 mmol) in toluene-$d_8$ (1.00 mL) and the resulting reaction mixture was stirred for 10 min. The reaction mixture was placed in a freezer at −30° C. for 30 minutes. To this cooled reaction mixture was added a cold (−30° C.) solution of iododiphenylphosphine (0.11 g, 0.34 mmol) in 1.06 mL of toluene-$d_8$ with formation of a white precipitate. The reaction mixture was stirred for 30 min at ambient temperature. Solvent was removed under vacuum. The crude product was redissolved in a diethyl ether and toluene (50/50 v/v) solvent mixture (5 mL) and filtered through a 5-cm plug of activated neutral alumina and the solvent was evaporated under vacuum giving solid product which was recrystallized from cold pentane at −30° C. to produce pure product. Yield 0.059 g (36.3%). $^1$H NMR (400 MHz, C$_6$D$_6$) δ 7.39-7.28 (m, 4H), 7.23 (dt, J=8.1, 1.5 Hz, 2H), 7.17 (dd, J=8.5, 6.8 Hz, 2H), 7.12-6.91 (m, 12H), 4.13 (dddd, J=11.5, 7.7, 6.0, 3.3 Hz, 1H), 3.38-3.10 (m, 1H), 3.07-2.86 (m, 1H), 2.36 (ddddd, J=14.1, 12.8, 7.7, 5.0, 1.2 Hz, 1H), 2.23-1.93 (m, 2H), 1.66-1.39 (m, 1H), 0.68-0.44 (m, 1H), 0.13--0.09 (m, 1H), —0.13--0.42 (m, 2H). $^{13}$C NMR (101 MHz, C$_6$D$_6$) δ 144.56 (d, J=22.6 Hz), 140.01 (d, J=21.1 Hz), 139.48 (d, J=1.8 Hz), 137.10 (dd, J=17.5, 1.5 Hz), 135.04 (d, J=22.5 Hz), 131.25 (d, J=18.3 Hz), 128.72, 128.63, 128.53, 128.49 (d, J=1.4 Hz), 128.33, 128.17, 127.95, 127.72, 127.32, 125.77 (d, J=2.5 Hz), 125.33 (d, J=1.8 Hz), 53.70 (t, J=22.2 Hz), 52.18 (dd, J=25.6, 2.5 Hz), 37.28 (d, J=2.3 Hz), 35.18 (dd, J=27.8, 6.3 Hz), 33.04 (dd, J=7.5, 2.9 Hz), 9.21 (d, J=12.6 Hz), 8.42 (d, J=21.1 Hz). $^{31}$P NMR (162 MHz, C$_6$D$_6$) δ 95.14 (d, J=16.2 Hz), 61.52 (d, J=16.2 Hz).

Preparation of rac-N-cyclobutyl-N-(diphenylphosphanyl)-2,5-diphenylphospholan-1-amine, L613

Step 1. Preparation of rac-N-cyclobutyl-2,5-diphenylphospholan-1-amine

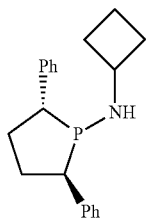

A solution of cyclobutylamine (0.54 mL, 6.6 mmol) in hexanes (5.00 mL) was added to a solution of rac-1-chloro-2,5-diphenyl-phospholane (0.60 g, 2.2 mmol) in hexanes (5.00 mL). The reaction mixture was stirred at room temperature overnight. The reaction mixture was filtered through a disposable filter funnel and then through a 5-cm plug of activated neutral alumina. Solvent was evaporated under vacuum to give a white solid. Yield 0.40 g (58.8%). $^1$H NMR (400 MHz, C$_6$D$_6$) δ 7.25 (dt, J=8.0, 1.7 Hz, 2H), 7.15 (qd, J=7.5, 1.6 Hz, 4H), 7.09-6.94 (m, 4H), 3.09-2.89 (m, 2H), 2.89-2.78 (m, 1H), 2.12 (dddd, J=20.3, 11.0, 7.1, 5.3 Hz, 1H), 2.06-1.93 (m, 1H), 1.77 (dddd, J=19.7, 9.3, 4.8, 2.1 Hz, 2H), 1.61-1.43 (m, 1H), 1.42-1.24 (m, 3H), 1.14 (qd, J=9.6, 9.0, 4.9 Hz, 1H), 1.08-0.78 (m, 2H). $^{13}$C NMR (101 MHz, C$_6$D$_6$) δ 143.96 (d, J=18.7 Hz), 139.79, 127.92, 127.65, 127.62, 127.54, 127.41, 125.60 (d, J=2.4 Hz), 125.24 (d, J=1.9 Hz), 55.71 (d, J=14.1 Hz), 53.95 (d, J=22.7 Hz), 50.00 (d, J=22.9 Hz), 34.30 (d, J=3.4 Hz), 34.20 (d, J=7.9 Hz), 33.89 (d, J=2.4 Hz), 31.32 (d, J=2.3 Hz), 13.49. $^{31}$P NMR (162 MHz, C$_6$D$_6$) δ 69.19.

Step 2. Preparation of rac-N-cyclobutyl-N-(diphenylphosphanyl)-2,5-diphenylphospholan-1-amine, L613

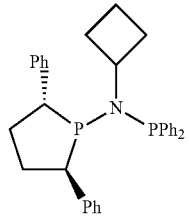

A cold solution (−30° C.) of triethylamine (0.049 g, 0.48 mmol) in toluene-d$_8$ (0.98 mL) was added to a cold (−30° C.) solution of rac-N-cyclobutyl-2,5-diphenylphospholan-1-amine (3) (0.15 g, 0.48 mmol) in toluene-d$_8$ (1.50 mL). The resulting mixture was stirred for 10 min, then was placed in a freezer at −30° C. for 30 minutes. To this cooled mixture was added a cold (−30° C.) solution of iododiphenylphosphine (0.15 g, 0.48 mmol) in toluene-d$_8$ (1.51 mL) with formation of a white precipitate. The reaction mixture was stirred for 30 min at ambient temperature. Solvent was removed under vacuum. The crude product was extracted with a diethyl ether and toluene (50/50 v/v) solvent mixture (5 mL) and filtered through a 5-cm plug of activated neutral alumina. The solvent was evaporated under vacuum giving solid material which was recrystallized from cold pentane at −30° C. to produce pure product. Yield 0.19 g (79.4%). $^1$H NMR (400 MHz, C$_6$D$_6$) δ 7.41 (td, J=7.0, 3.4 Hz, 2H), 7.30 (d, J=7.6 Hz, 2H), 7.14 (dq, J=19.9, 5.9, 4.8 Hz, 4H), 7.09-6.87 (m, 10H), 6.63 (q, J=6.2 Hz, 2H), 4.05 (tt, J=8.0, 4.0 Hz, 1H), 3.62 (dq, J=16.2, 8.7, 8.1 Hz, 1H), 3.36 (ddd, J=25.9, 13.1, 4.9 Hz, 1H), 3.00 (d, J=13.2 Hz, 1H), 2.37 (dt, J=23.9, 13.9 Hz, 2H), 2.11 (dtd, J=17.9, 10.1, 4.6 Hz, 2H), 1.73-1.43 (m, 3H), 1.32 (d, J=10.4 Hz, 1H), 1.01 (t, J=10.0 Hz, 1H). $^{13}$C NMR (101 MHz, C$_6$D$_6$) δ 143.78 (d, J=21.0 Hz), 140.85 (d, J=24.2 Hz), 139.11-138.57 (m), 132.32 (d, J=21.8 Hz), 131.81 (d, J=18.9 Hz), 128.66 (t, J=2.7 Hz), 128.42, 128.20, 128.12, 128.07, 128.01, 127.92, 127.47, 125.59 (d, J=2.6 Hz), 125.23 (d, J=1.9 Hz), 57.37 (d, J=25.4 Hz), 55.28-53.43 (m), 50.15 (d, J=21.8 Hz), 35.69 (d, J=3.5 Hz), 33.26 (d, J=13.4 Hz), 33.00-32.76 (m), 32.52 (d, J=12.5 Hz), 14.41. $^{31}$P NMR (162 MHz, C$_6$D$_6$, 60° C.) δ 77.62, 59.27. HRMS: Expected (M+1): 494.216; Found (M+1): 494.2169

Preparation of 2S,5S)—N-(bis(3,4,5-trifluorophenyl)phosphanyl)-N-butyl-2,5-diphenylphospholan-1-amine, L615

Step 1. Preparation of bis(3,4,5-trifluorophenyl)dimethylaminophosphine

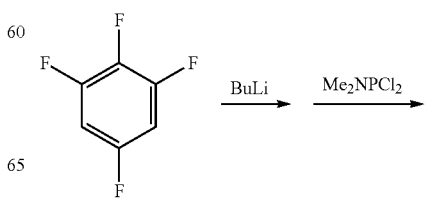

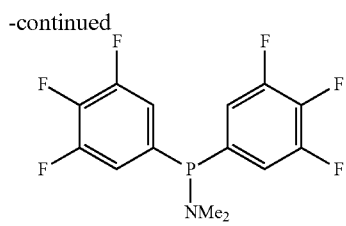

5-Bromo-1,2,3-trifluorobenzene (19.855 g, 94.110 mmol) was added slowly dropwise to a chilled (−85 to −80° C. (liquid nitrogen/acetone)) solution of n-butyllithium (9.10 mL, 2.38 M, 21.7 mmol combined with 45.5 mL, 1.57 M, 71.4 mmol; total: 93.1 mmol) in ether (200 mL) such that the temperature did not exceed −89° C. The temperature was allowed to increase to between −78 and −75° C. for 2.5 hours (dry ice bath) with formation of white precipitate. The reaction mixture was cooled to −85° C. A solution of dimethylphosphoramidous dichloride (6.791 g, 46.53 mmol) in ether (10 mL) was added very slowly dropwise such that the temperature did not exceed −80° C. Dry ice was added to the bath and the reaction mixture was allowed to stir overnight while warming to ambient temperature. $^{31}$P and $^{19}$F NMR spectra showed the product to be about 99.5% desired product. The reaction mixture was filtered and the volatiles were removed under reduced pressure. The residue was extracted with hexane, filtered, and the volatiles were removed under reduced pressure to give 5 as a pale yellow oil, 13.50 g, 86.04%. $^{1}$H NMR (500 MHz, CDCl$_3$) δ 6.95 (dt, J=7.5, 6.4 Hz, 4H), 2.64 (d, J=9.7 Hz, 6H). $^{13}$C NMR (101 MHz, CDCl$_3$) δ 151.35 (dddd, J=254.1, 10.0, 8.2, 3.0 Hz), 140.00 (dtd, J=254.5, 15.5, 2.2 Hz), 134.44 (dq, J=21.9, 3.7 Hz), 115.41 (ddd, J=21.7, 15.1, 5.5 Hz), 41.47 (d, J=16.3 Hz). $^{31}$P NMR (202 MHz, CDCl$_3$) δ 65.05. $^{19}$F NMR (376 MHz, CDCl$_3$) δ −133.39−−133.55 (m), −159.17 (ttd, J=20.3, 6.7, 3.4 Hz).

Step 2. Preparation of bis(3,4,5-trifluorophenyl)chlorophosphine

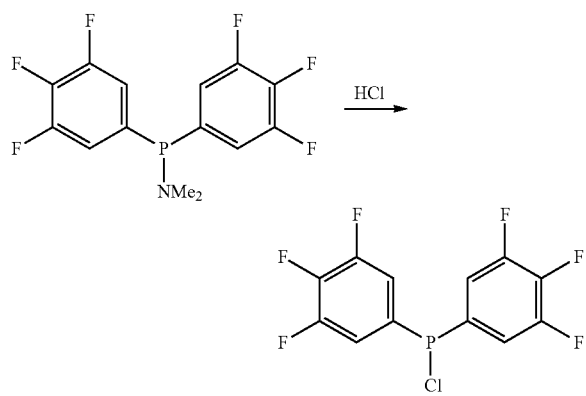

Anhydrous HCl in ether (55.0 mL, 2.0 M, 110 mmol) was added to a chilled (−35 to −30° C.) solution of bis(3,4,5-trifluorophenyl)dimethylaminophosphine (13.30 g, 39.44 mmol) in methylene chloride (125 mL) (in two portions—NMR spectra after the first portion showed the reaction was incomplete) with formation of some precipitate. The reaction mixture was stirred for two hours. NMR spectra after the second portion showed the reaction was complete. Hexane (100 mL) was added and the reaction mixture was filtered. The volatiles were removed under reduced pressure to give an oil containing precipitate. The residue was extracted with hexane and filtered. The volatiles were removed under reduced pressure to give clear yellow oil, 12.74 g, 98.3%. $^{1}$H NMR (400 MHz, CDCl$_3$) δ 7.19 (dtd, J=7.1, 6.3, 1.0 Hz, 1H). $^{13}$C NMR (101 MHz, CDCl$_3$) δ 151.45 (dtd, J=256.3, 10.1, 3.1 Hz), 141.38 (dtd, J=258.1, 15.2, 2.0 Hz), 133.93 (dq, J=37.9, 4.8 Hz), 115.64 (ddd, J=26.9, 15.6, 6.2 Hz). $^{31}$P NMR (162 MHz, CDCl$_3$) δ 74.93 (t, J=3.1 Hz). $^{19}$F NMR (376 MHz, CDCl$_3$) δ −131.41 (dd, J=20.2, 6.7 Hz), —155.11 (ttd, J=20.0, 6.5, 3.0 Hz).

Step 3. Preparation of bis(3,4,5-trifluorophenyl)iodophosphine

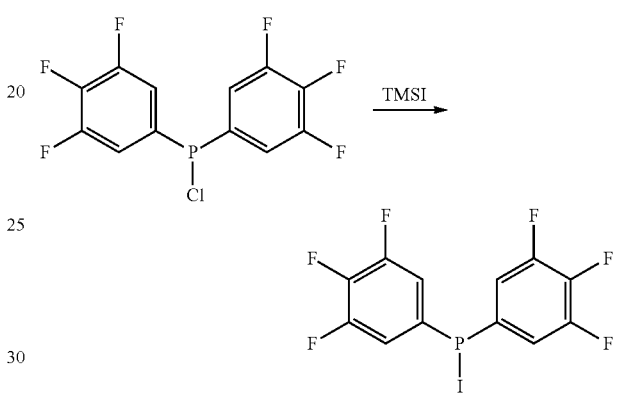

Iodotrimethylsilane (TMSI) (9.960 g, 49.78 mmol) is added quickly dropwise to a solution of bis(3,4,5-trifluorophenyl)chlorophosphine (12.50 g 38.04 mmol) in toluene to give a yellow solution. The reaction mixture was stirred overnight. The volatiles were removed under reduced pressure to give the product as yellow oil. Addition of hexane caused precipitation to occur, however the precipitate appeared to be less than about one or two grams in amount. The hexane mother liquor was very yellow, indicating the presence of much dissolved product. The volatiles were removed under reduced pressure to give the product as yellow oil which is a mixture of bis(3,4,5-trifluorophenyl)iodophosphine (94%) and diiodo(3,4,5-trifluorophenyl)phosphine (6%). The yield was 13.006 g, 81.39%. $^{1}$H NMR (400 MHz, CDCl$_3$) δ 7.28 (pseudo quartet, J=7.2 Hz, 4H). $^{13}$C NMR (101 MHz, CDCl$_3$) δ 151.10 (dddd, J=256.3, 10.3, 9.2, 3.3 Hz), 141.09 (dtd, J=258.4, 15.2, 2.3 Hz), 130.29 (dq, J=43.0, 4.8 Hz), 117.75 (ddd, J=25.5, 15.5, 6.1 Hz). $^{31}$P NMR (162 MHz, CDCl$_3$) δ 30.25 (t, J=3.1 Hz). $^{19}$F NMR (376 MHz, CDCl$_3$) δ −131.52 (dd, J=20.3, 6.8 Hz), —155.14 (ttd, J=20.0, 6.3, 2.9 Hz).

Step 4. Preparation of (2S,5S)—N-(bis(3,4,5-trifluorophenyl)phosphanyl)-N-butyl-2,5-diphenylphospholan-1-amine, L615

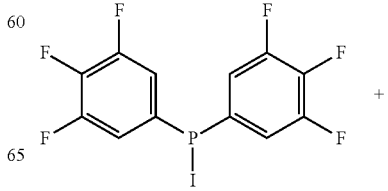

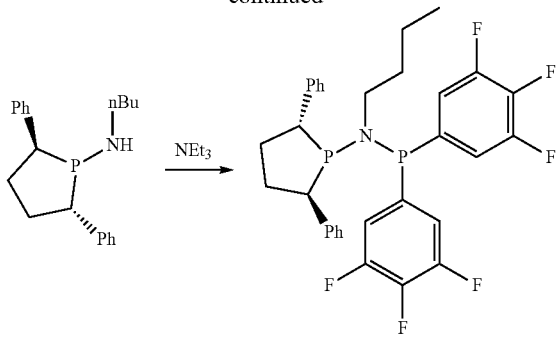

A solution of bis(3,4,5-trifluorophenyl)iodophosphine (0.302 g, 0.720 mmol) in ether (5 mL) was added slowly to a solution of N-butyl-2,5-diphenylphospholan-1-amine (0.224 g, 0.72 mmol) and triethylamine (0.728 g, 7.19 mmol) in ether (5 mL). Once about 80% of the bis(3,4,5-trifluorophenyl)iodophosphine had been added, NMR spectra were taken which showed excess phospholane was present. Additional bis(3,4,5-trifluorophenyl)iodophosphine was added. NMR spectra showed the reaction was still incomplete. The remaining bis(3,4,5-trifluorophenyl)iodophosphine was added and the mixture was allowed to stir overnight. The reaction mixture was filtered and the volatiles were removed under reduced pressure. The residue was recrystallized twice from hexane and dried under reduced pressure to give the product as a colorless powder, 0.1322 g, 30.5%. $^1$H NMR (400 MHz, CDCl$_3$) δ 7.68-7.48 (m, 10H), 7.17 (qd, J=6.3, 1.1 Hz, 2H), 6.57 (dt, J=7.5, 6.4 Hz, 2H), 4.00 (ddt, J=12.7, 7.6, 3.9 Hz, 1H), 3.87 (ddd, J=25.1, 13.2, 5.9 Hz, 1H), 3.34-3.18 (m, 1H), 3.18-3.05 (m, 1H), 2.94-2.81 (m, 1H), 2.74 (tt, J=11.0, 5.3 Hz, 1H), 2.10 (dtdd, J=13.2, 11.1, 5.2, 2.6 Hz, 1H), 1.66-1.55 (m, 1H), 1.30-1.09 (m, 3H), 1.02-0.92 (m, 1H), 0.90 (t, J=7.2 Hz, 3H). $^{13}$C NMR (126 MHz, CDCl$_3$) δ 151.15 (dddd, J=255.0, 10.5, 8.4, 2.9 Hz), 150.71 (dddd, J=253.6, 18.5, 8.8, 3.0 Hz), 142.64 (d, J=20.2 Hz), 140.97 (dtd, J=40.1, 15.4, 2.1 Hz), 138.94 (dtd, J=39.4, 15.4, 2.3 Hz), 138.17 (d, J=2.9 Hz), 135.56 (d, J=28.1 Hz), 133.97 (dq, J=21.5, 4.1 Hz), 128.65, 128.55-128.42 (m), 127.88 (d, J=9.0 Hz), 126.24 (d, J=2.4 Hz), 126.18 (d, J=1.9 Hz), 116.05, 115.93 (dddd, J=27.5, 21.5, 15.8, 4.9 Hz), 55.54 (dd, J=22.1, 14.1 Hz), 54.11 (d, J=24.0 Hz), 50.87 (dd, J=22.5, 4.2 Hz), 36.27 (d, J=3.7 Hz), 33.69 (dd, J=5.9, 2.5 Hz), 32.92 (dd, J=6.0, 3.2 Hz), 19.66, 13.50. $^{31}$P NMR (162 MHz, CDCl$_3$) δ 98.98 (d, J=15.9 Hz), 58.18 (d, J=15.7 Hz). $^{19}$F NMR (376 MHz, CDCl$_3$) δ −132.78 (m), −133.64 (m), −157.93 (m), −159.15 (m). HRMS: Expected (M+1): 604.1751. Found (M+1): 604.1754.

Preparation of rac-N-butyl-2,5-bis(3,5-dimethylphenyl)-N-(diphenylphosphanyl)phospholan-1-amine, L618

Step 1. Preparation of (3,5-dimethylphenyl)magnesium bromide

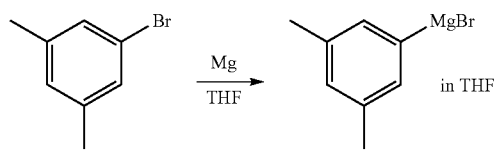

A two-necked flask, equipped with a stir bar and a Stevens (spiral tube-type) condenser, was charged with magnesium turnings (8.94 g, 368.0 mmol) and THF (20 mL). 1,2-Dibromoethane (2 drops) was added to the resulting mixture. The mixture was allowed to stir for 5 min to allow activate the magnesium turnings. In a separate container, 1-bromo-3,5-dimethylbenzene (50.0 mL, 368.0 mmol) was diluted with THF (100 mL) and sucked up in a syringe. A small amount (approximately 0.5 mL) of the 1-bromo-3,5-dimethylbenzene solution was added to the magnesium turnings and stirred until a color change was observed. With a fan circulating air over the Stevens condenser, the remaining 1-bromo-3,5-dimethylbenzene solution was slowly added over a few minutes and the reaction mixture was allowed to stir for a few minutes until the refluxing stopped. Additional THF (17.5 mL) was added to the solution. The reaction mixture was heated to 65° C. and allowed to stir overnight. A large amount of precipitate had formed. The remainder of the THF (229.5 mL) was added, and the reaction mixture was filtered through a plastic frit into an oven-dried jar. The resulting Grignard solution was titrated using salicylaldehyde phenylhydrazone following the procedure of Love et al. (Love, B. E.; Jones, E. G. *J. Org. Chem.* 1999, 64, 3755) which confirmed the concentration to be 1.0 M. The Grignard solution was used as-is in subsequent reactions.

Step 2. Preparation of (E,E)-1,4-bis(3,5-dimethylphenyl)-1,3-butadiene

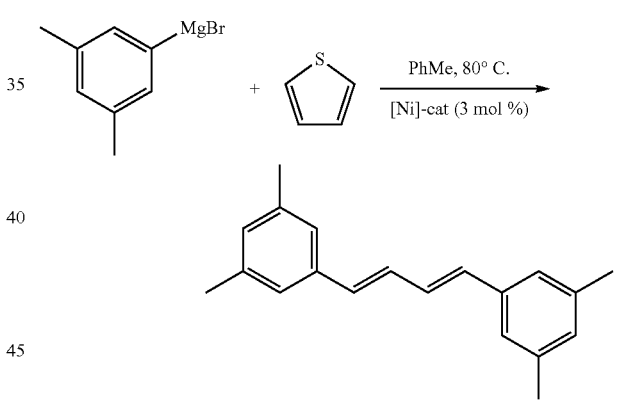

(E,E)-1,4-Bis(3,5-dimethylphenyl)-1,3-butadiene was prepared according to a procedure adapted from Hintermann et al. (Hintermann, L.; Schmitz, M.; Chen, Y. *Adv. Synth. Catal.* 2010, 352, 2411). Toluene (200 mL) was added to a small vial containing NiCl$_2$(tricyclohexylphosphine)$_2$ (3.80 g, 5.51 mmol, 3 mol %). The mixture was stirred and thiophene (14.7 mL, 183.6 mmol) and (3,5-dimethylphenyl)magnesium bromide (367.2 mL, 1.0 M, 367.2 mmol) were added sequentially. The reaction vial was heated to 86° C. while stirring was continued. The reaction was monitored by GC/MS. Upon completion the reaction mixture was cooled, diluted with 2-4 volumes of toluene, and quenched by careful addition of an equal volume of saturated aqueous NH$_4$Cl (caution: H$_2$S gas is generated). The organic phase was washed with equal volumes of HCl (2.4 M), NaOH (2 M), and water and was then dried over anhydrous MgSO$_4$. The solution was filtered and concentrated on a rotary evaporator. Purification of the material was achieved by chromatography on silica gel using a mixture of ethyl acetate/hexanes as an eluent. Volatiles were removed under vacuum, yielding a pale yellow powder (11.00 g, 23%). $^1$H NMR (400 MHz, CDCl$_3$) δ 7.07 (s, 4H), 6.93 (d, J=12.2 Hz, 2H), 6.89 (s, 2H), 6.60 (d, J=14.0 Hz, 2H), 2.33 (s, 12H). $^1$H NMR (400 MHz, C$_6$D$_6$) δ 7.07 (s, 2H), 7.01-6.90 (m, 1H), 6.76 (s, 1H), 6.66-6.55 (m, 1H), 2.18 (s, 6H). $^{13}$C NMR (101 MHz, C$_6$D$_6$) δ 138.07, 137.95, 133.33, 129.72, 129.62, 124.95, 21.38.

Step 3. Preparation of (1 S,2R,5S)-1-(dimethylamino)-2,5-bis(3,5-dimethylphenyl)-2,5-dihydrophosphole 1-oxide

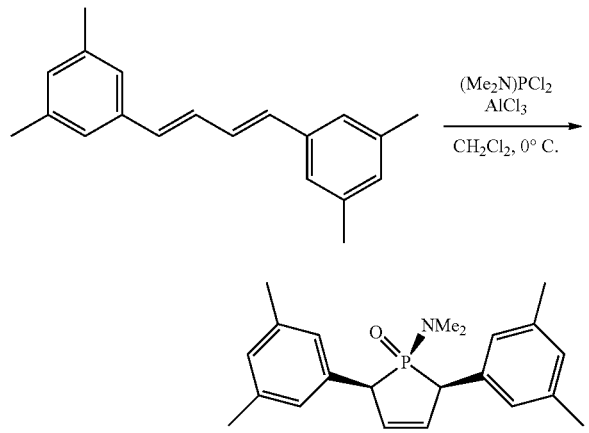

In a reaction not carried out in a glovebox, dimethylphosphoramidous dichloride (4.30 g, 37.4 mmol) was added to a stirred suspension of aluminum chloride (4.72 g, 35.4 mmol) in dichloromethane (50 mL) in a large jacketed multi-neck flask purged with nitrogen. After 45 min, the colorless solution that had formed and a solution of (E,E)-1,4-bis(3,5-dimethylphenyl)-1,3-butadiene (8.00 g, 34.1 mmol) in dichloromethane (125 mL) were each cooled to 0° C. After cooling, the 1,4-(3,5-dimethylphenyl)butadiene solution was slowly added to the mixture of dimethylphosphoramidous dichloride and aluminum chloride. The mixture was allowed to stir overnight at 0° C. A suspension of aqueous EDTA (ethylenediamine tetraacetic acid, 0.2 M, 200 mL) and saturated NaHCO$_3$(100 mL) cooled in ice water was then added to the reaction mixture. The mixture was stirred at 0° C. for 4 h, filtered through Celite, decanted, and the aqueous layer was extracted with dichloromethane. The organic layers were washed with NaHCO$_3$, 1.0 M HCl, brine, and dried over anhydrous MgSO$_4$. The volatiles were removed under vacuum to yield a yellow solid. The yellow solid was triturated with diethyl ether, the solid was collected by filtration, washed with additional diethyl ether, and dried. (Yield: 6.63 g, 50%). $^1$H NMR (400 MHz, CDCl$_3$) δ 6.94 (s, 4H), 6.86 (s, 2H), 6.49 (d, J=29.0 Hz, 1H), 4.22 (d, J=18.7 Hz, 1H), 2.29 (s, 12H), 1.93 (d, J=8.3 Hz, 6H). $^{13}$C NMR (101 MHz, CDCl$_3$) δ 138.02 (d, J=2.5 Hz), 135.79 (d, J=8.2 Hz), 130.84 (d, J=16.9 Hz), 128.39 (d, J=2.9 Hz), 125.06 (d, J=4.8 Hz), 77.36, 49.13 (d, J=71.7 Hz), 36.22 (d, J=1.8 Hz), 21.39. $^{31}$P NMR (162 MHz, CDCl$_3$) δ 69.13.

Step 4. Preparation of rac-1-(dimethylamino)-2,5-bis(3,5-dimethylphenyl)phospholane 1-oxide

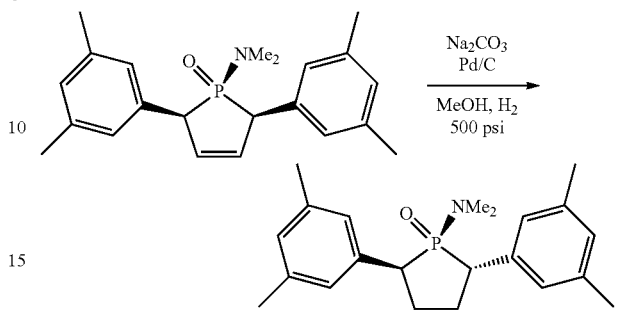

In a reaction not carried out in a glovebox, an 800-mL stainless steel pressure reactor was charged with (1S,2R,5S)-1-(dimethylamino)-2,5-bis(3,5-dimethylphenyl)-2,5-dihydrophosphole 1-oxide (6.10 g, 17.25 mmol), 10% Pd/C (918 mg, 0.086 mmol, 5 mol %), and methanol (200 mL). The reactor was purged with nitrogen and hydrogen, and then pressurized to 500 psi (3.45 MPa) of hydrogen and stirred for 8 hr at room temperature. Under an atmosphere of nitrogen, the solution was filtered through a plug of Celite (danger: methanol and Pd/C can spark a fire in the presence of oxygen; perform under inert atmosphere), and the volatiles were removed under vacuum. The solid was redissolved in CH$_2$Cl$_2$, filtered through Celite, and the volatiles were removed under vacuum. (Yield: 5.8 g, 94%; purity: 99.4%). On a plastic filter funnel, the solid was washed with acetone to remove trace impurities. The solid was dried under vacuum and then analyzed by NMR spectroscopy, confirming the removal of the impurities (Yield: 4.2 g, 68%). $^1$H NMR (400 MHz, C$_6$D$_6$) δ 7.13 (s, 2H), 6.97 (s, 2H), 6.76 (s, 1H), 6.72 (s, 1H), 3.53 (ddd, J=24.4, 13.0, 7.5 Hz, 1H), 2.99-2.84 (m, 1H), 2.20 (s, 6H), 2.15 (s, 6H), 2.15 (s, 3H), 2.12 (s, 3H), 2.09-1.99 (m, 2H), 1.95 (ddt, J=14.0, 7.5, 3.1 Hz, 1H), 1.76-1.53 (m, 1H). $^{13}$C NMR (101 MHz, C$_6$D$_6$) δ 137.90 (d, J=4.6 Hz), 137.73 (d, J=2.2 Hz), 137.70 (d, J=1.7 Hz), 137.55 (d, J=5.0 Hz), 128.60 (d, J=2.1 Hz), 128.18 (d, J=2.5 Hz), 127.53, 127.48, 125.37 (d, J=5.0 Hz), 47.72 (d, J=74.1 Hz), 42.75 (d, J=77.6 Hz), 35.92 (d, J=2.2 Hz), 30.57 (d, J=11.9 Hz), 27.50 (d, J=9.1 Hz), 21.51, 21.40. $^{31}$P NMR (162 MHz, C$_6$D$_6$) δ 56.62.

Step 5. Preparation of rac-1-chloro-2,5-bis(3,5-dimethylphenyl)phospholane

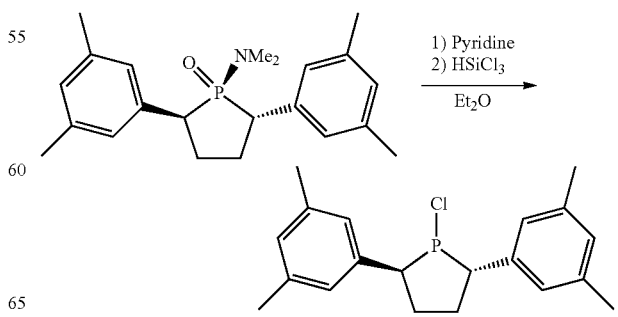

Rac-1-(Dimethylamino)-2,5-bis(3,5-dimethylphenyl)phospholane-1-oxide (2.36 g, 6.64 mmol) was mixed in ether (total reaction volume of 30 mL). Pyridine (0.59 mL, 7.30 mmol) and trichlorosilane (0.38 mL, 7.30 mmol) were sequentially added and the mixture was stirred overnight (~18 h) at ambient temperature. The volatiles were removed and pentane (10 mL) was added to the resulting slurry, which was stirred for a few minutes and then filtered through a plug of activated acidic alumina. The filtrate was concentrated, placed in a freezer at −35° C. overnight to form a white precipitate. The solvent was decanted and the solid was redissolved in pentane and again placed in the freezer to precipitate a white solid after a few minutes. The solid was isolated by filtration, and dried under vacuum (Yield: 1.95 g, 83%). $^1$H NMR (400 MHz, $C_6D_6$) δ 7.00 (s, 2H), 6.80 (s, 2H), 6.75 (s, 1H), 6.72 (s, 1H), 3.84 (td, J=8.9, 2.3 Hz, 1H), 3.24 (ddd, J=33.3, 12.5, 5.7 Hz, 1H), 2.56 (qdd, J=12.2, 6.8, 3.4 Hz, 1H), 2.43 (dtdd, J=13.4, 8.3, 6.7, 1.6 Hz, 1H), 2.16 (d, J=6.9 Hz, 12H), 1.80-1.63 (m, 1H). $^{13}$C NMR (101 MHz, $C_6D_6$) δ 141.82, 141.62, 138.12, 137.44, 136.64, 128.30 (d, J=2.4 Hz), 126.14, 125.66, 57.84 (d, J=32.1 Hz), 53.52 (d, J=31.1 Hz), 34.50, 31.69, 21.03. $^{31}$P NMR (162 MHz, $CDCl_3$) δ 137.06.

Step 6. Preparation of rac-N-butyl-2,5-bis(3,5-dimethylphenyl)phospholan-1-amine

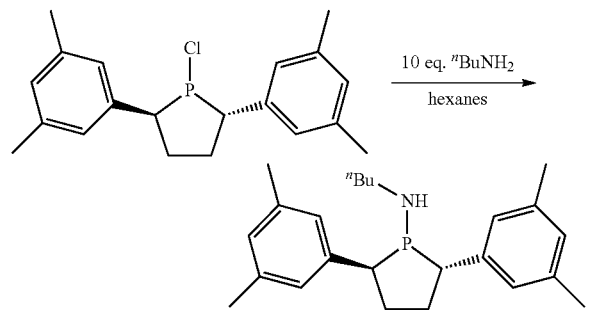

A 40-mL, oven-dried vial was charged with rac-1-chloro-2,5-bis(3,5-dimethylphenyl) phospholane (376 mg, 1.14 mmol) and pentane (20 mL). A separate vial was charged with n-butylamine (0.83 mL, 11.4 mmol) and pentane (10 mL). The reagents were cooled to −30° C., and the n-butylamine solution was slowly added (while stirring) to the solution of rac-1-chloro-2,5-bis(3,5-dimethylphenyl) phospholane, allowing it to reach room temperature. After stirring for 30 min, an aliquot was analyzed by NMR spectroscopy which confirmed complete conversion. The slurry which resulted was filtered through a plug of neutral alumina. The alumina was then rinsed with an additional 10 mL of pentane. The filtrate was dried under vacuum for 1 hr, then dissolved in a minimum amount of pentane, and placed in the freezer at −35° C. Overnight a white precipitate was formed, which was then isolated using a plastic filter funnel. Analysis by NMR spectroscopy revealed the presence of residual n-butylamine. The solid was recrystallized from pentane. The white powder was dried under vacuum and analyzed by NMR spectroscopy which confirmed complete removal of residual n-butylamine (Yield: 306 mg, 73%). $^1$H NMR (400 MHz, $C_6D_6$) δ 7.09 (s, 2H), 6.91 (s, 2H), 6.76 (s, 1H), 6.75 (s, 1H), 3.14 (ddd, J=21.6, 12.6, 6.0 Hz, 1H), 3.04-2.93 (m, 1H), 2.55 (ddq, J=12.6, 10.4, 6.9 Hz, 1H), 2.41-2.25 (m, 1H), 2.23 (s, 12H), 2.22-2.08 (m, 1H), 1.91 (qdd, J=12.5, 5.1, 2.6 Hz, 1H), 1.70 (qdd, J=12.6, 5.1, 2.5 Hz, 1H), 1.11 (m, 1H), 1.07-0.85 (m, 4H), 0.69 (t, J=6.9 Hz, 3H). $^{13}$C NMR (101 MHz, $C_6D_6$) δ 144.41 (d, J=17.8 Hz), 140.13, 137.87, 137.65-137.46 (m), 127.41 (d, J=1.8 Hz), 126.29 (d, J=3.2 Hz), 126.15, 126.07, 56.17 (d, J=14.3 Hz), 50.55 (d, J=22.3 Hz), 47.95 (d, J=23.1 Hz), 35.56 (d, J=6.9 Hz), 34.68, 31.93 (d, J=2.2 Hz), 21.55 (d, J=2.0 Hz), 20.11, 14.05. $^{31}$P NMR (162 MHz, $C_6D_6$) δ 72.65.

Step 7. Preparation of rac-N-butyl-2,5-bis(3,5-dimethylphenyl)-N-(diphenylphosphanyl)-phospholan-1-amine, L618

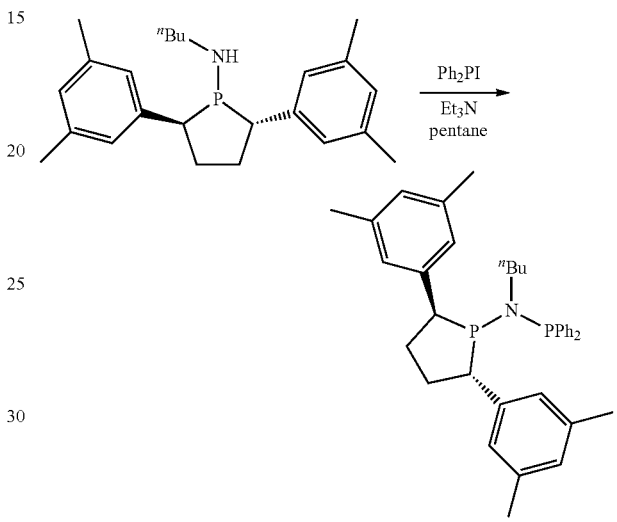

A cold (−35° C.) solution of iododiphenylphosphine (0.212 g, 0.680 mmol) in pentane (3 mL) was added dropwise to a cold (−35° C.) solution of rac-N-butyl-2,5-bis(3,5-dimethylphenyl)phospholan-1-amine (250 mg, 0.680 mmol) and triethylamine (0.072 g, 0.71 mmol) in pentane (3 mL) causing immediate precipitation of a white powder. An aliquot was analyzed by NMR spectroscopy, confirming complete conversion to the desired product. The pentane slurry was filtered through a small alumina plug, and the solvent was removed under vacuum. A minimum amount of pentane was added to the solid, and the material was placed in the freezer (−35° C.). Overnight a white solid precipitated. The solution was decanted, and the resulting solid was dried under vacuum (Yield: 260 mg, 69%). $^1$H NMR (400 MHz, $C_6D_6$) δ 7.48 (tt, J=6.5, 1.6 Hz, 2H), 7.23 (s, 2H), 7.19-7.10 (m, 4H), 7.01 (s, 3H), 7.00-6.93 (m, 3H), 6.87 (ddd, J=8.4, 6.8, 1.6 Hz, 2H), 6.78 (d, J=10.8 Hz, 2H), 4.08 (ddt, J=12.3, 7.3, 4.7 Hz, 1H), 3.46 (ddd, J=24.2, 13.3, 5.5 Hz, 1H), 3.29-3.13 (m, 1H), 3.11-2.88 (m, 1H), 2.57-2.39 (m, 1H), 2.31 (td, J=10.2, 4.9 Hz, 1H), 2.24 (s, 6H), 2.18 (s, 6H), 1.71 (qdt, J=12.9, 4.7, 2.1 Hz, 1H), 1.04-0.84 (m, 1H), 0.74-0.49 (m, 2H), 0.43 (t, J=7.0 Hz, 3H). $^{13}$C NMR (101 MHz, $C_6D_6$) δ 144.61 (d, J=20.6 Hz), 141.12 (d, J=22.9 Hz), 139.37 (d, J=2.5 Hz), 139.23, 139.07, 137.79 (d, J=2.9 Hz), 133.30 (d, J=19.8 Hz), 132.77 (d, J=20.2 Hz), 128.68, 128.49 (d, J=5.3 Hz), 128.37, 127.89, 127.55-127.44 (m), 127.29 (d, J=1.7 Hz), 127.26 (d, J=1.7 Hz), 126.86, 126.78, 56.45-55.86 (m), 54.81 (dd, J=34.0, 6.8 Hz), 52.74-51.81 (m), 36.79, 34.46 (d, J=6.6 Hz), 33.24 (d, J=3.4 Hz), 33.16 (d, J=3.3 Hz), 21.48, 20.04, 13.97. $^{31}$P NMR (162 MHz, $C_6D_6$) δ 100.18-98.20 (broad d, 1P), 56.83 (d, J=26.5 Hz, 1P).

Preparation of rac-N-cyclohexyl-N-(diphenylphosphanyl)-2,5-diphenylphospholan-1-amine, L619

Step 1. Preparation of rac-N-cyclohexyl-2,5-diphenylphospholan-1-amine

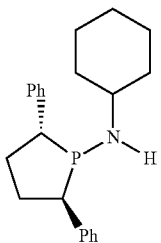

A solution of cyclohexylamine (0.38 mL, 3.3 mmol) in hexanes (5.00 mL) was added to a solution of rac-1-chloro-2,5-diphenyl-phospholane (0.30 g, 1.1 mmol) in hexanes (5.00 mL). The reaction mixture was stirred at room temperature overnight. The solid was removed by filtration and the resulting solution was passed through a 5-cm plug of activated neutral alumina. The solvent was evaporated under vacuum to give a white solid. Yield 0.35 g (94.6%). $^1$H NMR (400 MHz, $C_6D_5CD_3$) δ 7.30 (dt, J=8.0, 1.6 Hz, 2H), 7.19 (dt, J=17.0, 7.6 Hz, 4H), 7.11-7.02 (m, 4H), 3.03 (ddd, J=22.3, 12.4, 6.0 Hz, 1H), 2.83 (ddd, J=12.6, 7.1, 5.9 Hz, 1H), 2.28-2.12 (m, 1H), 2.04 (m, 1H), 1.80 (m, 1H), 1.72-1.51 (m, 3H), 1.51-1.21 (m, 3H), 1.03 (dd, J=10.8, 7.3 Hz, 2H), 0.98-0.73 (m, 4H), 0.58-0.36 (m, 1H). $^{13}$C NMR (101 MHz, $C_6D_5CD_3$) δ 144.00 (d, J=17.8 Hz), 140.05, 128.24, 127.99 (d, J=3.3 Hz), 127.94, 127.43, 125.47 (d, J=2.4 Hz), 125.13 (d, J=1.8 Hz), 56.81 (d, J=15.3 Hz), 56.15 (d, J=24.6 Hz), 49.78 (d, J=22.1 Hz), 36.80 (d, J=5.9 Hz), 36.08 (d, J=5.2 Hz), 33.59 (d, J=3.2 Hz), 31.39 (d, J=2.1 Hz), 25.67, 25.11 (d, J=13.9 Hz). $^{31}$P NMR (162 MHz, $C_6D_5CD_3$) δ 71.46.

Step 2. Preparation of rac-N-cyclohexyl-N-(diphenylphosphanyl)-2,5-diphenylphospholan-1-amine, L619

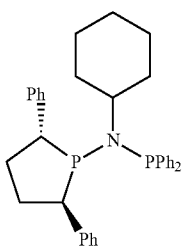

A cold solution (−30° C.) of triethylamine (0.058 g, 0.57 mmol) dissolved in $CH_2Cl_2$ (0.576 mL) was added to a cold (−30° C.) solution of rac-N-cyclohexyl-2,5-diphenylphospholan-1-amine (0.16 g, 0.47 mmol) dissolved in $CH_2Cl_2$ (1.60 mL). The resulting mixture was stirred for 10 min and placed in a freezer at −30° C. for 30 minutes. A cold (−30° C.) solution of bromodiphenylphosphine (0.13 g, 0.47 mmol) in 1.26 mL of $CH_2Cl_2$ was added to the cold mixture. The solution was stirred at ambient temperature overnight. Solvent was removed under vacuum. The crude product was redissolved in a diethyl ether and toluene (50/50 v/v) solvent mixture (5 mL) and filtered through a 5-cm plug of activated neutral alumina. The solvent was evaporated under vacuum giving solid product which was recrystallized from cold pentane at −30° C. to yield pure product. Yield 0.16 g (63.9%). $^1$H NMR (400 MHz, $C_6D_6$, 70° C.) δ 7.49 (d, J=7.0 Hz, 2H), 7.22 (d, J=7.6 Hz, 3H), 7.16-7.07 (m, 2H), 7.07-6.93 (m, 11H), 6.86 (h, J=6.3 Hz, 2H), 4.09 (s, 1H), 3.34 (ddd, J=25.7, 13.1, 5.7 Hz, 1H), 2.98 (s, 1H), 2.86 (qdd, J=11.3, 7.6, 3.4 Hz, 1H), 2.42 (td, J=15.4, 14.0, 6.4 Hz, 1H), 2.14 (tt, J=11.1, 5.5 Hz, 1H), 1.78 (q, J=12.0 Hz, 1H), 1.69-1.51 (m, 1H), 1.48-1.30 (m, 2H), 1.30-1.14 (m, 3H), 1.11-0.92 (m, 1H), 0.79 (tq, J=23.4, 12.4 Hz, 3H). $^{13}$C NMR (101 MHz, $C_6D_6$) δ 144.08 (d, J=20.7 Hz), 141.19 (d, J=24.0 Hz), 139.72, 139.23 (d, J=2.8 Hz), 133.10 (d, J=23.6 Hz), 132.51, 128.69 (d, J=3.1 Hz), 128.53, 128.23-127.96 (m), 127.85, 127.37, 127.32, 125.51 (d, J=2.5 Hz), 125.15 (d, J=1.8 Hz), 61.24 (d, J=14.7 Hz), 50.42 (d, J=23.3 Hz), 36.18 (d, J=3.9 Hz), 35.69 (d, J=10.2 Hz), 34.77, 33.02-32.64 (m), 26.19, 25.96, 25.24. $^{31}$P NMR (162 MHz, $C_6D_6$, 70° C.) δ 83.47, 58.30. HRMS: Expected (M+1): 522.2473; Found (M+1): 522.2483.

Preparation of (rac)-N-(bis(3,5-di-tert-butyl-4-methoxyphenyl)phosphanyl)-N-butyl-2,5-diphenylphospholan-1-amine, L620

Step 1. Preparation of bis(3,5-di-t-butyl-4-methoxyphenyl)iodophosphine

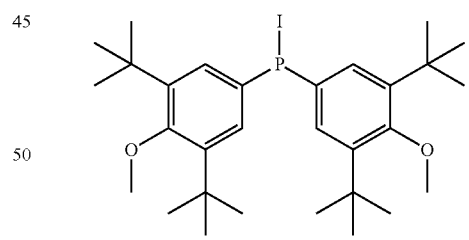

Bis(3,5-di-t-butyl-4-methoxyphenyl)chlorophosphine (0.90 g, 1.8 mmol) was dissolved in toluene (4.0 mL). Iodotrimethylsilane (0.30 mL, 2.1 mmol) was added and the orange solution was stirred at ambient temperature overnight. Some yellow solid had formed. The mixture was filtered to remove the yellow solid and the filtrate was concentrated under vacuum to yield the product. Yield (1.0 g, 97%). $^1$H NMR (400 MHz, $C_6D_6$) δ 7.90 (d, J=7.7 Hz, 4H), 3.31 (s, 6H), 1.37 (s, 36H). $^{13}$C NMR (101 MHz, $C_6D_6$) δ 161.96, 144.37 (d, J=6.1 Hz), 133.06, 132.81, 64.21, 36.20, 32.12. $^{31}$P NMR (162 MHz, $C_6D_6$) δ 47.18.

Step 2. Preparation of (rac)-N-(bis(3,5-di-tert-butyl-4-methoxyphenyl)phosphanyl)-N-butyl-2,5-diphenylphospholan-1-amine, L620

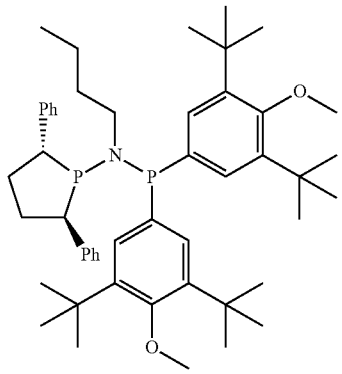 [SMILES: CCCCN(P(c1cc(C(C)(C)C)c(OC)c(C(C)(C)C)c1)c1cc(C(C)(C)C)c(OC)c(C(C)(C)C)c1)P1[C@@H](c2ccccc2)CC[C@@H]1c1ccccc1]

A cold (−30° C.) solution of bis(3,5-di-t-butyl-4-methoxyphenyl)iodophosphine (0.29 g, 0.48 mmol) in toluene (5.0 mL) was added dropwise to a cold (−30° C.) solution of (rac)-N-butyl-2,5-diphenylphospholan-1-amine (0.15 g, 0.48 mmol) and triethylamine (0.074 uL, 0.53 mmol) in toluene (5.0 mL), causing immediate solid formation. After mixing, the volatiles were removed under vacuum. The residue was extracted with ether and filtered through a plug of activated neutral alumina. The volatiles were removed to yield the product as a white solid. Yield (0.31 g, 81%). $^1$H NMR (400 MHz, C$_6$D$_6$) δ 7.77 (t, J=3.1 Hz, 2H), 7.56-7.44 (m, 2H), 7.40 (d, J=6.7 Hz, 2H), 7.33-7.23 (m, 2H), 7.21-7.11 (m, 4H), 7.08-7.00 (m, 1H), 7.00-6.91 (m, 1H), 4.59-4.16 (m, 1H), 3.38 (d, J=10.9 Hz, 6H), 3.31 (s, 5H), 3.24-3.04 (m, 3H), 1.49 (d, J=3.0 Hz, 3H), 1.33 (s, 36H), 0.40 (d, J=7.3 Hz, 3H). $^{13}$C NMR (101 MHz, C$_6$D$_6$) δ 160.36-160.07 (m), 144.84 (d, J=21.4 Hz), 143.48-143.22 (m), 142.73 (d, J=6.6 Hz), 139.20 (d, J=1.7 Hz), 135.18 (d, J=19.5 Hz), 133.33 (t, J=13.5 Hz), 131.88 (d, J=23.1 Hz), 130.84 (t, J=4.4 Hz), 130.31 (d, J=21.2 Hz), 128.80 (t, J=2.8 Hz), 128.39 (d, J=9.8 Hz), 128.31, 127.93 (d, J=1.4 Hz), 125.50 (dd, J=15.7, 2.2 Hz), 63.88 (d, J=5.6 Hz), 63.58, 36.82, 35.68, 35.56 (d, J=4.6 Hz), 34.24 (d, J=7.3 Hz), 31.93, 31.86 (d, J=4.6 Hz), 19.77, 13.52. $^{31}$P NMR (162 MHz, C$_6$D$_6$) δ 100.55 (d, J=25.7 Hz), 57.14 (d, J=25.7 Hz). HRMS (ESI-TOF) m/z: [M+H]+ Calcd for C$_{50}$H$_{71}$NO$_2$P$_2$ 780.5033; Found 780.5048.

Preparation of (2S,5S)—N-(bis(2,6-difluorophenyl)phosphanyl)-N-buty-2,5-diphenylphospholan-1-amine, L627

Step 1. Preparation of bis(2,6-difluorophenyl)dimethylaminophosphine

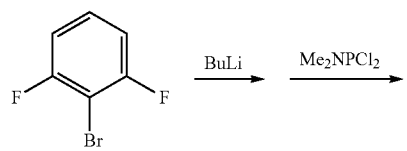

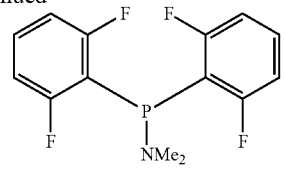

1-Bromo-3,5-difluorobenzene (19.00 g, 98.45 mmol) was added slowly dropwise to a chilled (−90 to −85° C. (liquid nitrogen/acetone)) solution of n-butyllithium (42.0 mL, 2.34 M in hexanes, 98.3 mmol) in ether (250 mL) such that the temperature did not exceed −85° C. The temperature was allowed to increase to between −78 and −74° C. for 2 hours (dry ice bath) with no formation of white precipitate, even after warming to −65° C. for 1 h. The mixture was cooled to −78° C. and a solution of dimethylphosphoramidous dichloride (7.161 g, 49.06 mmol) in ether (20 mL total) was added slowly dropwise at a rate such that the temperature did not exceed −65° C. Precipitate formed during the addition and the colorless mixture turned light brown. The reaction mixture was allowed to warm to ambient temperature while stirring overnight. The color has turned red. The reaction mixture was filtered and the volatiles were removed under reduced pressure to give a deep red solid. The solid was extracted with hexane, filtered, and the volatiles were removed under reduced pressure to give large colorless crystals coated with red liquid. The liquid was decanted. The crystals were collected on a frit, washed with hexane, and dried under reduced pressure to give bulk crystalline material which is pink due to some surface red liquid. Yield=7.135 g (48.3%). $^1$H NMR (400 MHz, CDCl$_3$) δ 7.32-7.21 (m, 1H), 6.89-6.73 (m, 2H), 2.73 (dp, J=10.5, 0.7 Hz, 3H). $^{13}$C NMR (101 MHz, CDCl$_3$) δ 163.16 (dt, J=246.7, 10.2 Hz), 130.82 (t, J=10.9 Hz), 115.15 (dtt, J=34.4, 23.7, 3.1 Hz), 111.69-111.06 (m), 42.46 (dt, J=17.3, 2.1 Hz). $^{31}$P NMR (162 MHz, CDCl$_3$) δ 25.62 (p, J=31.8 Hz). $^{19}$F NMR (376 MHz, CDCl$_3$) δ −104.67 (dt, J=31.7, 7.0 Hz).

Step 2. Preparation of bis(2,6-difluorophenyl)chlorophosphine

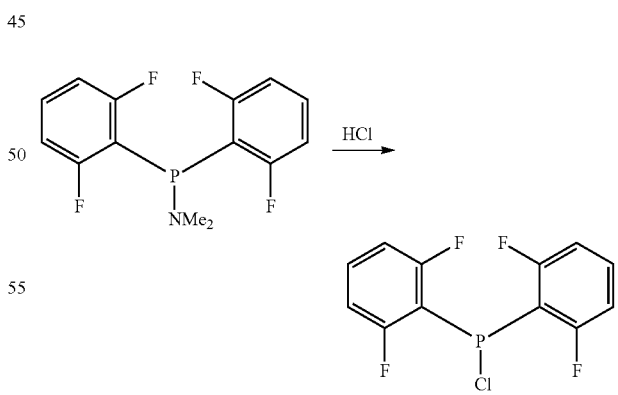

Anhydrous HCl in ether (35.0 mL, 2 M, 70.0 mmol) is added to a solution of bis(2,6-difluorophenyl)dimethylaminophosphine (7.00 g, 23.24 mmol) in methylene chloride (20 mL) causing decolorizing of the red-orange reaction mixture and formation of precipitate. The reaction mixture is stirred for 30 minutes. The mixture is filtered and the volatiles removed under reduced pressure. The residue is extracted with ether and filtered. The volatiles are removed under reduced pressure to give the product as a light yellow solid, 6.492 g, 95.5%. $^1$H NMR (500 MHz, CDCl$_3$) δ 7.42-7.41 (m, 1H), 6.91 (td, J=8.2, 2.5 Hz, 2H). $^{13}$C NMR (126 MHz, CDCl$_3$) δ 163.69 (dm, J=252.0 Hz), 133.73-133.33 (m), 113.50-112.37 (m), 112.15-111.48 (m). $^{31}$P NMR (162 MHz, CDCl$_3$) δ 39.58 (p, J=43.5 Hz). $^{19}$F NMR (376 MHz, CDCl$_3$) δ −100.55 (dt, J=43.5, 7.0 Hz).

Step 3. Preparation of bis(2,6-difluorophenyl)iodophosphine

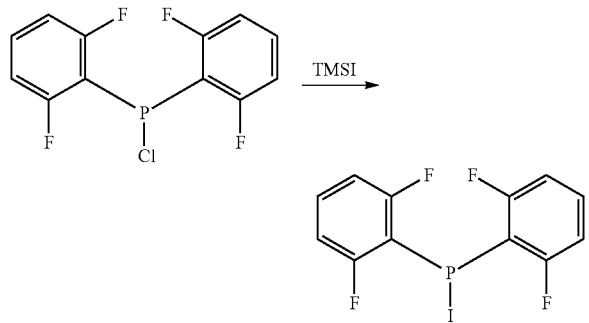

Iodotrimethylsilane (5.308 g, 26.53 mmol) was slowly added to a solution of bis(2,6-difluorophenyl)chlorophosphine (6.40 g, 21.9 mmol) in methylene chloride (20 mL). The reaction mixture instantly turned deep yellow. The mixture was allowed to stir for 1 hour. The volatiles were removed under reduced pressure. The residue was extracted with ether, filtered, and the volatiles were removed under reduced pressure to give the product as an orange-yellow crystalline solid, 8.3852 g, 99.8%. $^1$H NMR (500 MHz, CDCl$_3$) δ 7.46-7.33 (m, 1H), 6.91 (dtd, J=10.6, 8.1, 7.4, 3.3 Hz, 2H). $^{13}$C NMR (126 MHz, CDCl$_3$) δ 163.85 (dm, J=251.8 Hz), 133.41-132.88 (m), 111.99-111.35 (m), 110.35-108.83 (m). $^{31}$P NMR (202 MHz, CDCl$_3$) δ −29.81 (p, J=36.9 Hz). $^{19}$F NMR (470 MHz, CDCl$_3$) δ −96.87 (dt, J=36.4, 6.8 Hz).

Step 4. Preparation of (2S,5S)—N-(bis(2,6-difluorophenyl)phosphanyl)-N-butyl-2,5-diphenylphospholan-1-amine, L627

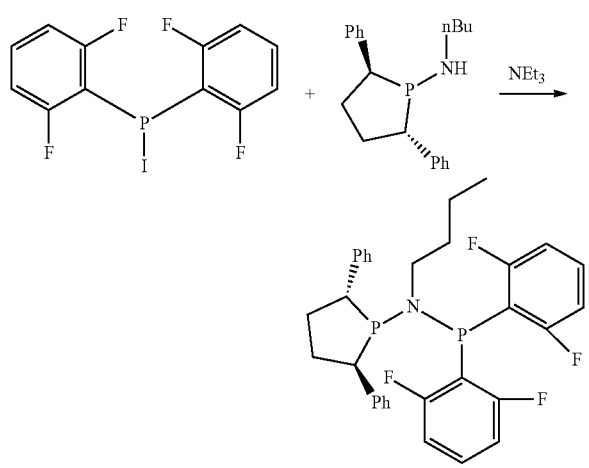

About 90% of a solution of bis(2,6-difluorophenyl)iodophosphine (0.394 g, 1.03 mmol) in diethyl ether (6 mL) was added slowly to a solution of N-butyl-2,5-diphenylphospholan-1-amine (0.3198 g, 1.03 mmol) and triethylamine (1.34 g, 13.2 mmol) in diethyl ether (6 mL) with formation of precipitate. $^{31}$P NMR spectra showed a slight excess of phospholane to be present. Additional bis(2,6-difluorophenyl)iodophosphine solution was added. The reaction mixture was stirred overnight. $^{31}$P NMR spectra still showed about 3% phospholane to be present. The rest of the bis(2,6-difluorophenyl)iodophosphine solution was added. The reaction mixture was stirred for several hours, then filtered, and the volatiles were removed under reduced pressure. The residue was extracted with ether, filtered, and the volatiles were removed under reduced pressure to give a beige solid. The residue was triturated with hexanes, filtered, and dried under reduced pressure to give the product as a beige powder, 0.4365 g, 74.89%. $^1$H NMR (500 MHz, CDCl$_3$) δ 7.38-7.26 (m, 7H), 7.21-7.17 (m, 1H), 7.15 (ddt, J=8.2, 6.4, 1.5 Hz, 1H), 7.00 (t, J=7.7 Hz, 2H), 6.89 (t, J=7.4 Hz, 1H), 6.85 (td, J=8.2, 2.2 Hz, 1H), 6.63 (td, J=8.2, 2.5 Hz, 2H), 4.11 (ddt, J=12.2, 7.9, 4.5 Hz, 1H), 3.50 (dddd, J=24.9, 13.4, 5.3, 1.7 Hz, 1H), 3.24-3.01 (m, 2H), 2.71 (ddddd, J=14.4, 13.0, 7.8, 5.1, 1.1 Hz, 1H), 2.40 (dq, J=17.0, 5.3 Hz, 1H), 1.82 (tdd, J=12.9, 11.2, 5.2 Hz, 1H), 0.71 (dddd, J=21.0, 15.0, 9.3, 3.7 Hz, 3H), 0.42 (t, J=7.2 Hz, 3H), 0.41-0.28 (m, 1H). $^{13}$C NMR (101 MHz, CDCl$_3$) δ 163.51 (ddd, J=247.8, 11.4, 8.8 Hz), 162.57 (dt, J=247.4, J=10.2 Hz), 143.97 (d, J=20.7 Hz), 138.02 (d, J=2.3 Hz), 131.82 (t, J=11.0 Hz), 129.88 (t, J=10.8 Hz), 128.30 (dm, J=3.0 Hz), 128.01 (d, J=8.4 Hz), 127.66 (d, J=1.3 Hz), 125.63 (d, J=2.6 Hz), 125.43 (d, J=1.9 Hz), 116.27-114.92 (m), 111.91-111.49 (m), 111.49-111.07 (m), 58.69 (dm, J=33.5 Hz), 55.44 (dd, J=21.9, 17.7 Hz), 52.16 (dd, J=21.4, 7.0 Hz), 36.42, 33.87 (d, J=6.9 Hz), 32.57 (dd, J=9.0, 3.7 Hz), 19.60, 13.42. $^{31}$P NMR (202 MHz, CDCl$_3$) δ 109.47 (d, J=29.8 Hz), 15.41 (pd, J=39.5, 30.0 Hz). $^{19}$F NMR (470 MHz, CDCl$_3$) δ −101.75 (dt, J=39.7, 7.6 Hz), —103.51 (dt, J=39.2, 7.4 Hz). HRMS: Expected (M+1): 568.1868. Found (M+1): 568.1940.

Preparation of (2S,5S)—N-(bis(3,5-difluorophenyl)phosphanyl)-N-butyl-2,5-diphenylphospholan-1-amine, L628

Step 1. Preparation of bis(3,5-difluorophenyl)dimethylaminophosphine

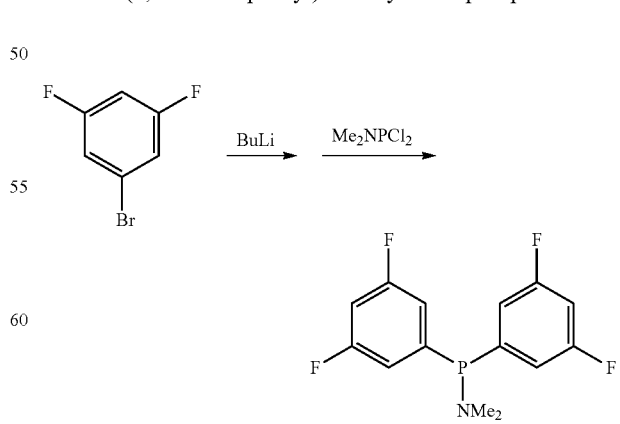

1-Bromo-3,5-difluorobenzene (19.469 g, 100.9 mmol) was added slowly dropwise to a chilled (−100 to −93° C.

(liquid nitrogen/acetone)) solution of n-butyllithium in hexanes (42.0 mL, 2.39 M, 100 mmol total) in ether (250 mL) such that the temperature did not exceed −88° C. The temperature was allowed to increase to between −78 and −74° C. for 1 hours (dry ice bath) with formation of white precipitate. A solution of dimethylphosphoramidous dichloride (7.030 g, 48.17 mmol) in ether (20 mL total) was added slowly dropwise at a rate such that the temperature did not exceed −64° C. The reaction mixture was allowed to warm while stirring overnight. By morning the temperature had reached 14° C. and the mixture color was reddish-purple. The flask was taken into the glovebox. The volatiles were removed under high vacuum to give a reddish-brown solid. The solid was extracted with hexane, filtered, and the volatiles were removed under reduced pressure to give a red oil. The oil was re-extracted with hexane, filtered from a trace of gray solid, and the volatiles were removed under reduced pressure to give the product as a red oil, 6.532 g, 44.3%. $^1$H NMR (400 MHz, CDCl$_3$) δ 6.89 (tdd, J=6.4, 2.3, 1.5 Hz, 4H), 6.77 (ttd, J=8.8, 2.3, 0.9 Hz, 2H), 2.65 (d, J=9.6 Hz, 6H). $^{13}$C NMR (101 MHz, CDCl$_3$) δ 163.00 (ddd, J=252.1, 11.3, 8.0 Hz), 142.66 (dt, J=20.9, 5.5 Hz), 114.05 (ddd, J=20.5, 18.2, 6.4 Hz), 104.28 (td, J=25.4, 1.6 Hz), 41.78 (d, J=16.0 Hz). $^{31}$P NMR (162 MHz, CDCl$_3$) δ 65.58. $^{19}$F NMR (376 MHz, CDCl$_3$) δ −109.14 (m).

Step 2. Preparation of bis(3,5-difluorophenyl)chlorophosphine

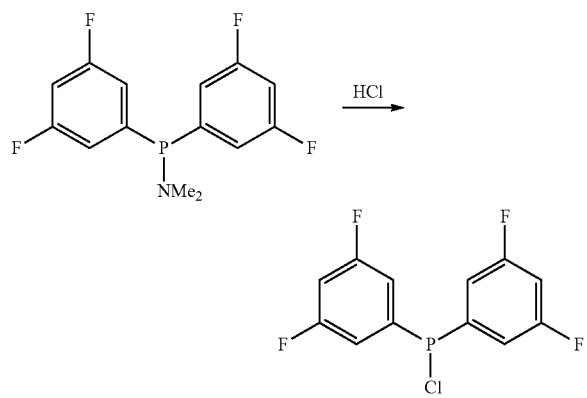

Anhydrous HCl in ether (35.0 mL, 2 M, 70.0 mmol) was added to a cooled (ice bath) solution of bis(3,5-difluorophenyl)dimethylaminophosphine (8.00 g, 26.6 mmol) in methylene chloride (20 mL), causing decolorizing of the yellow-orange reaction mixture and formation of precipitate. The reaction mixture was stirred for several days. The volatiles were removed under reduced pressure. The residue was extracted with ether and filtered. The volatiles were removed under reduced pressure to give the product as pale yellow liquid. The yield was 7.5385 g, 94.8%. $^1$H NMR (400 MHz, CDCl$_3$) δ 7.10 (dddd, J=7.8, 5.6, 2.3, 1.5 Hz, 4H), 6.87 (tt, J=8.7, 2.3 Hz, 2H). $^{13}$C NMR (101 MHz, CDCl$_3$) δ 163.00 (ddd, J=254.0, 11.4, 9.6 Hz), 141.96 (dt, J=37.0, 6.5 Hz), 114.51-113.89 (m), 106.42 (td, J=25.2, 1.4 Hz). $^{31}$P NMR (162 MHz, CDCl$_3$) δ 75.35. $^{19}$F NMR (376 MHz, CDCl$_3$) δ −107.44--107.51 (m).

Step 3. Preparation of bis(3,5-difluorophenyl)iodophosphine

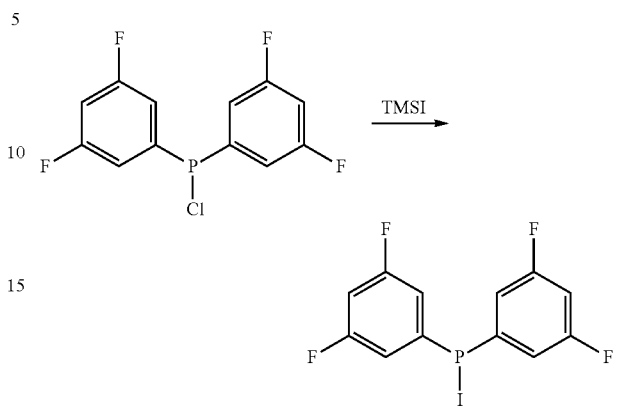

Iodotrimethylsilane (6.081 g, 30.39 mmol) was added to a solution of bis(3,5-difluorophenyl)chlorophosphine (7.410 g, 25.32 mmol) in ether (10 mL). The reaction mixture instantly turned deep yellow. The mixture was allowed to stir overnight. The reaction mixture was filtered and the volatiles were removed under reduced pressure to give 7.3738 g of crude product. The residue was extracted with ether, filtered, and the volatiles were removed under reduced pressure to give the product as a dark yellow oil.). Some solid particles were present. NMR spectra showed about 88% purity. The product was dissolved in ether, filtered from some brownish solid, and the volatiles were removed under reduced pressure to give a yellow oil. The product was subjected to trap-to-trap distillation: The water bath temperature was 85° C. at the pot end and liquid nitrogen at the receiver end. The vacuum was achieved on an oil diffusion pump vacuum line (0.6 mTorr). Only a very small amount (0.1-0.2 g) of dark yellow oil distilled over. The pot material appears to be less yellow. By $^{31}$P NMR, the distillate has peaks at 48.1 ppm (69%, undesired product), 33.8 ppm (9%, desired product), 0.6 ppm (22%, new undesired product), while the pot is enriched in desired product: 48.1 ppm (4.3%, undesired product), 33.8 ppm (91.6%, desired product), —9.3 ppm (4.1%, old undesired product). The pot residue of this first distillation was distilled in a second distillation at a slightly higher temperature of 90° C. to give the product as quite pure yellow oil, 3.5184 g, 35.18%. $^1$H NMR (400 MHz, CDCl$_3$) δ 7.18-7.13 (m, 2H), 6.83 (tt, J=8.6, 2.3 Hz, 1H). $^{13}$C NMR (101 MHz, CDCl$_3$) δ 162.73 (ddd, J=254.0, 11.5, 8.8 Hz), 138.28 (dt, J=42.1, 6.7 Hz), 116.77-116.10 (m), 106.28 (td, J=25.2, 1.5 Hz). $^{31}$P NMR (162 MHz, CDCl$_3$) δ 30.22. $^{19}$F NMR (376 MHz, CDCl$_3$) δ −107.32--107.42 (m).

Step 4. Preparation of (2S,5S)—N-(bis(3,5-difluorophenyl)phosphanyl)-N-butyl-2,5-diphenylphospholan-1-amine, L628

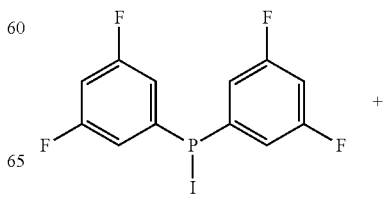

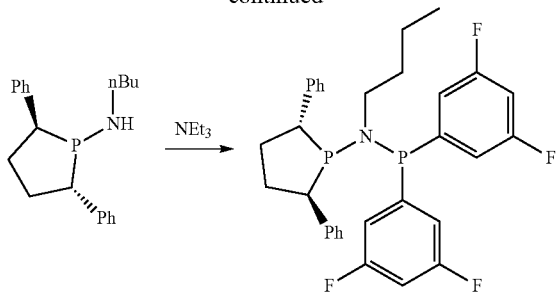

A solution of bis(3,5-difluorophenyl)iodophosphine (0.518 g, 1.35 mmol) in diethyl ether (6 mL) was added slowly to a solution of N-butyl-2,5-diphenylphospholan-1-amine (0.400 g, 1.28 mmol) and triethylamine (1.300 g, 12.84 mmol) in diethyl ether (6 mL) with formation of precipitate. The reaction mixture was stirred overnight. $^{31}$P NMR spectra showed the reaction to be complete. The reaction mixture was filtered, and the volatiles were removed under reduced pressure. The residue was extracted with ether, filtered, and the volatiles were removed under reduced pressure to give a yellow oil. The residue was triturated with hexanes, but the product all dissolved except for a trace of white solids. The solution was filtered, and the volatiles were removed under reduced pressure to give a yellow oil that solidified to a yellow solid. Yield: 0.6745 g, 92.5%. $^1$H NMR (500 MHz, CDCl$_3$) δ 7.39 (d, J=7.6 Hz, 2H), 7.36-7.30 (m, 2H), 7.29-7.21 (m, 5H), 7.20 (d, J=7.4 Hz, 1H), 6.87-6.76 (m, 3H), 6.66 (tm, J=8.8 Hz, 1H), 6.18 (td, J=6.2, 2.0 Hz, 2H), 3.77 (tt, J=7.9, 3.9 Hz, 1H), 3.60 (ddd, J=25.0, 13.2, 5.8 Hz, 1H), 2.93 (dddt, J=13.3, 11.3, 9.0, 3.6 Hz, 2H), 2.83 (dddd, J=15.6, 9.4, 5.3, 1.7 Hz, 1H), 2.60 (tdd, J=12.7, 9.9, 4.8 Hz, 1H), 2.44 (dq, J=11.0, 5.5 Hz, 1H), 1.82 (dddd, J=15.5, 13.2, 7.8, 5.4 Hz, 1H), 0.93-0.69 (m, 3H), 0.64-0.55 (m, 1H), 0.52 (td, J=7.2, 1.6 Hz, 3H). $^{13}$C NMR (126 MHz, CDCl$_3$) δ 163.62 (ddd, J=63.0, 11.3, 8.2 Hz), 161.61 (ddd, J=61.7, 11.4, 8.3 Hz), 143.90 (dt, J=27.8, 5.4 Hz), 143.00 (d, J=20.5 Hz), 141.92 (dt, J=21.1, 6.0 Hz), 138.10 (d, J=2.6 Hz), 128.56-128.47 (m), 128.48 (d, J=26.5 Hz), 127.95 (d, J=8.8 Hz), 126.15 (d, J=2.0 Hz), 126.07 (d, J=2.5 Hz), 114.58 (dddd, J=21.0, 19.6, 15.5, 5.6 Hz), 104.60 (td, J=25.3, 1.8 Hz), 104.03 (td, J=25.3, 1.8 Hz), 56.02 (dd, J=21.9, 16.3 Hz), 54.37 (dd, J=28.6, 3.8 Hz), 51.01 (dd, J=21.9, 4.4 Hz), 36.26 (d, J=3.3 Hz), 33.55 (d, J=6.7 Hz), 32.71 (dd, J=6.7, 3.6 Hz), 19.57, 13.42. $^{31}$P NMR (202 MHz, CDCl$_3$) δ 100.26 (d, J=16.7 Hz), 58.12 (d, J=16.7 Hz). $^{19}$F NMR (470 MHz, CDCl$_3$) d −108.73−−108.86 (m), −109.51−−109.69 (m).

Preparation of rac-N-cyclobutyl-N-(bis(2-fluorophenyl)phosphinyl)-2,5-diphenylphospholan-1-amine, L629

Step 1. Preparation of rac-N-cyclobutyl-N-(bis(2-fluorophenyl)phosphinyl)-2,5-diphenylphospholan-1-amine, L629

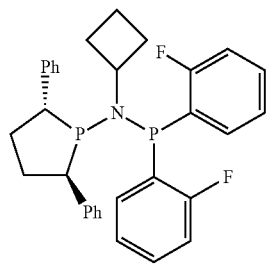 [SMILES: Fc1ccccc1P(c1ccccc1F)N(C1CCC1)P1[C@@H](c2ccccc2)CC[C@@H]1c1ccccc1]

A cold solution (−30° C.) of triethylamine (0.063 g, 0.62 mmol) dissolved in toluene (1.3 mL) was added to a cold (−30° C.) solution of rac-N-cyclobutyl-2,5-diphenylphospholan-1-amine (0.16 g, 0.52 mmol) dissolved in toluene (1.6 mL) and the resulting mixture was stirred for 10 min. The mixture was placed in a freezer at −30° C. for 30 minutes. A cold (−30° C.) solution of bis(2-fluorophenyl)iodophosphine (0.18 g, 0.52 mmol) in 1.8 mL of toluene was added to the cooled mixture of triethylamine and rac-N-cyclobutyl-2,5-diphenylphospholan-1-amine, with formation of a white precipitate. The reaction mixture was stirred for 30 min at ambient temperature, then was filtered through a 5-cm plug of activated neutral alumina. The volatiles were removed under vacuum giving solid product which was recrystallized from cold pentane at −30° C. to produce pure product. Yield 0.25 g (92%). $^1$H NMR (400 MHz, C$_6$D$_6$, 70° C.) δ 7.34 (d, J=7.5 Hz, 2H), 7.15 (q, J=7.3 Hz, 4H), 7.05-6.74 (m, 7H), 6.68-6.46 (m, 5H), 4.47-4.30 (m, 1H), 3.65 (dt, J=16.2, 8.0 Hz, 1H), 3.23 (m, 2.89 (d, J=13.6 Hz, 1H), 2.71-2.42 (m, 2H), 2.15-1.99 (m, 1H), 1.90 (s, 1H), 1.74-1.51 (m, 2H), 1.28 (d, J=9.9 Hz, 2H), 1.01 (m, 1H). $^{13}$C NMR (101 MHz, C$_6$D$_6$, 70° C.) δ 165.39 (d, J=17.9 Hz), 163.96 (d, J=17.2 Hz), 162.95 (d, J=18.1 Hz), 161.53 (d, J=16.9 Hz), 144.44 (d, J=21.7 Hz), 138.71 (d, J=2.3 Hz), 133.15 (t, J=5.5 Hz), 130.95 (d, J=8.6 Hz), 129.59 (d, J=8.1 Hz), 128.34 (d, J=3.9 Hz), 128.25, 128.10, 128.01, 127.86, 125.43 (dd, J=20.0, 2.3 Hz), 123.80 (dd, J=20.1, 3.2 Hz), 115.04 (d, J=24.1 Hz), 114.38 (d, J=23.2 Hz), 57.83 (d, J=23.3 Hz), 53.73-51.41 (m), 51.00 (dd, J=22.6, 3.7 Hz), 36.16 (d, J=1.8 Hz), 32.85 (dd, J=22.9, 8.6 Hz), 31.94 (d, J=14.6 Hz), 14.37. $^{31}$P NMR (162 MHz, C$_6$D$_6$, 70° C.) δ 81.24, 32.49. $^{19}$F NMR (376 MHz, C$_6$D$_6$) δ −103.57 (m).

Preparation of rac-N-cyclopentyl-N-(bis(2-fluorophenyl)phosphinyl)-2,5-diphenylphospholan-1-amine, L630

Step 1. Preparation of rac-N-cyclopentyl-2,5-diphenylphospholan-1-amine

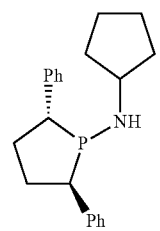 [SMILES: c1ccc([C@H]2CC[C@H](c3ccccc3)P2NC2CCCC2)cc1]

A solution of cyclopentylamine (0.64 mL, 6.5 mmol) in hexanes (5.0 mL) was added to a solution of rac-1-chloro-2,5-diphenyl-phospholane (0.60 g, 2.2 mmol) in hexanes (5.0 mL). The reaction mixture was stirred at room temperature overnight. The solid was removed by filtration using a disposable filter funnel and the resulting solution was passed through a 5-cm plug of activated neutral alumina. The volatiles were removed under vacuum to give a white solid. Yield 0.58 g (78%). $^1$H NMR (400 MHz, C$_6$D$_6$) δ 7.29 (dt, J=8.0, 1.7 Hz, 2H), 7.17 (m, J=17.1, 7.5, 1.6 Hz, 4H), 7.11-6.98 (m, 4H), 3.13-2.95 (m, 1H), 2.92-2.71 (m, 2H), 2.22-1.92 (m, 2H), 1.75 (m, 1H), 1.53 (m, 1H), 1.46-1.19 (m, 2H), 1.19-0.96 (m, 4H), 0.68-0.50 (m, 1H). $^{13}$C NMR (101 MHz, C$_6$D$_6$) δ 144.03 (d, J=18.3 Hz), 139.99 (d, J=1.3 Hz), 128.34 (d, J=1.2 Hz), 128.05 (d, J=1.1 Hz), 127.94 (d, J=3.4 Hz), 127.54 (d, J=8.1 Hz), 125.58 (d, J=2.4 Hz), 125.24 (d, J=1.8 Hz), 59.24 (d, J=22.4 Hz), 56.25 (d, J=15.0 Hz), 49.74 (d, J=22.3 Hz), 36.01-34.91 (m), 33.58 (d, J=3.0 Hz), 31.45 (d, J=2.1 Hz), 23.03 (d, J=3.4 Hz). $^{31}$P NMR (162 MHz, C$_6$D$_6$) δ 68.29.

Step 2. Preparation of rac-N-cyclopentyl-N-(bis(2-fluorophenyl)phosphinyl)-2,5-diphenylphospholan-1-amine, L630

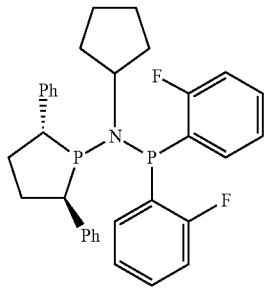 [SMILES: Fc1ccccc1P(c1ccccc1F)N(C1CCCC1)P1[C@@H](c2ccccc2)CC[C@@H]1c1ccccc1]

A cold solution (−30° C.) of triethylamine (0.049 g, 0.48 mmol) in toluene (0.98 mL) was added to a cold (−30° C.) solution of rac-N-cyclopentyl-2,5-diphenylphospholan-1-amine (0.13 g, 0.40 mmol) in toluene (1.3 mL) and the resulting reaction mixture was stirred for 10 min. The reaction mixture was placed in a freezer at −30° C. for 30 minutes. To this cooled reaction mixture was added a cold (−30° C.) solution of bis(2-fluorophenyl)iodophosphine (0.14 g, 0.40 mmol) in 1.4 mL of toluene with formation of a white precipitate. The reaction mixture was stirred for 30 min at ambient temperature. The reaction mixture was filtered through a 5-cm plug of activated neutral alumina and the volatiles were removed under vacuum giving solid product which was recrystallized from cold pentane at −30° C. to produce pure product. Yield 0.11 g (50.3%). $^{1}$H NMR (400 MHz, C$_6$D$_6$, 70° C.) δ 7.37 (d, J=7.5 Hz, 2H), 7.16 (t, J=7.2 Hz, 4H), 7.02 (q, J=7.8, 5.7 Hz, 2H), 6.97-6.75 (m, 5H), 6.66 (dt, J=13.3, 4.5 Hz, 4H), 6.55 (d, J=6.6 Hz, 1H), 4.40 (d, J=11.5 Hz, 1H), 3.58-3.39 (m, 1H), 3.26 (m, 1H), 2.97 (s, 1H), 2.52 (m, 1H), 2.05 (m, 2H), 1.50 (m, 3H), 1.35-0.75 (m, 5H). $^{13}$C NMR (101 MHz, C$_6$D$_6$, 70° C.) δ 144.45 (d, J=21.4 Hz), 138.75 (d, J=2.4 Hz), 133.58, 133.09, 131.11 (d, J=8.8 Hz), 129.39 (d, J=8.2 Hz), 128.39 (d, J=3.0 Hz), 128.23 (d, J=3.6 Hz), 128.12, 127.87, 125.45 (dd, J=15.9, 2.4 Hz), 123.75 (d, J=3.4 Hz), 115.08 (d, J=24.4 Hz), 114.36 (d, J=23.1 Hz), 63.81 (d, J=19.5 Hz), 51.01 (d, J=23.6 Hz), 36.68 (d, J=2.4 Hz), 35.75-34.84 (m), 33.70 (d, J=14.6 Hz), 32.84, 24.02. $^{31}$P NMR (162 MHz, C$_6$D$_6$, 70° C.) δ 83.83, 33.05. $^{19}$F NMR (376 MHz, C$_6$D$_6$) δ −105.88 (m).

Preparation of (2S,5S)—N-(bis(2,4,6-trifluorophenyl)phosphanyl)-N-butyl-2,5-diphenylphospholan-1-amine. L636

Step 1. Preparation of bis(2,4,6-trifluorophenyl)dimethylaminophosphine

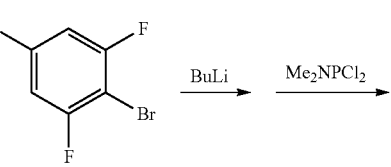

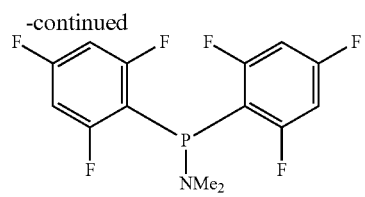

1-Bromo-2,4,6-trifluorobenzene (21.022 g, 99.64 mmol) was added slowly dropwise to a chilled (−99 to −89° C. (liquid nitrogen/acetone)) solution of n-butyllithium (42.0 mL, 2.35 M, 98.7 mmol) in hexanes in ether (250 mL) such that the temperature did not exceed −89° C. The temperature was allowed to increase to between −78 and −74° C. for 2 hours (dry ice bath) with no formation of precipitate. A solution of dimethylphosphoramidous dichloride (6.860 g, 47.00 mmol) in ether (20 mL total) was added slowly dropwise at a rate such that the temperature did not exceed −65° C. Precipitate formed during the addition and the colorless reaction mixture turned light brown. The reaction mixture was allowed to warm to ambient temperature while stirring overnight. The color has turned red-brown. The reaction mixture was filtered and the volatiles were removed under reduced pressure to give a brownish-red oil. The solid was extracted with hexane, filtered, and the volatiles were removed under reduced pressure to give a red oil. The yield was 12.121 g, 76.479%. $^{1}$H NMR (400 MHz, CDCl$_3$) δ 6.61 (tdd, J=8.9, 1.8, 1.1 Hz, 4H), 2.70 (dt, J=10.6, 0.8 Hz, 6H)$^{13}$C NMR (101 MHz, CDCl$_3$) δ 165.09-164.35 (m), 162.60-161.89 (m), 111.53-110.41 (m), 100.48 (ddd, J=30.7, 24.9, 3.3 Hz), 42.32 (dp, J=17.9, 1.9 Hz). $^{31}$P NMR (162 MHz, CDCl$_3$) δ 24.73 (td, J=31.0, 2.9 Hz). $^{19}$F NMR (376 MHz, CDCl$_3$) δ −101.74 (dt, J=31.1, 8.1 Hz), —107.33 (pd, J=8.6, 2.7 Hz).

Step 2. Preparation of bis(2,4,6-trifluorophenyl)chlorophosphine

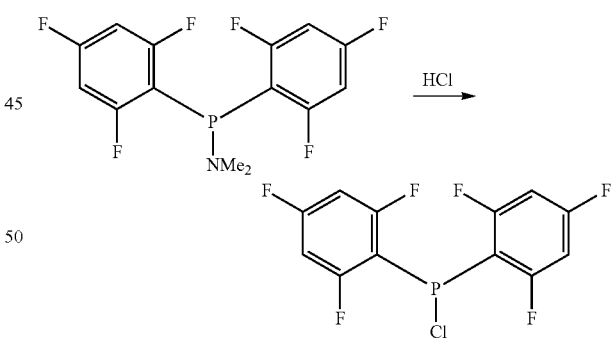

Anhydrous HCl in ether (45.0 mL, 2 M, 90 mmol) was added to a cooled (−35° C.) solution of bis(2,4,6-trifluorophenyl)dimethylaminophosphine (12.000 g, 35.590 mmol) in methylene chloride (100 mL) with decolorizing of the orange-red reaction mixture and formation of precipitate. The reaction mixture was stirred overnight, then filtered and the volatiles were removed under reduced pressure. The residue was extracted with ether and filtered. The volatiles were removed under reduced pressure to give the product as a dark yellow liquid. By $^{31}$P NMR, the compound contains mostly desired product (pentet, δ 37.34, 91.7%), dichloro (2,4,6-trifluorophenyl)phosphine (triplet, δ 72.00, J=51.6 Hz, 7.1%), and a downfield peak (singlet, δ 114.22, 1.2%). A trap-to-trap distillation was set up to remove the dichloro (2,4,6-trifluorophenyl)phosphine. The water-white more volatile fraction was compose of desired product (80.4%), dichloro(2,4,6-trifluorophenyl)phosphine (16.3%), downfield peak (3.2%). The dark yellow pot residue was composed of desired product (97.2%), dichloro(2,4,6-trifluorophenyl)phosphine (2.9%), and no downfield peak. The distillation was continued ($2^{nd}$ distillation): Distillate: desired product (97.5%), dichloro(2,4,6-trifluorophenyl) phosphine (2.3%), downfield peak (none). The distillate was a colorless liquid which solidified to a white solid, 3.924 g of white solid, 33.56%. $^1$H NMR (400 MHz, CDCl$_3$) δ 6.74-6.65 (m, 1H). $^{13}$C NMR (126 MHz, CDCl$_3$) δ 165.37 (dtm, J=255.2, 16.1 Hz), 164.19 (dddd, J=253.1, 14.5, 13.3, 10.6 Hz), 109.28-108.33 (m), 101.11 (tm, J=25.1 Hz). $^{31}$P NMR (162 MHz, CDCl$_3$) δ 37.34 (pt, J=43.1, 2.1 Hz). $^{19}$F NMR (376 MHz, CDCl$_3$) δ −97.32 (dt, J=43.6, 9.0 Hz), —102.19 (pm, J=8.6 Hz).

Step 3. Preparation of bis(2,4,6-trifluorophenyl)iodophosphine

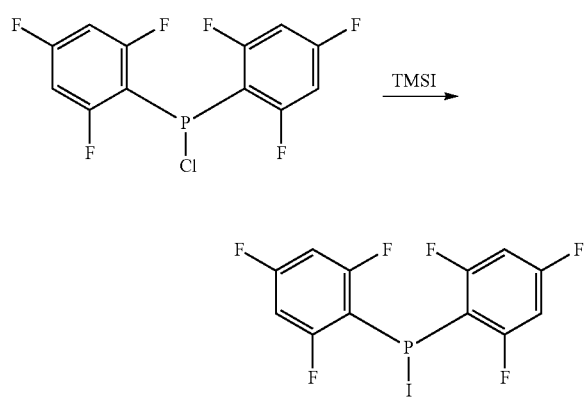 [SMILES: "TMSI" ; Fc1cc(F)c(P(Cl)c2c(F)cc(F)cc2F)c(F)c1 ; Fc1cc(F)c(P(I)c2c(F)cc(F)cc2F)c(F)c1]

Iodotrimethylsilane (3.205 g, 16.02 mmol) was slowly added to a solution of bis(2,4,6-trifluorophenyl)chlorophosphine (3.824 g, 11.64 mmol) in ether (20 mL). The reaction mixture instantly turned deep yellow. A $^{31}$P NMR spectrum taken within 10 minutes of the addition showed the reaction was complete. The volatiles were removed under reduced pressure. The residue was extracted with ether, filtered, and the volatiles were removed under reduced pressure to give an orange oil, 5.0782 g. The residue was extracted with a mixture of hexane and ether and filtered. The volatiles were removed under reduced pressure to give the product as an orange oil, 4.83 g, 98.8%. $^1$H NMR (500 MHz, CDCl$_3$) δ 6.69 (dddm, J=8.7, 7.8, 2.0 Hz, 1H). $^{13}$C NMR (126 MHz, CDCl$_3$) δ 165.24 (dt, J=255.1, 16.0 Hz), 165.29 (dddd, J=252.8, 15.2, 13.2, 10.4 Hz), 105.40 (dtm, J=58.2, 21.4 Hz). $^{31}$P NMR (202 MHz, CDCl$_3$) δ −31.87 (pt, J=36.4, 2.5 Hz). $^{19}$F NMR (470 MHz, CDCl$_3$) δ −93.83 (dtm, J=36.5, 9.1 Hz), —102.58 (pm, J=8.7 Hz).

Step 4. Preparation of (2S,5S)—N-(bis(2,4,6-trifluorophenyl)phosphanyl)-N-butyl-2,5-diphenylphospholan-1-amine, L636

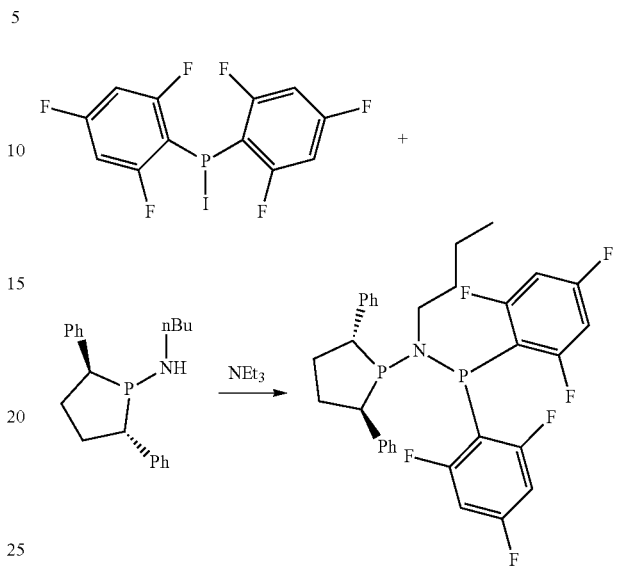

A solution of bis(2,4,6-trifluorophenyl)iodophosphine (0.446 g, 1.06 mmol) in diethyl ether (6 mL) was added slowly to a solution of N-butyl-2,5-diphenylphospholan-1-amine (0.328 g, 1.05 mmol) and triethylamine (1.530 g, 15.13 mmol) in diethyl ether (6 mL) with formation of precipitate. The reaction mixture was stirred overnight. $^{31}$P NMR spectroscopy showed the reaction to be complete. The reaction mixture was filtered, and the volatiles were removed under reduced pressure to give a pale yellow solid with small crystallites. The solid was extracted with ether, filtered, and the volatiles were removed under reduced pressure to give the product as a solid. The residue was triturated with hexanes, filtered, and the volatiles were removed under reduced pressure (overnight vacuum at 36° C.) to give the product as an off-white solid, 0.5740 g, 90.30%. $^1$H NMR (400 MHz, CDCl$_3$) δ 7.36-7.24 (m, 7H), 7.20 (tq, J=7.1, 1.5 Hz, 1H), 7.02 (t, J=7.6 Hz, 2H), 6.92 (t, J=7.4 Hz, 1H), 6.63 (ddd, J=9.2, 7.9, 1.8 Hz, 2H), 6.39 (td, J=8.4, 2.1 Hz, 2H), 4.00 (ddt, J=12.1, 8.2, 4.4 Hz, 1H), 3.52 (ddd, J=24.6, 13.5, 5.5 Hz, 1H), 3.16-2.95 (m, 3H), 2.67 (dddd, J=15.5, 13.3, 7.7, 5.0 Hz, 1H), 2.39 (tt, J=10.9, 5.3 Hz, 1H), 1.79 (qm, J=12.7 Hz, 1H), 0.82-0.70 (m, 3H), 0.45 (t, J=7.1 Hz, 3H). $^{13}$C NMR (101 MHz, CDCl$_3$) δ 165.72-164.88 (m), 164.47-163.62 (m), 163.16-162.41 (m), 161.97-161.08 (m), 143.72, 143.51, 138.00 (d, J=2.5 Hz), 128.40, 128.30 (t, J=3.2 Hz), 128.05, 127.96, 127.73, 125.80 (d, J=2.6 Hz), 125.48 (d, J=2.2 Hz), 100.75 (ddd, J=30.9, 24.8, 3.4 Hz), 100.29 (ddd, J=30.8, 24.8, 3.0 Hz), 58.62 (d, J=30.5 Hz), 55.70 (dd, J=22.3, 16.2 Hz), 51.76 (dd, J=21.2, 7.7 Hz), 36.45 (d, J=1.9 Hz), 34.04 (d, J=7.3 Hz), 32.56 (dd, J=8.8, 3.8 Hz), 19.65, 13.45. $^{31}$P NMR (162 MHz, CDCl$_3$) δ 108.88 (d, J=30.6 Hz), 14.07 (h, J=39.0 Hz). $^{19}$F NMR (376 MHz, CDCl$_3$) δ −98.36 (t, J=8.9 Hz), —98.47 (t, J=8.8 Hz), —100.72 (dt, J=38.6, 8.4 Hz), —105.13 (p, J=8.9 Hz), —108.85 (pd, J=8.6, 2.2 Hz).

Preparation of (2S,5S)—N-(bis(2,4-difluorophenyl)phosphanyl)-N-butyl-2,5-diphenylphospholan-1-amine, L638

Step 1. Preparation of bis(2,4-difluorophenyl)dimethylaminophosphine

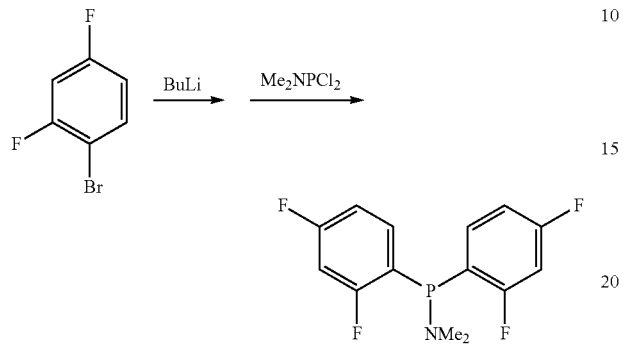

1-Bromo-2,4-difluorobenzene (19.469 g, 100.9 mmol) was added slowly dropwise to a chilled (−96 to −91° C. (liquid nitrogen/acetone)) solution of n-butyllithium in hexanes (41.5 mL, 2.39 M, 99.19 mmol total) in ether (250 mL) such that the temperature did not exceed −88° C. The temperature was allowed to increase to between −78 and −74° C. for 1 hour (dry ice bath) with formation of white precipitate. A solution of dimethylphosphoramidous dichloride (7.000 g, 47.96 mmol) in ether (20 mL total) was added slowly dropwise at a rate such that the temperature did not exceed −64° C. The reaction mixture was allowed to warm while stirring overnight. By morning the color was reddish-purple. The flask was taken into a glovebox. $^{31}$P NMR spectroscopy showed a major triplet peak at 43.5 ppm (88%) from the desired product, a minor doublet peak (presumed to be the monoaryl compound, dimethylamino(chloro)(2,4-difluorophenyl)phosphine) at 50.9 ppm (8.5%), and a small broad multiplet at about 36 ppm (3.5%). The volatiles were removed under reduced pressure to about 150 mL. Hexane (about 150 mL) was added and the mixture was filtered. The volatiles were removed under reduced pressure to give a deep red oil. The solid was extracted with hexane, filtered, and the volatiles were removed under reduced pressure overnight to give a deep red-purple oil. The oil was trap-to-trap transferred to give a pale yellow liquid. Much of the liquid was colorless as it came over, but a small amount of splatter sent some color over, yield: 9.8384 g. The product contains 9.3% of the monoaryl compound and 90.7% desired bis(2,4-difluorophenyl)dimethylaminophosphine compound. The distillate was partially distilled into two fractions: Distillate, 3.952 g, which contains 16.9% of the monoaryl compound and 83.1% desired bis(2,4-difluorophenyl)dimethylaminophosphine compound, and pot residue, 5.633 g, 39.28%, which contains 2.7% of the monoaryl compound and 97.3% desired bis(2,4-difluorophenyl)dimethylaminophosphine compound. $^{1}$H NMR (500 MHz, CDCl$_3$) δ 7.07-6.99 (m, 1H), 6.73 (td, J=8.3, 2.5 Hz, 1H), 6.64 (tdd, J=9.3, 3.4, 2.4 Hz, 1H), 2.49 (d, J=9.8 Hz, 3H). $^{13}$C NMR (101 MHz, CDCl$_3$) δ 163.88 (dd, J=250.6, 11.9 Hz), 163.52 (ddd, J=247.2, 16.8, 11.8 Hz), 133.27 (dt, J=9.5, 7.4 Hz), 120.41 (dddd, J=22.1, 20.3, 3.7, 2.3 Hz), 111.55 (ddd, J=20.3, 3.4, 1.2 Hz), 103.76 (dd, J=27.4, 25.2 Hz), 41.92 (d, J=17.4 Hz). $^{31}$P (162 MHz, CDCl$_3$) δ 43.50 (tt, J=42.4, 3.5 Hz). $^{19}$F NMR (376 MHz, CDCl$_3$) δ −101.86 (dq, J=42.4, 8.9 Hz), —109.38 (pd, J=9.2, 8.7, 3.4 Hz). $^{31}$P NMR for dimethylamino(chloro)(2,4-difluorophenyl)phosphine (162 MHz, CDCl$_3$) δ 50.87 (dd, J=26.4, 3.3 Hz).

Step 2. Preparation of bis(2,4-difluorophenyl)chlorophosphine

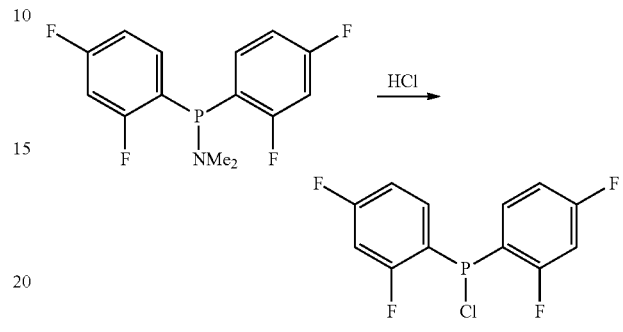

Anhydrous HCl in ether (55.0 mL, 2 M, 110 mmol) was added to a solution of bis(2,4-difluorophenyl)dimethylaminophosphine (8.00 g, 26.6 mmol) in methylene chloride (50 mL) with substantial decolorizing of the deep reddish-brown reaction mixture to light orange. A $^{31}$P NMR spectrum showed the reaction to be complete with about 10% of the putative dichloro(2,4-difluorophenyl)phosphine compound being present as well as the desired product. The volatiles were removed under reduced pressure. The residue was extracted with a mixture of ether and hexanes (50/50) and filtered. The volatiles were removed under reduced pressure to give the product as an orange oil. NMR spectra showed about 8% of putative dichloro(2,4-difluorophenyl)phosphine, 3% of another impurity, and 88% of bis(2,4-difluorophenyl)chlorophosphine. The oil was trap-to-trap vacuum transferred (hot water bath/liquid nitrogen) at 90° C. A small amount of liquid distilled over which was enriched in the dichloro(2,4-difluorophenyl)phosphine impurity. The distillation was continued with use of a heat gun to increase the temperature to obtain the product as a water-white liquid, 4.561 g, 58.69%, which contained about 3.7% of putative 2,4-difluorophenylphosphine dichloride, identified by a doublet in the $^{31}$P NMR spectrum, δ 86.39 (d, J=54.9 Hz). $^{1}$H NMR (500 MHz, CDCl$_3$) δ 7.57 (tdd, J=8.3, 6.3, 5.3 Hz, 1H), 6.97 (td, J=8.3, 2.4 Hz, 1H), 6.82 (tdd, J=9.1, 3.5, 2.4 Hz, 1H). $^{13}$C NMR (126 MHz, CDCl$_3$) δ 165.26 (dd, J=254.4, 12.2 Hz), 163.93 (ddd, J=250.8, 19.4, 12.2 Hz), 134.21 (ddd, J=12.6, 9.9, 5.7 Hz), 119.92 (ddm, J=40.32, 16.4 Hz), 112.34 (dt, J=21.0, 3.1 Hz), 104.34 (t, J=26.0 Hz). $^{31}$P NMR (202 MHz, CDCl$_3$) δ 58.97 (tt, J=60.5, 2.9 Hz). $^{19}$F NMR (470 MHz, CDCl$_3$) δ −101.04 (dq, J=60.5, 9.4 Hz), —105.13 (pd, J=8.8, 2.6 Hz).

Step 3. Preparation of bis(2,4-difluorophenyl)iodophosphine

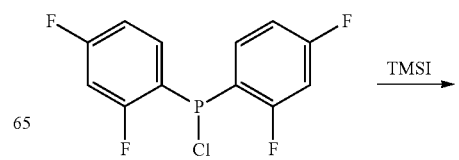

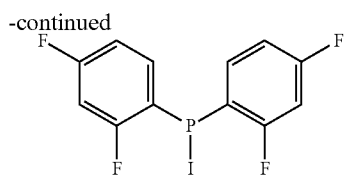

Iodotrimethylsilane (2.000 g, 9.99 mmol) was slowly added to a solution of bis(2,4-difluorophenyl)chlorophosphine (2.000 g, 6.84 mmol) in ether (10 mL). The reaction mixture instantly turned deep yellow. A $^{31}$P NMR spectrum taken within 10 minutes of the addition showed the reaction was complete. The volatiles were removed under reduced pressure to give a yellow oil. Yield was 2.543 g, 96.88%. $^1$H NMR (500 MHz, CDCl$_3$) δ 7.55 (tdd, J=8.4, 6.4, 4.6 Hz, 1H), 6.93 (td, J=8.3, 2.5 Hz, 1H), 6.82 (dddd, J=9.5, 8.7, 3.6, 2.4 Hz, 1H). $^{13}$C NMR (126 MHz, CDCl$_3$) δ 165.42 (dd, J=254.7, 12.0 Hz), 163.56 (dddd, J=251.2, 19.3, 12.3 Hz), 137.63 (td, J=10.4, 4.8 Hz), 116.22 (dddd, J=46.3, 17.4, 4.1, 1.8 Hz), 112.50 (ddd, J=21.0, 3.6, 2.1 Hz), 104.33 (dd, J=26.7, 25.3 Hz). $^{31}$P NMR (202 MHz, CDCl$_3$) δ 8.27 (tt, J=59.5, 2.0 Hz). $^{19}$F NMR (470 MHz, CDCl$_3$) δ −97.05 (dq, J=59.7, 9.6 Hz), −105.12 (p, J=8.7 Hz).

Step 4. Preparation of (2S,5S)—N-(bis(2,4-difluorophenyl)phosphanyl)-N-butyl-2,5-diphenylphospholan-1-amine, L638

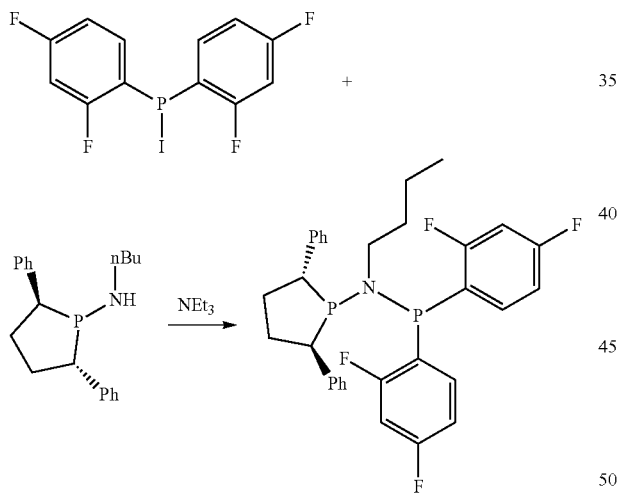

A solution of bis(2,4-difluorophenyl)iodophosphine (0.490 g, 1.28 mmol) in diethyl ether (6 mL) was added slowly to a solution of N-butyl-2,5-diphenylphospholan-1-amine (0.394 g, 1.27 mmol) and triethylamine (1.64 g, 16.2 mmol) in diethyl ether (6 mL) with formation of precipitate. The reaction mixture was stirred overnight. $^{31}$P NMR spectra showed the reaction to be complete. The reaction mixture was filtered, and the volatiles were removed under reduced pressure to give a pale yellow solid with small crystallites. The solid was extracted with ether, filtered, and the volatiles were removed under reduced pressure. The solid residue was triturated with hexanes, filtered, washed with hexane, and the volatiles were removed under reduced pressure to give the product as colorless powder, 0.5106 g, 71.11%. $^1$H NMR (500 MHz, CDCl$_3$) δ 7.37-7.28 (m, 7H), 7.22 (ddq, J=7.5, 6.4, 1.6 Hz, 1H), 7.10 (tm, J=7.4 Hz, 2H), 7.07-7.00 (m, 1H), 6.90-6.82 (m, 1H), 6.79 (tm, 9.1 Hz, 1H), 6.70-6.60 (m, 2H), 6.54 (td, J=8.4, 2.4 Hz, 1H), 6.44 (qd, J=7.9, 4.5 Hz, 1H), 4.06 (ddd, J=12.1, 7.8, 4.1 Hz, 1H), 3.46 (ddd, J=23.7, 13.5, 5.7 Hz, 1H), 3.04-2.86 (m, 4H), 2.74-2.61 (m, 1H), 2.38 (tt, J=10.8, 5.3 Hz, 1H), 1.78 (qd, J=12.9, 5.0 Hz, 1H), 0.94-0.82 (m, 1H), 0.76 (tt, J=14.2, 7.2 Hz, 2H), 0.48 (t, J=7.3 Hz, 4H). $^{13}$C NMR (126 MHz, CDCl$_3$) δ 164.27 (dd, J=252.0, 12.2 Hz), 164.06 (ddd, J=247.8, 19.2, 11.9 Hz), 163.35 (dd, J=250.0, 11.9 Hz), 162.09 (ddd, J=247.0, 17.4, 11.9 Hz), 143.76 (d, J=20.6 Hz), 138.34 (d, J=2.3 Hz), 133.89 (tt, J=12.3, 6.8 Hz), 128.46, 128.35 (dd, J=3.7, 1.8 Hz), 128.13, 128.08, 128.01, 125.78 (dd, J=11.4, 2.3 Hz), 121.44 (ddd, J=26.3, 18.8, 3.2 Hz), 120.54 (ddt, J=22.1, 18.9, 3.0 Hz), 111.51 (dd, J=7.1, 3.3 Hz), 111.35 (dd, J=7.4, 3.3 Hz), 103.87 (dd, J=27.9, 24.8 Hz), 103.27 (dd, J=27.2, 24.9 Hz), 54.64, 54.43, 51.84 (dd, J=21.9, 4.6 Hz), 36.48 (d, J=1.8 Hz), 33.83 (dd, J=6.7, 2.1 Hz), 32.62 (dd, J=7.6, 3.4 Hz), 19.63, 13.48. $^{31}$P NMR (162 MHz, CDCl$_3$) δ 102.16, 31.55 (ddd, J=53.8, 41.6, 22.0 Hz). $^{19}$F NMR (376 MHz, CDCl$_3$) δ −100.50 (dq, J=41.6, 9.0 Hz), −100.97 (dq, J=53.9, 9.3 Hz), −108.02 (t, J=8.9 Hz), −110.30 (t, J=9.0 Hz).

Preparation of rac-N-(bis(2-fluorophenyl)phosphanyl)-N-butyl-2,5-bis(4-methylphenyl)phospholan-1-amine, L645

Step 1. Preparation of 4-methylphenylmagnesium bromide in THF

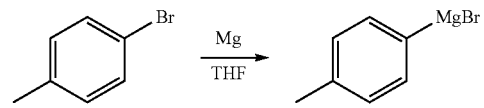

A two-necked flask, equipped with a stir bar and a Stevens (spiral tube-type) condenser, was charged with magnesium turnings (7.46 g, 306.9 mmol) and 100 mL of THF. Two drops of 1,2 dibromoethane were added to the resulting mixture. The mixture was allowed to stir for 5 min to activate the magnesium turnings. In a separate container, 4-bromotoluene (50.00 g, 321.6 mmol) was diluted with 60 mL of THF and drawn into a syringe. With a fan circulating air over the condenser, the solution of 4-bromotoluene was carefully added in 5- or 10-mL portions, allowing the mixture to stir for a few minutes between additions until the refluxing stopped. The container previously containing the solution of 4-bromotoluene was rinsed with 162 mL of THF, the rinse solvent was drawn with the same syringe used earlier and added to the reaction mixture. The Grignard solution that resulted was filtered through a disposable plastic fritted funnel to remove excess magnesium and titrated using salicylaldehyde phenylhydrazone to confirm a concentration of 1.0 M. The Grignard solution was used as-is in subsequent reactions.

Step 2. Preparation of (E,E)-1,4-bis(4-methylphenyl)-1,3-butadiene

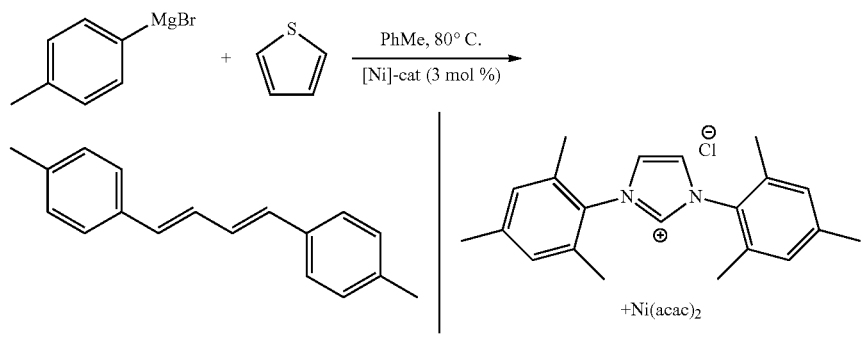

(E,E)-1,4-Bis-(4-methylphenyl)-1,3-butadiene was prepared according to a procedure adapted from Hintermann et al. (Hintermann, L.; Schmitz, M.; Chen, Y. Adv. Synth. Catal. 2010, 352, 2411). A 1-L three-necked, oven-dried flask was charged with toluene (300 mL), nickel (II) acetylacetonate, (Ni(acac)$_2$), (1.02 g, 3.98 mmol, 3 mol %) and 1,3-bis(2,4,6-trimethylphenyl)imidazolium chloride (3.38 g, 9.96 mmol, 7.5 mol %). While stirring, thiophene (12.8 mL, 159.4 mmol) and the 4-methylphenylmagnesium bromide solution (1.0 M, 321.6 mL, 321.6 mmol) were added sequentially to the reaction mixture. The reaction mixture was heated to 80° C. and stirred overnight, then monitored by NMR spectroscopy. Upon completion of the reaction, the reaction mixture was cooled (with an ice bath), diluted with 2-4 volumes of toluene, and quenched by careful addition of an equal volume of saturated aqueous NH$_4$Cl (caution H$_2$S gas is generated). The organic phase was washed with equal volumes of HCl (2.4 M), NaOH (2 M), and water and was then dried over anhydrous MgSO$_4$. The solution was then filtered through a silica gel plug. The plug was rinsed several times with dichloromethane. Solvent was removed on a rotary evaporator, the solid was triturated with pentane, collected on a fritted plastic filter, and dried under reduced pressure. The solid was analyzed by X-ray fluorescence spectroscopy (XFS) and determined to contain approximately 4% sulfur. The sample was passed through basic alumina using dichloromethane as the eluent, dried under vacuum, and analyzed by XFS: minimal reduction in sulfur content was observed. Four separate 100 mg samples were dissolved in dichloromethane and three solutions were each treated with H$_2$O$_2$ (dilute in H$_2$O), NaOCl (dilute in H$_2$O), or Na$_2$S$_2$O$_3$ (solid). The remaining sample, the control, was not treated. The samples were stirred overnight, separated from the aqueous layer (when applicable), filtered through basic alumina, dried under vacuum, and then analyzed by XFS. All samples, except for the control, showed a significant reduction in sulfur. The bulk of the material was purified with sodium thiosulfate and basic alumina, and then used as-is in subsequent steps (Yield: 15.3 g, 49%). $^1$H NMR (400 MHz, CDCl$_3$) δ 7.40-7.31 (m, 2H), 7.15 (d, J=7.8 Hz, 2H), 6.98-6.86 (m, 1H), 6.69-6.58 (m, 1H), 2.36 (s, 3H). $^{13}$C NMR (100 MHz, CDCl$_3$): δ=137.3, 134.6, 132.2, 129.3, 128.4, 126.2, 21.4.

Step 3. Preparation of (1S,2S,5R)-1-(dimethylamino)-2,5-bis(4-methylphenyl)-2,5-dihydrophosphole 1-oxide

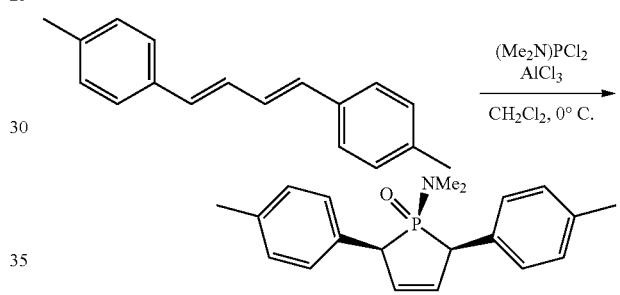

In a reaction not carried out in a glovebox, dimethylphosphoramidous dichloride (3.60 g, 31.3 mmol) was added to a stirred suspension of aluminum chloride (3.95 g, 29.6 mmol) in dichloromethane (50 mL) in a large jacketed multi-neck flask purged with nitrogen. After 45 min, the resulting greenish solution and a solution of (E,E)-1,4-bis(4-methylphenyl)-1,3-butadiene (6.70 g, 28.6 mmol) in dichloromethane (125 mL) were each cooled to 0° C. After cooling, the (E,E)-1,4-bis(4-methylphenyl)-1,3-butadiene solution was slowly added to the dimethylphosphoramidous dichloride-aluminum chloride solution. The mixture was allowed to stir overnight at 0° C. A solution of aqueous EDTA (ethylenediamine tetraacetic acid, 0.2 M, 200 mL) and saturated NaHCO$_3$(100 mL) cooled in ice water was then added to the reaction mixture. The mixture was stirred at 0° C. for 4 h, filtered through Celite, decanted, and the aqueous layer was extracted with dichloromethane. The organic layers were washed with NaHCO$_3$, 1 M HCl, brine, and dried over anhydrous MgSO$_4$. The solution was concentrated on a rotary evaporator and the resulting yellow oil was triturated with diethyl ether to yield a pale yellow solid (Yield: 7.5 g, 81%). $^1$H NMR (400 MHz, C$_6$D$_6$) δ 7.20 (dd, J=8.2, 2.2 Hz, 4H), 6.95 (d, J=7.8 Hz, 4H), 6.11 (d, J=27.9 Hz, 2H), 4.21 (d, J=18.2 Hz, 2H), 2.09 (s, 6H), 1.91 (s, 3H), 1.89 (s, 4H). $^{13}$C NMR (101 MHz, C$_6$D$_6$) δ 136.04 (d, J=2.6 Hz), 133.63 (d, J=8.3 Hz), 130.75 (d, J=16.0 Hz), 129.33 (d, J=2.3 Hz), 127.27 (d, J=4.7 Hz), 49.08 (d, J=70.8 Hz), 36.21, 36.20, 21.04. $^{31}$P NMR (162 MHz, C$_6$D$_6$) δ 66.68.

Step 4. Preparation of rac-1-(dimethylamino)-2,5-bis(4-methylphenyl)phospholane 1-oxide

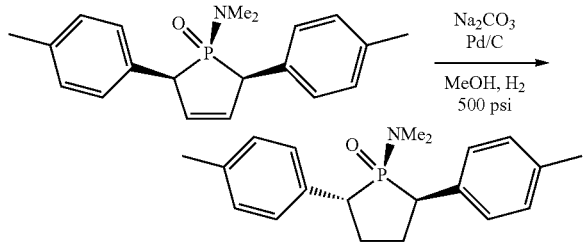

In a reaction not carried out in a glovebox, a pressure reactor was charged with (1S,2S,5R)-1-(dimethylamino)-2,5-bis(4-methylphenyl)-2,5-dihydrophosphole 1-oxide (6.69 g, 20.6 mmol), 10% Pd/C (438 mg, 0.41 mmol), sodium carbonate (1.09 g, 10.28 mmol), and methanol (100 mL). The reactor was purged with hydrogen, and then pressurized to 500 psi of hydrogen. After 2.5 h, an aliquot was taken and analyzed by NMR spectroscopy, confirming complete hydrogenation. The reaction mixture was filtered through Celite, and then heated to 40° C. for 1 hr and 40 min under an atmosphere of nitrogen. An aliquot was analyzed by NMR spectroscopy, confirming incomplete isomerization. Additional sodium carbonate was added (150 mg) and the reaction mixture was allowed to react overnight at room temperature; no change was observed by NMR spectroscopy. The reaction mixture was heated for 2.5 hr, and an aliquot was taken, confirming complete conversion. The solvent was removed under vacuum and the solid was treated with water. The product was then extracted with dichloromethane using a separatory funnel. The solution was dried using anhydrous MgSO$_4$, then filtered through Celite. The solvent was removed under vacuum. The solid was triturated with a few milliliters of acetone for 2 min, and the undissolved solid was isolated using a disposable fritted funnel. The white powder was dried under vacuum (Yield: 4.02 g, 59.7%). $^1$H NMR (400 MHz, CDCl$_3$) δ 7.26-7.18 (m, 4H), 7.14 (d, J=7.9 Hz, 4H), 3.57 (ddd, J=23.4, 12.4, 7.7 Hz, 1H), 3.24 (td, J=12.9, 7.1 Hz, 1H), 2.57-2.41 (m, 1H), 2.46-2.35 (m, 1H), 2.34 (s, 3H), 2.33 (s, 3H), 2.31 (s, 3H), 2.31 (s, 3H), 2.31-2.14 (m, 1H), 2.07 (qdd, J=12.9, 5.0, 2.2 Hz, 1H). $^{13}$C NMR (101 MHz, CDCl$_3$) δ 136.40 (d, J=2.4 Hz), 136.12 (d, J=2.8 Hz), 134.13 (d, J=4.7 Hz), 133.37 (d, J=5.4 Hz), 129.41 (d, J=2.0 Hz), 129.22 (d, J=2.2 Hz), 128.75 (d, J=5.1 Hz), 127.24 (d, J=5.0 Hz), 46.97 (d, J=75.8 Hz), 42.21 (d, J=77.9 Hz), 36.14, 36.12, 29.97 (d, J=12.1 Hz), 27.86 (d, J=9.5 Hz), 21.17 (d, J=3.0 Hz). $^{31}$P NMR (162 MHz, CDCl$_3$) δ 59.51.

Step 5. Preparation of rac-1-chloro-2,5-bis(4-methylphenyl)phospholane

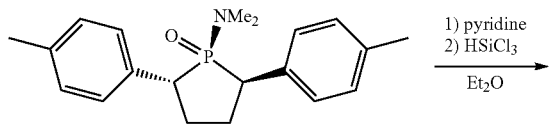

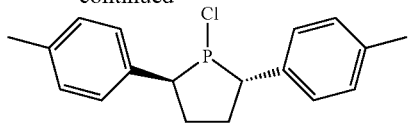

An oven-dried vial was charged with rac-1-(dimethylamino)-2,5-bis(4-methylphenyl)phospholane-1-oxide (1.50 g, 4.60 mmol) mixed in ether (total reaction volume of 30 mL). Pyridine (0.410 mL, 5.06 mmol) and trichlorosilane (0.511 mL, 5.06 mmol) were added sequentially, and the mixture was stirred overnight (approximately 18 hr) at room temperature. Pentane (10 mL) was added to the resulting slurry and it was filtered through a disposable fritted filter. The filtrate was then concentrated to dryness. The solid was dissolved in pentane (20 mL) and passed through a plug of acidic alumina. The alumina was rinsed with another 20 mL of pentane. The filtrate was then concentrated and placed in the freezer at −35° C. Overnight, a precipitate was formed which was then isolated via filtration. The resulting white solid was dried under vacuum (Yield: 601 mg, 43%). $^1$H NMR (400 MHz, C$_6$D$_6$) δ 7.19 (d, J=7.7 Hz, 2H), 7.02 (d, J=7.9 Hz, 2H), 6.98 (s, 4H), 3.80 (td, J=8.7, 2.2 Hz, 1H), 3.17 (ddd, J=33.6, 12.4, 5.8 Hz, 1H), 2.55-2.39 (m, 1H), 2.43-2.29 (m, 1H), 2.13 (s, 6H), 2.07 (dddd, J=13.2, 9.3, 5.8, 1.8 Hz, 1H), 1.71-1.54 (m, 1H). $^{13}$C NMR (101 MHz, C$_6$D$_6$) δ 139.06 (d, J=19.4 Hz), 136.23 (d, J=3.1 Hz), 136.17 (d, J=2.0 Hz), 134.19, 129.82, 129.36, 128.53, 128.49, 57.83 (d, J=31.8 Hz), 53.36 (d, J=32.6 Hz), 34.69 (d, J=2.6 Hz), 32.11 (d, J=3.3 Hz), 21.07, 21.02. $^{31}$P NMR (162 MHz, C$_6$D$_6$) δ 137.01.

Step 6. Preparation of rac-N-butyl-2,5-bis(4-methylphenyl)phospholan-1-amine

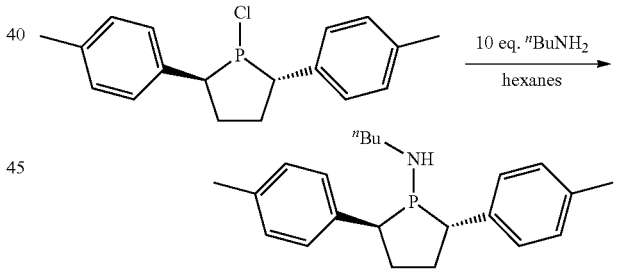

A solution of rac-1-chloro-2,5-bis(4-methylphenyl)phospholane (601 mg, 1.98 mmol) in pentane (30 mL) was treated with n-butylamine (1.45 g, 19.8 mmol) in 5 mL of pentane. After stirring for 30 min, an aliquot was removed for NMR analysis which confirmed complete conversion. The resulting slurry was filtered through a plug of neutral alumina. The alumina was rinsed with an additional 10 mL of pentane. The filtrate was concentrated under vacuum to yield the product as a colorless oil. The oil was dissolved in a small amount of pentane and placed in the freezer at −35° C. After a few hours, a precipitate was formed. The white powder was isolated by filtration and dried under vacuum (Yield: 550 mg, 82%). $^1$H NMR (400 MHz, C$_6$D$_6$) δ 7.31 (dd, J=8.1, 1.8 Hz, 2H), 7.15-7.02 (m, 7H), 3.09 (ddd, J=22.0, 12.5, 6.0 Hz, 1H), 2.95 (dt, J=12.6, 6.7 Hz, 1H), 2.60-2.40 (m, 1H), 2.37-2.23 (m, 1H), 2.19 (s, 3H), 2.17 (s, 3H), 2.15-2.05 (m, 1H), 1.85 (qdd, J=12.5, 5.1, 2.6 Hz, 1H), 1.62 (qdd, J=12.6, 5.1, 2.5 Hz, 1H), 1.08-0.98 (m, 1H), 1.01-0.87 (m, 4H), 0.68 (t, J=6.9 Hz, 3H). $^{13}$C NMR (101 MHz, C$_6$D$_6$) δ 141.47 (d, J=18.3 Hz), 137.32, 135.13 (d, J=2.6 Hz), 134.77 (d, J=2.4 Hz), 129.50-129.45 (d, J=5 Hz), 129.27-129.20 (d, J=5 Hz), 128.22 (d, J=3.4 Hz), 127.97, 55.67 (d, J=14.3 Hz), 50.04 (d, J=22.6 Hz), 47.88 (d, J=23.1 Hz), 35.59 (d, J=6.8 Hz), 34.43 (d, J=2.8 Hz), 31.95 (d, J=2.1 Hz), 21.08, 20.06, 14.01. $^{31}$P NMR (162 MHz, C$_6$D$_6$) δ 72.29.

Step 7. Preparation of rac-N-(bis(2-fluorophenyl) phosphanyl)-N-butyl-2,5-bis(4-methylphenyl)phospholan-1-amine, L645

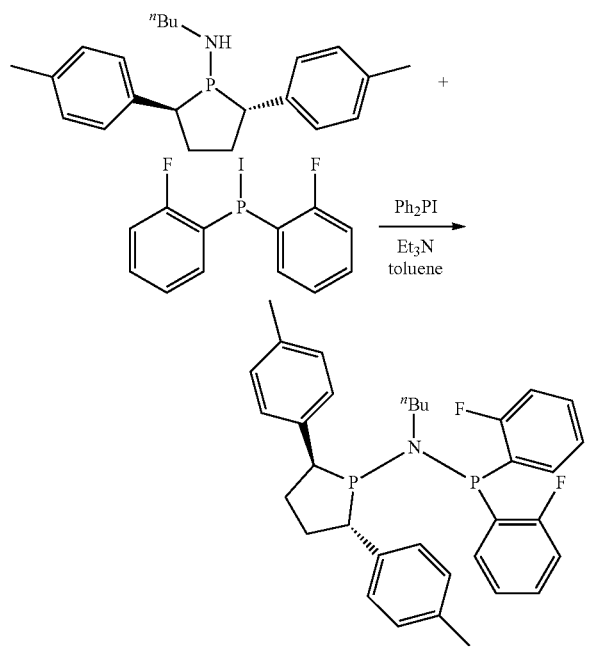

A cold (−30° C.) solution of bis(2-fluorophenyl)iodophosphine (200 mg, 0.574 mmol) in pentane (10 mL) was added to a cold (−30° C.) solution of rac-N-butyl-2,5-bis(4-methylphenyl)phospholan-1-amine (195 mg, 0.574 mmol) and triethylamine (64 mg, 0.631 mmol) in pentane (20 mL), causing immediate formation of precipitate. After 1 hr, an aliquot was analyzed by $^{31}$P NMR which showed complete conversion to the desired product. The reaction mixture was filtered through a small neutral alumina plug, additional pentane was used to wash the alumina, and the solvent was removed under vacuum. A small quantity of pentane was added and a white powder began to precipitate. The material was placed in the freezer at −35° C. for several days. The solution was decanted, and the resulting solid was dried under vacuum. A small sample was taken and analyzed by NMR spectroscopy: 2% rac-N-butyl-2,5-bis(4-methylphenyl)phospholan-1-amine was observed. The solid was stirred in pentane, the solution was decanted, and the solid was dried under vacuum. NMR spectroscopy confirmed the absence of starting material (Yield: 230 mg, 72%). $^{1}$H NMR (400 MHz, C$_6$D$_6$) δ 7.41 (dd, J=8.0, 1.7 Hz, 2H), 7.31 (d, J=7.7 Hz, 2H), 7.10 (d, J=7.7 Hz, 2H), 7.09-6.99 (m, 1H), 6.85 (dddd, J=9.7, 7.8, 5.0, 2.1 Hz, 2H), 6.79 (d, J=7.9 Hz, 2H), 6.75 (ddd, J=8.4, 4.2, 1.3 Hz, 1H), 6.72-6.56 (m, 4H), 4.42 (ddt, J=12.2, 8.3, 4.4 Hz, 1H), 3.33 (ddd, J=24.2, 13.5, 5.4 Hz, 1H), 3.21-2.99 (m, 3H), 2.69-2.52 (m, 1H), 2.17 (s, 3H), 2.15-2.10 (m, 1H), 2.08 (s, 3H), 1.64 (qd, J=12.8, 4.8 Hz, 1H), 1.13 (ddt, J=16.5, 13.7, 7.1 Hz, 1H), 0.70-0.47 (m, 3H), 0.36 (t, J=7.2 Hz, 3H). $^{13}$C NMR (101 MHz, C$_6$D$_6$) δ 166.40-163.73 (m), 163.80-161.28 (m), 141.94, 135.94 (d, J=2.3 Hz), 135.20 (d, J=2.6 Hz), 134.83 (d, J=2.1 Hz), 133.81-133.45 (m), 131.72 (d, J=8.6 Hz), 129.61, 129.50, 129.23, 128.88-128.76 (m), 128.68 (d, J=8.6 Hz), 126.76 (dd, J=27.2, 18.7 Hz), 126.29 (dd, J=19.0, 2.6 Hz), 126.06 (dd, J=18.8, 2.4 Hz), 124.31 (d, J=3.3 Hz), 124.14 (d, J=3.2 Hz), 115.58 (d, J=24.2 Hz), 114.75 (d, J=23.0 Hz), 55.27 (dd, J=31.6, 4.6 Hz), 55.49 (dd, J=13.5, 3.8 Hz), 55.38-55.16 (m), 52.09 (dd, J=21.6, 5.2 Hz), 37.20, 34.35 (d, J=7.4 Hz), 33.00 (dd, J=8.7, 3.5 Hz), 21.11 (d, J=3.0 Hz), 20.00, 13.69. $^{31}$P NMR (162 MHz, C$_6$D$_6$) δ 102.13 (d, J=30.8 Hz), 31.82 (ddd, J=57.1, 42.1, 30.5 Hz). $^{19}$F NMR (376 MHz, C$_6$D$_6$) δ −103.50 (ddt, J=41.9, 10.4, 6.0 Hz), −104.52 (dq, J=57.1, 7.1 Hz).

Preparation of rac-N-(bis(2-fluorophenyl)phosphanyl)-N-butyl-2,5-bis(3,5-dimethylphenyl) phospholan-1-amine, L647

Step 1. Preparation of rac-N-(bis(2-fluorophenyl) phosphanyl)-N-butyl-2,5-bis(3,5-dimethylphenyl) phospholan-1-amine, L647

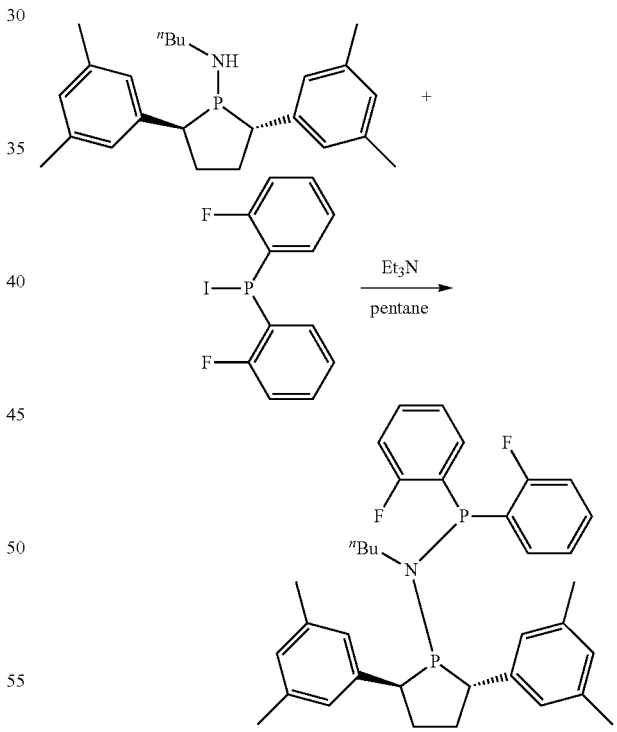

A cold (−30° C.) solution of bis(2-fluorophenyl)iodophosphine (100 mg, 0.288 mmol) in pentane (10 mL) was added dropwise to a cold (−30° C.) solution of rac-N-butyl-2,5-bis(3,5-dimethylphenyl)phospholan-1-amine (106 mg, 0.288 mmol) and triethylamine in pentane (20 mL), causing immediate solid formation. After 30 min, an aliquot was analyzed by $^{31}$P-NMR which confirmed complete conversion to the desired product. The reaction mixture was filtered through a small alumina plug and the solvent was removed under vacuum. The residue was extracted with pentane, the resulting solution was filtered through Celite, and placed in the freezer. White crystals formed overnight. The solution was decanted, and the resulting solid was dried under vacuum (Yield: 65 mg, 38%). $^1$H NMR (400 MHz, C$_6$D$_6$) δ 7.14 (d, J=3.3 Hz, 4H), 7.14-7.06 (m, 1H), 6.92-6.80 (m, 2H), 6.83-6.74 (m, 2H), 6.74-6.60 (m, 4H), 6.53 (s, 1H), 4.37 (ddt, J=12.3, 8.4, 4.5 Hz, 1H), 3.38 (ddd, J=23.7, 13.5, 5.3 Hz, 1H), 3.29-3.02 (m, 2H), 2.73-2.56 (m, 1H), 2.24 (s, 6H), 2.07 (s, 6H), 1.72 (qd, J=12.6, 4.9 Hz, 1H), 1.04 (tdd, J=13.5, 7.5, 3.7 Hz, 1H), 0.69-0.48 (m, 3H), 0.38 (t, J=7.1 Hz, 3H). $^{13}$C NMR (101 MHz, C$_6$D$_6$) δ 166.27-163.84 (m), 163.84-161.19 (m), 144.71 (d, J=20.6 Hz), 138.89 (d, J=2.2 Hz), 137.94-137.74 (m), 137.70-137.50 (m), 133.68 (t, J=5.2 Hz), 133.50 (dd, J=8.3, 5.2 Hz), 131.65 (d, J=8.4 Hz), 130.05 (d, J=8.2 Hz), 128.70, 127.72, 127.71, 127.10-126.84 (m), 126.70 (d, J=8.4 Hz), 126.60-125.98 (m), 124.28 (d, J=3.2 Hz), 124.09 (d, J=3.2 Hz), 115.56 (d, J=23.9 Hz), 114.69 (d, J=23.1 Hz), 55.89-55.41 (m), 55.39 (dd, J=32.3, 5.2 Hz), 52.67 (dd, J=22.1, 4.6 Hz), 36.81, 34.63 (d, J=7.2 Hz), 32.95 (dd, J=8.5, 3.5 Hz), 21.53, 21.39, 20.01, 13.80. $^{31}$P NMR (162 MHz, C$_6$D$_6$) δ 103.43 (d, J=31.1 Hz), 32.16 (ddd, J=55.9, 38.8, 31.4 Hz). $^{19}$F{$^1$H} NMR (376 MHz, C$_6$D$_6$) δ −103.26 (d, J=38.7 Hz), −104.27 (d, J=55.6 Hz). $^{19}$F NMR (376 MHz, C$_6$D$_6$) δ −103.26 (ddt, J=38.4, 9.5, 5.7 Hz), −104.27 (dq, J=55.4, 7.3 Hz).

Preparation of rac-(2S,5S)—N-(bis(2-fluorophenyl)phosphanyl)-N-butyl-2,5-bis(4-(tert-butyl)phenyl)phospholan-1-amine, L648

Step 1. Preparation of 1,4-bis(4-tert-butylphenyl)-1,3-butadiene

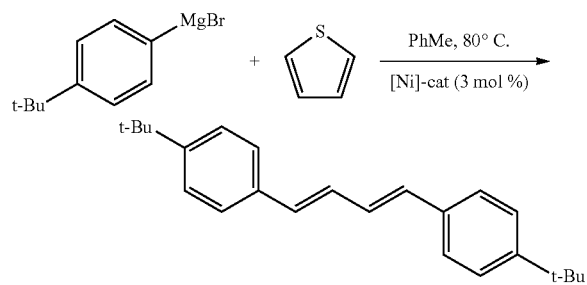

Toluene (100 mL) was added to a round-bottomed flask containing Ni(acetylacetonate)$_2$ (0.193 g, 0.75 mmol, 3 mol %) and 1,3-bis(2,4,6-trimethylphenyl)imidazolium chloride (0.639 g, 1.87 mmol, 7.5 mol %). The toluene mixture was stirred while thiophene (2.0 mL) and 4-tert-butylphenylmagnesium bromide (57.5 mL, 57.5 mmol, 1.0 M) were added sequentially. The reaction vessel was heated to 80° C. The reaction was monitored by GC/MS. Upon completion, the reaction mixture was cooled, diluted with 4 volumes of toluene, and quenched by careful addition of an equal volume of saturated aqueous NH$_4$Cl (caution H$_2$S gas is generated). The organic phase was washed with equal volumes of HCl (2.4 M), NaOH (2 M), and water and was then dried over anhydrous MgSO$_4$. The solution was filtered and concentrated on a rotary evaporator. Initial attempts at purification by recrystallization from hexane were unsuccessful. The material was purified by column chromatography on silica eluting with a mixture of hexane and ethyl acetate (25%). Two fractions were collected and the volatiles were removed under reduced pressure. Fraction 1 (4.2 g) contained a mixture of the desired product (68%) and the homocoupled product, 4,4'-di-tert-butyl-biphenyl (32%). Fraction 2 (1.1 g) contained the desired trans-trans diene product and an impurity which we tentatively assigned as the cis-trans or cis-cis isomers of the product. Total yield of the desired material from the two fractions was approximately 4 g (50% yield). These fractions were combined and used in the subsequent step without further purification. $^1$H NMR (400 MHz, CDCl$_3$) δ: 7.41-7.32 (m, 8H), 6.98-6.85 (m, 2H), 6.71-6.57 (m, 2H), 1.32 (s, 18H). $^{13}$C NMR (101 MHz, CDCl$_3$) δ: 150.61, 134.72, 132.15, 128.76, 126.06, 125.58, 34.62, 31.29.

Step 2. Preparation of rac-(1 S,2R,5 S)-2,5-bis(4-tert-butylphenyl)-1-(dimethylamino)-2,5-dihydrophosphole-1-oxide

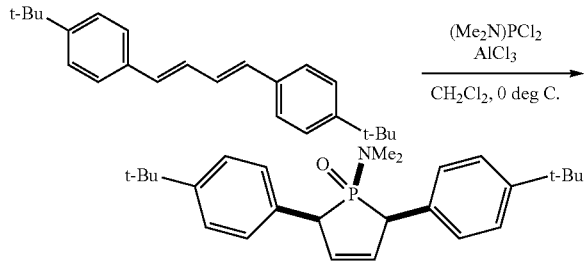

In a reaction not carried out in a glovebox, dimethylphosphoramidous dichloride (4.78 mL, 41.6 mmol) was added to a stirred suspension of aluminum chloride (5.25 g, 39.6 mmol) in dichloromethane (50 mL) in a large jacketed multi-neck flask purged with nitrogen. After 45 min, the resulting greenish solution and a solution of 1,4-bis(4-t-butylphenyl)butadiene (12.1 g, 38.0 mmol) in dichloromethane (125 mL) were both cooled to 0° C. After cooling, the 1,4-bis(4-t-butylphenyl)butadiene solution was slowly added to the dimethylphosphoramidous dichloride-aluminum chloride solution. The mixture was allowed to stir overnight at 0° C. A solution of aqueous EDTA (ethylenediamine tetraacetic acid, 0.2 M, 200 mL) and saturated NaHCO$_3$(100 mL) cooled in ice water was then added to the reaction mixture. The mixture was stirred at 0° C. for 4 h, filtered through Celite, decanted, and the aqueous layer was extracted with dichloromethane. The organic layers were washed with NaHCO$_3$(100 mL), 1M HCl (100 mL), brine (100 mL), and dried over anhydrous MgSO$_4$. The solution was concentrated on a rotary evaporator and the resulting yellow oil was triturated with ether to yield a white solid (6 g, 38%). A second crop was obtained from the washings (4.3 g, 27%) (total yield: 10.3 g, 65%). $^1$H NMR (400 MHz, CDCl$_3$) δ: 7.33 (d, J=8.3 Hz, 4H), 7.24 (dd, J=8.5, 2.2 Hz, 4H), 6.51 (d, J=29.3 Hz, 2H), 4.26 (d, J=18.7 Hz, 2H), 1.88 (d, J=8.3 Hz, 6H), 1.29 (s, 18H). $^{13}$C NMR (101 MHz, CDCl$_3$) δ: 149.78, 149.75, 132.76, 132.68, 130.75 (d, $^2J_{C-P}$=17.0 Hz), 126.81, 126.76, 125.31, 125.28, 48.83 (d, $^1J_{C-P}$=71.9 Hz), 35.89 (d, $^2J_{C-N-P}$=2.0 Hz), 34.45, 31.36. $^{31}$P NMR (162 MHz, CDCl$_3$) δ: 67.72 (ddp, J=45.6, 25.4, 9.7, 9.2 Hz).

Step 3. Preparation of rac-(1S,2R,5 S)-2,5-bis(4-t-butylphenyl)-1-(dimethylamino)phospholane-1-oxide

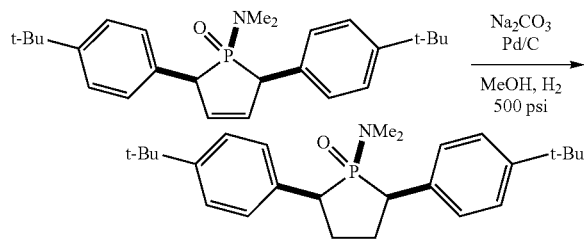

In a reaction not carried out in a glovebox, a pressure reactor was charged with rac-(1S,2R,5S)-2,5-bis(4-t-butylphenyl)-1-(dimethylamino)-2,5-dihydrophosphole-1-oxide (2) (2.5 g, 6.1 mmol), 10% Pd on carbon (0.065 g, 0.06 mmol), sodium carbonate (0.32 g, 3.05 mmol), and methanol (100 mL). The reactor was purged with hydrogen, then pressurized to 500 psi with hydrogen. After 5 h, the reaction mixture was filtered through Celite and the solvent was removed in vacuo to yield a colorless oil, which crystallized upon addition of ether (1.24 g, 49%). $^1$H NMR (400 MHz, CDCl$_3$) δ: 7.30 (d, J=8.4 Hz, 4H), 7.26-7.21 (m, 4H), 3.69-3.62 (m, 1H), 3.62-3.55 (m, 1H), 2.63-2.41 (m, 3H), 1.83 (d, J=8.2 Hz, 6H), 1.28 (s, 18H). $^{31}$P NMR (162 MHz, CDCl$_3$) δ: 66.56. $^{13}$C NMR (101 MHz, CDCl$_3$) δ: 149.34, 149.31, 133.86, 133.81, 126.65, 126.60, 125.16, 125.14, 45.22 (d, $^1J_{C-P}$=72.7 Hz), 35.28 (d, $^2J_{C-N-P}$=2.4 Hz), 34.37, 31.35, 26.78 (d, $^2J_{C-P}$=13.3 Hz).

Step 4. Preparation of rac-(1S,2S,5S)-2,5-bis(4-tert-butylphenyl)-1-(dimethylamino)phospholane-1-oxide

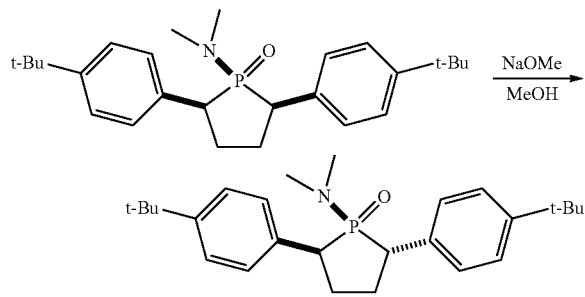

A solution of sodium methoxide (0.33 g, 6.1 mmol) in methanol (20 mL) was added to a vial containing (1S,2R,5S)-2,5-bis(4-tert-butylphenyl)-1-(dimethylamino)phospholane 1-oxide (3) (1.25 g, 3.03 mmol) and a magnetic stir bar. The reaction mixture was stirred for 5 hours and placed in the freezer overnight at −35° C. The following morning the vial was taken out of the freezer and allowed to warm to room temperature, after which point a second addition of sodium methoxide (0.16 g, 3.0 mmol) was made and the reaction mixture was stirred for an additional 6 hours. The solution was then poured into a separatory funnel containing toluene (100 mL) and 1 M HCl (100 mL). The combined organic layer was washed sequentially with the HCl solution, water, brine, and dried over anhydrous MgSO$_4$. After filtration the volatiles were removed on a rotary evaporator and the white solid obtained was recrystallized from hot acetone (~40 mL) to yield the product as a white solid (0.9 g, 72%). $^1$H NMR (400 MHz, CDCl$_3$) δ: 7.36 (dd, J=8.3, 3.5 Hz, 4H), 7.27 (dt, J=8.3, 1.8 Hz, 4H), 3.59 (ddd, J=23.2, 12.3, 7.8 Hz, 1H), 3.26 (td, J=12.8, 7.1 Hz, 1H), 2.57-2.46 (m, 1H), 2.46-2.38 (m, 1H), 2.31 (d, J=8.8 Hz, 6H), 2.28-2.16 (m, 1H), 2.10 (qdd, J=12.6, 4.9, 2.2 Hz, 1H), 1.32 (s, 9H), 1.30 (s, 9H). $^{13}$C NMR (101 MHz, CDCl$_3$) δ: 149.55, 149.52, 149.31, 149.28, 134.08, 134.03, 133.27, 133.21, 128.47, 128.42, 126.97, 126.92, 125.54, 125.52, 125.25, 125.23, 46.90 (d, $^1J_{C-P}$=75.8 Hz), 41.91 (d, $^1J_{C-P}$=78.1 Hz), 36.06, 36.04, 34.44, 34.41, 31.39, 31.36, 30.03 (d, $^2J_{C-P}$=12.3 Hz), 27.68 (d, $^2J_{C-P}$=9.5 Hz). $^{31}$P NMR (162 MHz, CDCl$_3$) δ: 58.87 (m).

Step 5. Preparation of rac-(2S,5S)-2,5-bis(4-tert-butylphenyl)-1-chlorophospholane

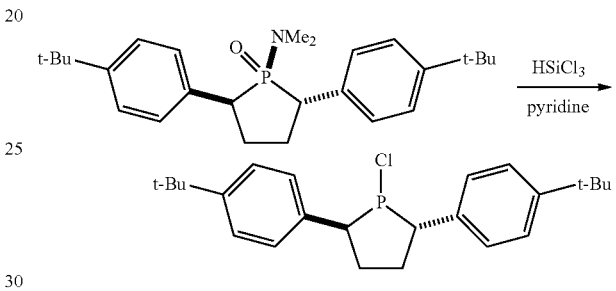

Pyridine (0.74 mL, 9.0 mmol) and trichlorosilane (0.93 mL, 0.89 mmol) were added to a solution of rac-(1S,2S,5S)-2,5-bis(4-tert-butylphenyl)-1-(dimethylamino)phospholane-1-oxide (3.43 g, 8.31 mmol) in ether (80 mL). After stirring overnight, pentane (10 mL) was added to the reaction mixture which was filtered through a disposable fritted filter. The filtrate was concentrated to dryness under reduced pressure to yield a white solid. The white solid was suspended in pentane (20 mL) and placed in the freezer glovebox freezer at −35° C. overnight. The mixture was filtered and the white solid was rinsed sparingly with cold pentane. The white solid was then transferred to a vial and dried under reduced pressure. A second crop was isolated by concentration of the pentane washings followed by cooling in the glovebox freezer to yield a white solid which was isolated by filtration, washed sparingly with cold pentane, and dried under reduced pressure. The combined yield of the two crops was 3.0 g (93%). $^1$H NMR (400 MHz, C$_6$D$_6$) δ: 7.30 (d, J=2.3 Hz, 4H), 7.27 (d, J=8.2 Hz, 2H), 7.09-7.02 (m, 2H), 3.86 (td, J=8.6, 2.2 Hz, 1H), 3.35-3.14 (m, 1H), 2.54 (ddd, J=11.3, 7.2, 3.3 Hz, 1H), 2.42 (dq, J=15.7, 8.1 Hz, 1H), 2.14 (pd, J=10.7, 8.8, 5.3 Hz, 1H), 1.81-1.63 (m, 1H), 1.24 (d, J=2.0 Hz, 18H). $^{13}$C NMR (101 MHz, C$_6$D$_6$) δ: 149.50, 139.10, 138.91, 134.24, 128.41, 127.94, 126.07, 125.57, 57.94, 57.62, 53.49, 53.16, 34.66, 34.48, 32.34, 32.30, 31.49. $^{31}$P NMR (162 MHz, C$_6$D$_6$) δ: 135.93

Step 6. Preparation of rac-(2S,5S)—N-butyl-2,5-bis(4-tert-butylphenyl)phospholan-1-amine

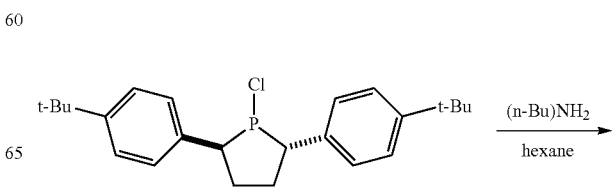

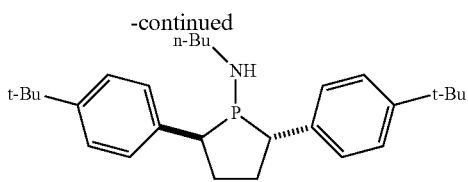

A solution of rac-(2S,5S)-2,5-bis(4-tert-butylphenyl)-1-chlorophospholane (1.0 g, 2.58 mmol) in hexane (45 mL) was added to n-butylamine (2.6 mL, 25.8 mmol) in hexane (45 mL). After stirring for 30 minutes, the resulting slurry was filtered through a plug of neutral alumina. The alumina was rinsed with an additional 45 mL of hexane. The filtrate was concentrated under vacuum to yield the product as an oily white solid. Repeated rinsing of the white residue with cold pentane yielded the product as a white solid upon drying (1.04 g, 95%). $^1$H NMR (400 MHz, C$_6$D$_6$) δ: 7.41-7.34 (m, 4H), 7.33-7.28 (m, 2H), 7.18 (d, J=8.2 Hz, 2H), 3.16 (ddd, J=22.1, 12.5, 6.1 Hz, 1H), 2.99 (dt, J=12.6, 6.7 Hz, 1H), 2.49 (s, 1H), 2.33-2.19 (m, 2H), 2.19-2.09 (m, 1H), 1.90 (qdd, J=12.5, 5.1, 2.6 Hz, 1H), 1.68 (qdd, J=12.6, 5.1, 2.6 Hz, 1H), 1.29 (s, 9H), 1.27 (s, 9H), 1.05 (s, 1H), 1.01-0.81 (m, 4H), 0.68 (t, J=7.0 Hz, 3H). $^{13}$C NMR (101 MHz, C$_6$D$_6$) δ: 148.48, 148.46, 148.26, 141.54, 141.35, 137.32, 125.70, 125.39, 55.64, 55.50, 50.08, 49.85, 47.97, 47.75, 35.53, 35.46, 34.59, 34.56, 34.44, 34.42, 32.03, 32.01, 31.64, 31.61, 20.08, 14.07. $^{31}$P NMR (162 MHz, C$_6$D$_6$) δ: 71.44.

Step 7. Preparation of rac-(2S,5S)—N-(bis(2-fluorophenyl)phosphanyl)-N-butyl-2,5-bis(4-tert-butylphenyl)phospholan-1-amine, L648

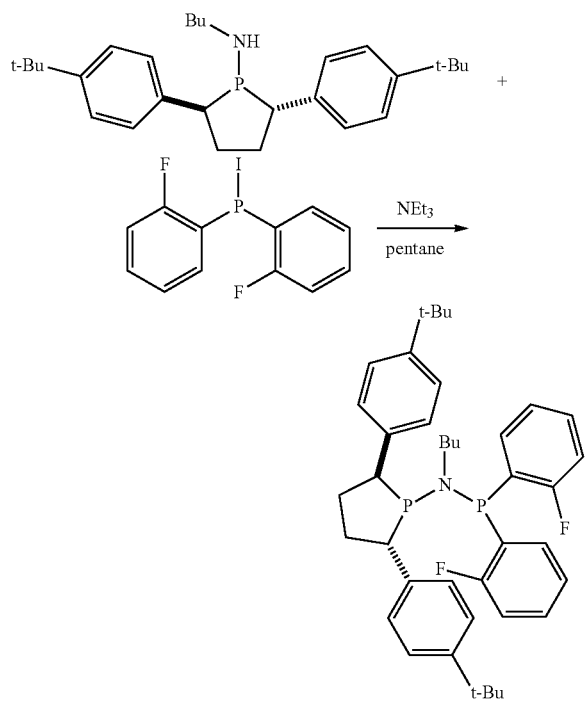

A cold (−35° C.) solution of rac-(2S,5S)—N-butyl-2,5-bis(4-tert-butylphenyl)phospholan-1-amine (6) (0.25 g, 0.59 mmol) and triethylamine (0.09 mL, 0.65 mmol) in pentane (20 mL) was combined with a cold (−35° C.) solution of bis(2-fluorophenyl)iodophosphine (0.21 g, 0.59 mmol) in pentane (20 mL), resulting in the rapid formation of a solid. After 2 h the reaction mixture was filtered through Celite and concentrated. After the volatiles were removed, the residue was extracted with diethyl ether and filtered through neutral alumina. The volatiles were removed under vacuum to yield the product (0.28 g, 74%). $^1$H NMR (400 MHz, C$_6$D$_6$) δ: 7.44 (dd, J=8.3, 1.7 Hz, 2H), 7.37 (t, J=8.8 Hz, 4H), 7.14-7.05 (m, 3H), 6.90-6.80 (m, 3H), 6.77 (dddd, J=9.6, 8.3, 4.2, 1.2 Hz, 1H), 6.73-6.61 (m, 3H), 4.42 (ddt, J=12.2, 8.4, 4.5 Hz, 1H), 3.33 (ddd, J=23.6, 13.5, 5.3 Hz, 1H), 3.23-2.97 (m, 3H), 2.74-2.53 (m, 1H), 2.19 (tt, J=10.6, 5.3 Hz, 1H), 1.68 (qd, J=12.5, 4.9 Hz, 1H), 1.27 (d, J=4.5 Hz, 18H), 0.98 (d, J=8.0 Hz, 0H), 0.71-0.53 (m, 3H), 0.40 (t, J=7.0 Hz, 3H). $^{13}$C NMR (101 MHz, C$_6$D$_6$) δ: 165.66, 164.48, 164.32, 163.40, 162.05, 148.56, 148.53, 148.11, 142.01, 141.81, 136.13, 136.11, 134.19, 134.12, 133.55, 133.50, 131.55, 131.47, 130.41, 130.33, 128.75, 128.72, 128.70, 128.58, 128.49, 128.18, 127.94, 125.72, 125.35, 124.30, 124.26, 124.21, 115.70, 115.47, 115.11, 114.88, 55.48, 55.19, 54.86, 52.65, 52.46, 52.42, 37.25, 34.47, 34.38, 34.33, 34.26, 33.39, 33.35, 33.30, 31.68, 31.61, 20.05, 13.82. $^{31}$P NMR (162 MHz, C$_6$D$_6$) δ: 101.00, 32.49-30.79 (m). $^{19}$F NMR (376 MHz, C$_6$D$_6$) δ: −102.79 (d, J=42.1 Hz), —104.27 (d, J=53.0 Hz).

Preparation of rac-N-cyclobutyl-N-(bis(2,4-difluorophenyl)phosphinyl)-2,5-diphenylphospholan-1-amine, L651

Step 1. Preparation of rac-N-cyclobutyl-N-(bis(2,4-difluorophenyl)phosphinyl)-2,5-diphenylphospholan-1-amine, L651

A cold solution (−30° C.) of triethylamine (0.079 g, 0.78 mmol) in toluene (1.6 mL) was added to a cold (−30° C.) solution of rac-N-cyclobutyl-2,5-diphenylphospholan-1-amine (0.20 g, 0.64 mmol) in toluene (2.0 mL) and the resulting mixture was stirred for 10 min. The mixture was placed in a freezer at −30° C. for 30 minutes. To this cooled reaction mixture was added a cold (−30° C.) solution of bis(2,4-difluorophenyl)iodophosphine (0.22 g, 0.57 mmol) in 2.2 mL of toluene with formation of a white precipitate. The reaction mixture was stirred for 30 min at ambient temperature. The reaction mixture was passed through a 5-cm plug of activated neutral alumina and the solvent was evaporated under vacuum giving solid product which was recrystallized from cold pentane at −30° C. to produce pure product. Yield 0.24 g (66.2%). $^1$H NMR (400 MHz, C$_6$D$_6$, 70° C.) δ 7.27 (d, J=8.1 Hz, 2H), 7.17 (d, J=7.5 Hz, 2H), 7.12-7.01 (m, 3H), 6.96-6.75 (m, 4H), 6.45-6.25 (m, 5H), 4.14 (s, 1H), 3.59 (p, J=8.9 Hz, 1H), 3.19 (m, 1H), 2.75 (d, J=15.2 Hz, 1H), 2.61 (m, 1H), 2.43 (m, 1H), 2.09-1.91 (m, 2H), 1.72-1.31 (m, 4H), 1.11 (q, J=9.5 Hz, 1H). ¹³C NMR (101 MHz, C₆D₆, 70° C.) δ 165.48 (d, J=12.1 Hz), 162.98 (d, J=12.7 Hz), 162.41 (d, J=11.8 Hz), 143.85 (d, J=21.3 Hz), 138.59 (d, J=2.6 Hz), 134.74-133.69 (m), 128.32, 128.27 (d, J=4.1 Hz), 128.02, 127.95, 125.75 (d, J=2.6 Hz), 125.47 (d, J=1.9 Hz), 111.11 (t, J=18.6 Hz), 103.48 (d, J=23.2 Hz), 57.71 (d, J=15.5 Hz), 52.96 (d, J=19.8 Hz), 50.80 (dd, J=23.1, 3.4 Hz), 36.21 (d, J=2.5 Hz), 33.07 (dd, J=8.1, 2.7 Hz), 31.79 (dd, J=12.8, 4.1 Hz), 14.39. ³¹P NMR (162 MHz, C₆D₆, 70° C.) δ 81.98, 29.68. ¹⁹F NMR (376 MHz, C₆D₆ 70° C.) δ 1.84-0.86 (m), —6.90, –8.98.

Preparation of rac-N-cyclopentyl-N-(bis(2,4-difluorophenyl)phosphinyl)-2,5-diphenylphospholan-1-amine, L652

Step 1. Preparation of rac-N-cyclopentyl-N-(bis(2,4-difluorophenyl)phosphinyl)-2,5-diphenylphospholan-1-amine, L652

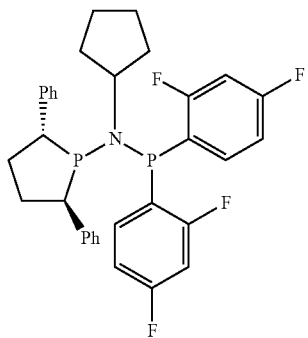 [SMILES: Fc1ccc(P(c2ccc(F)cc2F)N(C2CCCC2)P2[C@@H](c3ccccc3)CC[C@@H]2c2ccccc2)c(F)c1]

A cold solution (−30° C.) of triethylamine (0.075 g, 0.74 mmol) in toluene (1.5 mL) was added to a cold (−30° C.) solution of rac-N-cyclopentyl-2,5-diphenylphospholan-1-amine (0.20 g, 0.62 mmol) in toluene (2.0 mL) and the resulting mixture was stirred for 10 min. The mixture was placed in a freezer at −30° C. for 30 minutes. To this cooled mixture was added a cold (−30° C.) solution of bis(2,4-difluorophenyl)iodophosphine (0.21 g, 0.54 mmol) in 2.1 mL of toluene, with formation of a white precipitate. The reaction mixture was stirred for 30 min at ambient temperature. The reaction mixture was passed through a 5-cm plug of activated neutral alumina and the volatiles were removed under vacuum giving solid product which was recrystallized from cold pentane at −30° C. to produce pure product. Yield 0.14 g (39.1%). ¹H NMR (400 MHz, C₆D₆, 70° C.) δ 7.28 (d, J=7.6 Hz, 2H), 7.19-7.06 (m, 4H), 7.02 (t, J=7.2 Hz, 1H), 6.92 (t, J=7.5 Hz, 2H), 6.84 (dd, J=9.7, 5.4 Hz, 2H), 6.55 (s, 1H), 6.50-6.25 (m, 4H), 4.12 (s, 1H), 3.39 (m, 1H), 3.23 (m, 1H), 2.80 (s, 1H), 2.56-2.33 (m, 1H), 2.12-1.84 (m, 2H), 1.50 (m, 2H), 1.44-0.89 (m, 6H). ¹³C NMR (101 MHz, C₆D₆, 70° C.) δ 165.53 (d, J=12.9 Hz), 164.88, 163.03 (d, J=12.5 Hz), 162.27, 143.87 (d, J=21.2 Hz), 138.61 (d, J=2.7 Hz), 134.68 (q, J=8.8, 8.3 Hz), 134.05, 128.29 (d, J=3.0 Hz), 128.07 (d, J=9.4 Hz), 127.93, 125.62 (dd, J=21.6, 2.4 Hz), 121.45 (d, J=18.7 Hz), 111.03 (d, J=19.9 Hz), 103.21 (d, J=51.9, 26.8 Hz), 63.76 (d, J=15.7 Hz), 53.62, 50.82 (dd, J=22.9, 3.7 Hz), 36.67 (d, J=3.0 Hz), 35.05 (dd, J=7.3, 3.2 Hz), 33.65 (dd, J=12.4, 3.9 Hz), 32.95, 24.06 (d, J=5.9 Hz).

³¹P NMR (162 MHz, C₆D₆, 70° C.) δ 84.22, 30.88. ¹⁹F NMR (376 MHz, C₆D₆ 70° C.) 6-99.62 (m), —107.76, –110.46.

Preparation of (rac)-N-butyl-N-(di(thiophen-2-yl)phosphanyl)-2,5-diphenylphospholan-1-amine. L653

Step 1. Preparation of N,N-dimethyl-1,1-di(thiophen-2-yl)phosphanamine

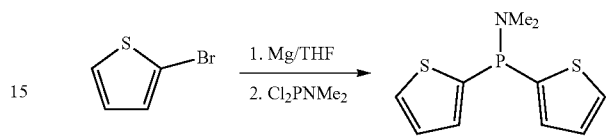

A 50-mL jar equipped with a stir bar and charged with THF (20 mL) and magnesium turnings (0.825 g, 33.9 mmol) was cooled in the freezer to −30° C. 2-Bromothiophene (5.00 g, 30.8 mmol) dissolved in THF (10 mL) was added slowly to the stirring solution, and the reaction mixture was stirred overnight. Analysis (a small aliquot was removed and quenched with deuterated water) by GC/MS showed the reaction to form the thiophenyl Grignard reagent was complete and the jar was placed in the freezer at −30° C. A 200-mL jar equipped with a stir bar and charged with dimethylphosphoramidous dichloride (2.20 g, 15.1 mmol) in THF (75 mL) was cooled in the freezer at −30° C. for 1 h. The cold thiophenyl Grignard reagent (5.60 g, 30.1 mmol) was added slowly to the cold dimethylphosphoramidous dichloride solution. The reaction mixture was allowed to warm to room temperature while stirring overnight. The reaction was checked by ³¹P NMR spectroscopy and found to be complete. The reaction mixture was concentrated to dryness under vacuum and the residue was slurried in toluene (100 mL). The toluene mixture was then passed through a filter which was washed with more toluene (25 mL). The volatiles were removed and the residue was taken up in diethyl ether and filtered. The filtrate was concentrated down and the residue was dissolved in toluene. One third of the solution was saved for a different reaction. Two-thirds of the solution was collected and the solvent was removed under vacuum to yield the product, 1.2 g, overall yield 1.8 g (79%). ¹H NMR (400 MHz, C₆D₆) δ 7.21 (ddd, J=4.6, 3.5, 1.1 Hz, 2H), 7.14 (dd, J=4.9, 1.1 Hz, 2H), 6.81 (ddd, J=4.8, 3.5, 1.3 Hz, 2H), 2.56 (d, J=10.8 Hz, 6H). ¹³C NMR (101 MHz, C₆D₆) δ 141.39 (d, J=30.9 Hz), 134.13 (d, J=24.3 Hz), 130.91 (d, J=2.3 Hz), 127.97 (d, J=6.1 Hz), 41.35 (d, J=15.2 Hz). ³¹P NMR (162 MHz, C₆D₆) δ 41.94.

Step 2. Preparation of iododi(thiophen-2-yl)phosphine

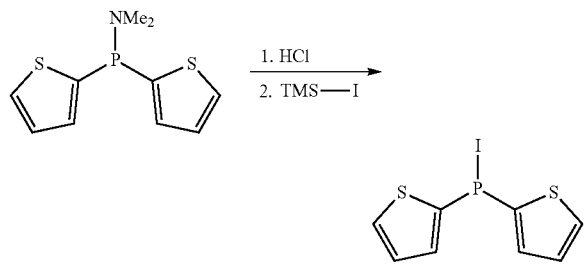

A 50-mL jar was equipped with a stir bar and charged with N,N-dimethyl-1,1-di(thiophen-2-yl)phosphanamine (1.20 g, 4.97 mmol) and toluene (7 mL). HCl in ether (1.00 M, 5.00 mL, 4.97 mmol) was added slowly to the stirring reaction mixture. The reaction mixture was stirred at room temperature overnight. The following day the reaction mixture was checked by $^{31}$P NMR spectroscopy whereupon it was determined some starting material (10%) was still present. Additional HCl in ether (1 mL) was added to the reaction mixture and it was stirred overnight at room temperature. When checked by $^{31}$P NMR spectroscopy the following day, the reaction had gone to completion. The solution was concentrated under vacuum to afford crude chlorodi(thiophen-2-yl)phosphine (Yield 0.63 g, 54%). $^{31}$P NMR (162 MHz, toluene-d$_8$) δ 47.92 (t, J=3.1 Hz). The crude chlorodi(thiophen-2-yl)phosphine was dissolved in toluene (7 mL) and transferred to a 40-mL vial equipped with a stir bar. The mixture was cooled to –30° C. in the freezer and cold (–30° C.) iodotrimethylsilane (813 µL, 5.71 mmol) was added to the stirring reaction mixture causing an instant color change from light yellow to dark yellow. The reaction mixture stirred at room temperature for several days. Analysis by $^{31}$P NMR spectroscopy showed the reaction to be complete. The reaction mixture was concentrated down to afford the product as an orange solid. Yield (0.78 g, 89%). $^1$H NMR (400 MHz, C$_6$D$_6$) δ 7.26 (ddd, J=6.0, 3.6, 1.1 Hz, 2H), 7.05 (ddd, J=4.9, 1.2, 0.4 Hz, 2H), 6.56 (ddd, J=4.9, 3.6, 1.7 Hz, 2H). $^{13}$C NMR (101 MHz, C$_6$D$_6$) δ 136.41 (d, J=34.3 Hz), 134.45 (d, J=1.5 Hz), 128.39. $^{31}$P NMR (162 MHz, C$_6$D$_6$) δ 2.45.

Step 3. Preparation of (rac)-N-butyl-N-(di(thiophen-2-yl)phosphanyl)-2,5-diphenylphospholan-1-amine, L653

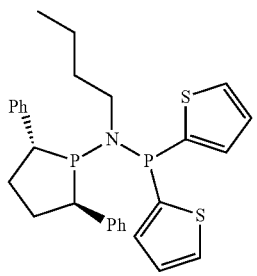 [SMILES: CCCCN(P(c1cccs1)c1cccs1)P1[C@@H](c2ccccc2)CC[C@@H]1c1ccccc1]

A cold (–30° C.) solution of iododi(thiophen-2-yl)phosphine (0.130 g, 0.402 mmol) in toluene (5 mL) was added dropwise to a cold (–30° C.) solution of (rac)-N-butyl-2,5-diphenylphospholan-1-amine (0.125 g, 0.402 mmol) and triethylamine (62 µL, 0.40 mmol) in toluene (5 mL) causing immediate solid formation. After stirring for 1 hour, the reaction mixture was analyzed by $^{31}$P NMR spectroscopy which showed complete conversion to the product. The toluene was removed under vacuum and the residue was extracted with ether. The mixture was filtered through a plug of neutral activated alumina. The ether was removed under vacuum to yield a white solid. The solid was triturated with pentane and dried, affording the product as a white solid. Yield (0.133 g, 65.1%). $^1$H NMR (400 MHz, C$_6$D$_6$) δ 7.41 (m, 2H), 7.31-7.19 (m, 5H), 7.16-6.99 (m, 6H), 6.77 (ddd, J=4.8, 3.5, 1.2 Hz, 1H), 6.74-6.70 (m, 2H), 4.22 (m, 1H), 3.38-3.12 (m, 3H), 3.09-2.96 (m, 1H), 2.51-2.38 (m, 1H), 2.25-2.12 (m, 1H), 1.68-1.53 (m, 1H), 1.29-1.16 (m, 1H), 0.93-0.75 (m, 3H), 0.60-0.54 (m, 3H). $^{13}$C NMR (101 MHz, C$_6$D$_6$) δ 144.63 (d, J=21.0 Hz), 143.59 (d, J=35.6 Hz), 140.51 (dd, J=32.1, 1.4 Hz), 139.43 (d, J=2.2 Hz), 135.42 (d, J=27.9 Hz), 133.82 (d, J=23.2 Hz), 131.07 (dd, J=30.1, 1.9 Hz), 129.10 (dd, J=3.4, 2.2 Hz), 128.87-128.46 (m), 127.51 (d, J=7.3 Hz), 125.97 (dd, J=35.2, 2.2 Hz), 55.23-55.10 (m), 54.96-54.69 (m), 52.02 (dd, J=22.9, 3.4 Hz), 36.33 (d, J=2.4 Hz), 34.10 (d, J=8.3 Hz), 33.38 (dd, J=8.1, 3.3 Hz), 20.18, 13.92. $^{31}$P NMR (162 MHz, C$_6$D$_6$) δ 97.24 (d, J=27.6 Hz), 33.93 (d, J=27.6 Hz). HRMS (ESI-TOF) m/z: [M+H]+ Calcd for C$_{28}$H$_{31}$NP$_2$S$_2$ 508.1446; Found 508.1438.

Preparation of (rac)-N-(diphenylphosphanyl)-N,2,5-triphenylphospholan-1-amine, L654

Step 1. Preparation of N,1,1-triphenylphosphanamine

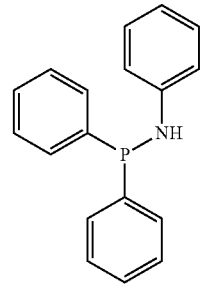 [SMILES: c1ccc(NP(c2ccccc2)c2ccccc2)cc1]

A solution of chlorodiphenylphosphine (1.0 mL, 5.4 mmol) in hexanes (5.0 mL) was added to aniline (1.1 mL, 12 mmol), causing a white precipitate to form. After stirring for 1 h, the mixture was filtered to remove the salts and the filtrate was concentrated to yield the product as a white solid. Yield (1.3 g, 86%). $^1$H NMR (400 MHz, C$_6$D$_6$) δ 7.44-7.33 (m, 4H), 7.13-7.02 (m, 8H), 6.97-6.87 (m, 2H), 6.81-6.69 (m, 1H), 4.09 (d, J=7.6 Hz, 1H). $^{13}$C NMR (101 MHz, C$_6$D$_6$) δ 147.04 (d, J=17.1 Hz), 140.72 (d, J=13.0 Hz), 131.59 (d, J=20.6 Hz), 129.56 (d, J=1.3 Hz), 129.18, 128.83, 128.77, 119.87 (d, J=1.2 Hz), 116.52 (d, J=13.0 Hz). $^{31}$P NMR (162 MHz, C$_6$D$_6$) δ 28.93.

Step 2. Preparation of (rac)-N-(diphenylphosphanyl)-N,2,5-triphenylphospholan-1-amine, L654

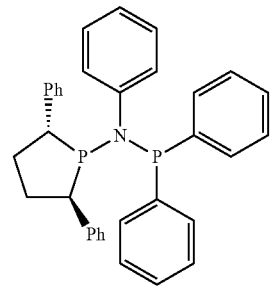 [SMILES: c1ccc([C@H]2CC[C@H](c3ccccc3)P2N(c2ccccc2)P(c2ccccc2)c2ccccc2)cc1]

A cold (–30° C.) solution of N,1,1-triphenylphosphanamine (0.25 g, 0.90 mmol) and triethylamine (151 µL, 1.08 mmol) in toluene (2 mL) was combined with a cold (–30°

C.) solution of (rac)-2,5-diphenyliodophospholane (0.33 g, 0.90 mmol) in toluene (2 mL) and placed back in the freezer for 30 minutes. The solvent was then removed under vacuum and the residue was extracted with ether and passed through a plug of activated neutral alumina. After removing the volatiles, the product was dissolved in pentane and crashed out in the freezer to yield the product as a white solid. Yield 0.25 g, 54%. $^{1}$H NMR (400 MHz, C$_6$D$_6$) δ 7.56-7.46 (m, 1H), 7.45-7.33 (m, 4H), 7.29-7.15 (m, 6H), 7.15-6.85 (m, 10H), 6.71-6.62 (m, 2H), 6.42-6.32 (m, 2H), 4.08 (ddt, J=10.9, 6.8, 3.4 Hz, 1H), 3.20 (ddd, J=25.1, 13.3, 5.8 Hz, 1H), 2.35-2.09 (m, 2H), 2.08-1.91 (m, 1H), 1.57-1.30 (m, 1H). $^{13}$C NMR (101 MHz, Benzene-d$_6$) δ 146.39 (t, J=4.6 Hz), 144.04 (d, J=22.0 Hz), 139.49, 133.44 (d, J=20.8 Hz), 133.15 (d, J=22.0 Hz), 130.52 (d, J=2.8 Hz), 128.83 (d, J=4.9 Hz), 128.65, 128.53 (d, J=3.8 Hz), 128.43, 128.34, 127.65 (d, J=6.8 Hz), 125.97 (d, J=2.5 Hz), 125.43, 125.03, 52.97 (d, J=14.3 Hz), 52.81, 52.72 (d, J=9.8 Hz), 52.50 (d, J=6.1 Hz), 36.29 (d, J=2.1 Hz), 32.16 (d, J=4.1 Hz). $^{31}$P NMR (162 MHz, C$_6$D$_6$) δ 100.50 (d, J=117.5 Hz), 68.64 (d, J=118.9 Hz).

Preparation of rac-N-butyl-N-(bis(4-chloro-2-fluoro-phenyl)phosphinyl)-2,5-diphenylphospholan-1-amine, L664

Step 1. Preparation of bis(4-chloro-2-fluorophenyl)diethylaminophosphine

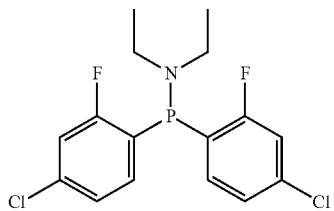 [SMILES: CCN(CC)P(c1ccc(Cl)cc1F)c1ccc(Cl)cc1F]

n-Butyllithium in hexane (4.9 mL, 1.6 M, 7.8 mmol) was added slowly to a cold (−78° C.) solution of 4-chloro-2-fluoro-1-iodobenzene (2.00 g, 7.80 mmol) in ether (20.0 mL). The resulting reaction mixture was stirred for one hour at −78° C. A solution of diethylphosphoramidous dichloride (0.62 g, 3.6 mmol) in ether (1.0 mL) was added slowly at −78° C. The reaction mixture was allowed to warm while stirring overnight. The volatiles were removed under reduced pressure. The solid was extracted with hexanes, filtered, and the volatiles were removed under reduced pressure overnight to give a dark brown solid. Yield 1.14 g (89.1%). $^{1}$H NMR (400 MHz, C$_6$D$_6$) δ 6.91 (m, 2H), 6.85-6.75 (m, 2H), 6.69 (m, 2H), 2.78 (dq, J=9.8, 7.1 Hz, 4H), 0.71 (t, J=7.1 Hz, 6H). $^{13}$C NMR (101 MHz, C$_6$D$_6$) δ 164.42 (d, J=17.5 Hz), 161.95 (d, J=17.4 Hz), 135.86 (d, J=11.3 Hz), 132.90 (t, J=6.9 Hz), 124.55 (d, J=3.7 Hz), 116.01 (d, J=27.1 Hz), 44.67 (d, J=17.4 Hz), 14.04 (d, J=3.7 Hz). $^{31}$P NMR (162 MHz, C$_6$D$_6$) δ 37.31 (t, J=44.0 Hz). $^{19}$F NMR (376 MHz, C$_6$D$_6$) δ −102.23 (dt, J=44.0, 8.4 Hz).

Step 2. Preparation of bis(4-chloro-2-fluorophenyl)chlorophosphine

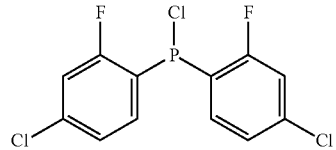

A solution of HCl in ether (7.87 mL, 1.0 M, 7.87 mmol) was added to a cold (−30° C.) solution of bis(4-chloro-2-fluorophenyl)diethylaminophosphine (1.14 g, 3.15 mmol) in diethyl ether (10.0 mL). The reaction mixture was allowed to stir for 1 h while warming to ambient temperature. The reaction mixture was filtered and the volatiles were removed under reduced pressure. The residue was extracted with hexanes and filtered. The volatiles were removed under reduced pressure to give the product as a dark brown solid. $^{31}$P NMR spectra showed 59.9% of the desired product. Yield 0.47 g (46.1%). The product was used in the next step without further purification. $^{1}$H NMR (400 MHz, C$_6$D$_6$) δ 7.14 (m, 2H), 6.71 (m, 2H), 6.56 (m, 1H). $^{13}$C NMR (101 MHz, C$_6$D$_6$) δ 164.34 (d, J=18.7 Hz), 161.84 (d, J=18.7 Hz), 138.36 (d, J=11.0 Hz), 133.34 (ddd, J=13.0, 3.9, 1.6 Hz), 125.47-124.30 (m), 116.27 (d, J=26.3 Hz). $^{31}$P NMR (162 MHz, C$_6$D$_6$) δ 63.95-53.04 (m). $^{19}$F NMR (376 MHz, C$_6$D$_6$) δ −102.09--103.21 (m).

Step 3. Preparation of bis(4-chloro-2-fluorophenyl)iodophosphine

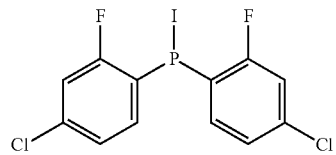 [SMILES: Fc1cc(Cl)ccc1P(I)c1ccc(Cl)cc1F]

Iodotrimethylsilane (0.48 g, 2.2 mmol) was added to a solution of bis(4-chloro-2-fluorophenyl)chlorophosphine (0.47 g, 1.4 mmol) in toluene (5.0 mL) to form an orange solution. The mixture was stirred at room temperature overnight. The reaction mixture was filtered to remove the dark precipitate which was suspended in the solution after the reaction. The volatiles were evaporated under reduced pressure to give a yellowish liquid. $^{31}$P NMR spectra showed 71.4% of the desired product. Yield (0.51 g, 85%). $^{1}$H NMR (400 MHz, C$_6$D$_6$) δ 7.15-7.03 (m, 2H), 6.63 (ddt, J=8.3, 2.0, 0.6 Hz, 2H), 6.51 (ddd, J=9.3, 3.7, 2.0 Hz, 2H). $^{13}$C NMR (101 MHz, C$_6$D$_6$) δ 164.11 (d, J=18.4 Hz), 161.61 (d, J=18.5 Hz), 138.46 (d, J=10.5 Hz), 136.78 (dd, J=11.6, 4.2 Hz), 125.15 (dd, J=3.8, 1.9 Hz), 116.25 (d, J=26.3 Hz). $^{31}$P NMR (162 MHz, C$_6$D$_6$) δ 6.07 (t, J=57.2 Hz). $^{19}$F NMR (376 MHz, C$_6$D$_6$) δ −98.59 (dt, J=57.2, 8.5 Hz).

Step 4. Preparation of rac-N-butyl-N-(bis(4-chloro-2-fluorophenyl)phosphinyl)-2,5-diphenylphospholan-1-amine, L664

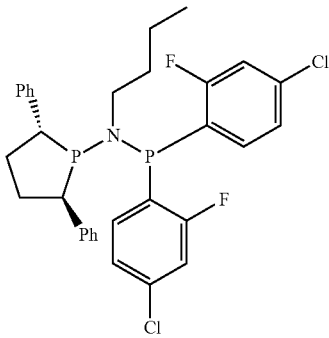 [SMILES: CCCCN(P(c1ccc(Cl)cc1F)c1ccc(Cl)cc1F)P1[C@@H](c2ccccc2)CC[C@@H]1c1ccccc1]

A cold solution (−30° C.) of triethylamine (0.063 g, 0.63 mmol) in toluene-d₈ (1.3 mL) was added to a cold (−30° C.) solution of rac-N-butyl-2,5-diphenylphospholan-1-amine (0.13 g, 0.42 mmol) in toluene-d₈ (1.3 mL) and the resulting mixture was stirred for 10 min. The mixture was placed in a freezer at −30° C. for 30 minutes. To this cooled mixture was added a cold (−30° C.) solution of bis(4-chloro-2-fluorophenyl)iodophosphine (0.17 g, 0.42 mmol) in toluene (1.7 mL), with formation of a white precipitate. The reaction mixture was stirred for 30 min at ambient temperature. The reaction mixture was passed through a 5-cm plug of activated neutral alumina and the solvent was evaporated under vacuum giving solid product which was recrystallized from cold pentane at −30° C. to produce pure product. Yield 0.05 g (20%). $^1$H NMR (400 MHz, C₆D₆) δ 7.31 (dt, J=8.0, 1.5 Hz, 2H), 7.19 (ddd, J=7.8, 4.3, 2.9 Hz, 4H), 7.06 (td, J=7.3, 1.3 Hz, 1H), 6.90 (dd, J=8.2, 6.6 Hz, 2H), 6.82 (t, J=7.3 Hz, 1H), 6.75-6.58 (m, 5H), 6.37 (td, J=7.7, 4.4 Hz, 1H), 4.10 (m, 1H), 3.16 (m, 1H), 2.98-2.71 (m, 3H), 2.54-2.34 (m, 1H), 2.00 (dq, J=11.1, 5.3 Hz, 1H), 1.48 (dd, J=12.7, 5.0 Hz, 1H), 1.01 (m, 1H), 0.61 (h, J=7.5, 7.0 Hz, 3H), 0.36 (t, J=7.1 Hz, 3H). $^{13}$C NMR (101 MHz, C₆D₆) δ 165.00 (d, J=19.4 Hz), 163.11 (d, J=17.3 Hz), 162.52 (d, J=19.3 Hz), 160.64 (d, J=17.2 Hz), 143.80 (d, J=20.9 Hz), 138.38 (d, J=2.3 Hz), 136.75 (d, J=10.5 Hz), 135.56-134.57 (m), 133.63 (d, J=6.1 Hz), 128.44, 128.41-128.31 (m), 128.27 (d, J=6.4 Hz), 128.15, 128.07, 125.89 (d, J=2.5 Hz), 125.63 (d, J=1.9 Hz), 124.56 (d, J=3.4 Hz), 124.41 (d, J=3.4 Hz), 116.10 (d, J=27.5 Hz), 115.39 (d, J=26.8 Hz), 54.59 (d, J=27.2 Hz), 51.79 (dd, J=22.5, 4.6 Hz), 36.65 (d, J=1.8 Hz), 33.84 (dd, J=6.7, 2.2 Hz), 32.53 (dd, J=7.6, 3.5 Hz), 22.31, 19.54, 13.86, 13.26. $^{31}$P NMR (162 MHz, C₆D₆) δ 101.47, 32.98-28.58 (m). $^{19}$F NMR (376 MHz, C₆D₅CD₃) 6-112.24-−112.40 (m), −112.71 (m).

Preparation of (2R,5R)—N-butyl-N-(di(thiophen-3-yl)phosphanyl)-2,5-diphenylphospholan-1-amine, L665

Step 1. Preparation of N,N-dimethyl-1,1-di(thiophen-3-yl)phosphanamine

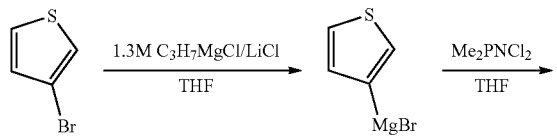

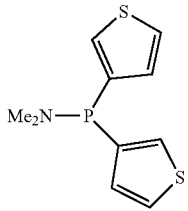

A 40-mL vial equipped with a stir bar and charged with THF (5 mL) and 3-bromothiophene (1.109 g, 6.852 mmol) was placed in the freezer (∼−30° C.) for two hours. Once removed from the freezer, isopropylmagnesium chloride-lithium chloride complex solution in THF (5.270 mL, 1.30 M, 6.85 mmol) that had also been in the freezer was added slowly to the stirring solution. The reaction mixture was stirred for two hours at room temperature and then placed back in the freezer. A new 40-mL vial was charged with dimethylphosphoroamidous dichloride (0.500 g, 3.43 mmol) in THF (10 mL) and placed in the freezer for 1 hour. Both reagents were removed and the 3-bromothiophene and isopropylmagnesium chloride-lithium chloride complex reaction mixture was slowly added to the dimethylphosphoroamidous dichloride solution. The reaction mixture stirred at room temperature for two and a half hours. The reaction was followed by $^{31}$P NMR spectroscopy and was determined to be complete. The reaction mixture was concentrated down, extracted with toluene, and filtered through a plug of neutral alumina. The filtrate was used in the next step as-is. $^1$H NMR (400 MHz, C₆D₆) δ 7.14-7.11 (m, 2H), 6.97-6.95 (m, 4H), 2.45 (d, J=10.3 Hz, 6H). $^{13}$C NMR (101 MHz, C₆D₆) δ 130.60 (d, J=17.9 Hz), 129.55 (d, J=21.7 Hz), 126.20 (d, J=5.7 Hz), 41.53 (d, J=14.8 Hz). $^{31}$P NMR (162 MHz, C₆D₆) δ 44.62.

Step 2. Preparation of chlorodi(thiophen-3-yl)phosphine

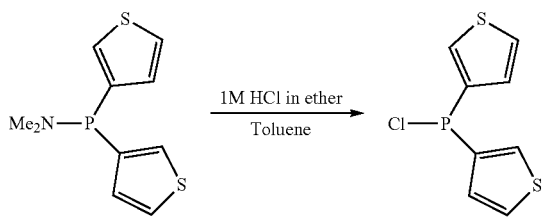 [SMILES: CN(C)P(c1ccsc1)c1ccsc1 ; "1M HCl in ether" ; "Toluene" ; ClP(c1ccsc1)c1ccsc1]

A mixture of N,N-dimethyl-1,1-di(thiophen-3-yl)phosphanamine and toluene in a 40 mL-vial was stirred while HCl in diethyl ether (4.25 mL, 1.0 M, 4.25 mmol) was added slowly. The reaction mixture was stirred at room temperature for three and a half hours. The reaction was checked by $^{31}$P NMR spectroscopy and was determined to be complete. The reaction mixture was filtered and concentrated down to afford 0.5305 g, 67.31%. $^1$H NMR (400 MHz, C₆D₆) δ 7.11 (dddd, J=4.6, 2.8, 1.2, 0.4 Hz, 2H), 6.95 (dddd, J=5.0, 2.2, 1.2, 0.4 Hz, 2H), 6.72 (dddd, J=5.0, 2.8, 1.1, 0.4 Hz, 2H). $^{13}$C NMR (101 MHz, C₆D₆) δ 138.88 (d, J=35.5 Hz), 131.99 (d, J=33.5 Hz), 129.34 (d, J=16.0 Hz), 127.17 (d, J=5.1 Hz). $^{31}$P NMR (162 MHz, C₆D₆) δ 57.83.

Step 3. Preparation of iododi(thiophen-3-yl)phosphine

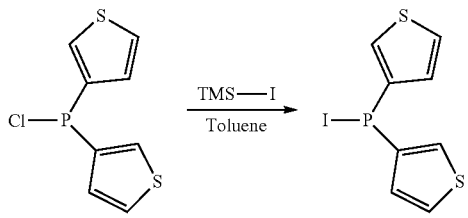

A 40-mL vial was equipped with a stir bar and charged with chlorodi(thiophen-3-yl)phosphine (0.484 g, 2.0814 mmol) in toluene (7 mL). The vial was placed in the freezer (about −30° C.) for fifteen minutes. Once removed from the freezer, iodotrimethylsilane (355 µL, 2.50 mmol) that had also been in the freezer was added slowly to the stirring solution. The reaction mixture immediately changed from light yellow to dark yellow. The reaction mixture was stirred for three and a half hours. The course of the reaction was checked by $^{31}$P NMR spectroscopy and was determined to be complete. The reaction mixture was concentrated down to afford 0.591 g, 87.6%. $^1$H NMR (400 MHz, C$_6$D$_6$) δ 7.14-7.07 (m, 4H), 6.77 (ddd, J=5.0, 2.8, 1.1 Hz, 2H). $^{13}$C NMR (101 MHz, C$_6$D$_6$) δ 132.50 (d, J=32.3 Hz), 131.89 (d, J=15.0 Hz), 127.52 (d, J=4.8 Hz). $^{31}$P NMR (162 MHz, C$_6$D$_6$) δ 5.90.

Step 4. Preparation of (2R,5R)—N-butyl-N-(di(thiophen-3-yl)phosphanyl)-2,5-diphenylphospholan-1-amine, L665

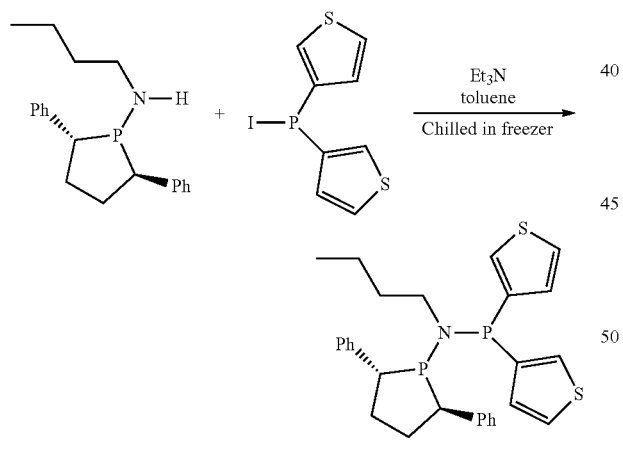

A cold (−30° C.) solution of iododi(thiophen-3-yl)phosphine (0.260 g, 0.836 mmol) in toluene (5 mL) was added dropwise to a cold (−30° C.) solution of (rac)-N-butyl-2,5-diphenylphospholan-1-amine (0.200 g, 0.643 mmol) and triethylamine (99 µL, 0.707 mmol) toluene (5 mL) causing immediate solid formation. After stirring for 1 hour, the sample was analyzed by $^{31}$P NMR spectroscopy which showed complete conversion to the product. The toluene was removed under vacuum, the residue was extracted with ether, and filtered through a plug of neutral activated alumina. The ether was removed under vacuum to yield a white solid. The solid was triturated with cold pentane and dried, affording 0.220 g, 67.53% as a white solid. $^1$H NMR (400 MHz, C$_6$D$_6$) δ 7.46-7.40 (m, 2H), 7.30-7.13 (m, 7H), 7.12-7.06 (m, 3H), 6.90-6.88 (m, 2H), 6.77 (ddd, J=4.9, 2.8, 1.3 Hz, 1H), 6.58 (td, J=2.9, 1.2 Hz, 1H), 6.38 (ddd, J=4.9, 2.0, 1.2 Hz, 1H), 4.04 (ddt, J=12.3, 7.4, 4.7 Hz, 1H), 3.39-3.25 (m, 1H), 3.08-2.85 (m, 3H), 2.44-2.31 (m, 1H), 2.21-2.11 (m, 1H), 1.10-0.98 (m, 1H), 0.78-0.61 (m, 3H), 0.53-0.47 (m, 3H). $^{13}$C NMR (101 MHz, C$_6$D$_6$) δ 144.65 (d, J=20.9 Hz), 141.81 (d, J=25.3 Hz), 139.78 (d, J=2.3 Hz), 139.17 (d, J=18.4 Hz), 131.37-130.22 (m), 129.52 (d, J=19.2 Hz), 129.31-129.14 (m), 128.89-128.52 (m), 126.50 (d, J=5.7 Hz), 126.23 (d, J=2.5 Hz), 125.85 (d, J=1.9 Hz), 125.33 (d, J=5.9 Hz), 55.85-55.31 (m), 54.63 (dd, J=31.5, 5.9 Hz), 51.87 (dd, J=22.5, 3.4 Hz), 36.77 (d, J=2.7 Hz), 34.14 (d, J=7.2 Hz), 33.26 (dd, J=7.9, 3.4 Hz), 20.10, 13.89. $^{31}$P NMR (162 MHz, C$_6$D$_6$) δ 97.06 (d, J=24.4 Hz), 37.46 (d, J=24.4 Hz).

Preparation of (2R,5R)—N-butyl-N-(di(furan-3-yl)phosphanyl)-2,5-diphenylphospholan-1-amine, L696

Step 1. Preparation of N,N-dimethyl-1,1-di(furan-3-yl)phosphanamine

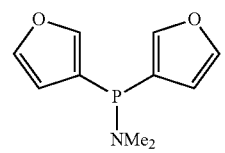

n-Butyllithium (6.86 mL, 2.5 M, 17 mmol) was slowly added to a chilled (−70° C. (dry-ice acetone bath)) solution of 3-bromofuran (2.832 g, 19.270 mmol) in THF (~40 mL) in a 250-mL three-necked round bottom flask equipped with a stir bar and a thermocouple. The reaction mixture was stirred at −70° C. for 2 hours. A solution of dimethylphosphoramidous dichloride (1.250 g, 8.565 mmol) in THF (~40 mL) was then slowly added by syringe. The reaction mixture was stirred for 2 hours. Analysis of the crude reaction mixture by $^{31}$P NMR spectroscopy showed the reaction was complete. The bright yellow reaction mixture was carried on to the next step as is. $^{31}$P NMR (162 MHz, THF) δ 20.41 (s).

Step 2. Preparation of chlorodi(furan-3-yl)phosphine

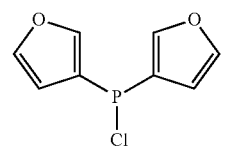 [SMILES: ClP(c1ccoc1)c1ccoc1]

To the reaction mixture (comprising N,N-dimethyl-1,1-di(furan-3-yl)phosphanamine in THF) from the previous step, still at −70° C., was added a solution of HCl in diethyl ether (18.85 mL, 1.0 M, 19 mmol). The reaction mixture was stirred overnight while warming up to room temperature. Analysis of the crude reaction mixture by $^{31}$P NMR spectroscopy showed the reaction was complete. The reaction mixture was taken back into a glovebox and the crude mixture was filtered through Celite and concentrated down to afford 0.922 g, 53.68% of light yellow solid. $^1$H NMR (400 MHz, $C_6D_6$) δ 7.24-7.22 (m, 1H), 7.14 (dd, J=1.5, 0.9 Hz, 1H), 7.04-7.00 (m, 1H), 6.94 (td, J=1.7, 0.9 Hz, 1H), 6.35-6.33 (m, 1H), 6.31 (td, J=1.8, 0.9 Hz, 1H). $^{13}$C NMR (101 MHz, $C_6D_6$) δ 147.79 (d, J=20.2 Hz), 147.46 (d, J=4.5 Hz), 144.71 (d, J=5.0 Hz), 143.91 (t, J=2.5 Hz), 113.55 (t, J=6.1 Hz), 111.82 (d, J=8.2 Hz). $^{31}$P NMR (162 MHz, $C_6D_6$) δ 40.26.

Step 3. Preparation of di(furan-3-yl)iodophosphane

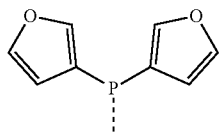

A 40-mL vial equipped with a stir bar and containing a solution of chlorodi(furan-3-yl)phosphane (0.500 g, 85% pure by $^{31}$P NMR, 2.493 mmol) in toluene (7 mL) was placed in the freezer (−30° C.) for 45 minutes. Cold iodotrimethylsilane (362 μL, 2.543 mmol) that had been in the freezer was added to the stirring reaction mixture. The reaction mixture was allowed to warm to ambient temperature. Analysis after 15 minutes by $^{31}$P NMR spectroscopy showed the reaction was complete. The reaction mixture was concentrated down to afford 0.3059 g, 49.43% of dark yellow oil. $^1$H NMR (400 MHz, $C_6D_6$) δ 7.26-7.20 (m, 1H), 7.12-7.08 (m, 1H), 7.05-7.00 (m, 1H), 6.99-6.94 (m, 1H), 6.35-6.30 (m, 2H). $^{13}$C NMR (101 MHz, $C_6D_6$) δ 147.34, 146.92, 144.60 (d, J=5.1 Hz), 143.90 (t, J=2.4 Hz), 114.13 (d, J=8.1 Hz), 113.55 (t, J=6.1 Hz). $^{31}$P NMR (162 MHz, $C_6D_6$) δ −14.79.

Preparation of (2R,5R)—N-butyl-N-(di(furan-3-yl)phosphanyl)-2,5-diphenylphospholan-1-amine, L696

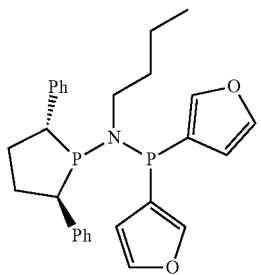 [SMILES: CCCCN(P(c1ccoc1)c1ccoc1)P1[C@@H](c2ccccc2)CC[C@@H]1c1ccccc1]

A cold (30 minutes in a −30° C. freezer) solution of di(furan-3-yl)iodophosphane (0.255 g, 60% pure by $^{31}$P NMR, 0.857 mmol) in toluene (5 mL) was added dropwise to a cold (30 minutes in a −30° C. freezer) solution of (rac)-N-butyl-2,5-diphenylphospholan-1-amine (0.160 g, 0.514 mmol) and triethylamine (79 μL, 0.565 mmol) in toluene (5 mL), causing immediate formation of precipitate. The reaction mixture was stirred for 45 minutes. Analysis by $^{31}$P-NMR spectroscopy showed the reaction had reached complete conversion. The toluene was removed under vacuum, the residue was extracted with ether and filtered through a plug of neutral activated alumina. The ether was removed under vacuum to yield an oil which was analyzed by $^{31}$P-NMR and found to contain some impurities. The product was purified by passing a toluene solution of the oil through a plug of basic alumina. The filtrate was concentrated down to afford the product as a light yellow oil, 41.3 mg, 16.9%. $^1$H NMR (500 MHz, $C_6D_6$) δ 7.40-7.35 (m, 2H), 7.27-7.21 (m, 3H), 7.20-7.16 (m, 2H), 7.14-7.11 (m, 2H), 7.06-7.00 (m, 3H), 6.96 (q, J=1.5 Hz, 1H), 6.69 (dt, J=1.4, 0.7 Hz, 1H), 6.15 (dt, J=1.9, 1.0 Hz, 1H), 5.70 (dt, J=1.9, 1.0 Hz, 1H), 4.00 (ddt, J=12.3, 7.4, 4.7 Hz, 1H), 3.34-3.21 (m, 1H), 3.00-2.79 (m, 3H), 2.41-2.29 (m, 1H), 2.12 (ddt, J=14.8, 13.0, 5.2 Hz, 1H), 1.61-1.48 (m, 1H), 1.26-1.13 (m, 1H), 0.88-0.65 (m, 3H), 0.56-0.52 (m, 3H). $^{13}$C NMR (126 MHz, $C_6D_6$) δ 147.01 (d, J=29.6 Hz), 146.24 (d, J=29.5 Hz), 143.84 (d, J=5.3 Hz), 143.07 (d, J=5.7 Hz), 139.85 (d, J=2.4 Hz), 129.23-129.08 (m), 128.91-128.46 (m), 126.23 (d, J=2.4 Hz), 125.84 (d, J=1.6 Hz), 112.99 (d, J=12.7 Hz), 112.59 (d, J=12.8 Hz), 55.14 (t, J=21.3 Hz), 54.19 (dd, J=30.4, 5.7 Hz), 51.49 (dd, J=22.4, 3.8 Hz), 36.32 (d, J=2.9 Hz), 34.22 (d, J=7.7 Hz), 33.17 (dd, J=7.8, 3.4 Hz), 20.15, 13.93. $^{31}$P NMR (202 MHz, $C_6D_6$) δ 96.13 (d, J=22.8 Hz), 15.59 (d, J=22.9 Hz).

Preparation of a mixture of 4,8-di-tert-butyl-N-butyl-N-((2S,5S)-2,5-diphenylphospholan-1-yl)-S-1,2,10,11-tetramethyldibenzo[d,f][1,3,21]dioxaphosphepin-6-amine and 4,8-di-tert-butyl-N-butyl-N-((2R,5R)-2,5-diphenylphospholan-1-yl)-S-1,2,10,11-tetramethyldibenzo[d,f][1,3,2]-dioxaphosphepin-6-amine, L699

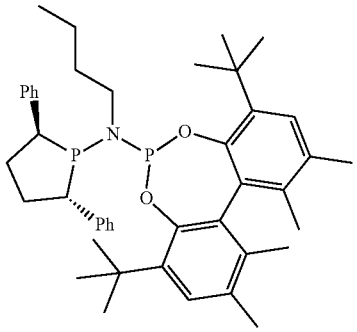 [SMILES: CCCCN(P1[C@H](c2ccccc2)CC[C@H]1c1ccccc1)p1oc2c(C(C)(C)C)cc(C)c(C)c2c2c(C)c(C)cc(C(C)(C)C)c2o1]

A cold solution (−30° C.) of triethylamine (0.117 g, 1.16 mmol) in toluene (1.2 mL) was added to a cold (−30° C.) solution of rac-N-butyl-2,5-diphenylphospholan-1-amine (0.30 g, 0.96 mmol) in toluene (3.0 mL) and the resulting reaction mixture was stirred for 10 min. The reaction mixture was placed in a freezer at −30° C. for 30 minutes. To this cooled reaction mixture, was added a cold (−30° C.) solution of S-4,8-di-tert-butyl-6-iodo-1,2,10,11-tetramethyldibenzo[d,f][1,3,2] dioxaphosphepine (0.49 g, 0.96 mmol) in 4.9 mL of toluene.

After the addition of the solution was complete, a white precipitate was observed. The solution was stirred for 30 min at ambient temperature. The volatiles were removed under vacuum. The crude product was extracted with toluene (10 mL) and filtered through 5 cm of activated neutral alumina. The volatiles were removed from the filtrate under vacuum giving solid product which was recrystallized from cold pentane at −30° C. to yield a mixture of two isomeric products. Yield 0.38 g (69.9%). $^1$H NMR (400 MHz, $C_6D_6$) δ 7.46 (m, 4H), 7.39-7.32 (m, 2H), 7.29 (m, 2H), 7.25-7.13 (m, 8H), 7.10-6.89 (m, 8H), 4.77 (m, 1H), 3.90 (m, 1H), 3.30 (m, 1H), 3.09-2.33 (m, 9H), 2.31-2.09 (m, 2H), 2.09-1.91

(m, 12H), 0.71 (s, 3H), 1.70 (s, 3H), 1.69 (s, 9H), 1.68 (s, 9H), 1.65-1.47 (m, 8H), 1.43 (s, 9H), 1.34-1.23 (m, 1H), 1.09 (s, 9H), 0.89-0.46 (m, 9H), 0.35 (m, 6H), 0.26-0.10 (m, 1H). $^{13}$C NMR (101 MHz, $C_6D_6$) δ 148.53, 148.43, 148.30, 148.24, 147.87, 147.58, 146.07, 145.82, 144.66, 144.45, 138.79, 137.73 (d, J=2.4 Hz), 137.67-137.34 (m), 137.22, 136.66, 134.87 (d, J=8.3 Hz), 134.08, 133.72, 132.30 (d, J=5.0 Hz), 131.99, 131.81, 130.44, 130.34 (d, J=3.0 Hz), 130.20, 129.96, 128.90, 128.87-128.76 (m), 128.64, 128.57 (d, J=3.7 Hz), 128.39, 128.34 (d, J=2.3 Hz), 128.29, 128.20 (t, J=2.3 Hz), 128.13, 126.06 (d, J=1.9 Hz), 125.98-125.69 (m), 125.26, 59.15 (d, J=27.2 Hz), 54.83 (d, J=27.5 Hz), 54.07-53.06 (m), 52.11-50.21 (m), 37.95, 37.40, 35.94 (d, J=12.2 Hz), 35.35 (d, J=7.7 Hz), 35.23-34.37 (m), 33.90, 33.15 (d, J=3.6 Hz), 31.69-30.74 (m), 30.36, 21.01, 20.58-19.33 (m), 16.56-14.90 (m), 12.70 (d, J=26.3 Hz). $^{31}$P NMR (162 MHz, $C_6D_6$ δ 143.44-143.17 (m), 102.02 (d, J=27.6 Hz), 92.14 (d, J=13.5 Hz).

Ligating Compound-Chromium Complex Preparation

Preparation of 1,2-bis[(2S,5S)-2,5-dimethylphospholano]benzene-CrCl$_3$((tetrahydrofuran)), (Me-DuPhos-CrCl$_3$(THF)), L372

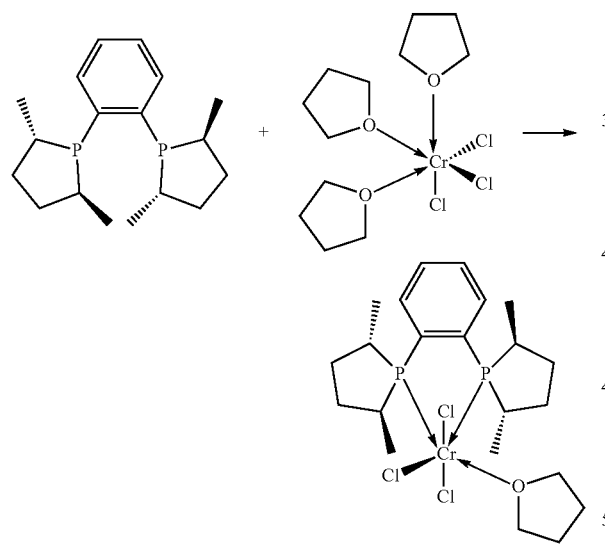

THF (15 mL) was added to a vial containing 1,2-bis[(2S,5S)-2,5-dimethylphospholano]benzene, (Me-DuPhos), (0.60 g, 1.96 mmol) and trichlorotris(tetrahydrofuran)chromium (CrCl$_3$(THF)$_3$), 0.56 g, 1.51 mmol). The resulting solution was stirred for 30 min at ambient temperature and then heated for 1 h at 60° C. The THF was concentrated with formation of more crystalline material. The supernatant was pipetted away from the solids. The solids were dried under reduced pressure to give violet-black crystalline material, 0.4776 g, 59.0%. Crystals suitable for X-ray diffraction analysis were grown by slow evaporation of a THF solution at ambient temperature. Elemental Analysis: Calculated: C, 49.22; H, 6.76. Found: C, 49.24; H, 6.69. Crystal structure is given in FIG. 1.

Preparation of (1,2-bis[(2S,5S)-2,5-dimethylphospholano]benzene-CrCl$_3$)$_2$ ((Me-DuPhos-CrCl$_3$)$_2$), L423

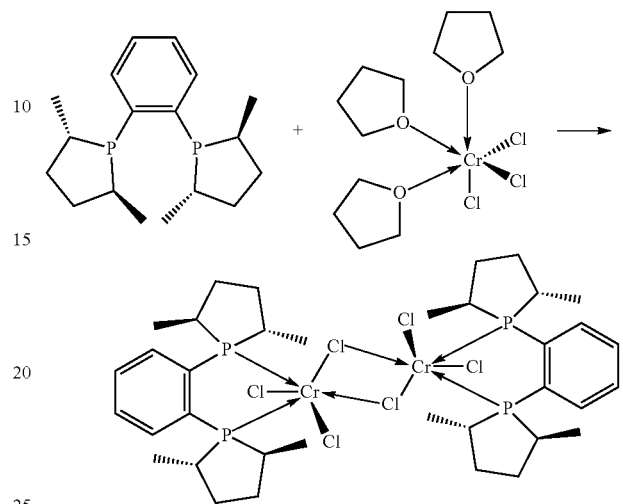

Figure 2:
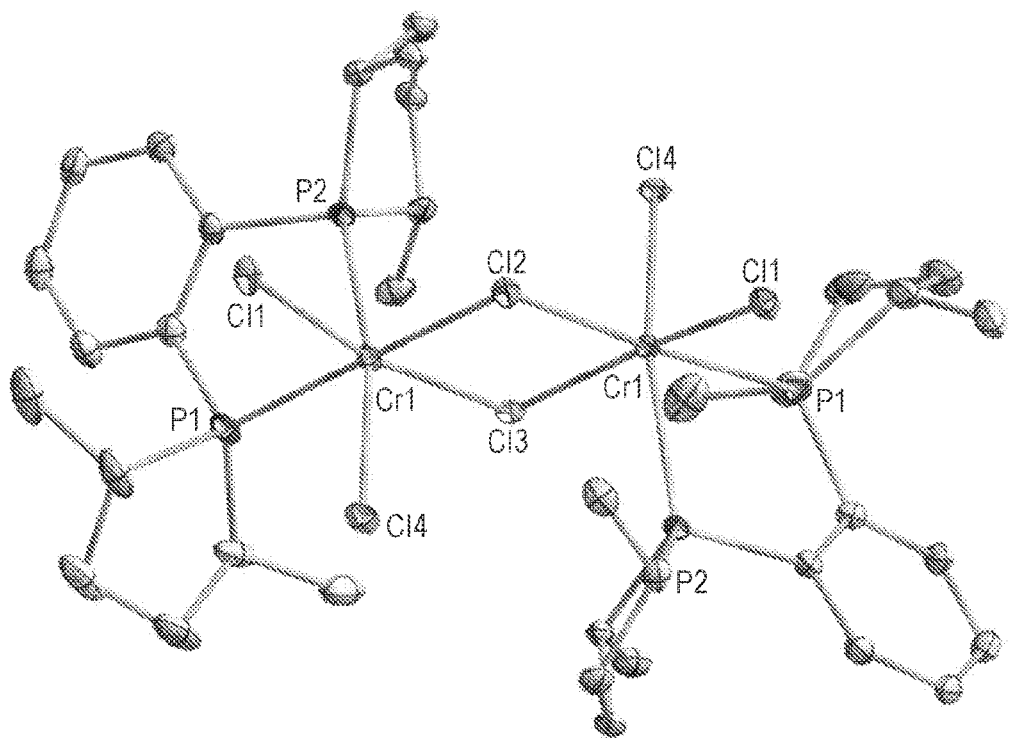
FIG. 2. Crystal structure of di-2-chlorotetrachlorobis[[1,2-bis[(2S,5S)-2,5-dimethylphospholano]benzene]]dichromium, (4), drawn with 50% thermal ellipsoid probability. Hydrogen atoms are omitted for clarity. Carbon atoms are represented by gray thermal ellipsoids.

Toluene (8 mL) was added to a vial containing 1,2-bis[(2S,5S)-2,5-dimethylphospholano]benzene (0.588 g, 1.92 mmol) and CrCl$_3$(THF)$_3$ (0.7133 g, 1.92 mmol). The reaction mixture was heated overnight at 80° C., giving a suspension. The suspension was filtered without cooling to yield an amorphous solid product. The product was washed with 2 mL of toluene and 8 mL of hexanes, and was then dried under reduced pressure giving 0.7655 g (yield=85.8%) of crystalline material. Elemental Analysis: Calculated: C, 46.52; H, 6.07. Found: C, 46.32; H, 5.97. Crystals suitable for X-ray diffraction analysis were grown from a CD$_2$Cl$_2$/hexanes solution of the material at ambient temperature. Crystal structure is given in FIG. 2.

Preparation of (1,2-bis[(2R,5R)-2,5-diethylphospholano]benzene-CrCl$_3$(THF) (Et-DuPhos-CrCl$_3$(THF), L403)

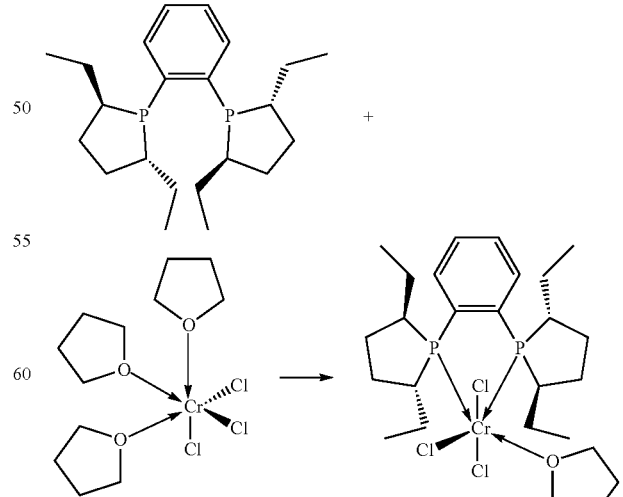

Figure 3:
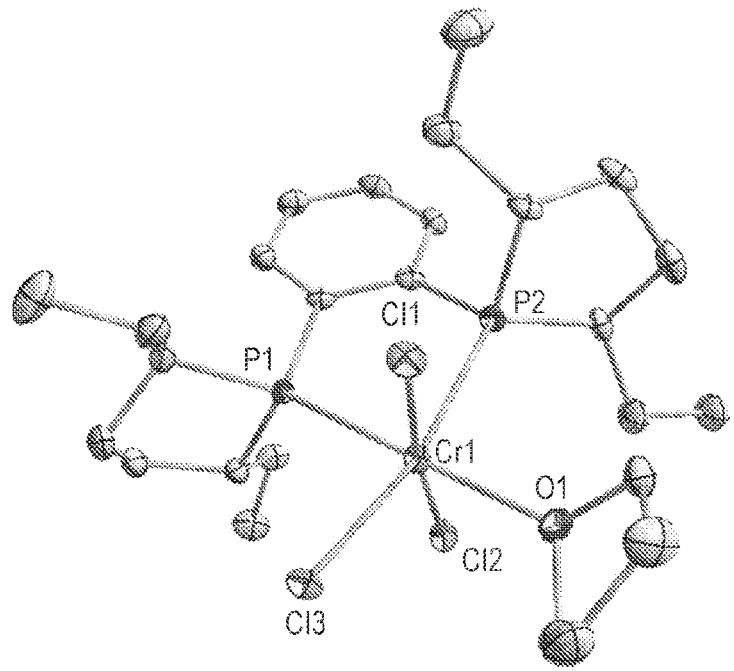
FIG. 3. Crystal structure of trichloro[1,2-bis[(2R,5R)-2,5-diethylphospholano]benzene](tetrahydrofuran)chromium, (6), drawn with 50% thermal ellipsoid probability. Hydrogen atoms are omitted for clarity. Carbon atoms are represented by gray thermal ellipsoids.

CrCl₃(THF)₃ (513 mg, 1.38 mmol) was dissolved in THF (5 mL) to give a purple solution. A solution of 1,2-bis[(2R,5R)-2,5-diethylphospholano]benzene, (Et-DuPhos), (500 mg, 0.60 mmol) in THF (5 mL) was added dropwise to the CrCl₃(THF)₃ solution. Almost immediately upon addition of the ligand, the solution color changed to a deep cobalt blue. The reaction mixture was stirred for 8 hours and then the solvent was removed in vacuo. The resulting blue solid was dried under vacuum at 60° C. overnight. Yield 506.7 mg, 62%. Crystals suitable for X-ray diffraction analysis were grown by evaporation of a THF/hexanes solution at ambient temperature. Elemental Analysis: Calculated: C, 52.67; H, 7.48; N, 0.00. Found: C, 52.43; H, 7.26. Crystal structure is given in FIG. 3.

Preparation of 1,2-bis[(2R,5R)-2,5-dimethylphospholano]ethane-CrCl₃(THF) (Me-BPE-CrCl₃(THF), L421)

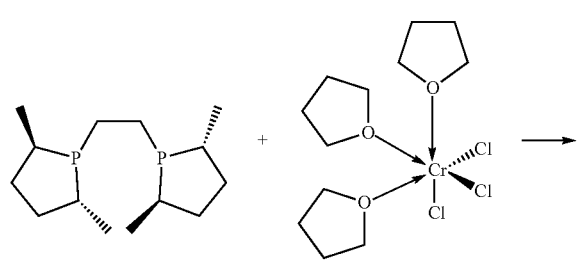

Figure 4:
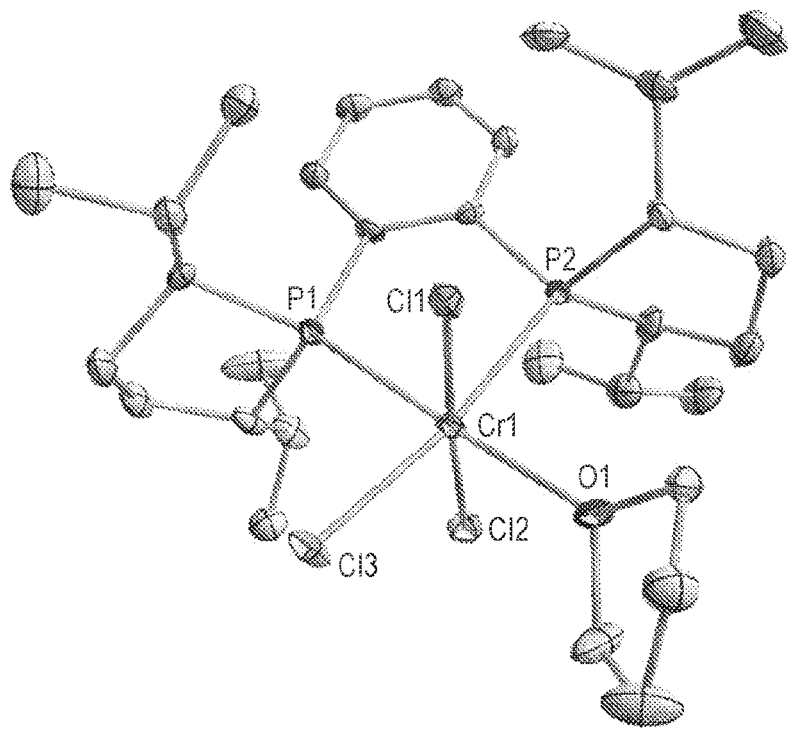
FIG. 4. Crystal structure of trichloro[1,2-bis[(2S,5S)-2,5-di-(1-methylethyl)phospholano]benzene](tetrahydrofuran) chromium, (8), drawn with 50% thermal ellipsoid probability. Hydrogen atoms are omitted for clarity. Carbon atoms are represented by gray thermal ellipsoids.

CrCl₃(THF)₃ (360 mg, 0.97 mmol) was dissolved in THF (5 mL) to give a purple solution. A solution of 1,2-bis[(2R,5R)-2,5-dimethylphospholano]ethane, (Me-BPE), (250 mg, 0.97 mmol) in THF (5 mL) was added dropwise to the CrCl₃(THF)₃ solution. The solution color immediately changed from purple to a dark cobalt blue. The solution was allowed to stir overnight at ambient temperature. The THF was removed in vacuo and the residue was redissolved in a minimal amount of THF (~5 mL), followed by addition of hexanes (~30 mL). This suspension was filtered through a frit, and the solvent was removed from the filtrate in vacuo to yield 299.9 mg of a blue solid. Yield 63.4%. Crystals suitable for X-ray diffraction analysis were grown by evaporation of a THF/hexanes solution at ambient temperature. Elemental Analysis: Calculated: C, 44.23; H, 7.42; N, 0.00. Found: C, 42.93; H, 7.25. Crystal structure is given in FIG. 4.

Preparation of 1,2-bis[(2R,5R)-2,5-diethylphospholano]ethane-CrCl₃(THF), (Et-BPE-CrCl₃(THF), L422)

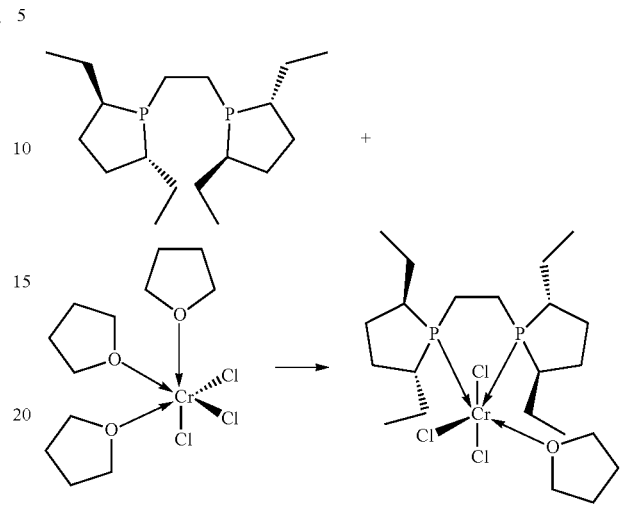

Figure 5:
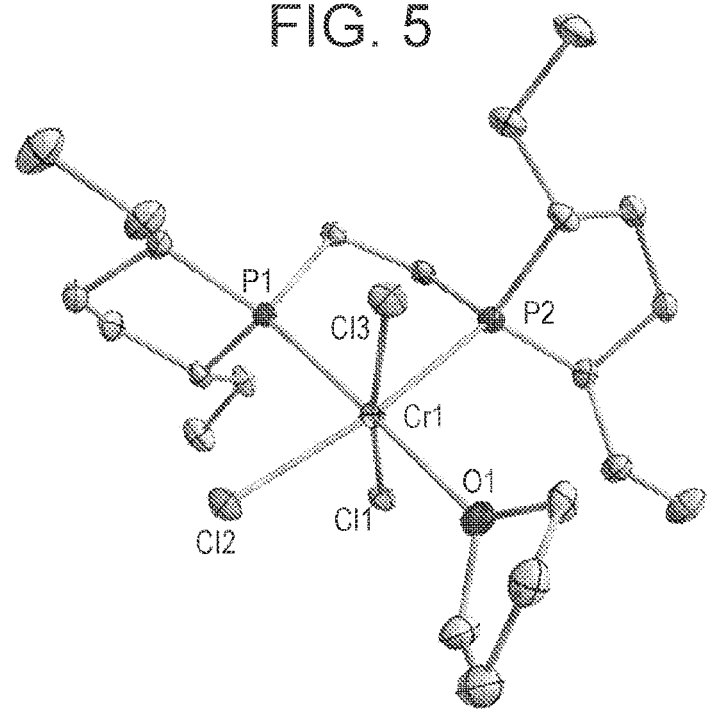
FIG. 5. Crystal structure of trichloro[1,2-bis[(2R,5R)-2,5-diethylphospholano]ethane](tetrahydrofuran)chromium, (12), drawn with 50% thermal ellipsoid probability. Hydrogen atoms are omitted for clarity. Carbon atoms are represented by gray thermal ellipsoids.

CrCl₃(THF)₃ (295 mg, 0.80 mmol) was dissolved in THF (5 mL) to give a purple solution. A solution of 1,2-bis[(2R,5R)-2,5-diethylphospholano]ethane, (Et-BPE), (250 mg, 0.80 mmol) in THF (5 mL) was added to the CrCl₃(THF)₃ solution. The reaction mixture was allowed to stir overnight at ambient temperature and then 30 mL of hexanes were added. The resulting suspension was filtered through a frit. The solvent was removed from the filtrate in vacuo to yield 354 mg of a blue solid. Yield 81.7%. Crystals suitable for X-ray diffraction analysis were grown by evaporation of a THF/hexanes solution at ambient temperature. Elemental Analysis: Calculated: C, 48.49; H, 8.14; N, 0.00. Found: C, 43.79; H, 7.84. Crystal structure is given in FIG. 5.

Preparation of (1R, 1'R,2S,2'S)-2,2'-di-tert-butyl-2,3,2',3'-tetrahydro-1H,1'H-(1,1')biisophosphindolyl-CrCl₃(THF), (DuanPhos-CrCl₃(THF) L455)

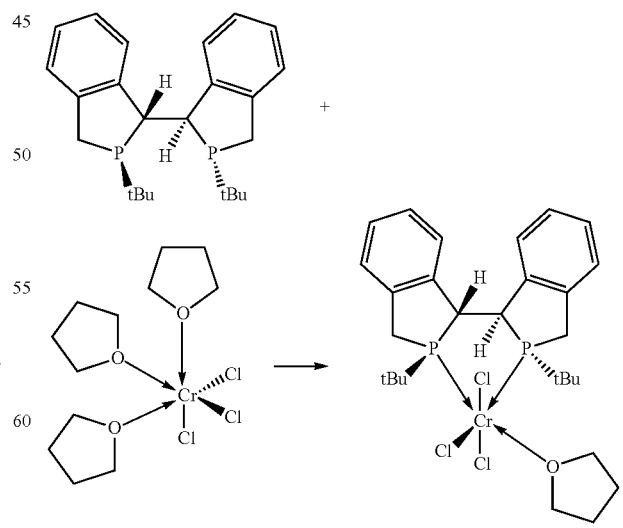

Cr(THF)₃Cl₃ (98.0 mg, 0.26 mmol) was dissolved in THF (3 mL) to give a purple solution. A solution of (1R,1'R,2S, 2'S)-2,2'-di-tert-butyl-2,3,2',3'-tetrahydro-1H,1'H-(1,1')bi-isophosphindolyl, (DuanPhos) (100 mg, 0.26 mmol) in THF (5 mL) was added to the Cr(THF)$_3$Cl$_3$ solution. The solution color changed from purple to blue within minutes of the ligand addition. The reaction mixture was allowed to stir for four days at ambient temperature. Hexanes (30 mL) was added to the reaction mixture, and the resulting suspension was filtered through a frit, yielding 108.2 mg of a blue solid. Yield 67.5%. Crystals of suitable for X-ray diffraction analysis were grown from CD$_2$Cl$_2$ and hexanes at ambient temperature. The resulting crystal structure is of the dimer complex: (DuanPhos-CrCl$_3$)$_2$. Because elemental analysis indicated a monomeric structure, it is apparent that the complex dimerized under the crystallization conditions. Elemental Analysis: Calculated: C, 54.87; H, 6.58. Found: C, 55.48; H, 6.96.

Preparation of ((rac)-N-(diphenylphosphanyl)-N-methyl-2,5-diphenylphospholan-1-amine)-CrCl$_3$(THF), L560

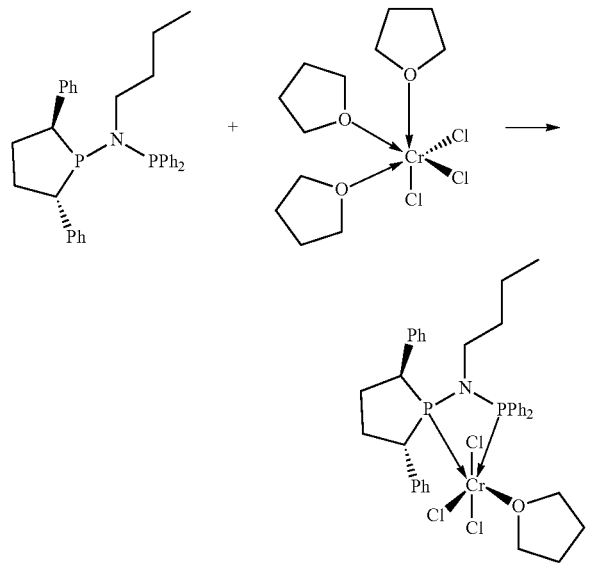

Figure 7:
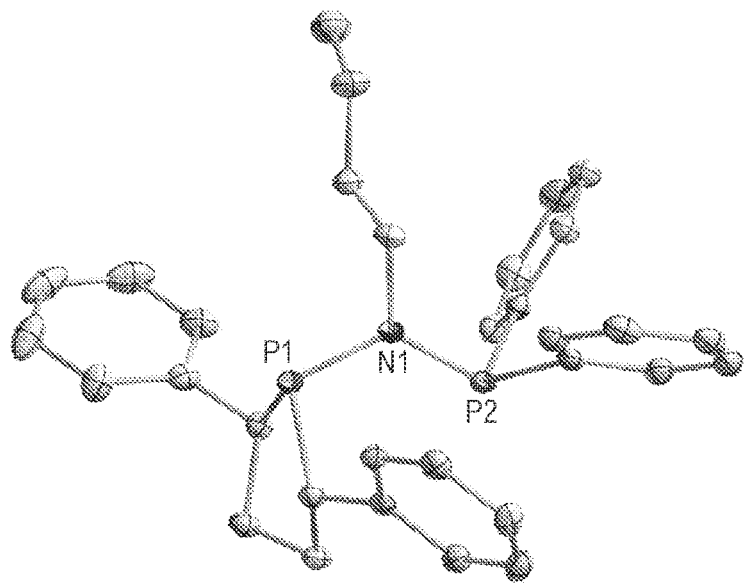
FIG. 7. Crystal structure of (2S,5S)—N-butyl-N-(2,5-diphenylphospholan-1-yl)-N-diphenylphosphinoamine, (17), drawn with 50% thermal ellipsoid probability. Hydrogen atoms are omitted for clarity. Carbon atoms are represented by gray thermal ellipsoids.
Figure 8:
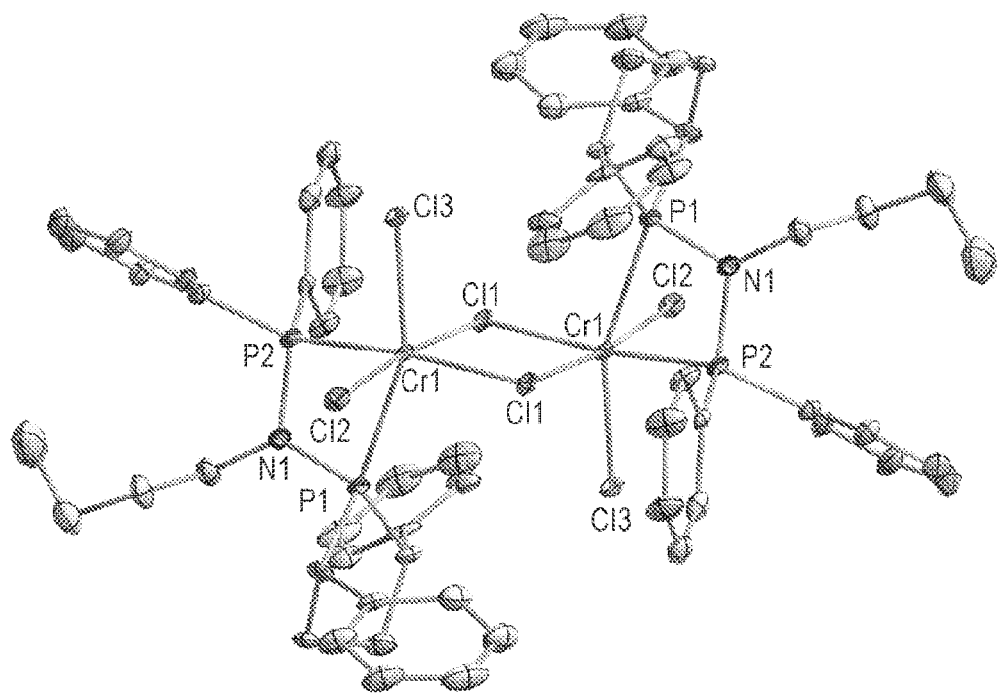
FIG. 8. Crystal structure of di-$\mu_2$-chlorotetrachlorobis [(2S,5S)—N-butyl-N-(2,5-diphenylphospholan-1-yl)-N-diphenylphosphinoamide]dichromium, (19), drawn with 50% thermal ellipsoid probability. Hydrogen atoms are omitted for clarity. Carbon atoms are represented by gray thermal ellipsoids.

CrCl$_3$(THF)$_3$ (65.2 mg, 0.17 mmol) was dissolved in toluene (2 mL) to give a purple solution. A solution of ((rac)-N-(diphenylphosphanyl)-N-methyl-2,5-diphenylphospholan-1-amine) (86.3 mg, 0.17 mmol) in toluene (8 mL) was added to the Cr(THF)$_3$Cl$_3$ solution. The solution color changed to a dark purple-black. The reaction mixture was allowed to stir overnight at ambient temperature. The reaction mixture was filtered and the solvent was removed in vacuo, yielding 54.5 mg of a blue solid. Yield 43.1%. Elemental Analysis: Calculated: C, 41.94; H, 5.63. Found: C, 41.89; H, 5.57. Purple, plate-like crystals suitable for X-ray diffraction were grown from a mixture of dichloromethane and chloroform at −20° C. Because elemental analysis confirmed the bulk composition to be the monomeric species, it is apparent that the dimer structure formed under the crystallization conditions. Crystal structure is shown in FIG. 7.

Comparative Example (CEx) A—Preparation of trichloro[N,N-bis(diphenylphosphino)-N-isopropylamine](tetrahydrofuran)chromium, L404a

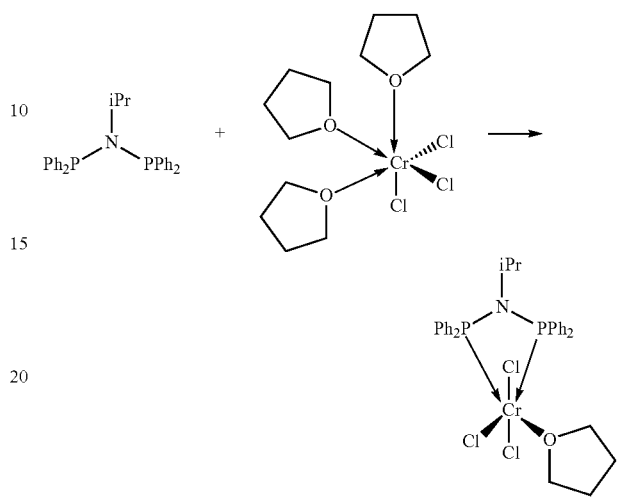

Figure 6:
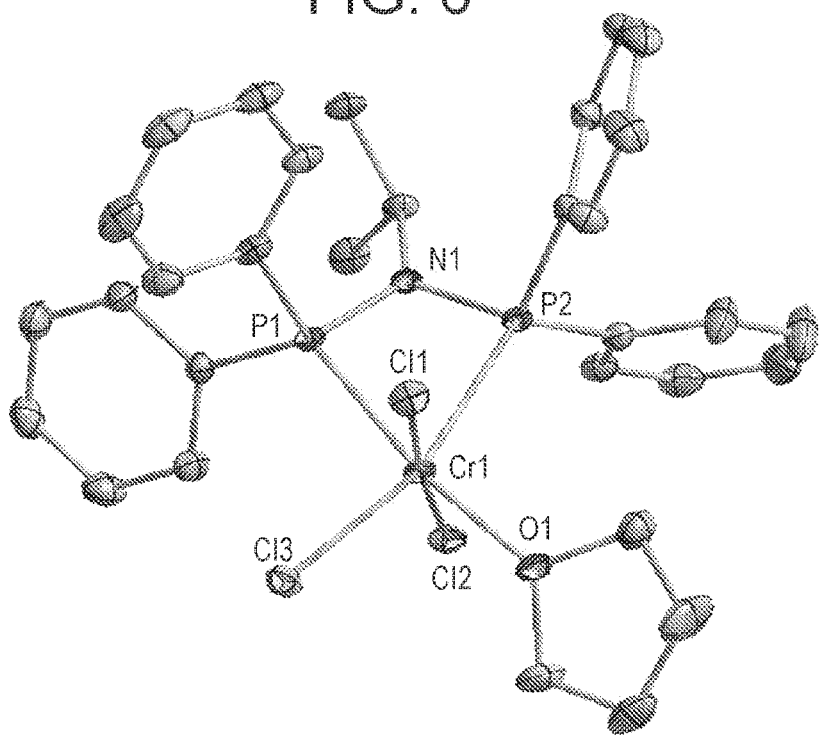
FIG. 6. Crystal structure of trichloro[N,N-bis(diphenylphosphino)-N-isopropylamine](tetrahydrofuran) chromium*toluene, (14), drawn with 50% thermal ellipsoid probability. Hydrogen atoms and the solvate toluene molecule are omitted for clarity. Carbon atoms are represented by gray thermal ellipsoids.

A 20 mL vial was charged with solid N, N-bis(diphenylphosphino)-isopropylamine, (obtained as described in Bollmann et al., ("Ethylene Tetramerization: A New Route to Produce 1-Octene in Exceptionally High Selectivities", Bollmann, A.; Blann, K.; Dixon, J. T.; Hess, F. M.; Killian, E.; Maumela, H.; McGuinness, D. S.; Morgan, D. H.; Neveling, A.; Otto, S.; Overett, M.; Slawin, A. M. Z.; Wasserscheid, P.; Kuhlmann, S. *J. Am. Chem. Soc.* 2004, 126, 14712-14713)), (0.100 g, 0.234 mmol) and solid trichlorotris(tetrahydrofuran)chromium, (2), (0.087 g, 0.213 mmol). Toluene (8 mL) was added to the vial and the vial contents were shaken. A deep blue-black color developed within 5 minutes in the solution which contained a significant amount of undissolved solids. The vial contents were shaken well and allowed to stand overnight to yield a solution with very little undissolved solids. The solution was filtered using a syringe filter into a 20-mL vial and the contents of the vial were allowed to stand overnight during which time several very large crystals formed. The crystals, once recovered from the vial and dried, were analyzed by single crystal XRD. Elemental analysis for trichloro[N,N-bis(diphenylphosphino)-N-isopropylamine](tetrahydrofuran)chromium as a mono toluene solvate: calculated: C, 60.85; H, 5.78; N, 1.87. found: C, 60.28; H, 5.69, N, 1.62. Crystal structure is shown in FIG. 6.

Comparative Example (CEx) B—Preparation of trichloro[N,N-bis(1,3,2-dioxaphospholane)-N-isopropylamine](tetrahydrofuran)chromium, L430

Step 1. Preparation of N,N-bis(1,3,2-dioxaphospholanyl)-N-isopropylamine, L429

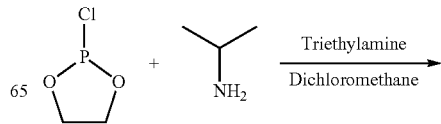

-continued

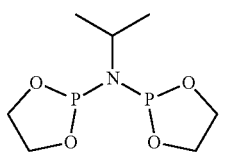

Triethylamine (9.8 mL, 70.6 mmol) was added to a solution of 2-chloro-1,3,2-dioxaphospholane (1.7 mL, 19.1 mmol) in dichloromethane. The reaction mixture was cooled to −28° C. and allowed to sit at that temperature for one hour. Isopropyl amine (0.7 mL, 8.6 mmol) was added and the reaction mixture was allowed to warm to ambient temperature and stir overnight. A white precipitate was observed. The reaction mixture was filtered and the filtrate was concentrated in vacuo. The residue was dissolved in a small amount of hexanes. The product precipitated from the hexanes as 0.86 g of a white solid. Yield 42%. $^1$H NMR (400 MHz, CDCl$_3$) δ 4.16-4.04 (m, 4H), 3.92-3.78 (m, 4H), 3.50-3.33 (m, 1H), 1.27 (s, 3H), 1.25 (s, 3H). $^{13}$C NMR (101 MHz, CDCl$_3$) δ 64.30 (m), 45.88 (s), 44.97 (t), 25.58 (t). $^{31}$P NMR (162 MHz, CDCl$_3$) δ 143.50.

Step 2. Preparation of trichloro[N,N-bis(1,3,2-dioxaphospholane)-N-isopropylamine]-(tetrahydrofuran)chromium, L430

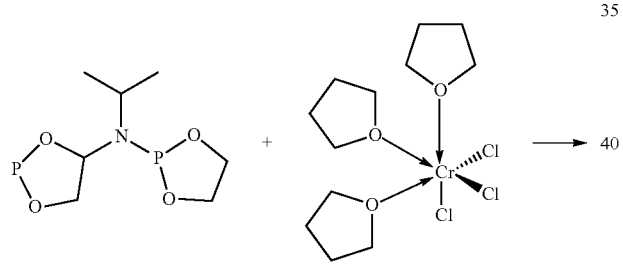

A solution of N,N-bis(1,3,2-dioxaphospholanyl)-N-isopropylamine (100 mg, 0.42 mmol) in toluene (5 mL) was added to a purple mixture of CrCl$_3$(THF)$_3$ (156.7 mg, 0.42 mmol) in toluene (5 mL) giving a blue solution. The reaction mixture was allowed to stir overnight at ambient temperature. The reaction mixture was filtered, yielding 97.5 mg of a blue solid. Yield 49.7%. Elemental Analysis: Calculated: C, 28.2; H, 4.73; N, 2.99. Found: C, 29.15; H, 5.18; N, 3.20.

Comparative Example (CEx) C—Preparation of trichloro[N,N-bis(5,5-dimethyl-1,3,2-dioxaphosphorinanyl)-N-isopropylamine](tetrahydrofuran)chromium, L431

Step 1. Preparation of N,N-bis(5,5-dimethyl-1,3,2-dioxaphosphorinanyl)-N-isopropylamine, L417

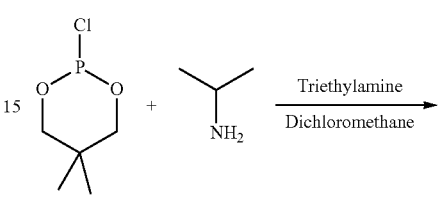

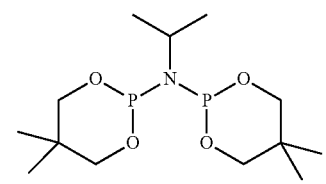

Triethylamine (9.6 mL, 69.3 mmol) was added to a solution of 2-chloro-5,5-dimethyl-1,3,2-dioxaphosphorinane (2.6 mL, 18.7 mmol) in dichloromethane. The reaction mixture was cooled to −28° C. and allowed to sit at that temperature for one hour. Isopropyl amine (0.7 mL, 8.6 mmol) was added and the reaction mixture was allowed to warm to ambient temperature and stir overnight. A white precipitate was observed. The reaction mixture was filtered and the filtrate was concentrated in vacuo. The residue was dissolved in a small amount of hexanes. The product precipitated from the hexanes and was filtered out to yield 1.2 g (44% yield) of a white solid. $^1$H NMR (400 MHz, CD$_2$Cl$_2$) δ 4.39-4.23 (m, 1H), 3.85-3.66 (m, 8H), 1.35 (s, 3H), 1.33 (s, 3H), 1.15 (s, 6H), 0.81 (s, 6H). $^{13}$C NMR (101 MHz, CD$_2$Cl$_2$) δ 74.87 (t), 45.69 (t), 33.26 (t), 26.17 (t), 23.35 (t), 22.07 (s). $^{31}$P NMR (162 MHz, CD$_2$Cl$_2$) δ 143.12.

Step 2. Preparation of trichloro[N,N-bis(5,5-dimethyl-1,3,2-dioxaphosphorinanyl)-N-isopropylamine]-(tetrahydrofuran)chromium, L431

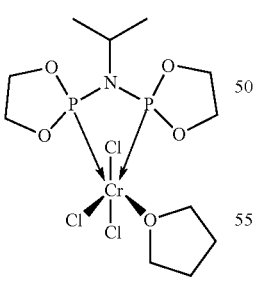

+

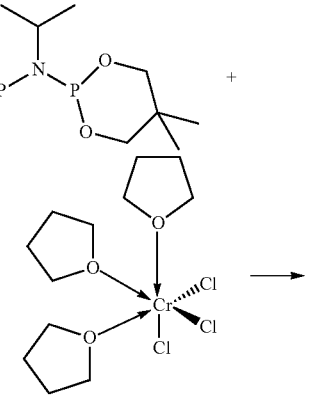

-continued

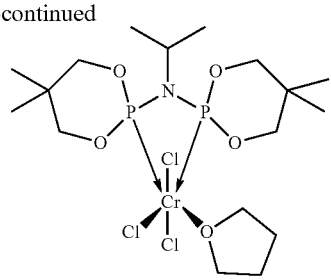

A solution of N,N-bis(5,5-dimethyl-1,3,2-dioxaphosphorinanyl)-N-isopropylamine (100 mg, 0.31 mmol) in toluene (5 mL) was added to a purple mixture of $CrCl_3(THF)_3$ (115.9 mg, 0.31 mmol) in toluene (5 mL) giving a blue solution. The reaction mixture was allowed to stir overnight at ambient temperature. The reaction mixture was filtered, yielding 57.3 mg of a blue solid. Yield 33.5%. Crystals suitable for X-ray diffraction analysis were grown by evaporation of a THF/hexanes solution of the product at ambient temperature.

Comparative Example (CEx) D—Preparation of trichloro[1,2-bis(5,5-dimethyl-1,3,2-dioxaphosphorinan-2-yl)benzene](tetrahydrofuran)chromium, L453

Step 1. Preparation of 1,2-bis(5,5-dimethyl-1,3,2-dioxaphosphorinan-2-yl)benzene

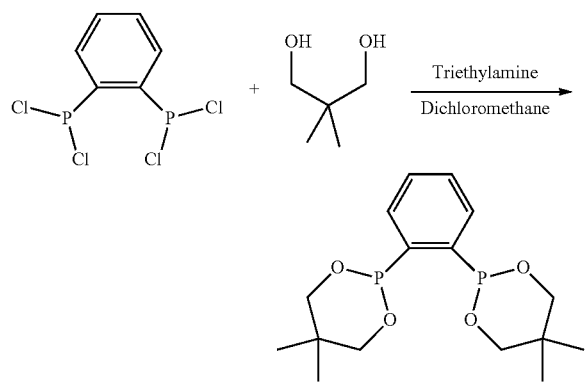

A solution of triethylamine (1.79 mL, 12.86 mmol) and 1,2-bis(dichlorophosphanyl)benzene (0.8 mL, 2.86 mmol) in dichloromethane (30 mL) was cooled to −35° C. for one hour. 2,2-Dimethylpropane-1,3-diol (0.56 g, 5.72 mmol) was slowly added to the cold solution over 15 minutes, causing the formation of a white precipitate. The resulting slurry was allowed to stir for ~24 h before being filtered. The filtrate was concentrated in vacuo giving an off-white solid. Recrystallization from hot hexanes afforded 0.6 g of the product as a white solid. Yield 61%. $^1H$ NMR (500 MHz, $CDCl_3$) δ 7.60-7.56 (br m, 2H), 7.45 (t, 2H), 3.68-3.43 (m, 9H), 1.29 (s, 6H), 0.55 (s, 6H). $^{13}C$ NMR (101 MHz, $CDCl_3$) δ 143.32 (d, $J_{C-P}$=14.51 Hz), 142.79 (d, $J_{C-P}$=14.68 Hz), 130.97, 130.85, 129.23, 129.21, 72.02, 72.00, 71.98, 71.96, 33.17, 33.13, 22.63, 22.58. $^{31}P$ NMR (202 MHz, $CDCl_3$) δ 147.53.

Step 2. Preparation of trichloro[1,2-bis(5,5-dimethyl-1,3,2-dioxaphosphorinan-2-yl) benzene](tetrahydrofuran)chromium, L453

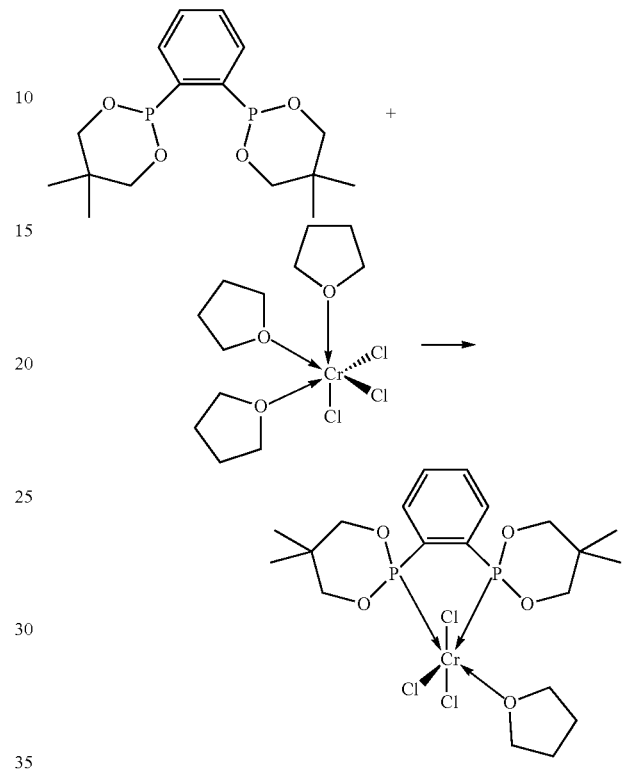

A solution of 1,2-bis(5,5-dimethyl-1,3,2-dioxaphosphorinan-2-yl)benzene (150 mg, 0.44 mmol) in toluene (5 mL) was added to a purple mixture of $CrCl_3(THF)_3$ (164.2 mg, 0.44 mmol) in toluene (5 mL) to give a blue solution. The reaction mixture was allowed to stir overnight at ambient temperature. The reaction mixture was filtered and the solvent was removed in vacuo, yielding 164.8 mg of a blue solid. Yield 70.1%. Elemental Analysis: Calculated: C, 41.94; H, 5.63. Found: C, 41.89; H, 5.57.

Ethylene Oligomerization Reactions

Solvents and gases used in the ethylene oligomerization reactions were purified as follows: The nitrogen and ethylene gas feeds and methylcyclohexane solvent were passed through purification columns containing activated A2 alumina and Q5 reactant. Chlorobenzene and nonane were passed through activated A-204 alumina. The methylcyclohexane, chlorobenzene, and nonane were stored over activated 3 Å molecular sieves. The A2 alumina, A204 alumina, and molecular sieves were activated as described above. MMAO-3A was obtained from AkzoNobel.

High-Throughput Experimental Information

The hot-oil pressure reactor (HOPR), a high-throughput reactor housed in a nitrogen-filled glovebox in which reactions are performed in some or all of 24 individual cells in a stainless steel block fitted with 8-mL glass inserts, is used to perform a series of oligomerization experiments using certain of the catalyst systems prepared above. The cells in the HOPR can be pressurized up to 500 pounds per square inch (psi) (3.45 megapascals (MPa)); however, all the cells share a common headspace and gas uptake profiles for individual reactions cannot be monitored with this apparatus. Efficient mixing is achieved through the use of magnetic stir bars.

Library Studio software from Freeslate was used to make designs for running the libraries of 24 experiments in the HOPR. In running the library, each glass insert was equipped with a stir bar and then the glass insert and stir bar combination was weighed to use as a basis for determining the weight of residual solids after completing an experimental run. The inserts were arranged in a 24-sample reactor plate (6×4) and a predetermined amount of methylcyclohexane solvent was added via a liquid handler such that the final volume after the addition of all other components would be 4 mL. The liquid handler then delivered a solution of 10 wt % nonane, the GC internal standard, in methylcyclohexane, for a total of 50 mg of nonane in each glass insert. The components of the catalyst system (comprising a solution of the selected activator and a solution of the selected precatalyst) were then added to the glass inserts via an Eppendorf pipette to form reaction mixtures. The activator (MMAO-3A as a 50 mM solution in methylcyclohexane) was added first to the glass inserts. The precatalyst was then added to the glass insert as a precatalyst solution comprising the ligating compound and chromium source of the catalyst system in chlorobenzene. The ligating compound and chromium source were selected either from the preformed ligating compound-chromium complexes of the above working examples or from the ligating compounds of the above working examples combined with a selected chromium source (in these ethylene oligomerization Examples, either $CrCl_3(THF)_3$ or tris(2,4-pentanedionato-O,O')chromium, $(Cr(acac)_3)$.

The in situ precatalyst solutions were prepared as follows: A 1 mM chlorobenzene solution of $CrCl_3(THF)_3$ or $Cr(acac)_3$ was combined with a 1 mM chlorobenzene solution of the selected ligating compound in a 1:1.2 ratio in 8-mL vials in a 24-sample plate (3×8). The samples were mixed for 30 minutes on a shaker before transferring them to the appropriate glass inserts in the HOPR cells. Preformed ligating compound-chromium complex solutions were prepared by mixing a preformed ligating compound-chromium complex prepared as shown in the above working examples (e.g., Ex 1, CEx A) in chlorobenzene to form 1 mM solutions before transferring them to the appropriate glass inserts in the HOPR cells. For comparison, the N,N-bis(diphenylphosphino)-N-isopropylamine ligating compound 100 was included in each library as a standard. Consistent activity and selectivity of this standard between libraries allowed for the catalysis results to be compared across libraries. Each library comprised twelve individual experiments designed to have the amount of chromium indicated at the bottom of each High-Throughput Oligomerization Results table present in 4 mL of total solution volume (with the exception that one library was run with a total solution volume of 5 mL), with a duplicate of each experiment, in each HOPR run.

Following the preparation of the reaction mixtures, the glass tubes were distributed in a 3×8 configuration in the HOPR cells and the reactor was sealed. The cells were pressurized with 100 psi (0.689 megapascals (MPa)) of ethylene and heated to the desired temperature (45° C.), as monitored by five thermocouples in the stainless steel block. Once the reaction temperature was reached, the cells were pressurized up to 500 psi with ethylene. After 30 minutes, the reactions were terminated by stopping the ethylene feed and cooling to room temperature. The reactor was slowly vented at room temperature in order to limit loss of low-boiling analytes (e.g., 1-hexene). A liquid sample from each cell was removed for gas chromatographic (GC) analysis, and the remainder of the liquid present was removed in vacuo on a Savant SC250EX SpeedVac Concentrator (Thermo Fisher). The glass tubes were then weighed to determine the amount of residual solids present. The residual solids present comprised any polymer which formed and catalyst system residues. At the activator to ligating compound+chromium source or activator to ligating compound-chromium complex ratios used in the following oligomerization examples, over 95% of the mass of the catalyst system residues arose from the MMAO-3A activator. Thus the weight of the residual solids from a control experiment tube containing only MMAO-3A solution is subtracted from the weight of the total residual solids in the oligomerization reaction tubes to give a good approximation of the amount of polymer produced in each oligomerization reaction tube. The chromium to activator (Cr:MMAO-3A) ratios and chromium loading levels are shown beneath the tables of oligomerization results. A summary of the conditions for the high-throughput ethylene oligomerization experiments is given in Table 1.

TABLE 1

Summary of conditions for high-throughput ethylene oligomerization experiments

| Parameter | Value |
| --- | --- |
| Chromium source | $CrCl_3(THF)_3$ |
| Chromium source:ligating compound | 1:1.2 |
| Ethylene pressure | 500 psi |
| Reaction temperature | 45° C. |
| Reaction time | 30 minutes |
| Solvent | Methylcyclohexane |
| Activator | 1000 equiv MMA0-3A; Source: AkzoNobel |
| GC internal standard | 50 mg nonane |

Activity and selectivity calculations include all major reaction products: 1-octene, 1-hexene, polymer, cyclic C6 products (methylcyclopentane and methylenecyclopentane), and higher $C_{10-18}$ olefin oligomers. The amounts of the cyclic products (methylcyclopentane and methylenecyclopentane) and higher $C_{10-18}$ olefin oligomers were quantified to obtain complete mass balance, however, only the activities and selectivities for the main products of interest (1-octene, 1-hexene, polymer, and, for one set of results, higher $C_{10-18}$ olefin oligomers) for the high-throughput ethylene oligomerization experiments are summarized in the High-Throughput Oligomerization Results tables below (see Table 4-9). The activity and selectivity values given here are the averages of two replicates.

Batch Reactor Experimental Information

The ethylene oligomerization reactions were conducted in a 300-mL Parr batch reactor equipped with a 10-mL catalyst shot tank and an agitator. The reactor was heated by an electrical resistive heating mantle and cooled by an internal cooling coil. Both the reactor and the temperature-control system were controlled and monitored by a Camile TG automation system.

All reactor manipulations and solution preparations were performed in a nitrogen-purged glovebox. For precatalysts prepared in situ, a solution of 1.2 equiv of the selected ligating compound in methylcyclohexane (2 mM) was added in a dropwise fashion to a solution of 1 equiv of the Cr precursor in chlorobenzene (2 mM), and the resulting solution was stirred for 30 minutes. For precatalysts comprising preformed ligating compound-chromium complexes, a solution of the selected preformed ligating compound-chromium complex was prepared in chlorobenzene (2 mM). Methylcyclohexane (100 mL) was added to the reactor body in a glovebox, along with MMAO-3A (1.77 M in heptane) and nonane, which served as the internal standard for GC analysis. The precatalyst solution was loaded into a 10-mL catalyst shot tank. Residual precatalyst solution in the vial and syringes used to handle the precatalyst solution was rinsed with 2.5 mL of methylcyclohexane into the shot tank. The reactor was sealed and removed from the glovebox.

The reactor was then transferred to a reactor stand with the heating mantle, and connections were made to the nitrogen and ethylene feed lines, cooling lines, a knockout pot, and a vent line. The agitator was turned on. The knockout pot was then purged with nitrogen for five minutes while the reactor was pressure tested to 750 psi (5.17 MPa) with nitrogen. After the pressure test, the reactor was slowly vented to about 10 psi (68.9 kilopascal (KPa)) and then slowly heated to 70° C. Once this temperature was reached, ethylene was added through a Brooks thermal mass flow meter to the desired reaction pressure. Once the reactor temperature and pressure stabilized, the catalyst shot tank was pressurized to 200 psi (1.38 MPa) over the reactor pressure with nitrogen, and the precatalyst solution was injected into the reactor, beginning the reaction. Ethylene was fed on demand through the Brooks thermal mass flow controller and the temperature was controlled by adjusting the mantle temperature and the flow through the internal cooling coil.

After the 30-minute reaction time, the ethylene feed was stopped and the reactor was cooled to 35° C., then vented at a rate of 1-4 psi (6.89-27.6 KPa) per second until 10 psi was reached. At this point, the reactor was returned to the nitrogen-filled glovebox where it was opened. The reactor contents were sampled for GC analysis, then emptied into a pan. Any residual polymer remaining in the reactor was thoroughly cleaned out and added to the reactor contents in the pan. The bulk of the solvent was allowed to evaporate off and the residual solids were dried in a vacuum oven. The resulting polymer residue was weighed to give the polymer yield for the reaction.

Activity and selectivity calculations include all major reaction products: 1-octene, 1-hexene, polymer, cyclic C6 products (methylcyclopentane and methylenecyclopentane), and higher $C_{10-18}$ olefin oligomers. The amounts of the cyclic products (methylcyclopentane and methylenecyclopentane) and higher $C_{10-18}$ olefin oligomers were quantified to obtain complete mass balance, however, only the activities and selectivities for the main products of interest (1-octene, 1-hexene, and polymer) for the batch reactor ethylene oligomerization experiments are summarized in the Batch Reactor Oligomerization Results tables below (see Tables 10-12). Unless otherwise indicated, the activity and selectivity values given were obtained from single runs (not averaged from multiple runs)

Analytical Procedures

The liquid reaction products were analyzed on an Agilent 7890 GC System. The GC conditions for the Agilent 7890 system are listed in Table 2 below.

TABLE 2

| | GC conditions |
|---|---|
| GC | Agilent 7890 Series |
| Column | Agilent (DB-5MS), 30 m × 32 μm, 1 μm film |

TABLE 2-continued

| | GC conditions |
|---|---|
| Oven | 70° C. for 8 min, ramp 50° C./min to 300° C. (hold 3.4 min) Total time-16 min |
| Inlet | 300° C., Split, 30:1 split ratio |
| Carrier Gas | Hydrogen, 1.33 mL/min constant flow |
| Flame Ionization Detector | 320° C., 45 mL/min H$_2$, 450 mL/min air |
| Injection Volume | 1 μL, chlorobenzene wash solvent |

Samples for GC analysis for the high-throughput and batch reactor experiments were prepared by quenching 75 μL of the reaction mixture with 25 μL of methanol. The response factors were determined for 1-octene, 1-hexene, methylcyclopentane, and methylenecyclopentane by calibration using a standard solution with known concentrations. The response factors used for the C10 to C18 fractions were determined using the terminal olefins of the same carbon length (e.g., 1-decene for the C10 fraction). The GC retention times for the C10-C18 olefins used as standards are given in Table 3. The concentrations of the reaction products were reported by the GC instrument on a g/(g nonane) basis because nonane was included as an internal standard at a known concentration in the reaction tubes. The amounts of the various reaction products produced were calculated relative to the amount of nonane added to the reaction mixture.

Activity, defined as the ratio of the amount of a selected product obtained from a given run to the amount of chromium used in the given run divided by the length of the given run in hours, is calculated for a given run by obtaining the ratio of the amount in grams of a selected reaction product (e.g., 1-octene, 1-hexene, polymer, cyclics, $C_{10-18}$ oligomers, total of all products) from the given run to the amount in grams of chromium used in the given run and dividing that ratio by the time of the given run in hours. Selectivity, defined as the ratio of the amount of a selected product obtained from a given run to the total amount of all products from the given run, is calculated for a given run by obtaining the ratio of the amount in grams of a selected reaction product (e.g., 1-octene, 1-hexene, polymer, cyclics, $C_{10-18}$ oligomers) to the total amount in grams of all products from the given run. The term "all products" with respect to the activity and the selectivity means the sum of the 1-octene, 1-hexene, polymer, cyclics, and $C_{10-18}$ oligomers.

TABLE 3

| Retention times for C10-C18 olefins. | |
|---|---|
| Product | Retention time (min) |
| Decenes | 10.00-11.00 |
| Dodecenes | 11.30-11.80 |
| Tetradecenes | 11.81-12.70 |
| Hexadecenes | 13.00-13.50 |
| Octadecenes | 13.70-14.20 |

TABLE 4

High-Throughput Oligomerization Results - in situ catalyst formation*

| Example | Ligating compound | Activity (g/g Cr h) | | | | Selectivity (wt %) | | |
|---|---|---|---|---|---|---|---|---|
| | | 1-Octene | 1-Hexene | Polymer | Total | 1-Octene | 1-Hexene | Polymer |
| 1 | 100 | 1,220,000 | 205,000 | 26,000 | 1,451,000 | 74.1 | 12.6 | 1.52 |
| 2 | 553 | 4,665,000 | 1,391,000 | 28,000 | 6,084,000 | 67.1 | 20.0 | 0.39 |
| 3 | 565 | 937,000 | 758,000 | 19,000 | 1,714,000 | 48.2 | 39.0 | 0.91 |
| 4 | 592 | 5,802,000 | 3,104,000 | 28,000 | 8,934,000 | 58.7 | 30.8 | 0.30 |
| 5 | 594 | 4,780,000 | 3,047,000 | 30,000 | 7,857,000 | 54.9 | 34.4 | 0.36 |
| 6 | 601 | 6,364,000 | 5,130,000 | 29,000 | 11,523,000 | 50.9 | 40.4 | 0.25 |
| 7 | 603 | 6,878,000 | 4,508,000 | 33,000 | 11,419,000 | 53.6 | 35.2 | 0.26 |
| 8 | 604 | 8,857,000 | 5,072,000 | 58,000 | 13,987,000 | 57.9 | 33.2 | 0.38 |
| 9 | 606 | 4,406,000 | 1,860,000 | 27,000 | 6,293,000 | 63.1 | 26.5 | 0.38 |
| 10 | 607 | 1,334,000 | 990,000 | 29,000 | 2,353,000 | 52.6 | 37.3 | 1.31 |
| 11 | 608 | 4,446,000 | 2,618,000 | 25,000 | 7,089,000 | 56.7 | 33.4 | 0.31 |
| 12 | 613 | 4,265,000 | 1,149,000 | 19,000 | 5,433,000 | 72.3 | 19.5 | 0.32 |
| 13 | 615 | 1,600,000 | 553,000 | 77,000 | 2,230,000 | 62.0 | 21.3 | 3.02 |
| 14 | 618 | 3,380,000 | 1,051,000 | 20,000 | 4,451,000 | 68.1 | 21.2 | 0.39 |
| 15 | 619 | 1,694,000 | 1,190,000 | 17,000 | 2,901,000 | 53.9 | 38.1 | 0.54 |
| 16 | 620 | 888,000 | 1,113,000 | 6,000 | 2,007,000 | 40.0 | 50.0 | 0.29 |
| 17 | 627 | 1,018,000 | 3,302,000 | 45,000 | 4,365,000 | 22.2 | 71.8 | 0.91 |
| 18 | 628 | 1,681,000 | 629,000 | 53,000 | 2,363,000 | 62.4 | 23.4 | 1.96 |
| 19 | 629 | 3,841,000 | 888,000 | 22,000 | 4,751,000 | 77.0 | 17.8 | 0.45 |
| 20 | 630 | 4,952,000 | 1,988,000 | 18,000 | 6,958,000 | 68.1 | 27.3 | 0.24 |
| 21 | 636 | 834,000 | 2,965,000 | 74,000 | 3,873,000 | 20.8 | 73.3 | 1.85 |
| 22 | 637 | 864,000 | 1,307,000 | 22,000 | 2,193,000 | 36.8 | 55.4 | 0.98 |
| 23 | 638 | 6,672,000 | 4,272,000 | 109,000 | 11,053,000 | 55.1 | 34.7 | 0.94 |
| 24 | 645 | 4,171,000 | 1,662,000 | 24,000 | 5,857,000 | 65.1 | 26.0 | 0.37 |
| 25 | 647 | 4,303,000 | 2,098,000 | 25,000 | 6,426,000 | 60.1 | 29.3 | 0.35 |
| 26 | 648 | 4,617,000 | 2,895,000 | 31,000 | 7,543,000 | 55.7 | 34.6 | 0.38 |
| 27 | 651 | 8,553,000 | 3,603,000 | 51,000 | 12,207,000 | 64.8 | 27.3 | 0.39 |
| 28 | 652 | 5,485,000 | 3,426,000 | 26,000 | 8,937,000 | 58.0 | 36.2 | 0.27 |
| 29 | 653 | 5,811,000 | 2,610,000 | 29,000 | 8,450,000 | 59.8 | 26.7 | 0.28 |
| 30 | 654 | 2,480,000 | 1,867,000 | 27,000 | 4,374,000 | 53.1 | 40.0 | 0.61 |
| 31 | 664 | 3,030,000 | 1,355,000 | 130,000 | 4,515,000 | 61.4 | 27.4 | 2.62 |
| 32 | 665 | 2,793,000 | 762,000 | 14,000 | 3,569,000 | 68.4 | 18.6 | 0.32 |
| 33 | 699 | 389,000 | 1,450,000 | 43000 | 1,882,000 | 19.3 | 71.9 | 2.11 |

*Oligomerization Conditions: 45° C.; 500 psi ethylene; Cr:MMAO-3A = 1:1000; run time = 50 minutes; chromium source: $CrCl_3(THF)_3$; chromium loading level: 0.008 μmol

TABLE 5

High-Throughput Oligomerization Results - preformed complexes as precatalysts*

| Example | Ligating compound or ligating compound-chromium complex | Activity (g/g Cr h) | | | | Selectivity (wt %) | | |
|---|---|---|---|---|---|---|---|---|
| | | 1-Octene | 1-Hexene | Polymer | Total | 1-Octene | 1-Hexene | Polymer |
| 34 | 100 | 1,220,000 | 205,000 | 26,000 | 1,451,000 | 74.1 | 12.6 | 1.52 |
| 35 | 403 | 177,000 | 1,000,000 | 15,000 | 1,192,000 | 13.4 | 75.6 | 1.19 |
| 36 | 421 | 291,000 | 123,000 | 10,000 | 424,000 | 55.2 | 23.3 | 1.55 |
| 37 | 422 | 160,000 | 931,000 | 14,000 | 1,105,000 | 13.4 | 77.7 | 1.18 |
| 38 | 560 | 5,362,000 | 1,898,000 | 50,000 | 7,310,000 | 64.7 | 22.9 | 0.60 |

*Oligomerization Conditions: 45° C.; 500 psi ethylene; Cr:MMAO-3A = 1:1000; run time = 30 minutes; chromium source for Example 100: $CrCl_3(THF)_3$; chromium loading level: 0.008 μmol.

TABLE 6

High-Throughput Oligomerization Results - preformed complexes as precatalysts*

| Example | Ligating compound or ligating compound-chromium complex | Activity (g/g Cr h) | | | | Selectivity (wt %) | | |
|---|---|---|---|---|---|---|---|---|
| | | 1-Octene | 1-Hexene | Polymer | Total | 1-Octene | 1-Hexene | Polymer |
| 39 | 100 | 511,000 | 107,000 | 13,000 | 631,000 | 69.94 | 14.67 | 1.76 |
| 40 | 421 | 305,000 | 148,000 | 8,000 | 461,000 | 52.56 | 25.46 | 1.33 |
| 41 | 422 | 121,000 | 958,000 | 6,000 | 1,085,000 | 10.10 | 79.46 | 0.50 |
| 42 | 455 | 68,000 | 232,000 | 6,000 | 306,000 | 19.85 | 68.14 | 1.69 |

*Oligomerization Conditions: 45° C.; 500 psi ethylene; Cr:MMAO-3A = 1:1000; run time = 30 minutes; chromium source for Example 100: $CrCl_3(THF)_3$; chromium loading level: 0.05 μmol

TABLE 7

High-Throughput Oligomerization Results - preformed complexes as precatalysts*

| Example | Ligating compound or ligating compound-chromium complex | Activity (g/g Cr h) | | | | Selectivity (wt %) | | |
|---|---|---|---|---|---|---|---|---|
| | | 1-Octene | 1-Hexene | Polymer | Total | 1-Octene | 1-Hexene | Polymer |
| 43 | 100 | 297,000 | 64,000 | 10,000 | 371,000 | 69.2 | 15.0 | 2.30 |
| 44 | 372 | 172,000 | 58,000 | 6,000 | 236,000 | 56.0 | 18.8 | 2.09 |
| 45 | 403 | 91,000 | 777,000 | 5,000 | 873,000 | 9.19 | 78.2 | 0.46 |
| 46 | 421 | 264,000 | 154,000 | 6,000 | 424,000 | 49.6 | 28.8 | 1.07 |
| 47 | 422 | 68,000 | 495,000 | 6,000 | 569,000 | 10.8 | 78.7 | 0.88 |
| 48 | 596 | 18,000 | 809,000 | 57,000 | 884,000 | 1.98 | 86.2 | 5.32 |

*Oligomerization Conditions: 45° C.; 500 psi ethylene; Cr:MMAO-3A = 1:1000; run time = 30 minutes; chromium source for Example 100: CrCl$_3$(THF)$_3$; chromium loading level: 0.1 µmol

TABLE 8

High-Throughput Oligomerization Results - Comparative Examples*

| Example | Ligating compound or ligating compound-chromium complex | Activity (g/g Cr h) | | | | Selectivity (wt %) | | |
|---|---|---|---|---|---|---|---|---|
| | | 1-Octene | 1-Hexene | Polymer | Total | 1-Octene | 1-Hexene | Polymer |
| C1 | 100 | 278,000 | 72,000 | 8,000 | 358,000 | 73.2 | 19.0 | 2.0 |
| C2 | 404 | 368,000 | 95,000 | 13,000 | 477,000 | 72.6 | 18.8 | 2.6 |
| C3 | 430 | 21,000 | 21,000 | 15,000 | 57,000 | 32.8 | 32.9 | 22.8 |
| C4 | 431 | 2,000 | 3,000 | 1,000 | 6,000 | 24.4 | 41.4 | 20.3 |
| C5 | 453 | 9,000 | 6,000 | 4,000 | 19,000 | 31.8 | 22.7 | 13.7 |

*Oligomerization Conditions: 45° C.; 500 psi ethylene; Cr:MMAO-3A = 1:1000; run time = 30 minutes; chromium source for Example 100: CrCl$_3$(THF)$_3$; chromium loading level: 0.1 µmol; total volume 5 mL

TABLE 9

High-Throughput Oligomerization Results - in situ catalyst formation*

| Example | Ligating compound | Total Activity (g/g Cr h) | C10-C18 Selectivity (wt %) |
|---|---|---|---|
| 49 | 100 | 1,451,000 | 6.38 |
| 50 | 594 | 7,857,000 | 5.45 |
| 51 | 601 | 11,523,000 | 3.45 |
| 52 | 603 | 11,419,000 | 4.38 |
| 53 | 607 | 2,353,000 | 2.80 |
| 54 | 613 | 5,433,000 | 4.68 |
| 55 | 615 | 2,230,000 | 6.07 |
| 56 | 620 | 2,007,000 | 2.84 |
| 57 | 627 | 4,365,000 | 4.58 |
| 58 | 629 | 4,751,000 | 3.47 |
| 59 | 630 | 6,958,000 | 3.50 |
| 60 | 636 | 3,873,000 | 3.47 |
| 61 | 637 | 2,193,000 | 4.25 |
| 62 | 651 | 12,207,000 | 6.11 |
| 63 | 652 | 8,937,000 | 4.59 |
| 64 | 654 | 4,374,000 | 4.24 |

*Oligomerization Conditions: 45° C.; 500 psi ethylene; Cr:MMAO-3A = 1:1000; run time = 30 minutes; chromium source: CrCl$_3$(THF)$_3$; chromium loading level: 0.008 µmol

TABLE 10

Batch Reactor Oligomerization Results*

| Example | Ligating compound or ligating compound-chromium complex | Activity (g/g Cr h) | | | | Selectivity (wt %) | | |
|---|---|---|---|---|---|---|---|---|
| | | 1-Octene | 1-Hexene | Polymer | Total | 1-Octene | 1-Hexene | Polymer |
| 65 | 100** | 747,000 | 230,198 | 14,508 | 991,706 | 68.6 | 21.2 | 1.3 |
| 66 | 404** | 792,440 | 252,358 | 21,138 | 1,065,936 | 68.1 | 21.7 | 1.8 |
| 67 | 372** | 501,461 | 273,254 | 9,200 | 783,915 | 54.8 | 29.9 | 1.0 |
| 68 | 403† | 342,991 | 1,657,579 | 12,212 | 2,012,782 | 16.0 | 77.1 | 0.6 |
| 69 | 553† | 3,399,495 | 1,487,577 | 16,615 | 4,903,687 | 64.0 | 28.0 | 0.3 |
| 70 | 560† | 3,864,789 | 1,783,422 | 24,981 | 5,673,192 | 62.4 | 28.8 | 0.4 |

*Oligomerization Conditions: 70° C.; 700 psi ethylene; Cr:MMAO-3A = 1:1000; run time = 30 minutes; chromium source for Examples 100 and 553: CrCl$_3$(THF)$_3$
**Chromium loading level: 0.05 µmol
†Chromium loading level: 0.2 µmol

TABLE 11

Batch Reactor Oligomerization Results with Cr(acac)₃*

| | Ligating | Activity (g/g Cr h) | | | | Selectivity (wt %) | | |
|---|---|---|---|---|---|---|---|---|
| Example | compound | 1-Octene | 1-Hexene | Polymer | Total | 1-Octene | 1-Hexene | Polymer |
| 71 | 100** | 742,000 | 242,000 | 16,000 | 1,000,000 | 67.2 | 22.2 | 1.60 |
| 72 | 553† | 2,404,000 | 1,129,000 | 20,000 | 3,553,000 | 61.6 | 29.0 | 0.57 |

*Oligomerization Conditions: 70° C.; 700 psi ethylene; Cr:MMAO-3A = 1:1000; run time = 30 minutes; chromium source: Cr(acac)₃; catalyst loading = 0.2 μmol
**Average of three runs in the batch reactor at the given conditions
†Average of eight runs in the batch reactor at the given conditions

TABLE 12

Batch Reactor Oligomerization Results with Varying Chromium Concentrations and Cr:MMAO ratios*

| | Ligating | [Al] | [Cr] | Activity (g/g Cr h) | | | | Selectivity (wt %) | | |
|---|---|---|---|---|---|---|---|---|---|---|
| Example | compound | (mM) | (μM) | 1-Octene | 1-Hexene | Polymer | Total | 1-Octene | 1-Hexene | Polymer |
| 73 | 553‡ | 1.0 | 1.0** | 2,871,000 | 1,334,000 | 48,000 | 4,253,000 | 62.5 | 29.0 | 1.02 |
| 74 | 100‡ | | | 577,000 | 189,000 | 29,000 | 795,000 | 68.1 | 22.3 | 3.45 |
| 75 | 553‡ | | 2.0† | 1,917,000 | 903,000 | 20,000 | 2,840,000 | 62.0 | 29.2 | 0.65 |
| 76 | 100‖ | | | 553,000 | 183,000 | 57,000 | 793,000 | 63.8 | 21.1 | 6.63 |
| 77 | 553†† | 2.0 | 2.0** | 2,404,000 | 1,129,000 | 20,000 | 3,553,000 | 61.6 | 29.0 | 0.57 |
| 78 | 100‖ | | | 742,000 | 242,000 | 16,000 | 1,000,000 | 67.2 | 22.2 | 1.60 |
| 80 | 553‖ | | 4.0† | 2,841,000 | 1,487,000 | 19,000 | 4,347,000 | 57.9 | 30.2 | 0.45 |
| 81 | 100‡ | | | 1,089,000 | 364,000 | 18,000 | 1,471,000 | 66.4 | 22.2 | 1.10 |
| 82 | 553‡ | 3.0 | 3.0** | 1,914,000 | 910,000 | 22,000 | 2,846,000 | 61.1 | 29.0 | 0.69 |
| 83 | 100‡ | | | 842,000 | 276,000 | 20,000 | 1,138,000 | 67.2 | 21.9 | 1.65 |
| 84 | 553‡ | | 6.0† | 1,475,000 | 712,000 | 56,000 | 2,243,000 | 59.1 | 28.5 | 2.25 |
| 85 | 100‡ | | | 559,000 | 177,000 | 22,000 | 758,000 | 67.2 | 21.4 | 2.67 |

*Oligomerization Conditions: 70° C.; 700 psi ethylene; run time = 30 minutes; chromium source: Cr(acac)₃
**Cr:MMAO-3A = 1:1000
†Cr:MMAO-3A = 1:500
‡Average of two runs in the batch reactor at the given conditions
‖Average of three runs in the batch reactor at the given conditions
††Average of seven runs in the batch reactor at the given conditions

What is claimed is:

1. A phosphacycle-containing ligating compound-chromium complex catalyst comprising a) a source of chromium selected from the group consisting of CrCl₃(THF)₃ (trichlorotris(tetrahydrofuran)chromium), CrBr₃(THF)₃, CrI₃(THF)₃, CrCl₃, CrBr₃, CrI₃, CrCl₂, CrCl₂(THF)₂, Cr(acac)₃(chromium (III) acetylacetonate), Cr(acetate)₃ (chromium (Ill) acetate), Cr(2-ethylhexanoate)₃ (chromium (Ill) 2-ethylhexanoate), (THF)₃CrMeCl₂, (Mes)₃Cr(THF), ((TFA)₂Cr(OEt)₂)₂, (THF)₃CrPh₃, Cr(NMe₂)₂Cl₃, Cr(neopentyl)₃(THF)₃, Cr(CH₂-C₆H₄-o-NMe₂)₃, Cr(TFA)₃, Cr(CH(SiMe₃)₂)₃, Cr(Mes)₂(THF)₃, Cr(Mes)₂(THF), Cr(Mes)₂(THF)₂, Cr(Mes)Cl(THF)₂, Cr(Mes)Cl(THF)₀.₅, Cr(p-tolyl)Cl₂(THF)₃, Cr(diisopropylamide)₃, Cr(picolinate)₃, Cr(NO₃)₃, Cr(hexafluoroacetylacetonato)₃, (THF)₃Cr(η²-2,2"biphenyl)Br, Cr(CO)₆, Cr(CO)₃(THF)₃, Cr(CO)₃(NCCH₃)₃, (benzene)Cr(CO)₃, (toluene)Cr(CO)₃ chromium (Ill) acetylacetonate, chromium (Ill) acetate and mixtures thereof;
   b) one or more activators selected from the group consisting of (hydrocarbyl)aluminum compounds, (hydrocarbyl)gallium compounds, (hydrocarbyl)boron compounds, (hydrocarbyl)zinc compounds, non-coordinating, ion-forming compounds, an organic salt, an inorganic acid and salt, Brønsted acid salts, salts of a cationic oxidizing agent and a non-coordinating, compatible anion, carbenium salts, and silylium salts; and
   c) at least one phosphacycle-containing ligating compound of the formula:

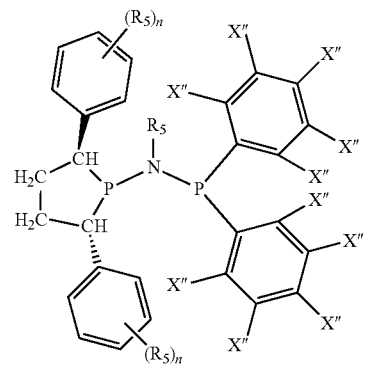

wherein: R₅ attached to N is independently C₁₋₄₀ substituted or unsubstituted alkyl, C₁₋₄₀ substituted or unsubstituted aryl; each R₅ attached to the phenyl group is independently halogen, C₁₋₄₀ substituted or unsubstituted alkyl, C₁₋₄₀ substituted or unsubstituted aryl; n is an integer from 0 to 5; and each X" is independently hydrogen, halogen, C₁₋₄ alkyl or substituted alkyl, C₆₋₁₀ aryl or substituted aryl, cyano or nitro.

2. The catalyst of claim 1, wherein the source of chromium is selected from the group consisting of trichlorotris(tetrahydrofuran)chromium, chromium (Ill) acetylacetonate, chromium (Ill) 2-ethylhexanoate, and chromium (Ill) acetate.

3. The catalyst of claim 1, wherein the source of chromium and the ligating compound are contacted in proportions to provide Cr: ligating compound ratios from 1000:1 to 1:1000.

4. The catalyst of claim 1, wherein the activator is an alkylaluminoxane.

5. The catalyst of claim 1, wherein the source of chromium and the aluminoxane are combined in proportions to provide chromium:

activator molar ratios from 1:1 to 1:10,000.

6. The catalyst of claim 1 wherein the phosphacycle-containing ligating compound is selected from the group consisting of:

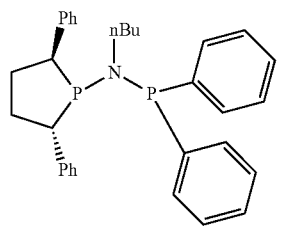

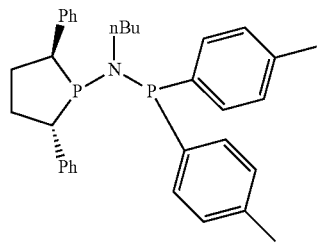

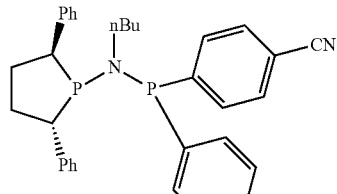

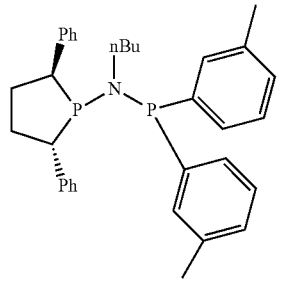

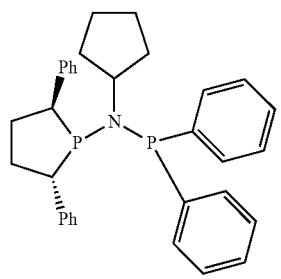

-continued

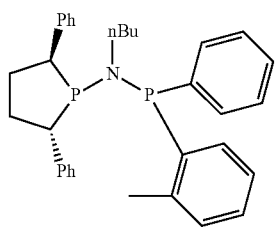

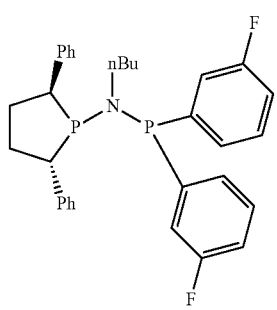

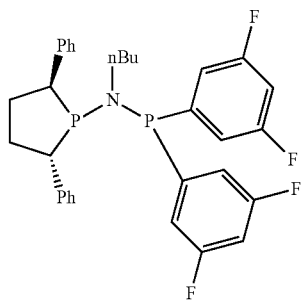

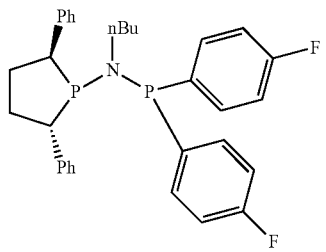

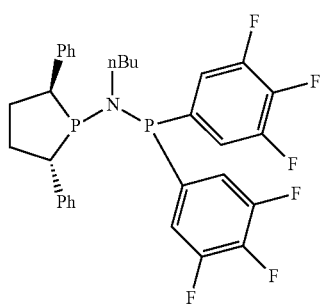

369
-continued
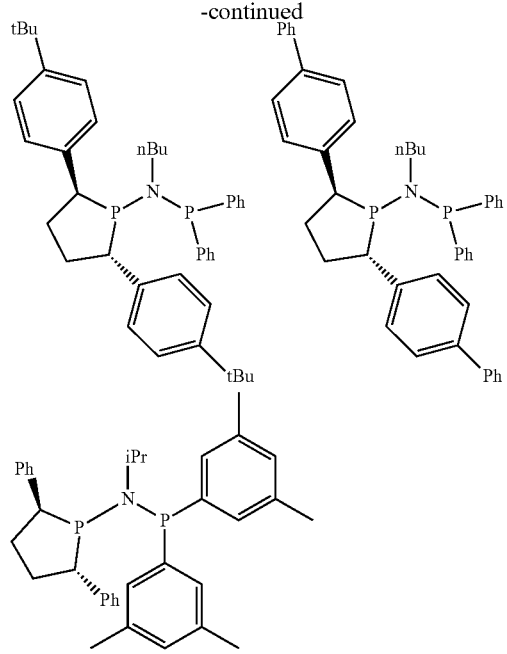
370
-continued
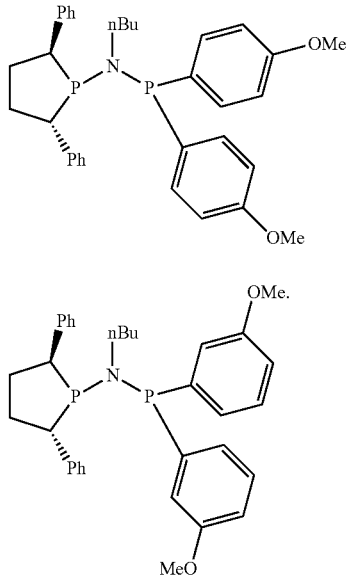
* * * * *